(12) United States Patent
Ding et al.

(10) Patent No.: US 8,952,157 B2
(45) Date of Patent: Feb. 10, 2015

(54) APOPTOSIS-INDUCING AGENTS FOR THE TREATMENT OF CANCER AND IMMUNE AND AUTOIMMUNE DISEASES

(71) Applicants: AbbVie Inc., North Chicago, IL (US); The Walter and Eliza Hall Institue of Medical Research, Parkville (AU)

(72) Inventors: Hong Ding, Gurnee, IL (US); George A. Doherty, Libertyville, IL (US); Steven W. Elmore, Northbrook, IL (US); Laura Hexamer, Grayslake, IL (US); Aaron R. Kunzer, Arlington Heights, IL (US); Cheol-Min Park, Gurnee, IL (US); Xiahong Song, Grayslake, IL (US); Andrew J. Souers, Evanston, IL (US); Gerard M. Sullivan, Lake Villa, IL (US); Zhi-Fu Tao, Gurnee, IL (US); Le Wang, Vernon Hills, IL (US); Michael D. Wendt, Vernon Hills, IL (US); Peter Edward Czabotar, North Melbourne (AU); Guillaume Laurent Lessene, Bundoora (AU); Peter Malcolm Colman, East Melbourne (AU)

(73) Assignees: AbbVie Inc., North Chicago, IL (US); The Walter and Eliza Hall Institute of Medical Research, Victoria (AU)

(*) Notice: Subject to any disclaimer, the term of this patent is extended or adjusted under 35 U.S.C. 154(b) by 0 days.

(21) Appl. No.: 13/952,278

(22) Filed: Jul. 26, 2013

(65) Prior Publication Data
US 2014/0066621 A1    Mar. 6, 2014

Related U.S. Application Data

(63) Continuation of application No. 12/631,367, filed on Dec. 4, 2009, now abandoned.

(60) Provisional application No. 61/119,844, filed on Dec. 4, 2008.

(51) Int. Cl.
| | | |
|---|---|---|
| C07D 241/12 | (2006.01) |
| C07D 401/10 | (2006.01) |
| C07D 401/12 | (2006.01) |
| C07D 209/08 | (2006.01) |
| C07D 211/58 | (2006.01) |
| C07D 213/74 | (2006.01) |
| C07D 213/84 | (2006.01) |
| C07D 231/56 | (2006.01) |
| C07D 235/06 | (2006.01) |
| C07D 277/24 | (2006.01) |
| C07D 295/30 | (2006.01) |
| C07D 309/04 | (2006.01) |
| C07D 401/14 | (2006.01) |
| C07D 403/12 | (2006.01) |
| C07D 405/12 | (2006.01) |
| C07D 405/14 | (2006.01) |
| C07D 413/12 | (2006.01) |
| C07D 417/12 | (2006.01) |
| C07D 471/04 | (2006.01) |
| C07D 309/08 | (2006.01) |

(52) U.S. Cl.
CPC ............ *C07D 401/12* (2013.01); *C07D 209/08* (2013.01); *C07D 211/58* (2013.01); *C07D 213/74* (2013.01); *C07D 213/84* (2013.01); *C07D 231/56* (2013.01); *C07D 235/06* (2013.01); *C07D 277/24* (2013.01); *C07D 295/30* (2013.01); *C07D 309/04* (2013.01); *C07D 401/14* (2013.01); *C07D 403/12* (2013.01); *C07D 405/12* (2013.01); *C07D 405/14* (2013.01); *C07D 413/12* (2013.01); *C07D 417/12* (2013.01); *C07D 471/04* (2013.01); *C07D 309/08* (2013.01)
USPC ........................................ 544/358; 544/360

(58) Field of Classification Search
CPC ...................................................... C07D 241/12
USPC .................................................. 544/358, 360
See application file for complete search history.

(56) References Cited

U.S. PATENT DOCUMENTS

| | | | |
|---|---|---|---|
| 5,661,159 | A | 8/1997 | Matsuo et al. |
| 6,410,584 | B1 | 6/2002 | Pamukcu et al. |
| 6,720,338 | B2 | 4/2004 | Augeri et al. |
| 6,949,545 | B2 | 9/2005 | Pikul et al. |
| 7,390,799 | B2 | 6/2008 | Bruncko et al. |
| 7,504,512 | B2 | 3/2009 | Augeri et al. |
| 7,511,013 | B2 | 3/2009 | Molino et al. |
| 7,514,068 | B2 | 4/2009 | Tung |

(Continued)

FOREIGN PATENT DOCUMENTS

| | | |
|---|---|---|
| EA | 005373 | 2/2005 |
| EA | 006973 | 6/2005 |

(Continued)

OTHER PUBLICATIONS

International Searching Authority, "International Search Report for Application No. PCT/US2010/036198 ISR," (Apr. 29, 2005), 3 pp.
Becker D.P., et al., "Azaadamantane Benzamide 5-HT4 Agonists: Gastrointestinal Prokinetic SC-54750" Bioorganic and Medicinal Chemistry Letters, (2004), vol. 14, No. 22, pp. 5509-5512.
Cross, L.C., et al., "IUPAC Commission on Nomenclature of Organic Chemistry: Rules for the Nomenclature of Organic Chemistry, Section E: Stereochemistry," Pure and Applied Chemistry, (1976), vol. 45, pp. 13-30.
Del Gaizo Moore, V., et al., "BCL-2 Dependence and ABT-737 Sensitivity in Acute Lymphoblastic Leukemia," Blood, (2008), vol. 111, No. 4. pp. 2300-2309.
Corbett, Thomas H. et al., "Discovery and Preliminary Antitumor efficacy evaluations of LY32262 and LY33169," Investigational New Drugs, (2003), vol. 21, pp. 33-45.

(Continued)

Primary Examiner — Shawquia Jackson
(74) Attorney, Agent, or Firm — Jones Day

(57) ABSTRACT

Disclosed are compounds which inhibit the activity of anti-apoptotic Bcl-2 proteins, compositions containing the compounds and methods of treating diseases during which is expressed anti-apoptotic Bcl-2 protein.

5 Claims, No Drawings

(56) References Cited

U.S. PATENT DOCUMENTS

| | | |
|---|---|---|
| 7,521,421 B2 | 4/2009 | Naicker et al. |
| 7,528,131 B2 | 5/2009 | Persichetti et al. |
| 7,531,685 B2 | 5/2009 | Czarnik |
| 7,534,814 B2 | 5/2009 | Ascher et al. |
| 7,538,189 B2 | 5/2009 | Naicker et al. |
| 7,642,260 B2 | 1/2010 | Bruncko et al. |
| 7,709,467 B2 | 5/2010 | Bruncko et al. |
| 7,754,886 B2 | 7/2010 | Augeri et al. |
| 7,767,684 B2 | 8/2010 | Bruncko et al. |
| 7,851,637 B2 | 12/2010 | Castro et al. |
| 7,973,161 B2 | 7/2011 | Bruncko et al. |
| 8,084,607 B2 | 12/2011 | Bruncko et al. |
| 8,173,811 B2 | 5/2012 | Bruncko et al. |
| 8,354,404 B2 | 1/2013 | Bruncko et al. |
| 8,546,399 B2 | 10/2013 | Bruncko et al. |
| 8,557,983 B2 | 10/2013 | Doherty et al. |
| 8,563,735 B2 | 10/2013 | Bruncko et al. |
| 8,580,794 B2 | 11/2013 | Doherty et al. |
| 8,586,754 B2 | 11/2013 | Bruncko et al. |
| 8,614,318 B2 | 12/2013 | Bruncko et al. |
| 8,686,136 B2 | 4/2014 | Bruncko et al. |
| 2002/0055631 A1 | 5/2002 | Augeri et al. |
| 2002/0086887 A1 | 7/2002 | Augeri et al. |
| 2005/0159427 A1 | 7/2005 | Bruncko et al. |
| 2006/0128706 A1 | 6/2006 | Bruncko et al. |
| 2006/0258657 A1 | 11/2006 | Bruncko et al. |
| 2007/0015787 A1 | 1/2007 | Bruncko et al. |
| 2007/0027135 A1 | 2/2007 | Bruncko et al. |
| 2007/0072860 A1 | 3/2007 | Bruncko et al. |
| 2008/0076779 A1 | 3/2008 | Elmore et al. |
| 2008/0182845 A1 | 7/2008 | Bardwell et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0022773 A1 | 1/2010 | Bruncko et al. |
| 2010/0152183 A1 | 6/2010 | Bruncko et al. |
| 2010/0160322 A1 | 6/2010 | Bruncko et al. |
| 2010/0184750 A1 | 7/2010 | Hexamer et al. |
| 2010/0184766 A1 | 7/2010 | Kunzer et al. |
| 2010/0227838 A1 | 9/2010 | Shah |
| 2010/0240715 A1 | 9/2010 | Bruncko et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2011/0124628 A1 | 5/2011 | Bruncko et al. |
| 2011/0256129 A1 | 10/2011 | Bruncko et al. |
| 2013/0267514 A1 | 10/2013 | Bruncko et al. |
| 2013/0267534 A1 | 10/2013 | Bruncko et al. |
| 2013/0296295 A1 | 11/2013 | Bruncko et al. |
| 2014/0057889 A1 | 2/2014 | Bruncko et al. |
| 2014/0057890 A1 | 2/2014 | Bruncko et al. |
| 2014/0088106 A1 | 3/2014 | Bruncko et al. |
| 2014/0094471 A1 | 4/2014 | Bruncko et al. |
| 2014/0107119 A1 | 4/2014 | Bruncko et al. |
| 2014/0113910 A1 | 4/2014 | Bruncko et al. |

FOREIGN PATENT DOCUMENTS

| | | |
|---|---|---|
| EP | 0527378 B1 | 2/1993 |
| RU | 2000104859 | 11/2001 |
| RU | 2208609 C2 | 7/2003 |
| RU | 2232751 C2 | 7/2004 |
| RU | 2245876 C2 | 2/2005 |
| RU | 2263666 C1 | 11/2005 |
| UA | 74889 C2 | 2/2004 |
| WO | 9304046 A1 | 3/1993 |
| WO | 9507271 A1 | 3/1995 |
| WO | 9710223 | 3/1997 |
| WO | 9906433 A1 | 2/1999 |
| WO | 9942443 | 8/1999 |
| WO | 0001389 A1 | 1/2000 |
| WO | 0037436 A1 | 6/2000 |
| WO | 0112189 A1 | 2/2001 |
| WO | 0170693 A2 | 9/2001 |
| WO | 0224636 A2 | 3/2002 |
| WO | 02066470 A1 | 8/2002 |
| WO | 02098848 A1 | 12/2002 |
| WO | 03040107 A1 | 5/2003 |
| WO | 2004043950 A1 | 5/2004 |
| WO | 2004048329 A1 | 6/2004 |
| WO | 2005049593 A2 | 6/2005 |
| WO | 2005049594 A1 | 6/2005 |
| WO | 2005099353 A2 | 10/2005 |
| WO | 2006008754 A1 | 1/2006 |
| WO | 2006009869 A1 | 1/2006 |
| WO | 2008030836 A2 | 3/2008 |
| WO | 2010065824 A2 | 6/2010 |
| WO | 2010065865 A2 | 6/2010 |
| WO | 2010083441 A2 | 7/2010 |
| WO | 2010138588 A2 | 12/2010 |

OTHER PUBLICATIONS

United States Patent and Trademark Office, "Non-Final Office Action issued in U.S. Appl. No. 12/631,404," (Feb. 18, 2011).

United States Patent and Trademark Office, "Final Office Action issued in U.S. Appl. No. 12/631,404," (Jul. 28, 2011).

United States Patent and Trademark Office, "Non-Final Office Action issued in U.S. Appl. No. 12/793,418," (Apr. 2, 2012).

United States Patent and Trademark Office, "Non-Final Office Action issued in U.S. Appl. No. 12/631,367," (Jun. 29, 2012).

United States Patent and Trademark Office, "Non-Final Office Action issued in U.S. Appl. No. 12/793,413," (Aug. 2, 2012).

United States Patent and Trademark Office, "Non-Final Office Action issued in U.S. Appl. No. 12/787,682," (Sep. 17, 2012).

United States Patent and Trademark Office, "Non-Final Office Action issued in U.S. Appl. No. 12/793,418," (Oct. 9, 2012).

United States Patent and Trademark Office, "Non-Final Office Action issued in U.S. Appl. No. 13/839,060," (May 6, 2014).

Patel, N. B., et al., "Synthesis and antimicrobial activity of sulfonamides and 4-(p-nitrobenzoyl)piperazine incorporated fluoroquinolones," Indian Journal of Heterocyclic Chemistry, (2006), vol. 16. No. 2, pp. 205-206.

File Registry (STN) [online], CAS Registry No. 745034-46-2, 378189-42-5.

File Registry (STN) [online], CAS Registry No. 739342-14-4, 395090-67-2, 328028-74-6, 303228-76-4.

File Registry (STN) [online], CAS Registry No. 753468-40-5, 745034-46-2, 745028-47-1, 716373-52-3, 380557-27-7, 378189-42-5.

Oltersdorf, T., et al., "An inhibitor of Bcl-2 family proteins induces regression of solid tumours," Nature, (2005), vol. 435, pp. 677-681.

Bardwell, P.D., et al., "The Bcl-2 family antagonist ABT-737 significantly inhibits multiple animal models of autoimmunity," J. Immunol., (2009), vol. 182, No. 12, pp. 7482-7489.

Humerickhouse, R., "Clinical Activity of the Potent and Selective Bcl-2 Inhibitor ABT-199: Proving the Concept," Symposium presentation, (Apr. 9, 2016), American Association for Cancer Research (AACR) Annual Meeting (Washington, D.C.), pp. 1-31.

Beylot M., et al., "In vivo studies of intrahepatic metabolic pathways," Diabetes Metabolism, 1997, 23 (3), 251-257.

Blagojevic N., et al., "Role of heavy water in Boron Neutron Capture Therapy," in Topics in Dosimetry & Treatment Planning for Neutron Capture Therapy, Advanced Medical Publishing, (1994), pp. 125-134, Madison, WI.

Blake et al., "Studies with deuterated drugs," J. Pharm. Sci., (1975), pp. 367-391, vol. 64, Issue 3.

Brickner S. J., et al., "Synthesis and antibacterial activity of U-100592 and U-100766, two oxazolidinone antibacterial agents for the potential treatment of multidrug-resistant gram-positive bacterial infections," J. Med Chem., (1996), pp. 673-679, vol. 39, Issue 3.

(56) References Cited

OTHER PUBLICATIONS

Bruncko M., et al., "Studies leading to potent, dual inhibitors of Bcl-2 and Bcl-xl" Journal of Medicinal Chemistry, (2007), pp. 641-662, vol. 50, Issue 4.

Certo M., et al., "Mitochondria primed by death signals determine cellular addiction to antiapoptotic BCL-2 family members," Cancer Cell, (2006), pp. 351-365, vol. 9, Issue 5.

Czajka D. M., "Effect of deuterium oxide on the reproductive potential of mice," Ann NY Acad Sci, (1960), pp. 770-779, vol. 84.

Czajka D.M., et al., "Physiological effects of deuterium on dogs," Am. J. Physiol., (1961), pp. 357-362, vol. 201, Issue 2.

Eliel, E. L. et al., "Stereochemistry of Organic Compounds," (1994), pp. 119-120, vol. 1206, John Wiley & Sons, Inc. New York.

Foster, A.B., et al., "Deuterium Isotope Effects in the Metabolism of Drugs and Xenobiotics: Implications for Drug Design," Advances in Drug Research, (1985), pp. 2-36, vol. 14, Academic Press, London.

Harada H., et al., "Survival factor-induced extracellular signal-regulated kinase phosphorylates BIM, inhibiting its association with BAX and proapoptotic activity," Proc Natl Acad Sci (2004). vol. 101, Issue 43, pp. 15313-15317, USA.

Holzelova et al., "Autoimmune Lymphoproliferative Syndrome with Somatic Fas Mutations," New England Journal of Medicine, (2004), pp. 1409-1418, vol. 351.

International Searching Authority, "International Search Report for Application No. PCT/US2010/036919," (Aug. 19, 2010), 5 pages.

International Searching Authority, "International Search Report for Application No. PCT/US2009/066790," (Jul. 28, 2010), 5 pages.

International Searching Authority, "International Search Report for Application No. PCT/US2009/066722," (Aug. 4, 2010), 4 pages.

International Searching Authority, "International Search Report for Application No. PCT/US2010/036844," (Aug. 16, 2010), 5 pages.

IUPAC, "Commission on Nomenclature of Organic Chemistry: Rules for the Nomenclature of Organic Chemistry Section E: Stereochemistry," Pure Appl Chem, (1976), pp. 11-30, vol. 45.

Jones C.D et al., "Effects of Substituent Modification on Face Selection in Reduction," Journal Org. Chem, (1998), pp. 2758-2760, vol. 63.

Kato et al., "Synthesis of Deuterated Mosapride Citrate," J. Labelled Comp. Radiopharmaceut, (1995), pp. 927-932, vol. 36, Issue 10.

Korolkova, A., "Essentials of Medicinal Chemistry," John Wiley-Interscience-Interscience Publications, John Wiley & Sons, (1988), pp. 97-118, New York.

Kushner et al., "Pharmacological uses and perspectives of heavy water and deuterated compounds," Can J Physiol Pharmacal, (1999), pp. 79-88, vol. 77.

Lizondo J., et al., "Linezolid: Oxazolidinone antibacterial," Drugs of the Future, (1996), pp. 1116-1123, vol. 21, Issue 11.

Mallesham B., et al., "Highly efficient CuI-catalyzed coupling of aryl bromides with oxazolidinones using Buchwald's protocol: a short route to linezolid and toloxatone," Org. Lett., (2003), pp. 963-965, vol. 5, Issue 7.

Mason, K.D. et al, "Programmed a nuclear cell death delimits platelet life span," Cell, (2007), pp. 1173-1186, vol. 128.

Park, C.M., et al., "Discovery of an orally bioavailable small molecule inhibitor of prosurvival B-cell lymphoma 2 proteins," Journal of Medicinal Chemistry, (2008), pp. 6902-6915, vol. 51, Issue 21.

Puck et al., "Immune Disorders Caused by Defects in the Caspase Cascade," Current Allergy and Asthma Reports, (2003), pp. 378-384, vol. 3.

Rengan et al., "Actin cytoskeletal function is spared, but apoptosis is increased, in WAS patient hematopoietic cells," Blood, (2000), pp. 1283-1292, vol. 95, Issue 4.

Shimazaki et al., "Evaluation of apoptosis as a prognostic factor in myelodysplastic syndromes," British J Hematology, (2000), pp. 584-590, vol. 110, Issue 3.

Sutton V.R., et al. "Bcl-2 prevents apoptosis induced by perforin and granzyme B, but not that mediated by whole cytotoxic lymphocytes", Journal of Immunology, (1997), pp. 5783-5790, vol. 158, Issue 12.

Thomson J. F., "Physiological effects of D20 in mammals," Ann. New York Acad. Sci., (1960), pp. 736-744, vol. 84.

Tse et al., "ABT-263: A Potent and Orally Bioavailable Bcl-2 Family Inhibitor," Cancer Research, (2008), pp. 3421-3428, vol. 68, Issue 9.

Wang Z.X., "An exact mathematical expression for describing competitive binding of two different ligands to a protein molecule," FEBS Lett, (1995); pp. 111-114, vol. 360, Issue 2.

Wendt Michael, "Discovery of ABT-263, a Bcl-family protein inhibitor: observations on targeting a large protein-protein interaction", Expert Opin Drug Discov, (2008), pp. 1123-1143, vol. 3, Issue 9.

International Searching Authority, "Written Opinion for Application No. PCT/US2010/036844," (Jun. 5, 2012), 10 pages.

International Searching Authority, "Written Opinion for Application No. PCT/US2010/036919," (Jun. 5, 2012), 9 pages.

Zhang H. et al., "Bcl-2 family proteins are essential for platelet survival," Cell Death and Differentiation, (2007), pp. 943-951, vol. 14, Issue 5.

International Searching Authority, "Written Opinion for App. No. PCT/US2009/066722," (Aug. 4, 2010), 8 pages.

Lala et al., "Role of nitric oxide in tumor progression: Lessons from experimental tumors," Cancer and Metastasis Reviews (1998), vol. 17, Issue 1, pp. 91-106.

Golub et al., "Molecular Classification of Cancer: Class Discovery and Class Prediction by Gene Expression Monitoring," Science (1999), vol. 286, pp. 531-537.

Cancer [online], [retrieved on Jul. 6, 2007]. Retrieved from the internet, URL http://www.nlm.nih.gov/medlineplus/cancer.html>.

Cancer [online], [retrieved on Jul. 6, 2007]. Retrieved from the internet, URL: http://en.wikipedia.org/wiki/Cancer.

International Searching Authority, Supplementary International Search Report for Application No. PCT/US2010/036844, (Februrary 16, 2012), 4 pages.

International Searching Authority, Supplementary International Search Report for Application No. \ PCT/US2009/066722, (Feb. 24, 2011), 2 pages.

English translation to RU2263666 Abstract, 009 http://worldwide.espacenet.com/publicationDetails/biblio?DB=EPODOC&adjacent=true&locale=en EP&FT=D&date=2005111 O&CC=RU&NR=2263666C1 &KC=C1.

US 8,952,157 B2

APOPTOSIS-INDUCING AGENTS FOR THE TREATMENT OF CANCER AND IMMUNE AND AUTOIMMUNE DISEASES

This application claims priority to U.S. Provisional Application Ser. No. 61/119,844 filed Dec. 4, 2008, which is incorporated by reference in its entirety.

FIELD OF THE INVENTION

This invention pertains to compounds which inhibit the activity of Bcl-2 anti-apoptotic proteins, compositions containing the compounds, and methods of treating diseases during which anti-apoptotic Bcl-2 proteins are expressed.

BACKGROUND OF THE INVENTION

Anti-apoptotic Bcl-2 proteins are associated with a number of diseases. There is therefore an existing need in the therapeutic arts for compounds which inhibit the activity of anti-apoptotic Bcl-2 proteins.

Overexpression of Bcl-2 proteins correlates with resistance to chemotherapy, clinical outcome, disease progression, overall prognosis or a combination thereof in various cancers and disorders of the immune system.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418. Involvement of Bcl-2 proteins in arthritis is disclosed in commonly-owned U.S. Provisional Patent Application Ser. No. 60/988,479. Involvement of Bcl-2 proteins in bone marrow transplant rejection is disclosed in commonly-owned U.S. patent application Ser. No. 11/941,196.

SUMMARY OF THE INVENTION

One embodiment of this invention, therefore, pertains to compounds or therapeutically acceptable salts, prodrugs or salts of prodrugs thereof, which are useful as inhibitors of anti-apoptotic Bcl-2 proteins, the compounds having Formula I

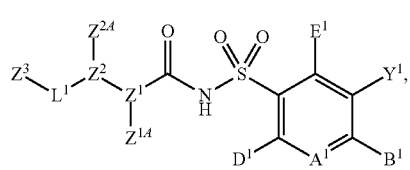

wherein
$A^1$ is N or $C(A^2)$;
$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$ $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, C(O)NH, or $C(O)OR^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; and $Y^1$ is H, CN, $NO_2$, C(O)OH, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2NHSO_2NHR^1$, $NHSO_7N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; or $Y^1$ and $B^1$, together with the atoms to which they are attached, are benzene, naphthylene, heteroarene cycloalkane, cycloalkene, heterocycloalkane or heterocycloalkene; and $A^2$, $D^1$, and $E^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; or $A^2$ and $B^1$, together with the atoms to which they are attached, are benzene, naphthylene, heteroarene cycloalkane, cycloalkene, heterocycloalkane or heterocycloalkene; and $D^1$, $E^1$, and $Y^1$ are independently selected H, $R^1$, $OR^1$, $SR^1$, $S(O)R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$; or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, C(O)H, CHNOH, $CH(NOCH_3)$, $CF_3$, C(O)OH, $C(O)NH_2$ or $C(O)OR^{1A}$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane or heterocycloalkane;

$R^3$ is heteroaryl, which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three of independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH(CH_3)NHC(O)CH(CH_3)NH_2$, $NHC(O)CH(CH_3)NHC(O)CH(CH_3)NHR^1$, OH, (O), C(O)OH, $N_3$, CN, $NH_2$, $CF_3$, $CF_2CF_3$, F, Cl, Br or I;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or $R^{11}$;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^2C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$; is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl, which is unfused or fused with benzene, heteroarene or $R^{18A}$; $R^{18A}$ is cycloalkane, cycloalkene, heterocycloalkane or heterocycloalkene;

$R^{19}$ is heteroaryl, which is unfused or fused with benzene, heteroarene or $R^{19A}$; $R^{19A}$ is cycloalkane, cycloalkene, heterocycloalkane or heterocycloalkene;

$R^{20}$ is cycloalkyl, cycloalkenyl, heterocycloalkyl or heterocycloalkenyl each of which is unfused or fused with benzene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three of independently selected $R^{22}$, $OR^{22}$, $SR^{22}$, $S(O)R^{22}$, $SO_2R^{22}$, $C(O)R^{22}$, $CO(O)R^{22}$, $OC(O)R^{22}$, $OC(O)OR^{22}$, $NH_2$, $NHR^{22}$, $N(R^{22})_2$, $NHC(O)R^{22}$, $NR^{22}C(O)R^{22}$, $NHS(O)_2R^{22}$, $NR^{22}S(O)_2R^{22}$, $NHC(O)OR^{22}$, $NR^2C(O)OR^{22}$, $NHC(O)NH_2$, $NHC(O)NHR^{22}$, $NHC(O)N(R^{22})_2$, $NR^2C(O)NHR^{22}$, $NR^{22}C(O)N(R^{22})_2$, $C(O)NH_2$, $C(O)NHR^{22}$, $C(O)N(R^{22})_2$, $C(O)NHOH$, $C(O)NHOR^{22}$, $C(O)NHSO_2R^{22}$, $C(O)NR^{22}SO_2R^{22}$, $SO_2NH_2$, $SO_2NHR^{22}$, $SO_2N(R^{22})_2$, C(O)H, C(O)OH, C(N)

NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is R$^{23}$, R$^{24}$ or R$^{25}$;

R$^{23}$ is phenyl, which is unfused or fused with benzene, heteroarene or R$^{23A}$; R$^{23A}$ is cycloalkane, cycloalkene, heterocycloalkane or heterocycloalkene;

R$^{24}$ is heteroarene, which is unfused or fused with benzene, heteroarene or R$^{24A}$; R$^{24A}$ is cycloalkane, cycloalkene, heterocycloalkane or heterocycloalkene;

R$^{25}$ is cycloalkyl, cycloalkenyl, heterocycloalkyl or heterocycloalkenyl each of which is unfused or fused with benzene, heteroarene or R$^{25A}$; R$^{25A}$ is cycloalkane, cycloalkene, heterocycloalkane or heterocycloalkene;

Z$^1$ is R$^{26}$ or R$^{27}$;

Z$^2$ is R$^{28}$, R$^{29}$ or R$^{30}$;

Z$^{1A}$ and Z$^{2A}$ are both absent or are taken together to form CH$_2$, CH$_2$CH$_2$ or Z$^{12A}$;

Z$^{12A}$ is C$_2$-C$_6$-alkylene having one or two CH$_2$ moieties replaced by NH, N(CH$_3$), S, S(O) or SO$_2$;

L$_1$ is a R$^{37}$, OR$^{37}$, SR$^{37}$, S(O)R$^{37}$, SO$_2$R$^{37}$, C(O)R$^{37}$, CO(O)R$^{37}$, OC(O)R$^{37}$, OC(O)OR$^{37}$, NHR$^{37}$, C(O)NH, C(O)NR$^{37}$, C(O)NHOR$^{37}$, C(O)NHSO$_2$R$^{37}$, SO$_2$NH, SO$_2$NHR$^{37}$, C(N)NH, C(N)NHR$^{37}$;

R$^{26}$ is phenylene, which is unfused or fused with benzene or heteroarene or R$^{26A}$; R$^{26A}$ is cycloalkane, cycloalkene, heterocycloalkane or heterocycloalkene;

R$^{27}$ is heteroarylene, which is unfused or fused with benzene or heteroarene or R$^{27A}$; R$^{27A}$ is cycloalkane, cycloalkene, heterocycloalkane or heterocycloalkene;

R$^{28}$ is phenylene, which is unfused or fused with benzene, heteroarene or R$^{28A}$; R$^{28A}$ is cycloalkane, cycloalkene, heterocycloalkane or heterocycloalkene;

R$^{29}$ is heteroarylene, which is unfused or fused with benzene or heteroarene or R$^{29A}$; R$^{29A}$ is cycloalkane, cycloalkene, heterocycloalkane or heterocycloalkene;

R$^{30}$ is cycloalkylene, cycloalkenylene, heterocycloalkylene or heterocycloalkenylene, each of which is unfused or fused with benzene, heteroarene or R$^{30A}$; R$^{30A}$ is cycloalkane, cycloalkene, heterocycloalkane or heterocycloalkene;

R$^{37}$ is a bond or R$^{37A}$;

R$^{37A}$ is alkylene, alkenylene, or alkynylene, each of which is unsubstituted or substituted with one or two or three independently selected R$^{37B}$, OR$^{37B}$, SR$^{37B}$, S(O)R$^{37B}$, SO$_2$R$^{37B}$, C(O)R$^{37B}$, CO(O)R$^{37B}$, OC(O)R$^{37B}$, OC(O)OR$^{37B}$, NH$_2$, NHR$^{37B}$, N(R$^{37B}$)$_2$, NHC(O)R$^{37B}$, NR$^{37B}$C(O)R$^{37B}$, NHS(O)$_2$R$^{37B}$, NR$^{37B}$S(O)$_2$R$^{37B}$, NHC(O)OR$^{37B}$, NR$^{37B}$C(O)OR$^{37B}$, NHC(O)NH$_2$, NHC(O)NHR$^{37B}$, NHC(O)N(R$^{37B}$)$_2$, NR$^{37B}$C(O)NHR$^{37B}$, NR$^{37B}$C(O)N(R$^{37B}$)$_2$, C(O)NH$_2$, C(O)NHR$^{37B}$, C(O)N(R$^{37B}$)$_2$, C(O)NHOH, C(O)NHOR$^{37B}$, C(O)NHSO$_2$R$^{37B}$, C(O)NR$^{37B}$SO$_2$R$^{37B}$, SO$_2$NH$_2$, SO$_2$NHR$^{37B}$, SO$_2$N(R$^{37B}$)$_2$, C(O)H, C(O)OH, C(N)NH$_2$, C(N)NHR$^{37B}$, C(N)N(R$^{37B}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br and I substituents;

R$^{37B}$ is alkyl, alkenyl, alkynyl, phenyl, heteroaryl, cycloalkyl, cycloalkenyl, heterocycloalkyl, or heterocycloalkenyl;

Z$^3$ is R$^{38}$, R$^{39}$ or R$^{40}$;

R$^{38}$ is phenyl, which is unfused or fused with benzene, heteroarene or R$^{38A}$; R$^{38A}$ is cycloalkane, cycloalkene, heterocycloalkane or heterocycloalkene;

R$^{39}$ is heteroaryl, which is unfused or fused with benzene, heteroarene or R$^{39A}$; R$^{39A}$ is cycloalkane, cycloalkene, heterocycloalkane or heterocycloalkene;

R$^{40}$ is cycloalkyl, cycloalkenyl, heterocycloalkyl or heterocycloalkenyl, each of which is unfused or fused with benzene, heteroarene or R$^{40A}$; R$^{40A}$ is cycloalkane, cycloalkene, heterocycloalkane or heterocycloalkene;

wherein the moieties represented by R$^{26}$ and R$^{27}$ are substituted (i.e., if Z$^{1A}$ and Z$^{2A}$ are absent) or further substituted (i.e., if Z$^{1A}$ and Z$^{2A}$ are present) with one or two or three or four of independently selected R$^{41}$, OR$^{41}$, SR$^{41}$, S(O)R$^{41}$, SO$_2$R$^{41}$, C(O)R$^{41}$, CO(O)R$^{41}$, OC(O)R$^{41}$, OC(O)OR$^{41}$, NH$_2$, NHR$^{41}$, N(R$^{41}$)$_2$, NHC(O)R$^{41}$, NR$^{41}$C(O)R$^{41}$, NHS(O)$_2$R$^{41}$, NR$^{41}$S(O)$_2$R$^{41}$, NHC(O)OR$^{41}$, NR$^{41}$C(O)OR$^{41}$, NHC(O)NH$_2$, NHC(O)NHR$^{41}$, NHC(O)N(R$^{41}$)$_2$, NR$^{41}$C(O)NHR$^{41}$, NR$^{41}$C(O)N(R$^{41}$)$_2$, C(O)NH$_2$, C(O)NHR$^{41}$, C(O)N(R$^{41}$)$_2$, C(O)NHOH, C(O)NHOR$^{41}$, C(O)NHSO$_2$R$^{41}$, C(O)NR$^{41}$SO$_2$R$^{41}$, SO$_2$NH$_2$, SO$_2$NHR$^{41}$, SO$_2$N(R$^{41}$)$_2$, C(O)H, C(O)OH, C(N)NH$_2$, C(N)NHR$^{41}$, C(N)N(R$^{41}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{41}$ is R$^{42}$, R$^{43}$, R$^{44}$ or R$^{45}$;

R$^{42}$ is phenyl, which is unfused or fused with benzene, heteroarene or R$^{42A}$; R$^{42A}$ is cycloalkane, cycloalkene, heterocycloalkane or heterocycloalkene;

R$^{43}$ is heteroaryl, which is unfused or fused with benzene, heteroarene or R$^{43A}$; R$^{43A}$ is cycloalkane, cycloalkene, heterocycloalkane or heterocycloalkene;

R$^{44}$ is cycloalkyl, cycloalkenyl, heterocycloalkyl or heterocycloalkenyl, each of which is unfused or fused with benzene, heteroarene or R$^{44A}$; R$^{44A}$ is cycloalkane, cycloalkene, heterocycloalkane or heterocycloalkene;

R$^{45}$ is alkyl, alkenyl or alkynyl, each of which is unsubstituted or substituted with one or two or three of independently selected R$^{46}$, OR$^{46}$, SR$^{46}$, S(O)R$^{46}$, SO$_2$R$^{46}$, C(O)R$^{46}$, CO(O)R$^{46}$, OC(O)R$^{46}$, OC(O)OR$^{46}$, NH$_2$, NHR$^{46}$, N(R$^{46}$)$_2$, NHC(O)R$^{46}$, NR$^{46}$C(O)R$^{46}$, NHS(O)$_2$R$^{46}$, NR$^{46}$S(O)$_2$R$^{46}$, NHC(O)OR$^{46}$, NR$^{46}$C(O)OR$^{46}$, NHC(O)NH$_2$, NHC(O)NHR$^{46}$, NHC(O)N(R$^{46}$)$_2$, NR$^{46}$C(O)NHR$^{46}$, NR$^{46}$C(O)N(R$^{46}$)$_2$, C(O)NH$_2$, C(O)NHR$^{46}$, C(O)N(R$^{46}$)$_2$, C(O)NHOH, C(O)NHOR$^{46}$, C(O)NHSO$_2$R$^{46}$, C(O)NR$^{46}$SO$_2$R$^{46}$, SO$_2$NH$_2$, SO$_2$NHR$^{46}$, SO$_2$N(R$^{46}$)$_2$, C(O)H, C(O)OH, C(N)NH$_2$, C(N)NHR$^{46}$, C(N)N(R$^{46}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{46}$ is alkyl, alkenyl, alkynyl, R$^{47}$, R$^{48}$ or R$^{49}$;

R$^{47}$ is phenyl, which is unfused or fused with benzene, heteroarene or R$^{47A}$; R$^{47A}$ is cycloalkane, cycloalkene, heterocycloalkane or heterocycloalkene;

R$^{48}$ is heteroaryl, which is unfused or fused with benzene, heteroarene or R$^{48A}$; R$^{48A}$ is cycloalkane, cycloalkene, heterocycloalkane or heterocycloalkene;

R$^{49}$ is cycloalkyl, cycloalkenyl, heterocycloalkyl or heterocycloalkenyl, each of which is unfused or fused with benzene, heteroarene or R$^{49A}$; R$^{49A}$ is cycloalkane, cycloalkene, heterocycloalkane or heterocycloalkene;

wherein the moieties represented by R$^{42}$, R$^{42A}$, R$^{43}$, R$^{43A}$, R$^{44}$, R$^{44A}$, R$^{47}$, R$^{47A}$, R$^{48}$, R$^{48A}$, R$^{49}$, and R$^{49A}$ are independently substituted with one or two or three or four of independently selected R$^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_2$, NHR$^{50}$, N(R$^{50}$)$_2$, NHC(O)R$^{50}$, NR$^{50}$C(O)R$^{50}$, NHS(O)$_2$R$^{50}$, NR$^{50}$S(O)$_2$R$^{50}$, NHC(O)OR$^{50}$, NR$^{50}$C(O)OR$^{50}$, NHC(O)NH$_2$, NHC(O)NHR$^{50}$, NHC(O)N(R$^{50}$)$_2$, NR$^{50}$C(O)NHR$^{50}$, NR$^{50}$, C(O)N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{50}$SO$_2$R$^{50}$, SO$_2$NH$_2$, SO$_2$NHR$^{50}$, SO$_2$N(R$^{50}$)$_2$, C(O)H, C(O)OH, C(N)NH$_2$, C(N)NHR$^{50}$, C(N)N(R$^{50}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{50}$ is R$^{51}$, R$^{52}$, R$^{53}$ or R$^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three of independently selected $R^{55}$, $OR^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{55}$ is alkyl, alkenyl, alkynyl, phenyl, heteroaryl, cycloalkyl, cycloalkenyl, heterocycloalkyl or heterocycloalkenyl; and wherein each foregoing cyclic moiety is independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{57A}$ is spirocyclyl;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{59A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^2$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl or alkenyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{7}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^7$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl or alkenyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{73}$ is alkyl, alkenyl, alkenyl, phenyl, heteroaryl, cycloalkyl, cycloalkenyl, heterocycloalkyl or heterocycloalkenyl; and the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, OH, (O), CN, $N_3$, $NO_2$, $CF_3$, $CF_2CF_3$, $OCF_3$, $OCF_2CF_3$, F, Cl, Br or I.

Another embodiment pertains to a compound having Formula (II)

(II)

or a therapeutically acceptable salt thereof, wherein
$R^{100}$ is as described for substituents on $R^{26}$;
n is 0, 1, 2, or 3;
$R^{101}$ is as described for substituents on $R^{42}$;
m is 1, 2, 3, 4, or 5;
$A^1$ is N or $C(A^2)$;
$A^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NHSO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$; and $Y^1$ is H, CN, $NO_2$, $C(O)OH$, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$; or $Y^1$ and $B^1$, together with the atoms to which they are attached, are benzene, naphthylene, heteroarene cycloalkane, cycloalkene, heterocycloalkane or heterocycloalkene; and $A^2$, $D^1$, and $E^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$; or $A^2$ and $B^1$, together with the atoms to which they are attached, are benzene, naphthylene, heteroarene cycloalkane, cycloalkene, heterocycloalkane or heterocycloalkene; and $D^1$, $E^1$, and $Y^1$ are independently selected H, $R^1$, $ORE$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1.4}$; or A¹ and D¹, together with the atoms to which they are attached, are benzene, naphthalene, heteroarene, cycloalkane, cycloalkene, heterocycloalkane or heterocycloalkene; and B¹, E¹, and Y¹ are independently selected H, R¹, OR¹, SR¹, S(O)R¹, SO₂R¹, C(O)R¹, C(O)OR¹, OC(O)R¹, NHR¹, N(R¹)₂, C(O)NHR¹, C(O)N(R¹)₂, NHC(O)R¹, NR¹C(O)R¹, NHC(O)OR¹, NR¹C(O)OR¹, NHC(O)NH₂, NHC(O)NHR¹, NHC(O)N(R¹)₂, NR¹C(O)NHR¹, NR¹C(O)N(R¹)₂, SO₂NH₂, SO₂NHR¹, SO₂N(R¹)₂, NHSO₂R¹, NR¹SO₂R¹, NHSO₂NHR¹, NHSO₂N(R¹)₂, NR¹SO₂NHR¹, NR¹SO₂N(R¹)₂, C(O)NHNOH, C(O)NHNOR¹, C(O)NHSO₂R¹, C(NH)NH₂, C(NH)NHR¹, C(NH)N(R¹)₂, NHSO₂NHR¹, NHSO₂N(CH₃)R¹, N(CH₃)SO₂N(CH₃)R¹, F, Cl, Br, I, CN, NO₂, N₃, OH, C(O)H, CHNOH, CH(NOCH₃), CF₃, C(O)OH, C(O)NH₂ or C(O)OR¹·⁴;

R¹ is R², R³, R⁴ or R⁵;

R¹·⁴ is cycloalkyl, cycloalkenyl or cycloalkynyl;

R² is phenyl, which is unfused or fused with benzene, heteroarene or R²·⁴; R²·⁴ is cycloalkane or heterocycloalkane;

R³ is heteroaryl, which is unfused or fused with benzene, heteroarene or R³·⁴; R³·⁴ is cycloalkane or heterocycloalkane;

R⁴ is cycloalkyl, cycloalkenyl, heterocycloalkyl or heterocycloalkenyl, each of which is unfused or fused with benzene, heteroarene or R⁴·⁴; R⁴·⁴ is cycloalkane, cycloalkene, heterocycloalkane or heterocycloalkene;

R⁵ is alkyl, alkenyl or alkynyl, each of which is unsubstituted or substituted with one or two or three of independently selected R⁶, NC(R⁶·⁴)(R⁶·ᴮ), R⁷, OR⁷, SR⁷, S(O)R⁷, SO₂R⁷, NHR⁷, N(R⁷)₂, C(O)R⁷, C(O)NH₂, C(O)NHR⁷, C(O)N(R⁷)₂, NHC(O)R⁷, NR⁷C(O)R⁷, NHSO₂R⁷, NHC(O)OR⁷, SO₂NH₂, SO₂NHR⁷, SO₂N(R⁷)₂, NHC(O)NH₂, NHC(O)NHR⁷, NHC(O)CH(CH₃)NHC(O)CH(CH₃)NH₂, NHC(O)CH(CH₃)NHC(O)CH(CH₃)NHR¹, OH, (O), C(O)OH, N₃, CN, NH₂, CF₃, CF₂CF₃, F, Cl, Br or I;

R⁶ is C₂-C₅-spiroalkyl, each of which is unsubstituted or substituted with OH, (O), N₃, CN, CF₃, CF₂CF₃, F, Cl, Br, I, NH₂, NH(CH₃) or N(CH₃)₂;

R⁶·⁴ and R⁶·ᴮ are independently selected alkyl or, together with the N to which they are attached, R⁶·ᶜ;

R⁶·ᶜ is aziridin-1-yl, azetidin-1-yl, pyrrolidin-1-yl or piperidin-1-yl, each having one CH₂ moiety unreplaced or replaced with O, C(O), CNOH, CNOCH₃, S, S(O), SO₂ or NH;

R⁷ is R⁸, R⁹, R¹⁰ or R¹¹;

R⁸ is phenyl, which is unfused or fused with benzene, heteroarene or R⁸·⁴; R⁸·⁴ is cycloalkane, cycloalkene, heterocycloalkane or heterocycloalkene;

R⁹ is heteroaryl, which is unfused or fused with benzene, heteroarene or R⁹·⁴; R⁹·⁴ is cycloalkane, cycloalkene, heterocycloalkane or heterocycloalkene;

R¹⁰ is cycloalkyl, cycloalkenyl, heterocycloalkyl or heterocycloalkenyl each of which is unfused or fused with benzene, heteroarene or R¹⁰·⁴; R¹⁰·⁴ is cycloalkane, cycloalkene, heterocycloalkane or heterocycloalkene;

R¹¹ is alkyl, alkenyl or alkynyl, each of which is unsubstituted or substituted with one or two or three of independently selected R¹², OR¹², SR¹², S(O)R¹², SO₂R¹², C(O)R¹², CO(O)R¹, OC(O)R¹², OC(O)OR¹², NH₂, NHR¹², N(R¹²)₂, NHC(O)R¹², NR¹²C(O)R¹, NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, (O), CN, N₃, NO₂, CF₃, CF₂CF₃, OCF₃, OCF₂CF₃, F, Cl, Br or I;

R¹² is R¹³, R¹⁴, R¹⁵ or R¹⁶;

R¹³ is phenyl, which is unfused or fused with benzene, heteroarene or R¹³·⁴; R¹³·⁴ is cycloalkane, cycloalkene, heterocycloalkane or heterocycloalkene;

R¹⁴ is heteroaryl, which is unfused or fused with benzene, heteroarene or R¹⁴·⁴; R¹⁴·⁴ is cycloalkane, cycloalkene, heterocycloalkane or heterocycloalkene;

R¹⁵ is cycloalkane, cycloalkene, heterocycloalkane or heterocycloalkene, each of which is unfused or fused with benzene, heteroarene or R¹⁵·⁴; R¹⁵·⁴ is cycloalkane, cycloalkene, heterocycloalkane or heterocycloalkene;

R¹⁶ is alkyl, alkenyl or alkynyl;

R¹⁷ is R¹⁸, R¹⁹, R²⁰ or R²¹;

R¹⁸ is phenyl, which is unfused or fused with benzene, heteroarene or R¹⁸·⁴; R¹⁸·⁴ is cycloalkane, cycloalkene, heterocycloalkane or heterocycloalkene;

R¹⁹ is heteroaryl, which is unfused or fused with benzene, heteroarene or R¹⁹·⁴; R¹⁹·⁴ is cycloalkane, cycloalkene, heterocycloalkane or heterocycloalkene;

R²⁰ is cycloalkyl, cycloalkenyl, heterocycloalkyl or heterocycloalkenyl each of which is unfused or fused with benzene, heteroarene or R²⁰·⁴; R²⁰·⁴ is cycloalkane, cycloalkene, heterocycloalkane or heterocycloalkene;

R²¹ is alkyl, alkenyl or alkynyl, each of which is unsubstituted or substituted with one or two or three of independently selected R²², OR¹, SR²², S(O)R²², SO₂R²², C(O)R²², CO(O)R²², OC(O)R²², OC(O)OR²², NH₂, NHR¹, N(R²²)₂, NHC(O)R²², NR¹C(O)R²², NHS(O)₂R²², NR²²S(O)₂R²², NHC(O)OR²², NR²²C(O)OR²², NHC(O)NH₂, NHC(O)NHR²², NHC(O)N(R²²)₂, NR²²C(O)NHR²², NR²²C(O)N(R²²)₂, C(O)NH₂, C(O)NHR²², C(O)N(R²²)₂, C(O)NHOH, C(O)NHOR²², C(O)NHSO₂R²², C(O)NR²²SO₂R²², SO₂NH₂, SO₂NHR²², SO₂N(R²²)₂, C(O)H, C(O)OH, C(N)NH₂, C(N)NHR²², C(N)N(R²²)₂, CNOH, CNOCH₃, OH, (O), CN, N₃, NO₂, CF₃, CF₂CF₃, OCF₃, OCF₂CF₃, F, Cl, Br or I;

R²² is R²³, R²⁴ or R²⁵;

R²³ is phenyl, which is unfused or fused with benzene, heteroarene or R²³·⁴; R²³·⁴ is cycloalkane, cycloalkene, heterocycloalkane or heterocycloalkene;

R²⁴ is heteroarene, which is unfused or fused with benzene, heteroarene or R²⁴·⁴; R²⁴·⁴ is cycloalkane, cycloalkene, heterocycloalkane or heterocycloalkene;

R²⁵ is cycloalkyl, cycloalkenyl, heterocycloalkyl or heterocycloalkenyl each of which is unfused or fused with benzene, heteroarene or R²⁵·⁴; R²⁵·⁴ is cycloalkane, cycloalkene, heterocycloalkane or heterocycloalkene;

Z² is R²⁸, R²⁹ or R³⁰;

Z¹·⁴ and Z²·⁴ are both absent or are taken together to form CH₂, CH₂CH₂ or Z¹²·⁴;

Z¹²·⁴ is C₂-C₆-alkylene having one or two CH₂ moieties replaced by NH, N(CH₃), S, S(O) or SO₂;

L¹ is a R³⁷, OR³⁷, SR³⁷, S(O)R³⁷, SO₂R³⁷, C(O)R³⁷, CO(O)R³⁷, OC(O)R³⁷, OC(O)OR³⁷, NHR³⁷, C(O)NH, C(O)NR³⁷, C(O)NHOR³⁷, C(O)NHSO₂R³⁷, SO₂NH, SO₂NHR³⁷, C(N)NH, C(N)NHR³⁷;

R²⁸ is phenylene, which is unfused or fused with benzene, heteroarene or R²⁸·⁴; R²⁸·⁴; is cycloalkane, cycloalkene, heterocycloalkane or heterocycloalkene;

R²⁹ is heteroarylene, which is unfused or fused with benzene or heteroarene or R²⁹·⁴; R²⁹·⁴ is cycloalkane, cycloalkene, heterocycloalkane or heterocycloalkene;

R³⁰ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37}$, $OR^{37B}$, $SR^{37B}$, $S(O)R^{37B}$, $SO_2R^{37B}$, $C(O)R^{37B}$, $CO(O)R^{37}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^{37B}$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, $C(O)H$, $C(O)OH$, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $OCF_2CF_3$, F, Cl, Br and I substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{42}$ are independently substituted with one or two or three or four of independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}$, $C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three of independently selected $R^{55}$, $OR^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{55}$ is alkyl, alkenyl, alkynyl, phenyl, heteroaryl, cycloalkyl, cycloalkenyl, heterocycloalkyl or heterocycloalkenyl; and wherein each foregoing cyclic moiety is independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{57A}$ is spirocyclyl;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl or alkenyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{57A}$, R$^{58}$, R$^{59}$, R$^{60}$, R$^{63}$, R$^{64}$, R$^{65}$, and R$^{67}$ are unsubstituted or substituted with one or two or three or four of independently selected R$^{68}$, OR$^{68}$, SR$^{68}$, S(O)R$^{68}$, SO$_2$R$^{68}$, C(O)R$^{68}$, CO(O)R$^{68}$, OC(O)R$^{68}$, OC(O)OR$^{68}$, NH$_2$, NHR$^{68}$, N(R$^{68}$)$_2$, NHC(O)R$^{68}$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^{68}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl or alkenyl, each of which is unsubstituted or substituted with one or two or three of independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO$_2$NH$_2$, SO$_2$NHR$^{73}$, SO$_2$N(R$^{73}$)$_2$, C(O)H, C(O)OH, C(N)NH$_2$, C(N)NHR$^{73}$, C(N)N(R$^{73}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{73}$ is alkyl, alkenyl, alkenyl, phenyl, heteroaryl, cycloalkyl, cycloalkenyl, heterocycloalkyl or heterocycloalkenyl; and the moieties represented by R$^{69}$, R$^{70}$, and R$^{71}$ are unsubstituted or substituted with one or two or three or four of independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I.

Still another embodiment pertains to a compound of Formula I or Formula II, wherein A$^1$ is C(A$^2$); and A$^2$ is H.

Still another embodiment pertains to a compound of Formula I or Formula II, wherein A$^1$ is C(A$^2$); A$^2$ is H; and B$^1$ is NHR$^1$.

Still another embodiment pertains to a compound of Formula I or Formula II, wherein A$^1$ is C(A$^2$); A$^2$ is H; B$^1$ is NHR$^1$; and D$^1$ is H.

Still another embodiment pertains to a compound of Formula I or Formula II, wherein A$^1$ is C(A$^2$); A$^2$ is H; B$^1$ is NHR$^1$; D$^1$ is H; and E$^1$ is H.

Still another embodiment pertains to a compound of Formula I or Formula II, wherein A$^1$ is C(A$^2$); A$^2$ is H; B$^1$ is NHR$^1$; D$^1$ is H; E$^1$ is H; and Y$^1$ is NO$_2$.

Still another embodiment pertains to compounds having Formula I, which are 4-(4-((4'-chloro-1,1'-biphenyl-2-yl)methyl)piperazin-1-yl)-2-(3-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(methylamino)phenoxy)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(hydroxymethyl)phenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((1-methyl-1H-indol-4-yl)oxy)benzamide;

2-(3-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-(4-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-(3-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-methoxyphenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(dimethylamino)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-6-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-5-yl)oxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-methyl-1,3-benzothiazol-5-yl)oxy)benzamide;

4-(4-((4'-chloro-1,1'-biphenyl-2-yl)methyl)piperazin-1-yl)-2-(2-(3-(dimethylamino)-3-oxopropyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)-2-oxoethyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(3-(dimethylamino)propyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)ethyl)phenoxy)-N-((3-nitro-4-((tetrahydro-2H-pyran-4-ylmethyl)amino)phenyl)sulfonyl)benzamide;

2-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)-N,N-dimethylbenzamide;

4-(4-((4'-chloro-1,1'-biphenyl-2-yl)methyl)piperazin-1-yl)-2-(2-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-morpholin-4-ylphenoxy)benzamide;

4-(4-((4'-chloro-1,1'-biphenyl-2-yl)methyl)piperazin-1-yl)-2-(3-(2,4-dimethyl-1,3-thiazol-5-yl)phenoxy)-N-((4-((3-morpholin-4-ylpropyl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(3,5-dichlorophenoxy)-N-((4-((1-methylpiperidin-4-yl)amino)-3-nitrophenyl)sulfonyl)benzamide;

2-(3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((4'-chloro-4-(2-(dimethylamino)ethoxy)-1,1'-biphenyl-2-yl)methyl)piperazin-1-yl)-2-(3-chlorophenoxy)-N-((4-((1-methylpiperidin-4-yl)amino)-3-nitrophenyl)sulfonyl)benzamide;

2-(2-chlorophenoxy)-4-(4-((4-(4-chlorophenyl)-6,6-dimethyl-5,6-dihydro-2H-pyran-3-yl)methyl)piperazin-1-yl)-N-((4-((1-methylpiperidin-4-yl)amino)-3-nitrophenyl)sulfonyl)benzamide;

4-(4-((4'-chloro-1,1'-biphenyl-2-yl)methyl)piperazin-1-yl)-2-(3-(2-(dimethylamino)ethoxy)phenoxy)-N-((3-nitro-4-((tetrahydro-2H-pyran-4-ylmethyl)amino)phenyl)sulfonyl)benzamide;

2-(4-amino-3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-isopropylpiperidin-4-yl)amino)-3-nitrophenyl)sulfonyl)benzamide;

2-(2-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)cyclohex-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((1-methylpiperidin-4-yl)amino)-3-nitrophenyl)sulfonyl)benzamide;

2-(3-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-ethylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((3-nitro-4-((1,2,2,6,6-pentamethylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((3-nitro-4-((1-tetrahydro-2H-pyran-4-ylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-((7-fluoro-1H-indol-5-yl)oxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((3-morpholin-4-ylpropyl)amino)-3-nitrophenyl)sulfonyl)benzamide;

2-(4-amino-3-chlorophenoxy)-4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)benzamide;

2-(3-chlorophenoxy)-4-(4-((4'-chloro-4-(2-pyrrolidin-1-ylethyl)-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-2-(2,3-dichlorophenoxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-((1-methylpiperidin-4-yl)amino)-3-nitrophenyl)sulfonyl)benzamide;

2-(2-chlorophenoxy)-4-(4-((2-(4-chlorophenyl)cyclohept-1-en-1-yl)methyl)piperazin-1-yl)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(((1-methylpiperidin-4-yl)amino)-3-nitrophenyl)sulfonyl)-2-(3-(trifluoromethyl)phenoxy)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-oxo-1,2,3,4-tetrahydroquinolin-5-yl)oxy)benzamide;

2-(2-chlorophenoxy)-4-(4-((2-(4-chlorophenyl)-4,4-dimethylcyclohex-1-en-1-yl)methyl)piperazin-1-yl)-N-((4-(((1-methylpiperidin-4-yl)amino)-3-((trifluoromethyl)sulfonyl)phenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-(((1-methylpiperidin-4-yl)amino)-3-nitrophenyl)sulfonyl)benzamide;

2-(2-chloro-4-fluorophenoxy)-4-(4-((2-(4-chlorophenyl)-4,4-dimethylcyclohex-1-en-1-yl)methyl)piperazin-1-yl)-N-((4-(((1-methylpiperidin-4-yl)amino)-3-nitrophenyl)sulfonyl)benzamide;

2-(2-chlorophenoxy)-4-(4-((2-(4-chlorophenyl)-4,4-dimethylcyclopent-1-en-1-yl)methyl)piperazin-1-yl)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2-chloro-3-(trifluoromethyl)phenoxy)-N-((4-(((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-(((1-cyclopropylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-((1-methyl-1H-indol-4-yl)oxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-morpholin-4-ylphenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((3-(3-morpholin-4-yl-3-oxopropyl)-1H-indol-5-yl)oxy)benzamide;

2-(3-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-morpholin-4-yl-3-oxopropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-morpholin-4-ylpropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(1H-imidazol-1-yl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((4-((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

4-(4-((4'-chloro-1,1'-biphenyl-2-yl)methyl)piperazin-1-yl)-2-(4-((ethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-((ethylamino)methyl)phenoxy)-N-((3-nitro-4-((tetrahydro-2H-pyran-4-ylmethyl)amino)phenyl)sulfonyl)benzamide;

2-(4-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-2-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-3-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(2-(dimethylamino)ethyl)phenoxy)-N-((3-nitro-4-((tetrahydro-2H-pyran-4-ylmethyl)amino)phenyl)sulfonyl)benzamide;

2-(4-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-morpholin-4-ylphenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-5-yl)oxy)-N-((3-nitro-4-((tetrahydro-2H-pyran-4-ylmethyl)amino)phenyl)sulfonyl)benzamide;

tert-butyl 4-(3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenyl)piperazine-1-carboxylate;

2-(3-(benzyloxy)phenoxy)-4-(4-((4'-chloro-1,1'-biphenyl-2-yl)methyl)piperazin-1-yl)-N-((4-((3-(dimethylamino)propyl)amino)-3-nitrophenyl)sulfonyl)benzamide;

2-(3-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-(2-morpholin-4-ylethoxy)phen oxy)-N-((3-nitro-4-((tetrahydro-2H-pyran-4-ylmethyl)amino)phenyl)sulfonyl)benzamide;

4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)-2-((2-oxo-1,2,3,4-tetrahydroquinolin-5-yl)oxy)benzamide;

2-(4-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

tert-butyl 4-(4-(5-(4-((4'-chloro-1,1'-biphenyl-2-yl)methyl)piperazin-1-yl)-2-((((4-((3-morpholin-4-ylpropyl)amino)-3-nitrophenyl)sulfonyl)amino)carbonyl)phenoxy)phenyl)piperazine-1-carboxylate;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(3-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-3-ylphenoxy)benzamide;

4-(4-((4'-chloro-1,1'-biphenyl-2-yl)methyl)piperazin-1-yl)-2-(4-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((1-methyl-1H-benzimidazol-5-yl)oxy)-N-((4-((3-morpholin-4-ylpropyl)amino)-3-nitrophenyl)sulfonyl)benzamide;

4-(4-((4'-chlorobiphenyl-2-yl)methyl)piperazin-1-yl)-2-(3-(methylcarbamoyl)phenoxy)-N-(4-(3-morpholinopropylamino)-3-nitrophenylsulfonyl)benzamide;

4-(4-((4'-chlorobiphenyl-2-yl)methyl)piperazin-1-yl)-N-(4-(3-(dimethylamino)propylamino)-3-nitrophenylsulfonyl)-2-(3-(methylcarbamoyl)phenoxy)benzamide;

4-(4-((4'-chloro-1,1'-biphenyl-2-yl)methyl)piperazin-1-yl)-2-(3-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-(dimethylamino)propyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-(hydroxymethyl)phenoxy)benzamide;

4-(4-((4'-chloro-1,1'-biphenyl-2-yl)methyl)piperazin-1-yl)-2-((4-methoxybenzyl)oxy)-N-((3-nitro-4-((tetrahydro-2H-pyran-4-ylmethyl)amino)phenyl)sulfonyl)benzamide;

N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide;

4-(4-(1-(4'-chlorobiphenyl-2-yl)ethyl)piperazin-1-yl)-2-(2-chlorophenoxy)-N-(3-nitro-4-((tetrahydro-2H-pyran-4-yl)methylamino)phenylsulfonyl)benzamide;

N-{[4-{4-[(4'-chloro-1,1'-biphenyl-2-yl)methyl]piperazin-1-yl}-2-(3,5-dichlorophenoxy)phenyl]sulfonyl}-4-[(1-methylpiperidin-4-yl)amino]-3-nitrobenzamide;

4-(4-{[2-(4-chlorophenyl)-4,4-dimethylcyclohex-1-en-1-yl]methyl}piperazin-1-yl)-2-(3-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({3-nitro-4-[(1-tetrahydro-2H-pyran-4-ylpiperidin-4-yl)amino]phenyl})sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl)}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(4-fluorophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(3-fluorophenoxy)benzamide;

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-({4-[(2-morpholin-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2,3-difluorophenoxy)-N-[(3-nitro-4-{[1-(thien-3-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(2-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(3-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(4-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[1-(2-fluoroethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(4-methylpiperazin-1-yl)propyl]amino}-3-nitrophenyl)sulfonyl]benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(1-methylpiperidin-4-yl)amino]-3-nitrophenyl}sulfonyl)benzamide;

N-({4-[(1-allylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(2,3-difluorophenoxy)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(4-fluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[3-(methoxymethoxy)-2-methylphenoxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-hydroxy-2-methylphenoxy)-N-({4-[(1-methylpiperidin-4-yl)amino]-3-nitrophenyl}sulfonyl)benzamide;

2-(3-bromophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(3-iodophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(2-phenylethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(3,4-dichlorophenoxy)-N-({4-[(1-methylpiperidin-4-yl)amino]-3-nitrophenyl}sulfonyl)benzamide;

2-(2-chloro-3,5-difluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[3-(hydroxymethyl)phenoxy]-N-({4-[(1-methylpiperidin-4-yl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-{[4-({1-[2-(2-methoxyethoxy)ethyl]piperidin-4-yl}amino)-3-nitrophenyl]sulfonyl}benzamide;

2-(2-chloro-3-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(3-phenylpropyl)piperidin-4-yl]amino}phenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-methoxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(1-ethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-hydroxyphenoxy)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-methylphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methylphenoxy)-N-({4-[(1-methylpiperidin-4-yl)amino]-3-nitrophenyl}sulfonyl)benzamide;

2-(2-chlorophenoxy)-4-(4-{[6-(4-chlorophenyl)-1,3-benzodioxol-5-yl]methyl}piperazin-1-yl)-N-({4-[(1-methylpiperidin-4-yl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(4-methylpiperazin-1-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide;

2-(2-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-{[4-({-[2-(dimethylamino)-2-oxoethyl]piperidin-4-yl}amino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-morpholin-4-ylethyl)piperidin-4-yl]amino}-3-nitrophenyl)sulfonyl]benzamide;

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3S)-1-methylpyrrolidin-3-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3R)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[3-(1H-pyrrol-2-yl)phenoxy]benzamide;

4-(4-{[2-(4-chlorophenyl)-4,4-dimethylcyclohex-1-en-1-yl]methyl}piperazin-1-yl)-2-(3-fluorophenoxy)-N-[(4-{[(4-hydroxy-1-methylpiperidin-4-yl)methyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(1-tetrahydro-2H-pyran-4-ylpiperidin-4-yl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)-1H-indole-1-carboxylate;

2-(3-chlorophenoxy)-4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]benzamide;

Trans-2-(3-chlorophenoxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

4-{4-[1-(4'-chloro-1,1'-biphenyl-2-yl)ethyl]piperazin-1-yl}-2-(2-chlorophenoxy)-N-({4-[(1-methylpiperidin-4-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({3-nitro-4-[(1-tetrahydro-2H-pyran-4-ylpiperidin-4-yl)amino]phenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-[(trifluoromethyl)sulfonyl]phenyl}sulfonyl)benzamide;

2-({1,3-bis[(4-methylpiperazin-1-yl)methyl]-1H-indol-4-yl}oxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-({3-[(4-methylpiperazin-1-yl)methyl]-1H-indol-4-yl}oxy)benzamide;

2-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)-N,N-dimethylbenzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[2-(trifluoromethyl)-1H-indol-4-yl]oxy}benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-{[6-(trifluoromethyl)-1H-indol-5-yl]oxy}benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[6-(trifluoromethyl)-1H-indol-5-yl]oxy}benzamide;

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide;

tert-butyl 4-[(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)methyl]-1,3-thiazol-2-ylcarbamate;

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(2-chlorophenyl)amino]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-methoxy-1H-indol-5-yl)oxy]-N-({3-nitro-4-[(1-tetrahydro-2H-pyran-4-ylpiperidin-4-yl)amino]phenyl}sulfonyl)benzamide;

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[(2-chlorophenyl)amino]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

tert-butyl 5-[5-(4-{[2-(4-chlorophenyl)-4,4-dimethylcyclohex-1-en-1-yl]methyl}piperazin-1-yl)-2-({[(4-{[3-(dimethylamino)propyl]amino}-3-nitrophenyl)sulfonyl]amino}carbonyl)phenoxy]-1H-indole-1-carboxylate;

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[3-(3-oxopiperazin-1-yl)propyl]amino}phenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide;

Trans-4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6,7-difluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-hydroxy-1-tetrahydro-2H-pyran-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-({[4-(hydroxymethyl)tetrahydro-2H-pyran-4-yl]methyl}amino)-3-nitrophenyl]sulfonyl}benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(1-(1,3-thiazol-4-ylmethyl)piperidin-4-yl]amino}phenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(4-amino-3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(3S,4R)-3-hydroxy-1-(1,3-thiazol-4-ylmethyl)piperidin-4-yl]amino}-3-nitrophenyl)sulfonyl]benzamide;

2-(2-chlorophenoxy)-4-(4-({[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylamino)phenyl]sulfonyl}benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-(morpholin-4-ylamino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}benzamide;

2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide;

2-(6-aminopyridin-3-yl)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{1-[2-(4-chlorophenyl)-4,4-dimethylcyclohex-1-en-1-yl]ethyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-tetrahydro-2H-pyran-3-ylmethyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3R)-tetrahydro-2H-pyran-3-ylmethyl]amino}phenyl)sulfonyl]benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-3,4-dihydroisoquinoline-2(1H)-carboxylate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-5,5-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-methoxyethyl)amino]-3-nitrophenyl}sulfonyl)benzamide;

4-(4-({[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylmethoxy)phenyl]sulfonyl}benzamide;

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-5-yl)oxy]benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(2-methoxyethyl)amino]-3-nitrophenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-{[2-(4-chlorophenyl)-4,4-dimethylcyclohex-1-en-1-yl]methyl}piperazin-1-yl)-2-{[({3-nitro-4-[(1-tetrahydro-2H-pyran-4-ylpiperidin-4-yl)amino]phenyl}sulfonyl)amino]carbonyl}phenoxy)pyridin-2-ylcarbamate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-ylcarbamate;

2-[(5-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-hydroxypyridin-3-yl)oxy]-N-({3-nitro-4-[(tetrahydro-2H-pyran-4-ylmethyl)amino]phenyl}sulfonyl)benzamide;

2-{[6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-[(6-fluoro-1H-indol-5-yl)oxy]benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-[(2-oxo-2,3-dihydro-1H-indol-4-yl)oxy]benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-[(6-fluoro-1H-indol-5-yl)oxy]benzamide;

Trans-2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

Trans-2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

2-[(6-amino-5-fluoropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(1-oxo-1,2,3,4-tetrahydroisoquinolin-5-yl)oxy]benzamide;

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-[(6-fluoro-1H-indol-5-yl)oxy]benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-N-({5-bromo-6-[(4-morpholin-4-ylcyclohexyl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-[(6-fluoro-1H-indol-5-yl)oxy]benzamide;

2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)oxy]-3-nitrophenyl}sulfonyl)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-[(2-oxo-2,3-dihydro-1H-indol-4-yl)oxy]benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-[(trifluoromethyl)sulfonyl]phenyl}sulfonyl)benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylbut-2-ynyl)oxy]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[1-(methylsulfonyl)piperidin-4-yl]amino}-3-nitrophenyl)sulfonyl]benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide;

4-(4-{[4-(4-chlorophenyl)-6,6-dimethyl-5,6-dihydro-2H-pyran-3-yl]methyl}piperazin-1-yl)-N-{([5-ethynyl-6-(tetrahydro-2H-pyran-4-ylmethoxy)pyridin-3-yl]sulfonyl}-2-[(6-fluoro-1H-indol-5-yl)oxy]benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}-4-sulfonyl)-2-[(6-fluoro-1H-indol-5-yl)oxy]benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}-4-piperazin-1-yl)-N-(({4-[(1-cyclopropylpiperidin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-1-tetrahydro-2H-pyran-4-ylpiperidin-3-yl]amino}phenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}-4-piperazin-1-yl)-2-[(6-fluoro-1H-indol-5-yl)oxy]-N-(({3-nitro-4-[(tetrahydrofuran-3-ylmethyl)amino]phenyl}sulfonyl)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(tetrahydro-2H-pyran-4-ylamino)cyclohexyl]amino}phenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(4-tetrahydro-2H-pyran-4-ylpiperazin-1-yl)cyclohexyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-fluorotetrahydro-2H-pyran-4-yl)methyl]amino}-3-nitrophenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-hydroxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-{[1-(4-methoxybenzyl)-1H-1,2,3-benzotriazol-4-yl]oxy}-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{4-(1,4-dioxan-2-ylmethoxy)-3-nitrophenyl]sulfonyl}benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(3-morpholin-4-ylpropyl)amino]-3-[(trifluoromethyl)sulfonyl]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)nicotinamide;

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-[(6-fluoro-1H-indol-5-yl)oxy]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)benzamide;

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

Trans-2-[(6-amino-5-bromopyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(3-methyl-2-oxo-2,3-dihydro-1H-benzimidazol-4-yl)oxy]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({4-fluoro-1-[2-fluoro-1-(fluoromethyl)ethyl]piperidin-4-yl}methoxy)-3-nitrophenyl]sulfonyl}benzamide;

tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino)phenylsulfonylcarbamoyl)phenoxy)pyridine-2,6-diyldicarbamate;

4-(4-{[2-(4-chlorophenyl)-4,4-dimethylcyclohex-1-en-1-yl]methyl}piperazin-1-yl)-2-{[6-(cyclopropylamino)pyridin-3-yl]oxy}-N-({3-nitro-4-[(tetrahydro-2H-pyran-4-ylmethyl)amino]phenyl}sulfonyl)benzamide;

Trans-4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-({3-nitro-4-[(tetrahydro-2H-pyran-4-ylmethyl)amino]phenyl}sulfonyl)benzamide;

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[({4-[2-fluoro-1-(fluoromethyl)ethyl]morpholin-2-yl}methyl)amino]-3-nitrophenyl}sulfonyl)benzamide;

2-[(2-amino-6-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(2,6-diaminopyridin-4-yl)oxy]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]piperidin-3-yl}amino)-3-nitrophenyl]sulfonyl}benzamide;

tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

4-(4-{[2-(4-chlorophenyl)-4,4-dimethylcyclohex-1-en-1-yl]methyl}piperazin-1-yl)-2-[(4-chloro-1H-pyrrolo[2,3-b]pyridin-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide;

2-[(6-amino-5-chloropyridin-3-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)benzamide;

2-[(6-amino-5-chloropyridin-3-yl)oxy]-4-[4-({9-(4-chlorophenyl)-3-[2-fluoro-1-(fluoromethyl)ethyl]-3-azaspiro[5.5]undec-8-en-8-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}benzamide;

2-[(2-amino-5-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

2-[(6-amino-5-chloropyridin-3-yl)oxy]-4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-N-{5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide;

2-[(6-amino-5-chloropyridin-3-yl)oxy]-N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide;

2-[2-(2-aminopyridin-3-yl)phenoxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-5-yl)phenoxy]benzamide;

2-[(6-amino-5-chloropyridin-3-yl)oxy]-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-({5-chloro-6-[(4,4-difluorocyclohexyl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-[(6-fluoro-1H-indol-5-yl)oxy]benzamide;

and therapeutically acceptable salts, prodrugs, salts of prodrugs and metabolites thereof.

Still another embodiment pertains to 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; and therapeutically acceptable salts, prodrugs, salts of prodrugs and metabolites thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of the compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Variable moieties herein are represented by identifiers (capital letters with numerical and/or alphabetical superscripts) and may be specifically embodied.

It is meant to be understood that proper valences are maintained for all moieties and combinations thereof, that monovalent moieties having more than one atom are drawn from left to right and are attached through their left ends, and that divalent moieties are also drawn from left to right.

It is also meant to be understood that a specific embodiment of a variable moiety herein may be the same or different as another specific embodiment having the same identifier.

The term "alkenyl" as used herein, means a straight or branched hydrocarbon chain containing from 2 to 10 carbons and containing at least one carbon-carbon double bond. The term "$C_x$-$C_y$ alkyl" means a straight or branched hydrocarbon chain containing at least one carbon-carbon double bond containing x to y carbon atoms. The term "$C_2$-$C_4$ alkenyl" means an alkenyl group containing 2-4 carbon atoms. Representative examples of alkenyl include, but are not limited to buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double bond. The term "$C_x$-$C_y$ alkylene" means a divalent group derived from a straight or branched hydrocarbon chain containing at least one carbon-carbon double bond and containing x to y carbon atoms. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. The term "$C_x$-$C_y$ alkylene" means a divalent group derived from a straight or branched chain, saturated hydrocarbon containing x to y carbon atoms. For example "$C_2$-$C_6$ alkylene" means a straight or branched chain, saturated hydrocarbon containing 2 to 6 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_x$-$C_y$ alkynyl" means a straight or branched chain hydrocarbon group containing from x to y carbon atoms. Representative examples of alkynyl include, but are not limited, to acetylenyl, 1-propynyl, 2-propynyl, 3-butynyl, 2-pentynyl, and 1-butynyl.

The term "alkynylene," as used herein, means a divalent radical derived from a straight or branched chain hydrocarbon group containing from 2 to 10 carbon atoms and containing at least one carbon-carbon triple bond.

The term "aryl" as used herein, means phenyl.

The term "cyclic moiety," as used herein, means benzene, phenyl, phenylene, cycloalkane, cycloalkyl, cycloalkylene, cycloalkene, cycloalkenyl, cycloalkenylene, cycloalkyne, cycloalkynyl, cycloalkynylene, heteroarene, heteroaryl, heterocycloalkane, heterocycloalkyl, heterocycloalkene, heterocycloalkenyl and spiroalkyl.

The term "cycloalkylene" or "cycloalkyl" or "cycloalkane" as used herein, means a monocyclic or bridged hydrocarbon ring system. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and bridged cycloalkyl can be attached to the parent molecular moiety through any substitutable atom contained within the ring system.

The term "cycloalkenylene," or "cycloalkenyl" or "cycloalkene" as used herein, means a monocyclic or a bridged hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems.

The term "cycloalkyne," or "cycloalkynyl," or "cycloalkynylene," as used herein, means a monocyclic or a bridged hydrocarbon ring system. The monocyclic cycloalkynyl has eight or more carbon atoms, zero heteroatoms, and one or more triple bonds. The monocyclic cycloalkynyl ring may contain one or two alkylene bridges, each consisting of one, two, or three carbon atoms, each linking two non-adjacent carbon atoms of the ring system. The monocyclic and bridged cycloalkynyl can be attached to the parent molecular moiety through any substitutable atom contained within the ring systems.

The term "heteroarene," or "heteroaryl," or "heteroarylene," as used herein, means a five-membered or six-membered aromatic ring having at least one carbon atom and one or more than one independently selected nitrogen, oxygen or sulfur atom. The heteroarenes of this invention are connected through any adjacent atoms in the ring, provided that proper valences are maintained. Representative examples of heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, thiazolyl, thienyl (including, but not limited thereto, thien-2-yl, thien-3-yl), triazolyl, and triazinyl.

The term "heterocycloalkane," or "heterocycloalkyl," or "heterocycloalkylene," as used herein, means monocyclic or bridged three-, four-, five-, six-, seven-, or eight-membered ring containing at least one heteroatom independently selected from the group consisting of O, N, and S and zero double bonds. The monocyclic and bridged heterocycloalkane are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkane groups include, but are not limited to, Representative examples of heterocycloalkane groups include, but are not limited to, morpholinyl, tetrahydropyranyl, pyrrolidinyl, piperidinyl, dioxolanyl, tetrahydrofuranyl, thiomorpholinyl, dioxanyl, tetrahydrothienyl, tetrahydrothiopyranyl, oxetanyl, piperazinyl, imidazolidinyl, azetidine, azepanyl, aziridinyl, diazepanyl, dithiolanyl, dithianyl, isoxazolidinyl, isothiazolidinyl, oxadiazolidinyl, oxazolidinyl, pyrazolidinyl, tetrahydrothienyl, thiadiazolidinyl, thiazolidinyl, thiomorpholinyl, trithianyl, and trithianyl.

The term "heterocycloalkene," or "heterocycloalkenyl," or "heterocycloalkenylene," as used herein, means monocyclic or bridged three-, four-, five-, six-, seven-, or eight-membered ring containing at least one heteroatom independently selected from the group consisting of O, N, and S and one or more double bonds. The monocyclic and bridged heterocycloalkene are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized. Representative examples of heterocycloalkene groups include, but are not limited to, tetrahydrooxocinyl, 1,4,5,6-tetrahydropyridazinyl, 1,2,3,6-tetrahydropyridinyl, dihydropyranyl, imidazolinyl, isothiazolinyl, oxadiazolinyl, isoxazolinyl, oxazolinyl, pyranyl, pyrazolinyl, pyrrolinyl, thiadiazolinyl, thiazolinyl, and thiopyranyl.

The term "phenylene," as used herein, means a divalent radical formed by removal of a hydrogen atom from phenyl.

The term "spiroalkyl," as used herein, means alkylene, both ends of which are attached to the same carbon atom and is exemplified by $C_2$-spiroalkyl, $C_3$-spiroalkyl, $C_4$-spiroalkyl, $C_5$-spiroalkyl, $C_6$-spiroalkyl, $C_7$-spiroalkyl, $C_8$-spiroalkyl, $C_9$-spiroalkyl and the like.

The term "spiroheteroalkyl," as used herein, means spiroalkyl having one or two $CH_2$ moieties replaced with independently selected O, C(O), CNOH, CNOCH$_3$, S, S(O), SO$_2$ or NH and one or two CH moieties unreplaced or replaced with N.

The term "spiroheteroalkenyl," as used herein, means spiroalkenyl having one or two $CH_2$ moieties replaced with independently selected O, C(O), CNOH, CNOCH$_3$, S, S(O), SO$_2$ or NH and one or two CH moieties unreplaced or replaced with N and also means spiroalkenyl having one or two $CH_2$ moieties unreplaced or replaced with independently selected O, C(O), CNOH, CNOCH$_3$, S, S(O), SO$_2$ or NH and one or two CH moieties replaced with N.

The term, "spirocyclo," as used herein, means two substituents on the same carbon atom, that, together with the carbon atom to which they are attached, form a cycloalkane, heterocycloalkane, cycloalkene, or heterocycloalkene ring.

The term "$C_2$-$C_5$-spiroalkyl," as used herein, means $C_2$-spiroalkyl, $C_3$-spiroalkyl, $C_4$-spiroalkyl, and $C_5$-spiroalkyl.

The term "$C_2$-spiroalkyl," as used herein, means eth-1,2-ylene, both ends of which replace hydrogen atoms of the same $CH_2$ moiety.

The term "$C_3$-spiroalkyl," as used herein, means prop-1,3-ylene, both ends of which replace hydrogen atoms of the same $CH_2$ moiety.

The term "$C_4$-spiroalkyl," as used herein, means but-1,4-ylene, both ends of which replace hydrogen atoms of the same $CH_2$ moiety.

The term "$C_5$-spiroalkyl," as used herein, means pent-1,5-ylene, both ends of which replace hydrogen atoms of the same $CH_2$ moiety.

The term "$C_6$-spiroalkyl," as used herein, means hex-1,6-ylene, both ends of which replace hydrogen atoms of the same $CH_2$ moiety.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloroethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl) ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Calhn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble *J. Org. Chem.* 1998, 63, 2758-2760 and E. L. Eliel, and S. H. Wilen. (1994) *Stereochemistry of Organic Compounds*. New York, N.Y.: John Wiley & Sons, Inc.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Compounds of this invention containing NH, C(O)OH, OH or SH moieties may have attached thereto prodrug-forming moieties. The prodrug-forming moieties are removed by metabolic processes and release the compounds having the freed hydroxyl, amino or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance. An example of a compound with a prodrug-forming moiety is [3-chloro-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-2-iminopyridin-1(2H)-yl]methyl dihydrogen phosphate (EXAMPLE 397), which is a prodrug of 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide (EXAMPLE 318).

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}$H, $^{3}$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^{2}$H), tritium ($^{3}$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-2 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to Bcl-2 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-istopic compound.

Amides, Esters and Prodrugs

Prodrugs are derivatives of an active drug designed to ameliorate some identified, undesirable physical or biological property. The physical properties are usually solubility (too much or not enough lipid or aqueous solubility) or stability related, while problematic biological properties include too rapid metabolism or poor bioavailability which itself may be related to a physicochemical property.

Prodrugs are usually prepared by: a) formation of ester, hemi esters, carbonate esters, nitrate esters, amides, hydroxamic acids, carbamates, imines, Mannich bases, phosphates, phosphate esters, and enamines of the active drug, b) functionalizing the drug with azo, glycoside, peptide, and ether functional groups, c) use of aminals, hemi-aminals, polymers, salts, complexes, phosphoramides, acetals, hemiacetals, and ketal forms of the drug. For example, see Andrejus Korolkovas's, "Essentials of Medicinal Chemistry", John Wiley-Interscience Publications, John Wiley and Sons, New York (1988), pp. 97-118, which is incorporated in its entirety by reference herein.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

Scheme 1

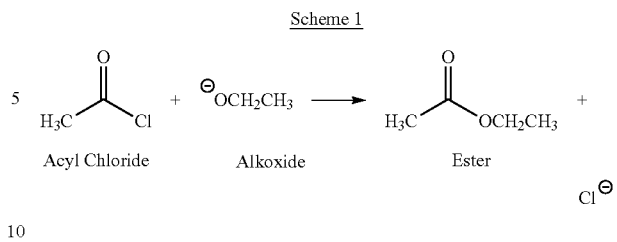

Amides can be prepared from substrates of formula (I) containing either an amino group or a carboxy group in similar fashion. Esters can also react with amines or ammonia to form amides.

Scheme 2

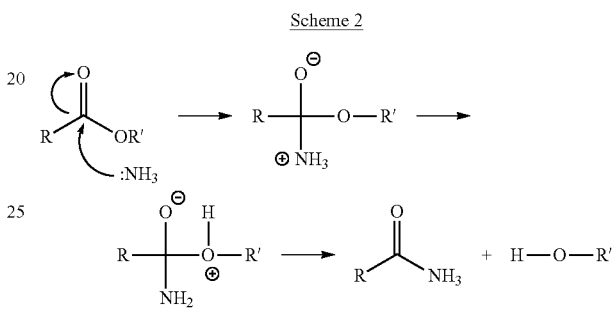

Another way to make amides from compounds of formula (I) is to heat carboxylic acids and amines together.

Scheme 3

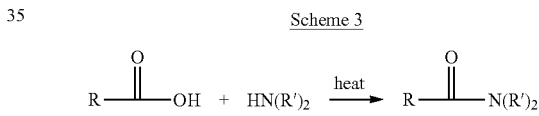

In Schemes 2 and 3 above, R and R' are independently substrates of formula (I), alkyl or hydrogen.

Suitable groups for $A^1, B^1, D^1, E^1, Y^1, L^1, Z^{1A}, Z^{2A}, Z^1, Z^2$, and $Z^3$ in compounds of Formula (I) are independently selected. The described embodiments of the present invention may be combined. Such combination is contemplated and within the scope of the present invention. For example, it is contemplated that embodiments for any of $A^1, B^1, D^1, E^1, Y^1, L^1, Z^{1A}, Z^{2A}, Z^1, Z^2$, and $Z^3$ can be combined with embodiments defined for any other of $A^1, B^1, D^1, E^1, Y^1, L^1, Z^{1A}, Z^{2A}, Z^1, Z^2$, and $Z^3$.

One embodiment of this invention, therefore, pertains to compounds or therapeutically acceptable salts, prodrugs or salts of prodrugs thereof, which are useful as inhibitors of anti-apoptotic Bcl-2 proteins, the compounds having Formula (I)

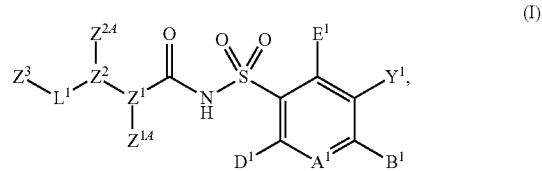

(I)

wherein $A^1$ is N or $C(A^2)$;

$A^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NRSO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$; and $Y^1$ is H, CN, $NO_2$, $C(O)OH$, F, Cl, Br, I, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$; or $Y^1$ and $B^1$, together with the atoms to which they are attached, are benzene, naphthylene, heteroarene cycloalkane, cycloalkene, heterocycloalkane or heterocycloalkene; and $A^2$, $D^1$, and $E^1$ are independently selected H, $R^1$, OR, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$; or $A^2$ and $B^1$, together with the atoms to which they are attached, are benzene, naphthylene, heteroarene cycloalkane, cycloalkene, heterocycloalkane or heterocycloalkene; and $D^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, OH, $C(O)H$, CHNOH, $CH(NOCH_3)$, $CF_3$, $C(O)OH$, $C(O)NH_2$ or $C(O)OR^{1A}$; or $A^2$ and $D^1$, together with the atoms to which they are attached, are benzene, naphthalene, heteroarene, cycloalkane, cycloalkene, heterocycloalkane or heterocycloalkene; and $B^1$, $E^1$, and $Y^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, $NO_2$, OH, $C(O)H$, CHNOH, $CH(NOCH_3)$, $CF_3$, $C(O)OH$, $C(O)NH_2$ or $C(O)OR^{1A}$;

$R^1$ is $R^2$, $R^3$, $R^4$ or $R^5$;

$R^{1A}$ is cycloalkyl, cycloalkenyl or cycloalkynyl;

$R^2$ is phenyl, which is unfused or fused with benzene, heteroarene or $R^{2A}$; $R^{2A}$ is cycloalkane or heterocycloalkane;

$R^3$ is heteroaryl, which is unfused or fused with benzene, heteroarene or $R^{3A}$; $R^{3A}$ is cycloalkane or heterocycloalkane;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one or two or three of independently selected $R^6$, $NC(R^{6A})(R^{6B})$, $R^7$, $OR^7$, $SR^7$, $S(O)R^7$, $SO_2R^7$, $NHR^7$, $N(R^7)_2$, $C(O)R^7$, $C(O)NH_2$, $C(O)NHR^7$, $C(O)N(R^7)_2$, $NHC(O)R^7$, $NR^7C(O)R^7$, $NHSO_2R^7$, $NHC(O)OR^7$, $SO_2NH_2$, $SO_2NHR^7$, $SO_2N(R^7)_2$, $NHC(O)NH_2$, $NHC(O)NHR^7$, $NHC(O)CH_3)NHC(O)CH(CH_3)NH_2$, $NHC(O)CH(CH_3)NHC(O)CH(CH_3)NHR^1$, OH, (O), $C(O)OH$, $N_3$, CN, $NH_2$, $CF_3$, $CF_2CF_3$, F, Cl, Br or I;

$R^6$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{6A}$ and $R^{6B}$ are independently selected alkyl or, together with the N to which they are attached, $R^{6C}$;

$R^{6C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^7$ is $R^8$, $R^9$, $R^{10}$ or R;

$R^8$ is phenyl, which is unfused or fused with benzene, heteroarene or $R^{8A}$; $R^{8A}$ is cycloalkane, cycloalkene, heterocycloalkane or heterocycloalkene;

$R^9$ is heteroaryl, which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl or alkynyl, each of which is unsubstituted or substituted with one or two or three of independently selected $R^{12}$, $OR^{12}$, $SR^{12}$, $S(O)R^{12}$, $SO_2R^{12}$, $C(O)R^{12}$, $CO(O)R^{12}$, $OC(O)R^{12}$, $OC(O)OR^{12}$, $NH_2$, $NHR^{12}$, $N(R^{12})_2$, $NHC(O)R^{12}$, $NR^{12}C(O)R^{12}$, $NHS(O)_2R^{12}$, $NR^{12}S(O)_2R^{12}$, $NHC(O)OR^{12}$, $NR^{12}C(O)OR^{12}$, $NHC(O)NH_2$, $NHC(O)NHR^{12}$, $NHC(O)N(R^{12})_2$, $NR^{12}C(O)NHR^{12}$, $NR^{12}C(O)N(R^{12})_2$, $C(O)NH_2$, $C(O)NHR^{12}$, $C(O)N(R^{12})_2$, $C(O)NHOH$, $C(O)NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, C(O)H, C(O)OH, $C(N)NH_2$, $C(N)NHR^{12}$, $C(N)N(R^{12})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{17}$ is $R^{18}$, $R^{19}$, $R^{20}$ or $R^{21}$;

$R^{18}$ is phenyl, which is unfused or fused with benzene, heteroarene or $R^{18A}$; $R^{18A}$ is cycloalkane, cycloalkene, heterocycloalkane or heterocycloalkene;

$R^{19}$ is heteroaryl, which is unfused or fused with benzene, heteroarene or $R^{19A}$; $R^{19A}$ is cycloalkane, cycloalkene, heterocycloalkane or heterocycloalkene;

$R^{20}$ is cycloalkyl, cycloalkenyl, heterocycloalkyl or heterocycloalkenyl each of which is unfused or fused with benzene, heteroarene or $R^{20A}$; $R^{20A}$ is cycloalkane, cycloalkene, heterocycloalkane or heterocycloalkene;

$R^{21}$ is alkyl, alkenyl or alkynyl, each of which is unsubstituted or substituted with one or two or three of independently selected $R^{22}$, $OR^{22}$, $SR^{22}$, $S(O)R^{22}$, $SO_2R^{22}$, $C(O)R^{22}$, $CO(O)R^{22}$, $OC(O)R^{22}$, $OC(O)OR^{22}$, $NH_2$, $NHR^{22}$, $N(R^{22})_2$, $NHC(O)R^{22}$, $NR^{22}C(O)R^{22}$, $NHS(O)_2R^{22}$, $NR^{22}S(O)_2R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $C(O)NH_2$, $C(O)NHR^{22}$, $C(O)N(R^{22})_2$, $C(O)NHOH$, $C(O)NHOR^{22}$, $C(O)NHSO_2R^{22}$, $C(O)NR^{22}SO_2R^{22}$, $SO_2NH_2$, $SO_2NHR^{22}$, $SO_2N(R^{22})_2$, C(O)H, C(O)OH, $C(N)NH_2$, $C(N)NHR^{22}$, $C(N)N(R^{22})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{22}$ is $R^{23}$, $R^{24}$ or $R^{25}$;

$R^{23}$ is phenyl, which is unfused or fused with benzene, heteroarene or $R^{23A}$; $R^{23A}$ is cycloalkane, cycloalkene, heterocycloalkane or heterocycloalkene;

$R^{24}$ is heteroarene, which is unfused or fused with benzene, heteroarene or $R^{24A}$; $R^{24A}$ is cycloalkane, cycloalkene, heterocycloalkane or heterocycloalkene;

$R^{25}$ is cycloalkyl, cycloalkenyl, heterocycloalkyl or heterocycloalkenyl each of which is unfused or fused with benzene, heteroarene or $R^{25A}$; $R^{25A}$ is cycloalkane, cycloalkene, heterocycloalkane or heterocycloalkene;

$Z^1$ is $R^{26}$ or $R^{27}$;

$Z^2$ is $R^{28}$, $R^{19}$ or $R^{30}$;

$Z^{1A}$ and $Z^{2A}$ are both absent or are taken together to form $CH_2$, $CH_2CH_2$ or $Z^{12A}$;

$Z^{12A}$ is $C_2$-$C_6$-alkylene having one or two $CH_2$ moieties replaced by NH, $N(CH_3)$, S, S(O) or $SO_2$;

$L^1$ is a $R^{37}$, $OR^{37}$, $SR^{37}$, $S(O)R^{37}$, $SO_2R^{37}$, $C(O)R^{37}$, $CO(O)R^{37}$, $OC(O)R^{37}$, $OC(O)OR^{37}$, $NHR^{37}$, $C(O)NH$, $C(O)NR^{37}$, $C(O)NHOR^{37}$, $C(O)NHSO_2R^{37}$, $SO_2NH$, $SO_2NHR^{37}$, $C(N)NH$, $C(N)NHR^{37}$;

$R^{26}$ is phenylene, which is unfused or fused with benzene or heteroarene or $R^{26A}$; $R^{26A}$ is cycloalkane, cycloalkene, heterocycloalkane or heterocycloalkene;

$R^{27}$ is heteroarylene, which is unfused or fused with benzene or heteroarene or $R^{27A}$; $R^{27A}$ is cycloalkane, cycloalkene, heterocycloalkane or heterocycloalkene;

$R^{28}$ is phenylene, which is unfused or fused with benzene, heteroarene or $R^{28A}$; $R^{28A}$ is cycloalkane, cycloalkene, heterocycloalkane or heterocycloalkene;

$R^{29}$ is heteroarylene, which is unfused or fused with benzene or heteroarene or $R^{29A}$; $R^{29A}$ is cycloalkane, cycloalkene, heterocycloalkane or heterocycloalkene;

$R^{30}$ is cycloalkylene, cycloalkenylene, heterocycloalkylene or heterocycloalkenylene, each of which is unfused or fused with benzene, heteroarene or $R^{30A}$; $R^{30A}$ is cycloalkane, cycloalkene, heterocycloalkane or heterocycloalkene;

$R^{37}$ is a bond or $R^{37A}$;

$R^{37A}$ is alkylene, alkenylene, or alkynylene, each of which is unsubstituted or substituted with one or two or three independently selected $R^{37B}$, $OR^{37B}$, $SR^{37B}$, $S(O)R^{37B}$, $SO_2R^{37B}$, $C(O)R^{37B}$, $CO(O)R^{37B}$, $OC(O)R^{37B}$, $OC(O)OR^{37B}$, $NH_2$, $NHR^{37B}$, $N(R^{37B})_2$, $NHC(O)R^{37B}$, $NR^{37B}C(O)R^{37B}$, $NHS(O)_2R^{37B}$, $NR^{37B}S(O)_2R^7$, $NHC(O)OR^{37B}$, $NR^{37B}C(O)OR^{37B}$, $NHC(O)NH_2$, $NHC(O)NHR^{37B}$, $NHC(O)N(R^{37B})_2$, $NR^{37B}C(O)NHR^{37B}$, $NR^{37B}C(O)N(R^{37B})_2$, $C(O)NH_2$, $C(O)NHR^{37B}$, $C(O)N(R^{37B})_2$, $C(O)NHOH$, $C(O)NHOR^{37B}$, $C(O)NHSO_2R^{37B}$, $C(O)NR^{37B}SO_2R^{37B}$, $SO_2NH_2$, $SO_2NHR^{37B}$, $SO_2N(R^{37B})_2$, C(O)H, C(O)OH, $C(N)NH_2$, $C(N)NHR^{37B}$, $C(N)N(R^{37B})_2$, CNOH, $CNOCH_3$, OH, (O), CN, $N_3$, $NO_2$, $CF_3$, $CF_2CF_3$, $OCF_3$, $OCF_2CF_3$, F, Cl, Br and I substituents;

$R^{37B}$ is alkyl, alkenyl, alkynyl, phenyl, heteroaryl, cycloalkyl, cycloalkenyl, heterocycloalkyl, or heterocycloalkenyl;

$Z^3$ is $R^{38}$, $R^{39}$ or $R^{40}$;

$R^{38}$ is phenyl, which is unfused or fused with benzene, heteroarene or $R^{38A}$; $R^{38A}$ is cycloalkane, cycloalkene, heterocycloalkane or heterocycloalkene;

$R^{39}$ is heteroaryl, which is unfused or fused with benzene, heteroarene or $R^{39A}$; $R^{39A}$ is cycloalkane, cycloalkene, heterocycloalkane or heterocycloalkene;

$R^{40}$ is cycloalkyl, cycloalkenyl, heterocycloalkyl or heterocycloalkenyl, each of which is unfused or fused with benzene, heteroarene or $R^{40A}$; $R^{40A}$ is cycloalkane, cycloalkene, heterocycloalkane or heterocycloalkene;

wherein the moieties represented by $R^{26}$ and $R^{27}$ are substituted (i.e., if $Z^{1A}$ and $Z^{2A}$ are absent) or further substituted (i.e., if $Z^{1A}$ and $Z^{2A}$ are present) with one or two or three or four of independently selected $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $NR^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, $C(O)H$, $C(O)OH$, $C(N)NH_2$, $C(N)NHR^{41}$, $C(N)N(R^{41})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{41}$ is $R^{42}$, $R^{43}$, $R^{44}$ or $R^{45}$;

$R^{42}$ is phenyl, which is unfused or fused with benzene, heteroarene or $R^{42A}$; $R^{42A}$ is cycloalkane, cycloalkene, heterocycloalkane or heterocycloalkene;

$R^{43}$ is heteroaryl, which is unfused or fused with benzene, heteroarene or $R^{43A}$; $R^{43A}$ is cycloalkane, cycloalkene, heterocycloalkane or heterocycloalkene;

$R^{44}$ is cycloalkyl, cycloalkenyl, heterocycloalkyl or heterocycloalkenyl, each of which is unfused or fused with benzene, heteroarene or $R^{44A}$; $R^{44A}$ is cycloalkane, cycloalkene, heterocycloalkane or heterocycloalkene;

$R^{45}$ is alkyl, alkenyl or alkynyl, each of which is unsubstituted or substituted with one or two or three of independently selected $R^{46}$, $OR^{46}$, $SR^{46}$, $S(O)R^{46}$, $SO_2R^{46}$, $C(O)R^{46}$, $CO(O)R^{46}$, $OC(O)R^{46}$, $OC(O)OR^{46}$, $NH_2$, $NHR^{46}$, $N(R^{46})_2$, $NHC(O)R^{46}NR^{46}C(O)R^{46}$, $NHS(O)_2R^{46}$, $NR^{46}S(O)_2R^{46}$, $NHC(O)OR^{46}$, $NR^{46}C(O)OR^{46}$, $NHC(O)NH_2$, $NHC(O)NHR^{46}$, $NHC(O)N(R^{46})_2$, $NR^{46}C(O)NHR^{46}$, $NR^{46}C(O)N(R^{46})_2$, $C(O)NH_2$, $C(O)NHR^{46}$, $C(O)N(R^{46})_2$, $C(O)NHOH$, $C(O)NHOR^{46}$, $C(O)NHSO_2R^{46}$, $C(O)NR^{46}SO_2R^{46}$, $SO_2NH_2$, $SO_2NHR^{46}$, $SO_2N(R^{46})_2$, $C(O)H$, $C(O)OH$, $C(N)NH_2$, $C(N)NHR^{46}$, $C(N)N(R^{46})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{46}$ is alkyl, alkenyl, alkynyl, $R^{47}$, $R^{48}$ or $R^{49}$;

$R^{47}$ is phenyl, which is unfused or fused with benzene, heteroarene or $R^{47A}$; $R^{47A}$ is cycloalkane, cycloalkene, heterocycloalkane or heterocycloalkene;

$R^{48}$ is heteroaryl, which is unfused or fused with benzene, heteroarene or $R^{48A}$; $R^{48A}$ is cycloalkane, cycloalkene, heterocycloalkane or heterocycloalkene;

$R^{49}$ is cycloalkyl, cycloalkenyl, heterocycloalkyl or heterocycloalkenyl, each of which is unfused or fused with benzene, heteroarene or $R^{49A}$; $R^{49A}$ is cycloalkane, cycloalkene, heterocycloalkane or heterocycloalkene;

wherein the moieties represented by $R^{42}$, $R^{42A}$, $R^{43}$, $R^{43A}$, $R^{44}$, $R^{44A}$, $R^{47}$, $R^{47A}$, $R^{48}$, $R^{48A}$, $R^{49}$, and $R^{49A}$ are independently substituted with one or two or three or four of independently selected $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three of independently selected $R^{55}$, $OR^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{55}$ is alkyl, alkenyl, alkynyl, phenyl, heteroaryl, cycloalkyl, cycloalkenyl, heterocycloalkyl or heterocycloalkenyl; and wherein each foregoing cyclic moiety is independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{57A}$ is spirocyclyl;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl or alkenyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^{68}SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or I;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl or alkenyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or I;

$R^{73}$ is alkyl, alkenyl, alkenyl, phenyl, heteroaryl, cycloalkyl, cycloalkenyl, heterocycloalkyl or heterocycloalkenyl; and the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, $F$, $Cl$, $Br$ or I.

Another embodiment of this invention pertains to compounds of Formula (I), wherein $A^1$ is N or $C(A^2)$;

$A^2$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, $F$, $Cl$, $Br$, $I$, $CN$, $NO_2$, $N_3$, $OH$, $C(O)H$, $CHNOH$, $CH(NOCH_3)$, $CF_3$, $C(O)OH$, $C(O)NH_2$ or $C(O)OR^{1A}$;

$B^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, $F$, $Cl$, $Br$, $I$, $CN$, $NO_2$, $N_3$, $OH$, $C(O)H$, $CHNOH$, $CH(NOCH_3)$, $CF_3$, $C(O)OH$, $C(O)NH_2$ or $C(O)OR^{1A}$;

$D^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, $F$, $Cl$, $Br$, $I$, $CN$, $NO_2$, $N_3$, $OH$, $C(O)H$, $CHNOH$, $CH(NOCH_3)$, $CF_3$, $C(O)OH$, $C(O)NH_2$ or $C(O)OR^{1A}$;

$E^1$ is H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NH_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, $F$, $Cl$, $Br$, $I$, $CN$, $NO_2$, $N_3$, $OH$, $C(O)H$, $CHNOH$, $CH(NOCH_3)$, $CF_3$, $C(O)OH$, $C(O)NH_2$ or $C(O)OR^{1A}$; and $Y^1$ is H, $CN$, $NO_2$, $C(O)OH$, $F$, $Cl$, $Br$, $I$, $CF_3$, $OCF_3$, $CF_2CF_3$, $OCF_2CF_3$, $R^{17}$, $OR^{17}$, $C(O)R^{17}$, $C(O)OR^{17}$, $SR^{17}$, $SO_2R^{17}$, $NH_2$, $NHR^{17}$, $N(R^{17})_2$, $NHC(O)R^{17}$, $C(O)NH_2$, $C(O)NHR^{17}$, $C(O)N(R^{17})_2$, $NHS(O)R^{17}$ or $NHSO_2R^{17}$; or $E^1$ and $Y^1$, together with the atoms to which they are attached, are benzene, naphthylene, heteroarene cycloalkane, cycloalkene, heterocycloalkane or heterocycloalkene; and $A^2$, $B^1$, and $D^1$ are independently selected H, $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$, NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, OH, C(O)H, CHNOH, CH(NOCH$_3$), CF$_3$, C(O)OH, C(O)NH$_2$ or C(O)OR$^{1A}$; or Y$^1$ and B$^1$, together with the atoms to which they are attached, are benzene, naphthylene, heteroarene cycloalkane, cycloalkene, heterocycloalkane or heterocycloalkene; and A$^2$, D$^1$, and E$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$, NHSO$_2$NHR$^1$, NHSO$_2$N(CH$_3$)R$^1$, N(CH$_3$)SO$_2$N(CH$_3$)R$^1$, F, Cl, Br, I, CN, NO$_2$N$_3$, OH, C(O)H, CHNOH, CH(NOCH$_3$), CF$_3$, C(O)OH, C(O)NH$_2$ or C(O)OR$^{1A}$; or A$^2$ and B$^1$, together with the atoms to which they are attached, are benzene, naphthylene, heteroarene cycloalkane, cycloalkene, heterocycloalkane or heterocycloalkene; and D$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$, NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, N$_3$, OH, C(O)H, CHNOH, CH(NOCH$_3$), CF$_3$, C(O)OH, C(O)NH$_2$ or C(O)OR$^{1A}$; or A$^2$ and D$^1$, together with the atoms to which they are attached, are benzene, naphthalene, heteroarene, cycloalkane, cycloalkene, heterocycloalkane or heterocycloalkene; and B$^1$, E$^1$, and Y$^1$ are independently selected H, R$^1$, OR$^1$, SR$^1$, S(O)R$^1$, SO$_2$R$^1$, C(O)R$^1$, C(O)OR$^1$, OC(O)R$^1$, NHR$^1$, N(R$^1$)$_2$, C(O)NHR$^1$, C(O)N(R$^1$)$_2$, NHC(O)R$^1$, NR$^1$C(O)R$^1$, NHC(O)OR$^1$, NR$^1$C(O)OR$^1$, NHC(O)NH$_2$, NHC(O)NHR$^1$, NHC(O)N(R$^1$)$_2$, NR$^1$C(O)NHR$^1$, NR$^1$C(O)N(R$^1$)$_2$, SO$_2$NH$_2$, SO$_2$NHR$^1$, SO$_2$N(R$^1$)$_2$, NHSO$_2$R$^1$, NR$^1$SO$_2$R$^1$, NHSO$_2$NHR$^1$, NHSO$_2$N(R$^1$)$_2$, NR$^1$SO$_2$NHR$^1$, NR$^1$SO$_2$N(R$^1$)$_2$, C(O)NHNOH, C(O)NHNOR$^1$, C(O)NHSO$_2$R$^1$, C(NH)NH$_2$, C(NH)NHR$^1$, C(NH)N(R$^1$)$_2$, NHSO$_2$NHR$^1$, NHSO$_2$N(CH$_3$)R$^1$, N(CH$_3$)SO$_2$N(CH$_3$)R$^1$, F, Cl, Br, I, CN, NO$_2$, OH, C(O)H, CHNOH, CH(NOCH$_3$), CF$_3$, C(O)OH, C(O)NH$_2$ or C(O)OR$^{1A}$;

R$^1$ is R$^2$, R$^3$, R$^4$ or R;

R$^{1A}$ is cycloalkyl, cycloalkenyl or cycloalkynyl;

R$^2$ is phenyl, which is unfused or fused with benzene, heteroarene or R$^{2A}$; R$^{2A}$ is cycloalkane or heterocycloalkane;

R$^3$ is heteroaryl, which is unfused or fused with benzene, heteroarene or R$^{3A}$; R$^{3A}$ is cycloalkane or heterocycloalkane;

R$^4$ is cycloalkyl, cycloalkenyl, heterocycloalkyl or heterocycloalkenyl, each of which is unfused or fused with benzene, heteroarene or R$^{4A}$; R$^{4A}$ is cycloalkane, cycloalkene, heterocycloalkane or heterocycloalkene;

R$^5$ is alkyl, alkenyl or alkynyl, each of which is unsubstituted or substituted with one or two or three of independently selected R$^6$, NC(R$^{6A}$)(R$^{6B}$), R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, NHC(O)CH(CH$_3$)NHC(O)CH(CH$_3$)NHR$^7$, OH, (O), C(O)OH, N$_3$, CN, NH$_2$, CF$_3$, CF$_2$CF$_3$, F, Cl, Br or I;

R$^6$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{6A}$ and R$^{6B}$ are independently selected alkyl or, together with the N to which they are attached, R$^{6C}$;

R$^{6C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^7$ is R$^8$, R$^9$, R$^{10}$ or R$^{11}$;

R$^8$ is phenyl, which is unfused or fused with benzene, heteroarene or R$^{8A}$; R$^{8A}$ is cycloalkane, cycloalkene, heterocycloalkane or heterocycloalkene;

R$^9$ is heteroaryl, which is unfused or fused with benzene, heteroarene or R$^{9A}$; R$^{9A}$ is cycloalkane, cycloalkene, heterocycloalkane or heterocycloalkene;

R$^{10}$ is cycloalkyl, cycloalkenyl, heterocycloalkyl or heterocycloalkenyl each of which is unfused or fused with benzene, heteroarene or R$^{10A}$; R$^{10A}$ is cycloalkane, cycloalkene, heterocycloalkane or heterocycloalkene;

R$^{11}$ is alkyl, alkenyl or alkynyl, each of which is unsubstituted or substituted with one or two or three of independently selected R$^{12}$, OR$^{12}$, SR, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N(R$^{12}$)$_2$, NR$^{12}$C(O)NHR$^{12}$, NR$^{12}$C(O)N(R$^{12}$)$_2$, C(O)NH$_2$, C(O)NHR$^{12}$, C(O)N(R$^{12}$)$_2$, C(O)NHOH, C(O)NHOR$^{12}$, C(O)NHSO$_2$R$^{17}$, C(O)NR$^{12}$SO$_2$R$^{12}$, SO$_2$NH$_2$, SO$_2$NHR$^{12}$, SO$_2$N(R$^{12}$)$_2$, C(O)H, C(O)OH, C(N)NH$_2$, C(N)NHR$^{12}$, C(N)N(R$^{12}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{12}$ is R$^{13}$, R$^{14}$, R$^{15}$ or R$^{16}$;

R$^{13}$ is phenyl, which is unfused or fused with benzene, heteroarene or R$^{13A}$; R$^{13A}$ is cycloalkane, cycloalkene, heterocycloalkane or heterocycloalkene;

R$^{14}$ is heteroaryl, which is unfused or fused with benzene, heteroarene or R$^{14A}$; R$^{14A}$ is cycloalkane, cycloalkene, heterocycloalkane or heterocycloalkene;

R$^{15}$ is cycloalkane, cycloalkene, heterocycloalkane or heterocycloalkene, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkynyl;

R$^{17}$ is R$^{18}$, R$^{19}$, R$^{20}$ or R$^{21}$;

R$^{18}$ is phenyl, which is unfused or fused with benzene, heteroarene or R$^{18A}$; R$^{18A}$ is cycloalkane, cycloalkene, heterocycloalkane or heterocycloalkene;

R$^{19}$ is heteroaryl, which is unfused or fused with benzene, heteroarene or R$^{19A}$; R$^{19A}$ is cycloalkane, cycloalkene, heterocycloalkane or heterocycloalkene;

R$^{20}$ is cycloalkyl, cycloalkenyl, heterocycloalkyl or heterocycloalkenyl each of which is unfused or fused with benzene, heteroarene or R$^{20A}$; R$^{20A}$ is cycloalkane, cycloalkene, heterocycloalkane or heterocycloalkene;

R$^{21}$ is alkyl, alkenyl or alkynyl, each of which is unsubstituted or substituted with one or two or three of independently selected R$^{22}$, OR$^{22}$, SR$^{22}$, S(O)R$^{22}$, SO$_2$R$^{22}$, C(O)R$^{22}$, CO(O)R$^{22}$, OC(O)R$^{22}$, OC(O)OR$^{22}$, NH$_2$, NHR$^{22}$, N(R$^{22}$)$_2$, NHC(O)R$^{22}$, NR$^{22}$C(O)R$^{22}$, NHS(O)$_2$R$^{22}$, NR$^{22}$S(O)$_2$R$^{22}$, NHC(O)OR$^{22}$, NR$^{22}$C(O)OR$^{22}$, NHC(O)NH$_2$, NHC(O)NHR$^{22}$, NHC(O)N(R$^{22}$)$_2$, NR$^{22}$C(O)NHR$^{22}$, NR$^{22}$C(O)N(R$^{22}$)$_2$, C(O)NH$_2$, C(O)NHR$^{22}$, C(O)N(R$^{22}$)$_2$, C(O)NHOH, C(O)NHOR$^{22}$, C(O)NHSO$_2$R$^{22}$, C(O)NR$^{22}$SO$_2$R$^{22}$, SO$_2$NH$_2$, SO$_2$NHR$^{22}$, SO$_2$N(R$^{22}$)$_2$, C(O)H, C(O)OH, C(N)NH$_2$, C(N)NHR$^{22}$, C(N)N(R$^{22}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{22}$ is R$^{23}$, R$^{24}$ or R$^{25}$;

R$^{23}$ is phenyl, which is unfused or fused with benzene, heteroarene or R$^{23A}$; R$^{23A}$ is cycloalkane, cycloalkene, heterocycloalkane or heterocycloalkene;

R$^{24}$ is heteroarene, which is unfused or fused with benzene, heteroarene or R$^{24A}$; R$^{24A}$ is cycloalkane, cycloalkene, heterocycloalkane or heterocycloalkene;

R$^{25}$ is cycloalkyl, cycloalkenyl, heterocycloalkyl or heterocycloalkenyl each of which is unfused or fused with benzene, heteroarene or R$^{25A}$; R$^{25A}$ is cycloalkane, cycloalkene, heterocycloalkane or heterocycloalkene;

Z$^1$ is R$^{26}$ or R$^{27}$;

Z$^2$ is R$^{28}$, R$^{29}$ or R$^{30}$;

Z$^{1A}$ and Z$^{2A}$ are both absent or are taken together to form CH$_2$, CH$_2$CH$_2$ or Z$^{12A}$;

Z$^{2A}$ is C$_2$-C$_6$-alkylene having one or two CH$_2$ moieties replaced by NH, N(CH$_3$), S, S(O) or SO$_2$;

L$^1$ is a R$^{37}$, OR$^{37}$, SR$^{37}$, S(O)R$^{37}$, SO$_2$R$^{37}$, C(O)R$^{37}$, CO(O)R$^{37}$, OC(O)R$^{37}$, OC(O)OR$^{37}$, NHR$^{37}$, C(O)NH, C(O)NR$^{37}$, C(O)NHOR$^{37}$, C(O)NHSO$_2$R$^{37}$, SO$_2$NH, SO$_2$NHR$^{37}$, C(N)NH, C(N)NHR$^{37}$;

R$^{26}$ is phenylene, which is unfused or fused with benzene or heteroarene or R$^{26A}$; R$^{26A}$ is cycloalkane, cycloalkene, heterocycloalkane or heterocycloalkene;

R$^{27}$ is heteroarylene, which is unfused or fused with benzene or heteroarene or R$^{27A}$; R$^{27A}$ is cycloalkane, cycloalkene, heterocycloalkane or heterocycloalkene;

R$^{28}$ is phenylene, which is unfused or fused with benzene, heteroarene or R$^{28A}$; R$^{28A}$ is cycloalkane, cycloalkene, heterocycloalkane or heterocycloalkene;

R$^{29}$ is heteroarylene, which is unfused or fused with benzene or heteroarene or R$^{29A}$; R$^{29A}$ is cycloalkane, cycloalkene, heterocycloalkane or heterocycloalkene;

R$^{30}$ is cycloalkylene, cycloalkenylene, heterocycloalkylene or heterocycloalkenylene, each of which is unfused or fused with benzene, heteroarene or R$^{30A}$; R$^{30A}$ is cycloalkane, cycloalkene, heterocycloalkane or heterocycloalkene;

R$^{37}$ is a bond or R$^{37A}$;

R$^{37A}$ is alkylene, alkenylene, or alkynylene, each of which is unsubstituted or substituted with one or two or three independently selected R$^{37B}$, OR$^{37B}$, SR$^{37B}$, S(O)R$^{37B}$, SO$_2$R$^{37B}$, C(O)R$^{37B}$, CO(O)R$^{37B}$, OC(O)R$^{37B}$, OC(O)OR$^{37B}$, NH$_2$, NHR$^{37B}$, N(R$^{37B}$)$_2$, NHC(O)R$^{37B}$, NR$^{37B}$C(O)R$^{37B}$, NHS(O)$_2$R$^{37B}$, NR$^{37B}$S(O)$_2$R$^{37B}$, NHC(O)OR$^{37B}$, NR$^{37B}$C(O)OR$^{37B}$, NHC(O)NH$_2$, NHC(O)NHR$^{37B}$, NHC(O)N(R$^{37B}$)$_2$, NR$^{37B}$C(O)NHR$^{37B}$, NR$^{37B}$C(O)N(R$^{37B}$)$_2$, C(O)NH$_2$, C(O)NHR$^{37B}$, C(O)N(R$^{37B}$)$_2$, C(O)NHOH, C(O)NHOR$^{37B}$, C(O)NHSO$_2$R$^{37B}$, C(O)NR$^{37B}$SO$_2$R$^{37B}$, SO$_2$NH$_2$, SO$_2$NHR$^{37B}$, SO$_2$N(R$^{37B}$)$_2$, C(O)H, C(O)OH, C(N)NH$_2$, C(N)NHR$^{37B}$, C(N)N(R$^{37B}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br and I substituents;

R$^{37B}$ is alkyl, alkenyl, alkynyl, phenyl, heteroaryl, cycloalkyl, cycloalkenyl, heterocycloalkyl, or heterocycloalkenyl;

Z$^3$ is R$^{38}$, R$^{39}$ or R$^{40}$;

R$^{38}$ is phenyl, which is unfused or fused with benzene, heteroarene or R$^{38A}$; R$^{38A}$ is cycloalkane, cycloalkene, heterocycloalkane or heterocycloalkene;

R$^{39}$ is heteroaryl, which is unfused or fused with benzene, heteroarene or R$^{39A}$; R$^{39A}$ is cycloalkane, cycloalkene, heterocycloalkane or heterocycloalkene;

R$^{40}$ is cycloalkyl, cycloalkenyl, heterocycloalkyl or heterocycloalkenyl, each of which is unfused or fused with benzene, heteroarene or R$^{40A}$; R$^{40A}$ is cycloalkane, cycloalkene, heterocycloalkane or heterocycloalkene;

wherein the moieties represented by R$^{26}$ and R$^{27}$ are substituted with OR$^{41}$;

R$^{41}$ is R$^{42}$, R$^{43}$, R$^{44}$ or R$^{45}$;

R$^{42}$ is phenyl, which is unfused or fused with benzene, heteroarene or R$^{42A}$; R$^{42A}$ is cycloalkane, cycloalkene, heterocycloalkane or heterocycloalkene;

R$^{43}$ is heteroaryl, which is unfused or fused with benzene, heteroarene or R$^{43A}$; R$^{43A}$ is cycloalkane, cycloalkene, heterocycloalkane or heterocycloalkene;

R$^{44}$ is cycloalkyl, cycloalkenyl, heterocycloalkyl or heterocycloalkenyl, each of which is unfused or fused with benzene, heteroarene or R$^{44A}$; R$^{44A}$ is cycloalkane, cycloalkene, heterocycloalkane or heterocycloalkene;

R$^{45}$ is alkyl, alkenyl or alkynyl, each of which is unsubstituted or substituted with one or two or three of independently selected R$^{46}$, OR$^{46}$, SR$^{46}$, S(O)R$^{46}$, SO$_2$R$^{46}$, C(O)R$^{46}$, CO(O)R$^{46}$, OC(O)R$^{46}$, OC(O)OR$^{46}$, NH$_2$, NHR$^{46}$, N(R$^{46}$)$_2$, NHC(O)R$^{46}$, NR$^{46}$C(O)R$^{46}$, NHS(O)$_2$R$^{46}$, NR$^{46}$S(O)$_2$R$^{46}$, NHC(O)OR$^{46}$, NR$^{46}$C(O)OR$^{46}$, NHC(O)NH$_2$, NHC(O)NHR$^{46}$, NHC(O)N(R$^{46}$)$_2$, NR$^{46}$C(O)NHR$^{46}$, NR$^{46}$C(O)N(R$^{46}$)$_2$, C(O)NH$_2$, C(O)NHR$^{46}$, C(O)N(R$^{46}$)$_2$, C(O)NHOH, C(O)NHOR$^{46}$, C(O)NHSO$_2$R$^{46}$, C(O)NR$^{46}$SO$_2$R$^{46}$, SO$_2$NH$_2$, SO$_2$NHR$^{46}$, SO$_2$N(R$^{46}$)$_2$, C(O)H, C(O)OH, C(N)NH$_2$, C(N)NHR$^{46}$, C(N)N(R$^{46}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{46}$ is alkyl, alkenyl, alkynyl, R$^{47}$, R$^{48}$ or R$^{49}$;

R$^{47}$ is phenyl, which is unfused or fused with benzene, heteroarene or R$^{47A}$; R$^{47A}$ is cycloalkane, cycloalkene, heterocycloalkane or heterocycloalkene;

R$^{48}$ is heteroaryl, which is unfused or fused with benzene, heteroarene or R$^{48A}$; R$^{48A}$ is cycloalkane, cycloalkene, heterocycloalkane or heterocycloalkene;

R$^{49}$ is cycloalkyl, cycloalkenyl, heterocycloalkyl or heterocycloalkenyl, each of which is unfused or fused with benzene, heteroarene or R$^{49A}$; R$^{49A}$ is cycloalkane, cycloalkene, heterocycloalkane or heterocycloalkene;

wherein the moieties represented by R$^{42}$, R$^{42A}$, R$^{43}$, R$^{43A}$, R$^{44}$, R$^{44A}$, R$^{47}$R$^{47A}$, R$^{48}$, R$^{48A}$, R$^{49}$, and R$^{49A}$ independently substituted with one or two or three or four of independently selected R$^{50}$, OR$^{50}$, SR$^{50}$, S(O)R$^{50}$, SO$_2$R$^{50}$, C(O)R$^{50}$, CO(O)R$^{50}$, OC(O)R$^{50}$, OC(O)OR$^{50}$, NH$_2$, NHR$^{50}$, N(R$^{50}$)$_2$, NHC(O)R$^{50}$, NR$^{50}$C(O)R$^{50}$, NHS(O)$_2$R$^{50}$, NR$^{50}$S(O)$_2$R$^{50}$, NHC(O)OR$^{50}$, NR$^{50}$C(O)OR$^{50}$, NHC(O)NH$_2$, NHC(O)NHR$^{50}$, NHC(O)N(R$^{50}$)$_2$, NR$^{50}$C(O)NHR$^{50}$, NR$^{50}$C(O)N(R$^{50}$)$_2$, C(O)NH$_2$, C(O)NHR$^{50}$, C(O)N(R$^{50}$)$_2$, C(O)NHOH, C(O)NHOR$^{50}$, C(O)NHSO$_2$R$^{50}$, C(O)NR$^{50}$SO$_2$R$^{50}$, SO$_2$NH$_2$, SO$_2$NHR$^{50}$, SO$_2$N(R$^{50}$)$_2$, C(O)H, C(O)OH, C(N)NH$_2$, C(N)NHR$^{50}$, C(N)N(R$^{50}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{50}$ is R$^{51}$, R$^{52}$, R$^{53}$ or R$^{54}$;

R$^{51}$ is phenyl, which is unfused or fused with benzene, heteroarene or R$^{51A}$; R$^{51A}$ is cycloalkane, cycloalkene, heterocycloalkane or heterocycloalkene;

R$^{52}$ is heteroaryl, which is unfused or fused with benzene, heteroarene or R$^{52A}$; R$^{52A}$ is cycloalkane, cycloalkene, heterocycloalkane or heterocycloalkene;

R$^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three of independently selected $R^{55}$, $OR^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{55}$ is alkyl, alkenyl, alkynyl, phenyl, heteroaryl, cycloalkyl, cycloalkenyl, heterocycloalkyl or heterocycloalkenyl; and wherein each foregoing cyclic moiety is independently unsubstituted, further unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC(O)NH_2$, $NHC(O)NHR^{57}$, $NHC(O)N(R^{57})_2$, $NR^{57}C(O)NHR^{57}$, $NR^{57}C(O)N(R^{57})_2$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{57}$ is $R^{58}$, $R^{59}$, $R^{60}$ or $R^{61}$;

$R^{57A}$ is spirocyclyl;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^{67}$, $OC(O)OR^{67}$, $NH_2$, $NHR^{67}$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R^{68}$, $SO_2R^{68}$, $C(O)R^{68}$, $CO(O)R^{68}$, $OC(O)R^6$, $OC(O)OR^{68}$, $NH_2$, $NHR^{68}$, $N(R^{68})_2$, $NHC(O)R^{68}$, $NR^{68}C(O)R^{68}$, $NHS(O)_2R^{68}$, $NR^{68}S(O)_2R^{68}$, $NHC(O)OR^{68}$, $NR^{68}C(O)OR^{68}$, $NHC(O)NH_2$, $NHC(O)NHR^{68}$, $NHC(O)N(R^{68})_2$, $NR^{68}C(O)NHR^{68}$, $NR^{68}C(O)N(R^{68})_2$, $C(O)NH_2$, $C(O)NHR^{68}$, $C(O)N(R^{68})_2$, $C(O)NHOH$, $C(O)NHOR^{68}$, $C(O)NHSO_2R^{68}$, $C(O)NR^6SO_2R^{68}$, $SO_2NH_2$, $SO_2NHR^{68}$, $SO_2N(R^{68})_2$, $C(O)H$, $C(O)OH$, $C(N)NH_2$, $C(N)NHR^{68}$, $C(N)N(R^{68})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{68}$ is $R^{69}$, $R^{70}$, $R^{71}$ or $R^{72}$;

$R^{69}$ is phenyl, which is unfused or fused with benzene, heteroarene or $R^{69A}$; $R^{69A}$ is cycloalkane, cycloalkene, heterocycloalkane or heterocycloalkene;

$R^{70}$ is heteroaryl, which is unfused or fused with benzene, heteroarene or $R^{70A}$; $R^{70A}$ is cycloalkane, cycloalkene, heterocycloalkane or heterocycloalkene;

$R^{71}$ is cycloalkyl, cycloalkenyl, heterocycloalkyl or heterocycloalkenyl, each of which is unfused or fused with benzene, heteroarene or $R^{71A}$; $R^{71A}$ is cycloalkane, cycloalkene, heterocycloalkane or heterocycloalkene;

$R^{72}$ is alkyl, alkenyl or alkynyl, each of which is unsubstituted or substituted with one or two or three of independently selected $R^{73}$, $OR^{73}$, $SR^{73}$, $S(O)R^{73}$, $SO_2R^{73}$, $C(O)R^{73}$, $CO(O)R^{73}$, $OC(O)R^{73}$, $OC(O)OR^{73}$, $NH_2$, $NHR^{73}$, $N(R^{73})_2$, $NHC(O)R^{73}$, $NR^{73}C(O)R^{73}$, $NHS(O)_2R^{73}$, $NR^{73}S(O)_2R^{73}$, $NHC(O)OR^{73}$, $NR^{73}C(O)OR^{73}$, $NHC(O)NH_2$, $NHC(O)NHR^{73}$, $NHC(O)N(R^{73})_2$, $NR^{73}C(O)NHR^{73}$, $NR^{73}C(O)N(R^{73})_2$, $C(O)NH_2$, $C(O)NHR^{73}$, $C(O)N(R^{73})_2$, $C(O)NHOH$, $C(O)NHOR^{73}$, $C(O)NHSO_2R^{73}$, $C(O)NR^{73}SO_2R^{73}$, $SO_2NH_2$, $SO_2NHR^{73}$, $SO_2N(R^{73})_2$, $C(O)H$, $C(O)OH$, $C(N)NH_2$, $C(N)NHR^{73}$, $C(N)N(R^{73})_2$, $CNOH$, $CNOCH_3$, $OH$, (O), $CN$, $N_3$, $NO_2$, $CF_3$, $CF_2CF_3$, $OCF_3$, $OCF_2CF_3$, F, Cl, Br or I;

$R^{73}$ is alkyl, alkenyl, alkenyl, phenyl, heteroaryl, cycloalkyl, cycloalkenyl, heterocycloalkyl or heterocycloalkenyl; and the moieties represented by $R^{69}$, $R^{70}$, and $R^{71}$ are unsubstituted or substituted with one or two or three or four of independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, (O), $CN$, $N_3$, $NO_2$, $CF_3$, $CF_2CF_3$, $OCF_3$, $OCF_2CF_3$, F, Cl, Br or I.

In one embodiment of Formula (I), $A^1$ is N. In another embodiment of Formula (I), $A^1$ is $C(A^2)$. In another embodiment of Formula (I), $A^1$ is $C(A^2)$; and $A^2$ is H.

In one embodiment of Formula (I), $B^1$ is $OR^1$, or $NHR^1$. In another embodiment of Formula (I), $A^1$ is $C(A^2)$; $A^2$ is H; and $B^1$ is $NHR^1$. In another embodiment of Formula (I), $A^1$ is $C(A^2)$; $A^2$ is H; and $B^1$ is $OR^1$.

In one embodiment of Formula (I), $D^1$ is H. In another embodiment of Formula (I), $A^1$ is $C(A^2)$; $A^2$ is H; $B^1$ is $NHR^1$; and $D^1$ is H. In another embodiment of Formula (I), $A^1$ is $C(A^2)$; $A^2$ is H; $B^1$ is $OR^1$; and $D^1$ is H.

In one embodiment of Formula (I), $E^1$ is H. In another embodiment of Formula (I), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (I), $Y^1$ is H, CN, $NO_2$, F, Cl, Br, $CF_3$, $R^{17}$, or $SO_2R^{17}$.

In another embodiment of Formula (I), $Y^1$ is $NO_2$. In another embodiment of Formula (I), $Y^1$ is Cl. In another embodiment of Formula (I), $Y^1$ is $SO_2R^7$; wherein $R^{17}$ is as defined herein. In another embodiment of Formula (I), $Y^1$ is $SO_2R^{17}$; wherein $R^{17}$ is alkyl. In another embodiment of Formula (I), $Y^1$ is $R^{17}$; wherein $R^{17}$ is alkynyl. In another embodiment of Formula (I), $A^1$ is $C(A^2)$; $A^2$ is H; $B^1$ is $NHR^1$; $D^1$ is H; $E^1$ is H; and $Y^1$ is $NO_2$ or $SO_2R^7$; wherein $R^{17}$ is alkyl or alkynyl. In another embodiment of Formula (I), $A^1$ is $C(A^2)$; $A^2$ is H; $B^1$ is $NHR^1$; $D^1$ is H; $E^1$ is H; and $Y^1$ is $NO_2$. In another embodiment of Formula (I), $A^1$ is $C(A^2)$; $A^2$ is H; $B^1$ is $NHR^1$; $D^1$ is H; $E^1$ is H; and $Y^1$ is $SO_2R^{17}$, wherein $R^{17}$ is alkyl substituted with three F. In another embodiment of Formula (I), $A^1$ is $C(A^2)$; $A^2$ is H; $B^1$ is $OR^1$; $D^1$ is H; $E^1$ is H; and $Y^1$ is Cl.

In one embodiment of Formula (I), $R^1$ is $R^4$ or $R^5$. In one embodiment of Formula (I), $R^1$ is $R^4$. In one embodiment of Formula (I), $R^1$ is $R^5$. In one embodiment of Formula (I), $R^1$ is $R^4$; and $R^4$ is cycloalkyl, or heterocycloalkyl. In one embodiment of Formula (I), $R^1$ is $R^4$; and $R^4$ is cycloalkyl. In one embodiment of Formula (I), $R^1$ is $R^4$; and $R^4$ is heterocycloalkyl.

In one embodiment of Formula (I), $R^1$ is $R^4$; and $R^4$ is cycloalkyl; wherein $R^4$ is unsubstituted or substituted as defined herein. In another embodiment of Formula (I), $R^1$ is $R^4$; and $R^4$ is cycloalkyl; wherein the cycloalkyl ring is substituted as defined herein. In another embodiment of Formula (I), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (I), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (I), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (I), $R^1$ is $R^4$; and $R^4$ is cycloalkyl; wherein the cycloalkyl ring is substituted with $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (I), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{61}$ is alkyl which is unsubstituted. In another embodiment of Formula (I), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{60}$ is cycloalkyl which is unsubstituted. In another embodiment of Formula (I), $R^1$ is $R^4$; and $R^4$ is cycloalkyl; wherein the cycloalkyl ring is substituted with $NHR^{57}$. In another embodiment of Formula (I), $R^1$ is $R^4$; and $R^4$ is cycloalkyl; wherein the cycloalkyl ring is cyclohexyl; and wherein the cyclohexyl ring is substituted with $NHR^{57}$. In another embodiment of Formula (I), $R^1$ is $R^4$; and $R^4$ is cycloalkyl; wherein the cycloalkyl ring is cyclohexyl; and wherein the cyclohexyl ring is substituted with $NHR^{57}$, $R^{57}$ is $R^{60}$, and $R^{60}$ is heterocycloalkyl which is unsubstituted.

In one embodiment of Formula (I), $R^1$ is $R^4$; and $R^4$ is heterocycloalkyl; wherein $R^4$ is unsubstituted or substituted as defined herein. In another embodiment of Formula (I), $R^1$ is $R^4$; and $R^4$ is heterocycloalkyl; wherein the heterocycloalkyl ring is substituted as defined herein. In another embodiment of Formula (I), $R^1$ is $R^4$; and $R^4$ is heterocycloalkyl; wherein the heterocycloalkyl ring is substituted with $R^{57}$. In another embodiment of Formula (I), $R^1$ is $R^4$; and $R^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more $R^{57}$; $SO_2R^{57}$, or OH, and $R^{57}$ is $R^{60}$ or $R^{61}$. In another embodiment of Formula (I), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is cycloalkyl or heterocycloalkyl; and $R^{61}$ is alkyl. In another embodiment of Formula (I), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is heterocycloalkyl, wherein the heterocycloalkyl is tetrahydropyranyl or oxetanyl. In another embodiment of Formula (I), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is cycloalkyl, wherein the cycloalkyl is cyclopropyl or cyclopentyl. In another embodiment of Formula (I), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl. In another embodiment of Formula (I), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl; wherein the $C_1$-alkyl, $C_2$-alkyl, or $C_3$-alkyl are unsubstituted or substituted.

In one embodiment of Formula (I), $R^1$ is $R^5$; and $R^5$ is alkyl which is unsubstituted or substituted. In one embodiment of Formula (I), $R^1$ is $R^5$; and $R^5$ is alkyl which is unsubstituted or substituted with $R^7$, $OR^7$, $N(R^7)_2$, or OH.

In one embodiment of Formula (I), $R^7$ is $R^{10}$ or $R^{11}$ which are unsubstituted or substituted as defined herein. In another embodiment of Formula (I), $R^7$ is $R^{10}$ which is unsubstituted or substituted as defined herein. In another embodiment of Formula (I), $R^7$ is $R^{11}$ which is unsubstituted or substituted as defined herein.

In one embodiment of Formula (I), $R^{10}$ is cycloalkyl or heterocycloalkyl which are unsubstituted or substituted as defined herein. In another embodiment of Formula (I), $R^{10}$ is heterocycloalkyl which is unsubstituted or substituted as defined herein. In another embodiment of Formula (I), $R^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (I), $R^{10}$ is tetrahydropyranyl, which is unsubstituted or substituted as defined herein. In another embodiment of Formula (I), $R^{10}$ is morpholinyl, which is unsubstituted or substituted as defined herein. In another embodiment of Formula (I), $R^{10}$ is cycloalkyl which is unsubstituted or substituted as defined herein. In another embodiment of Formula (I), $R^{10}$ is cyclohexyl which is unsubstituted or substituted as defined herein.

In one embodiment of Formula (I), $R^{11}$ is alkyl which is unsubstituted. In another embodiment of Formula (I), $R^{11}$ is methyl, which is unsubstituted or substituted as defined herein. In another embodiment of Formula (I), $R^{11}$ is alkyl, which is substituted as defined herein. In another embodiment of Formula (I), $R^{11}$ is alkyl, which is substituted with $OR^{12}$, $R^{12}$ is $R^{16}$, and $R^{16}$ is alkyl.

Another embodiment of this invention pertains to compounds of Formula (I), wherein
  $A^1$ is N or $C(A^2)$;
  $A^2$ is H;
  $B^1$ is $OR^1$, $NHR^1$;
  $D^1$ is H;
  $E^1$ is H; and
  $Y^1$ is H, CN, $NO_2$, F, Cl, Br, $CF_3$, $R^{17}$, or $SO_2R^{17}$;
  $R^1$ is $R^4$ or $R^5$;
  $R^4$ is cycloalkyl, or heterocycloalkyl;
  $R^5$ is alkyl or alkynyl, each of which is unsubstituted or substituted with one or two or three of independently selected $R^7$, $OR^7$, $N(R^7)_2$, OH, F, Cl, Br or I;
  $R^7$ is $R^{10}$ or $R^{11}$;
  $R^{10}$ is cycloalkyl or heterocycloalkyl;
  $R^{11}$ is alkyl, each of which is unsubstituted or substituted with one or two or three of independently selected F, Cl, Br or I;
  $R^{17}$ is $R^{21}$;
  $R^{21}$ is alkyl, or alkynyl, each of which is unsubstituted or substituted with one or two or three of independently selected F, Cl, Br or I;
  $Z^1$ is $R^{26}$;
  $Z^2$ is $R^{30}$;
  $Z^{1A}$ and $Z^{2A}$ are both absent;
  $L^1$ is a $R^{37}$;
  $R^{26}$ is phenylene;
  $R^{30}$ is heterocycloalkylene;
  $R^{37}$ is $R^{37A}$;
  $R^{37A}$ is alkylene, alkenylene, or alkynylene, each of which is unsubstituted or substituted with one or two or three independently selected F, Cl, Br and I substituents;
  $Z^3$ is $R^{38}$, or $R^{40}$;
  $R^{38}$ is phenyl, which is unfused or fused with $R^{38A}$; $R^{38A}$ is heterocycloalkane;
  $R^{40}$ is cycloalkenyl, or heterocycloalkenyl;
  wherein the moieties represented by $R^{26}$ and $R^{27}$ are substituted (i.e., if $Z^{1A}$ and $Z^{2A}$ are absent) or further substituted (i.e., if $Z^{1A}$ and $Z^{2A}$ are present) with one or two or three or four of independently selected $R^{41}$, $OR^{41}$, or $NHR^{41}$;
  $R^{41}$ is $R^{42}$, $R^{43}$, or $R^{45}$;
  $R^{42}$ is phenyl, which is unfused or fused with heteroarene or $R^{42A}$; $R^{42A}$ is heterocycloalkane;
  $R^{43}$ is heteroaryl, which is unfused or fused with heteroarene;
  $R^{45}$ is alkyl, each of which is unsubstituted or substituted with one or two or three of independently selected $R^{46}$, F, Cl, Br or I;
  $R^{46}$ is $R^{47}$, or $R^{48}$;
  $R^{47}$ is phenyl;
  $R^{48}$ is heteroaryl;
  wherein the moieties represented by $R^{42}$, $R^{42A}$, $R^{43}$, $R^{43A}$, $R^{44}$, $R^{44A}$, $R^{47}$, $R^{47A}$, $R^{48}$, $R^{48A}$, $R^{49}$, and $R^{49A}$ are independently substituted with one or two or three or four of independently selected $R^{50}$, $OR^{50}$, $CO(O)R^{50}$, $NH_2$, $NHR^{50}$, $N(R^{50})_2$, $NHC(O)R^{50}$, $NHS(O)_2R^{50}$, $NHC(O)OR^{50}$, $C(O)NH_2$, $C(O)NHR^{50}$, $C(O)N(R^{50})_2$, OH, (O), CN, $NO_2$, $CF_3$, F, Cl, Br or I;
  $R^{50}$ is $R^{51}$, $R^{52}$, $R^{53}$ or $R^{54}$;
  $R^{51}$ is phenyl;
  $R^{52}$ is heteroaryl;
  $R^{53}$ is cycloalkyl or heterocycloalkyl;
  $R^{54}$ is alkyl, each of which is unsubstituted or substituted with one or two or three of independently selected $R^{55}$, $OR^{55}$, $C(O)R^{55}$, $NH_2$, $NHR^{55}$, $N(R^{55})_2$, $NR^{55}C(O)OR^{55}$, $C(O)N(R^{55})_2$, OH, F, Cl, Br or I;
  $R^{55}$ is alkyl, phenyl, or heterocycloalkyl; and
  wherein each foregoing cyclic moiety is independently unsubstituted, further unsubstituted, substituted or further substituted with one or two or three or four or five of independently selected $R^{57A}$, $R^{57}$, $OR^{57}$, $SO_2R^{57}$, $C(O)R^{57}$, $CO(O)R^{57}$, $NH_2$, $NHR^{57}$, $N(R^{57})_2$, OH, (O), CN, F, Cl, Br or I;
  $R^{57A}$ is spirocyclyl;
  $R^{57}$ is $R^{58}$, $R^{60}$ or $R^{61}$;
  $R^{58}$ is phenyl;
  $R^{60}$ is cycloalkyl, or heterocycloalkyl;
  $R^{61}$ is alkyl, or alkenyl, each of which is unsubstituted or substituted with one or two or three of independently selected $R^{62}$, $OR^{62}$, $N(R^{62})_2$, $C(O)N(R^{62})_2$, OH, F, Cl, Br or I;
  $R^{62}$ is $R^{63}$, $R^{64}$, $R^{65}$ or $R^{66}$;
  $R^{63}$ is phenyl;
  $R^{64}$ is heteroaryl;
  $R^{65}$ is cycloalkyl, or heterocycloalkyl;
  $R^{66}$ is alkyl, each of which is unsubstituted or substituted with one or two or three of independently selected $OR^{67}$, F, Cl, Br or I substituents;
  $R^{67}$ is alkyl;
  wherein the moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, F, Cl, Br or I;
  $R^{68}$ is $R^{71}$ or $R^{72}$;
  $R^{71}$ is heterocycloalkyl; and
  $R^{72}$ is alkyl which is unsubstituted or substituted with one or two or three of independently selected F, Cl, Br or I.

Still another embodiment pertains to compounds having Formula (I), which are 4-(4-((4'-chloro-1,1'-biphenyl-2-yl)methyl)piperazin-1-yl)-2-(3-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(methylamino)phenoxy)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(hydroxymethyl)phenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((1-methyl-1H-indol-4-yl)oxy)benzamide;

2-(3-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-(4-aminophenoxy)-4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)benzamide;

2-(3-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-methoxyphenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-dimethylamino)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-6-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-5-yl)oxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-methyl-1,3-benzothiazol-5-yl)oxy)benzamide;

4-(4-((4'-chloro-1,1'-biphenyl-2-yl)methyl)piperazin-1-yl)-2-(2-(3-(dimethylamino)-3-oxopropyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)-2-oxoethyl)phen oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(3-(dimethylamino)propyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)ethyl)phenoxy)-N-((3-nitro-4-((tetrahydro-2H-pyran-4-ylmethyl)amino)phenyl)sulfonyl)benzamide;

2-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)-N,N-dimethylbenzamide;

4-(4-((4'-chloro-1,1'-biphenyl-2-yl)methyl)piperazin-1-yl)-2-(2-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-morpholin-4-ylphenoxy)benzamide;

4-(4-((4'-chloro-1,1'-biphenyl-2-yl)methyl)piperazin-1-yl)-2-(3-(2,4-dimethyl-1,3-thiazol-5-yl)phenoxy)-N-((4-((3-morpholin-4-ylpropyl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(3,5-dichlorophenoxy)-N-((4-((1-methylpiperidin-4-yl)amino)-3-nitrophenyl)sulfonyl)benzamide;

2-(3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((4'-chloro-4-(2-(dimethylamino)ethoxy)-1,1'-biphenyl-2-yl)methyl)piperazin-1-yl)-2-(3-chlorophenoxy)-N-((4-((1-methylpiperidin-4-yl)amino)-3-nitrophenyl)sulfonyl)benzamide;

2-(2-chlorophenoxy)-4-(4-((4-(4-chlorophenyl)-6,6-dimethyl-5,6-dihydro-2H-pyran-3-yl)methyl)piperazin-1-yl)-N-((4-((1-methylpiperidin-4-yl)amino)-3-nitrophenyl)sulfonyl)benzamide;

4-(4-((4'-chloro-1,1'-biphenyl-2-yl)methyl)piperazin-1-yl)-2-(3-(2-(dimethylamino)ethoxy)phenoxy)-N-((3-nitro-4-((tetrahydro-2H-pyran-4-ylmethyl)amino)phenyl)sulfonyl)benzamide;

2-(4-amino-3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-isopropylpiperidin-4-yl)amino)-3-nitrophenyl)sulfonyl)benzamide;

2-(2-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)cyclohex-1-en-1-yl)methyl)piperazin-1-yl)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-(((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((1-methylpiperidin-4-yl)amino)-3-nitrophenyl)sulfonyl)benzamide;

2-(3-bromophenoxy)-4-(4-((2-(4-chlorophenyl)-4,4-dimethylcyclohex-1-en-1-yl)methyl)piperazin-1-yl)-N-((4-(((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-(((1-ethylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((3-nitro-4-((1,2,2,6,6-pentamethylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((3-nitro-4-((1-tetrahydro-2H-pyran-4-ylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-((7-fluoro-1H-indol-5-yl)oxy)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((3-morpholin-4-ylpropyl)amino)-3-nitrophenyl)sulfonyl)benzamide;

2-(4-amino-3-chlorophenoxy)-4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)benzamide;

2-(3-chlorophenoxy)-4-(4-((4'-chloro-4-(2-pyrrolidin-1-ylethyl)-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-2-(2,3-dichlorophenoxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-(((1-methylpiperidin-4-yl)amino)-3-nitrophenyl)sulfonyl)benzamide;

2-(2-chlorophenoxy)-4-(4-((2-(4-chlorophenyl)cyclohept-1-en-1-yl)methyl)piperazin-1-yl)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-(((1-methylpiperidin-4-yl)amino)-3-nitrophenyl)sulfonyl)-2-(3-(trifluoromethyl)phenoxy)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-oxo-1,2,3,4-tetrahydroquinolin-5-yl)oxy)benzamide;

2-(2-chlorophenoxy)-4-(4-((2-(4-chlorophenyl)-4,4-dimethylcyclohex-1-en-1-yl)methyl)piperazin-1-yl)-N-((4-(((1-methylpiperidin-4-yl)amino)-3-((trifluoromethyl)sulfonyl)phenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-(((1-methylpiperidin-4-yl)amino)-3-nitrophenyl)sulfonyl)benzamide;

2-(2-chloro-4-fluorophenoxy)-4-(4-((2-(4-chlorophenyl)-4,4-dimethylcyclohex-1-en-1-yl)methyl)piperazin-1-yl)-N-((4-(((1-methylpiperidin-4-yl)amino)-3-nitrophenyl)sulfonyl)benzamide;

2-(2-chlorophenoxy)-4-(4-((2-(4-chlorophenyl)-4,4-dimethylcyclopent-1-en-1-yl)methyl)piperazin-1-yl)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-(((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2-chloro-3-(trifluoromethyl)phenoxy)-N-((4-(((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-(((1-cyclopropylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-(((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-((1-methyl-1H-indol-4-yl)oxy)-N-((4-(((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-morpholin-4-ylphenoxy)-N-((4-(((3-morpholin-4-ylpropyl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((3-(3-morpholin-4-yl-3-oxopropyl)-1H-indol-5-yl)oxy)benzamide;

2-(3-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-morpholin-4-yl-3-oxopropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-morpholin-4-ylpropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(1H-imidazol-1-yl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((4-(((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

4-(4-((4'-chloro-1,1'-biphenyl-2-yl)methyl)piperazin-1-yl)-2-(4-((ethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-((ethylamino)methyl)phenoxy)-N-((3-nitro-4-((tetrahydro-2H-pyran-4-ylmethyl)amino)phenyl)sulfonyl)benzamide;

2-(4-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-2-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-3-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(2-(dimethylamino)ethyl)phenoxy)-N-((3-nitro-4-((tetrahydro-2H-pyran-4-ylmethyl)amino)phenyl)sulfonyl)benzamide;

2-(4-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-morpholin-4-ylphenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((2-methyl-1,3-benzothiazol-5-yl)oxy)-N-((3-nitro-4-((tetrahydro-2H-pyran-4-ylmethyl)amino)phenyl)sulfonyl)benzamide;

tert-butyl 4-(3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenyl)piperazine-1-carboxylate;

2-(3-(benzyloxy)phenoxy)-4-(4-((4'-chloro-1,1'-biphenyl-2-yl)methyl)piperazin-1-yl)-N-((4-((3-(dimethylamino)propyl)amino)-3-nitrophenyl)sulfonyl)benzamide;

2-(3-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-(2-morpholin-4-ylethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-((2-oxo-1,2,3,4-tetrahydroquinolin-5-yl)oxy)benzamide;

2-(4-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

tert-butyl 4-(4-(5-(4-((4'-chloro-1,1'-biphenyl-2-yl)methyl)piperazin-1-yl)-2-((((4-((3-morpholin-4-ylpropyl)amino)-3-nitrophenyl)sulfonyl)amino)carbonyl)phenoxy)phenyl)piperazine-1-carboxylate;

4-(4-((4'-chloro-1,1-biphenyl-2-yl)methyl)piperazin-1-yl)-N-((4-((3-morpholin-4-ylpropyl)amino)-3-nitrophenyl)sulfonyl)-2-(3-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-3-ylphenoxy)benzamide;

4-(4-((4'-chloro-1,1'-biphenyl-2-yl)methyl)piperazin-1-yl)-2-(4-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((1-methyl-1H-benzimidazol-5-yl)oxy)-N-((4-((3-morpholin-4-ylpropyl)amino)-3-nitrophenyl)sulfonyl)benzamide;

4-(4-((4'-chlorobiphenyl-2-yl)methyl)piperazin-1-yl)-2-(3-(methylcarbamoyl)phenoxy)-N-(4-(3-morpholinopropylamino)-3-nitrophenylsulfonyl)benzamide;

4-(4-((4'-chlorobiphenyl-2-yl)methyl)piperazin-1-yl)-N-(4-(3-(dimethylamino)propylamino)-3-nitrophenylsulfonyl)-2-(3-(methylcarbamoyl)phenoxy)benzamide;

4-(4-((4'-chloro-1,1'-biphenyl-2-yl)methyl)piperazin-1-yl)-2-(3-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-(dimethylamino)propyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-(hydroxymethyl)phenoxy)benzamide;

4-(4-((4'-chloro-1,1'-biphenyl-2-yl)methyl)piperazin-1-yl)-2-((4-methoxybenzyl)oxy)-N-((3-nitro-4-((tetrahydro-2H-pyran-4-ylmethyl)amino)phenyl)sulfonyl)benzamide;

N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide;

4-(4-(1-(4'-chlorobiphenyl-2-yl)ethyl)piperazin-1-yl)-2-(2-chlorophenoxy)-N-(3-nitro-4-((tetrahydro-2H-pyran-4-yl)methylamino)phenylsulfonyl)benzamide;

N-{[4-{4-[(4'-chloro-1,1'-biphenyl-2-yl)methyl]piperazin-1-yl}-2-(3,5-dichlorophenoxy)phenyl]sulfonyl}-4-[(1-methylpiperidin-4-yl)amino]-3-nitrobenzamide;

4-(4-{[2-(4-chlorophenyl)-4,4-dimethylcyclohex-1-en-1-yl]methyl}piperazin-1-yl)-2-(3-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(4-fluorophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(3-fluorophenoxy)benzamide;

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl)}piperazin-1-yl)-N-({4-[(1-cyclopentylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-({4-[(2-morpholin-4-ylethyl)amino]-3-nitrophenyl}sulfonyl)benzamide;

4-(4-{[2-(4-chlorophenyl)-4,4-dimethylcyclohex-1-en-1-yl]methyl}-4-piperazin-1-yl)-2-(2,3-difluorophenoxy)-N-[(3-nitro-4-{[1-(thien-3-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(2-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(3-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(4-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[1-(2-fluoroethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}) piperazin-1-yl)-N-[(4-{[3-(4-methylpiperazin-1-yl)propyl]amino}-3-nitrophenyl)sulfonyl]benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(1-methylpiperidin-4-yl)amino]-3-nitrophenyl}sulfonyl)benzamide;

N-({4-[(1-allylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(2,3-difluorophenoxy)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(4-fluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[3-(methoxymethoxy)-2-methylphenoxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-hydroxy-2-methylphenoxy)-N-({4-[(1-methylpiperidin-4-yl)amino]-3-nitrophenyl}sulfonyl)benzamide;

2-(3-bromophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(3-iodophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(2-phenylethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(3,4-dichlorophenoxy)-N-({4-[(1-methylpiperidin-4-yl)amino]-3-nitrophenyl}sulfonyl)benzamide;

2-(2-chloro-3,5-difluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[3-(hydroxymethyl)phenoxy]-N-({4-[(1-methylpiperidin-4-yl)amino]-3-nitrophenyl}sulfonyl)benzamide;

2-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-{[4-({1-[2-(2-methoxyethoxy)ethyl]piperidin-4-yl}amino)-3-nitrophenyl]sulfonyl}benzamide;

2-(2-chloro-3-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(3-phenylpropyl)piperidin-4-yl]amino}phenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-methoxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(1-ethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-hydroxyphenoxy)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-methylphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methylphenoxy)-N-({4-[(1-methylpiperidin-4-yl)amino]-3-nitrophenyl}sulfonyl)benzamide;

2-(2-chlorophenoxy)-4-(4-{[6-(4-chlorophenyl)-1,3-benzodioxol-5-yl]methyl}piperazin-1-yl)-N-({4-[(1-methylpiperidin-4-yl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(4-methylpiperazin-1-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl-4-piperazin-1-yl)-N-[(4-{[1-(cyclopropylmethyl)piperidin-4-yl]amino}-3-nitrophenyl)sulfonyl]benzamide;

2-(2-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-{4-({1-[2-(dimethylamino)-2-oxoethyl]piperidin-4-yl}amino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-morpholin-4-ylethyl)piperidin-4-yl]amino}-3-nitrophenyl)sulfonyl]benzamide;

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3S)-1-methylpyrrolidin-3-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3R)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[3-(1H-pyrrol-2-yl)phenoxy]benzamide;

4-(4-{[2-(4-chlorophenyl)-4,4-dimethylcyclohex-1-en-1-yl]methyl}piperazin-1-yl)-2-(3-fluorophenoxy)-N-[(4-{[(4-hydroxy-1-methylpiperidin-4-yl)methyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(1-tetrahydro-2H-pyran-4-ylpiperidin-4-yl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)-1H-indole-1-carboxylate;

2-(3-chlorophenoxy)-4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]benzamide;

2-(3-chlorophenoxy)-4-(4-({[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]benzamide;

Trans-2-(3-chlorophenoxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

4-{4-[1-(4'-chloro-1,1'-biphenyl-2-yl)ethyl]piperazin-1-yl}-2-(2-chlorophenoxy)-N-({4-[(1-methylpiperidin-4-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({3-nitro-4-[(1-tetrahydro-2H-pyran-4-ylpiperidin-4-yl)amino]phenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-[(trifluoromethyl)sulfonyl]phenyl}sulfonyl)benzamide;

2-({1,3-bis[(4-methylpiperazin-1-yl)methyl]-1H-indol-4-yl}oxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-({3-[(4-methylpiperazin-1-yl)methyl]-1H-indol-4-yl}oxy)benzamide;

2-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)-N,N-dimethylbenzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[2-(trifluoromethyl)-1H-indol-4-yl]oxy}benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-{[6-(trifluoromethyl)-1H-indol-5-yl]oxy}benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[6-(trifluoromethyl)-1H-indol-5-yl]oxy}benzamide;

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide;

tert-butyl 4-[(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)methyl]-1,3-thiazol-2-ylcarbamate;

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(2-chlorophenyl)amino]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-methoxy-1H-indol-5-yl)oxy]-N-({3-nitro-4-[(1-tetrahydro-2H-pyran-4-ylpiperidin-4-yl)amino]phenyl}sulfonyl)benzamide;

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[(2-chlorophenyl)amino]-4-(4-{[2-(4-chlorophenyl)-4,4-dimethylcyclohex-1-en-1-yl]methyl}piperazin-1-yl)-N-({4-[(1-methylpiperidin-4-yl)amino]-3-r nitrophenyl}sulfonyl)benzamide;

tert-butyl 5-[5-(4-{[2-(4-chlorophenyl)-4,4-dimethylcyclohex-1-en-1-yl]methyl}piperazin-1-yl)-2-({[(4-{[3-(dimethylamino)propyl]amino}-3-nitrophenyl)sulfonyl]amino}carbonyl)phenoxy]-1H-indole-1-carboxylate;

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[3-(3-oxopiperazin-1-yl)propyl]amino}phenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide;

Trans-4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6,7-difluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-hydroxy-1-tetrahydro-2H-pyran-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-({[4-(hydroxymethyl)tetrahydro-2H-pyran-4-yl]methyl}amino)-3-nitrophenyl]sulfonyl}benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[1-(1,3-thiazol-4-ylmethyl)piperidin-4-yl]amino}phenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(4-amino-3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(3S,4R)-3-hydroxy-1-(1,3-thiazol-4-ylmethyl)piperidin-4-yl]amino}-3-nitrophenyl)sulfonyl]benzamide;

2-(2-chlorophenoxy)-4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylamino)phenyl]sulfonyl}benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-(morpholin-4-ylamino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}benzamide;

2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide;

2-(6-aminopyridin-3-yl)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{1-[2-(4-chlorophenyl)-4,4-dimethylcyclohex-1-en-1-yl]ethyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-[(3-nitro-4-{[3-(3-oxopiperazin-1-yl)propyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-tetrahydro-2H-pyran-3-ylmethyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3R)-tetrahydro-2H-pyran-3-ylmethyl]amino}phenyl)sulfonyl]benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-3,4-dihydroisoquinoline-2(1H)-carboxylate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

4-(4-{[2-(4-chlorophenyl)-5,5-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-methoxyethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylmethoxy)phenyl]sulfonyl}benzamide;

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-5-yl)oxy]benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(2-methoxyethyl)amino]-3-nitrophenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-{[2-(4-chlorophenyl)-4,4-dimethylcyclohex-1-en-1-yl]methyl}piperazin-1-yl)-2-{[({3-nitro-4-[(1-tetrahydro-2H-pyran-4-ylpiperidin-4-yl)amino]phenyl}sulfonyl)amino]carbonyl}phenoxy)pyridin-2-ylcarbamate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-ylcarbamate;

2-[(5-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-hydroxypyridin-3-yl)oxy]-N-({3-nitro-4-[(tetrahydro-2H-pyran-4-ylmethyl)amino]phenyl}sulfonyl)benzamide;

2-{[6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-[(6-fluoro-1H-indol-5-yl)oxy]benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-[(2-oxo-2,3-dihydro-1H-indol-4-yl)oxy]benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-[(6-fluoro-1H-indol-5-yl)oxy]benzamide;

Trans-2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

Trans-2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

2-[(6-amino-5-fluoropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(1-oxo-1,2,3,4-tetrahydroisoquinolin-5-yl)oxy]benzamide:

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-[(6-fluoro-1H-indol-5-yl)oxy]benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-N-({5-bromo-6-[(4-morpholin-4-ylcyclohexyl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-[(6-fluoro-1H-indol-5-yl)oxy]benzamide;

2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)oxy]-3-nitrophenyl}sulfonyl)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-[(2-oxo-2,3-dihydro-1H-indol-4-yl)oxy]benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-[(trifluoromethyl)sulfonyl]phenyl}sulfonyl)benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylbut-2-ynyl)oxy]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-(4-{[1-(methylsulfonyl)piperidin-4-yl]amino}-3-nitrophenyl)sulfonyl]benzamide;

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-[(2-oxo-2,3-dihydro-1H-indol-4-yl)oxy]benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide;

4-(4-{[4-(4-chlorophenyl)-6,6-dimethyl-5,6-dihydro-2H-pyran-3-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-[(6-fluoro-1H-indol-5-yl)oxy]benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-1-tetrahydro-2H-pyran-4-ylpiperidin-3-yl]amino}phenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydrofuran-3-ylmethyl)amino]phenyl}sulfonyl)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(tetrahydro-2H-pyran-4-ylamino)cyclohexyl]amino}phenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(4-tetrahydro-2H-pyran-4-ylpiperazin-1-yl)cyclohexyl]amino}phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-fluorotetrahydro-2H-pyran-4-yl)methyl]amino}-3-nitrophenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-hydroxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-{[1-(4-methoxybenzyl)-1H-1,2,3-benzotriazol-4-yl]oxy}-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(3-morpholin-4-ylpropyl)amino]-3-[(trifluoromethyl)sulfonyl]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}) sulfonyl)amino]carbonyl}phenoxy)nicotinamide;

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-[(6-fluoro-1H-indol-5-yl)oxy]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)benzamide;

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

Trans-2-[(6-amino-5-bromopyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[(3-methyl-2-oxo-2,3-dihydro-1H-benzimidazol-4-yl)oxy]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({4-fluoro-1-[2-fluoro-1-(fluoromethyl)ethyl]piperidin-4-yl}methoxy)-3-nitrophenyl]sulfonyl}benzamide;

tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino)phenylsulfonylcarbamoyl)phenoxy)pyridine-2,6-diyldicarbamate;

4-(4-{[2-(4-chlorophenyl)-4,4-dimethylcyclohex-1-en-1-yl]methyl}piperazin-1-yl)-2-{6-(cyclopropylamino)pyridin-3-yl]oxy}-N-(({3-nitro-4-[(tetrahydro-2H-pyran-4-ylmethyl)amino]phenyl}sulfonyl)benzamide;

Trans-4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-({3-nitro-4-[(tetrahydro-2H-pyran-4-ylmethyl)amino]phenyl}sulfonyl)benzamide;

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[({4-[2-fluoro-1-(fluoromethyl)ethyl]morpholin-2-yl}methyl)amino]-3-nitrophenyl}sulfonyl)benzamide;

2-[(2-amino-6-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(2,6-diaminopyridin-4-yl)oxy]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{3-nitro-4-(tetrahydro-2H-pyran-4-ylmethoxy)phenyl]sulfonyl}benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]piperidin-3-yl}amino)-3-nitrophenyl]sulfonyl}benzamide;

tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

4-(4-{[2-(4-chlorophenyl)-4,4-dimethylcyclohex-1-en-1-yl]methyl}piperazin-1-yl)-2-[(4-chloro-1H-pyrrolo[2,3-b]pyridin-5-yl)oxy]-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide;

2-[(6-amino-5-chloropyridin-3-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)benzamide;

2-[(6-amino-5-chloropyridin-3-yl)oxy]-4-[4-({9-(4-chlorophenyl)-3-[2-fluoro-1-(fluoromethyl)ethyl]-3-azaspiro[5.5]undec-8-en-8-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}benzamide;

2-[(2-amino-5-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

2-[(6-amino-5-chloropyridin-3-yl)oxy]-4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-N-{5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide;

2-[(6-amino-5-chloropyridin-3-yl)oxy]-N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide;

2-[2-(2-aminopyridin-3-yl)phenoxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-(({3-nitro-4-[(tetrahydro-2H-pyran-4-ylmethyl)amino]phenyl}sulfonyl)-2-[2-(1H-pyrazol-5-yl)phenoxy]benzamide;

2-[(6-amino-5-chloropyridin-3-yl)oxy]-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

N-({5-chloro-6-[(4,4-difluorocyclohexyl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-[(6-fluoro-1H-indol-5-yl)oxy]benzamide;

and therapeutically acceptable salts, prodrugs, salts of prodrugs and metabolites thereof.

Still another embodiment pertains to 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; and therapeutically acceptable salts, prodrugs, salts of prodrugs and metabolites thereof.

Still another embodiment pertains to [3-chloro-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-2-iminopyridin-1(2H)-yl]methyl dihydrogen phosphate; and therapeutically acceptable salts, and metabolites thereof.

In another aspect, the present invention provides compounds of Formula (II)

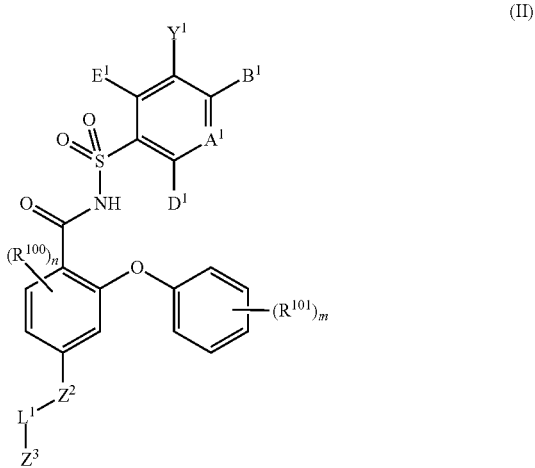

(II)

and therapeutically acceptable salts, prodrugs, salts of prodrugs and metabolites thereof, wherein $A^1$, $B^1$, $D^1$, $E^1$, $Y^1$, $Z^2$, $L^1$, and $Z^3$ are as described herein for Formula (I), n is 0, 1, 2, or 3; describing the number of additional substituents on $R^{26}$, and $R^{100}$ is as described for substituents on $R^{26}$, m is 1, 2, 3, 4, or 5; describing the number of substituents on $R^{42}$, and $R^{101}$ is as described for substituents on $R^{42}$.

In one embodiment of Formula (II), $A^1$ is N. In another embodiment of Formula (II), $A^1$ is $C(A^2)$. In another embodiment of Formula (II), $A^1$ is $C(A^2)$; and $A^2$ is H.

In one embodiment of Formula (II), $B^1$ is $OR^1$, or $NHR^1$. In another embodiment of Formula (II), $A^1$ is $C(A^2)$; $A^2$ is H; and $B^1$ is $NHR^1$. In another embodiment of Formula (II), $A^1$ is $C(A^2)$; $A^2$ is H; and $B^1$ is $OR^1$.

In one embodiment of Formula (II), $D^1$ is H. In another embodiment of Formula (II), $A^1$ is $C(A^2)$; $A^2$ is H; $B^1$ is $NHR^1$; and $D^1$ is H. In another embodiment of Formula (II), $A^1$ is $C(A^2)$; $A^2$ is H; $B^1$ is $OR^1$; and $D^1$ is H.

In one embodiment of Formula (II), $E^1$ is H. In another embodiment of Formula (II), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (II), $Y^1$ is H, CN, $NO_2$, F, Cl, Br, $CF_3$, $R^{17}$, or $SO_2R^{17}$. In another embodiment of Formula (II), $Y^1$ is $NO_2$. In another embodiment of Formula (II), $Y^1$ is Cl. In another embodiment of Formula (II), $Y^1$ is $SO_2R^{17}$; wherein $R^{17}$ is as defined herein. In another embodiment of Formula (II), $Y^1$ is $SO_2R^{17}$; wherein $R^{17}$ is alkyl. In another embodiment of Formula (II), $Y^1$ is $R^{17}$; wherein $R^{17}$ is alkynyl. In another embodiment of Formula (II), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (II), $A^1$ is $C(A^2)$; $A^2$ is H; $B^1$ is $NHR^1$; $D^1$ is H; $E^1$ is H; and $Y^1$ is $NO_2$. In another embodiment of Formula (II), $A^1$ is $C(A^2)$; $A^2$ is H; $B^1$ is $NHR^1$; $D^1$ is H; $E^1$ is H; and $Y^1$ is $SO_2R^{17}$, wherein $R^{17}$ is alkyl substituted with three F. In another embodiment of Formula (II), $A^1$ is $C(A^2)$; $A^2$ is H; $B^1$ is $OR^1$; $D^1$ is H; $E^1$ is H; and $Y^1$ is Cl.

In one embodiment of Formula (II), $R^1$ is $R^4$ or $R^5$. In one embodiment of Formula (II), $R^1$ is $R^4$. In one embodiment of Formula (II), $R^1$ is $R^5$. In one embodiment of Formula (II), $R^1$ is $R^4$; and $R^4$ is cycloalkyl, or heterocycloalkyl. In one embodiment of Formula (II), $R^1$ is $R^4$; and $R^4$ is cycloalkyl. In one embodiment of Formula (II), $R^1$ is $R^4$; and $R^4$ is heterocycloalkyl.

In one embodiment of Formula (II), $R^1$ is $R^4$; and $R^4$ is cycloalkyl; wherein $R^4$ is unsubstituted or substituted as defined herein. In another embodiment of Formula (II), $R^1$ is $R^4$; and $R^4$ is cycloalkyl; wherein the cycloalkyl ring is substituted as defined herein. In another embodiment of Formula (II), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (II), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (II), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (II), $R^1$ is $R^4$; and $R^4$ is cycloalkyl; wherein the cycloalkyl ring is substituted with $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (II), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{61}$ is alkyl which is unsubstituted. In another embodiment of Formula (II), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{61}$ is cycloalkyl which is unsubstituted. In another embodiment of Formula (II), $R^1$ is $R^4$; and $R^4$ is cycloalkyl; wherein the cycloalkyl ring is substituted with $NHR^{57}$. In another embodiment of Formula (II), $R^1$ is $R^4$; and $R^4$ is cycloalkyl; wherein the cycloalkyl ring is cyclohexyl; and wherein the cyclohexyl ring is substituted with $NHR^{57}$. In another embodiment of Formula (II), $R^1$ is $R^4$; and $R^4$ is cycloalkyl; wherein the cycloalkyl ring is cyclohexyl; and wherein the cyclohexyl ring is substituted with $NHR^{57}$, $R^{57}$ is $R^{60}$, and $R^{60}$ is heterocycloalkyl which is unsubstituted.

In one embodiment of Formula (II), $R^1$ is $R^4$; and $R^4$ is heterocycloalkyl; wherein $R^4$ is unsubstituted or substituted as defined herein. In another embodiment of Formula (II), $R^1$ is $R^4$; and $R^4$ is heterocycloalkyl; wherein the heterocycloalkyl ring is substituted as defined herein. In another embodiment of Formula (II), $R^1$ is $R^4$; and $R^4$ is heterocycloalkyl; wherein the heterocycloalkyl ring is substituted with $R^{57}$. In another embodiment of Formula (II), $R^1$ is $R^4$; and $R^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more $R^{57}$; $SO_2R^{57}$, or OH, and $R^{57}$ is $R^{60}$ or $R^{61}$. In another embodiment of Formula (II), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is cycloalkyl or heterocycloalkyl; and $R^{61}$ is alkyl. In another embodiment of Formula (II), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is heterocycloalkyl, wherein the heterocycloalkyl is tetrahydropyranyl or oxetanyl. In another embodiment of Formula (II), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is cycloalkyl, wherein the cycloalkyl is cyclopropyl or cyclopentyl. In another embodiment of Formula (II), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl. In another embodiment of Formula (II), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl; wherein the $C_1$-alkyl, $C_2$-alkyl, or $C_3$-alkyl are unsubstituted or substituted.

In one embodiment of Formula (II), $R^1$ is $R^5$; and $R^5$ is alkyl which is unsubstituted or substituted. In one embodiment of Formula (II), $R^1$ is $R^5$; and $R^5$ is alkyl which is unsubstituted or substituted with $R^7$, $OR^7$, $N(R^7)_2$, or OH.

In one embodiment of Formula (I), $R^7$ is $R^{10}$ or $R^{11}$ which are unsubstituted or substituted as defined herein. In another embodiment of Formula (II), $R^7$ is $R^{10}$ which is unsubstituted or substituted as defined herein. In another embodiment of Formula (II), $R^7$ is $R^{11}$ which is unsubstituted or substituted as defined herein.

In one embodiment of Formula (II), $R^{10}$ is cycloalkyl or heterocycloalkyl which are unsubstituted or substituted as defined herein. In another embodiment of Formula (II), $R^{10}$ is heterocycloalkyl which is unsubstituted or substituted as defined herein. In another embodiment of Formula (II), $R^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (II), $R^{10}$ is tetrahydropyranyl, which is unsubstituted or substituted as defined herein. In another embodiment of Formula (II), $R^{10}$ is morpholinyl, which is unsubstituted or substituted as defined herein. In another embodiment of Formula (II), $R^{10}$ is cycloalkyl which is unsubstituted or substituted as defined herein. In another embodiment of Formula (II), $R^{10}$ is cyclohexyl which is unsubstituted or substituted as defined herein.

In one embodiment of Formula (II), $R^{11}$ is alkyl which is unsubstituted. In another embodiment of Formula (II), $R^{11}$ is methyl, which is unsubstituted or substituted as defined herein. In another embodiment of Formula (II), $R^{11}$ is alkyl, which is substituted as defined herein. In another embodiment of Formula (II), $R^{11}$ is alkyl, which is substituted with $OR^{12}$, $R^{12}$ is $R^{16}$, and $R^{16}$ is alkyl.

Still another embodiment pertains to compounds having Formula (II), which are 4-(4-((4'-chloro-1,1'-biphenyl-2-yl)methyl)piperazin-1-yl)-2-(3-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(methylamino)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-chlorophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(hydroxymethyl)phenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(2-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-chlorophenoxy)-N-((4-((3-(dimethylamino)propyl)amino)-3-nitrophenyl)sulfonyl)benzamide;

4-(4-((4'-chloro-1,1'-biphenyl-2-yl)methyl)piperazin-1-yl)-2-(4-chlorophenoxy)-N-((4-((3-(dimethylamino)propyl)amino)-3-nitrophenyl)sulfonyl)benzamide;

2-(3-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-(4-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

2-(3-aminophenoxy)-4-(4-((4'-chloro-1,1-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-methoxyphenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-(dimethylamino)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(3-(dimethylamino)-3-oxopropyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)-2-oxoethyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(3-(dimethylamino)propyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(2-(2-(dimethylamino)ethyl)phenoxy)-N-((3-nitro-4-((tetrahydro-2H-pyran-4-ylmethyl)amino)phenyl)sulfonyl)benzamide;

2-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)-N,N-dimethylbenzamide;

4-(4-((4'-chloro-1,1'-biphenyl-2-yl)methyl)piperazin-1-yl)-2-(2-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-morpholin-4-ylphenoxy)benzamide;

4-(4-((4'-chloro-1,1'-biphenyl-2-yl)methyl)piperazin-1-yl)-2-(3-(2,4-dimethyl-1,3-thiazol-5-yl)phenoxy)-N-((4-((3-morpholin-4-ylpropyl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(3,5-dichlorophenoxy)-N-((4-((1-methylpiperidin-4-yl)amino)-3-nitrophenyl)sulfonyl)benzamide;

2-(3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

4-(4-((4'-chloro-4-(2-(dimethylamino)ethoxy)-1,1'-biphenyl-2-yl)methyl)piperazin-1-yl)-2-(3-chlorophenoxy)-N-((4-((1-methylpiperidin-4-yl)amino)-3-nitrophenyl)sulfonyl)benzamide;

2-(2-chlorophenoxy)-4-(4-((4-(4-chlorophenyl)-6,6-dimethyl-5,6-dihydro-2H-pyran-3-yl)methyl)piperazin-1-yl)-N-((4-((1-methylpiperidin-4-yl)amino)-3-nitrophenyl)sulfonyl)benzamide;

4-(4-((4'-chloro-1,1'-biphenyl-2-yl)methyl)piperazin-1-yl)-2-(3-(2-(dimethylamino)ethoxy)phenoxy)-N-((3-nitro-4-((tetrahydro-2H-pyran-4-ylmethyl)amino)phenyl)sulfonyl)benzamide;

2-(2-amino-3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-isopropylpiperidin-4-yl)amino)-3-nitrophenyl)sulfonyl)benzamide;

2-(2-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)cyclohex-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((1-methylpiperidin-4-yl)amino)-3-nitrophenyl)sulfonyl)benzamide;

2-(3-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-ethylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((3-nitro-4-((1,2,2,6,6-pentamethylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((3-nitro-4-((1-tetrahydro-2H-pyran-4-ylpiperidin-4-yl)amino)phenyl)sulfonyl)benzamide;

4-(4-((2-(4-chlorophenyl)-4,4-dimethylcyclohex-1-en-1-yl)methyl)piperazin-1-yl)-2-(2,3-difluorophenoxy)-N-((4-((3-morpholin-4-ylpropyl)amino)-3-nitrophenyl)sulfonyl)benzamide;

2-(4-amino-3-chlorophenoxy)-4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)benzamide;

2-(3-chlorophenoxy)-4-(4-((4'-chloro-4-(2-pyrrolidin-1-ylethyl)-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((2-(4-chlorophenyl)-4,4-dimethylcyclohex-1-en-1-yl)methyl)piperazin-1-yl)-2-(2,3-dichlorophenoxy)-N-((4-((1-methylpiperidin-4-yl)amino)-3-nitrophenyl)sulfonyl)benzamide;

2-(2-chlorophenoxy)-4-(4-((2-(4-chlorophenyl)cyclohept-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-(3-(trifluoromethyl)phenoxy)benzamide;

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-((trifluoromethyl)sulfonyl)phenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-((1-methylpiperidin-4-yl)amino)-3-nitrophenyl)sulfonyl)benzamide;

2-(2-chloro-4-fluorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclopent-1-en-1-yl)methyl)piperazin-1-yl)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2-chloro-3-(trifluoromethyl)phenoxy)-N-((4-((1-methylpiperidin-4-yl)amino)-3-nitrophenyl)sulfonyl)benzamide;

2-(2-chlorophenoxy)-4-(4-((2-(4-chlorophenyl)-4,4-dimethylcyclohex-1-en-1-yl)methyl)piperazin-1-yl)-N-((4-((1-cyclopropylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-(2,5-dichlorophenoxy)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(3-morpholin-4-ylphenoxy)-N-((4-((3-morpholin-4-ylpropyl)amino)-3-nitrophenyl)sulfonyl)benzamide;

2-(3-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-cyanophenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-((dimethylamino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(1H-imidazol-1-yl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-nitrophenoxy)-N-((4-((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate;

4-(4-((4'-chloro-1,1'-biphenyl-2-yl)methyl)piperazin-1-yl)-2-(4-((ethyl amino)methyl)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-((ethylamino)methyl)phenoxy)-N-((3-nitro-4-((tetrahydro-2H-pyran-4-ylmethyl)amino)phenyl)sulfonyl)benzamide;

2-(4-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-2-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate;

2-(1,1'-biphenyl-3-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(4-(2-(dimethylamino)ethyl)phenoxy)-N-((3-nitro-4-((tetrahydro-2H-pyran-4-ylmethyl)amino)phenyl)sulfonyl)benzamide;

2-(4-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-(3-morpholin-4-ylphenoxy)-N-((3-nitro-4-((tetrahydro-2H-pyran-4-ylmethyl)amino)phenyl)sulfonyl)benzamide;

tert-butyl 4-(3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenyl)piperazine-1-carboxylate;

2-(3-(benzyloxy)phenoxy)-4-(4-((4'-chloro-1,1'-biphenyl-2-yl)methyl)piperazin-1-yl)-N-((4-((3-(dimethylamino)propyl)amino)-3-nitrophenyl)sulfonyl)benzamide;

2-(3-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

4-(4-((4'-chloro-1,1'-biphenyl-2-yl)methyl)piperazin-1-yl)-2-(4-(2-morpholin-4-ylethoxy)phenoxy)-N-((3-nitro-4-((tetrahydro-2H-pyran-4-ylmethyl)amino)phenyl)sulfonyl)benzamide;

2-(4-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide;

tert-butyl 4-(4-(5-(4-((4'-chloro-1,1-biphenyl-2-yl)methyl)piperazin-1-yl)-2-((((4-((3-morpholin-4-ylpropyl)amino)-3-nitrophenyl)sulfonyl)amino)carbonyl)phenoxy)phenyl)piperazine-1-carboxylate;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(3-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-4-ylphenoxy)benzamide;

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-3-ylphenoxy)benzamide;

4-(4-((4'-chloro-1,1'-biphenyl-2-yl)methyl)piperazin-1-yl)-2-(4-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chlorobiphenyl-2-yl)methyl)piperazin-1-yl)-2-(3-(methylcarbamoyl)phenoxy)-N-(4-(3-morpholinopropylamino)-3-nitrophenylsulfonyl)benzamide;

4-(4-((4'-chlorobiphenyl-2-yl)methyl)piperazin-1-yl)-N-(4-(3-(dimethylamino)propylamino)-3-nitrophenylsulfonyl)-2-(3-(methylcarbamoyl)phenoxy)benzamide;

4-(4-((4'-chloro-1,1'-biphenyl-2-yl)methyl)piperazin-1-yl)-2-(3-(2-(dimethylamino)-2-oxoethoxy)phenoxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-(hydroxymethyl)phenoxy)benzamide;

N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide;

4-(4-(1-(4'-chlorobiphenyl-2-yl)ethyl)piperazin-1-yl)-2-(2-chlorophenoxy)-N-(3-nitro-4-((tetrahydro-2H-pyran-4-yl)methylamino)phenylsulfonyl)benzamide;

N-{[4-{4-[(4'-chloro-1,1'-biphenyl-2-yl}methyl]piperazin-1-yl)-2-(3,5-dichlorophenoxy)phenyl]sulfonyl}-4-[(1-methylpiperidin-4-yl)amino]-3-nitrobenzamide;

4-(4-{[2-(4-chlorophenyl)-4,4-dimethylcyclohex-1-en-1-yl]methyl}piperazin-1-yl)-2-(3-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(4-fluorophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2-fluorophenoxy)-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(3-fluorophenoxy)benzamide;

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2,3-difluorophenoxy)benzamide;

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-({4-[(2-morpholin-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2,3-difluorophenoxy)-N-[(3-nitro-4-{[1-(thien-3-ylmethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(2-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(3-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(4-fluorophenoxy)benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[1-(2-fluoroethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[3-(4-methylpiperazin-1-yl)propyl]amino}-3-nitrophenyl)sulfonyl]benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(1-methylpiperidin-4-yl)amino]-3-nitrophenyl}sulfonyl)benzamide;

N-({4-[(1-allylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(2,3-difluorophenoxy)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-6-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-[3-(methoxymethoxy)-2-methylphenoxy]-N-({4-[(1-methylpiperidin-4-yl)amino]-3-nitrophenyl)}sulfonyl)benzamide;

4-(4-{[2-(4-chlorophenyl)-4,4-dimethylcyclohex-1-en-1-yl]methyl}piperazin-1-yl)-2-(3-hydroxy-2-methylphenoxy)-N-({4-[(1-methylpiperidin-4-yl)amino]-3-nitrophenyl}sulfonyl)benzamide;

2-(3-bromophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(3-iodophenoxy)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(2-phenylethyl)piperidin-4-yl]amino}phenyl)sulfonyl]benzamide;

4-(4-{[2-(4-chlorophenyl)-4,4-dimethylcyclohex-1-en-1-yl]methyl}piperazin-1-yl)-2-(3,4-dichlorophenoxy)-N-({4-[(1-methylpiperidin-4-yl)amino]-3-nitrophenyl}sulfonyl)benzamide;

2-(2-chloro-3,5-difluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[3-(hydroxymethyl)phenoxy]-N-({4-[(1-methylpiperidin-4-yl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-({[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-{[4-({1-[2-(2-methoxyethoxy)ethyl]piperidin-4-yl}amino)-3-nitrophenyl]sulfonyl}benzamide;

2-(2-chloro-3-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(3-phenylpropyl)piperidin-4-yl]amino}phenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-methoxyethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(1-ethylpiperidin-4-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-hydroxyphenoxy)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-3-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2-methoxyphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-methylphenoxy)-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-methylphenoxy)-N-({4-[(1-methylpiperidin-4-yl)amino]-3-nitrophenyl}sulfonyl)benzamide;

2-(2-chlorophenoxy)-4-(4-{[6-(4-chlorophenyl)-1,3-benzodioxol-5-yl]methyl}piperazin-1-yl)-N-({4-[(1-methylpiperidin-4-yl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(4-methylpiperazin-1-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide;

2-(2-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-{[4-({1-[2-(dimethylamino)-2-oxoethyl]piperidin-4-yl}amino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-[(4-{[1-(2-morpholin-4-ylethyl)piperidin-4-yl]amino}-3-nitrophenyl)sulfonyl]benzamide;

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3S)-1-methylpyrrolidin-3-yl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[(3R)-1-methylpyrrolidin-3-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[3-(1H-pyrrol-2-yl)phenoxy]benzamide;

4-(4-{[2-(4-chlorophenyl)-4,4-dimethylcyclohex-1-en-1-yl]methyl}piperazin-1-yl)-2-(3-fluorophenoxy)-N-[(4-{[(4-hydroxy-1-methylpiperidin-4-yl)methyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]benzamide;

Trans-2-(3-chlorophenoxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

4-{4-[1-(4'-chloro-1,1'-biphenyl-2-yl)ethyl]piperazin-1-yl}-2-(2-chlorophenoxy)-N-({4-[(1-methylpiperidin-4-yl)amino]-3-nitrophenyl})sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-[(trifluoromethyl)sulfonyl]phenyl}sulfonyl)benzamide;

2-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)-N,N-dimethylbenzamide;

2-(2-chloro-4-hydroxyphenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide;

2-[3-(acetylamino)phenoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-yl)piperidin-4-yl)amino]phenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(4-amino-3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide;

2-(3-chlorophenoxy)-4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}benzamide;

2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide;

2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide;

2-[2-(2-aminopyridin-3-yl)phenoxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-5-yl)phenoxy]benzamide;

and therapeutically acceptable salts, prodrugs, salts of prodrugs and metabolites thereof.

In another aspect, the present invention provides compounds of Formula (III)

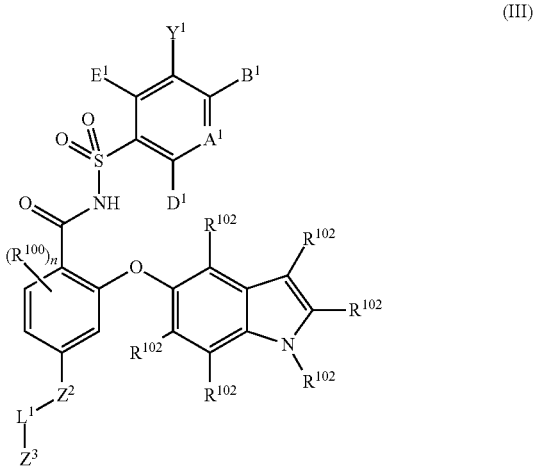

and therapeutically acceptable salts, prodrugs, salts of prodrugs and metabolites thereof, wherein $A^1$, $B^1$, $D^1$, $E^1$, $Y^1$, $Z^2$, $L^1$, and $Z^3$ are as described herein for Formula (I), n is 0, 1, 2, or 3; describing the number of additional substituents on $R^{26}$, and $R^{100}$ is as described for substituents on $R^{26}$, and at least one $R^{102}$ is a substituent as described for substituents on $R^{42}$ and $R^{42A}$, and the remainder are H.

In one embodiment of Formula (III), $A^1$ is N. In another embodiment of Formula (III), $A^1$ is $C(A^2)$. In another embodiment of Formula (III), $A^1$ is $C(A^2)$; and $A^2$ is H.

In one embodiment of Formula (III), $B^1$ is $OR^1$, or $NHR^1$. In another embodiment of Formula (III), $A^1$ is $C(A^2)$; $A^2$ is H; and $B^1$ is $NHR^1$. In another embodiment of Formula (III), $A^1$ is $C(A^2)$; $A^2$ is H; and $B^1$ is $OR^1$.

In one embodiment of Formula (III), $D^1$ is H. In another embodiment of Formula (III), $A^1$ is $C(A^2)$; $A^2$ is H; $B^1$ is $NHR^1$; and $D^1$ is H. In another embodiment of Formula (III), $A^1$ is $C(A^2)$; $A^2$ is H; $B^1$ is $OR^1$; and $D^1$ is H.

In one embodiment of Formula (III), $E^1$ is H. In another embodiment of Formula (III), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (III), $Y^1$ is H, CN, $NO_2$, F, Cl, Br, $CF_3$, $R^{17}$, or $SO_2R^{17}$. In another embodiment of Formula (III), $Y^1$ is $NO_2$. In another embodiment of Formula (III), $Y^1$ is Cl. In another embodiment of Formula (III), $Y^1$ is $SO_2R^{17}$; wherein $R^{17}$ is as defined herein. In another embodiment of Formula (III), $Y^1$ is $SO_2R^{17}$; wherein $R^{17}$ is alkyl. In another embodiment of Formula (III), $Y^1$ is $R^{17}$; wherein $R^{17}$ is alkynyl. In another embodiment of Formula (III), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (III), $A^1$ is $C(A^2)$; $A^2$ is H; $B^1$ is $NHR^1$; $D^1$ is H; $E^1$ is H; and $Y^1$ is $NO_2$. In another embodiment of Formula (III), $A^1$ is $C(A^2)$; $A^2$ is H; $B^1$ is $NHR^1$; $D^1$ is H; $E^1$ is H; and $Y^1$ is $SO_2R^{17}$, wherein $R^{17}$ is alkyl substituted with three F. In another embodiment of Formula (III), $A^1$ is $C(A^2)$; $A^2$ is H; $B^1$ is $OR^1$; $D^1$ is H; $E^1$ is H; and $Y^1$ is Cl.

In one embodiment of Formula (III), $R^1$ is $R^4$ or $R^5$. In one embodiment of Formula (III), $R^1$ is $R^4$. In one embodiment of Formula (III), $R^1$ is $R^5$. In one embodiment of Formula (III), $R^1$ is $R^4$; and $R^4$ is cycloalkyl, or heterocycloalkyl. In one embodiment of Formula (III), $R^1$ is $R^4$; and $R^4$ is cycloalkyl. In one embodiment of Formula (III), $R^1$ is $R^4$; and $R^4$ is heterocycloalkyl.

In one embodiment of Formula (III), $R^1$ is $R^4$; and $R^4$ is cycloalkyl; wherein $R^4$ is unsubstituted or substituted as defined herein. In another embodiment of Formula (III), $R^1$ is $R^4$; and $R^4$ is cycloalkyl; wherein the cycloalkyl ring is substituted as defined herein. In another embodiment of Formula (III), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (III), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (III), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (III), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (III), $R^1$ is $R^4$; and $R^4$ is cycloalkyl; wherein the cycloalkyl ring is substituted with $N(R^{57})_2$. In another embodiment of Formula (III), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (III), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{60}$ is alkyl which is unsubstituted. In another embodiment of Formula (III), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{60}$ is cycloalkyl which is unsubstituted. In another embodiment of Formula (III), $R^1$ is $R^4$; and $R^4$ is cycloalkyl; wherein the cycloalkyl ring is substituted with $NHR^{57}$. In another embodiment of Formula (III), $R^1$ is $R^4$; and $R^4$ is cycloalkyl; wherein the cycloalkyl ring is cyclohexyl; and wherein the cyclohexyl ring is substituted with $NHR^{57}$. In another embodiment of Formula (III), $R^1$ is $R^4$; and $R^4$ is cycloalkyl; wherein the cycloalkyl ring is cyclohexyl; and wherein the cyclohexyl ring is substituted with $NHR^{57}$, $R^{57}$ is $R^{60}$, and $R^{60}$ is heterocycloalkyl which is unsubstituted.

In one embodiment of Formula (III), $R^1$ is $R^4$; and $R^4$ is heterocycloalkyl; wherein $R^4$ is unsubstituted or substituted as defined herein. In another embodiment of Formula (III), $R^1$ is $R^4$; and $R^4$ is heterocycloalkyl; wherein the heterocycloalkyl ring is substituted as defined herein. In another embodiment of Formula (III), $R^1$ is $R^4$; and $R^4$ is heterocycloalkyl; wherein the heterocycloalkyl ring is substituted with $R^{57}$. In another embodiment of Formula (III), $R^1$ is $R^4$; and $R^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more $R^{57}$; $SO_2R^{57}$, or OH, and $R^{57}$ is $R^{60}$ or $R^{61}$. In another embodiment of Formula (III), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is cycloalkyl or heterocycloalkyl; and $R^{61}$ is alkyl. In another embodiment of Formula (III), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is heterocycloalkyl, wherein the heterocycloalkyl is tetrahydropyranyl or oxetanyl. In another embodiment of Formula (III), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is cycloalkyl, wherein the cycloalkyl is cyclopropyl or cyclopentyl. In another embodiment of Formula (III), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl. In another embodiment of Formula (III), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl; wherein the $C_1$-alkyl, $C_2$-alkyl, or $C_3$-alkyl are unsubstituted or substituted.

In one embodiment of Formula (III), $R^1$ is $R^5$; and $R^5$ is alkyl which is unsubstituted or substituted. In one embodiment of Formula (III), $R^1$ is $R^5$; and $R^5$ is alkyl which is unsubstituted or substituted with $R^7$, $OR^7$, $N(R^7)_2$, or OH.

In one embodiment of Formula (III), $R^7$ is $R^{10}$ or $R^{11}$ which are unsubstituted or substituted as defined herein. In another embodiment of Formula (III), $R^7$ is $R^{10}$ which is unsubstituted or substituted as defined herein. In another embodiment of Formula (III), $R^7$ is $R^{11}$ which is unsubstituted or substituted as defined herein.

In one embodiment of Formula (III), $R^{10}$ is cycloalkyl or heterocycloalkyl which are unsubstituted or substituted as defined herein. In another embodiment of Formula (III), $R^{10}$ is heterocycloalkyl which is unsubstituted or substituted as defined herein. In another embodiment of Formula (III), $R^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (III), $R^{10}$ is tetrahydropyranyl, which is unsubstituted or substituted as defined herein. In another embodiment of Formula (III), $R^{10}$ is morpholinyl, which is unsubstituted or substituted as defined herein. In another embodiment of Formula (III), $R^{10}$ is cycloalkyl which is unsubstituted or substituted as defined herein. In another embodiment of Formula (III), $R^{10}$ is cyclohexyl which is unsubstituted or substituted as defined herein.

In one embodiment of Formula (III), $R^{11}$ is alkyl which is unsubstituted. In another embodiment of Formula (III), $R^{11}$ is methyl, which is unsubstituted or substituted as defined herein. In another embodiment of Formula (III), $R^{11}$ is alkyl, which is substituted as defined herein. In another embodiment of Formula (III), $R^{11}$ is alkyl, which is substituted with $OR^{12}$, $R^{12}$ is $R^{16}$, and $R^{16}$ is alkyl.

Still another embodiment pertains to compounds having Formula (III), which are 4-(4-((2-(4-chlorophenyl)-4,4-dimethylcyclohex-1-en-1-yl)methyl)piperazin-1-yl)-2-((2-methyl-1H-indol-5-yl)oxy)-N-((4-((1-methylpiperidin-4-yl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((7-fluoro-1H-indol-5-yl)oxy)-N-((4-((1-methylpiperidin-4-yl)amino)-3-nitrophenyl)sulfonyl)benzamide;

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((3-(3-morpholin-4-yl-3-oxopropyl)-1H-indol-5-yl)oxy)benzamide;

4-(4-((4'-chloro-1,1'-biphenyl-2-yl)methyl)piperazin-1-yl)-2-((3-(3-morpholin-4-yl-3-oxopropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-morpholin-4-ylpropyl)-1H-indol-5-yl)oxy)-N-((3-nitro-4-((tetrahydro-2H-pyran-4-ylmethyl)amino)phenyl)sulfonyl)benzamide;

4-(4-((4'-chloro-1,1'-biphenyl-2-yl)methyl)piperazin-1-yl)-2-((3-(3-(dimethylamino)propyl)-1H-indol-5-yl)oxy)-N-((3-nitro-4-((tetrahydro-2H-pyran-4-ylmethyl)amino)phenyl)sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(4-fluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl})piperazin-1-yl)-2-[(6,7-difluoro-1H-indol-5-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(1-tetrahydro-2H-pyran-4-ylpiperidin-4-yl)amino]phenyl}sulfonyl)benzamide;

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-{[6-(trifluoromethyl)-1H-indol-5-yl]oxy}benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[6-(trifluoromethyl)-1H-indol-5-yl]oxy}benzamide;

4-(4-{[2-(4-chlorophenyl)-4,4-dimethylcyclohex-1-en-1-yl]
methyl}piperazin-1-yl)-2-[(6,7-difluoro-1H-indol-5-yl)
oxy]-N-({4-[(4-methylpiperazin-1-yl)amino]-3-
nitrophenyl}sulfonyl)benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-({4-[(4-methylpiperazin-1-yl)amino]-3-
nitrophenyl}sulfonyl)benzamide;

4-(4-{[2-(4-chlorophenyl)-4,4-dimethylcyclohex-1-en-1-yl]
methyl}piperazin-1-yl)-2-[(6-methoxy-1H-indol-5-yl)
oxy]-N-({3-nitro-4-[(1-tetrahydro-2H-pyran-4-ylpiperi-
din-4-yl)amino]phenyl}sulfonyl)benzamide;

tert-butyl 5-[5-(4-{[2-(4-chlorophenyl)-4,4-dimethylcyclo-
hex-1-en-1-yl]methyl}piperazin-1-yl)-2-({[(4-{[3-(dim-
ethylamino)propyl]amino}-3-nitrophenyl)sulfonyl]
amino}carbonyl)phenoxy]-1H-indole-1-carboxylate;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-[(3-nitro-4-{[3-(3-oxopiperazin-1-yl)propyl]
amino}phenyl)sulfonyl]benzamide;

Trans-4-(4-{[2-(4-chlorophenyl)-4,4-dimethylcyclohex-1-
en-1-yl]methyl}piperazin-1-yl)-2-[(6-fluoro-1H-indol-5-
yl)oxy]-N-({4-[(4-morpholin-4-ylcyclohexyl)amino]-3-
nitrophenyl}sulfonyl)benzamide;

Trans-4-(4-{[2-(4-chlorophenyl)-4,4-dimethylcyclohex-1-
en-1-yl]methyl}piperazin-1-yl)-2-[(6,7-difluoro-1H-in-
dol-5-yl)oxy]-N-({4-[(4-morpholin-4-ylcyclohexyl)
amino]-3-nitrophenyl}sulfonyl)benzamide;

4-(4-{[2-(4-chlorophenyl)-4,4-dimethylcyclohex-1-en-1-yl]
methyl}piperazin-1-yl)-N-[(4-{[1-(cyclopropylmethyl)
piperidin-4-yl]amino}-3-nitrophenyl)sulfonyl]-2-[(6-
fluoro-1H-indol-5-yl)oxy]benzamide;

4-(4-{[2-(4-chlorophenyl)-4,4-dimethylcyclohex-1-en-1-yl]
methyl}piperazin-1-yl)-N-[(4-{[1-(cyclopropylmethyl)
piperidin-4-yl]amino}-3-nitrophenyl)sulfonyl]-2-[(6,7-
difluoro-1H-indol-5-yl)oxy]benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-({3-nitro-4-[(tetrahydro-2H-pyran-4-ylmethyl)amino]
phenyl}sulfonyl)benzamide;

4-(4-{[2-(4-chlorophenyl)-4,4-dimethylcyclohex-1-en-1-yl]
methyl}piperazin-1-yl)-2-[(6,7-difluoro-1H-indol-5-yl)
oxy]-N-[(3-nitro-4-{[3-(3-oxopiperazin-1-yl)propyl]
amino}phenyl)sulfonyl]benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-({4-[(2-hydroxy-1-tetrahydro-2H-pyran-4-ylethyl)
amino]-3-nitrophenyl}sulfonyl)benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-{[4-({[4-(hydroxymethyl)tetrahydro-2H-pyran-4-yl]
methyl}amino)-3-nitrophenyl]sulfonyl}benzamide;

2-[(6-chloro-1H-indol-5-yl)oxy]-4-(4-{[2-(4-chlorophe-
nyl)-4,4-dimethylcyclohex-1-en-1-yl]methyl}piperazin-
1-yl)-N-({3-nitro-4-[(1-tetrahydro-2H-pyran-4-ylpiperi-
din-4-yl)amino]phenyl}sulfonyl)benzamide;

4-(4-{[2-(4-chlorophenyl)-4,4-dimethylcyclohex-1-en-1-yl]
methyl}piperazin-1-yl)-2-[(6,7-difluoro-1H-indol-5-yl)
oxy]-N-({3-nitro-4-[(tetrahydro-2H-pyran-4-ylmethyl)
amino]phenyl}sulfonyl)benzamide;

2-[(6-chloro-1H-indol-5-yl)oxy]-4-(4-{[2-(4-chlorophe-
nyl)-4,4-dimethylcyclohex-1-en-1-yl]methyl}piperazin-
1-yl)-N-({4-[(4-methylpiperazin-1-yl)amino]-3-
nitrophenyl}sulfonyl)benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-[(3-nitro-4-{[1-(1,3-thiazol-4-ylmethyl)piperidin-4-yl]
amino}phenyl)sulfonyl]benzamide;

N-[(4-{[(4-aminotetrahydro-2H-pyran-4-yl)methyl]amino}-
3-nitrophenyl)sulfonyl]-4-(4-{[2-(4-chlorophenyl)-4,4-
dimethylcyclohex-1-en-1-yl]methyl}piperazin-1-yl)-2-
[(6-fluoro-1H-indol-5-yl)oxy]benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-[(4-{[(3S,4R)-3-hydroxy-1-(1,3-thiazol-4-ylmethyl)pi-
peridin-4-yl]amino}-3-nitrophenyl)sulfonyl]benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-{[3-nitro-4-(tetrahydro-2H-pyran-4-ylamino)phenyl]
sulfonyl}benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-{[4-(morpholin-4-ylamino)-3-nitrophenyl]
sulfonyl}benzamide;

4-(4-{1-[2-(4-chlorophenyl)-4,4-dimethylcyclohex-1-en-1-
yl]ethyl}piperazin-1-yl)-2-[(6-fluoro-1H-indol-5-yl)
oxy]-N-({3-nitro-4-[(tetrahydro-2H-pyran-4-ylmethyl)
amino]phenyl}sulfonyl)benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-[(3-nitro-4-{[(3S)-tetrahydro-2H-pyran-3-ylmethyl]
amino}phenyl)sulfonyl]benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-[(3-nitro-4-{[(3R)-tetrahydro-2H-pyran-3-ylmethyl]
amino}phenyl)sulfonyl]benzamide;

4-(4-{[2-(4-chlorophenyl)-5,5-dimethylcyclohex-1-en-1-yl]
methyl}piperazin-1-yl)-2-[(6-fluoro-1H-indol-5-yl)oxy]-
N-({3-nitro-4-[(tetrahydro-2H-pyran-4-ylmethyl)amino]
phenyl}sulfonyl)benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-({4-[(2-methoxyethyl)amino]-3-nitrophenyl}sulfonyl)
benzamide;

4-(4-{[2-(4-chlorophenyl)-4,4-dimethylcyclohex-1-en-1-yl]
methyl}piperazin-1-yl)-2-[(6-fluoro-1H-indol-5-yl)oxy]-
N-{[3-nitro-4-(tetrahydro-2H-pyran-4-ylmethoxy)phe-
nyl]sulfonyl}benzamide;

2-[(3-chloro-1H-indol-5-yl)oxy]-4-(4-{[2-(4-chlorophe-
nyl)-4,4-dimethylcyclohex-1-en-1-yl]methyl}piperazin-
1-yl)-N-({3-nitro-4-[(tetrahydro-2H-pyran-4-ylmethyl)
amino]phenyl}sulfonyl)benzamide;

2-[(6-chloro-1H-indol-5-yl)oxy]-4-(4-{[4-(4-chlorophe-
nyl)-6,6-dimethyl-5,6-dihydro-2H-pyran-3-yl]
methyl}piperazin-1-yl)-N-({3-nitro-4-[(tetrahydro-2H-
pyran-4-ylmethyl)amino]phenyl}sulfonyl)benzamide;

2-[(6-chloro-1H-indol-5-yl)oxy]-4-(4-{[2-(4-chlorophe-
nyl)-4,4-dimethylcyclohex-1-en-1-yl]methyl}piperazin-
1-yl)-N-({3-nitro-4-[(tetrahydro-2H-pyran-4-ylmethyl)
amino]phenyl}sulfonyl)benzamide;

4-(4-{[4-(4-chlorophenyl)-6,6-dimethyl-5,6-dihydro-2H-
pyran-3-yl]methyl}piperazin-1-yl)-2-[(6-fluoro-1H-in-
dol-5-yl)oxy]-N-({3-nitro-4-[(tetrahydro-2H-pyran-4-yl-
methyl)amino]phenyl}sulfonyl)benzamide;

2-[(3-chloro-1H-indol-5-yl)oxy]-4-(4-{[2-(4-chlorophe-
nyl)-4,4-dimethylcyclohex-1-en-1-yl]methyl}piperazin-
1-yl)-N-({3-nitro-4-[(1-tetrahydro-2H-pyran-4-ylpiperi-
din-4-yl)amino]phenyl}sulfonyl)benzamide;

4-(4-{[2-(4-chlorophenyl)-4,4-dimethylcyclohex-1-en-1-yl]
methyl}piperazin-1-yl)-N-{[4-(1,4-dioxan-2-yl-
methoxy)-3-nitrophenyl]sulfonyl}-2-[(6-fluoro-1H-in-
dol-5-yl)oxy]benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}benzamide;

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-[(6-fluoro-1H-indol-5-yl)oxy]benzamide;

Trans-2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

Trans-2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-[(6-fluoro-1H-indol-5-yl)oxy]benzamide;

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-N-({5-bromo-6-[(4-morpholin-4-ylcyclohexyl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)oxy]-3-nitrophenyl}sulfonyl)benzamide;

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-[(trifluoromethyl)sulfonyl]phenyl}sulfonyl)benzamide;

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-nitrophenyl}sulfonyl)benzamide;

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylbut-2-ynyl)oxy]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[1-(methylsulfonyl)piperidin-4-yl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide;

4-(4-{[4-(4-chlorophenyl)-6,6-dimethyl-5,6-dihydro-2H-pyran-3-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-[(6-fluoro-1H-indol-5-yl)oxy]benzamide;

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-1-tetrahydro-2H-pyran-4-ylpiperidin-3-yl]amino}phenyl)sulfonyl]benzamide;

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydrofuran-3-ylmethyl)amino]phenyl}sulfonyl)benzamide;

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-[(6-fluoro-1H-indol-5-yl)oxy]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(tetrahydro-2H-pyran-4-ylamino)cyclohexyl]amino}phenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(4-tetrahydro-2H-pyran-4-ylpiperazin-1-yl)cyclohexyl]amino})phenyl)sulfonyl]benzamide;

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-fluorotetrahydro-2H-pyran-4-yl)methyl]amino}-3-nitrophenyl)sulfonyl]benzamide;

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-hydroxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-[(6-fluoro-1H-indol-5-yl)oxy]benzamide;

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

N-({5-chloro-6-[(4,4-difluorocyclohexyl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide;

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-[(6-fluoro-1H-indol-5-yl)oxy]benzamide;

and therapeutically acceptable salts, prodrugs, salts of prodrugs and metabolites thereof.

In another aspect, the present invention provides compounds of Formula (IV)

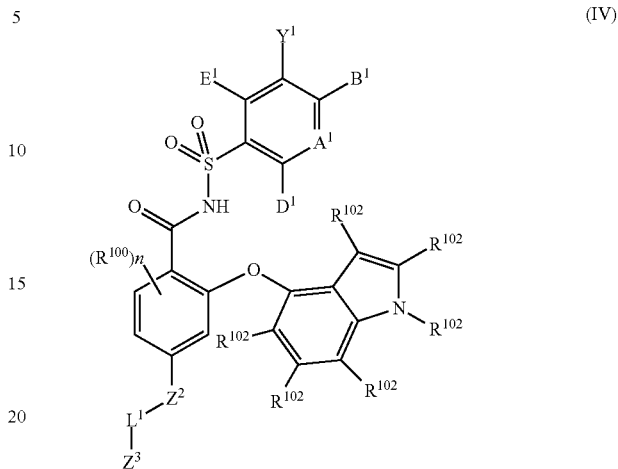

(IV)

and therapeutically acceptable salts, prodrugs, salts of prodrugs and metabolites thereof, wherein $A^1$, $B^1$, $D^1$, $E^1$, $Y^1$, $Z^2$, $L^1$, and $Z^3$ are as described herein for Formula (I), n is 0, 1, 2, or 3; describing the number of additional substituents on $R^{26}$, and $R^{100}$ is as described for substituents on $R^{26}$, and at least one $R^{102}$ is a substituent as described for substituents on $R^{42}$ and $R^{42A}$, and the remainder are H.

In one embodiment of Formula (IV), $A^1$ is N. In another embodiment of Formula (IV), $A^1$ is $C(A^2)$. In another embodiment of Formula (IV), $A^1$ is $C(A^2)$; and $A^2$ is H.

In one embodiment of Formula (IV), $B^1$ is $OR^1$, or $NHR^1$. In another embodiment of Formula (IV), $A^1$ is $C(A^2)$; $A^2$ is H; and $B^1$ is $NHR^1$. In another embodiment of Formula (IV), $A^1$ is $C(A^2)$; $A^2$ is H; and $B^1$ is $OR^1$.

In one embodiment of Formula (IV), $D^1$ is H. In another embodiment of Formula (IV), $A^1$ is $C(A^2)$; $A^2$ is H; $B^1$ is $NHR^1$; and $D^1$ is H. In another embodiment of Formula (IV), $A^1$ is $C(A^2)$; $A^2$ is H; $B^1$ is $OR^1$; and $D^1$ is H.

In one embodiment of Formula (IV), $E^1$ is H. In another embodiment of Formula (IV), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (IV), Y is H, CN, $NO_2$, F, Cl, Br, $CF_3$, $R^{17}$, or $SO_2R^{17}$. In another embodiment of Formula (IV), $Y^1$ is $NO_2$. In another embodiment of Formula (IV), $Y^1$ is Cl. In another embodiment of Formula (IV), $Y^1$ is $SO_2R^{17}$; wherein $R^{17}$ is as defined herein. In another embodiment of Formula (IV), $Y^1$ is $SO_2R^{17}$; wherein $R^{17}$ is alkyl. In another embodiment of Formula (IV), $Y^1$ is $R^{17}$; wherein $R^{17}$ is alkynyl. In another embodiment of Formula (IV), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (IV), $A^1$ is $C(A^2)$; $A^2$ is H; $B^1$ is $NHR^1$; $D^1$ is H; $E^1$ is H; and $Y^1$ is $NO_2$. In another embodiment of Formula (IV), $A^1$ is $C(A^2)$; $A^2$ is H; $B^1$ is $NHR^1$; $D^1$ is H; $E^1$ is H; and $Y^1$ is $SO_2R^{17}$, wherein $R^{17}$ is alkyl substituted with three F. In another embodiment of Formula (IV), $A^1$ is $C(A^2)$; $A^2$ is H; $B^1$ is $OR^1$; $D^1$ is H; $E^1$ is H; and $Y^1$ is Cl.

In one embodiment of Formula (IV), $R^1$ is $R^4$ or $R^5$. In one embodiment of Formula (IV), $R^1$ is $R^4$. In one embodiment of Formula (IV), $R^1$ is $R^5$. In one embodiment of Formula (IV), $R^1$ is $R^4$; and $R^4$ is cycloalkyl, or heterocycloalkyl. In one embodiment of Formula (IV), $R^1$ is $R^4$; and $R^4$ is cycloalkyl. In one embodiment of Formula (IV), $R^1$ is $R^4$; and $R^4$ is heterocycloalkyl.

In one embodiment of Formula (IV), $R^1$ is $R^4$; and $R^4$ is cycloalkyl; wherein $R^4$ is unsubstituted or substituted as defined herein. In another embodiment of Formula (IV), $R^1$ is $R^4$; and $R^4$ is cycloalkyl; wherein the cycloalkyl ring is substituted as defined herein. In another embodiment of Formula (IV), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (IV), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (IV), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (IV), $R^1$ is $R^4$; and $R^4$ is cycloalkyl; wherein the cycloalkyl ring is substituted with $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (IV), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{61}$ is alkyl which is unsubstituted. In another embodiment of Formula (IV), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{60}$ is cycloalkyl which is unsubstituted. In another embodiment of Formula (IV), $R^1$ is $R^4$; and $R^4$ is cycloalkyl; wherein the cycloalkyl ring is substituted with $NHR^{57}$. In another embodiment of Formula (IV), $R^1$ is $R^4$; and $R^4$ is cycloalkyl; wherein the cycloalkyl ring is cyclohexyl; and wherein the cyclohexyl ring is substituted with $NHR^{57}$. In another embodiment of Formula (IV), $R^1$ is $R^4$; and $R^4$ is cycloalkyl; wherein the cycloalkyl ring is cyclohexyl; and wherein the cyclohexyl ring is substituted with $NHR^{57}$, $R^{57}$ is $R^{60}$, and $R^{60}$ is heterocycloalkyl which is unsubstituted.

In one embodiment of Formula (IV), $R^1$ is $R^4$; and $R^4$ is heterocycloalkyl; wherein $R^4$ is unsubstituted or substituted as defined herein. In another embodiment of Formula (IV), $R^1$ is $R^4$; and $R^4$ is heterocycloalkyl; wherein the heterocycloalkyl ring is substituted as defined herein. In another embodiment of Formula (IV), $R^1$ is $R^4$; and $R^4$ is heterocycloalkyl; wherein the heterocycloalkyl ring is substituted with $R^{57}$. In another embodiment of Formula (IV), $R^1$ is $R^4$; and $R^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more $R^{57}$; $SO_2R^{57}$, or OH, and $R^{57}$ is $R^{60}$ or $R^{61}$. In another embodiment of Formula (IV), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is cycloalkyl or heterocycloalkyl; and $R^{61}$ is alkyl. In another embodiment of Formula (IV), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is heterocycloalkyl, wherein the heterocycloalkyl is tetrahydropyranyl or oxetanyl. In another embodiment of Formula (IV), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is cycloalkyl, wherein the cycloalkyl is cyclopropyl or cyclopentyl. In another embodiment of Formula (IV), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl. In another embodiment of Formula (IV), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl; wherein the $C_1$-alkyl, $C_2$-alkyl, or $C_3$-alkyl are unsubstituted or substituted.

In one embodiment of Formula (IV), $R^1$ is $R^5$; and $R^5$ is alkyl which is unsubstituted or substituted. In one embodiment of Formula (IV), $R^1$ is $R^5$; and $R^5$ is alkyl which is unsubstituted or substituted with $R^7$, $OR^7$, $N(R^7)_2$, or OH.

In one embodiment of Formula (IV), $R^7$ is $R^{10}$ or $R^{11}$ which are unsubstituted or substituted as defined herein. In another embodiment of Formula (IV), $R^7$ is $R^{10}$ which is unsubstituted or substituted as defined herein. In another embodiment of Formula (IV), $R^7$ is $R^{11}$ which is unsubstituted or substituted as defined herein.

In one embodiment of Formula (IV), $R^{10}$ is cycloalkyl or heterocycloalkyl which are unsubstituted or substituted as defined herein. In another embodiment of Formula (IV), $R^{10}$ is heterocycloalkyl which is unsubstituted or substituted as defined herein. In another embodiment of Formula (IV), $R^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (IV), $R^{10}$ is tetrahydropyranyl, which is unsubstituted or substituted as defined herein. In another embodiment of Formula (IV), $R^{10}$ is morpholinyl, which is unsubstituted or substituted as defined herein. In another embodiment of Formula (IV), $R^{10}$ is cycloalkyl which is unsubstituted or substituted as defined herein. In another embodiment of Formula (IV), $R^{10}$ is cyclohexyl which is unsubstituted or substituted as defined herein.

In one embodiment of Formula (IV), $R^{11}$ is alkyl which is unsubstituted. In another embodiment of Formula (IV), $R^{11}$ is methyl, which is unsubstituted or substituted as defined herein. In another embodiment of Formula (IV), $R^{11}$ is alkyl, which is substituted as defined herein. In another embodiment of Formula (IV), $R^{11}$ is alkyl, which is substituted with $OR^{12}$, $R^{12}$ is $R^{16}$, and $R^{16}$ is alkyl.

Still another embodiment pertains to compounds having Formula (IV), which are 4-(4-((4'-chloro-1,1'-biphenyl-2-yl)methyl)piperazin-1-yl)-N-((4-((3-(dimethylamino)propyl)amino)-3-nitrophenyl)sulfonyl)-2-((1-methyl-1H-indol-4-yl)oxy)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-((3-morpholin-4-ylpropyl)amino)-3-nitrophenyl)sulfonyl)benzamide;

4-(4-((2-(4-chlorophenyl)-4,4-dimethylcyclohex-1-en-1-yl)methyl)piperazin-1-yl)-2-((3-methyl-1H-indol-4-yl)oxy)-N-((4-((1-methylpiperidin-4-yl)amino)-3-nitrophenyl)sulfonyl)benzamide;

4-(4-((4'-chloro-1,1'-biphenyl-2-yl)methyl)piperazin-1-yl)-2-((1-methyl-1H-indol-4-yl)oxy)-N-((4-((3-morpholin-4-ylpropyl)amino)-3-nitrophenyl)sulfonyl)benzamide;

tert-butyl 4-(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)-1H-indole-1-carboxylate;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(1-methylpiperidin-4-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({3-nitro-4-[(1-tetrahydro-2H-pyran-4-ylpiperidin-4-yl)amino]phenyl}sulfonyl)benzamide;

2-({1,3-bis[(4-methylpiperazin-1-yl)methyl]-1H-indol-4-yl}oxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-({3-[(4-methylpiperazin-1-yl)methyl]-1H-indol-4-yl}oxy)benzamide;

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[2-(trifluoromethyl)-1H-indol-4-yl]oxy}benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-[(3-nitro-4-{[3-(3-oxopiperazin-1-yl)propyl]amino}phenyl)sulfonyl]benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(2-methoxyethyl)amino]-3-nitrophenyl}sulfonyl)benzamide;

2-[(3-chloro-1H-indol-4-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({4-[(4-methylpiperazin-1-yl)amino]-3-nitrophenyl}sulfonyl)benzamide; and therapeutically acceptable salts, prodrugs, salts of prodrugs and metabolites thereof.

In another aspect, the present invention provides compounds of Formula (V)

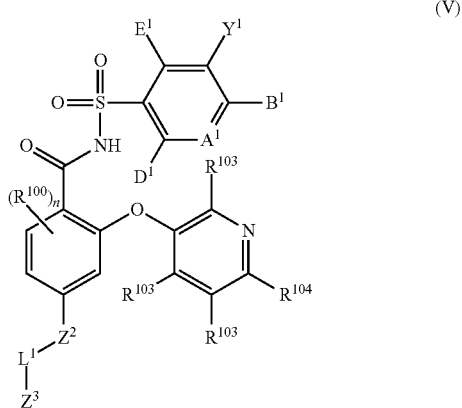

and therapeutically acceptable salts, prodrugs, salts of prodrugs and metabolites thereof, wherein $A^1$, $B^1$, $D^1$, $E^1$, $Y^1$, $Z^2$, $L^1$, and $Z^3$ are as described herein for Formula (I), n is 0, 1, 2, or 3; describing the number of additional substituents on $R^{26}$, and $R^{100}$ is as described for substituents on $R^{26}$, and at least one of $R^{103}$ or $R^{104}$ is a substituent as described for substituents on $R^{42}$ and $R^{42A}$ and the remainder are H.

In one embodiment of Formula (V), $R^{104}$ is $NH_2$ or $NHR^{50}$. In another embodiment of Formula (V), $R^{104}$ is $NH_2$.

In one embodiment of Formula (V), $A^1$ is N. In another embodiment of Formula (V), $A^1$ is $C(A^2)$. In another embodiment of Formula (V), $A^1$ is $C(A^2)$; and $A^2$ is H.

In one embodiment of Formula (V), $B^1$ is $OR^1$, or $NHR^1$. In another embodiment of Formula (V), $A^1$ is $C(A^2)$; $A^2$ is H; and $B^1$ is $NHR^1$. In another embodiment of Formula (V), $A^1$ is $C(A^2)$; $A^2$ is H; and $B^1$ is $OR^1$.

In one embodiment of Formula (V), $D^1$ is H. In another embodiment of Formula (V), $A^1$ is $C(A^2)$; $A^2$ is H; $B^1$ is $NHR^1$; and $D^1$ is H. In another embodiment of Formula (V), $A^1$ is $C(A^2)$; $A^2$ is H; $B^1$ is $OR^1$; and $D^1$ is H.

In one embodiment of Formula (V), $E^1$ is H. In another embodiment of Formula (V), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (V), $Y^1$ is H, CN, $NO_2$, F, Cl, Br, $CF_3$, $R^{17}$, or $SO_2R^{17}$. In another embodiment of Formula (V), $Y^1$ is $NO_2$. In another embodiment of Formula (V), $Y^1$ is Cl. In another embodiment of Formula (V), $Y^1$ is $SO_2R^{17}$; wherein $R^{17}$ is as defined herein. In another embodiment of Formula (V), $Y^1$ is $SO_2R^{17}$; wherein $R^{17}$ is alkyl. In another embodiment of Formula (V), $Y^1$ is $R^{17}$; wherein $R^{17}$ is alkynyl. In another embodiment of Formula (V), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (V), $A^1$ is $C(A^2)$; $A^2$ is H; $B^1$ is $NHR^1$; $D^1$ is H; $E^1$ is H; and $Y^1$ is $NO_2$. In another embodiment of Formula (V), $A^1$ is $C(A^2)$; $A^2$ is H; $B^1$ is $NHR^1$; $D^1$ is H; $E^1$ is H; and $Y^1$ is $SO_2R^7$, wherein $R^{17}$ is alkyl substituted with three F. In another embodiment of Formula (V), $A^1$ is $C(A^2)$; $A^2$ is H; $B^1$ is $OR^1$; $D^1$ is H; $E^1$ is H; and $Y^1$ is Cl.

In one embodiment of Formula (V), $R^1$ is $R^4$ or $R^5$. In one embodiment of Formula (V), $R^1$ is $R^4$. In one embodiment of Formula (V), $R^1$ is $R^5$. In one embodiment of Formula (V), $R^1$ is $R^4$; and $R^4$ is cycloalkyl, or heterocycloalkyl. In one embodiment of Formula (V), $R^1$ is $R^4$; and $R^4$ is cycloalkyl. In one embodiment of Formula (V), $R^1$ is $R^4$; and $R^4$ is heterocycloalkyl.

In one embodiment of Formula (V), $R^1$ is $R^4$; and $R^4$ is cycloalkyl; wherein $R^4$ is unsubstituted or substituted as defined herein. In another embodiment of Formula (V), $R^1$ is $R^4$; and $R^4$ is cycloalkyl; wherein the cycloalkyl ring is substituted as defined herein. In another embodiment of Formula (V), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (V), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^{60}$ is heterocycloalkyl. In another embodiment of Formula (V), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (V), $R^1$ is $R^4$; and $R^4$ is cycloalkyl; wherein the cycloalkyl ring is substituted with $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (V), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{61}$ is alkyl which is unsubstituted. In another embodiment of Formula (V), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{60}$ is cycloalkyl which is unsubstituted. In another embodiment of Formula (V), $R^1$ is $R^4$; and $R^4$ is cycloalkyl; wherein the cycloalkyl ring is substituted with $NHR^{57}$. In another embodiment of Formula (V), $R^1$ is $R^4$; and $R^4$ is cycloalkyl; wherein the cycloalkyl ring is cyclohexyl; and wherein the cyclohexyl ring is substituted with $NHR^{57}$. In another embodiment of Formula (V), $R^1$ is $R^4$; and $R^4$ is cycloalkyl; wherein the cycloalkyl ring is cyclohexyl; and wherein the cyclohexyl ring is substituted with $NHR^{57}$, $R^{57}$ is $R^{60}$, and $R^{60}$ is heterocycloalkyl which is unsubstituted.

In one embodiment of Formula (V), $R^1$ is $R^4$; and $R^4$ is heterocycloalkyl; wherein $R^4$ is unsubstituted or substituted as defined herein. In another embodiment of Formula (V), $R^1$ is $R^4$; and $R^4$ is heterocycloalkyl; wherein the heterocycloalkyl ring is substituted as defined herein. In another embodiment of Formula (V), $R^1$ is $R^4$; and $R^4$ is heterocycloalkyl; wherein the heterocycloalkyl ring is substituted with $R^{57}$. In another embodiment of Formula (V), $R^1$ is $R^4$; and $R^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more $R^{57}$; $SO_2R^{57}$, or OH, and $R^{57}$ is $R^{60}$ or $R^{61}$. In another embodiment of Formula (V), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$ or $R^{61}$; $R^{60}$ is cycloalkyl or heterocycloalkyl; and $R^{61}$ is alkyl. In another embodiment of Formula (V), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is heterocycloalkyl, wherein the heterocycloalkyl is tetrahydropyranyl or oxetanyl. In another embodiment of Formula (V), $R^1$ is $R^4$; $R^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with $R^{57}$; $R^{57}$ is $R^{60}$; $R^{60}$ is cycloalkyl, wherein the cycloalkyl is cyclopropyl or cyclopentyl. In another embodiment of Formula (V), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl. In another embodiment of Formula (V), $R^1$ is $R^4$; $R^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five $R^{57}$; $R^{57}$ is $R^{61}$; $R^{61}$ is alkyl; and the alkyl is $C_1$-alkyl, $C_2$-alkyl, or $C_3$-alkyl; wherein the $C_1$-alkyl, $C_2$-alkyl, or $C_3$-alkyl are unsubstituted or substituted.

In one embodiment of Formula (V), $R^1$ is $R^5$; and $R^5$ is alkyl which is unsubstituted or substituted. In one embodiment of Formula (V), $R^1$ is $R^5$; and $R^5$ is alkyl which is unsubstituted or substituted with $R^7$, $OR^7$, $N(R)_2$, or OH.

In one embodiment of Formula (V), $R^7$ is $R^{10}$ or $R^{11}$ which are unsubstituted or substituted as defined herein. In another embodiment of Formula (V), $R^7$ is $R^{10}$ which is unsubstituted or substituted as defined herein. In another embodiment of Formula (V), $R^7$ is $R^{11}$ which is unsubstituted or substituted as defined herein.

In one embodiment of Formula (V), $R^{10}$ is cycloalkyl or heterocycloalkyl which are unsubstituted or substituted as defined herein. In another embodiment of Formula (V), $R^{10}$ is heterocycloalkyl which is unsubstituted or substituted as defined herein. In another embodiment of Formula (V), $R^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (V), $R^{10}$ is tetrahydropyranyl, which is unsubstituted or substituted as defined herein. In another embodiment of Formula (V), $R^{10}$ is morpholinyl, which is unsubstituted or substituted as defined herein. In another embodiment of Formula (V), $R^{10}$ is cycloalkyl which is unsubstituted or substituted as defined herein. In another embodiment of Formula (V), $R^{10}$ is cyclohexyl which is unsubstituted or substituted as defined herein.

In one embodiment of Formula (V), $R^{11}$ is alkyl which is unsubstituted. In another embodiment of Formula (V), $R^{11}$ is methyl, which is unsubstituted or substituted as defined herein. In another embodiment of Formula (V), $R^{11}$ is alkyl, which is substituted as defined herein. In another embodiment of Formula (V), $R^{11}$ is alkyl, which is substituted with $OR^{12}$, $R^{12}$ is $R^{16}$, and $R^{16}$ is alkyl.

Still another embodiment pertains to compounds having Formula (V), which are 2-(6-aminopyridin-3-yl)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-{[2-(4-chlorophenyl)-4,4-dimethylcyclohex-1-en-1-yl]methyl}piperazin-1-yl)-2-{[({3-nitro-4-[(1-tetrahydro-2H-pyran-4-ylpiperidin-4-yl)amino]phenyl}sulfonyl)amino]carbonyl}phenoxy)pyridin-2-ylcarbamate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide;

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-ylcarbamate;

2-[(5-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(6-hydroxypyridin-3-yl)oxy]-N-({3-nitro-4-[(tetrahydro-2H-pyran-4-ylmethyl)amino]phenyl}sulfonyl)benzamide;

2-{[6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-fluoropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{4-(1,4-dioxan-2-ylmethoxy)-3-nitrophenyl]sulfonyl}benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(3-morpholin-4-ylpropyl)amino]-3-[(trifluoromethyl)sulfonyl]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)nicotinamide;

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[4-{[(3R)-1-(2,2-difluoroethyl)pyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide;

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[4-{[(4-fluorotetrahydro-2H-pyran-4-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)benzamide;

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

Trans-2-[(6-amino-5-bromopyridin-3-yl)oxy]-4-(4-{([2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-cyclopropylpyrrolidin-3-yl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({4-fluoro-1-[2-fluoro-1-(fluoromethyl)ethyl]piperidin-4-yl}methoxy)-3-nitrophenyl]sulfonyl}benzamide;

tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino)phenylsulfonylcarbamoyl)phenoxy)pyridine-2,6-diyldicarbamate;

4-(4-{[2-(4-chlorophenyl)-4,4-dimethylcyclohex-1-en-1-yl]methyl}piperazin-1-yl)-2-{[6-(cyclopropylamino)pyridin-3-yl]oxy}-N-({3-nitro-4-[(tetrahydro-2H-pyran-4-ylmethyl)amino]phenyl}sulfonyl)benzamide;

Trans-4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-({3-nitro-4-[(tetrahydro-2H-pyran-4-ylmethyl)amino]phenyl}sulfonyl)benzamide;

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[({4-[2-fluoro-1-(fluoromethyl)ethyl]morpholin-2-yl}methyl)amino]-3-nitrophenyl}sulfonyl)benzamide;

2-[(2-amino-6-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-[(2,6-diaminopyridin-4-yl)oxy]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]piperidin-3-yl}amino)-3-nitrophenyl]sulfonyl}benzamide;

tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide;

2-[(6-amino-5-chloropyridin-3-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)benzamide;

2-[(6-amino-5-chloropyridin-3-yl)oxy]-4-[4-({9-(4-chlorophenyl)-3-[2-fluoro-1-(fluoromethyl)ethyl]-3-azaspiro[5.5]undec-8-en-8-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}benzamide;

2-[(2-amino-5-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

2-[(6-amino-5-chloropyridin-3-yl)oxy]-4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)benzamide;

2-[(6-amino-5-chloropyridin-3-yl)oxy]-N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino)}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide;

2-[(6-amino-5-chloropyridin-3-yl)oxy]-N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}benzamide;

2-[(6-amino-5-chloropyridin-3-yl)oxy]-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide;

and therapeutically acceptable salts, prodrugs, salts of prodrugs and metabolites thereof.

In another aspect, the present invention provides compounds of Formula (VI)

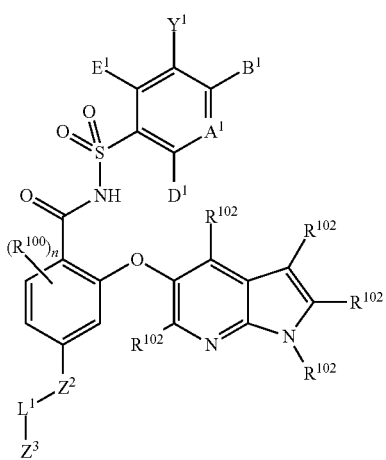

(VI)

and therapeutically acceptable salts, prodrugs, salts of prodrugs and metabolites thereof, wherein $A^1$, $B^1$, $D^1$, $E^1$, $Y^1$, $Z^2$, $L^1$, and $Z^3$ are as described herein for Formula (I), n is 0, 1, 2, or 3; describing the number of additional substituents on $R^{26}$, and $R^{100}$ is as described for substituents on $R^{26}$, and at least one $R^{102}$ is a substituent as described for substituents on $R^{42}$ and $R^{42A}$, and the remainder are H.

In one embodiment of Formula (VI), $A^1$ is N. In another embodiment of Formula (VI), $A^1$ is $C(A^2)$. In another embodiment of Formula (VI), $A^1$ is $C(A^2)$; and $A^2$ is H.

In one embodiment of Formula (VI), $B^1$ is $OR^1$, or $NHR^1$. In another embodiment of Formula (VI), $A^1$ is $C(A^2)$; $A^2$ is H; and $B^1$ is $NHR^1$. In another embodiment of Formula (VI), $A^1$ is $C(A^2)$; $A^2$ is H; and $B^1$ is $OR^1$.

In one embodiment of Formula (VI), $D^1$ is H. In another embodiment of Formula (VI), $A^1$ is $C(A^2)$; $A^2$ is H; $B^1$ is $NHR^1$; and $D^1$ is H. In another embodiment of Formula (VI), $A^1$ is $C(A^2)$; $A^2$ is H; $B^1$ is $OR^1$; and $D^1$ is H.

In one embodiment of Formula (VI), $E^1$ is H. In another embodiment of Formula (VI), $A^1$ is $C(A^2)$; $A^2$ is H; $B^1$ is $NHR^1$; $D^1$ is H; and $E^1$ is H. In another embodiment of Formula (I), $A^1$ is $C(A^2)$; $A^2$ is H; $B^1$ is $OR^1$; $D^1$ is H; and $E^1$ is H.

In one embodiment of Formula (VI), $Y^1$ is H, CN, $NO_2$, F, Cl, Br, $CF_3$, $R^{17}$, or $SO_2R^{17}$. In another embodiment of Formula (VI), $Y^1$ is $NO_2$. In another embodiment of Formula (VI), $Y^1$ is Cl. In another embodiment of Formula (VI), $Y^1$ is $SO_2R^{17}$; wherein $R^{17}$ is as defined herein. In another embodiment of Formula (VI), $Y^1$ is $SO_2R^{17}$; wherein $R^{17}$ is alkyl. In another embodiment of Formula (VI), $Y^1$ is $R^{17}$; wherein $R^{17}$ is alkynyl. In another embodiment of Formula (VI), $A^1$ is $C(A^2)$; $A^2$ is H; $B^1$ is $NHR^1$; $D^1$ is H; $E^1$ is H; and $Y^1$ is $NO_2$ or $SO_2R^{17}$; wherein $R^{17}$ is alkyl or alkynyl. In another embodiment of Formula (VI), $A^1$ is $C(A^2)$; $A^2$ is H; $B^1$ is $NHR^1$; $D^1$ is H; $E^1$ is H; and $Y^1$ is $NO_2$. In another embodiment of Formula (VI), $A^1$ is $C(A^2)$; $A^2$ is H; $B^1$ is $NHR^1$; $D^1$ is H; $E^1$ is H; and $Y^1$ is $SO_2R^{17}$, wherein $R^{17}$ is alkyl substituted with three F. In another embodiment of Formula (VI), $A^1$ is $C(A^2)$; $A^2$ is H; $B^1$ is $OR^1$; $D^1$ is H; $E^1$ is H; and $Y^1$ is Cl.

In one embodiment of Formula (VI), $R^1$ is $R^4$ or $R^5$. In one embodiment of Formula (VI), $R^1$ is $R^4$. In one embodiment of Formula (VI), $R^1$ is $R^5$. In one embodiment of Formula (VI), $R^1$ is $R^4$; and $R^4$ is cycloalkyl, or heterocycloalkyl. In one embodiment of Formula (VI), $R^1$ is $R^4$; and $R^4$ is cycloalkyl. In one embodiment of Formula (VI), $R^1$ is $R^4$; and $R^4$ is heterocycloalkyl.

In one embodiment of Formula (VI), $R^1$ is $R^4$; and $R^4$ is cycloalkyl; wherein $R^4$ is unsubstituted or substituted as defined herein. In another embodiment of Formula (VI), $R^1$ is $R^4$; and $R^4$ is cycloalkyl; wherein the cycloalkyl ring is substituted as defined herein. In another embodiment of Formula (VI), $R^1$ is $R^4$; and $R^4$ is cycloalkyl; wherein the cycloalkyl ring is substituted with $R^{57}$, $NHR^{57}$, or $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $R^{57}$; and $R^{57}$ is $R^{60}$. In another embodiment of Formula (VI), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; and $R^6$ is heterocycloalkyl. In another embodiment of Formula (VI), $R^1$ is $R^4$; $R^4$ is cycloalkyl; wherein the cycloalkyl ring is cyclohexyl; and wherein the cyclohexyl ring is substituted with $R^{57}$; $R^{57}$ is $R^{60}$; $R^{60}$ is heterocycloalkyl; wherein the heterocycloalkyl ring is morpholinyl or piperazinyl. In another embodiment of Formula (VI), $R^1$ is $R^4$; and $R^4$ is cycloalkyl; wherein the cycloalkyl ring is substituted with $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $N(R^{57})_2$. In another embodiment of Formula (VI), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{61}$, and $R^{61}$ is alkyl which is unsubstituted. In another embodiment of Formula (VI), $R^1$ is $R^4$; and $R^4$ is cycloalkyl; wherein the cycloalkyl ring is cyclohexyl; and wherein the cyclohexyl ring is substituted with $N(R^{57})_2$, $R^{57}$ is $R^{60}$, and $R^{60}$ is cycloalkyl which is unsubstituted. In another embodiment of Formula (VI), $R^1$ is $R^4$; and $R^4$ is cycloalkyl; wherein the cycloalkyl ring is substituted with $NHR^{57}$. In another embodiment of Formula (VI), $R^1$ is $R^4$; and $R^4$ is cycloalkyl; wherein the cycloalkyl ring is cyclohexyl; and wherein the cyclohexyl ring is substituted with NHR$^{57}$. In another embodiment of Formula (VI), R$^1$ is R$^4$; and R$^4$ is cycloalkyl; wherein the cycloalkyl ring is cyclohexyl; and wherein the cyclohexyl ring is substituted with NHR$^{57}$, R$^{57}$ is R$^{60}$, and R$^{60}$ is heterocycloalkyl which is unsubstituted.

In one embodiment of Formula (VI), R$^1$ is R$^4$; and R$^4$ is heterocycloalkyl; wherein R$^4$ is unsubstituted or substituted as defined herein. In another embodiment of Formula (VI), R$^1$ is R$^4$; and R$^4$ is heterocycloalkyl; wherein the heterocycloalkyl ring is substituted as defined herein. In another embodiment of Formula (VI), R$^1$ is R$^4$; and R$^4$ is heterocycloalkyl; wherein the heterocycloalkyl ring is substituted with R$^{57}$. In another embodiment of Formula (VI), R$^1$ is R$^4$; and R$^4$ is heterocycloalkyl; wherein the heterocycloalkyl ring is piperidinyl, pyrrolinyl, morpholinyl, or piperizinyl; and wherein the heterocycloalkyl ring is substituted with one or two or three or four or five more R$^{57}$; SO$_2$R$^{57}$, or OH, and R$^{57}$ is R$^{60}$ or R$^{61}$. In another embodiment of Formula (VI), R$^1$ is R$^4$; R$^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with R$^{57}$; R$^{57}$ is R$^{60}$ or R$^{61}$; R$^{60}$ is cycloalkyl or heterocycloalkyl; and R$^{61}$ is alkyl. In another embodiment of Formula (VI), R$^1$ is R$^4$; R$^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with R$^{57}$; R$^{57}$ is R$^{60}$; R$^{60}$ is heterocycloalkyl, wherein the heterocycloalkyl is tetrahydropyranyl or oxetanyl. In another embodiment of Formula (VI), R$^1$ is R$^4$; R$^4$ is heterocycloalkyl; wherein the heterocycloalkyl ring is piperidinyl, pyrrolinyl, morpholinyl, or piperizinyl; and wherein the piperidinyl, pyrrolinyl, morpholinyl, or piperizinyl; ring is substituted with R$^{57}$; R$^{57}$ is R$^{60}$; R$^{60}$ is cycloalkyl, wherein the cycloalkyl is cyclopropyl or cyclopentyl. In another embodiment of Formula (VI), R$^1$ is R$^4$; R$^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five R$^{57}$; R$^{57}$ is R$^{61}$; R$^{61}$ is alkyl; and the alkyl is C$_1$-alkyl, C$_2$-alkyl, or C$_3$-alkyl. In another embodiment of Formula (VI), R$^1$ is R$^4$; R$^4$ is heterocycloalkyl; wherein the heterocycloalkyl ring is piperidinyl, pyrrolinyl, morpholinyl, or piperizinyl, and wherein the piperidinyl, pyrrolinyl, morpholinyl, or piperizinyl ring is substituted with one or two or three or four or five R$^{57}$; R$^{57}$ is R$^{61}$; R$^{61}$ is alkyl; and the alkyl is C$_1$-alkyl, C$_2$-alkyl, or C$_3$-alkyl; wherein the C$_1$-alkyl, C$_2$-alkyl, or C$_3$-alkyl are unsubstituted or substituted.

In one embodiment of Formula (VI), R$^1$ is R$^5$; and R$^5$ is alkyl which is unsubstituted or substituted. In one embodiment of Formula (VI), R$^1$ is R$^5$; and R$^5$ is alkyl which is unsubstituted or substituted with R$^7$, OR$^7$, N(R$^7$)$_2$, or OH.

In one embodiment of Formula (VI), R$^7$ is R$^{10}$ or R$^{11}$ which are unsubstituted or substituted as defined herein. In another embodiment of Formula (VI), R$^7$ is R$^{10}$ which is unsubstituted or substituted as defined herein. In another embodiment of Formula (VI), R$^7$ is R$^{11}$ which is unsubstituted or substituted as defined herein.

In one embodiment of Formula (VI), R$^{10}$ is cycloalkyl or heterocycloalkyl which are unsubstituted or substituted as defined herein. In another embodiment of Formula (VI), R$^{10}$ is heterocycloalkyl which is unsubstituted or substituted as defined herein. In another embodiment of Formula (VI), R$^{10}$ is tetrahydrofuranyl, tetrahydropyranyl, morpholinyl, dioxanyl, piperidinyl, piperizinyl, or pyrrolidinyl, which are unsubstituted or substituted as defined herein. In another embodiment of Formula (VI), R$^{10}$ is tetrahydropyranyl, which is unsubstituted or substituted as defined herein. In another embodiment of Formula (VI), R$^{10}$ is morpholinyl, which is unsubstituted or substituted as defined herein. In another embodiment of Formula (VI), R$^{10}$ is cycloalkyl which is unsubstituted or substituted as defined herein. In another embodiment of Formula (VI), R$^{10}$ is cyclohexyl which is unsubstituted or substituted as defined herein.

In one embodiment of Formula (VI), R$^{11}$ is alkyl which is unsubstituted. In another embodiment of Formula (VI), R$^{11}$ is methyl, which is unsubstituted or substituted as defined herein. In another embodiment of Formula (VI), R$^{11}$ is alkyl, which is substituted as defined herein. In another embodiment of Formula (VI), R$^{11}$ is alkyl, which is substituted with OR$^{12}$, R$^{12}$ is R$^{16}$, and R$^{16}$ is alkyl.

Still another embodiment pertains to compounds having Formula (VI), which are 4-(4-{[2-(4-chlorophenyl)-4,4-dimethylcyclohex-1-en-1-yl]methyl}piperazin-1-yl)-2-[(4-chloro-1H-pyrrolo[2,3-b]pyridin-5-yl)oxy]-N-({3-nitro-4-[(tetrahydro-2H-pyran-4-ylmethyl)amino]phenyl}sulfonyl)benzamide;

and therapeutically acceptable salts, prodrugs, salts of prodrugs and metabolites thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-2 proteins are expressed, said compositions comprising an excipient and a therapeutically effective amount of the compound having Formula (I).

Still another embodiment pertains to methods of treating disease in a patient during which anti-apoptotic Bcl-2 proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-2 proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-2 proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-2 proteins.

Certain precursor compounds which may be metabolized in vitro or in vivo to form compounds having Formula (I) may also have utility for treating diseases associated with expression of anti-apoptotic Bcl-2 proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiqutin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN®(trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGTOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II, GA101, ofatumumab, ABT-806 (mAb-806), ErbB3 specific antibodies, BSG2 specific antibodies, DLL4 specific antibodies and C-met specific antibodies, and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAX-ANE™ (ABI-007), ABT-100 (farnesyl transferase inhibitor), ADVEXIN® (Ad5CMV-p53 vaccine), ALTOCOR® or MEVACOR® (lovastatin), AMPLIGEN®(poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARTX® (human papillomavirus vaccine), CHOP® (C: CYTOXAN®(cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-2 proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1,1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp (tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded Wang resin/vessel on an ABI 433A peptide synthesizer using 250 μmol scale Fastmoc™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with dichloromethane and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of N,N-dimethylformamide was flowed through the bed over 15 minutes. The resin was then washed thrice with N,N-dimethylformamide and filtered. Ninhydrin tests showed a strong signal for primary amine.

Resin Labeling with 6-Carboxyfluorescein-NHS (6-FAM-NHS)

The resin was treated with 2 equivalents 6-FAM-NHS in 1% DIEA/N,N-dimethylformamide and stirred or shaken at ambient temperature overnight. When complete, the resin was drained, washed thrice with N,N-dimethylformamide, thrice with (1×DCM and 1× methanol) and dried to provide an orange resin that was negative by ninhydrin test.

General Procedure for Cleavage and Deprotection of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 μm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D ChemStation software version A.03.04 (Hewlett-Packard. Palo Alto, Calif.) on a 4.6×250 mm YMC column packed with ODS-AQ 5 μm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

```
F-Bak:
Peptide Probe Acetyl-        (SEQ ID NO: 1)

GQVGRQLAIIGDK(6-FAM)-        (SEQ ID NO: 2)

INR-NH₂
```

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak:
Acetyl-(SEQ ID NO: 1)GQVGRQLAIIGDK(6-
FAM)-(SEQ ID NO:2)INR-NH$_2$ The protected peptide was assembled on 0.25 mmol Fmoc-Rink amide MBHA resin (Novabiochem) on an Applied Biosystems 433A automated peptide synthesizer running Fastmoc™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM: TIS:TFA (v/v/v) flowed through the resin over 15 minutes, followed by quenching with a flow of dimethylformamide. Single-isomer 6-carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)$^+$)).

Time Resolved-Fluorescence Resonance Energy Transfer (TR-FRET) Assay

Representative compounds were serially diluted in dimethyl sulfoxide (DMSO) starting at 50 µM (2× starting concentration; 10% DMSO) and 10 µL were transferred into a 384-well plate. Then 10 µL of a protein/probe/antibody mix was added to each well at final concentrations listed in TABLE 1. The samples are then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters. Inhibition constants (Ki) are shown in TABLE 2 below and were determined using Wang's equation (Wang Z.-X. An Exact Mathematical Expression For Describing Competitive Binding Of Two Different Ligands To A Protein Molecule. *FEBS Lett.* 1995, 360:111-4).

The samples were then mixed on a shaker for 1 minute and incubated for an additional 3 hours at room temperature. For each assay, the probe/antibody and protein/probe/antibody were included on each assay plate as negative and positive controls, respectively. Fluorescence was measured on the Envision (Perkin Elmer) using a 340/35 nm excitation filter and 520/525 (F-Bak peptide) and 495/510 nm (Tb-labeled anti-Histidine antibody) emission filters.

Inhibition constants ($K_i$) for compounds according to the invention are shown in TABLE 2 below. Where the $K_i$ for a compound is represented as ">" (greater than) a certain numerical value, it is intended to mean that the binding affinity value is greater than the limits of detection of the assay used. Where the $K_i$ for a compound is represented as "<" (less than) a certain numerical value, it is intended to mean that the binding affinity value is lower than the limit of detection of the assay used.

TABLE 2

| TR-FRET Bcl-2 Binding Ki (µM) | |
|---|---|
| Example No. | TR-FRET Binding: Bcl-2 Ki (µM) |
| 1 | 0.008354 |
| 2 | 0.031467 |
| 3 | 0.000827 |
| 4 | 0.002474 |
| 5 | 0.000746 |
| 6 | 0.000787 |
| 7 | 0.002592 |
| 8 | 0.003451 |
| 9 | 0.000754 |
| 10 | 0.00072 |
| 11 | 0.000171 |
| 12 | 0.000331 |
| 13 | 0.001621 |
| 14 | 0.000079 |
| 15 | 0.000586 |
| 16 | 0.003039 |
| 17 | 0.005578 |
| 18 | 0.002487 |
| 19 | 0.001679 |
| 20 | 0.003965 |
| 21 | 0.014054 |
| 22 | 0.005455 |
| 23 | 0.00827 |
| 24 | 0.014984 |
| 25 | 0.001501 |
| 26 | 0.000511 |
| 27 | 0.002212 |
| 28 | 0.001326 |
| 29 | 0.000903 |
| 30 | 0.000071 |
| 31 | 0.002007 |
| 32 | 0.001584 |
| 33 | 0.007173 |
| 34 | 0.000049 |
| 35 | 0.000022 |

TABLE 1

| Protein, Probe And Antibody Used For TR-FRET Assays | | | | | |
|---|---|---|---|---|---|
| Protein | Probe | Protein (nM) | Probe (nM) | Antibody | Antibody (nM) |
| GST-Bcl-2 | F-Bak Peptide Probe Acetyl-(SEQ ID NO: 1 GQVGRQLAIIGDK(6-FAM) SEQ ID NO: 2 INR-amide) | 1 | 100 | Tb-anti-GST | 1 |

6-FAM = 6-carboxyfluorescein.; Tb = terbium; GST = glutathione S-transferase

TABLE 2-continued

TR-FRET Bcl-2 Binding Ki (μM)

| Example No. | TR-FRET Binding: Bcl-2 Ki (μM) |
|---|---|
| 36 | 0.00007 |
| 37 | 0.000005 |
| 38 | 0.000013 |
| 39 | 0.000019 |
| 40 | 0.000019 |
| 41 | 0.000027 |
| 42 | 0.00003 |
| 43 | 0.000034 |
| 44 | 0.000036 |
| 45 | 0.000047 |
| 46 | 0.000047 |
| 47 | 0.00005 |
| 48 | 0.000053 |
| 49 | 0.000062 |
| 50 | 0.000062 |
| 51 | 0.000066 |
| 52 | 0.000072 |
| 53 | 0.000077 |
| 54 | 0.000082 |
| 55 | 0.00009 |
| 56 | 0.000106 |
| 57 | 0.000147 |
| 58 | 0.000155 |
| 59 | 0.000184 |
| 60 | 0.000187 |
| 61 | 0.00022 |
| 62 | 0.000227 |
| 63 | 0.000438 |
| 64 | 0.000458 |
| 65 | 0.00052 |
| 66 | 0.000592 |
| 67 | 0.000807 |
| 68 | 0.005934 |
| 69 | 0.008246 |
| 70 | 0.020421 |
| 71 | 0.031597 |
| 72 | 0.031666 |
| 73 | 0.03226 |
| 74 | 0.18943 |
| 75 | 0.076832 |
| 76 | 0.2395 |
| 77 | 0.45052 |
| 78 | >1.195000 |
| 79 | 0.099826 |
| 80 | 0.14872 |
| 81 | 0.031048 |
| 82 | 0.51156 |
| 83 | >1.195000 |
| 84 | 0.013654 |
| 85 | 0.005626 |
| 86 | 0.005263 |
| 87 | 0.26427 |
| 88 | >1.195000 |
| 89 | 0.006111 |
| 90 | 0.010626 |
| 91 | >1.195000 |
| 92 | 0.002569 |
| 93 | 0.01683 |
| 94 | 0.56121 |
| 95 | 0.000428 |
| 96 | >1.195000 |
| 97 | 0.14659 |
| 98 | 0.000959 |
| 99 | 0.071364 |
| 100 | 0.11299 |
| 101 | 0.6695 |
| 102 | 0.043518 |
| 103 | 0.006755 |
| 104 | 0.002321 |
| 105 | 0.003567 |
| 106 | 0.21452 |
| 107 | 0.000331 |
| 108 | nd |
| 109 | 0.000237 |
| 110 | 0.000039 |
| 111 | 0.01744 |
| 112 | 0.000042 |
| 113 | 0.000032 |
| 114 | 0.000036 |
| 115 | 0.000042 |
| 116 | 0.000123 |
| 117 | 0.000072 |
| 118 | 0.000151 |
| 119 | 0.000156 |
| 120 | 0.000214 |
| 121 | 0.000081 |
| 122 | <0.000001 |
| 123 | 0.00011 |
| 124 | 0.000033 |
| 125 | 0.000075 |
| 126 | 0.000068 |
| 127 | 0.00003 |
| 128 | 0.000064 |
| 129 | 0.000107 |
| 130 | 0.000067 |
| 131 | 0.000066 |
| 132 | 0.000211 |
| 133 | 0.000055 |
| 134 | 0.000181 |
| 135 | 0.000068 |
| 136 | 0.000177 |
| 137 | 0.000021 |
| 138 | 0.000016 |
| 139 | 0.000125 |
| 140 | 0.000223 |
| 141 | 0.000482 |
| 142 | 0.000071 |
| 143 | 0.000053 |
| 144 | 0.000028 |
| 145 | 0.000057 |
| 146 | 0.00004 |
| 147 | 0.000127 |
| 148 | 0.000106 |
| 149 | 0.00003 |
| 150 | 0.000759 |
| 151 | 0.006935 |
| 152 | 0.018589 |
| 154 | 0.000012 |
| 155 | 0.000062 |
| 156 | 0.000035 |
| 157 | 0.00072 |
| 158 | 0.000619 |
| 159 | 0.000526 |
| 160 | 0.000028 |
| 161 | 0.000031 |
| 162 | 0.000048 |
| 163 | 0.000686 |
| 164 | 0.000056 |
| 165 | 0.00012 |
| 166 | 0.000082 |
| 167 | 0.001345 |
| 168 | 0.028343 |
| 169 | 0.000498 |
| 170 | 0.000036 |
| 171 | 0.000066 |
| 172 | 0.000549 |
| 173 | 0.000019 |
| 174 | 0.000037 |
| 175 | 0.000046 |
| 176 | 0.00024 |
| 177 | 0.000037 |
| 178 | 0.000175 |
| 179 | 0.000036 |
| 180 | 0.000112 |
| 181 | 0.000119 |
| 182 | 0.000172 |
| 183 | 0.00253 |
| 184 | 0.000155 |

TABLE 2-continued

TR-FRET Bcl-2 Binding Ki (μM)

| Example No. | TR-FRET Binding: Bcl-2 Ki (μM) |
|---|---|
| 185 | 0.000083 |
| 186 | 0.000035 |
| 187 | 0.000054 |
| 188 | 0.000073 |
| 189 | 0.000036 |
| 190 | 0.000077 |
| 191 | 0.000552 |
| 192 | 0.000024 |
| 193 | 0.000064 |
| 194 | 0.000317 |
| 195 | 0.000684 |
| 197 | 0.00022 |
| 198 | <0.000010 |
| 199 | 0.000244 |
| 200 | 0.000081 |
| 201 | 0.00001 |
| 202 | 0.020043 |
| 203 | 0.000084 |
| 204 | 0.000075 |
| 205 | 0.000153 |
| 206 | 0.000037 |
| 207 | 0.000074 |
| 208 | 0.000261 |
| 209 | <0.000010 |
| 210 | 0.00002 |
| 211 | 0.001338 |
| 212 | 0.000375 |
| 213 | 0.000031 |
| 214 | 0.000221 |
| 215 | 0.002954 |
| 216 | 0.000027 |
| 217 | 0.000174 |
| 218 | 0.000175 |
| 219 | 0.014857 |
| 220 | 0.000127 |
| 221 | 0.000227 |
| 222 | >1.195000 |
| 223 | 0.010911 |
| 224 | 0.005603 |
| 225 | 0.003283 |
| 226 | 0.007586 |
| 227 | 0.000174 |
| 229 | 0.001085 |
| 230 | 0.002833 |
| 231 | 0.036946 |
| 232 | 0.001047 |
| 233 | 0.000037 |
| 234 | 0.000099 |
| 235 | 0.000039 |
| 236 | 0.000071 |
| 237 | 0.000197 |
| 238 | 0.000124 |
| 239 | 0.000105 |
| 240 | 0.000912 |
| 241 | 0.000141 |
| 242 | 0.000092 |
| 243 | 0.000069 |
| 244 | 0.001734 |
| 245 | 0.00048 |
| 246 | 0.000065 |
| 247 | 0.000039 |
| 248 | 0.000051 |
| 249 | 0.000168 |
| 250 | 0.000672 |
| 251 | 0.000435 |
| 252 | 0.001147 |
| 253 | 0.00005 |
| 254 | 0.000119 |
| 255 | 0.007013 |
| 256 | 0.000105 |
| 257 | 0.000097 |
| 258 | 0.000083 |
| 259 | 0.000165 |
| 260 | 0.011834 |
| 261 | 0.000186 |
| 262 | 0.000276 |
| 263 | 0.00011 |
| 264 | 0.000068 |
| 265 | 0.000363 |
| 266 | 0.00081 |
| 267 | 0.028426 |
| 268 | 0.000042 |
| 269 | 0.000469 |
| 270 | >1.195000 |
| 271 | 0.001908 |
| 272 | 0.00124 |
| 273 | 0.000516 |
| 274 | 0.000936 |
| 275 | 0.000081 |
| 276 | 0.000199 |
| 277 | 0.000017 |
| 278 | 0.039967 |
| 279 | 0.001703 |
| 280 | 0.00755 |
| 281 | 0.000111 |
| 282 | 0.001012 |
| 283 | 0.01721 |
| 284 | 0.079348 |
| 285 | 0.000037 |
| 286 | 0.003181 |
| 287 | 0.000131 |
| 288 | 0.000017 |
| 289 | <0.000010 |
| 290 | 0.000251 |
| 291 | 0.000273 |
| 292 | 0.000191 |
| 293 | 0.000233 |
| 294 | 0.000127 |
| 295 | 0.000077 |
| 296 | <0.000010 |
| 297 | <0.000010 |
| 298 | 0.000054 |
| 299 | 0.051687 |
| 300 | 0.013659 |
| 301 | 0.000113 |
| 302 | <0.000010 |
| 303 | 0.000092 |
| 304 | 0.000822 |
| 305 | 0.000146 |
| 306 | 0.000671 |
| 307 | 0.000524 |
| 308 | 0.00004 |
| 309 | 0.00069 |
| 310 | 0.000155 |
| 311 | 0.000185 |
| 312 | 0.000531 |
| 313 | <0.000010 |
| 314 | 0.003094 |
| 315 | 0.004555 |
| 316 | 0.000058 |
| 317 | 0.000205 |
| 318 | <0.000010 |
| 319 | 0.000198 |
| 320 | 0.000028 |
| 321 | 0.000029 |
| 322 | 0.00453 |
| 323 | 0.003484 |
| 324 | <0.000010 |
| 325 | 0.000183 |
| 326 | 0.000037 |
| 327 | 0.000212 |
| 328 | 0.000068 |
| 329 | 0.000108 |
| 330 | <0.000010 |
| 331 | 0.000238 |
| 332 | 0.000034 |
| 333 | 0.000107 |
| 334 | 0.000197 |

TABLE 2-continued

TR-FRET Bcl-2 Binding Ki (µM)

| Example No. | TR-FRET Binding: Bcl-2 Ki (µM) |
|---|---|
| 335 | <0.000010 |
| 336 | <0.000010 |
| 337 | 0.000049 |
| 338 | <0.000010 |
| 339 | 0.000057 |
| 340 | 0.000385 |
| 341 | 0.000017 |
| 342 | 0.003340 |
| 343 | 0.000009 |
| 344 | 0.000042 |
| 345 | 0.000005 |
| 346 | <0.000010 |
| 347 | 0.000377 |
| 348 | 0.003779 |
| 349 | 0.000019 |
| 350 | <0.000010 |
| 351 | 0.002843 |
| 352 | 0.000079 |
| 353 | 0.000016 |
| 354 | 0.000114 |
| 355 | 0.009567 |
| 356 | 0.002822 |
| 357 | 0.000177 |
| 358 | 0.000062 |
| 359 | 0.000110 |
| 360 | 0.000050 |
| 361 | 0.000015 |
| 362 | 0.000033 |
| 363 | <0.000010 |
| 364 | 0.000014 |
| 365 | 0.004551 |
| 366 | 0.006052 |
| 367 | 0.000012 |
| 368 | <0.000010 |
| 369 | 0.000014 |
| 370 | <0.000010 |
| 371 | <0.000010 |
| 372 | 0.014978 |
| 373 | 1.195000 |
| 374 | 0.005337 |
| 375 | 0.327810 |
| 376 | 0.057705 |
| 377 | 0.002323 |
| 378 | <0.000010 |
| 379 | 0.017948 |
| 380 | 0.008274 |
| 381 | 0.000020 |
| 382 | 0.000114 |
| 383 | 0.427490 |
| 384 | 0.006233 |
| 385 | 0.049293 |
| 386 | <0.000010 |
| 387 | <0.000010 |
| 388 | 0.000020 |
| 389 | <0.000010 |
| 390 | <0.000010 |
| 391 | <0.000010 |
| 392 | <0.000010 |
| 393 | <0.000010 |
| 394 | 0.000018 |
| 395 | 0.000077 |
| 396 | <0.000010 |
| 397 | 0.000137 |
| 398 | 0.000175 |
| 399 | <0.000010 |
| 400 | 0.000082 |
| 401 | 0.000035 |
| 402 | 0.000039 |
| 403 | 0.002136 |
| 404 | 0.000069 |
| 405 | 0.000354 |
| 406 | 0.000166 |
| 407 | 0.000946 |
| 408 | 0.001160 |
| 409 | 0.000686 |
| 410 | <0.000010 |
| 411 | 0.021291 |

The inhibition constant ($K_i$) is the dissociation constant of an enzyme-inhibitor complex or a protein/small molecule complex, wherein the small molecule is inhibiting binding of one protein to another protein. So a large $K_i$ value indicates a low binding affinity and a small $K_i$ value indicates a high binding affinity.

The data in TABLE 2 shows inhibition constants for the inhibition of a Bak BH3 peptide probe to Bcl-2 protein and indicate that compounds according to the invention have high binding affinities for anti-apoptotic Bcl-2 protein. The compounds are therefore expected to have utility in treatment of diseases during which anti-apoptotic Bcl-2 protein is expressed.

It is expected that, because compounds having Formula I bind to Bcl-2, they would also have utility as binders to anti-apoptotic proteins having close structural homology to Bcl-2, such as, for example, anti-apoptotic Bcl-$X_L$, Bcl-w, Mcl-1 and Bfl-1/A1 proteins.

Involvement of Bcl-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, chronic lymphocytic leukemia, myeloma, prostate cancer spleen cancer, and the like is described in commonly-owned PCT US 2004/36770, published as WO 2005/049593, and PCT US 2004/37911, published as WO 2005/024636.

Involvement of Bcl-2 proteins in immune and autoimmune diseases is described in *Current Allergy and Asthma Reports* 2003, 3, 378-384; *British Journal of Haematology* 2000, 110(3), 584-90; *Blood* 2000, 95(4), 1283-92; and *New England Journal of Medicine* 2004, 351(14), 1409-1418.

Involvement of Bcl-2 proteins in arthritis is disclosed in commonly-owned U.S. Provisional Patent Application Ser. No. 60/988,479.

Involvement of Bcl-2 proteins in bone marrow transplant rejection is disclosed in commonly-owned U.S. patent application Ser. No. 11/941,196.

Overexpression of Bcl-2 proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic)

leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

It is also expected that compounds having Formula (I) would inhibit growth of cells expressing Bcl-2 proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-$BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

SCHEME 1

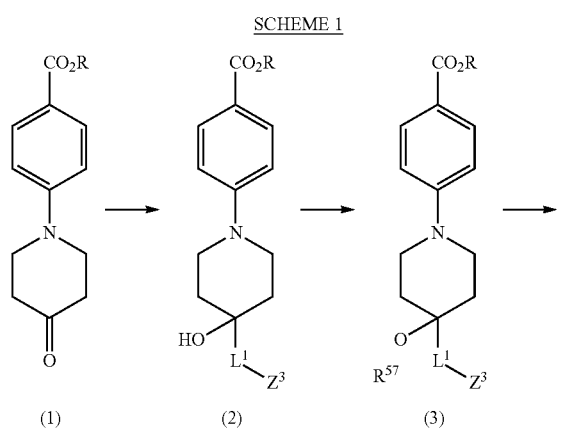

Compounds of Formula (4) can be prepared as shown in SCHEME 1, and can be used as described in SCHEME 8 to prepare compounds of Formula (I), which are representative of the compounds of the present invention. Compounds of Formula (I) wherein R is alkyl, can be converted to compounds of Formula (2) using $Z^3L^1MgX^1$, wherein $X^1$ is a halide, in a solvent such as but not limited to ether or tetrahydrofuran. Compounds of Formula (3) can be prepared from compounds of Formula (2) using a strong base such as NaH and $R^{57} \times 2$, wherein $X^2$ is a halide and $R^{57}$ is as described herein. Compounds of Formula (3), when treated with aqueous NaOH or LiOH, will provide compounds of Formula (4).

SCHEME 2

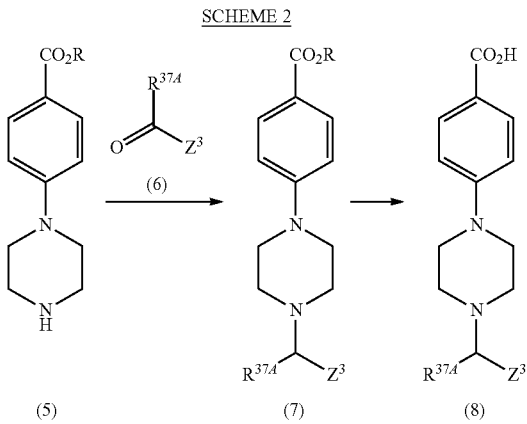

As shown in SCHEME 2, compounds of Formula (5) can be reacted with compounds of Formula (6) and a reducing agent to provide compounds of Formula (7). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, and dichloromethane or mixtures thereof. Compounds of Formula (8) can be prepared from compounds of Formula (7) as described in SCHEME 1, and can be used as described in SCHEME 8 to prepare compounds of Formula (I).

SCHEME 3

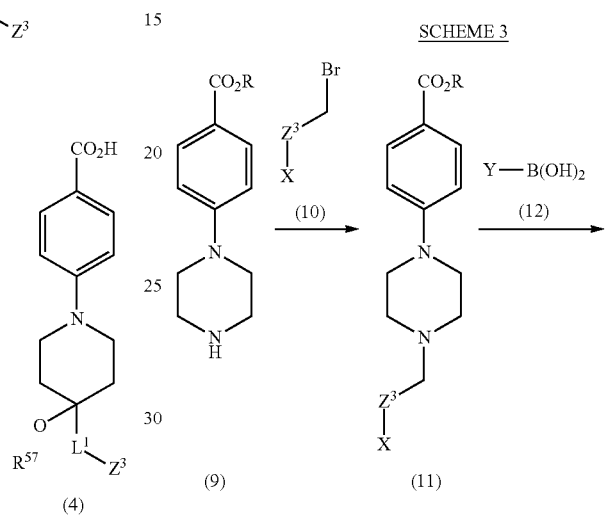

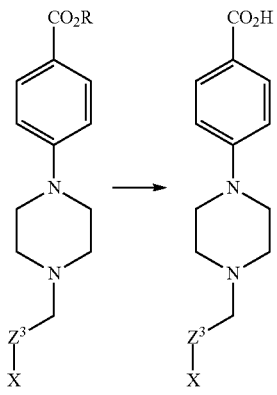

Compounds of Formula (9), when reacted with a compound a Formula (10) wherein X is a halide or triflate, and a base will provide a compound of Formula (11). Bases useful in the reaction include triethylamine, diisopropylethylamine and the like. Compounds of Formula (13), wherein Y is as described herein for substituents on $Z^3$, can be prepared from compounds of Formula (11) and compounds of Formula (12) using Suzuki coupling conditions known to those skilled in the art and readily available in the literature. Compounds of Formula (14) can be prepared from compounds of Formula (13) as described in SCHEME 1, and can be used as described in SCHEME 8 to prepare compounds of Formula (I).

SCHEME 4

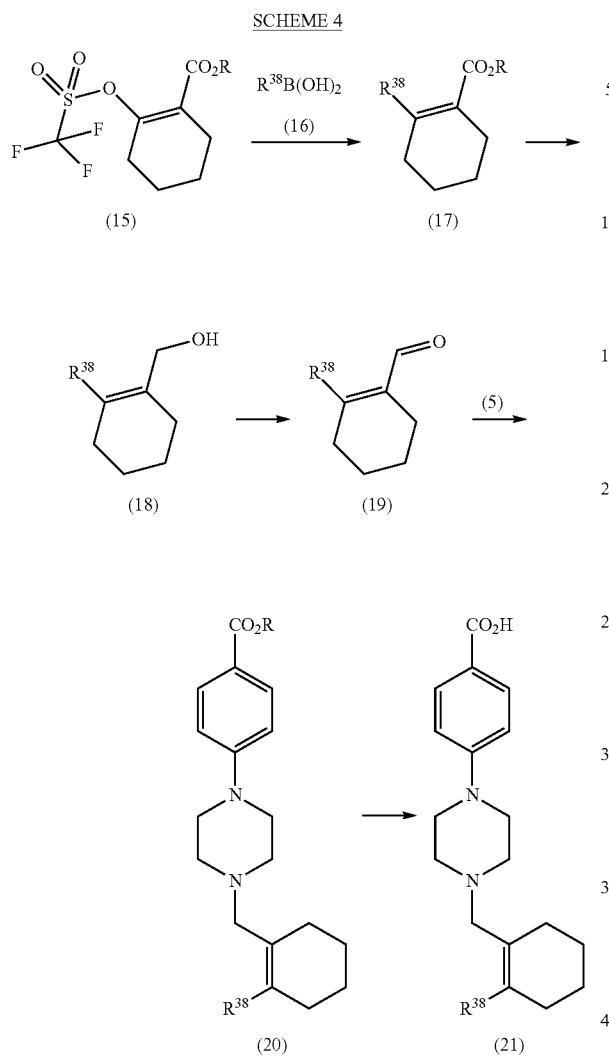

SCHEME 5

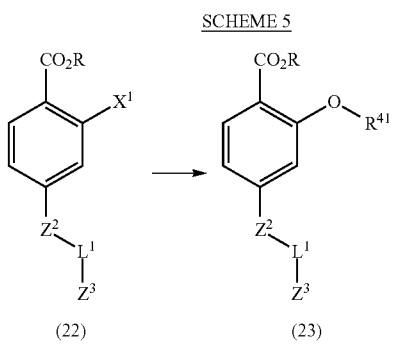

As shown in SCHEME 5, compounds of Formula (22), wherein R is alkyl, may be converted to compounds of Formula (23) by reacting the former, wherein $X^1$ is Cl, Br, I, or $CF_3SO_3$—, and compounds of Formula $R^{41}$—OH and a catalyst, with or without a first base. Examples of catalysts include copper(I) trifluoromethanesulfonate toluene complex, $PdCl_2$, $Pd(OAc)_2$, and $Pd_2(dba)_3$. Examples of first bases include triethylamine, N,N-diisopropylethylamine, $Cs_2CO_3$, $Na_2CO_3$, $K_3PO_4$, and mixtures thereof.

Compounds of Formula (22) may also be converted to compounds of Formula (23) by reacting the former, when $X^1$ is Cl, F, or $NO_2$, and compounds of Formula $R^{41}$—OH with a first base. Examples of first bases include triethylamine, N,N-diisopropylethylamine, $Cs_2CO_3$, $Na_2CO_3$, $K_3PO_4$, and mixtures thereof.

SCHEME 6

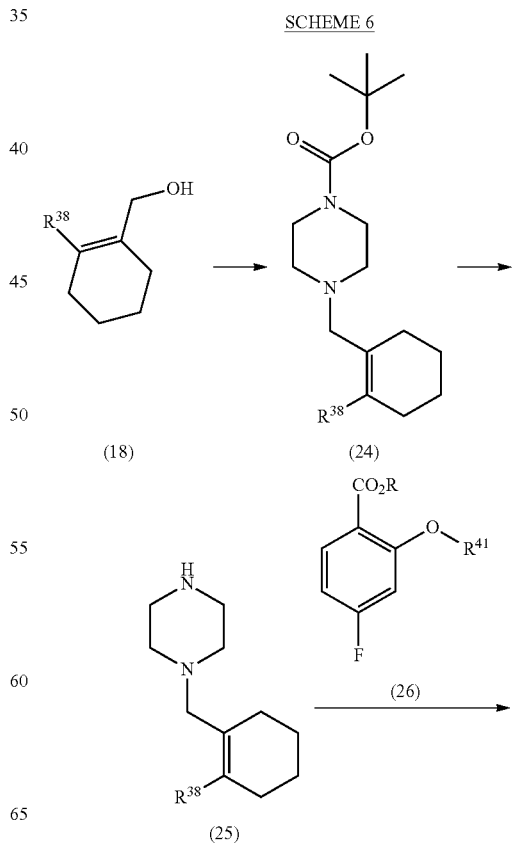

As shown in SCHEME 4, compounds of Formula (17) can be prepared from compounds of Formula (15) and compounds of Formula (16), wherein R is alkyl and $R^{38}$ is as described herein, using Suzuki coupling conditions known to those skilled in the art and readily available in the literature. Compounds of Formula (17) can be reduced to compounds of Formula (18) using a reducing agent such as $LiAlH_4$ in a solvent such as but not limited to diethyl ether or THF. Compounds of Formula (19) can be prepared from compounds of Formula (18) using Dess-Martin periodinane or Swern oxidation conditions known to those skilled in the art and readily available in the literature. Compounds of Formula (19) can be reacted with a compound of Formula (5) and a reducing agent to provide compounds of Formula (20). Examples of reducing agents include sodium borohydride, sodium cyanoborohydride, sodium triacetoxyborohydride, polymer supported cyanoborohydride, and the like. The reaction is typically performed in a solvent such as but not limited to methanol, tetrahydrofuran, 1,2-dichloroethane, and dichloromethane or mixtures thereof. Compounds of Formula (21) can be prepared from compounds of Formula (20) as described in SCHEME 1, and can be used as described in SCHEME 8 to prepare compounds of Formula (I).

-continued

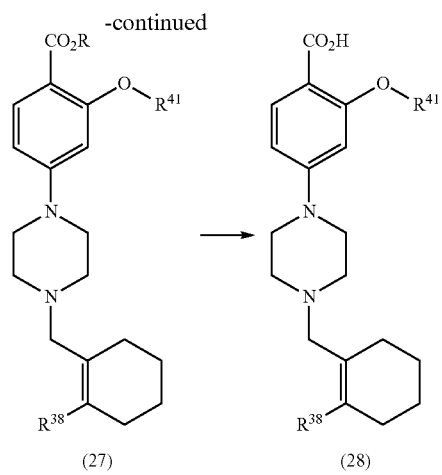

Compounds of Formula (18) can be reacted with mesyl chloride and a base such as but not limited to triethylamine, followed by N-t-butoxycarbonylpiperazine, to provide compounds of Formula (24). Compounds of Formula (25) can be prepared by reacting compounds of Formula (24) with triethylsilane and trifluoroacetic acid. Compounds of Formula (25) can be reacted with compounds of Formula (26) and $HK_2PO_4$ to provide compounds of Formula (27) in a solvent such as but not limited to dimethylsulfoxide. Compounds of Formula (28) can be prepared from compounds of Formula (27) as described in SCHEME 1, and can be used as described in SCHEME 8 to prepare compounds of Formula (I).

SCHEME 7

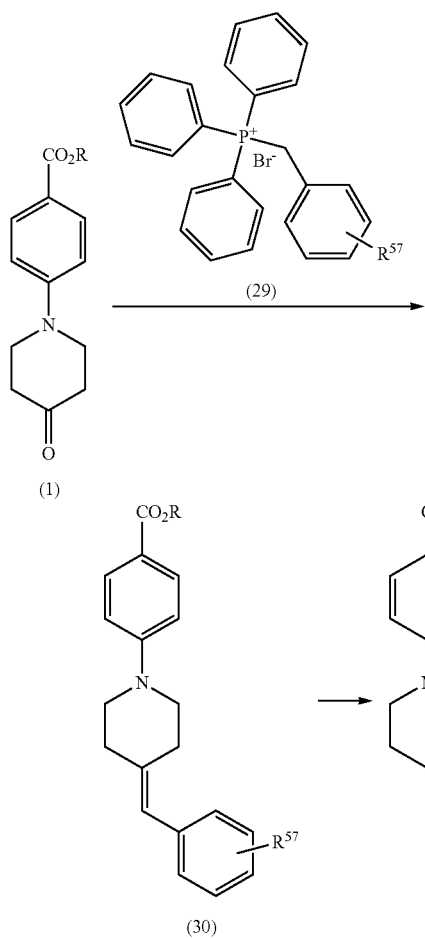

As shown in SCHEME 7, compounds of Formula (I) can be reacted with an appropriate triphenylphosphonium bromide of Formula (29) and a base such as but not limited to sodium hydride or n-butyllithium to provide compounds of Formula (30). The reaction is typically performed in a solvent such as THF or DMSO. Compounds of Formula (31) can be prepared from compounds of Formula (30) as described in SCHEME 1, and can be used as described in SCHEME 8 to prepare compounds of Formula (I).

SCHEME 8

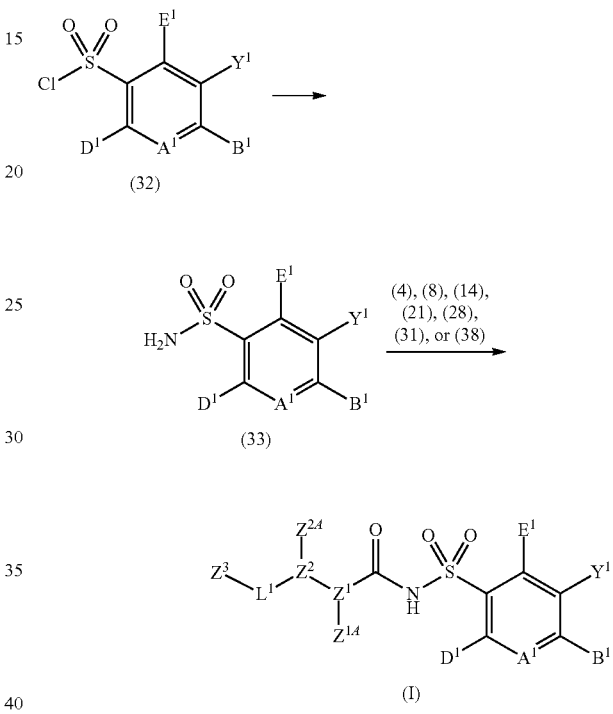

As shown in SCHEME 8, compounds of Formula (32), which can be prepared as described herein, may be converted to compounds of Formula (33) by reacting the former with ammonia. Compounds of Formula (33) may be converted to compounds of Formula (I) by reacting the former and compounds of Formula (4), (8), (14), (21), (28), (31), or (38) and a coupling agent, with or without a first base. Examples of coupling agents include 1-ethyl-3-[3-(dimethylamino)propyl]-carbodiimide hydrochloride, 1,1'-carbonyldiimidazole, and benzotriazol-1-yl-oxytripyrrolidinophosphonium hexafluorophosphate. Examples of first bases include triethylamine, N,N-diisopropylethylamine, 4-(dimethylamino)pyridine, and mixtures thereof.

SCHEME 9

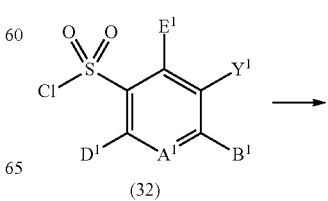

-continued

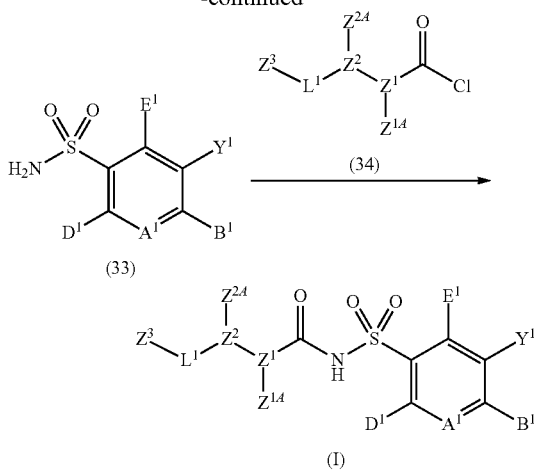

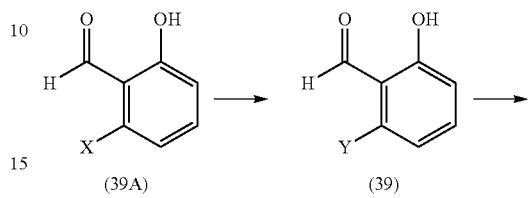

Compounds of Formula (33), prepared as described in SCHEME 8, may also be converted to compounds of Formula (I) by reacting the former and compounds of Formula (34) and a first base. Examples of first bases include but are not limited to sodium hydride, triethylamine, N,N-diisopropylethylamine, 4-(dimethylamino)pyridine, and mixtures thereof.

SCHEME 10

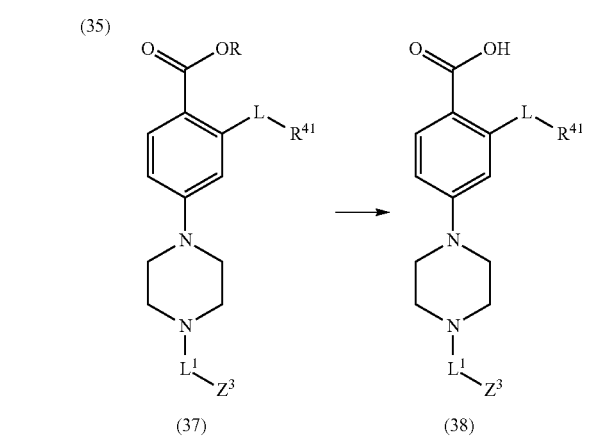

As shown in SCHEME 10, compounds of Formula (35), wherein L is a bond, alkyl, O, S, S(O), S(O)$_2$, NH, etc., can be reacted with compounds of Formula (36), to provide compounds of Formula (37). The reaction is typically performed at elevated temperatures in a solvent such as but not limited to dimethylsulfoxide, and may require the use of a base such as but not limited to potassium phosphate, potassium carbonate, and the like. Compounds of Formula (38) can be prepared from compounds of Formula (37) as described in SCHEME 1, and can be used as described in SCHEME 8 to prepare compounds of Formula (I).

SCHEME 11

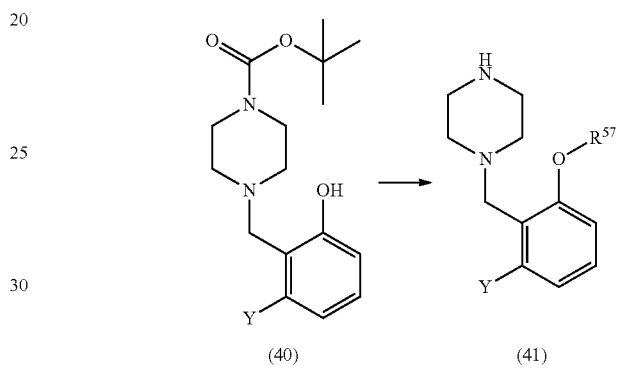

Compounds of Formula (39), wherein Y is as described herein for substituents on $Z^3$, can be prepared from compounds of Formula (39A) wherein X is a halide or triflate, and Y—B(OH)$_2$ using Suzuki coupling conditions known to those skilled in the art and readily available in the literature. Compounds of Formula (39) can be reacted with tert-butyl piperazine-1-carboxylate and a reducing agent such as sodium triacetoxyborohydride to provide compounds of Formula (40). The reaction is typically performed in a solvent such as but not limited to methylene chloride. Compounds of Formula (41) can be prepared from compounds of Formula (40) by reacting the latter with $R^{57}X$, wherein X is a halide, and NaH in a solvent such as N,N-dimethylformamide, and then the resulting material can be treated with triethylsilane and trifluoroacetic acid in dichloromethane. Compounds of Formula (41) can be used as described in Scheme 10 wherein $L^1$-$Z^3$ is as shown in Formula (41).

SCHEME 12

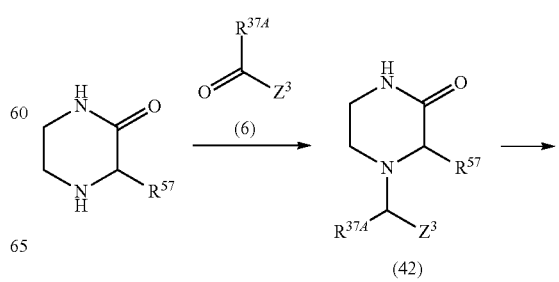

-continued

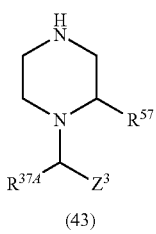

(43)

As shown in SCHEME 12, substituted piperazin-2-ones wherein $R^{57}$ is alkyl, can be reacted with compounds of Formula (6) and a reducing agent such as sodium triacetoxyborohydride in dichloromethane to provide compounds of Formula (42). Compounds of Formula (42) can be reduced to compounds of Formula (43) using a reducing agent such as but not limited to lithium aluminum hydride in a solvent such as but not limited to tetrahydrofuran. Compounds of Formula (43) can be used as described in Scheme 10 wherein $L^1$-$Z^3$ is as shown in Formula (43).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

4-(4-((4'-chloro-1,1'-biphenyl-2-yl)methyl)piperazin-1-yl)-2-(3-((dimethylamino)methyl)phenoxy)-N-((3-nitro-4-((tetrahydro-2H-pyran-4-ylmethyl)amino)phenyl)sulfonyl)benzamide Example 1A tert-butyl 4-((4'-chlorobiphenyl-2-yl)methyl)piperazine-1-carboxylate 4'-Chlorobiphenyl-2-carboxaldehyde (4.1 g), tert-butyl piperazine-1-carboxylate (4.23 g) and sodium triacetoxyborohydride (5.61 g) in $CH_2Cl_2$ (60 mL) were stirred for 24 hours. The mixture was treated with methanol and poured into ether. The extract was washed with water and brine and concentrated. The concentrate was chromatographed on silica gel with 2-25% ethyl acetate/hexanes.

Example 1B 1-((4'-chlorobiphenyl-2-yl)methyl)piperazine

EXAMPLE 1A (3.0 g) and triethylsilane (1 mL) were stirred in dichloromethane (30 mL) and trifluoroacetic acid (30 mL) for 2 hours. The mixture was concentrated, taken up in ether and concentrated again.

Example 1C methyl 2-bromo-4-(4-((4'-chlorobiphenyl-2-yl)methyl)piperazin-1-yl)benzoate Methyl 2-bromo-4-fluorobenzoate (3 g), EXAMPLE 1B (4.43 g), and $K_2CO_3$ (3.56 g) were stirred in DMSO (35 mL) at 125° C. for 24 hours. The mixture was cooled, taken up in ethyl acetate (500 mL), washed with water and brine, dried over $Na_2SO_4$, filtered and concentrated. The concentrate was chromatographed on silica gel with 5-25% ethyl acetate/hexanes.

Example 1D 3-((dimethylamino)methyl)phenol

3-Hydroxybenzaldehyde (1.0 g), 2M dimethylamine in THF (5 mL), and sodium triacetoxyborohydride (2 g) in $CH_2Cl_2$ (10 mL) were stirred for 24 hours. The mixture was treated with methanol and chromatographed on silica gel with 2-25% ethyl acetate/hexanes.

Example 1E methyl 4-(4-((4'-chlorobiphenyl-2-yl)methyl)piperazin-1-yl)-2-(3-((dimethylamino)methyl)phenoxy)benzoate EXAMPLE 1C (400 mg), EXAMPLE 1D (260 mg), $Cs_2CO_3$ (570 mg), 1-naphthoic acid (2.96 g), copper(I) triflate-toluene complex (245 mg), ethyl acetate (9 µL), and 4 Å sieves (30 mg) in toluene (2 mL) was stirred at 105° C. for 24 hours. The mixture was cooled and taken up in ethyl acetate (100 mL) and water (40 mL). The layers were separated and the extract was washed twice with $Na_2CO_3$ solution and brine, dried, and concentrated. The concentrate was chromatographed on silica gel with 25-50% ethyl acetate/hexanes.

Example 1F 4-(4-((4'-chlorobiphenyl-2-yl)methyl)piperazin-1-yl)-2-(3-((dimethylamino)methyl)phenoxy)benzoic acid EXAMPLE 1E (750 mg) was stirred in 25 mL 2:1 dioxane/1M NaOH at 80° C. for 4 hours. The solution was cooled and adjusted to pH 4 with $NaH_2PO_4$ solution and concentrated HCl, and extracted with ethyl acetate. The extract was washed with brine, dried ($Na_2SO_4$), and concentrated.

Example 1G 3-nitro-4-((tetrahydro-2H-pyran-4-yl)methylamino)benzenesulfonamide

4-Fluoro-3-nitrobenzenesulfonamide (2.18 g), (tetrahydropyran-4-yl)methylamine (1.14 g), and triethylamine (1 g) were stirred in THF (30 mL) for 24 hours. The solution was diluted with ethyl acetate, washed with $NaH_2PO_4$ solution and brine, and dried ($Na_2SO_4$), filtered and concentrated. The product was triturated from ethyl acetate.

Example 1H 4-(4-((4'-chloro-1,1'-biphenyl-2-yl)methyl)piperazin-1-yl)-2-(3-((dimethylamino)methyl)phenoxy)-N-((3-nitro-4-((tetrahydro-2H-pyran-4-ylmethyl)amino)phenyl)sulfonyl)benzamide EXAMPLE 1F (128 mg), EXAMPLE 1G (73 mg), 1-ethyl-3-(3-(dimethylamino)propyl)-carbodiimide hydrochloride (88 mg), and 4-dimethylaminopyridine (28 mg) were stirred in CH$_2$Cl$_2$ (3 mL) for 24 hours. The mixture was cooled and chromatographed on silica gel with 0-10% methanol/ethyl acetate. $^1$H NMR (300 MHz, DMSO-d$_6$) δ 11.15 (br s, 1H), 8.63 (dd, 1H), 8.49 (d, 1H), 7.80 (dd, 1H), 7.44-7.53 (m, 5H), 7.36 (m, 3H), 7.22 (m, 3H), 7.01 (s, 1H), 6.92 (d, 1H), 6.78 (d, 1H), 6.44 (s, 1H), 4.17 (m, 2H), 3.86 (dd, 2H), 3.33 (m, 6H), 3.16 (m, 4H), 2.66 (s, 6H), 2.37 (br s, 4H), 1.91 (m, 1H), 1.63 (d, 2H), 1.29 (m, 2H).

Example 2

4-(4-((4'-chloro-1,1'-biphenyl-2-yl)methyl)piperazin-1-yl)-2-(3-(methylamino)phenoxy)-N-((3-nitro-4-((tetrahydro-2H-pyran-4-ylmethyl)amino)phenyl)sulfonyl)benzamide

Example 2A 3-(methylamino)phenol

Ethylamine was bubbled into a solution of 4-hydroxybenzaldehyde (2.0 g) and sodium triacetoxyborohydride (5.2 g) in CH$_2$Cl$_2$ (60 mL) for 1 hour, and the mixture was stopped and stirred for 24 hours. 1M NaOH solution was added (10 mL), and di-tert-butyl dicarbonate (3.57 g) and triethylamine (2.28 mL) were then added and the mixture was stirred for 24 hours. The solution was cooled and adjusted to pH 4 with NaH$_2$PO$_4$ solution and concentrated HCl, and extracted with ethyl acetate. The extract was washed with brine, dried (Na$_2$SO$_4$), and concentrated. The concentrate was chromatographed on silica gel with 20% ethyl acetate/hexanes.

Example 2B methyl 4-(4-((4'-chlorobiphenyl-2-yl)methyl)piperazin-1-yl)-2-(3-(methylamino)phenoxy)benzoate EXAMPLE 1C (457 mg), EXAMPLE 2A (225 mg), cesium carbonate (595 mg), copper(I) triflate toluene complex (41 mg), and ethyl acetate (0.016 mL) in toluene (5 mL) were stirred at 110° C. for 72 hours. The mixture was cooled and chromatographed on silica gel with 5-25% ethyl acetate/hexanes.

Example 2C 4-(4-((4'-chlorobiphenyl-2-yl)methyl)piperazin-1-yl)-2-(3-(methylamino)phenoxy)benzoic acid This EXAMPLE was prepared by substituting EXAMPLE 2B for EXAMPLE 1E in EXAMPLE 1F.

Example 2D 4-(4-((4'-chloro-1,1'-biphenyl-2-yl)methyl)piperazin-1-yl)-2-(3-(methylamino)phenoxy)-N-((3-nitro-4-((tetrahydro-2H-pyran-4-ylmethyl)amino)phenyl)sulfonyl)benzamide This EXAMPLE was prepared by substituting EXAMPLE 2C for EXAMPLE 1F in EXAMPLE 1G. $^1$H NMR (500 MHz, DMSO-d$_6$) δ 11.60 (brs, 1H), 8.37 (s, 1H), 7.69 (d, 1H), 7.58 (d, 1H), 7.47 (m, 5H), 7.38 (m, 3H), 7.24 (m, 1H), 6.95 (d, 1H), 6.89 (dd, 1H), 6.61 (d, 1H), 6.26 (s, 1H), 6.13 (d, 1H), 5.97 (s, 1H), 5.92 (d, 1H), 5.59 (br s, 1H), 3.84 (dd, 2H), 3.37 (m, 6H), 3.03 (m, 4H), 2.89 (m, 2H), 2.59 (br s, 3H), 2.36 (br s, 4H), 1.91 (m, 1H), 1.62 (d, 2H), 1.24 (m, 2H).

Example 3

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((1-methylpiperidin-4-yl)amino)-3-nitrophenyl)sulfonyl)benzamide

Example 3A ethyl 4-fluoro-2-(2-methyl-1H-indol-5-yloxy)benzoate

Ethyl 2,4-difluorobenzoate (1.14 g), K$_3$PO$_4$ (1.30 g) and 2-methyl-5-indolol (0.90 g) were stirred at 110° C. in diglyme (12 mL) for 24 hours. The mixture was cooled and poured into ether. The solution was washed three times with 1M NaOH solution, and with brine, and dried. The solution was then concentrated. The concentrate was chromatographed on silica gel with 10% ethyl acetate/hexanes.

Example 3B methyl 4,4-dimethyl-2-(trifluoromethylsulfonyloxy)cyclohex-1-enecarboxylate To a suspension of hexane-washed NaH (17 g) in dichloromethane (700 mL) was added 5,5-dimethyl-2-methoxycarbonylcyclohexanone (38.5 g) dropwise at 0° C. After stirring for 30 minutes, the mixture was cooled to −78° C. and trifluoroacetic anhydride (40 mL) was added. The mixture was warmed to room temperature and stirred for 24 hours. The extract was washed with brine, dried and concentrated.

Example 3C methyl 2-(4-chlorophenyl)-4,4-dimethylcyclohex-1-enecarboxylate

EXAMPLE 3B (62.15 g), 4-chlorophenylboronic acid (32.24 g), CsF (64 g) and tetrakis(triphenylphosphine)palladium(0) (2 g) in 2:1 dimethoxyethane/methanol (600 mL) were heated to 70° C. for 24 hours. The mixture was concentrated. Ether was added, and the mixture was filtered and concentrated.

Example 3D (2-(4-chlorophenyl)-4,4-dimethylcyclohex-1-enyl)methanol

To a mixture of LiBH$_4$ (13 g), EXAMPLE 3C (53.8 g) and ether (400 mL), methanol (25 mL) was added slowly by syringe. The mixture was stirred at room temperature for 24 hours. The mixture was quenched with 1N HCl with ice-cooling. The mixture was diluted with water and extracted by ether (3×100 mL). The extracts were dried, and concentrated. The concentrate was chromatographed on silica gel with 0-30% ethyl acetate/hexanes.

Example 3E tert-butyl 4-((2-(4-chlorophenyl)-4,4-dimethylcyclohex-1-enyl)methyl)piperazine-1-carboxylate Mesyl chloride (7.5 mL) was added via syringe to EXAMPLE 3D (29.3 g) and triethylamine (30 mL) in CH$_2$Cl$_2$ (500 mL) at 0° C., and the mixture was stirred for 1 minute. N-t-butoxycarbonylpiperazine (25 g) was added and the mixture was stirred at room temperature for 24 hours. The suspension was washed with brine, dried, and concentrated. The concentrate was chromatographed on silica gel with 10-20% ethyl acetate/hexanes.

Example 3F 1-((2-(4-chlorophenyl)-4,4-dimethylcyclohex-1-enyl)methyl)piperazine This EXAMPLE was prepared by substituting EXAMPLE 3E for EXAMPLE 1A in EXAMPLE 1B.

Example 3G ethyl 4-(4-((2-(4-chlorophenyl)-4,4-dimethylcyclohex-1-enyl)methyl)piperazin-1-yl)-2-(2-methyl-1H-indol-5-yloxy)benzoate EXAMPLE 3F (1008 mg), EXAMPLE 3A (900 mg), and $HK_2PO_4$ (550 mg) were stirred in DMSO (7 mL) at 140° C. for 24 hours. The mixture was diluted with ethyl acetate, washed three times with water, washed with brine, dried, and concentrated. The concentrate was chromatographed on silica gel with 30% ethyl acetate/hexanes.

Example 3H 4-(4-((2-(4-chlorophenyl)-4,4-dimethylcyclohex-1-enyl)methyl)piperazin-1-yl)-2-(2-methyl-1H-indol-5-yloxy)benzoic acid This EXAMPLE was prepared by substituting EXAMPLE 3G for EXAMPLE 1E in EXAMPLE 1F.

Example 3I 4-(1-methylpiperidin-4-ylamino)-3-nitrobenzenesulfonamide

This EXAMPLE was prepared by substituting 4-amino-N-methylpiperidine for 3-(N-morpholinyl)-1-propylamine in EXAMPLE 4A.

Example 3J 4-(4-((2-(4-chlorophenyl)-4,4-dimethylcyclohex-1-en-1-yl)methyl)piperazin-1-yl)-2-((2-methyl-1H-indol-5-yl)oxy)-N-((4-((1-methylpiperidin-4-yl)amino)-3-nitrophenyl)sulfonyl)benzamide This EXAMPLE was prepared by substituting EXAMPLE 3H for EXAMPLE 1F and EXAMPLE 3I for EXAMPLE 1G in EXAMPLE 1H. $^1$H NMR (300 MHz, DMSO-$d_6$) δ 10.98 (s, 1H), 10.50 (br s, 1H), 8.55 (dd, 1H), 8.17 (d, 1H), 7.88 (dd, 1H), 7.51 (d, 1H), 7.34 (d, 2H), 7.24 (d, 1H), 7.14 (d, 1H), 7.05 (d, 2H), 7.00 (d, 1H), 6.72 (d, 1H), 6.55 (d, 1H), 6.08 (d, 2H), 3.85 (m, 1H), 3.45 (m, 4H), 2.98 (br s, 4H), 2.85 (m, 2H), 2.71 (br s, 2H), 2.63 (s, 2H), 2.38 (s, 2H), 2.15 (m, 6H), 1.95 (m, 4H), 1.80 (m, 2H), 1.38 (m, 2H), 0.92 (s, 6H).

Example 4

4-(4-((2-(4-chlorophenyl)-4,4-dimethylcyclohex-1-en-1-yl)methyl)piperazin-1-yl)-2-((2-methyl-1H-indol-5-yl)oxy)-N-((4-((3-morpholin-4-ylpropyl)amino)-3-nitrophenyl)sulfonyl)benzamide

Example 4A 4-(3-morpholinopropylamino)-3-nitrobenzenesulfonamide

4-Fluoro-3-nitrobenzenesulfonamide (550 mg), 3-(N-morpholinyl)-1-propylamine (1.00 g), and triethylamine (1 g) were stirred in THF (30 mL) for 24 hours. The mixture was diluted with ethyl acetate, washed with $NaH_2PO_4$ solution and brine, and dried ($Na_2SO_4$), filtered and concentrated. The product was triturated from ethyl acetate.

Example 4B 4-(4-((2-(4-chlorophenyl)-4,4-dimethylcyclohex-1-en-1-yl)methyl)piperazin-1-yl)-2-((2-methyl-1H-indol-5-yl)oxy)-N-((4-((3-morpholin-4-ylpropyl)amino)-3-nitrophenyl)sulfonyl)benzamide This EXAMPLE was prepared by substituting EXAMPLE 4A for EXAMPLE 1F and EXAMPLE 3H for EXAMPLE 1G in EXAMPLE 1H. $^1$H NMR (300 MHz, DMSO-$d_6$) δ 10.98 (m, 2H), 8.80 (dd, 1H), 8.58 (d, 1H), 7.82 (dd, 1H), 7.50 (d, 1H), 7.34 (d, 2H), 7.27 (d, 1H), 7.05 (m, 4H), 6.75 (d, 1H), 6.62 (d, 1H), 6.10 (d, 1H), 3.60 (m, 4H), 3.45 (m, 2H), 3.01 (br s, 4H), 2.71 (br s, 3H), 2.38 (m, 8H), 2.14 (br s, 6H), 1.95 (m, 2H), 1.81 (m, 2H), 1.38 (m, 2H), 0.92 (s, 6H).

Example 5

4-(4-((4'-chloro-1,1'-biphenyl-2-yl)methyl)piperazin-1-yl)-2-(2-chlorophenoxy)-N-((3-nitro-4-((tetrahydro-2H-pyran-4-ylmethyl)amino)phenyl)sulfonyl)benzamide

Example 5A methyl 4-(4-((4'-chlorobiphenyl-2-yl)methyl)piperazin-1-yl)-2-(2-chlorophenoxy)benzoate This EXAMPLE was prepared by substituting 2-chlorophenol for EXAMPLE 1D in EXAMPLE 1E.

Example 5B 4-(4-((4'-chlorobiphenyl-2-yl)methyl)piperazin-1-yl)-2-(2-chlorophenoxy)benzoic acid This EXAMPLE was prepared by substituting EXAMPLE 5A for EXAMPLE 1E in EXAMPLE 1F.

Example 5C 4-(4-((4'-chloro-1,1'-biphenyl-2-yl)methyl)piperazin-1-yl)-2-(2-chlorophenoxy)-N-((3-nitro-4-((tetrahydro-2H-pyran-4-ylmethyl)amino)phenyl)sulfonyl)benzamide This EXAMPLE was prepared by substituting EXAMPLE 5B for EXAMPLE 1F in EXAMPLE 1H. The crude product was purified by preparative HPLC using a 250×50 mm C18 column and eluting with 20-100% CH₃CN vs. 0.1% trifluoroacetic acid in water, giving the product as a trifluoroacetate salt. $^1$H NMR (300 MHz, DMSO-d$_6$) δ 11.77 (br s, 1H), 9.58 (v br s, 1H), 8.63 (t, 1H), 8.46 (d, 1H), 7.79 (dd, 1H), 7.71 (br s, 1H), 7.52 (m, 5H), 7.35 (m, 4H), 7.15 (d, 1H), 7.13 (m, 1H), 6.99 (m, 1H), 6.78 (dd, 1H), 6.65 (d, 1H), 6.40 (s, 1H), 4.35 (v br s, 1H), 3.90 (m, 2H), 3.80-2.80 (v br m, 7H), 3.36 (m, 4H), 3.27 (m, 2H), 1.90 (m, 1H), 1.63 (m, 2H), 1.28 (m, 2H).

Example 6

4-(4-((4'-chloro-1,1'-biphenyl-2-yl)methyl)piperazin-1-yl)-2-(3-chlorophenoxy)-N-((3-nitro-4-((tetrahydro-2H-pyran-4-ylmethyl)amino)phenyl)sulfonyl)benzamide

Example 6A methyl 4-(4-((4'-chlorobiphenyl-2-yl)methyl)piperazin-1-yl)-2-(3-chlorophenoxy)benzoate This EXAMPLE was prepared by substituting 3-chlorophenol for EXAMPLE 1D in EXAMPLE 1E.

Example 6B 4-(4-((4'-chlorobiphenyl-2-yl)methyl)piperazin-1-yl)-2-(3-chlorophenoxy)benzoic acid This EXAMPLE was prepared by substituting EXAMPLE 6A for EXAMPLE 1E in EXAMPLE 1F.

Example 6C 4-(4-((4'-chloro-1,1'-biphenyl-2-yl)methyl)piperazin-1-yl)-2-(3-chlorophenoxy)-N-((3-nitro-4-((tetrahydro-2H-pyran-4-ylmethyl)amino)phenyl)sulfonyl)benzamide This EXAMPLE was prepared by substituting EXAMPLE 6B for EXAMPLE 5B in EXAMPLE 5C. $^1$H NMR (300 MHz, DMSO-d$_6$) δ 11.85 (br s, 1H), 9.60 (v br s, 1H), 8.63 (t, 1H), 8.43 (d, 1H), 7.72 (dd, 1H), 7.70 (br s, 1H), 7.50 (m, 5H), 7.40 (d, 2H), 7.35 (m, 1H), 7.19 (dd, 1H), 7.14 (d, 1H), 6.95 (m, 1H), 6.80 (dd, 1H), 6.72 (m, 1H), 6.70 (m, 1H), 6.56 (d, 1H), 4.35 (v br s, 1H), 3.90 (m, 2H), 3.80-2.80 (v br m, 7H), 3.36 (m, 4H), 3.27 (m, 2H), 1.90 (m, 1H), 1.63 (m, 2H), 1.28 (m, 2H).

Example 7

4-(4-((4'-chloro-1,1'-biphenyl-2-yl)methyl)piperazin-1-yl)-2-(4-chlorophenoxy)-N-((3-nitro-4-((tetrahydro-2H-pyran-4-ylmethyl)amino)phenyl)sulfonyl)benzamide

Example 7A methyl 4-(4-((4'-chlorobiphenyl-2-yl)methyl)piperazin-1-yl)-2-(4-chlorophenoxy)benzoate This EXAMPLE was prepared by substituting 4-chlorophenol for EXAMPLE 1D in EXAMPLE 1E.

Example 7B 4-(4-((4'-chlorobiphenyl-2-yl)methyl)piperazin-1-yl)-2-(4-chlorophenoxy)benzoic acid This EXAMPLE was prepared by substituting EXAMPLE 7A for EXAMPLE 1E in EXAMPLE 1F.

Example 7C 4-(4-((4'-chloro-1,1'-biphenyl-2-yl)methyl)piperazin-1-yl)-2-(4-chlorophenoxy)-N-((3-nitro-4-((tetrahydro-2H-pyran-4-ylmethyl)amino)phenyl)sulfonyl)benzamide This EXAMPLE was prepared by substituting EXAMPLE 7B for EXAMPLE 5B in EXAMPLE 5C. $^1$H NMR (300 MHz, DMSO-d$_6$) δ 11.81 (br s, 1H), 9.58 (v br s, 1H), 8.63 (t, 1H), 8.46 (d, 1H), 7.73 (dd, 1H), 7.71 (br s, 1H), 7.50 (m, 5H), 7.38 (d, 2H), 7.33 (m, 1H), 7.25 (m, 2H), 7.15 (d, 1H), 6.79 (m, 3H), 6.50 (d, 1H), 4.35 (v br s, 1H), 3.90 (m, 2H), 3.80-2.80 (v br m, 7H), 3.36 (m, 4H), 3.27 (m, 2H), 1.90 (m, 1H), 1.63 (m, 2H), 1.28 (m, 2H).

Example 8

4-(4-((4'-chloro-1,1'-biphenyl-2-yl)methyl)piperazin-1-yl)-2-(3-nitrophenoxy)-N-((3-nitro-4-((tetrahydro-2H-pyran-4-ylmethyl)amino)phenyl)sulfonyl)benzamide

Example 8A methyl 4-(4-((4'-chlorobiphenyl-2-yl)methyl)piperazin-1-yl)-2-(3-nitrophenoxy)benzoate This EXAMPLE was prepared by substituting 3-nitrophenol for EXAMPLE 1D in EXAMPLE 1E.

Example 8B 4-(4-((4'-chlorobiphenyl-2-yl)methyl)piperazin-1-yl)-2-(3-nitrophenoxy)benzoic acid This EXAMPLE was prepared by substituting EXAMPLE 8A for EXAMPLE 1E in EXAMPLE 1F.

Example 8C 4-(4-((4'-chloro-1,1'-biphenyl-2-yl)methyl)piperazin-1-yl)-2-(3-nitrophenoxy)-N-((3-nitro-4-((tetrahydro-2H-pyran-4-ylmethyl)amino)phenyl)sulfonyl)benzamide This EXAMPLE was prepared by substituting EXAMPLE 8B for EXAMPLE 5B in EXAMPLE 5C. $^1$H NMR (300 MHz, DMSO-d$_6$) δ 11.81 (br s, 1H), 9.59 (v br s, 1H), 8.60 (t, 1H), 8.39 (d, 1H), 7.70 (m, 3H), 7.50 (m, 6H), 7.38 (m, 4H), 7.23 (m, 1H), 7.10 (d, 1H), 6.85 (dd, 1H), 6.63 (d, 1H), 4.35 (v br s, 1H), 3.90 (m, 2H), 3.80-2.80 (v br m, 7H), 3.36 (m, 4H), 3.27 (m, 2H), 1.90 (m, 1H), 1.63 (m, 2H), 1.28 (m, 2H).

Example 9

4-(4-((4'-chloro-1,1'-biphenyl-2-yl)methyl)piperazin-1-yl)-2-(3-(hydroxymethyl)phenoxy)-N-((4-((3-morpholin-4-ylpropyl)amino)-3-nitrophenyl)sulfonyl)benzamide

Example 9A methyl 4-(4-((4'-chlorobiphenyl-2-yl)methyl)piperazin-1-yl)-2-(3-(hydroxymethyl)phenoxy)benzoate This EXAMPLE was prepared by substituting 3-(hydroxymethyl)phenol for EXAMPLE 1D in EXAMPLE 1E.

Example 9B 4-(4-((4'-chlorobiphenyl-2-yl)methyl)piperazin-1-yl)-2-(3-(hydroxymethyl)phenoxy)benzoic acid This EXAMPLE was prepared by substituting EXAMPLE 9A for EXAMPLE 1E in EXAMPLE 1F.

Example 9C 4-(4-((4'-chloro-1,1'-biphenyl-2-yl)methyl)piperazin-1-yl)-2-(3-(hydroxymethyl)phenoxy)-N-((4-((3-morpholin-4-ylpropyl)amino)-3-nitrophenyl)sulfonyl)benzamide This EXAMPLE was prepared by substituting EXAMPLE 9B for EXAMPLE 1F and EXAMPLE 4A for EXAMPLE 1G in EXAMPLE 1H, except that the purification was performed by HPLC according to EXAMPLE 5C. $^1$H NMR (300 MHz, DMSO-$d_6$) δ 11.63 (br s, 1H), 9.60 (v br s, 2H), 8.70 (t, 1H), 8.50 (d, 1H), 7.80 (dd, 1H), 7.67 (br s, 1H), 7.50 (m, 5H), 7.40 (m, 2H), 7.35 (br s, 1H), 7.20 (m, 2H), 6.95 (d, 1H), 6.75 (m, 3H), 6.40 (s, 1H), 4.40 (s, 2H), 4.35-2.80 (m, 22H), 1.98 (m, 2H).

Example 10

4-(4-((4'-chloro-1,1'-biphenyl-2-yl)methyl)piperazin-1-yl)-2-(2-chlorophenoxy)-N-((4-((3-morpholin-4-ylpropyl)amino)-3-nitrophenyl)sulfonyl)benzamide This EXAMPLE was prepared by substituting EXAMPLE 5B for EXAMPLE 1F and EXAMPLE 4A for EXAMPLE 1G in EXAMPLE 1H, except that the purification was performed by HPLC according to EXAMPLE 5C. $^1$H NMR (300 MHz, DMSO-$d_6$) δ 11.77 (br s, 1H), 9.62 (v br s, 2H), 8.70 (t, 1H), 8.50 (d, 1H), 7.82 (dd, 1H), 7.71 (br s, 1H), 7.52 (m, 5H), 7.40 (m, 3H), 7.33 (br s, 1H), 7.16 (m, 2H), 7.02 (m, 1H), 6.79 (dd, 1H), 6.70 (d, 1H), 6.40 (s, 1H), 4.35-2.80 (m, 22H), 1.98 (m, 2H).

Example 11

4-(4-((4'-chloro-1,1'-biphenyl-2-yl)methyl)piperazin-1-yl)-2-(2-chlorophenoxy)-N-((4-((3-(dimethylamino)propyl)amino)-3-nitrophenyl)sulfonyl)benzamide

Example 11A 4-(3-(dimethylamino)propylamino)-3-nitrobenzenesulfonamide

This EXAMPLE was prepared by substituting 3-(dimethylamino)-1-propylamine for 3-(N-morpholinyl)-1-propylamine in EXAMPLE 4A.

Example 11B 4-(4-((4'-chloro-1,1'-biphenyl-2-yl)methyl)piperazin-1-yl)-2-(2-chlorophenoxy)-N-((4-((3-(dimethylamino)propyl)amino)-3-nitrophenyl)sulfonyl)benzamide This EXAMPLE was prepared by substituting EXAMPLE 5B for EXAMPLE 1F and EXAMPLE 11A for EXAMPLE 1G in EXAMPLE 1H, except that the purification was performed by HPLC according to EXAMPLE 5C. $^1$H NMR (300 MHz, DMSO-$d_6$) δ 11.77 (br s, 1H), 9.38 (v br s, 2H), 8.70 (t, 1H), 8.50 (d, 1H), 7.82 (dd, 1H), 7.65 (br s, 1H), 7.52 (m, 5H), 7.40 (m, 3H), 7.33 (br s, 1H), 7.16 (m, 2H), 7.02 (m, 1H), 6.79 (dd, 1H), 6.70 (d, 1H), 6.40 (s, 1H), 4.35-2.80 (m, 12H), 2.80 (s, 3H), 2.78 (s, 3H), 1.98 (m, 2H).

Example 12

4-(4-((4'-chloro-1,1'-biphenyl-2-yl)methyl)piperazin-1-yl)-2-(3-chlorophenoxy)-N-((4-((3-morpholin-4-ylpropyl)amino)-3-nitrophenyl)sulfonyl)benzamide This EXAMPLE was prepared by substituting EXAMPLE 6B for EXAMPLE 1F and EXAMPLE 4A for EXAMPLE 1G in EXAMPLE 1H, except that the purification was performed by HPLC according to EXAMPLE 5C. $^1$H NMR (300 MHz, DMSO-$d_6$) δ 11.85 (br s, 1H), 9.63 (v br s, 2H), 8.66 (t, 1H), 8.43 (d, 1H), 7.78 (dd, 1H), 7.67 (br s, 1H), 7.50 (m, 5H), 7.40 (d, 2H), 7.35 (m, 1H), 7.20 (dd, 1H), 7.14 (d, 1H), 6.95 (m, 1H), 6.80 (dd, 1H), 6.72 (m, 1H), 6.70 (m, 1H), 6.53 (s, 1H), 4.35-2.80 (m, 22H), 1.98 (m, 2H).

Example 13

4-(4-((4'-chloro-1,1'-biphenyl-2-yl)methyl)piperazin-1-yl)-2-(4-chlorophenoxy)-N-((4-((3-morpholin-4-ylpropyl)amino)-3-nitrophenyl)sulfonyl)benzamide This EXAMPLE was prepared by substituting EXAMPLE 7B for EXAMPLE 1F and EXAMPLE 4A for EXAMPLE 1G in EXAMPLE 1H, except that the purification was performed by HPLC according to EXAMPLE 5C. $^1$H NMR (300 MHz, DMSO-$d_6$) δ 11.81 (br s, 1H), 9.63 (v br s, 2H), 8.70 (t, 1H), 8.50 (d, 1H), 7.80 (dd, 1H), 7.69 (br s, 1H), 7.50 (m, 5H), 7.38

(d, 2H), 7.33 (m, 1H), 7.25 (m, 2H), 7.15 (d, 1H), 6.79 (m, 3H), 6.50 (d, 1H), 4.35-2.80 (m, 22H), 1.98 (m, 2H).

Example 14

4-(4-((4'-chloro-1,1'-biphenyl-2-yl)methyl)piperazin-1-yl)-2-(3-chlorophenoxy)-N-((4-((3-(dimethylamino)propyl)amino)-3-nitrophenyl)sulfonyl)benzamide This EXAMPLE was prepared by substituting EXAMPLE 6B for EXAMPLE 1F and EXAMPLE 11A for EXAMPLE 1G in EXAMPLE 1H, except that the purification was performed by HPLC according to EXAMPLE 5C. $^1$H NMR (300 MHz, DMSO-$d_6$) δ 11.85 (br s, 1H), 9.63 (v br s, 2H), 8.70 (t, 1H), 8.45 (d, 1H), 7.78 (dd, 1H), 7.70 (br s, 1H), 7.50 (m, 5H), 7.40 (d, 2H), 7.35 (m, 1H), 7.20 (dd, 1H), 7.14 (d, 1H), 6.95 (m, 1H), 6.80 (dd, 1H), 6.72 (m, 1H), 6.70 (m, 1H), 6.56 (s, 1H), 4.35-2.80 (m, 12H), 2.52 (s, 3H), 2.50 (s, 3H), 2.00 (m, 2H).

Example 15

4-(4-((4'-chloro-1,1'-biphenyl-2-yl)methyl)piperazin-1-yl)-2-(4-chlorophenoxy)-N-((4-((3-(dimethylamino)propyl)amino)-3-nitrophenyl)sulfonyl)benzamide This EXAMPLE was prepared by substituting EXAMPLE 7B for EXAMPLE 1F and EXAMPLE 11A for EXAMPLE 1G in EXAMPLE 1H, except that the purification was performed by HPLC according to EXAMPLE 5C. $^1$H NMR (300 MHz, DMSO-$d_6$) δ 11.81 (br s, 1H), 9.38 (v br s, 1H), 8.68 (t, 1H), 8.50 (d, 1H), 7.80 (dd, 1H), 7.69 (br s, 1H), 7.50 (m, 5H), 7.40 (d, 2H), 7.33 (m, 1H), 7.25 (m, 2H), 7.15 (d, 1H), 6.80 (m, 3H), 6.46 (s, 1H), 4.35-2.80 (m, 12H), 2.81 (s, 3H), 2.79 (s, 3H), 1.98 (m, 2H).

Example 16

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((1-methyl-1H-indol-4-yl)oxy)benzamide

Example 16A 1-(triisopropylsilyl)-1H-indol-4-ol

4-Benzyloxyindole (1 g) was treated with 60% oily NaH (135 mg) and triisopropylsilyl chloride (1 g) in THF, purified by flash chromatography (98/2 ethyl acetate/hexanes), then debenzylated in ethanol (35 mL) using Pearlman's catalyst (0.19 g) and a hydrogen balloon.

Example 16B methyl 2-(1H-indol-4-yloxy)-4-(4-((4'-chlorobiphenyl-2-yl)methyl)piperazin-1-yl)benzoate This EXAMPLE was prepared by substituting EXAMPLE 16A for EXAMPLE 1D in EXAMPLE 1E. The crude material from the ether formation was desilylated using tetrabutyl ammonium fluoride in THF/water 95/5 for 1 hour prior to purification.

Example 16C methyl 4-(4-((4'-chlorobiphenyl-2-yl)methyl)piperazin-1-yl)-2-(1-methyl-1H-indol-4-yloxy)benzoate EXAMPLE 16B (148 mg), 60% oily NaH (9 mg) and methyl iodide (57 mg) in THF (1 mL) were stirred at room temperature overnight. The mixture was chromatographed on silica gel with 20% ethyl acetate in hexanes.

Example 16D 4-(4-((4'-chlorobiphenyl-2-yl)methyl)piperazin-1-yl)-2-(1-methyl-1H-indol-4-yloxy)benzoic acid This EXAMPLE was prepared by substituting EXAMPLE 16C for EXAMPLE 1E in EXAMPLE 1F.

Example 16E 4-(4-((4'-chloro-1,1'-biphenyl-2-yl)methyl)piperazin-1-yl)-N-((4-((3-(dimethylamino)propyl)amino)-3-nitrophenyl)sulfonyl)-2-((1-methyl-1H-indol-4-yl)oxy)benzamide This EXAMPLE was prepared by substituting EXAMPLE 11A for EXAMPLE 1G and EXAMPLE 16D for EXAMPLE 1F in EXAMPLE 1H, except that the purification was performed by HPLC according to EXAMPLE 5C. $^1$H NMR (300 MHz, DMSO-$d_6$) δ 11.58 (br s, 1H), 9.42 (br s, 2H), 8.64 (t, 1H), 8.44 (d, 1H), 7.77 (dd, 1H), 7.66 (br s, 1H), 7.50 (m, 5H), 7.37 (d, 2H), 7.30 (m, 1H), 7.25 (d, 1H), 7.19 (d, 1H), 7.06 (d, 1H), 7.00 (dd, 1H), 6.75 (dd, 1H), 6.40 (d, 1H), 6.38 (s, 1H), 6.23 (d, 1H), 4.35-2.80 (m, 12H), 3.80 (s, 3H), 2.79 (s, 3H), 2.77 (s, 3H), 1.96 (m, 2H).

Example 17

2-(3-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide

Example 17A methyl 2-(3-acetamidophenoxy)-4-(4-((4'-chlorobiphenyl-2-yl)methyl)piperazin-1-yl)benzoate This EXAMPLE was prepared by substituting 3-acetamidophenol for EXAMPLE 1D in EXAMPLE 1E.

Example 17B 2-(3-acetamidophenoxy)-4-(4-((4'-chlorobiphenyl-2-yl)methyl)piperazin-1-yl)benzoic acid This EXAMPLE was prepared by substituting EXAMPLE 17A for EXAMPLE 1E in EXAMPLE 1F.

Example 17C 2-(3-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide This EXAMPLE was prepared by substituting EXAMPLE 17B for EXAMPLE 1F in EXAMPLE 1H. $^1$H NMR (300

MHz, DMSO-d$_6$) δ 11.48 (s, 1H), 9.89 (s, 1H), 8.59 (m, 1H), 8.50 (d, 1H), 7.71 (dd, 1H), 7.47 (m, 6H), 7.36 (m, 2H), 7.24 (m, 2H), 7.14 (m, 3H), 6.75 (dd, 1H), 6.50 (dd, 1H), 6.39 (d, 1H), 3.86 (dd, 2H), 3.37 (m, 2H), 3.30 (m, 6H), 3.16 (m, 4H), 2.35 (s, 4H), 2.00 (s, 3H), 1.89 (m, 1H), 1.63 (dd, 2H), 1.27 (m, 2H).

Example 18

2-(4-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide Example 18A methyl 2-(4-(tert-butoxycarbonylamino)phenoxy)-4-(4-((4'-chlorobiphenyl-2-yl)methyl)piperazin-1-yl)benzoate This EXAMPLE was prepared by substituting N-tert-butoxycarbonyl-4-aminophenol for EXAMPLE 1D in EXAMPLE 1E.

Example 18B 2-(4-(tert-butoxycarbonylamino)phenoxy)-4-(4-((4'-chlorobiphenyl-2-yl)methyl)piperazin-1-yl)benzoic acid This EXAMPLE was prepared by substituting EXAMPLE 18A for EXAMPLE 1E in EXAMPLE 1F.

Example 18C tert-butyl 4-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)phenylcarbamate This EXAMPLE was prepared by substituting EXAMPLE 18B for EXAMPLE 1F in EXAMPLE 1H.

Example 18D 2-(4-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide This EXAMPLE was prepared by substituting EXAMPLE 18C for EXAMPLE 1A in EXAMPLE 1B. $^1$H NMR (300 MHz, DMSO-d$_6$) δ ppm 11.41 (s, 1H), 9.54 (s, 1H), 8.66 (t, 1H), 8.59 (d, 1H), 7.86 (dd, 1H), 7.67 (m, 1H), 7.51 (dd, 5H), 7.38 (d, 2H), 7.31 (m, 1H), 7.25 (d, 1H), 6.82 (m, 4H), 6.69 (dd, 1H), 6.24 (m, 1H), 4.26 (s, 2H), 3.85 (dd, 2H), 3.35 (m, 4H), 3.26 (td, 4H), 3.04 (m, 4H), 2.81 (m, 2H), 1.91 (m, 1H), 1.62 (dd, 2H), 1.26 (m, 2H).

Example 19

2-(3-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide Example 19A methyl 2-(3-(tert-butoxycarbonylamino)phenoxy)-4-(4-((4'-chlorobiphenyl-2-yl)methyl)piperazin-1-yl)benzoate This EXAMPLE was prepared by substituting N-tert-butoxycarbonyl-3-aminophenol for EXAMPLE 1D in EXAMPLE 1E.

Example 19B 2-(3-(tert-butoxycarbonylamino)phenoxy)-4-(4-((4'-chlorobiphenyl-2-yl)methyl)piperazin-1-yl)benzoic acid This EXAMPLE was prepared by substituting EXAMPLE 19A for EXAMPLE 1E in EXAMPLE 1F.

Example 19C tert-butyl 3-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)phenylcarbamate This EXAMPLE was prepared by substituting EXAMPLE 19B for EXAMPLE 1F in EXAMPLE 1H.

Example 19D 2-(3-aminophenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide This EXAMPLE was prepared by substituting EXAMPLE 19C for EXAMPLE 1A in EXAMPLE 1B. $^1$H NMR (300 MHz, DMSO-d$_6$) δ ppm 11.39 (s, 1H), 9.50 (s, 1H), 8.64 (t, 1H), 8.54 (d, 1H), 7.75 (dd, 2H), 7.51 (d, 5H), 7.38 (m, 2H), 7.31 (m, 1H), 7.16 (d, 1H), 6.92 (t, 1H), 6.73 (dd, 1H), 6.38 (d, 1H), 6.28 (m, 1H), 6.09 (m, 1H), 6.02 (d, 1H), 5.24 (m, 1H), 4.36 (m, 1H), 3.86 (dd, 2H), 3.72 (m, 1H), 3.28 (m, 8H), 3.20 (m, 1H), 3.04 (m, 3H), 2.85 (m, 1H), 1.90 (m, 1H), 1.63 (dd, 2H), 1.27 (m, 2H).

Example 20

4-(4-((4'-chloro-1,1'-biphenyl-2-yl)methyl)piperazin-1-yl)-2-(3-methoxyphenoxy)-N-((3-nitro-4-((tetrahydro-2H-pyran-4-ylmethyl)amino)phenyl)sulfonyl)benzamide Example 20A methyl 4-(4-((4'-chlorobiphenyl-2-yl)methyl)piperazin-1-yl)-2-(3-methoxyphenoxy)benzoate This EXAMPLE was prepared by substituting 3-methoxyphenol for EXAMPLE 1D in EXAMPLE 1E.

Example 20B 4-(4-((4'-chlorobiphenyl-2-yl)methyl)piperazin-1-yl)-2-(3-methoxyphenoxy)benzoic acid This EXAMPLE was prepared by substituting EXAMPLE 20A for EXAMPLE 1E in EXAMPLE 1F.

Example 20C 4-(4-((4'-chloro-1,1'-biphenyl-2-yl)methyl)piperazin-1-yl)-2-(3-methoxyphenoxy)-N-((3-nitro-4-((tetrahydro-2H-pyran-4-ylmethyl)amino)phenyl)sulfonyl)benzamide This EXAMPLE was prepared by substituting EXAMPLE 20B for EXAMPLE 1F in EXAMPLE 1H. $^1$H NMR (300 MHz, DMSO-$d_6$) δ ppm 11.57 (s, 1H), 8.63 (t, 1H), 8.47 (d, 1H), 7.76 (dd, 1H), 7.47 (m, 6H), 7.36 (m, 2H), 7.24 (m, 1H), 7.11 (m, 2H), 6.76 (dd, 1H), 6.53 (ddd, 1H), 6.35 (m, 3H), 3.86 (m, 2H), 3.66 (s, 3H), 3.32 (m, 6H), 3.17 (m, 4H), 2.36 (m, 4H), 1.92 (m, 1H), 1.64 (dd, 2H), 1.27 (m, 2H).

Example 21

4-(4-((4'-chloro-1,1'-biphenyl-2-yl)methyl)piperazin-1-yl)-2-(3-(dimethylamino)phenoxy)-N-((3-nitro-4-((tetrahydro-2H-pyran-4-ylmethyl)amino)phenyl)sulfonyl)benzamide

Example 21A methyl 4-(4-((4'-chlorobiphenyl-2-yl)methyl)piperazin-1-yl)-2-(3-(dimethylamino)phenoxy)benzoate This EXAMPLE was prepared by substituting 3-(dimethylamino)phenol for EXAMPLE 1D in EXAMPLE 1E.

Example 21B 4-(4-((4'-chlorobiphenyl-2-yl)methyl)piperazin-1-yl)-2-(3-(dimethylamino)phenoxy)benzoic acid This EXAMPLE was prepared by substituting EXAMPLE 21A for EXAMPLE 1E in EXAMPLE 1F.

Example 21C 4-(4-((4'-chloro-1,1'-biphenyl-2-yl)methyl)piperazin-1-yl)-2-(3-(dimethylamino)phenoxy)-N-((3-nitro-4-((tetrahydro-2H-pyran-4-ylmethyl)amino)phenyl)sulfonyl)benzamide This EXAMPLE was prepared by substituting EXAMPLE 21B for EXAMPLE 1F in EXAMPLE 1H. $^1$H NMR (300 MHz, DMSO-$d_6$) δ ppm 11.36 (s, 1H), 8.63 (t, 1H), 8.51 (d, 1H), 7.79 (dd, 1H), 7.46 (m, 6H), 7.36 (m, 2H), 7.24 (m, 1H), 7.15 (d, 1H), 7.04 (t, 1H), 6.72 (m, 1H), 6.39 (dd, 1H), 6.33 (d, 1H), 6.24 (t, 1H), 6.10 (dd, 1H), 3.86 (dd, 2H), 3.32 (m, 6H), 3.13 (m, 4H), 2.83 (s, 6H), 2.34 (m, 4H), 1.90 (m, 1H), 1.63 (dd, 2H), 1.27 (m, 2H).

Example 22

4-(4-((4'-chloro-1,1'-biphenyl-2-yl)methyl)piperazin-1-yl)-2-(3-cyanophenoxy)-N-((3-nitro-4-((tetrahydro-2H-pyran-4-ylmethyl)amino)phenyl)sulfonyl)benzamide

Example 22A methyl 4-(4-((4'-chlorobiphenyl-2-yl)methyl)piperazin-1-yl)-2-(3-cyanophenoxy)benzoate This EXAMPLE was prepared by substituting 3-cyanophenol for EXAMPLE 1D in EXAMPLE 1E.

Example 22B 4-(4-((4'-chlorobiphenyl-2-yl)methyl)piperazin-1-yl)-2-(3-cyanophenoxy)benzoic acid A mixture of EXAMPLE 22A (0.081 g) in pyridine (2 mL) in a 10 mL microwave vial equipped with a magnetic stir bar was treated with LiI (0.402 g), flushed with nitrogen and heated in a CEM microwave reactor at 120° C. for 30 minutes. The mixture was concentrated, acidified with 1N HCl, extracted with ethyl acetate and dried (MgSO$_4$), filtered and concentrated. The concentrate was purified by column chromatography on silica gel, eluting with a gradient of 0-10% methanol in dichloromethane.

Example 22C 4-(4-((4'-chloro-1,1'-biphenyl-2-yl)methyl)piperazin-1-yl)-2-(3-cyanophenoxy)-N-((3-nitro-4-((tetrahydro-2H-pyran-4-ylmethyl)amino)phenyl)sulfonyl)benzamide This EXAMPLE was prepared by substituting EXAMPLE 22B for EXAMPLE 1F in EXAMPLE 1H. $^1$H NMR (300 MHz, DMSO-$d_6$) δ ppm 11.78 (s, 1H), 8.62 (t, 1H), 8.41 (d, 1H), 7.72 (dd, 1H), 7.48 (m, 6H), 7.34 (m, 4H), 7.25 (m, 1H), 7.08 (m, 3H), 6.82 (dd, 1H), 6.54 (d, 1H), 3.87 (dd, 2H), 3.33 (m, 6H), 3.22 (m, 4H), 2.38 (m, 4H), 1.93 (m, 1H), 1.65 (dd, 2H), 1.29 (m, 2H).

Example 23

4-(4-((4'-chloro-1,1'-biphenyl-2-yl)methyl)piperazin-1-yl)-2-((2-methyl-1,3-benzothiazol-6-yl)oxy)-N-((3-nitro-4-((tetrahydro-2H-pyran-4-ylmethyl)amino)phenyl)sulfonyl)benzamide

Example 23A methyl 4-(4-((4'-chlorobiphenyl-2-yl)methyl)piperazin-1-yl)-2-(2-methylbenzo[d]thiazol-6-yloxy)benzoate This EXAMPLE was prepared by substituting 2-methylbenzothiazol-6-ol for EXAMPLE 1D in EXAMPLE 1E.

Example 23B 4-(4-((4'-chlorobiphenyl-2-yl)methyl)piperazin-1-yl)-2-(2-methylbenzo[d]thiazol-6-yloxy)benzoic acid This EXAMPLE was prepared by substituting EXAMPLE 23A for EXAMPLE 1E in EXAMPLE 1F.

Example 23C 4-(4-((4'-chloro-1,1'-biphenyl-2-yl)methyl)piperazin-1-yl)-2-((2-methyl-1,3-benzothiazol-6-yl)oxy)-N-((3-nitro-4-((tetrahydro-2H-pyran-4-ylmethyl)amino)phenyl)sulfonyl)benzamide This EXAMPLE was prepared by substituting EXAMPLE 23B for EXAMPLE 1F in EXAMPLE 1H. $^1$H NMR (300 MHz, DMSO-$d_6$) δ 11.78 (s, 1H), 8.56 (t, 1H), 8.40 (d, 1H), 7.71 (d, 2H), 7.64 (dd, 1H), 7.51 (m, 5H), 7.37 (d, 2H), 7.32 (m, 1H), 7.28 (d, 1H), 6.98 (dd, 1H), 6.79 (dd, 1H), 6.51 (m, 1H), 4.33 (br s, 1H), 3.87 (dd, 2H), 3.69 (br s, 2H), 3.28 (m, 4H), 3.04 (br s, 2H), 2.84 (br s, 1H), 2.74 (s, 3H), 2.49 (m, 4H), 1.90 (br s, 1H), 1.63 (dd, 2H), 1.28 (m, 3H).

Example 24

4-(4-((4'-chloro-1,1'-biphenyl-2-yl)methyl)piperazin-1-yl)-2-((2-methyl-1,3-benzothiazol-5-yl)oxy)-N-((4-((3-morpholin-4-ylpropyl)amino)-3-nitrophenyl)sulfonyl)benzamide

Example 24A methyl 4-(4-((4'-chlorobiphenyl-2-yl)methyl)piperazin-1-yl)-2-(2-methylbenzo[d]thiazol-5-yloxy)benzoate This EXAMPLE was prepared by substituting 2-methylbenzothiazol-5-ol for EXAMPLE 1D in EXAMPLE 1E.

Example 24B 4-(4-((4'-chlorobiphenyl-2-yl)methyl)piperazin-1-yl)-2-(2-methylbenzo[d]thiazol-5-yloxy)benzoic acid This EXAMPLE was prepared by substituting EXAMPLE 24A for EXAMPLE 1E in EXAMPLE 1F.

Example 24C 4-(4-((4'-chloro-1,1'-biphenyl-2-yl)methyl)piperazin-1-yl)-2-((2-methyl-1,3-benzothiazol-5-yl)oxy)-N-((4-((3-morpholin-4-ylpropyl)amino)-3-nitrophenyl)sulfonyl)benzamide This EXAMPLE was prepared by substituting EXAMPLE 24B and EXAMPLE 4A for EXAMPLE 1F and EXAMPLE 1G respectively, in EXAMPLE 1H. $^1$H NMR (300 MHz, DMSO-$d_6$) δ 11.83 (s, 1H), 9.48 (br s, 1H), 8.64 (t, 1H), 8.45 (d, 1H), 7.88 (d, 1H), 7.76 (dd, 1H), 7.50 (m, 5H), 7.37 (m, 2H), 7.30 (m, 1H), 7.18 (m, 1H), 7.04 (d, 1H), 6.97 (dd, 1H), 6.78 (dd, 1H), 6.48 (br s, 1H), 4.35 (br s, 1H), 3.98 (m, 3H), 3.77 (br s, 2H), 3.60 (t, 4H), 3.49 (m, 2H), 3.15 (m, 4H), 3.04 (m, 4H), 2.75 (s, 3H), 2.56 (m, 2H), 1.94 (m, 2H).

Example 25

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-methyl-1,3-benzothiazol-5-yl)oxy)benzamide This EXAMPLE was prepared by substituting EXAMPLE 24B and EXAMPLE 11A for EXAMPLE 1F and EXAMPLE 1G respectively, in EXAMPLE 1H. $^1$H NMR (300 MHz, DMSO-$d_6$) δ 11.86 (s, 1H), 9.23 (br s, 1H), 8.63 (t, 1H), 8.46 (d, 1H), 7.88 (d, 1H), 7.77 (dd, 2H), 7.51 (m, 6H), 7.39 (m, 3H), 7.32 (br s, 1H), 7.19 (m, 1H), 7.04 (d, 1H), 6.98 (dd, 1H), 6.79 (dd, 1H), 6.49 (br s, 1H), 4.37 (br s, 1H), 3.76 (br s, 2H), 3.49 (m, 4H), 3.11 (m, 4H), 2.79 (s, 3H), 2.77 (s, 3H), 2.76 (s, 3H), 1.94 (m, 2H).

Example 26

4-(4-((4'-chloro-1,1'-biphenyl-2-yl)methyl)piperazin-1-yl)-2-(2-(3-(dimethylamino)-3-oxopropyl)phenoxy)-N-((3-nitro-4-((tetrahydro-2H-pyran-4-ylmethyl)amino)phenyl)sulfonyl)benzamide

Example 26A 3-(2-hydroxyphenyl)-N,N-dimethylpropanamide

A solution of chroman-2-one (444 mg) in THF (1 mL) was treated with dimethylamine (7.5 mL) and stirred at room temperature for 5 hours. The solution was concentrated. The concentrate was filtered through a small pad of silica gel.

Example 26B methyl 4-(4-((4'-chlorobiphenyl-2-yl)methyl)piperazin-1-yl)-2-(2-(3-(dimethylamino)-3-oxopropyl)phenoxy)benzoate This EXAMPLE was prepared by substituting EXAMPLE 26A for EXAMPLE 1D in EXAMPLE 1E.

Example 26C 4-(4-((4'-chlorobiphenyl-2-yl)methyl)piperazin-1-yl)-2-(2-(3-(dimethylamino)-3-oxopropyl)phenoxy)benzoic acid This EXAMPLE was prepared by substituting EXAMPLE 26B for EXAMPLE 1E in EXAMPLE 1F.

Example 26D 4-(4-((4'-chloro-1,1'-biphenyl-2-yl)methyl)piperazin-1-yl)-2-(2-(3-(dimethylamino)-3-oxopropyl)phenoxy)-N-((3-nitro-4-((tetrahydro-2H-pyran-4-ylmethyl)amino)phenyl)sulfonyl)benzamide This EXAMPLE was prepared by substituting EXAMPLE 26C for EXAMPLE 1F in EXAMPLE 1H. $^1$H NMR (500 MHz, DMSO-$d_6$) δ 11.74 (s, 1H), 8.65 (t, 1H), 8.44 (d, 1H), 7.73 (dd, 2H), 7.52 (m, 5H), 7.35 (d, 3H), 7.13 (dd, 2H), 6.96 (t, 1H), 6.87 (t, 1H), 6.75 (dd, 1H), 6.44 (d, 1H), 6.39 (d, 1H), 3.87 (dd, 2H), 3.67 (br, 8H), 3.34 (t, 2H), 3.28 (t, 2H), 3.00 (br, 2H), 2.91 (s, 3H), 2.79 (s, 3H), 2.74 (t, 2H), 2.55 (t, 2H), 1.91 (m, 1H), 1.64 (d, 2H), 1.29 (m, 2H).

Example 27

4-(4-((4'-chloro-1,1'-biphenyl-2-yl)methyl)piperazin-1-yl)-2-(2-(2-(dimethylamino)-2-oxoethyl)phenoxy)-N-((3-nitro-4-((tetrahydro-2H-pyran-4-ylmethyl)amino)phenyl)sulfonyl)benzamide Example 27A 2-(2-hydroxyphenyl)-N,N-dimethylacetamide This EXAMPLE was prepared by substituting benzofuran-2(3H)-one for chroman-2-one in EXAMPLE 26A.

Example 27B methyl 4-(4-((4'-chlorobiphenyl-2-yl)methyl)piperazin-1-yl)-2-(2-(2-(dimethylamino)-2-oxoethyl)phenoxy)benzoate This EXAMPLE was prepared by substituting EXAMPLE 27A for EXAMPLE 1D in EXAMPLE 1E.

Example 27C 4-(4-((4'-chlorobiphenyl-2-yl)methyl)piperazin-1-yl)-2-(2-(2-(dimethylamino)-2-oxoethyl)phenoxy)benzoic acid This EXAMPLE was prepared by substituting EXAMPLE 27B for EXAMPLE 1E in EXAMPLE 1F.

Example 27D 4-(4-((4'-chloro-1,1'-biphenyl-2-yl)methyl)piperazin-1-yl)-2-(2-(2-(dimethylamino)-2-oxoethyl)phenoxy)-N-((3-nitro-4-((tetrahydro-2H-pyran-4-ylmethyl)amino)phenyl)sulfonyl)benzamide This EXAMPLE was prepared by substituting EXAMPLE 27C for EXAMPLE 1F in EXAMPLE 1H. $^1$H NMR (400 MHz, DMSO-$d_6$) δ 8.64 (t, 1H), 8.52 (d, 1H), 7.82 (dd, 1H), 7.70 (s, 1H), 7.52 (dd, 5H), 7.37 (d, 2H), 7.33 (s, 1H), 7.19 (m, 2H), 7.14 (t, 1H), 7.03 (t, 1H), 6.70 (m, 2H), 6.23 (s, 1H), 3.86 (dd, 2H), 3.64 (s, 2H), 3.40 (br, 12H), 3.25 (t, 2H), 2.92 (s, 3H), 2.72 (s, 3H), 1.91 (s, 1H), 1.63 (d, 2H), 1.28 (m, 2H).

Example 28

4-(4-((4'-chloro-1,1'-biphenyl-2-yl)methyl)piperazin-1-yl)-2-(2-(3-(dimethylamino)propyl)phenoxy)-N-((3-nitro-4-((tetrahydro-2H-pyran-4-ylmethyl)amino)phenyl)sulfonyl)benzamide Example 28A methyl 4-(4-((4'-chlorobiphenyl-2-yl)methyl)piperazin-1-yl)-2-(2-(3-(dimethylamino)propyl)phenoxy)benzoate A solution of EXAMPLE 26B (211 mg) in THF (1.7 mL) at room temperature was treated with borane (689 μL) and stirred for 24 hours. The mixture was quenched with 1N HCl and heated at 50° C. overnight. The solution was concentrated. The concentrate was purified by flash chromatography (0-5% 7N NH$_3$ in 10% methanol/dichloromethane).

Example 28B 4-(4-((4'-chlorobiphenyl-2-yl)methyl)piperazin-1-yl)-2-(2-(3-(dimethylamino)propyl)phenoxy)benzoic acid This EXAMPLE was prepared by substituting EXAMPLE 28A for EXAMPLE 1E in EXAMPLE 1F.

Example 28C 4-(4-((4'-chloro-1,1'-biphenyl-2-yl)methyl)piperazin-1-yl)-2-(2-(3-(dimethylamino)propyl)phenoxy)-N-((3-nitro-4-((tetrahydro-2H-pyran-4-ylmethyl)amino)phenyl)sulfonyl)benzamide This EXAMPLE was prepared by substituting EXAMPLE 28B for EXAMPLE 1F in EXAMPLE 1H. $^1$H NMR (500 MHz, DMSO-$d_6$) δ 8.65 (t, 1H), 8.44 (d, 1H), 7.75 (dd, 1H), 7.51 (m, 6H), 7.39 (d, 2H), 7.32 (s, 1H), 7.16 (m, 2H), 6.98 (m, 1H), 6.90 (t, 1H), 6.76 (d, 1H), 6.48 (d, 1H), 6.37 (s, 1H), 3.87 (d, 2H), 3.35 (m, 2H), 3.29 (m, 2H), 3.07 (s, 2H), 2.79 (s, 6H), 2.61 (t, 2H), 1.94 (s, 2H), 1.64 (d, 2H), 1.30 (m, 2H).

Example 29

4-(4-((4'-chloro-1,1'-biphenyl-2-yl)methyl)piperazin-1-yl)-2-(2-(2-(dimethylamino)ethyl)phenoxy)-N-((3-nitro-4-((tetrahydro-2H-pyran-4-ylmethyl)amino)phenyl)sulfonyl)benzamide Example 29A methyl 4-(4-((4'-chlorobiphenyl-2-yl)methyl)piperazin-1-yl)-2-(2-(2-(dimethylamino)ethyl)phenoxy)benzoate This EXAMPLE was prepared by substituting EXAMPLE 27B for EXAMPLE 26B in EXAMPLE 28A.

Example 29B 4-(4-((4'-chlorobiphenyl-2-yl)methyl)piperazin-1-yl)-2-(2-(2-(dimethylamino)ethyl)phenoxy)benzoic acid This EXAMPLE was prepared by substituting EXAMPLE 29A for EXAMPLE 1E in EXAMPLE 1F.

Example 29C 4-(4-((4'-chloro-1,1'-biphenyl-2-yl)methyl)piperazin-1-yl)-2-(2-(2-(dimethylamino)ethyl)phenoxy)-N-((3-nitro-4-((tetrahydro-2H-pyran-4-ylmethyl)amino)phenyl)sulfonyl)benzamide This EXAMPLE was prepared by substituting EXAMPLE 29B for EXAMPLE 1F in EXAMPLE 1H. $^1$H NMR (400 MHz, DMSO-$d_6$) δ 8.64 (t, 1H), 8.44 (d, 1H), 7.72 (m, 2H), 7.53 (m, 5H), 7.38 (d, 2H), 7.32 (m, 1H), 7.19 (dd, 1H), 7.15 (d, 1H), 7.01 (td, 1H), 6.90 (t, 1H), 6.79 (dd, 1H), 6.49 (d, 1H), 6.42 (d, 1H), 3.88 (m, 2H), 3.60 (br, 10H), 3.35 (t, 2H), 3.29 (t, 4H), 2.97 (m, 2H), 2.81 (m, 6H), 1.92 (s, 1H), 1.65 (m, 2H), 1.30 (m, 2H).

Example 30

2-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)-N,N-dimethylbenzamide

Example 30A methyl 4-(4-((4'-chlorobiphenyl-2-yl)methyl)piperazin-1-yl)-2-(2-(dimethylcarbamoyl)phenoxy)benzoate This EXAMPLE was prepared by substituting 2-hydroxy-N,N-dimethylbenzamide for EXAMPLE 1D in EXAMPLE 1E.

Example 30B 4-(4-((4'-chlorobiphenyl-2-yl)methyl)piperazin-1-yl)-2-(2-(dimethylcarbamoyl)phenoxy)benzoic acid This EXAMPLE was prepared by substituting EXAMPLE 30A for EXAMPLE 1E in EXAMPLE 1F.

Example 30C 2-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)-N,N-dimethylbenzamide This EXAMPLE was prepared by substituting EXAMPLE 30B for EXAMPLE 1F in EXAMPLE 1H. $^1$H NMR (400 MHz, DMSO-d$_6$) δ 8.63 (t, 1H), 8.52 (d, 1H), 7.83 (dd, 1H), 7.71 (s, 1H), 7.51 (m, 5H), 7.30 (m, 5H), 7.20 (d, 1H), 7.13 (t, 1H), 6.82 (d, 1H), 6.74 (m, 1H), 6.24 (d, 1H), 4.30 (s, 1H), 3.80 (br, 11H), 3.34 (t, 2H), 3.27 (t, 2H), 2.79 (s, 3H), 2.66 (s, 3H), 1.90 (s, 1H), 1.62 (d, 2H), 1.27 (ddd, 2H).

Example 31

4-(4-((4'-chloro-1,1'-biphenyl-2-yl)methyl)piperazin-1-yl)-2-(2-((dimethylamino)methyl)phenoxy)-N-((3-nitro-4-((tetrahydro-2H-pyran-4-ylmethyl)amino)phenyl)sulfonyl)benzamide

Example 31A methyl 4-(4-((4'-chlorobiphenyl-2-yl)methyl)piperazin-1-yl)-2-(2-((dimethylamino)methyl)phenoxy)benzoate This EXAMPLE was prepared by substituting EXAMPLE 30A for EXAMPLE 26B in EXAMPLE 28A.

Example 31B 4-(4-((4'-chlorobiphenyl-2-yl)methyl)piperazin-1-yl)-2-(2-((dimethylamino)methyl)phenoxy)benzoic acid This EXAMPLE was prepared by substituting EXAMPLE 31A for EXAMPLE 1E in EXAMPLE 1F.

Example 31C 4-(4-((4'-chloro-1,1'-biphenyl-2-yl)methyl)piperazin-1-yl)-2-(2-((dimethylamino)methyl)phenoxy)-N-((3-nitro-4-((tetrahydro-2H-pyran-4-ylmethyl)amino)phenyl)sulfonyl)benzamide This EXAMPLE was prepared by substituting EXAMPLE 31B for EXAMPLE 1F in EXAMPLE 1H. $^1$H NMR (400 MHz, DMSO-d$_6$) δ 8.62 (m, 1H), 8.38 (d, 1H), 7.70 (dd, 1H), 7.61 (d, 1H), 7.51 (d, 4H), 7.39 (m, 4H), 7.33 (s, 1H), 7.15 (m, 2H), 6.97 (t, 1H), 6.84 (d, 1H), 6.61 (s, 1H), 6.43 (d, 1H), 4.33 (s, 2H), 3.88 (d, 2H), 3.55 (br, 10H), 3.35 (m, 2H), 3.29 (m, 2H), 2.78 (s, 6H), 1.92 (s, 1H), 1.64 (d, 2H), 1.31 (m, 2H).

Example 32

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-morpholin-4-ylphenoxy)benzamide

Example 32A methyl 4-(4-((4'-chlorobiphenyl-2-yl)methyl)piperazin-1-yl)-2-(3-morpholinophenoxy)benzoate This EXAMPLE was prepared by substituting 3-morpholinophenol for EXAMPLE 1D in EXAMPLE 1E.

Example 32B 4-(4-((4'-chlorobiphenyl-2-yl)methyl)piperazin-1-yl)-2-(3-morpholinophenoxy)benzoic acid This EXAMPLE was prepared by substituting EXAMPLE 32A for EXAMPLE 1E in EXAMPLE 1F.

Example 32C 4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-morpholin-4-ylphenoxy)benzamide This EXAMPLE was prepared by substituting EXAMPLE 32B for EXAMPLE 1F and EXAMPLE 11A for EXAMPLE 1G in EXAMPLE 1H. $^1$H NMR (400 MHz, DMSO-d$_6$) δ 11.61 (br s, 1H), 9.50 (br s, 1H), 8.69 (t, 1H), 8.51 (d, 1H), 7.83 (dd, 1H), 7.68 (m, 1H), 7.50 (m, 5H), 7.39 (m, 2H), 7.31 (m, 1H), 7.15 (d, 1H), 7.08 (m, 1H), 6.75 (dd, 1H), 6.59 (dd, 1H), 6.40 (m, 2H), 6.23 (m, 1H), 3.71 (m, 4H), 3.52 (m, 4H), 3.40 (m, 4H), 3.13 (m, 4H), 3.00 (m, 6H), 2.78 (s, 6H), 1.96 (m, 2H).

Example 33

4-(4-((4'-chloro-1,1'-biphenyl-2-yl)methyl)piperazin-1-yl)-2-(3-(2,4-dimethyl-1,3-thiazol-5-yl)phenoxy)-N-((4-((3-morpholin-4-ylpropyl)amino)-3-nitrophenyl)sulfonyl)benzamide

Example 33A methyl 2-(3-(benzyloxy)phenoxy)-4-(4-((4'-chlorobiphenyl-2-yl)methyl)piperazin-1-yl)benzoate This EXAMPLE was prepared by substituting 3-(benzyloxy)phenol for EXAMPLE 1D in EXAMPLE 1E.

Example 33B methyl 4-(4-((4'-chlorobiphenyl-2-yl)methyl)piperazin-1-yl)-2-(3-hydroxyphenoxy)benzoate EXAMPLE 33A (510 mg) in CH$_2$Cl$_2$ (5 mL) was cooled to 0° C., treated with 1M BBr$_3$ in CH$_2$Cl$_2$ (4 mL), and stirred at room temperature for 2 hours. The mixture was quenched with saturated NaHCO$_3$ solution and extracted with ethyl acetate. The extract was washed with water and brine, dried over Na$_2$SO$_4$ and concentrated. The concentrate was purified by flash column chromatography on silica gel with 0-30% ethyl acetate in hexane.

Example 33C methyl 4-(4-((4'-chlorobiphenyl-2-yl)methyl)piperazin-1-yl)-2-(3-(trifluoromethylsulfonyloxy)phenoxy)benzoate EXAMPLE 33B (180 mg) in THF (5 mL) was cooled to −78° C., and 0.5 mL of 1M lithium hexamethyldisilazide in THF was added. The mixture was stirred for 15 minutes then treated with 1,1,1-trifluoro-N-phenyl-N-(trifluoromethylsulfonyl)methanesulfonamide (146 mg). The mixture was warmed to room temperature overnight, quenched with saturated NH$_4$Cl solution and extracted with ethyl acetate. The extract was washed with water and brine, dried over Na$_2$SO$_4$ and concentrated.

Example 33D methyl 4-(4-((4'-chlorobiphenyl-2-yl)methyl)piperazin-1-yl)-2-(3-(2,4-dimethylthiazol-5-yl)phenoxy)benzoate EXAMPLE 33C (60 mg), 2,4-dimethyl-5-(4,4,5,5-tetramethyl-1,3,2-dioxaborolan-2-yl)thiazole (36 mg) and dichlorobis(triphenylphosphine) palladium(II) (2 mg) were dissolved in 5 mL of a dimethoxyethane:ethanol:2M Na$_2$CO$_3$ solution (7:2:2). The mixture was heated at 130° C. for 15 minutes in a microwave reactor and concentrated. The concentrate was purified by flash column chromatography with 0-30% ethyl acetate/hexanes.

Example 33E 4-(4-((4'-chlorobiphenyl-2-yl)methyl)piperazin-1-yl)-2-(3-(2,4-dimethylthiazol-5-yl)phenoxy)benzoic acid This EXAMPLE was prepared by substituting EXAMPLE 33D for EXAMPLE 1E in EXAMPLE 1F.

Example 33F 4-(4-((4'-chloro-1,1'-biphenyl-2-yl)methyl)piperazin-1-yl)-2-(3-(2,4-dimethyl-1,3-thiazol-5-yl)phenoxy)-N-((4-((3-morpholin-4-ylpropyl)amino)-3-nitrophenyl)sulfonyl)benzamide This EXAMPLE was prepared by substituting EXAMPLE 33E for EXAMPLE 1F and EXAMPLE 4A for EXAMPLE 1G in EXAMPLE 1H. $^1$H NMR (400 MHz, DMSO-d$_6$) δ 11.80 (br s, 1H), 9.67 (br s, 1H), 8.63 (t, 1H), 8.47 (d, 1H), 7.78 (dd, 1H), 7.68 (m, 1H), 7.52 (m, 5H), 7.35 (m, 4H), 7.10 (d, 1H), 7.05 (d, 1H), 6.77 (m, 3H), 6.57 (m, 1H), 3.95 (m, 2H), 3.60 (m, 6H), 3.45 (m, 6H), 3.16 (m, 4H), 3.07 (m, 4H), 2.51 (s, 3H), 2.26 (s, 3H), 1.95 (m, 2H).

Example 34

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 34A ethyl 2-(2-chlorophenoxy)-4-fluorobenzoate

This EXAMPLE was prepared by substituting 2-chlorophenol for 2-methyl-5-indolol in EXAMPLE 3A.

Example 34B ethyl 2-(2-chlorophenoxy)-4-(4-((2-(4-chlorophenyl)-4,4-dimethylcyclohex-1-enyl)methyl)piperazin-1-yl)benzoate This EXAMPLE was prepared by substituting EXAMPLE 34A for EXAMPLE 3A in EXAMPLE 3G.

Example 34C 2-(2-chlorophenoxy)-4-(4-((2-(4-chlorophenyl)-4,4-dimethylcyclohex-1-enyl)methyl)piperazin-1-yl) benzoic acid This EXAMPLE was prepared by substituting EXAMPLE 34B for EXAMPLE 1E in EXAMPLE 1F.

Example 34D 2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide This EXAMPLE was prepared by substituting EXAMPLE 34C for EXAMPLE 1F and EXAMPLE 3I for EXAMPLE 1G in EXAMPLE 1H. $^1$H NMR (500 MHz, pyridine-d$_5$) δ 8.37 (d, 1H), 8.08 (d, 1H), 7.76 (dd, 1H), 7.62 (d, 1H), 7.36 (d, 2H), 7.35 (d, 1H), 7.07 (d, 2H), 7.07-7.03 (m, 2H), 6.90 (td, 1H), 6.71 (dd, 1H), 6.55 (dd, 1H), 6.26 (d, 1H), 3.81 (m, 1H), 3.21 (m, 2H), 3.08 (m, 4H), 2.86 (m, 2H), 2.76 (s, 2H), 2.63 (s, 3H), 2.28-2.04 (m, 8H), 1.97 (s, 2H), 1.76 (m, 2H), 1.40 (t, 2H), 0.94 (s, 6H).

Example 35

4-(4-((2-(4-chlorophenyl)-4,4-dimethylcyclohex-1-en-1-yl)methyl)piperazin-1-yl)-2-(3,5-dichlorophenoxy)-N-((4-((1-methylpiperidin-4-yl)amino)-3-nitrophenyl)sulfonyl)benzamide

Example 35A ethyl 2-(3,5-dichlorophenoxy)-4-fluorobenzoate

This EXAMPLE was prepared by substituting 3,5-dichlorophenol for 2-methyl-5-indolol in EXAMPLE 3A.

Example 35B ethyl 4-(4-((2-(4-chlorophenyl)-4,4-dimethylcyclohex-1-enyl)methyl)piperazin-1-yl)-2-(3,5-dichlorophenoxy)benzoate This EXAMPLE was prepared by substituting EXAMPLE 35A for EXAMPLE 3A in EXAMPLE 3G.

Example 35C 4-(4-((2-(4-chlorophenyl)-4,4-dimethylcyclohex-1-enyl)methyl)piperazin-1-yl)-2-(3,5-dichlorophenoxy)benzoic acid This EXAMPLE was prepared by substituting EXAMPLE 35B for EXAMPLE 1E in EXAMPLE 1F.

Example 35D 4-(4-((2-(4-chlorophenyl)-4,4-dimethylcycohex-1-en-1-yl)methyl)piperazin-1-yl)-2-(3,5-dichlorophenoxy)-N-((4-((1-methylpiperidin-4-yl)amino)-3-nitrophenyl)sulfonyl)benzamide This EXAMPLE was prepared by substituting EXAMPLE 35C for EXAMPLE 1F and EXAMPLE 3I for EXAMPLE 1G in EXAMPLE 1H. $^1$H NMR (500 MHz, pyridine-$d_5$) δ 9.14 (d, 1H), 8.53 (m, 1H), 8.31 (m, 1H), 7.95 (d, 1H), 7.46 (d, 2H), 7.11 (d, 2H), 6.99 (m, 3H), 6.81 (m, 2H), 3.73 (m, 1H), 3.22 (m, 4H), 3.05 (m, 2H), 2.85 (s, 2H), 2.56 (m, 2H), 2.46 (s, 3H), 2.30 (m, 6H), 2.14 (m, 2H), 1.95 (m, 4H), 1.42 (m, 2H), 0.97 (s, 6H).

Example 36

2-(3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 36A ethyl 2-(3-chlorophenoxy)-4-fluorobenzoate

This EXAMPLE was prepared by substituting 2-chlorophenol for 2-methyl-5-indolol in EXAMPLE 3A.

Example 36B ethyl 2-(3-chlorophenoxy)-4-(4-((2-(4-chlorophenyl)-4,4-dimethylcyclohex-1-enyl)methyl)piperazin-1-yl)benzoate This EXAMPLE was prepared by substituting EXAMPLE 36A for EXAMPLE 3A in EXAMPLE 3G.

Example 36C 2-(3-chlorophenoxy)-4-(4-((2-(4-chlorophenyl)-4,4-dimethylcyclohex-1-enyl)methyl)piperazin-1-yl)benzoic acid This EXAMPLE was prepared by substituting EXAMPLE 36B for EXAMPLE 1E in EXAMPLE 1F.

Example 36D 2-(3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide This EXAMPLE was prepared by substituting EXAMPLE 36C for EXAMPLE 1F and EXAMPLE 3I for EXAMPLE 1G in EXAMPLE 1H. $^1$H NMR (500 MHz, pyridine-$d_5$) δ 9.12 (d, 1H), 8.51 (d, 1H), 8.31 (dd, 1H), 7.99 (d, 1H), 7.45 (d, 1H), 7.11 (m, 3H), 7.02 (m, 2H), 6.91 (dd, 1H), 6.82 (dd, 1H), 6.68 (d, 2H), 4.05 (br s, 1H), 3.55 (br s, 2H), 3.31 (s, 6H), 2.99 (s, 2H), 2.85 (s, 3H), 2.51 (br s, 3H), 2.41 (s, 6H), 1.99 (s, 2H), 1.41 (t, 2H), 0.95 (s, 6H).

Example 37

4-(4-((4'-chloro-4-(2-(dimethylamino)ethoxy)-1,1'-biphenyl-2-yl)methyl)piperazin-1-yl)-2-(3-chlorophenoxy)-N-((4-((1-methylpiperidin-4-yl)amino)-3-nitrophenyl)sulfonyl)benzamide

Example 37A

4'-chloro-4-hydroxybiphenyl-2-carbaldehyde 2-bromo-5-hydroxybenzaldehyde (20 g), 4-chlorophenylboronic acid (17.1 g) and dichlorobis(triphenylphosphine)palladium(I) (1.75 g) were dissolved in 475 mL of a dimethoxyethane:ethanol:2M $Na_2CO_3$ solution (7:2:2). The mixture was heated to reflux for 1 hour. The reaction mixture was then diluted with ethyl acetate, washed thoroughly with water and with brine, dried over $MgSO_4$, filtered and concentrated. The resulting solid was slurried in 500 mL of hexane:ether mixture (2:1). The title compound was collected by filtration.

Example 37B tert-butyl 4-((4'-chloro-4-hydroxybiphenyl-2-yl)methyl)piperazine-1-carboxylate The title compound was prepared by substituting EXAMPLE 37A for 4'-chlorobiphenyl-2-carboxaldehyde in EXAMPLE 1A.

Example 37C tert-butyl 4-((4'-chloro-4-(2-(dimethylamino)ethoxy)biphenyl-2-yl)methyl)piperazine-1-carboxylate EXAMPLE 37B (2 g), 2-chloro-N,N-dimethylethanamine hydrochloric acid salt (2.15 g), and cesium carbonate (9.70 g) were combined in 10 mL of N,N-dimethylformamide. The resulting mixture was heated to 80° C. overnight. The reaction was cooled to room temperature, diluted with ethyl acetate and poured into water. The aqueous layer was extracted with ethyl acetate, and the combined organic layers were washed thoroughly with water and with brine, dried over $MgSO_4$, filtered and concentrated. The crude material was slurried in 100 mL of ether and the product was obtained by filtration.

Example 37D 2-(4'-chloro-2-(piperazin-1-ylmethyl)biphenyl-4-yloxy)-N,N-dimethylethanamine The title compound was prepared by substituting EXAMPLE 37C for EXAMPLE 1A in EXAMPLE 1B.

Example 37E ethyl 4-(4-((4'-chloro-4-(2-(dimethylamino)ethoxy)biphenyl-2-yl)methyl)piperazin-1-yl)-2-(3-chlorophenoxy)benzoate The title compound was prepared by substituting EXAMPLE 36A for EXAMPLE 3A and EXAMPLE 37D for EXAMPLE 3F in EXAMPLE 3G.

Example 37F 4-(4-((4'-chloro-4-(2-(dimethylamino)ethoxy)biphenyl-2-yl)methyl)piperazin-1-yl)-2-(3-chlorophenoxy)benzoic acid The title compound was prepared by substituting EXAMPLE 37E for EXAMPLE 1E in EXAMPLE 1F.

Example 37G 4-(4-((4'-chloro-4-(2-(dimethylamino)ethoxy)-1,1'-biphenyl-2-yl)methyl)piperazin-1-yl)-2-(3-chlorophenoxy)-N-((4-((1-methylpiperidin-4-yl)amino)-3-nitrophenyl)sulfonyl)benzamide The title compound was prepared by substituting EXAMPLE 37F for EXAMPLE 1F and EXAMPLE 3I for EXAMPLE 1G in EXAMPLE 1H. $^1$H NMR (400 MHz, dimethylsulfoxide-$d_6$) δ 11.88 (br s, 1H), 9.52 (br s, 1H), 9.30 (br s, 1H), 8.45 (m, 1H), 8.21 (d, 1H), 7.78 (dd, 1H), 7.50 (m, 3H), 7.38 (m, 2H), 7.18 (m, 3H), 6.95 (m, 1H), 6.81 (dd, 1H), 6.72 (dd, 1H), 6.68 (m, 1H), 6.53 (m, 1H), 4.35 (m, 2H), 3.53 (m, 2H), 3.28 (m, 2H), 3.21 (m, 4H), 3.08 (m, 2H), 2.88 (s, 6H), 2.73 (m, 2H), 2.64 (m, 1H), 2.43 (s, 3H), 2.27 (m, 4H), 1.83 (m, 2H).

Example 38

2-(2-chlorophenoxy)-4-(4-((4-(4-chlorophenyl)-6,6-dimethyl-5,6-dihydro-2H-pyran-3-yl)methyl)piperazin-1-yl)-N-((4-((1-methylpiperidin-4-yl)amino)-3-nitrophenyl)sulfonyl)benzamide

Example 38A methyl 6,6-dimethyl-4-oxotetrahydro-2H-pyran-3-carboxylate

To a suspension of hexane-washed NaH (0.72 g, 60%) in tetrahydrofuran (30 mL) was added a solution of 2,2-dimethyldihydro-2H-pyran-4(3H)-one (2.0 g) in tetrahydrofuran (20 mL). The suspension was stirred at room temperature for 30 minutes. Dimethylcarbonate (6.31 mL) was added dropwise by syringe. The mixture was heated to reflux for 4 hours. The mixture was acidified with 5% aqueous HCl and extracted with dichloromethane (100 mL×3) and washed with water and brine, and dried over $Na_2SO_4$. After filtration and concentration, the crude product was loaded on a column and eluted with 10% ethyl acetate in hexane to give the product.

Example 38B methyl 6,6-dimethyl-4-(trifluoromethylsulfonyloxy)-5,6-dihydro-2H-pyran-3-carboxylate To a cooled (0° C.) stirring suspension of NaH (0.983 g 60% in mineral oil, washed with hexane three times) in ether (50 mL) was added EXAMPLE 38A (3.2 g). The mixture was stirred at 0° C. for 30 minutes before the addition of triflic anhydride (4.2 mL). The mixture was then stirred at room temperature overnight. The mixture was diluted with ether (200 mL) and washed with 5% HCl, water and brine. After drying over $Na_2SO_4$, evaporation of solvent gave the crude product which was used without further purification.

Example 38C methyl 4-(4-chlorophenyl)-6,6-dimethyl-5,6-dihydro-2H-pyran-3-carboxylate To a solution of EXAMPLE 38B (2.88 g), 4-chlorophenylboronic acid (1.88 g) and tetrakis(triphenylphosphine)palladium(0) (0.578 g) in toluene (40 mL) and ethanol (10 mL) was added 2N aqueous $Na_2CO_3$ (10 mL). The mixture was stirred at reflux overnight. The mixture was diluted with ether (300 mL) and washed with water, brine and dried over $Na_2SO_4$. After filtration and evaporation of solvent, the residue was loaded on a column and eluted with 3% ethyl acetate in hexane to give the product.

Example 38D (4-(4-chlorophenyl)-6,6-dimethyl-5,6-dihydro-2H-pyran-3-yl)methanol To a solution of EXAMPLE 38C (1.6 g) in ether (20 mL) was added LiAlH$_4$ (1.2 g). The mixture was stirred at room temperature for 4 hours. The mixture was acidified carefully with 5% aqueous HCl and extracted with ethyl acetate (100 mL×3) and the combined organic layers were washed with water, brine and dried over $Na_2SO_4$. After filtration and evaporation of solvent, the crude product was loaded on a column and eluted with 10% ethyl acetate in hexane to give the product.

Example 38E 4-(4-chlorophenyl)-6,6-dimethyl-5,6-dihydro-2H-pyran-3-carbaldehyde To a solution of oxalyl chloride (1.1 g) in dichloromethane (30 mL) at −78° C. was added dimethylsulfoxide (6.12 mL). The mixture was stirred at −78° C. for 30 minutes, and then a solution of EXAMPLE 38D (1.2 g) in dichloromethane (10 mL) was added. The mixture was stirred at −78° C. for 2 hours before the addition of triethylamine (10 mL). The mixture was stirred overnight and the temperature was allowed to rise to room temperature. The mixture was diluted with ether (300 mL) and washed with water, brine and dried over $Na_2SO_4$. After filtration and evaporation of solvent, the crude product was loaded on a column and eluted with 5% ethyl acetate in hexane to give the product.

Example 38F methyl 2-(2-chlorophenoxy)-4-(piperazin-1-yl)benzoate

This example was prepared by substituting piperazine for EXAMPLE 3F and EXAMPLE 34A for EXAMPLE 3A in EXAMPLE 3G.

Example 38G methyl 2-(2-chlorophenoxy)-4-(4-((4-(4-chlorophenyl)-6,6-dimethyl-5,6-dihydro-2H-pyran-3-yl)methyl)piperazin-1-yl)benzoate To a solution of EXAMPLE 38E (100 mg) and EXAMPLE 38F (177 mg) in dichloromethane (10 mL) was added sodium triacetoxyborohydride (154 mg). The mixture was stirred at room temperature overnight. The mixture was diluted with ethyl acetate (200 mL) and washed with 2 wt % aqueous NaOH, water and brine. After drying over Na$_2$SO$_4$ and filtration, the solvent was evaporated under vacuum and the residue was loaded on a column and eluted with 30% ethyl acetate in hexane to give the product.

Example 38H 2-(2-chlorophenoxy)-4-(4-((4-(4-chlorophenyl)-6,6-dimethyl-5,6-dihydro-2H-pyran-3-yl)methyl)piperazin-1-yl)benzoic acid To a solution of EXAMPLE 38G (254 mg) in tetrahydrofuran (4 mL), methanol (2 mL) and water (2 mL) was added LiOH H$_2$O (126 mg). The mixture was stirred at room temperature overnight. The mixture was then neutralized with 5% aqueous HCl and diluted with ethyl acetate (200 mL). After washing with brine, it was dried over Na$_2$SO$_4$. Filtration and evaporation of solvent gave the product.

Example 38I 2-(2-chlorophenoxy)-4-(4-((4-(4-chlorophenyl)-6,6-dimethyl-5,6-dihydro-2H-pyran-3-yl)methyl)piperazin-1-yl)-N-((4-((1-methylpiperidin-4-yl)amino)-3-nitrophenyl)sulfonyl)benzamide The title compound was prepared as described in EXAMPLE 1H by replacing EXAMPLE 1F and EXAMPLE 1G with EXAMPLE 38H and EXAMPLE 3I, respectively. $^1$H NMR (300 MHz, dimethylsulfoxide-d$_6$) δ 8.33 (d, 1H), 8.06 (d, 1H), 7.71 (dd, 1H), 7.64 (d, 1H), 7.38 (d, 2H), 7.33 (dd, 1H), 7.16 (d, 2H), 7.02 (m, 2H), 6.86 (m, 1H), 6.69 (dd, 1H), 6.49 (dd, 1H), 6.25 (d, 1H), 4.14 (m, 2H), 3.73 (m, 1H), 3.04 (m, 10H), 2.87 (m, 2H), 2.42 (m, 4H), 2.22 (m, 6H), 1.69 (m, 2H), 1.21 (s, 6H).

Example 39

4-(4-((4'-chloro-1,1'-biphenyl-2-yl)methyl)piperazin-1-yl)-2-(3-(2-(dimethylamino)ethoxy)phenoxy)-N-((3-nitro-4-((tetrahydro-2H-pyran-4-ylmethyl)amino)phenyl)sulfonyl)benzamide

Example 39A 2-(3-(benzyloxy)phenoxy)-N,N-dimethylethanamine

A solution of 3-(benzyloxy)phenol (2.002 g), 2-chloro-N,N-dimethylethanamine (1.459 g) in N,N-dimethylformamide (50 mL) was treated with cesium carbonate (3.91 g) and stirred at 50° C. overnight. The mixture was diluted with ethyl acetate and 1N aqueous NaOH and the layers were separated. The aqueous layer was extracted with ethyl acetate and the combined organic layers were dried over MgSO$_4$, filtered and concentrated. The residue was purified by flash chromatography (5% 7N NH$_3$ in methanol-dichloromethane) to give the desired product.

Example 39B 3-(2-(dimethylamino)ethoxy)phenol

EXAMPLE 39A (450 mg) was dissolved in ethyl acetate (10 mL). The flask was flushed with nitrogen three times followed by the addition of 10% Pd/C (45 mg). The reaction mixture was kept under 1 atm of hydrogen at room temperature overnight. The mixture was filtered and concentrated. The residue was filtered through a small pad of silica gel and used in the next step without further purification.

Example 39C methyl 4-(4-((4'-chlorobiphenyl-2-yl)methyl)piperazin-1-yl)-2-(3-(2-(dimethylamino)ethoxy)phenoxy)benzoate The title compound was prepared by substituting EXAMPLE 39B for EXAMPLE 1D in EXAMPLE 1E.

Example 39D 4-(4-((4'-chlorobiphenyl-2-yl)methyl)piperazin-1-yl)-2-(3-(2-(dimethylamino)ethoxy)phenoxy)benzoic acid The title compound was prepared by substituting EXAMPLE 39C for EXAMPLE 1E in EXAMPLE 1F.

Example 39E 4-(4-((4'-chloro-1,1'-biphenyl-2-yl)methyl)piperazin-1-yl)-2-(3-(2-(dimethylamino)ethoxy)phenoxy)-N-((3-nitro-4-((tetrahydro-2H-pyran-4-ylmethyl)amino)phenyl)sulfonyl)benzamide The title compound was prepared by substituting EXAMPLE 39D for EXAMPLE 1F in EXAMPLE 1H. $^1$H NMR (400 MHz, dimethylsulfoxide-d$_6$) δ 11.69 (m, 1H), 9.60 (m, 1H), 8.64 (s, 1H), 8.50 (d, 1H), 7.80 (d, 1H), 7.72 (s, 1H), 7.52 (d, 5H), 7.38 (d, 2H), 7.33 (s, 1H), 7.19 (m, 2H), 6.78 (d, 1H), 6.65 (d, 1H), 6.45 (dd, 3H), 4.24 (s, 2H), 3.86 (d, 2H), 3.67 (s, 10H), 3.48 (s, 2H), 3.35 (t, 2H), 3.27 (t, 2H), 2.85 (s, 6H), 1.91 (s, 1H), 1.63 (d, 2H), 1.27 (d, 2H).

Example 40

2-(4-amino-3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 40A ethyl 2-(4-amino-3-chlorophenoxy)-4-fluorobenzoate

The title compound was prepared by substituting 4-amino-3-chlorophenol for 2-methyl-5-indolol in EXAMPLE 3A.

Example 40B ethyl 2-(4-amino-3-chlorophenoxy)-4-(4-((2-(4-chlorophenyl)-4,4-dimethylcyclohex-1-enyl)methyl)piperazin-1-yl)benzoate The title compound was prepared by substituting EXAMPLE 40A for methyl-2-bromo-4-fluorobenzoate and EXAMPLE 3F for EXAMPLE 1B in EXAMPLE 1C.

Example 40C 2-(4-amino-3-chlorophenoxy)-4-(4-((2-(4-chlorophenyl)-4,4-dimethylcyclohex-1-enyl)methyl)piperazin-1-yl)benzoic acid The title compound was prepared by substituting EXAMPLE 40B for EXAMPLE 1E in EXAMPLE 1F.

Example 40D 2-(4-amino-3-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide The title compound was prepared by substituting EXAMPLE 40C for EXAMPLE 1F and EXAMPLE 3I for EXAMPLE 1G in EXAMPLE 1H. $^1$H NMR (300 MHz, dimethylsulfoxide-$d_6$) δ 10.70 (br s, 1H), 8.60 (s, 1H), 8.20 (dd, 1H), 7.90 (dd, 1H), 7.45 (d, 1H), 7.35 (d, 2H), 7.24 (d, 1H), 7.06 (d, 2H), 6.91 (d, 1H), 6.78 (s, 2H), 6.64 (d, 1H), 6.14 (d, 1H), 5.24 (s, 2H), 4.03 (m, 1H), 3.52 (m, 2H), 3.10 (m, 6H), 2.80 (m, 4H), 2.73 (s, 3H), 2.18 (m, 6H), 1.99 (m, 2H), 1.82 (m, 2H), 1.38 (m, 2H), 0.94 (s, 6H).

Example 41

2-(2-chlorophenoxy)-4-(4-((2-(4-chlorophenyl)-4,4-dimethylcyclohex-1-en-1-yl)methyl)piperazin-1-yl)-N-((4-((1-isopropylpiperidin-4-yl)amino)-3-nitrophenyl)sulfonyl)benzamide

Example 41A 4-(1-isopropylpiperidin-4-ylamino)-3-nitrobenzenesulfonamide

A suspension of 4-chloro-3-nitrobenzenesulfonamide (1.664 g) triethylamine (2 mL) and 1-isopropylpiperidin-4-amine (1 g) in dioxane (10 mL) was stirred for 16 hours at 90° C. The reaction mixture was cooled to room temperature and the solid material was filtered off. The solid material was washed with 20% methanol/dichloromethane, and the mixture was dried under vacuum, to provide the product.

Example 41B 2-(2-chlorophenoxy)-4-(4-((2-(4-chlorophenyl)-4,4-dimethylcyclohex-1-en-1-yl)methyl)piperazin-1-yl)-N-((4-((1-isopropylpiperidin-4-yl)amino)-3-nitrophenyl)sulfonyl)benzamide The title compound was prepared by substituting EXAMPLE 34C for EXAMPLE 1F and EXAMPLE 41A for EXAMPLE 1G in EXAMPLE 1H. $^1$H NMR (500 MHz, pyridine-$d_5$) δ 9.18 (d, 1H), 8.51 (d, 1H), 8.37 (dd, 1H), 8.01 (d, 1H), 7.40-7.49 (m, 3H), 7.10 (d, 2H), 7.00-7.06 (m, 2H), 6.94-6.99 (m, 1H), 6.86 (dd, 1H), 6.80 (dd, 1H), 6.54 (d, 2H), 3.90-3.99 (m, 1H), 3.41-3.55 (m, 3H), 3.10-3.21 (m, 6H), 2.87 (s, 2H), 2.24-2.45 (m, 10H), 1.99 (s, 2H), 1.41 (t, 2H), 1.25 (d, 6H), 0.95 (s, 6H).

Example 42

2-(2-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 42A

Ethyl 2-(2-bromophenoxy)-4-fluorobenzoate

The title compound was prepared by substituting 2-bromophenol for 2-methyl-5-indolol in EXAMPLE 3A.

Example 42B

Ethyl 2-(2-bromophenoxy)-4-(4-((2-(4-chlorophenyl)-4,4-dimethylcyclohex-1-enyl)methyl)piperazin-1-yl)benzoate The title compound was prepared by substituting EXAMPLE 42A for EXAMPLE 3A in EXAMPLE 3G.

Example 42C 2-(2-Bromophenoxy)-4-(4-((2-(4-chlorophenyl)-4,4-dimethylcyclohex-1-enyl)methyl)piperazin-1-yl) benzoic acid The title compound was prepared by substituting EXAMPLE 42B for EXAMPLE 1E in EXAMPLE 1F.

Example 42D 2-(2-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide The title compound was prepared by substituting EXAMPLE 42C for EXAMPLE 1F and EXAMPLE 3I for EXAMPLE 1G in EXAMPLE 1H. $^1$H NMR (300 MHz, dimethylsulfoxide-$d_6$) δ 11.81 (s, 1H), 9.24-9.76 (m, 2H), 8.48 (d, 1H), 8.21 (d, 1H), 7.84 (dd, 1H), 7.50-7.60 (m, 2H), 7.41 (d, 2H), 7.25 (d, 1H), 7.18 (t, 1H), 7.11 (d, 2H), 6.95 (t, 1H), 6.80 (dd, 1H), 6.69 (d, 1H), 6.39 (s, 1H), 4.03-4.13 (m, 1H), 3.47-3.65 (m, 5H), 3.20-3.40 (m, 3H), 3.01-3.19 (m, 4H), 2.70-2.91 (m, 5H), 2.14-2.26 (m, 4H), 2.04 (s, 2H), 1.73-1.93 (m, 2H), 1.48 (t, 2H), 0.96 (s, 6H).

Example 43

2-(2-chlorophenoxy)-4-(4-((2-(4-chlorophenyl)cyclohex-1-en-1-yl)methyl)piperazin-1-yl)-N-((4-((1-methylpiperidin-4-yl)amino)-3-nitrophenyl)sulfonyl)benzamide

Example 43A ethyl 2-(trifluoromethylsulfonyloxy)cyclohex-1-enecarboxylate

The title compound was prepared as described in EXAMPLE 38B by replacing EXAMPLE 38A with ethyl 2-oxocyclohexanecarboxylate.

Example 43B ethyl 2-(4-chlorophenyl)cyclohex-1-enecarboxylate

The title compound was prepared as described in EXAMPLE 38C by replacing EXAMPLE 38B with EXAMPLE 43A.

Example 43C (2-(4-chlorophenyl)cyclohex-1-enyl)methanol

The title compound was prepared as described in EXAMPLE 38D by replacing EXAMPLE 38C with EXAMPLE 43B.

Example 43D 2-(4-chlorophenyl)cyclohex-1-enecarbaldehyde

The title compound was prepared as described in EXAMPLE 38E by replacing EXAMPLE 38D with EXAMPLE 43C.

Example 43E methyl 2-(2-chlorophenoxy)-4-(4-((2-(4-chlorophenyl)cyclohex-1-enyl)methyl)piperazin-1-yl)benzoate The title compound was prepared as described in EXAMPLE 38G by replacing EXAMPLE 38E with EXAMPLE 43D.

Example 43F 2-(2-chlorophenoxy)-4-(4-((2-(4-chlorophenyl)cyclohex-1-enyl)methyl)piperazin-1-yl)benzoic acid The title compound was prepared as described in EXAMPLE 38H by replacing EXAMPLE 38G with EXAMPLE 43E.

Example 43G 2-(2-chlorophenoxy)-4-(4-((2-(4-chlorophenyl)cyclohex-1-en-1-yl)methyl)piperazin-1-yl)-N-((4-((1-methylpiperidin-4-yl)amino)-3-nitrophenyl)sulfonyl)benzamide The title compound was prepared as described in EXAMPLE 1H by replacing EXAMPLE 1F and EXAMPLE 1G with EXAMPLE 43F and EXAMPLE 3I, respectively. $^1$H NMR (300 MHz, dimethylsulfoxide-$d_6$) δ 8.36 (d, 1H), 8.07 (d, 1H), 7.74 (dd, 1H), 7.62 (d, 1H), 7.35 (d, 2H), 7.09 (d, 2H), 7.04 (d, 1H), 6.89 (m, 1H), 6.70 (dd, 1H), 6.54 (dd, 1H), 6.25 (d, 1H), 3.80 (m, 1H), 3.11 (m, 8H), 2.77 (m, 4H), 2.59 (m, 4H), 2.15 (m, 8H), 1.70 (m, 8H).

Example 44

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-((3-morpholin-4-ylpropyl)amino)-3-nitrophenyl)sulfonyl)benzamide

Example 44A 4-methoxy-3-methyl-1H-indazole

A solution of 1-(2-fluoro-6-methoxyphenyl)ethanone (1 g), hydrazine (1.04 g), and sodium acetate (0.49 g) was stirred for 72 hours in toluene (10 mL). The mixture was concentrated, taken up in DMSO (8 mL), and heated to 135° C. for 24 hours. The mixture was cooled, poured into ethyl acetate (200 mL), and rinsed with 3× water, and brine. The organic layer was concentrated and chromatographed on silica gel using 10-100% ethyl acetate/hexanes.

Example 44B 3-methyl-1H-indazol-4-ol

A 1M solution of $BBr_3$ (6.57 mL) was added to a solution of EXAMPLE 44A (0.71 g) in dichloromethane (30 mL), and the reaction was stirred for 18 hours. The reaction was quenched by the slow addition of methanol, and the mixture was concentrated and chromatographed on silica gel using 10% methanol/ethyl acetate.

Example 44C ethyl 4-fluoro-2-(3-methyl-1H-indazol-4-yloxy)benzoate

The title compound was prepared by substituting EXAMPLE 44B for 2-methyl-5-indolol in EXAMPLE 3A.

Example 44D ethyl 4-(4-((2-(4-chlorophenyl)-4,4-dimethylcyclohex-1-enyl)methyl)piperazin-1-yl)-2-(3-methyl-1H-indazol-4-yloxy)benzoate The title compound was prepared by substituting EXAMPLE 44C for methyl-2-bromo-4-fluorobenzoate and EXAMPLE 3F for EXAMPLE 1B in EXAMPLE 1C.

Example 44E 4-(4-((2-(4-chlorophenyl)-4,4-dimethylcyclohex-1-enyl)methyl)piperazin-1-yl)-2-(3-methyl-1H-indazol-4-yloxy)benzoic acid The title compound was prepared by substituting EXAMPLE 40B for EXAMPLE 1E in EXAMPLE 1F.

Example 44F 4-(4-((2-(4-chlorophenyl)-4,4-dimethylcyclohex-1-en-1-yl)methyl)piperazin-1-yl)-2-((3-methyl-1H-indazol-4-yl)oxy)-N-((4-((3-morpholin-4-ylpropyl)amino)-3-nitrophenyl)sulfonyl)benzamide The title compound was prepared by substituting EXAMPLE 44E for EXAMPLE 1F and EXAMPLE 4A for EXAMPLE 1G in EXAMPLE 1H. $^1$H NMR (300 MHz, dimethylsulfoxide-$d_6$) δ 11.95 (br s, 2H), 8.47 (m, 1H), 8.27 (d, 1H), 7.62 (d, 1H), 7.36 (d, 2H), 7.07 (d, 2H), 6.95 (m, 2H), 6.72 (m, 2H), 6.36 (s, 1H), 5.92 (d, 1H), 3.61 (m, 4H), 3.04 (m, 4H), 2.75 (m, 2H), 2.39 (m, 4H), 2.18 (m, 6H), 1.99 (s, 3H), 1.90 (m, 6H), 1.77 (m, 2H), 1.41 (m, 2H), 0.94 (s, 6H).

Example 45

4-(4-((2-(4-chlorophenyl)-4,4-dimethylcyclohex-1-en-1-yl)methyl)piperazin-1-yl)-2-(2,3-difluorophenoxy)-N-((4-((1-methylpiperidin-4-yl)amino)-3-nitrophenyl)sulfonyl)benzamide

Example 45A

Ethyl 2-(2,3-difluorophenoxy)-4-fluorobenzoate

The title compound was prepared by substituting 2,3-difluorophenol for 2-methyl-5-indolol in EXAMPLE 3A.

Example 45B

Ethyl 4-(4-((2-(4-chlorophenyl)-4,4-dimethylcyclohex-1-enyl)methyl)piperazin-1-yl)-2-(2,3-difluorophenoxy)benzoate The title compound was prepared by substituting EXAMPLE 45A for EXAMPLE 3A in EXAMPLE 3G.

Example 45C

This EXAMPLE was prepared by substituting EXAMPLE 45B for EXAMPLE 1E in EXAMPLE 1F.

Example 45D 4-(4-((2-(4-chlorophenyl)-4,4-dimethylcyclohex-1-en-1-yl)methyl)piperazin-1-yl)-2-(2,3-difluorophenoxy)-N-((4-((1-methylpiperidin-4-yl)amino)-3-nitrophenyl)sulfonyl)benzamide The title compound was prepared by substituting EXAMPLE 45C for EXAMPLE 1F and EXAMPLE 3I for EXAMPLE 1G in EXAMPLE 1H. $^1$H NMR (500 MHz, pyridine-$d_5$) 9.17 (d, 1H), 8.49 (d, 1H), 8.38 (dd, 1H), 7.99 (d, 1H), 7.46 (d, 2H), 7.10 (d, 2H), 7.01 (d, 1H), 6.85 (m, 3H), 6.69 (m, 2H), 3.70 (m, 1H), 3.21 (m, 4H), 3.05 (m, 2H), 2.84 (s, 2H), 2.57 (m, 2H), 2.46 (s, 3H), 2.28 (m, 6H), 2.11 (m, 2H), 1.94 (m, 4H), 1.42 (t, 2H), 0.96 (s, 6H).

Example 46

2-(3-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 46A

Ethyl 2-(3-bromophenoxy)-4-fluorobenzoate

The title compound was prepared by substituting 3-bromophenol for 2-methyl-5-indolol in EXAMPLE 3A.

Example 46B

Ethyl 2-(3-bromophenoxy)-4-(4-((2-(4-chlorophenyl)-4,4-dimethylcyclohex-1-enyl)methyl)piperazin-1-yl)benzoate The title compound was prepared by substituting EXAMPLE 46A for EXAMPLE 3A in EXAMPLE 3G.

Example 46C 2-(3-Bromophenoxy)-4-(4-((2-(4-chlorophenyl)-4,4-dimethylcyclohex-1-enyl)methyl)piperazin-1-yl)benzoic acid The title compound was prepared by substituting EXAMPLE 46B for EXAMPLE 1E in EXAMPLE 1F.

Example 46D 2-(3-bromophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide The title compound was prepared by substituting EXAMPLE 46C for EXAMPLE 1F and EXAMPLE 3I for EXAMPLE 1G in EXAMPLE 1H. $^1$H NMR (300 MHz, dimethylsulfoxide-$d_6$) δ 11.97 (s, 1H), 9.46 (s, 1H), 9.38 (s, 1H), 8.39-8.48 (m, 1H), 8.21 (d, 1H), 7.78 (dd, 1H), 7.53 (d, 1H), 7.41 (d, 2H), 7.08-7.24 (m, 5H), 6.75-6.86 (m, 3H), 6.58 (d, 1H), 4.08 (s, 1H), 3.62 (s, 3H), 3.55 (d, 4H), 3.23-3.39 (m, 3H), 3.05-3.20 (m, 4H), 2.78-2.91 (m, 5H), 2.70-2.78 (m, 1H), 2.13-2.28 (m, 4H), 2.05 (s, 2H), 1.78-1.92 (m, 2H), 1.48 (t, 2H), 0.96 (s, 6H).

Example 47

2-(2-chlorophenoxy)-4-(4-((2-(4-chlorophenyl)-4,4-dimethylcyclohex-1-en-1-yl)methyl)piperazin-1-yl)-N-((4-((1-ethylpiperidin-4-yl)amino)-3-nitrophenyl)sulfonyl)benzamide

Example 47A 4-(1-Ethylpiperidin-4-ylamino)-3-nitrobenzenesulfonamide

The title compound was prepared by substituting 1-ethylpiperidin-4-amine for 1-isopropylpiperidin-4-amine in EXAMPLE 41A.

Example 47B 2-(2-chlorophenoxy)-4-(4-((2-(4-chlorophenyl)-4,4-dimethylcyclohex-1-en-1-yl)methyl)piperazin-1-yl)-N-((4-((1-ethylpiperidin-4-yl)amino)-3-nitrophenyl)sulfonyl)benzamide The title compound was prepared by substituting EXAMPLE 34C for EXAMPLE 1F and EXAMPLE 47A for EXAMPLE 1G in EXAMPLE 1H. $^1$H NMR (500 MHz, pyridine-$d_5$) δ 9.18 (d, 1H), 8.50 (d, 1H), 8.36 (dd, 1H), 8.01 (d, 1H), 7.39-7.47 (m, 3H), 7.10 (d, 5H), 7.03-7.06 (m, 2H), 7.02 (dd, 1H), 6.96 (td, 2H), 6.85 (dd, 1H), 6.80 (dd, 1H), 6.54 (d, 1H), 3.93-4.00 (m, 1H), 3.55 (s, 2H), 3.13-3.21 (m, 5H), 3.10 (q, 2H), 2.90 (s, 2H), 2.28-2.37 (m, 8H), 2.22-2.28 (m, 2H), 1.98 (s, 2H), 1.40 (t, 2H), 1.26 (t, 3H), 0.95 (s, 6H).

Example 48

2-(2-chlorophenoxy)-4-(4-((2-(4-chlorophenyl)-4,4-dimethylcyclohex-1-en-1-yl)methyl)piperazin-1-yl)-N-((3-nitro-4-((1,2,2,6,6-pentamethylpiperidin-4-yl)amino)phenyl)sulfonyl)benzamide

Example 48A 4-(1,2,2,6,6-Pentamethylpiperidin-4-ylamino)-3-nitrobenzenesulfonamide The title compound was prepared by substituting 1,2,2,6,6-pentamethylpiperidin-4-ylamine for 1-isopropylpiperidin-4-amine in EXAMPLE 41A.

Example 48B 2-(2-chlorophenoxy)-4-(4-((2-(4-chlorophenyl)-4,4-dimethylcyclohex-1-en-1-yl)methyl)piperazin-1-yl)-N-((3-nitro-4-((1,2,2,6,6-pentamethylpiperidin-4-yl)amino)phenyl)sulfonyl)benzamide The title compound was prepared by substituting EXAMPLE 34C for EXAMPLE 1F and EXAMPLE 48A for EXAMPLE 1G in EXAMPLE 1H. $^1$H NMR (500 MHz, pyridine-$d_5$) δ 9.19 (d, 1H), 8.45 (d, 1H), 8.37 (dd, 1H), 8.01 (d, 1H), 7.45 (d, 3H), 7.09 (d, 2H), 7.06 (s, 1H), 7.02-7.05 (m, 2H), 6.99 (td, 1H), 6.86 (dd, 2H), 6.80 (dd, 1H), 6.53 (d, 1H), 4.16-4.25 (m, 1H), 3.16-3.23 (m, 4H), 2.90 (s, 2H), 2.82 (s, 3H), 2.45-2.54 (m, 2H), 2.31 (d, 6H), 2.17 (dd, 2H), 1.98 (s, 2H), 1.55 (s, 6H), 1.46 (s, 6H), 1.40 (t, 2H), 0.95 (s, 6H).

Example 49

4-(4-((2-(4-chlorophenyl)-4,4-dimethylcyclohex-1-en-1-yl)methyl)piperazin-1-yl)-2-(2,3-difluorophenoxy)-N-((3-nitro-4-((1-tetrahydro-2H-pyran-4-ylpiperidin-4-yl)amino)phenyl)sulfonyl)benzamide

Example 49A tert-butyl 1-(tetrahydro-2H-pyran-4-yl)piperidin-4-ylcarbamate

A mixture of tert-butyl piperidin-4-ylcarbamate (45 g) and dihydro-2H-pyran-4(3H)-one (24.74 g) in dichloromethane (1000 mL) was treated with sodium triacetoxyborohydride (61.9 g), stirred at room temperature for 16 hours, washed with 1M sodium hydroxide and dried with anhydrous sodium sulfate, filtered and concentrated. The concentrate was flash column chromatographed on silica gel with 10-20% methanol/dichloromethane.

Example 49B 1-(tetrahydro-2H-pyran-4-yl)piperidin-4-amine dihydrochloride salt A solution of EXAMPLE 49A (52.57 g) in dichloromethane (900 mL) was treated with 4M aqueous HCl (462 mL), mixed vigorously at room temperature for 16 hours and concentrated.

Example 49C 3-nitro-4-(1-(tetrahydro-2H-pyran-4-yl)piperidin-4-ylamino)benzenesulfonamide A mixture of EXAMPLE 49B (22.12 g), water (43 mL), and triethylamine (43.6 mL) in 1,4-dioxane (300 mL) was stirred at room temperature until EXAMPLE 49B completely dissolved. The solution was then treated with 4-chloro-3-nitrobenzenesulfonamide (20.3 g), heated at 90° C. for 16 hours, cooled and concentrated. 10% Methanol in dichloromethane was added, and the solution was stirred vigorously at room temperature until a fine suspension existed and then the mixture was filtered.

Example 49D 4-(4-((2-(4-chlorophenyl)-4,4-dimethylcyclohex-1-en-1-yl)methyl)piperazin-1-yl)-2-(2,3-difluorophenoxy)-N-((3-nitro-4-((1-tetrahydro-2H-pyran-4-ylpiperidin-4-yl)amino)phenyl)sulfonyl)benzamide The title compound was prepared by substituting EXAMPLE 45C for EXAMPLE 1F and EXAMPLE 49C for EXAMPLE 1G in EXAMPLE 1H. $^1$H NMR (500 MHz, pyridine-$d_5$) δ 9.18 (d, 1H), 8.53 (d, 1H), 8.40 (dd, 1H), 7.99 (d, 1H), 7.45 (d, 2H), 7.10 (d, 2H), 7.03 (d, 1H), 6.85 (m, 3H), 6.69 (m, 2H), 4.02 (m, 2H), 3.72 (m, 1H), 3.31 (t, 2H), 3.21 (m, 4H), 3.11 (m, 2H), 2.83 (m, 3H), 2.66 (m, 2H), 2.30 (m, 6H), 2.16 (m, 2H), 1.93 (m, 4H), 1.74 (m, 4H), 1.41 (t, 2H), 0.96 (s, 6H).

Example 50

4-(4-((2-(4-chlorophenyl)-4,4-dimethylcyclohex-1-en-1-yl)methyl)piperazin-1-yl)-2-((7-fluoro-1H-indol-5-yl)oxy)-N-((4-((1-methylpiperidin-4-yl)amino)-3-nitrophenyl)sulfonyl)benzamide

Example 50A ((3-fluoro-4-nitrophenoxy)methylene)dibenzene

Bromodiphenylmethane (3.5 g) and 3-fluoro-4-nitrophenol were dissolved in N,N-dimethylformamide (30 mL), and then $K_2CO_3$ (4.2 g) was added and the reaction stirred at room temperature for 60 hours. The reaction was partitioned between water and ethyl acetate. The organic layer was washed with 2M aqueous $Na_2CO_3$ and brine, then dried over $Na_2SO_4$. After filtration and concentration, the crude material was purified by column chromatography using 1.5-2.0% ethyl acetate in hexanes.

Example 50B 5-(benzhydryloxy)-7-fluoro-1H-indole

EXAMPLE 50A (2.0 g) was dissolved in tetrahydrofuran (60 mL), then that solution was cooled to −40° C. Vinylmagnesium bromide, 1.0M in tetrahydrofuran, (21 mL) was then added dropwise, keeping the temperature below −30° C. The reaction was stirred at −40° C. for 90 minutes, and was partitioned between saturated $NH_4Cl$ and ethyl acetate. The organic layer was washed with brine and dried over $Na_2SO_4$. After filtration and concentration, the crude material was purified by column chromatography using 2.5-3.0% ethyl acetate in hexanes.

Example 50C 7-fluoro-1H-indol-5-ol

EXAMPLE 50B (240 mg) was dissolved in ethyl acetate (1 mL) and methanol (9 mL), then palladium hydroxide on carbon (35 mg) was added and the reaction stirred at room temperature under a hydrogen balloon for 90 minutes. The reaction was filtered through celite and concentrated to give the crude product which was carried on in the next step without further purification.

Example 50D ethyl 4-fluoro-2-(7-fluoro-1H-indol-5-yloxy)benzoate

The title compound was prepared by substituting EXAMPLE 50C for 2-methyl-5-indolol in EXAMPLE 3A.

Example 50E ethyl 4-(4-((2-(4-chlorophenyl)-4,4-dimethylcyclohex-1-enyl)methyl)piperazin-1-yl)-2-(7-fluoro-1H-indol-5-yloxy)benzoate The title compound was prepared by substituting EXAMPLE 50D for EXAMPLE 3A in EXAMPLE 3G.

Example 50F 4-(4-((4'-chlorobiphenyl-2-yl)methyl)piperazin-1-yl)-2-(7-fluoro-1H-indol-5-yloxy)benzoic acid The title compound was prepared by substituting EXAMPLE 50E for EXAMPLE 1E in EXAMPLE 1F.

Example 50G 4-(4-((2-(4-chlorophenyl)-4,4-dimethylcyclohex-1-en-1-yl)methyl)piperazin-1-yl)-2-((7-fluoro-1H-indol-5-yl)oxy)-N-((4-((1-methylpiperidin-4-yl)amino)-3-nitrophenyl)sulfonyl)benzamide bis(2,2,2-trifluoroacetate)

EXAMPLE 50F (35 mg), EXAMPLE 3I (17 mg), 1-ethyl-3-[3-(dimethylamino)propyl]-carbodiimide hydrochloride (21 mg), and 4-dimethylaminopyridine (14 mg) were stirred in $CH_2Cl_2$ (1.5 mL) overnight. The reaction was concentrated and the crude material was purified by preparative HPLC using a 250×50 mm C18 column and eluting with 20-100% $CH_3CN$ vs. 0.1% trifluoroacetic acid in water, giving the product as a trifluoroacetate salt. $^1$H NMR (300 MHz, dimethylsulfoxide-$d_6$) δ 11.62 (br s, 1H), 9.65, 9.45 (both v br s, total 2H), 8.55 (d, 1H), 8.17 (br d, 1H), 7.84 (dd, 1H), 7.50 (d, 1H), 7.43 (t, 1H), 7.39 (d, 2H), 7.20 (d, 1H), 7.08 (d, 2H), 6.90 (d, 1H), 6.66 (m, 2H), 6.44 (m, 1H), 6.28 (d, 1H), 4.02, 3.82 (both br s, total 2H), 3.60 (v br m, 4H), 3.05 (v br m, 5H), 2.85, 2.80 (br m, br s, total 5H), 2.20 (br m, 5H), 2.00 (br s, 3H), 1.80 (v br m, 2H) 1.44 (br t, 2H), 0.95 (s, 6H).

Example 51

4-(4-((2-(4-chlorophenyl)-4,4-dimethylcyclohex-1-en-1-yl)methyl)piperazin-1-yl)-2-(2,3-difluorophenoxy)-N-((4-((3-morpholin-4-ylpropyl)amino)-3-nitrophenyl)sulfonyl)benzamide The title compound was prepared by substituting EXAMPLE 45C for EXAMPLE 1F and EXAMPLE 4A for EXAMPLE 1G in EXAMPLE 1H. $^1$H NMR (500 MHz, pyridine-$d_5$) δ 9.21 (d, 1H), 9.00 (m, 1H), 8.36 (dd, 1H), 7.97 (d, 1H), 7.45 (d, 2H), 7.10 (d, 2H), 6.97 (d, 1H), 6.85 (d, 3H), 6.69 (d, 2H), 3.82 (m, 4H), 3.38 (q, 2H), 3.21 (m, 4H), 2.86 (s, 2H), 2.45 (m, 6H), 2.28 (m, 6H), 1.99 (s, 2H), 1.80 (m, 2H), 1.41 (t, 2H), 0.96 (s, 6H).

Example 52

2-(4-amino-3-chlorophenoxy)-4-(4-((2-(4-chlorophenyl)-4,4-dimethylcyclohex-1-en-1-yl)methyl)piperazin-1-yl)-N-((4-((3-morpholin-4-ylpropyl)amino)-3-nitrophenyl)sulfonyl)benzamide The title compound was prepared by substituting EXAMPLE 40C for EXAMPLE 1F and EXAMPLE 4A for EXAMPLE 1G in EXAMPLE 1H. $^1$H NMR (300 MHz, dimethylsulfoxide-$d_6$) δ 11.10 (br s, 1H), 8.80 (t, 1H), 8.56 (s, 1H), 7.82 (dd, 1H), 7.45 (d, 1H), 7.35 (d, 2H), 7.17 (d, 1H), 7.06 (d, 2H), 6.89 (d, 1H), 6.77 (s, 2H), 6.63 (d, 1H), 6.14 (d, 1H), 5.20 (br s, 2H), 3.61 (m, 4H), 3.46 (m, 2H), 3.07 (m, 4H), 2.75 (m, 2H), 2.44 (m, 6H), 2.20 (m, 6H), 1.97 (m, 2H), 1.81 (m, 2H), 1.40 (m, 2H), 0.94 (s, 6H).

Example 53

2-(3-chlorophenoxy)-4-(4-((4'-chloro-4-(2-pyrrolidin-1-ylethyl)-1,1'-biphenyl-2-yl)methyl)piperazin-1-yl)-N-((3-nitro-4-((tetrahydro-2H-pyran-4-ylmethyl)amino)phenyl)sulfonyl)benzamide

Example 53A methyl 5-formyl-2-(trifluoromethylsulfonyloxy)benzoate

Triflic anhydride (7.74 mL) was added to methyl 5-formyl-2-hydroxybenzoate (7.5 g) in 150 mL $CH_2Cl_2$ at 0° C., and the reaction mixture was stirred and allowed to warm to room temperature over 3 hours. The reaction mixture was diluted with $CH_2Cl_2$ (150 mL), washed 3× with brine, dried over $Na_2SO_4$, filtered, and concentrated. The product was used without further purification.

Example 53B methyl 4'-chloro-4-formylbiphenyl-2-carboxylate

EXAMPLE 53A (14.5 g), 4-chlorophenylboronic acid (6.88 g) CsF (12.2 g), and tetrakis(triphenylphosphine)palladium(0) were stirred at 70° C. for 24 hours. The reaction mixture was cooled, filtered, and concentrated. The crude product was taken up in ethyl acetate (250 mL), washed with 3×μM aqueous NaOH, and brine, concentrated, and chromatographed on silica gel with 10% ethyl acetate/hexanes.

Example 53C methyl 4'-chloro-4-(2-oxoethyl)biphenyl-2-carboxylate

To a solution of (methoxymethyl)diphenylphosphine oxide (1.62 g) in 40 mL tetrahydrofuran at −78° C., was added lithium diisopropylamide (2M, 3.3 mL), and after stirring 3 minutes, EXAMPLE 53B (1.57 g) was added, and the solution was warmed to room temperature. NaH (230 mg), and 40 mL N,N-dimethylformamide were added, and the mixture was heated to 60° C. for 1 hour. The reaction mixture was cooled and poured into saturated aqueous $NaH_2PO_4$ solution. The resulting solution was extracted twice with ether, and the combined extracts were washed twice with water, and brine, and concentrated. The crude mixture of enol ethers was taken up in 1M aqueous HCl (50 mL) and dioxane (50 mL), and stirred at 60° C. for 3 hours. The reaction was cooled and poured into $NaHCO_3$ solution. The resulting solution was extracted twice with ether, and the combined extracts were washed with water, and brine, and concentrated. The product was used without further purification.

Example 53D methyl 4'-chloro-4-(2-(pyrrolidin-1-yl)ethyl)biphenyl-2-carboxylate The title compound was prepared by substituting EXAMPLE 53C for 4'-chlorobiphenyl-2-carboxaldehyde and pyrrolidine for tert-butyl piperazine-1-carboxylate in EXAMPLE 1A.

Example 53E (4'-chloro-4-(2-(pyrrolidin-1-yl)ethyl)biphenyl-2-yl)methanol

Diisobutylaluminum hydride (1M in hexanes, 7.8 mL) was added to a solution of EXAMPLE 53D (0.89 g) in dichloromethane (30 mL) at 0° C., and the reaction was stirred for 20 minutes. The reaction was quenched by the slow addition of methanol, and then poured into 1M aqueous NaOH (50 mL). The mixture was extracted twice with ethyl acetate, and extracts were combined, washed with brine, dried over $Na_2SO_4$, filtered, and concentrated.

Example 53F

4'-chloro-4-(2-(pyrrolidin-1-yl)ethyl)biphenyl-2-carbaldehyde

EXAMPLE 53E (0.85 g) and Dess-Martin periodinane (1.26 g) were stirred in dichloromethane (40 mL) for 90 minutes. The reaction was quenched with methanol (5 mL), concentrated, and chromatographed on silica gel with 10-50% ethyl acetate/hexanes.

Example 53G tert-butyl 4-(3-(3-chlorophenoxy)-4-(ethoxycarbonyl)phenyl)piperazine-1-carboxylate The title compound was prepared by substituting EXAMPLE 36A for methyl 2-bromo-4-fluorobenzoate and tert-butyl piperazine-1-carboxylate for EXAMPLE 1B in EXAMPLE 1C.

Example 53H ethyl 2-(3-chlorophenoxy)-4-(piperazin-1-yl)benzoate

The title compound was prepared by substituting EXAMPLE 53G for EXAMPLE 1A in EXAMPLE 1B.

Example 53I ethyl 4-(4-((4'-chloro-4-(2-(pyrrolidin-1-yl)ethyl)biphenyl-2-yl)methyl)piperazin-1-yl)-2-(3-chlorophenoxy)benzoate The title compound was prepared by substituting EXAMPLE 53F for 4'-chlorobiphenyl-2-carboxaldehyde and EXAMPLE 53H for tert-butyl piperazine-1-carboxylate in EXAMPLE 1A.

Example 53J 4-(4-((4'-chloro-4-(2-(pyrrolidin-1-yl)ethyl)biphenyl-2-yl)methyl)piperazin-1-yl)-2-(3-chlorophenoxy)benzoic acid The title compound was prepared by substituting EXAMPLE 53I for EXAMPLE 1E in EXAMPLE 1F.

Example 53K 2-(3-chlorophenoxy)-4-(4-((4'-chloro-4-(2-pyrrolidin-1-ylethyl)-1,1'-biphenyl-2-yl)methyl)piperazin-1-yl)-N-((3-nitro-4-((tetrahydro-2H-pyran-4-ylmethyl)amino)phenyl)sulfonyl)benzamide The title compound was prepared by substituting EXAMPLE 53J for EXAMPLE 1F in EXAMPLE 1H. $^1$H NMR (300 MHz, dimethylsulfoxide-$d_6$) δ 11.80 (br s, 1H), 8.66 (t, 1H), 8.45 (s, 1H), 8.00 (m, 1H), 7.72 (dd, 1H), 7.52 (d, 2H), 7.35 (m, 4H), 7.16 (m, 2H), 6.94 (d, 1H), 6.80 (d, 1H), 6.66 (d, 2H), 6.55 (m, 1H), 4.32 (m, 1H), 3.85 (m, 2H), 3.56 (m, 2H), 3.33 (m, 8H), 3.07 (m, 6H), 2.85 (m, 2H), 2.43 (m, 2H), 2.02 (m, 2H), 1.91 (m, 4H), 1.63 (m, 2H), 1.27 (m, 2H).

Example 54

4-(4-((2-(4-chlorophenyl)-4,4-dimethylcyclohex-1-en-1-yl)methyl)piperazin-1-yl)-2-(2,3-dichlorophenoxy)-N-((4-(((1-methylpiperidin-4-yl)amino)-3-nitrophenyl)sulfonyl)benzamide

Example 54A

Ethyl 2-(2,3-dichlorophenoxy)-4-fluorobenzoate

The title compound was prepared by substituting 2,3-dichlorophenol for 2-methyl-5-indolol in EXAMPLE 3A.

Example 54B

Ethyl 2-(2,3-dichlorophenoxy)-4-(4-((2-(4-chlorophenyl)-4,4-dimethylcyclohex-1-enyl)methyl)piperazin-1-yl)benzoate The title compound was prepared by substituting EXAMPLE 54A for EXAMPLE 3A in EXAMPLE 3G.

Example 54C 2-(2,3-dichlorophenoxy)-4-(4-((2-(4-chlorophenyl)-4,4-dimethylcyclohex-1-enyl)methyl)piperazin-1-yl) benzoic acid The title compound was prepared by substituting EXAMPLE 54B for EXAMPLE 1E in EXAMPLE 1F.

Example 54D 4-(4-((2-(4-chlorophenyl)-4,4-dimethylcyclohex-1-en-1-yl)methyl)piperazin-1-yl)-2-(2,3-dichlorophenoxy)-N-((4-((1-methylpiperidin-4-yl)amino)-3-nitrophenyl)sulfonyl)benzamide The title compound was prepared by substituting EXAMPLE 54C for EXAMPLE 1F and EXAMPLE 3I for EXAMPLE 1G in EXAMPLE 1H. $^1$H NMR (500 MHz, pyridine-$d_5$) δ 9.16 (d, 1H), 8.50 (d, 1H), 8.33 (dd, 1H), 7.99 (d, 1H), 7.45 (d, 2H), 7.11 (t, 3H), 7.04 (d, 1H), 6.95 (t, 1H), 6.84 (dd, 1H), 6.74 (d, 1H), 6.68 (d, 1H), 3.90-3.98 (m, 1H), 3.51 (d, 2H), 3.20-3.27 (m, 4H), 3.15 (t, 2H), 2.90 (s, 2H), 2.80 (s, 3H), 2.33 (d, 9H), 2.17-2.26 (m, 2H), 1.99 (s, 2H), 1.41 (t, 2H), 0.96 (s, 6H).

Example 55

4-(4-((2-(4-chlorophenyl)-4,4-dimethylcyclohex-1-en-1-yl)methyl)piperazin-1-yl)-2-((3-methyl-1H-indazol-4-yl)oxy)-N-((4-((1-methylpiperidin-4-yl)amino)-3-nitrophenyl)sulfonyl)benzamide The title compound was prepared by substituting EXAMPLE 44E for EXAMPLE 1F and EXAMPLE 3I for EXAMPLE 1G in EXAMPLE 1H. $^1$H NMR (300 MHz, dimethylsulfoxide-$d_6$) δ 11.95 (br s, 2H), 8.30 (d, 1H), 8.02 (d, 1H), 7.61 (d, 1H), 7.36 (d, 2H), 7.07 (d, 2H), 6.94 (m, 2H), 6.69 (m, 2H), 6.36 (s, 1H), 5.92 (d, 1H), 3.27 (m, 4H), 3.04 (m, 7H), 2.75 (m, 4H), 2.49 (m, 4H), 2.22 (m, 8H), 1.99 (s, 3H), 1.77 (m, 2H), 1.39 (m, 2H), 0.94 (s, 6H).

Example 56

2-(2-chlorophenoxy)-4-(4-((2-(4-chlorophenyl)cyclohept-1-en-1-yl)methyl)piperazin-1-yl)-N-((4-((1-methylpiperidin-4-yl)amino)-3-nitrophenyl)sulfonyl)benzamide

Example 56A (Z)-methyl 2-(trifluoromethylsulfonyloxy)cyclohept-1-enecarboxylate The title compound was prepared as described in EXAMPLE 38B by replacing EXAMPLE 38A with methyl 2-oxocycloheptanecarboxylate.

Example 56B (Z)-methyl 2-(4-chlorophenyl)cyclohept-1-enecarboxylate

The title compound was prepared as described in EXAMPLE 38C by replacing EXAMPLE 38B with EXAMPLE 56A.

Example 56C (Z)-(2-(4-chlorophenyl)cyclohept-1-enyl)methanol

The title compound was prepared as described in EXAMPLE 38D by replacing EXAMPLE 38C with EXAMPLE 56B.

Example 56D (Z)-2-(4-chlorophenyl)cyclohept-1-enecarbaldehyde

The title compound was prepared as described in EXAMPLE 38E by replacing EXAMPLE 38D with EXAMPLE 56C.

Example 56E (Z)-methyl 2-(2-chlorophenoxy)-4-(4-((2-(4-chlorophenyl)cyclohept-1-enyl)methyl)piperazin-1-yl)benzoate The title compound was prepared as described in EXAMPLE 38G by replacing EXAMPLE 38E with EXAMPLE 56D.

Example 56F (Z)-2-(2-chlorophenoxy)-4-(4-((2-(4-chlorophenyl)cyclohept-1-enyl)methyl)piperazin-1-yl)benzoic acid The title compound was prepared as described in EXAMPLE 38H by replacing EXAMPLE 38G with EXAMPLE 56E.

Example 56G 2-(2-chlorophenoxy)-4-(4-((2-(4-chlorophenyl)cyclohept-1-en-1-yl)methyl)piperazin-1-yl)-N-((4-((1-methylpiperidin-4-yl)amino)-3-nitrophenyl)sulfonyl)benzamide The title compound was prepared as described in EXAMPLE 1H by replacing EXAMPLE 1F and EXAMPLE 1G with EXAMPLE 56F and EXAMPLE 3I, respectively. $^1$H NMR (300 MHz, dimethylsulfoxide-$d_6$) δ 8.35 (d, 1H), 8.06 (d, 1H), 7.73 (dd, 1H), 7.63 (d, 1H), 7.35 (d, 2H), 7.04 (m, 4H), 6.88 (m, 1H), 6.69 (dd, 1H), 6.52 (dd, 1H), 6.25 (d, 1H), 3.78 (m, 1H), 3.06 (m, 6H), 2.70 (m, 4H), 2.38 (m, 4H), 2.26 (m, 5H), 2.07 (m, 4H), 1.73 (m, 5H), 1.52 (m, 5H).

Example 57

4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-(3-(trifluoromethyl)phenoxy)benzamide

Example 57A

Ethyl 4-fluoro-2-(3-(trifluoromethyl)phenoxy)benzoate

The title compound was prepared by substituting 3-(trifluoromethyl)phenol for 2-methyl-5-indolol in EXAMPLE 3A.

Example 57B

Ethyl 4-(4-((2-(4-chlorophenyl)-4,4-dimethylcyclohex-1-enyl)methyl)piperazin-1-yl)-2-(3-(trifluoromethyl)phenoxy)benzoate The title compound was prepared by substituting EXAMPLE 57A for EXAMPLE 3A in EXAMPLE 3G.

Example 57C 4-(4-((2-(4-chlorophenyl)-4,4-dimethylcyclohex-1-enyl)methyl)piperazin-1-yl)-2-(3-(trifluoromethyl)phenoxy)benzoic acid This EXAMPLE was prepared by substituting EXAMPLE 57B for EXAMPLE 1E in EXAMPLE 1F.

Example 57D 4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)-2-(3-(trifluoromethyl)phenoxy)benzamide The title compound was prepared by substituting EXAMPLE 57C for EXAMPLE 1F and EXAMPLE 3I for EXAMPLE 1G in EXAMPLE 1H. $^1$H NMR (400 MHz, dimethylsulfoxide-$d_6$) δ 8.32 (d, 1H), 8.04 (m, 1H), 7.66 (m, 2H), 7.35 (m, 3H), 7.16 (d, 1H), 7.06 (d, 2H), 6.95 (m, 3H), 6.73 (dd, 1H), 6.42 (d, 1H), 3.80 (m, 1H), 3.11 (m, 4H), 2.83 (m, 4H), 2.63 (m, 3H), 2.21 (m, 6H), 2.08 (m, 2H), 1.97 (m, 5H), 1.76 (m, 2H), 1.41 (t, 2H), 0.95 (s, 6H).

Example 58

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-oxo-1,2,3,4-tetrahydroquinolin-5-yl)oxy)benzamide

Example 58A methyl 4-(4-((4'-chlorobiphenyl-2-yl)methyl)piperazin-1-yl)-2-(2-oxo-1,2,3,4-tetrahydroquinolin-5-yloxy)benzoate The title compound was prepared by substituting 3,4-dihydro-5-hydroxy-1H-quinolin-2-one for EXAMPLE 1D in EXAMPLE 1E.

Example 58B 4-(4-((4'-chlorobiphenyl-2-yl)methyl)piperazin-1-yl)-2-(2-oxo-1,2,3,4-tetrahydroquinolin-5-yloxy)benzoic acid The title compound was prepared by substituting EXAMPLE 58A for EXAMPLE 1E in EXAMPLE 1F.

Example 58C 4-(4-((4'-chloro-1,1'-biphenyl-2-yl)methyl)piperazin-1-yl)-N-((4-((3-(dimethylamino)propyl)amino)-3-nitrophenyl)sulfonyl)-2-((2-oxo-1,2,3,4-tetrahydroquinolin-5-yl)oxy)benzamide The title compound was prepared by substituting EXAMPLE 58B for EXAMPLE 1F and EXAMPLE 11A for EXAMPLE 1G in EXAMPLE 1H. $^1$H NMR (300 MHz, dimethylsulfoxide-$d_6$) δ 11.68 (s, 1H), 10.08 (s, 1H), 8.64 (t, 1H), 8.48 (d, 1H), 7.81 (dd, 1H), 7.50 (m, 6H), 7.39 (m, 2H), 7.29 (m, 1H), 7.14 (d, 1H), 6.93 (t, 1H), 6.75 (dd, 1H), 6.51 (d, 1H), 6.39 (m, 1H), 6.13 (d, 1H), 4.36 (m, 1H), 3.72 (m, 1H), 3.40 (m, 6H), 3.13 (m, 4H), 2.80 (m, 4H), 2.78 (d, 6H), 2.40 (t, 2H), 1.96 (m, 2H).

Example 59

2-(2-chlorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-((trifluoromethyl)sulfonyl)phenyl)sulfonyl)benzamide The title compound was prepared by substituting EXAMPLE 34C for EXAMPLE 1F and EXAMPLE 131D for EXAMPLE 1G in EXAMPLE 1H. $^1$H NMR (400 MHz, dimethylsulfoxide-$d_6$) δ 7.99 (d, 1H), 7.88 (m, 1H), 7.62 (d, 1H), 7.38 (m, 3H), 7.06 (d, 3H), 7.01 (d, 1H), 6.93 (t, 1H), 6.69 (m, 1H), 6.56 (d, 1H), 6.50 (s, 1H), 6.24 (d, 1H), 3.25 (m, 10H), 3.07 (s, 2H), 3.07 (s, 3H), 2.77 (d, 3H), 2.20 (d, 5H), 2.04 (s, 2H), 1.96 (d, 2H), 1.63 (s, 2H), 1.40 (t, 2H), 0.94 (s, 6H).

Example 60

4-(4-((2-(4-chlorophenyl)-4,4-dimethylcyclohex-1-en-1-yl)methyl)piperazin-1-yl)-2-(2,5-dichlorophenoxy)-N-((4-((1-methylpiperidin-4-yl)amino)-3-nitrophenyl)sulfonyl)benzamide

Example 60A

Ethyl 2-(2,5-dichlorophenoxy)-4-fluorobenzoate

The title compound was prepared by substituting 2,5-dichlorophenol for 2-methyl-5-indolol in EXAMPLE 3A.

Example 60B

Ethyl 2-(2,5-dichlorophenoxy)-4-(piperazin-1-yl)benzoate

The title compound was prepared by substituting piperazine for EXAMPLE 3F and EXAMPLE 60A for EXAMPLE 3A in EXAMPLE 3G.

Example 60C

2-chloro-4,4-dimethylcyclohex-1-enecarbaldehyde

Into a 250 mL round-bottomed flask was added N,N-dimethylformamide (3.5 mL) in dichloromethane (30 mL) to give a colorless solution. The mixture was cooled to −10° C., and phosphoryl trichloride (4 mL) was added dropwise. The solution was warmed up to room temperature, and 3,3-dimethylcyclohexanone (5.5 mL) was added slowly. The mixture was heated to reflux for overnight. The reaction mixture was quenched by 0° C. solution of sodium acetate (25 g in 50 mL water). The aqueous layer was extracted with ether (3×200 mL). The organic layers were combined, dried over $Na_2SO_4$, filtered, and dried under vacuum.

Example 60D

2-(4-chlorophenyl)-4,4-dimethylcyclohex-1-enecarbaldehyde

Into a 1 L round-bottomed flask was added EXAMPLE 60C (6.8 g), 4-chlorophenylboronic acid (6.5 g) and palladium(II) acetate (0.2 g) in water (100 mL) to give a suspension. Potassium carbonate (15 g) and tetrabutylammonium bromide (10 g) were added. After degassing by subjecting to vacuum and nitrogen, the mixture was stirred at 45° C. for 4 hours. After filtering through silica gel, ether (4×200 mL) was used to extract the product. The combined organic layers were dried over $Na_2SO_4$ and filtered. The filtrate was concentrated and purified by flash chromatography on silica with 0 to 10% ethyl acetate in hexanes to provide the title compound.

Example 60E

Ethyl 4-(4-((2-(4-chlorophenyl)-4,4-dimethylcyclohex-1-enyl)methyl)piperazin-1-yl)-2-(2,5-dichlorophenoxy)benzoate The title compound was prepared by substituting EXAMPLE 60D for 4'-chlorobiphenyl-2-carboxaldehyde and EXAMPLE 60B for tert-butyl piperazine-1-carboxylate in EXAMPLE 1A.

Example 60F

4-(4-((2-(4-chlorophenyl)-4,4-dimethylcyclohex-1-enyl)methyl)piperazin-1-yl)-2-(2,5-dichlorophenoxy)benzoic acid The title compound was prepared by substituting EXAMPLE 60E for EXAMPLE 1E in EXAMPLE 1F.

Example 60G

4-(4-((2-(4-chlorophenyl)-4,4-dimethylcyclohex-1-en-1-yl)methyl)piperazin-1-yl)-2-(2,5-dichlorophenoxy)-N-((4-((1-methylpiperidin-4-yl)amino)-3-nitrophenyl)sulfonyl)benzamide The title compound was prepared by substituting EXAMPLE 60F for EXAMPLE 1F and EXAMPLE 3I for EXAMPLE 1G in EXAMPLE 1H. $^1$H NMR (400 MHz, dimethylsulfoxide-$d_6$) δ 12.01 (br.s, 1H), 9.92 (br.s, 1H), 9.68 (br.s, 1H), 8.43 (m, 1H), 8.19 (d, 1H), 7.80 (dd, 1H), 7.55 (d, 1H), 7.39 (m, 3H), 7.23 (d, 1H), 7.11 (d, 2H), 6.97 (dd, 1H), 6.85 (dd, 1H), 6.55 (m, 2H), 3.58 (m, 5H), 3.25 (m, 6H), 2.83 (m, 4H), 2.21 (m, 4H), 2.05 (s, 2H), 1.87 (m, 2H), 1.48 (t, 2H), 0.96 (s, 6H).

Example 61

2-(2-chloro-4-fluorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide

Example 61A

Ethyl 2-(2-chloro-4-fluorophenoxy)-4-fluorobenzoate

The title compound was prepared by substituting 2-chloro-4-fluorophenol for 2-methyl-5-indolol in EXAMPLE 3A.

Example 61B

Ethyl 2-(2-chloro-4-fluorophenoxy)-4-(piperazin-1-yl)benzoate

The title compound was prepared by substituting piperazine for EXAMPLE 3F and EXAMPLE 61A for EXAMPLE 3A in EXAMPLE 3G.

Example 61C

Ethyl 2-(2-chloro-4-fluorophenoxy)-4-(4-((2-(4-chlorophenyl)-4,4-dimethylcyclohex-1-enyl)methyl)piperazin-1-yl)benzoate The title compound was prepared by substituting EXAMPLE 60D for 4'-chlorobiphenyl-2-carboxaldehyde and EXAMPLE 61B for tert-butyl piperazine-1-carboxylate in EXAMPLE 1A.

Example 61D

2-(2-chloro-4-fluorophenoxy)-4-(4-((2-(4-chlorophenyl)-4,4-dimethylcyclohex-1-enyl)methyl)piperazin-1-yl)benzoic acid The title compound was prepared by substituting EXAMPLE 61C for EXAMPLE 1E in EXAMPLE 1F.

Example 61E

2-(2-chloro-4-fluorophenoxy)-4-(4-((2-(4-chlorophenyl)-4,4-dimethylcyclohex-1-en-1-yl)methyl)piperazin-1-yl)-N-((4-((1-methylpiperidin-4-yl)amino)-3-nitrophenyl)sulfonyl)benzamide The title compound was prepared by substituting EXAMPLE 61D for EXAMPLE 1F and EXAMPLE 3I for EXAMPLE 1G in EXAMPLE 1H. $^1$H NMR (400 MHz, dimethylsulfoxide-$d_6$) δ 8.40 (m, 1H), 8.08 (m, 1H), 7.78 (dd, 1H), 7.59 (d, 1H), 7.33 (m, 3H), 7.07 (m, 3H), 6.92 (m, 1H), 6.69 (dd, 1H), 6.59 (m, 1H), 6.25 (d, 1H), 3.84 (m, 1H), 3.08

(m, 4H), 2.77 (m, 8H), 2.16 (m, 8H), 1.97 (s, 2H), 1.75 (m, 2H), 1.40 (t, 2H), 0.94 (s, 6H).

Example 62

2-(2-chlorophenoxy)-4-(4-((2-(4-chlorophenyl)-4,4-dimethylcyclopent-1-en-1-yl)methyl)piperazin-1-yl)-N-((4-((1-methylpiperidin-4-yl)amino)-3-nitrophenyl)sulfonyl)benzamide

Example 62A methyl 4,4-dimethyl-2-oxocyclopentanecarboxylate

This compound was prepared according to WO 2006/035061 (page 53).

Example 62B methyl 4,4-dimethyl-2-(trifluoromethylsulfonyloxy)cyclopent-1-enecarboxylate The title compound was prepared as described in EXAMPLE 38B by replacing EXAMPLE 38A with EXAMPLE 62A.

Example 62C ethyl 2-(4-chlorophenyl)-4,4-dimethylcyclopent-1-enecarboxylate

The title compound was prepared as described in EXAMPLE 38C by replacing EXAMPLE 38B with EXAMPLE 62B.

Example 62D (2-(4-chlorophenyl)-4,4-dimethylcyclopent-1-enyl)methanol

The title compound was prepared as described in EXAMPLE 38D by replacing EXAMPLE 38C with EXAMPLE 62C.

Example 62E 2-(4-chlorophenyl)-4,4-dimethylcyclopent-1-enecarbaldehyde

The title compound was prepared as described in EXAMPLE 38E by replacing EXAMPLE 38D with EXAMPLE 62D.

Example 62F methyl 2-(2-chlorophenoxy)-4-(4-((2-(4-chlorophenyl)-4,4-dimethylcyclopent-1-enyl)methyl)piperazin-1-yl)benzoate The title compound was prepared as described in EXAMPLE 38G by replacing EXAMPLE 38E with EXAMPLE 62E.

Example 62G 2-(2-chlorophenoxy)-4-(4-((2-(4-chlorophenyl)-4,4-dimethylcyclopent-1-enyl)methyl)piperazin-1-yl)benzoic acid The title compound was prepared as described in EXAMPLE 38H by replacing EXAMPLE 38G with EXAMPLE 62F.

Example 62H 2-(2-chlorophenoxy)-4-(4-((2-(4-chlorophenyl)-4,4-dimethylcyclopent-1-en-1-yl)methyl)piperazin-1-yl)-N-((4-((1-methylpiperidin-4-yl)amino)-3-nitrophenyl)sulfonyl)benzamide The title compound was prepared as described in EXAMPLE 1H by replacing EXAMPLE 1F and EXAMPLE 1G with EXAMPLE 62G and EXAMPLE 3I, respectively. $^1$H NMR (300 MHz, dimethylsulfoxide-$d_6$) δ 8.35 (d, 1H), 8.06 (d, 1H), 7.73 (dd, 1H), 7.64 (d, 1H), 7.33 (m, 5H), 7.04 (m, 2H), 6.88 (m, 1H), 6.72 (dd, 1H), 6.52 (dd, 1H), 6.28 (d, 1H), 3.78 (d, 1H), 3.07 (d, 4H), 2.71 (m, 6H), 2.33 (m, 8H), 2.06 (m, 4H), 1.74 (m, 4H), 1.10 (m, 6H).

Example 63

4-(4-((2-(4-chlorophenyl)-4,4-dimethylcyclohex-1-en-1-yl)methyl)piperazin-1-yl)-2-((3-methyl-1H-indol-4-yl)oxy)-N-((4-((3-morpholin-4-ylpropyl)amino)-3-nitrophenyl)sulfonyl)benzamide

Example 63A ethyl 4-fluoro-2-(3-methyl-1H-indol-4-yloxy)benzoate

The title compound was prepared by substituting 3-methyl-4-indolol for 2-methyl-5-indolol in EXAMPLE 3A.

Example 63B ethyl 4-(4-((2-(4-chlorophenyl)-4,4-dimethylcyclohex-1-enyl)methyl)piperazin-1-yl)-2-(3-methyl-1H-indol-4-yloxy)benzoate The title compound was prepared by substituting EXAMPLE 63A for methyl-2-bromo-4-fluorobenzoate and EXAMPLE 3F for EXAMPLE 1B in EXAMPLE 1C.

Example 63C 4-(4-((2-(4-chlorophenyl)-4,4-dimethylcyclohex-1-enyl)methyl)piperazin-1-yl)-2-(3-methyl-1H-indol-4-yloxy)benzoic acid The title compound was prepared by substituting EXAMPLE 63B for EXAMPLE 1E in EXAMPLE 1F.

Example 63D 4-(4-((2-(4-chlorophenyl)-4,4-dimethylcyclohex-1-en-1-yl)methyl)piperazin-1-yl)-2-((3-methyl-1H-indol-4-yl)oxy)-N-((4-((3-morpholin-4-ylpropyl)amino)-3-nitrophenyl)sulfonyl)benzamide The title compound was prepared by substituting EXAMPLE 63C for EXAMPLE 1F and EXAMPLE 4A for EXAMPLE 1G in EXAMPLE 1H. $^1$H NMR (300 MHz, dimethylsulfoxide-d$_6$) δ 10.92 (br s, 2H), 8.77 (m, 1H), 8.57 (d, 1H), 7.82 (dd, 1H), 7.55 (d, 1H), 7.33 (d, 2H), 7.15 (m, 2H), 7.03 (d, 2H), 6.99 (m, 2H), 6.67 (d, 1H), 6.45 (d, 1H), 6.12 (d, 1H), 3.68 (m, 4H), 3.47 (m, 2H), 3.02 (m, 6H), 2.73 (m, 4H), 2.43 (m, 2H), 2.14 (m, 8H), 1.99 (s, 3H), 1.91 (m, 2H), 1.38 (m, 2H), 0.92 (s, 6H).

Example 64

4-(4-((2-(4-chlorophenyl)-4,4-dimethylcyclohex-1-en-1-yl)methyl)piperazin-1-yl)-2-(2-chloro-3-(trifluoromethyl)phenoxy)-N-((4-((1-methylpiperidin-4-yl)amino)-3-nitrophenyl)sulfonyl)benzamide Example 64A Ethyl 2-(2-chloro-3-(trifluoromethyl)phenoxy)-4-fluorobenzoate The title compound was prepared by substituting 2-chloro-3-(trifluoromethyl)phenol for 2-methyl-5-indolol in EXAMPLE 3A.

Example 64B

Ethyl 2-(2-chloro-3-(trifluoromethyl)phenoxy)-4-(4-((2-(4-chlorophenyl)-4,4-dimethylcyclohex-1-enyl)methyl)piperazin-1-yl)benzoate The title compound was prepared by substituting EXAMPLE 64A for EXAMPLE 3A in EXAMPLE 3G.

Example 64C 2-(2-chloro-3-(trifluoromethyl)phenoxy)-4-(4-((2-(4-chlorophenyl)-4,4-dimethylcyclohex-1-enyl)methyl)piperazin-1-yl)benzoic acid The title compound was prepared by substituting EXAMPLE 64B for EXAMPLE 1E in EXAMPLE 1F.

Example 64D 4-(4-((2-(4-chlorophenyl)-4,4-dimethylcyclohex-1-en-1-yl)methyl)piperazin-1-yl)-2-(2-chloro-3-(trifluoromethyl)phenoxy)-N-((4-((1-methylpiperidin-4-yl)amino)-3-nitrophenyl)sulfonyl)benzamide The title compound was prepared by substituting EXAMPLE 64C for EXAMPLE 1F and EXAMPLE 3I for EXAMPLE 1G in EXAMPLE 1H. $^1$H NMR (400 MHz, dimethylsulfoxide-d$_6$) δ 12.02 (s, 1H), 9.76 (s, 1H), 9.52 (s, 1H), 8.42 (m, 1H), 8.17 (d, 1H), 7.82 (dd, 1H), 7.58 (d, 1H), 7.41 (m, 3H), 7.27 (m, 2H), 7.11 (d, 2H), 6.93 (d, 1H), 6.84 (dd, 1H), 6.57 (d, 1H), 3.15 (m, 6H), 2.83 (m, 8H), 2.11 (m, 8H), 1.83 (m, 2H), 1.47 (t, 2H), 0.96 (s, 6H).

Example 65

2-(2-chlorophenoxy)-4-(4-((2-(4-chlorophenyl)-4,4-dimethylcyclohex-1-en-1-yl)methyl)piperazin-1-yl)-N-((4-(((1-cyclopropylpiperidin-4-yl)amino)-3-nitrophenyl)sulfonyl)benzamide Example 65A 4-(1-cyclopropylpiperidin-4-ylamino)-3-nitrobenzenesulfonamide To a solution of 4-fluoro-3-nitrobenzenesulfonamide (1.26 g) and 1-cyclopropylpiperidin-4-amine (0.802 g) in tetrahydrofuran (20 mL) was added N,N-diisopropylethylamine (2.22 g) and 4-dimethylaminopyridine (35 mg). The mixture was stirred at reflux overnight. The mixture was diluted with ethyl acetate (200 mL) and washed with aqueous NaHCO$_3$, water, and brine and dried over Na$_2$SO$_4$. After filtration and concentration, the residue was dissolved in dichloromethane and loaded on a column and eluted with dichloromethane (500 mL), 5% 7N NH$_3$ in 10% methanol in dichloromethane (1.5 L) to give the product.

Example 65B 2-(2-chlorophenoxy)-4-(4-((2-(4-chlorophenyl)-4,4-dimethylcyclohex-1-en-1-yl)methyl)piperazin-1-yl)-N-((4-(((1-cyclopropylpiperidin-4-yl)amino)-3-nitrophenyl)sulfonyl)benzamide The title compound was prepared as described in EXAMPLE 1H by replacing EXAMPLE 1F and EXAMPLE 1G with EXAMPLE 34C and EXAMPLE 65A, respectively. $^1$H NMR (300 MHz, dimethylsulfoxide-d$_6$) δ 8.46 (dd, 1H), 8.22 (t, 1H), 7.81 (m, 2H), 7.53 (d, 1H), 7.37 (m, 4H), 7.14 (m, 1H), 7.07 (m, 1H), 6.99 (m, 1H), 6.72 (m, 1H), 6.29 (d, 1H), 3.75 (m, 1H), 3.13 (s, 3H), 2.93 (d, 3H), 2.78 (s, 1H), 2.20 (m, 5H), 1.97 (m, 5H), 1.59 (m, 5H), 0.94 (s, 6H), 0.42 (m, 5H).

Example 66

4-(4-((2-(4-chlorophenyl)-4,4-dimethylcyclohex-1-en-1-yl)methyl)piperazin-1-yl)-2-((3-methyl-1H-indol-4-yl)oxy)-N-((4-(((1-methylpiperidin-4-yl)amino)-3-nitrophenyl)sulfonyl)benzamide The title compound was prepared by substituting EXAMPLE 63C for EXAMPLE 1F and EXAMPLE 3I for EXAMPLE 1G in EXAMPLE 1H. $^1$H NMR (300 MHz, dimethylsulfoxide-d$_6$) δ 10.86 (br s, 2H), 8.51 (br s, 1H), 8.15 (d, 1H), 7.82 (dd, 1H), 7.55 (d, 1H), 7.33 (d, 2H), 7.15 (m, 2H), 7.03 (d, 2H), 6.94 (m, 2H), 6.62 (d, 1H), 6.38 (d, 1H), 6.12 (d, 1H), 3.82 (m, 1H), 3.09 (m, 2H), 2.98 (m, 6H), 2.88 (m, 2H), 2.71 (m, 3H), 2.66 (m, 2H), 2.11 (m, 8H), 1.99 (s, 3H), 1.82 (m, 2H), 1.38 (m, 2H), 0.92 (s, 6H).

Example 67

4-(4-((2-(4-chlorophenyl)-4,4-dimethylcyclohex-1-en-1-yl)methyl)piperazin-1-yl)-2-(2,5-dichlorophenoxy)-N-((4-((3-morpholin-4-ylpropyl)amino)-3-nitrophenyl)sulfonyl)benzamide The title compound was prepared by substituting EXAMPLE 60D for EXAMPLE 1F and EXAMPLE 4A for EXAMPLE 1G in EXAMPLE 1H. $^1$H NMR (400 MHz, dimethylsulfoxide-d$_6$) δ 8.71 (m, 1H), 8.43 (d, 1H), 7.75 (dd, 1H), 7.54 (d, 1H), 7.36 (m, 3H), 7.07 (m, 3H), 6.94 (dd, 1H), 6.79 (dd, 1H), 6.46 (dd, 2H), 3.67 (m, 4H), 3.48 (q, 2H), 3.20 (m, 4H), 2.83 (s, 2H), 2.65 (m, 6H), 2.24 (m, 6H), 1.98 (s, 2H), 1.88 (m, 2H), 1.42 (t, 2H), 0.95 (s, 6H).

Example 68

4-(4-((4'-chloro-1,1'-biphenyl-2-yl)methyl)piperazin-1-yl)-2-((1-methyl-1H-indol-4-yl)oxy)-N-((4-((3-morpholin-4-ylpropyl)amino)-3-nitrophenyl)sulfonyl)benzamide The title compound was prepared by substituting EXAMPLE 16D for EXAMPLE 50F and EXAMPLE 4A for EXAMPLE 3I in EXAMPLE 50G. $^1$H NMR (300 MHz, 4 dimethylsulfoxide-$d_6$) δ 11.58 (br s, 1H), 9.78 (br s, 1H), 8.67 (t, 1H), 8.44 (d, 1H), 7.77 (dd, 1H), 7.66 (br s, 1H), 7.50 (m, 5H), 7.37 (d, 2H), 7.30 (m, 1H), 7.25 (d, 1H), 7.19 (d, 1H), 7.06 (d, 1H), 7.00 (dd, 1H), 6.75 (dd, 1H), 6.40 (d, 1H), 6.38 (s, 1H), 6.23 (d, 1H), 4.35-2.80 (series of br m, total 22H), 3.80 (s, 3H), 1.96 (m, 2H).

Example 69

4-(4-((4'-chloro-1,1'-biphenyl-2-yl)methyl)piperazin-1-yl)-2-(3-morpholin-4-ylphenoxy)-N-((4-((3-morpholin-4-ylpropyl)amino)-3-nitrophenyl)sulfonyl) benzamide The title compound was prepared by substituting EXAMPLE 32B for EXAMPLE 1F and EXAMPLE 4A for EXAMPLE 1G in EXAMPLE 1H. $^1$H NMR (400 MHz, dimethylsulfoxide-$d_6$) δ 11.63 (s, 1H), 9.86 (s, 1H), 8.71 (t, 1H), 8.50 (d, 1H), 7.83 (dd, 1H), 7.70 (s, 1H), 7.50 (m, 5H), 7.39 (d, 2H), 7.32 (m, 1H), 7.16 (d, 1H), 7.08 (m, 1H), 6.74 (dd, 1H), 6.59 (dd, 1H), 6.40 (m, 2H), 6.23 (dd, 1H), 4.24 (m, 2H), 3.97 (m, 2H), 3.70 (m, 4H), 3.63 (m, 4H), 3.54 (m, 4H), 3.18 (m, 4H), 3.07 (m, 4H), 3.00 (m, 4H), 2.83 (m, 2H), 1.98 (m, 2H).

Example 70

4-(4-((4'-chloro-1,1'-biphenyl-2-yl)methyl)piperazin-1-yl)-N-((4-((3-(dimethylamino)propyl)amino)-3-nitrophenyl)sulfonyl)-2-((3-(3-morpholin-4-yl-3-oxopropyl)-1H-indol-5-yl)oxy)benzamide Example 70A (Z)-tert-butyl 5-(benzyloxy)-3-(3-morpholino-3-oxoprop-1-enyl)-1H-indole-1-carboxylate A mixture of tert-butyl 5-(benzyloxy)-3-bromo-1H-indole-1-carboxylate (2.011 g), 1-morpholinoprop-2-en-1-one (0.776 g), palladium acetate (31 mg), tri-o-tolylphosphine (187 mg) and triethylamine (1.14 mL) in N,N-dimethylformamide (14 mL) under nitrogen atmosphere was stirred at 100° C. overnight. The mixture was diluted with ethyl acetate and saturated ammonium chloride. The aqueous layer was extracted with ethyl acetate and the combined organic layers were dried over MgSO$_4$, filtered and concentrated. The residue was purified by flash chromatography (80% ethyl acetate-hexane) to give the desired product.

Example 70B tert-butyl 5-hydroxy-3-(3-morpholino-3-oxopropyl)-1H-indole-1-carboxylate The title compound was prepared by substituting EXAMPLE 70A for EXAMPLE 39A in EXAMPLE 39B.

Example 70C tert-butyl 5-(5-(4-((4'-chlorobiphenyl-2-yl)methyl) piperazin-1-yl)-2-(methoxycarbonyl)phenoxy)-3-(3-morpholino-3-oxopropyl)-1H-indole-1-carboxylate The title compound was prepared by substituting EXAMPLE 70B for EXAMPLE 1D in EXAMPLE 1E.

Example 70D methyl 4-(4-((4'-chlorobiphenyl-2-yl)methyl)piperazin-1-yl)-2-(3-(3-morpholino-3-oxopropyl)-1H-indol-5-yloxy)benzoate A solution of EXAMPLE 70C (300 mg) in dioxane (2 mL) was treated with concentrated aqueous hydrogen chloride (0.378 mL) and stirred at room temperature overnight. The solution was concentrated and the residue was used for the next step without further purification.

Example 70E 4-(4-((4'-chlorobiphenyl-2-yl)methyl)piperazin-1-yl)-2-(3-(3-morpholino-3-oxopropyl)-1H-indol-5-yloxy)benzoic acid The title compound was prepared by substituting EXAMPLE 70D for EXAMPLE 1E in EXAMPLE 1F.

Example 70F 4-(4-((4'-chloro-1,1'-biphenyl-2-yl)methyl)piperazin-1-yl)-N-((4-((3-(dimethylamino)propyl)amino)-3-nitrophenyl)sulfonyl)-2-((3-(3-morpholin-4-yl-3-oxopropyl)-1H-indol-5-yl)oxy)benzamide The title compound was prepared by substituting EXAMPLE 70E for EXAMPLE 1F and EXAMPLE 11A for EXAMPLE 1G in EXAMPLE 1H. $^1$H NMR (400 MHz, dimethylsulfoxide-$d_6$) δ 11.37 (s, 1H), 10.88 (s, 1H), 9.33 (s, 1H), 8.64 (m, 2H), 7.88 (d, 1H), 7.66 (s, 1H), 7.51 (dd, 5H), 7.35 (dd, 3H), 7.29 (s, 1H), 7.21 (s, 1H), 7.13 (d, 2H), 6.82 (dd, 1H), 6.67 (d, 1H), 6.21 (s, 1H), 3.42 (s, 20H), 3.12 (s, 2H), 2.85 (m, 2H), 2.78 (d, 6H), 2.61 (m, 2H), 1.95 (m, 2H).

Example 71

2-(3-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl) sulfonyl)benzamide Example 71A 2-(3-(benzyloxy)phenoxy)-4-(4-((4'-chlorobiphenyl-2-yl)methyl)piperazin-1-yl)benzoic acid The title compound was prepared by substituting EXAMPLE 33A for EXAMPLE 1E in EXAMPLE 1F.

Example 71B 2-(3-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl) sulfonyl)benzamide The title compound was prepared by substituting EXAMPLE 71A for EXAMPLE 1F in EXAMPLE 1H. $^1$H NMR (400 MHz, dimethylsulfoxide-$d_6$) δ 11.69 (m, 1H), 8.62 (m, 1H), 8.48 (d, 1H), 7.76 (dd, 1H), 7.65 (m, 1H), 7.50 (m, 5H), 7.38 (m, 6H), 7.32 (m, 2H), 7.11 (m, 2H), 6.77 (dd, 1H), 6.62 (dd, 1H), 6.41 (m, 2H), 6.35 (m, 1H), 4.98 (s, 2H), 3.83 (m, 2H), 3.28 (m, 12H), 3.17 (m, 2H), 1.89 (m, 1H), 1.59 (m, 2H), 1.26 (m, 2H).

Example 72

4-(4-((4'-chloro-1,1'-biphenyl-2-yl)methyl)piperazin-1-yl)-2-(4-cyanophenoxy)-N-((3-nitro-4-((tetrahydro-2H-pyran-4-ylmethyl)amino)phenyl)sulfonyl)benzamide

Example 72A methyl 4-(4-((4'-chlorobiphenyl-2-yl)methyl)piperazin-1-yl)-2-(4-cyanophenoxy)benzoate The title compound was prepared by substituting 4-cyanophenol for EXAMPLE 1D in EXAMPLE 1E.

Example 72B 4-(4-((4'-chlorobiphenyl-2-yl)methyl)piperazin-1-yl)-2-(4-cyanophenoxy)benzoic acid The title compound was prepared by substituting EXAMPLE 72A for EXAMPLE 1E in EXAMPLE 1F.

Example 72C 4-(4-((4'-chloro-1,1'-biphenyl-2-yl)methyl)piperazin-1-yl)-2-(4-cyanophenoxy)-N-((3-nitro-4-((tetrahydro-2H-pyran-4-ylmethyl)amino)phenyl)sulfonyl)benzamide The title compound was prepared by substituting EXAMPLE 72B for EXAMPLE 1G in EXAMPLE 1H. $^1$H NMR (300 MHz, dimethylsulfoxide-$d_6$) δ 11.97 (s, 1H), 9.54 (s, 1H), 8.62 (t, 1H), 8.44 (d, 1H), 7.66 (m, 4H), 7.53 (m, 5H), 7.37 (m, 3H), 7.12 (d, 1H), 6.82 (m, 3H), 6.64 (d, 1H), 4.37 (m, 1H), 3.86 (dd, 2H), 3.49 (m, 2H), 3.26 (m, 8H), 3.10 (m, 2H), 2.84 (s, 1H), 1.92 (m, 1H), 1.64 (dd, 2H), 1.28 (m, 2H).

Example 73

4-(4-((4'-chloro-1,1'-biphenyl-2-yl)methyl)piperazin-1-yl)-2-((3-(3-morpholin-4-yl-3-oxopropyl)-1H-indol-5-yl)oxy)-N-((3-nitro-4-((tetrahydro-2H-pyran-4-ylmethyl)amino)phenyl)sulfonyl)benzamide The title compound was prepared by substituting EXAMPLE 70E for EXAMPLE 1F in EXAMPLE 1H. $^1$H NMR (400 MHz, dimethylsulfoxide-$d_6$) δ 11.38 (s, 1H), 10.87 (s, 1H), 8.59 (m, 2H), 7.79 (dd, 1H), 7.68 (s, 1H), 7.51 (dd, 5H), 7.34 (dd, 4H), 7.20 (s, 1H), 7.10 (d, 2H), 6.81 (dd, 1H), 6.68 (d, 1H), 6.23 (s, 1H), 3.85 (d, 2H), 3.44 (s, 18H), 3.28 (m, 4H), 2.84 (m, 2H), 2.60 (t, 2H), 1.89 (s, 1H), 1.63 (m, 2H), 1.27 (m, 2H).

Example 74

4-(4-((4'-chloro-1,1'-biphenyl-2-yl)methyl)piperazin-1-yl)-2-((3-(3-morpholin-4-ylpropyl)-1H-indol-5-yl)oxy)-N-((3-nitro-4-((tetrahydro-2H-pyran-4-ylmethyl)amino)phenyl)sulfonyl)benzamide

Example 74A methyl 4-(4-((4'-chlorobiphenyl-2-yl)methyl)piperazin-1-yl)-2-(3-(3-morpholinopropyl)-1H-indol-5-yloxy)benzoate EXAMPLE 70C (107 mg) was dissolved in anhydrous tetrahydrofuran (0.7 mL), followed by the addition of 1M borane in tetrahydrofuran solution (0.57 mL). The reaction mixture was stirred at room temperature overnight. The reaction was quenched with 1N HCl aqueous solution (1.5 mL). The resulting solution was heated at 50° C. overnight. The solvent was removed under vacuum. The residue was purified by flash column chromatography on silica gel using 10-50% ethyl acetate in hexanes to afford the product.

Example 74B 4-(4-((4'-chlorobiphenyl-2-yl)methyl)piperazin-1-yl)-2-(3-(3-morpholinopropyl)-1H-indol-5-yloxy)benzoic acid The title compound was prepared by substituting EXAMPLE 74A for EXAMPLE 1E in EXAMPLE 1F.

Example 74C 4-(4-((4'-chloro-1,1'-biphenyl-2-yl)methyl)piperazin-1-yl)-2-((3-(3-morpholin-4-ylpropyl)-1H-indol-5-yl)oxy)-N-((3-nitro-4-((tetrahydro-2H-pyran-4-ylmethyl)amino)phenyl)sulfonyl)benzamide The title compound was prepared by substituting EXAMPLE 74B for EXAMPLE 1F in EXAMPLE 1H. $^1$H NMR (400 MHz, dimethylsulfoxide-$d_6$) δ 11.35 (m, 1H), 10.95 (s, 1H), 9.58 (m, 1H), 8.60 (m, 2H), 7.86 (dd, 1H), 7.63 (m, 1H), 7.50 (dd, 5H), 7.35 (t, 3H), 7.28 (s, 1H), 7.22 (dd, 2H), 7.17 (d, 1H), 6.84 (d, 1H), 6.65 (d, 1H), 6.16 (s, 1H), 3.93 (s, 1H), 3.84 (d, 2H), 3.50 (m, 15H), 3.32 (m, 2H), 3.26 (m, 2H), 3.13 (m, 2H), 3.03 (s, 2H), 2.68 (t, 2H), 1.97 (d, 2H), 1.89 (s, 1H), 1.61 (d, 2H), 1.27 (m, 2H).

Example 75

4-(4-((4'-chloro-1,1'-biphenyl-2-yl)methyl)piperazin-1-yl)-2-(4-((dimethylamino)methyl)phenoxy)-N-((3-nitro-4-((tetrahydro-2H-pyran-4-ylmethyl)amino)phenyl)sulfonyl)benzamide

Example 75A 4-((dimethylamino)methyl)phenol

The title compound was prepared by substituting 4-hydroxybenzaldehyde for 4'-chlorobiphenyl-2-carboxaldehyde and dimethylamine for tert-butyl piperazine-1-carboxylate in EXAMPLE 1A.

Example 75B methyl 4-(4-((4'-chlorobiphenyl-2-yl)methyl)piperazin-1-yl)-2-(4-((dimethylamino)methyl)phenoxy)benzoate The title compound was prepared by substituting EXAMPLE 75A for EXAMPLE 1D in EXAMPLE 1E.

Example 75C 4-(4-((4'-chlorobiphenyl-2-yl)methyl)piperazin-1-yl)-2-(4-((dimethylamino)methyl)phenoxy)benzoic acid The title compound was prepared by substituting EXAMPLE 75B for EXAMPLE 1E in EXAMPLE 1F.

Example 75D 4-(4-((4'-chloro-1,1'-biphenyl-2-yl)methyl)piperazin-1-yl)-2-(4-((dimethylamino)methyl)phenoxy)-N-((3-nitro-4-((tetrahydro-2H-pyran-4-ylmethyl)amino)phenyl)sulfonyl)benzamide The title compound was prepared by substituting EXAMPLE 75C for EXAMPLE 1F in EXAMPLE 1H. $^1$H NMR (300 MHz, dimethylsulfoxide-d$_6$) δ 11.80 (br s, 1H), 9.60 (br s, 1H), 8.59 (m, 1H), 8.48 (m, 1H), 7.80 (d, 1H), 7.50 (d, 2H), 7.46 (m, 2H), 7.36 (m, 4H), 7.24 (m, 2H), 6.90 (d, 2H), 6.77 (d, 1H), 6.44 (d, 1H), 4.16 (m, 2H), 3.84 (dd, 2H), 3.30 (m, 8H), 3.15 (m, 4H), 2.68 (m, 4H), 2.35 (m, 4H), 1.88 (m, 1H), 1.61 (dd, 2H), 1.23 (m, 2H).

Example 76

4-(4-((4'-chloro-1,1'-biphenyl-2-yl)methyl)piperazin-1-yl)-2-(4-(1H-imidazol-1-yl)phenoxy)-N-((3-nitro-4-((tetrahydro-2H-pyran-4-ylmethyl)amino)phenyl)sulfonyl)benzamide

Example 76A methyl 2-(4-(1H-imidazol-1-yl)phenoxy)-4-(4-((4'-chlorobiphenyl-2-yl)methyl)piperazin-1-yl)benzoate The title compound was prepared by substituting 4-(1H-imidazol-1-yl)phenol for EXAMPLE 1D in EXAMPLE 1E.

Example 76B 2-(4-(1H-imidazol-1-yl)phenoxy)-4-(4-((4'-chlorobiphenyl-2-yl)methyl)piperazin-1-yl)benzoic acid The title compound was prepared by substituting EXAMPLE 76A for EXAMPLE 1E in EXAMPLE 1F.

Example 76C 4-(4-((4'-chloro-1,1'-biphenyl-2-yl)methyl)piperazin-1-yl)-2-(4-(1H-imidazol-1-yl)phenoxy)-N-((3-nitro-4-((tetrahydro-2H-pyran-4-ylmethyl)amino)phenyl)sulfonyl)benzamide The title compound was prepared by substituting EXAMPLE 76B for EXAMPLE 1F in EXAMPLE 1H. $^1$H NMR (300 MHz, dimethylsulfoxide-d$_6$) δ 8.50 (s, 1H), 8.17 (d, 1H), 7.78 (m, 1H), 7.66 (m, 1H), 7.40-7.58 (m, 8H), 7.37 (d, 2H), 7.25 (m, 1H), 7.10 (d, 2H), 6.94 (d, 1H), 6.75 (d, 1H), 6.63 (d, 1H), 6.43 (d, 1H), 3.82 (m, 2H), 3.37 (m, 4H), 3.08-3.21 (m, 6H), 2.35 (m, 4H), 1.82 (m, 1H), 1.58 (m, 2H), 1.40 (m, 2H).

Example 77

4-(4-((4'-chloro-1,1'-biphenyl-2-yl)methyl)piperazin-1-yl)-2-(3-nitrophenoxy)-N-((4-((tetrahydro-2H-pyran-4-ylmethyl)amino)phenyl)sulfonyl)benzamide

Example 77A 4-((tetrahydro-2H-pyran-4-yl)methylamino)benzenesulfonamide

4-Aminobenzenesulfonamide (6.80 g), tetrahydropyran-4-carboxaldehyde (4.96 g), and sodium triacetoxyborohydride (16.74 g) in tetrahydrofuran (300 mL) and acetic acid (15 mL) were stirred at room temperature for 24 hours. The reaction was concentrated and taken up in ethyl acetate. The resulting solution was washed with water and brine, concentrated, and chromatographed on silica gel with 50% ethyl acetate/hexanes.

Example 77B 4-(4-((4'-chloro-1,1'-biphenyl-2-yl)methyl)piperazin-1-yl)-2-(3-nitrophenoxy)-N-((4-((tetrahydro-2H-pyran-4-ylmethyl)amino)phenyl)sulfonyl)benzamide 2,2,2-trifluoroacetate The title compound was prepared by substituting EXAMPLE 8B for EXAMPLE 50F and EXAMPLE 77A for EXAMPLE 3I in EXAMPLE 50G. $^1$H NMR (300 MHz, dimethylsulfoxide-d$_6$) δ 11.58 (br s, 1H), 9.58 (br s, 1H), 7.86 (m, 1H), 7.71 (br s, 1H), 7.52 (m, 7H), 7.40 (m, 5H), 7.30 (m, 1H), 6.82 (dd, 1H), 6.71 (br s, 1H), 6.60 (d, 1H), 6.47 (d, 2H), 4.37 (v br s, 1H), 3.83 (dd, 2H), 3.70 (v br s, 1H), 3.50-3.40 (envelope, 6H), 3.26, (m, 2H), 3.05, 2.96, 2.94, 2.85 (all br s, total 4H), 1.79 (m, 1H), 1.65 (m, 2H), 1.22 (m, 2H).

Example 78 tert-butyl 4-(5-(4-((4'-chloro-1,1'-biphenyl-2-yl)methyl)piperazin-1-yl)-2-((((3-nitro-4((tetrahydro-2H-pyran-4-ylmethyl)amino)phenyl)sulfonyl)amino)carbonyl)phenoxy)benzyl(ethyl)carbamate

Example 78A tert-butyl ethyl(4-hydroxybenzyl)carbamate

Diethylamine gas was bubbled into a solution of 4-hydroxybenzaldehyde (2.0 g) and sodium triacetoxyborohydride (5.2 g) in dichloromethane (60 mL) until saturated. The reaction flask was stoppered and the reaction stirred for 24 hours. 1M NaOH (10 mL) was then added, followed by di-tert-butyl dicarbonate (3.57 g) and triethylamine (2.28 mL), and the reaction was stirred for 24 hours. The reaction was acidified with saturated NaH$_2$PO$_4$ solution, extracted twice with ethyl acetate, and the combined extracts were washed with brine and concentrated. The crude product was chromatographed on silica gel using 20% ethyl acetate/hexanes as the eluent to give the product.

Example 78B methyl 2-(4-((tert-butoxycarbonyl(ethyl)amino)methyl)phenoxy)-4-(4-((4'-chlorobiphenyl-2-yl)methyl)piperazin-1-yl)benzoate The title compound was prepared by substituting EXAMPLE 78A for EXAMPLE 1D in EXAMPLE 1E.

Example 78C 2-(4-((tert-butoxycarbonyl(ethyl)amino)methyl)phenoxy)-4-(4-((4'-chlorobiphenyl-2-yl)methyl)piperazin-1-yl)benzoic acid The title compound was prepared by substituting EXAMPLE 78B for EXAMPLE 1E in EXAMPLE 1F.

Example 78D tert-butyl 4-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)benzyl(ethyl)carbamate The title compound was prepared by substituting EXAMPLE 78C for EXAMPLE 1F in EXAMPLE 1H.

Example 79 tert-butyl 3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)benzyl(ethyl)carbamate

Example 79A tert-butyl ethyl(4-hydroxybenzyl)carbamate

The title compound was prepared by substituting 3-hydroxybenzaldehyde for 4-hydroxybenzaldehyde in EXAMPLE 78A.

Example 79B methyl 2-(3-((tert-butoxycarbonyl(ethyl)amino)methyl)phenoxy)-4-(4-((4'-chlorobiphenyl-2-yl)methyl)piperazin-1-yl)benzoate The title compound was prepared by substituting EXAMPLE 79A for EXAMPLE 1D in EXAMPLE 1E.

Example 79C 2-(3-((tert-butoxycarbonyl(ethyl)amino)methyl)phenoxy)-4-(4-((4'-chlorobiphenyl-2-yl)methyl)piperazin-1-yl)benzoic acid The title compound was prepared by substituting EXAMPLE 79B for EXAMPLE 1E in EXAMPLE 1F.

Example 79D tert-butyl 3-(5-(4-((4'-chlorobiphenyl-2-yl)methyl)piperazin-1-yl)-2-(3-nitro-4-((tetrahydro-2H-pyran-4-yl)methylamino)phenylsulfonylcarbamoyl)phenoxy)benzyl(ethyl)carbamate The title compound was prepared by substituting EXAMPLE 79C for EXAMPLE 1F in EXAMPLE 1H.

Example 80

4-(4-((4'-chloro-1,1'-biphenyl-2-yl)methyl)piperazin-1-yl)-2-(4-((ethylamino)methyl)phenoxy)-N-((3-nitro-4-((tetrahydro-2H-pyran-4-ylmethyl)amino)phenyl)sulfonyl)benzamide The title compound was prepared by substituting EXAMPLE 78D for EXAMPLE 1A in EXAMPLE 1B. $^1$H NMR (300 MHz, dimethylsulfoxide-$d_6$) δ 8.63 (br s, 1H), 8.52 (br s, 1H), 8.43 (s, 1H), 7.78 (dd, 1H), 7.60 (d, 1H), 7.46 (s, 4H), 7.35 (d, 2H), 7.31 (m, 1H), 7.24 (d, 1H), 7.13 (d, 1H), 6.84 (d, 2H), 6.72 (d, 1H), 6.36 (s, 1H), 4.04 (s, 2H), 3.84 (dd, 2H), 3.27 (m, 6H), 3.11 (m, 4H), 2.94 (m, 2H), 2.36 (m, 4H), 1.91 (m, 1H), 1.62 (dd, 2H), 1.23 (m, 2H), 1.17 (t, 3H).

Example 81

4-(4-((4'-chloro-1,1'-biphenyl-2-yl)methyl)piperazin-1-yl)-2-(3-((ethylamino)methyl)phenoxy)-N-((3-nitro-4-((tetrahydro-2H-pyran-4-ylmethyl)amino)phenyl)sulfonyl)benzamide The title compound was prepared by substituting EXAMPLE 79D for EXAMPLE 1A in EXAMPLE 1B. $^1$H NMR (300 MHz, dimethylsulfoxide-$d_6$) δ 11.60 (br s, 1H), 8.80 (br s, 1H), 8.62 (br s, 1H), 8.51 (s, 1H), 7.82 (dd, 1H), 7.30-7.55 (m, 7H), 7.24 (m, 2H), 7.19 (d, 1H), 7.04 (d, 1H), 6.89 (d, 1H), 6.77 (d, 1H), 6.36 (s, 1H), 4.06 (s, 2H), 3.86 (dd, 2H), 3.27 (m, 6H), 3.11 (m, 4H), 2.96 (m, 2H), 2.34 (m, 4H), 1.90 (m, 1H), 1.61 (dd, 2H), 1.24 (m, 2H), 1.19 (t, 3H).

Example 82

2-(4-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide

Example 82A methyl 2-(4-acetamidophenoxy)-4-(4-((4'-chlorobiphenyl-2-yl)methyl)piperazin-1-yl)benzoate The title compound was prepared by substituting 4-acetamidophenol for EXAMPLE 1D in EXAMPLE 1E.

Example 82B 2-(4-acetamidophenoxy)-4-(4-((4'-chlorobiphenyl-2-yl)methyl)piperazin-1-yl)benzoic acid The title compound was prepared by substituting EXAMPLE 82A for EXAMPLE 1E in EXAMPLE 1F.

Example 82C 2-(4-(acetylamino)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide The title compound was prepared by substituting EXAMPLE 82B for EXAMPLE 1G in EXAMPLE 1H. $^1$H NMR (300 MHz, dimethylsulfoxide-$d_6$) δ 11.58 (s, 1H), 9.91 (s, 1H), 8.62 (t, 1H), 8.54 (d, 1H), 7.76 (dd, 1H), 7.68 (m, 1H), 7.51 (m, 7H), 7.34 (m, 3H), 7.16 (d, 1H), 6.85 (d, 2H), 6.72 (dd, 1H), 6.30 (m, 1H), 4.35 (s, 1H), 3.85 (dd, 2H), 3.68 (m, 1H), 3.27 (m, 9H), 3.02 (m, 2H), 2.83 (m, 1H), 2.04 (s, 3H), 1.89 (m, 1H), 1.62 (dd, 2H), 1.24 (m, 2H).

Example 83 tert-butyl 4-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenylcarbamate This EXAMPLE was prepared by substituting EXAMPLE 18B for EXAMPLE 1F in EXAMPLE 1H. $^1$H NMR (300

MHz, dimethylsulfoxide-d$_6$) δ 11.37 (s, 1H), 9.32 (s, 1H), 8.61 (t, 1H), 8.57 (d, 1H), 7.81 (dd, 1H), 7.44 (m, 8H), 7.34 (m, 2H), 7.22 (m, 2H), 6.88 (d, 2H), 6.69 (dd, 1H), 6.20 (d, 1H), 3.85 (m, 2H), 3.28 (m, 6H), 3.09 (m, 4H), 2.33 (m, 4H), 1.90 (m, 1H), 1.63 (m, 2H), 1.47 (m, 9H), 1.26 (m, 2H).

Example 84

2-(1,1'-biphenyl-2-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide Example 84A methyl 2-(biphenyl-2-yloxy)-4-(4-((4'-chlorobiphenyl-2-yl)methyl)piperazin-1-yl)benzoate The title compound was prepared by substituting 2-phenylphenol for EXAMPLE 1D in EXAMPLE 1E.

Example 84B 2-(biphenyl-2-yloxy)-4-(4-((4'-chlorobiphenyl-2-yl)methyl)piperazin-1-yl)benzoic acid The title compound was prepared by substituting EXAMPLE 84A for EXAMPLE 1E in EXAMPLE 1F.

Example 84C 2-(1,1'-biphenyl-2-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide 2,2,2-trifluoroacetate The title compound was prepared by substituting EXAMPLE 84B for EXAMPLE 50F and EXAMPLE 1G for EXAMPLE 3I in EXAMPLE 50G. $^1$H NMR (300 MHz, dimethylsulfoxide-d$_6$) δ 11.56 (v br s, 1H), 9.50 (v br s, 1H), 8.62 (t, 1H), 8.45 (d, 1H), 7.76 (dd, 1H), 7.70 (br s, 1H), 7.50 (m, 7H), 7.37 (d, 2H), 7.27 (m, 5H), 7.12 (m, 2H), 7.04 (m, 1H), 6.70 (dd, 1H), 6.64 (d, 1H), 6.27 (s, 1H), 4.35 (v br s, 1H), 3.83 (dd, 2H), 3.70 (v br s, 1H), 3.40 (m, 4H), 3.25, 3.20 (both m, total 4H), 3.00, 2.80 (both br s, total 4H), 1.83 (m, 1H), 1.59 (m, 2H), 1.24 (m, 2H).

Example 85 tert-butyl 3-(5-(4-((4'-chloro-1,1'-biphenyl-2-yl)methyl)-1-yl)-2-((((3-nitro-4-((tetrahydro-2H-pyran-4-ylmethyl)amino)phenyl)sulfonyl)amino)carbonyl)phenoxy)phenylcarbamate The title compound was prepared as described in EXAMPLE 19C. $^1$H NMR (300 MHz, dimethylsulfoxide-d$_6$) δ 11.45 (s, 1H), 9.34 (s, 1H), 8.62 (t, 1H), 8.52 (d, 1H), 7.75 (dd, 1H), 7.46 (m, 6H), 7.36 (m, 2H), 7.23 (m, 1H), 7.11 (m, 4H), 6.74 (dd, 1H), 6.42 (m, 1H), 6.36 (d, 1H), 3.86 (dd, 2H), 3.30 (m, 6H), 3.15 (m, 4H), 2.35 (m, 4H), 1.90 (qd, 1H), 1.63 (dd, 2H), 1.45 (s, 9H), 1.27 (m, 2H).

Example 86

2-(1,1'-biphenyl-3-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide Example 86A methyl 2-(biphenyl-3-yloxy)-4-(4-((4'-chlorobiphenyl-2-yl)methyl)piperazin-1-yl)benzoate The title compound was prepared by substituting 3-phenylphenol for EXAMPLE 1D in EXAMPLE 1E.

Example 86B 2-(biphenyl-3-yloxy)-4-(4-((4'-chlorobiphenyl-2-yl)methyl)piperazin-1-yl)benzoic acid The title compound was prepared by substituting EXAMPLE 86A for EXAMPLE 1E in EXAMPLE 1F.

Example 86C 2-(1,1'-biphenyl-3-yloxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide 2,2,2-trifluoroacetate The title compound was prepared by substituting EXAMPLE 86B for EXAMPLE 50F and EXAMPLE 1G for EXAMPLE 3I in EXAMPLE 50G. $^1$H NMR (300 MHz, dimethylsulfoxide-dc) δ 11.82 (v br s, 1H), 9.60 (v br s, 1H), 8.72 (t, 1H), 8.42 (d, 1H), 7.70 (br s, 1H), 7.69 (dd, 1H), 7.55-7.20 (m, 15H), 7.00 (d, 1H), 6.96 (s, 1H), 6.80 (m, 2H), 6.53 (d, 1H), 4.35 (v br s, 1H), 3.83 (dd, 2H), 3.70 (v br s, 1H), 3.40 (m, 4H), 3.25, 3.20 (both m, total 4H), 3.00, 2.80 (both br s, total 4H), 1.81 (m, 1H), 1.58 (m, 2H), 1.22 (m, 2H).

Example 87

4-(4-((4'-chloro-1,1'-biphenyl-2-yl)methyl)piperazin-1-yl)-2-(4-(2-(dimethylamino)ethyl)phenoxy)-N-((3-nitro-4-((tetrahydro-2H-pyran-4-ylmethyl)amino)phenyl)sulfonyl)benzamide Example 87A methyl 4-(4-((4'-chlorobiphenyl-2-yl)methyl)piperazin-1-yl)-2-(4-(2-(dimethylamino)ethyl)phenoxy)benzoate The title compound was prepared by substituting 4-(2-(dimethylamino)ethyl)phenol for EXAMPLE 1D in EXAMPLE 1E.

Example 87B 4-(4-((4'-chlorobiphenyl-2-yl)methyl)piperazin-1-yl)-2-(4-(2-(dimethylamino)ethyl)phenoxy)benzoic acid The title compound was prepared by substituting EXAMPLE 87A for EXAMPLE 1E in EXAMPLE 1F.

Example 87C 4-(4-((4'-chloro-1,1'-biphenyl-2-yl)methyl)piperazin-1-yl)-2-(4-(2-(dimethylamino)ethyl)phenoxy)-N-((3-nitro-4-((tetrahydro-2H-pyran-4-ylmethyl)amino)phenyl)sulfonyl)benzamide The title compound was prepared by substituting EXAMPLE 87B for EXAMPLE 1F in EXAMPLE 1H. $^1$H NMR (400 MHz, dimethylsulfoxide-$d_6$) δ 11.67 (s, 1H), 9.51 (s, 1H), 8.66 (t, 1H), 8.52 (d, 1H), 7.84 (dd, 1H), 7.70 (s, 1H), 7.51 (dd, 5H), 7.36 (m, 3H), 7.22 (m, 3H), 6.84 (d, 2H), 6.76 (m, 1H), 6.42 (s, 1H), 3.85 (m, 2H), 3.52 (s, 10H), 3.35 (m, 2H), 3.26 (dd, 4H), 2.90 (m, 2H), 2.83 (d, 6H), 1.91 (s, 1H), 1.61 (d, 2H), 1.27 (dt, 2H).

Example 88

2-(4-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide

Example 88A

Methyl 2-(4-(benzyloxy)phenoxy)-4-(4-((4'-chlorobiphenyl-2-yl)methyl)piperazin-1-yl)benzoate The title compound was prepared by substituting 4-(benzyloxy)phenol for EXAMPLE 1D in EXAMPLE 1E.

Example 88B 2-(4-(benzyloxy)phenoxy)-4-(4-((4'-chlorobiphenyl-2-yl)methyl)piperazin-1-yl)benzoic acid The title compound was prepared by substituting EXAMPLE 88A for EXAMPLE 1E in EXAMPLE 1F.

Example 88C 2-(4-(benzyloxy)phenoxy)-4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)benzamide The title compound was prepared by substituting EXAMPLE 88B for EXAMPLE 1F in EXAMPLE 1H. $^1$H NMR (400 MHz, dimethylsulfoxide-$d_6$) δ 11.50 (m, 1H), 8.63 (t, 1H), 8.55 (d, 1H), 7.82 (dd, 1H), 7.66 (m, 1H), 7.41 (m, 13H), 7.20 (m, 1H), 6.96 (d, 2H), 6.88 (d, 2H), 6.70 (dd, 1H), 6.25 (m, 1H), 5.04 (m, 2H), 3.27 (m, 10H), 2.90 (m, 6H), 1.88 (m, 1H), 1.57 (m, 2H), 1.23 (m, 2H).

Example 89

4-(4-((4'-chloro-1,1'-biphenyl-2-yl)methyl)piperazin-1-yl)-2-(3-morpholin-4-ylphenoxy)-N-((3-nitro-4-((tetrahydro-2H-pyran-4-ylmethyl)amino)phenyl)sulfonyl)benzamide The title compound was prepared by substituting EXAMPLE 32B for EXAMPLE 1F in EXAMPLE 1H. $^1$H NMR (400 MHz, dimethylsulfoxide-$d_6$) δ 11.58 (s, 1H), 8.63 (t, 1H), 8.49 (d, 1H), 7.78 (dd, 1H), 7.69 (m, 1H), 7.52 (m, 5H), 7.38 (d, 2H), 7.33 (m, 1H), 7.15 (d, 1H), 7.07 (m, 1H), 6.74 (dd, 1H), 6.58 (dd, 1H), 6.40 (m, 2H), 6.22 (dd, 1H), 4.29 (m, 2H), 3.86 (m, 2H), 3.70 (m, 6H), 3.30 (m, 6H), 3.00 (m, 6H), 2.83 (m, 2H), 1.91 (m, 1H), 1.63 (d, 2H), 1.28 (m, 2H).

Example 90

4-(4-((4'-chloro-1,1'-biphenyl-2-yl)methyl)piperazin-1-yl)-2-((2-methyl-1,3-benzothiazol-5-yl)oxy)-N-((3-nitro-4-((tetrahydro-2H-pyran-4-ylmethyl)amino)phenyl)sulfonyl)benzamide The title compound was prepared by substituting EXAMPLE 24B for EXAMPLE 1F in EXAMPLE 1H. $^1$H NMR (300 MHz, dimethylsulfoxide-$d_6$) δ 11.83 (s, 1H), 9.48 (br s, 1H), 8.64 (t, 1H), 8.45 (d, 1H), 7.88 (d, 1H), 7.76 (dd, 1H), 7.50 (m, 5H), 7.37 (m, 2H), 7.30 (m, 1H), 7.18 (m, 1H), 7.04 (d, 1H), 6.97 (dd, 1H), 6.78 (dd, 1H), 6.48 (br s, 1H), 3.84 (dd, 2H), 3.37 (m, 6H), 3.23 (m, 4H), 2.89 (m, 2H), 2.75 (s, 3H), 2.36 (m, 3H), 1.62 (d, 2H), 1.24 (m, 2H).

Example 91 tert-butyl 4-(3-(5-(4-((4'-chloro-1,1'-biphenyl-2-yl)methyl)piperazin-1-yl)-2-((((3-nitro-4-((tetrahydro-2H-pyran-4-ylmethyl)amino)phenyl)sulfonyl)amino)carbonyl)phenoxy)phenyl)piperazine-1-carboxylate

Example 91A tert-butyl 4-(3-(5-(4-((4'-chlorobiphenyl-2-yl)methyl)piperazin-1-yl)-2-(methoxycarbonyl)phenoxy)phenyl)piperazine-1-carboxylate The title compound was prepared by substituting 1-(3-hydroxy-phenyl)-piperazine-4-carboxylic acid tert-butyl ester for EXAMPLE 1D in EXAMPLE 1E.

Example 91B 2-(3-(4-(tert-butoxycarbonyl)piperazin-1-yl)phenoxy)-4-(4-((4'-chlorobiphenyl-2-yl)methyl)piperazin-1-yl)benzoic acid The title compound was prepared by substituting EXAMPLE 91A for EXAMPLE 1E in EXAMPLE 1F.

Example 91C tert-butyl 4-(3-(5-(4-((4'-chloro-1,1'-biphenyl-2-yl)methyl)piperazin-1-yl)-2-(((((3-nitro-4-((tetrahydro-2H-pyran-4-ylmethyl)amino)phenyl)sulfonyl)amino)carbonyl)phenoxy)phenyl)piperazine-1-carboxylate The title compound was prepared by substituting EXAMPLE 91B for EXAMPLE 1F in EXAMPLE 1H. $^1$H NMR (400 MHz, dimethylsulfoxide-$d_6$) δ 11.65 (s, 1H), 8.65 (t, 1H), 8.47 (d, 1H), 7.76 (dd, 1H), 7.72 (m, 1H), 7.50 (m, 5H), 7.37 (d, 2H), 7.33 (m, 1H), 7.15 (d, 1H), 7.05 (m, 1H), 6.75 (dd, 1H), 6.57 (dd, 1H), 6.41 (m, 2H), 6.21 (dd, 1H), 4.31 (m, 2H), 3.86 (dd, 2H), 3.41 (m, 6H), 3.34 (t, 2H), 3.27 (m, 4H), 3.00 (m, 6H), 2.85 (m, 2H), 1.91 (m, 1H), 1.63 (d, 2H), 1.40 (m, 9H), 1.28 (m, 2H).

Example 92

2-(3-(benzyloxy)phenoxy)-4-(4-((4'-chloro-1,1'-biphenyl-2-yl)methyl)piperazin-1-yl)-N-((4-((3-(dimethylamino)propyl)amino)-3-nitrophenyl)sulfonyl)benzamide The title compound was prepared by substituting EXAMPLE 71A for EXAMPLE 11F and EXAMPLE 11A for EXAMPLE 1G in EXAMPLE 1H. $^1$H NMR (400 MHz, dimethylsulfoxide-$d_6$) δ 11.72 (s, 1H), 9.52 (s, 1H), 8.69 (t, 1H), 8.50 (d, 1H), 7.81 (dd, 1H), 7.65 (s, 1H), 7.50 (m, 5H), 7.39 (m, 6H), 7.32 (m, 2H), 7.13 (m, 2H), 6.77 (dd, 1H), 6.64 (dd, 1H), 6.42 (s, 2H), 6.38 (m, 1H), 4.99 (s, 2H), 3.50 (m, 10H), 3.11 (m, 4H), 2.77 (s, 6H), 1.95 (m, 2H).

Example 93

2-(3-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide The title compound was prepared by substituting EXAMPLE 71A for EXAMPLE 1F and EXAMPLE 4A for EXAMPLE 1G in EXAMPLE 1H. $^1$H NMR (400 MHz, dimethylsulfoxide-$d_6$) δ 11.74 (m, 1H), 9.78 (s, 1H), 8.71 (m, 1H), 8.50 (d, 1H), 7.82 (dd, 1H), 7.67 (s, 1H), 7.50 (m, 5H), 7.39 (m, 6H), 7.32 (m, 2H), 7.13 (m, 1H), 6.77 (dd, 1H), 6.64 (dd, 1H), 6.39 (m, 3H), 4.99 (s, 2H), 3.96 (m, 2H), 3.60 (s, 2H), 3.51 (m, 6H), 3.17 (m, 10H), 2.67 (m, 2H), 1.94 (m, 2H).

Example 94

4-(4-((4'-chloro-1,1'-biphenyl-2-yl)methyl)piperazin-1-yl)-2-(4-(2-morpholin-4-ylethoxy)phenoxy)-N-((3-nitro-4-((tetrahydro-2H-pyran-4-ylmethyl)amino)phenyl)sulfonyl)benzamide

Example 94A 4-(2-(4-(benzyloxy)phenoxy)ethyl)morpholine

The title compound was prepared by substituting 4-(2-chloroethyl)morpholine for 2-chloro-N,N-dimethylethanamine and 4-(benzyloxy)phenol for 3-(benzyloxy)phenol in EXAMPLE 39A.

Example 94B 4-(2-morpholinoethoxy)phenol

The title compound was prepared by substituting EXAMPLE 94A for EXAMPLE 39A in EXAMPLE 39B.

Example 94C methyl 4-(4-((4'-chlorobiphenyl-2-yl)methyl)piperazin-1-yl)-2-(4-(2-morpholinoethoxy)phenoxy)benzoate The title compound was prepared by substituting EXAMPLE 94B for EXAMPLE 1D in EXAMPLE 1E.

Example 94D 4-(4-((4'-chlorobiphenyl-2-yl)methyl)piperazin-1-yl)-2-(4-(2-morpholinoethoxy)phenoxy)benzoic acid The title compound was prepared by substituting EXAMPLE 94C for EXAMPLE 1E in EXAMPLE 1F.

Example 94E 4-(4-((4'-chloro-1,1'-biphenyl-2-yl)methyl)piperazin-1-yl)-2-(4-(2-morpholin-4-ylethoxy)phenoxy)-N-((3-nitro-4-((tetrahydro-2H-pyran-4-ylmethyl)amino)phenyl)sulfonyl)benzamide The title compound was prepared by substituting EXAMPLE 94D for EXAMPLE 1F in EXAMPLE 1H. $^1$H NMR (400 MHz, dimethylsulfoxide-$d_6$) δ 11.46 (m, 1H), 9.98 (m, 1H), 8.64 (d, 1H), 8.55 (d, 1H), 7.87 (d, 1H), 7.49 (m, 5H), 7.39 (d, 2H), 7.31 (s, 1H), 7.25 (d, 1H), 6.96 (m, 5H), 6.71 (d, 1H), 6.29 (s, 1H), 4.30 (s, 2H), 3.98 (s, 2H), 3.85 (d, 2H), 3.72 (s, 2H), 3.42 (s, 16H), 3.27 (m, 2H), 1.91 (s, 1H), 1.62 (d, 2H), 1.28 (m, 2H).

Example 95

4-(4-((4'-chloro-1,1'-biphenyl-2-yl)methyl)piperazin-1-yl)-N-((3-nitro-4-((tetrahydro-2H-pyran-4-ylmethyl)amino)phenyl)sulfonyl)-2-((2-oxo-1,2,3,4-tetrahydroquinolin-5-yl)oxy)benzamide The title compound was prepared by substituting EXAMPLE 58B for EXAMPLE 1F in EXAMPLE 1H. $^1$H NMR (300 MHz, dimethylsulfoxide-$d_6$) δ 11.50 (s, 1H), 10.07 (s, 1H), 8.60 (t, 1H), 8.47 (d, 1H), 7.74 (dd, 1H), 7.46 (m, 6H), 7.36 (m, 2H), 7.24 (m, 1H), 7.14 (d, 1H), 6.92 (t, 1H), 6.74 (dd, 1H), 6.51 (d, 1H), 6.35 (d, 1H), 6.13 (d, 1H), 3.86 (dd, 2H), 3.36 (m, 4H), 3.25 (m, 2H), 3.16 (m, 4H), 2.83 (t, 2H), 2.41 (dd, 2H), 2.35 (m, 4H), 1.90 (m, 1H), 1.64 (dd, 2H), 1.28 (m, 2H).

Example 96

2-(4-(benzyloxy)phenoxy)-4-(4-((4'-chloro-1,1'-biphenyl-2-yl)methyl)piperazin-1-yl)-N-((4-((3-morpholin-4-ylpropyl)amino)-3-nitrophenyl)sulfonyl)benzamide The title compound was prepared by substituting EXAMPLE 88B for EXAMPLE 1F and EXAMPLE 4A for EXAMPLE 1G in EXAMPLE 1H. $^1$H NMR (400 MHz, dimethylsulfoxide-$d_6$) δ 11.53 (s, 1H), 9.74 (s, 1H), 8.69 (m, 1H), 8.59 (d, 1H), 7.90 (dd, 1H), 7.67 (m, 1H), 7.41 (m, 13H), 7.21 (d, 1H), 6.99 (m, 2H), 6.91 (m, 2H), 6.70 (dd, 1H), 6.23 (s, 1H), 5.07 (s, 2H), 4.28 (m, 2H), 3.95 (s, 2H), 3.51 (m, 6H), 3.16 (m, 10H), 2.73 (d, 2H), 1.98 (m, 2H).

Example 97 tert-butyl 4-(4-(5-(4-(((4'-chloro-1,1'-biphenyl-2-yl)methyl)piperazin-1-yl)-2-((((4-((3-morpholin-4-ylpropyl)amino)-3-nitrophenyl)sulfonyl)amino)carbonyl)phenoxy)phenyl)piperazine-1-carboxylate

Example 97A tert-butyl 4-(4-(5-(4-(((4'-chlorobiphenyl-2-yl)methyl)piperazin-1-yl)-2-(methoxycarbonyl)phenoxy)phenyl)piperazine-1-carboxylate The title compound was prepared by substituting 1-(4-hydroxy-phenyl)-piperazine-4-carboxylic acid tert-butyl ester for EXAMPLE 1D in EXAMPLE 1E.

Example 97B 2-(4-(4-(tert-butoxycarbonyl)piperazin-1-yl)phenoxy)-4-(4-((4'-chlorobiphenyl-2-yl)methyl)piperazin-1-yl)benzoic acid The title compound was prepared by substituting EXAMPLE 97A for EXAMPLE 1E in EXAMPLE 1F.

Example 97C tert-butyl 4-(4-(5-(4-(((4'-chloro-1,1'-biphenyl-2-yl)methyl)piperazin-1-yl)-2-((((4-((3-morpholin-4-ylpropyl)amino)-3-nitrophenyl)sulfonyl)amino)carbonyl)phenoxy)phenyl)piperazine-1-carboxylate The title compound was prepared by substituting EXAMPLE 97B for EXAMPLE 1F and EXAMPLE 4A for EXAMPLE 1G in EXAMPLE 1H. $^1$H NMR (400 MHz, dimethylsulfoxide-$d_6$) δ 11.44 (m, 1H), 9.67 (s, 1H), 8.70 (t, 1H), 8.59 (d, 1H), 7.91 (dd, 1H), 7.69 (s, 1H), 7.49 (m, 7H), 7.30 (m, 1H), 7.21 (d, 1H), 6.91 (m, 4H), 6.69 (dd, 1H), 6.24 (s, 1H), 3.95 (m, 2H), 3.67 (m, 4H), 3.52 (m, 10H), 3.17 (s, 4H), 3.04 (m, 10H), 1.97 (d, 2H), 1.43 (s, 9H).

Example 98

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(3-pyridin-4-ylphenoxy)benzamide

Example 98A 4-(3-(benzyloxy)phenyl)pyridine

The title compound was prepared by substituting 1-(benzyloxy)-3-bromobenzene for EXAMPLE 33C and pyridin-4-ylboronic acid for 2,4-dimethyl-5-(4,4,5,5-tetramethyl-1,3,2-dioxaborolan-2-yl)thiazole in EXAMPLE 33D.

Example 98B 3-(pyridin-4-yl)phenol

The title compound was prepared by substituting EXAMPLE 98A for EXAMPLE 33A in EXAMPLE 33B.

Example 98C methyl 4-(4-((4'-chlorobiphenyl-2-yl)methyl)piperazin-1-yl)-2-(3-(pyridin-4-yl)phenoxy)benzoate The title compound was prepared by substituting EXAMPLE 98B for EXAMPLE 1D in EXAMPLE 1E.

Example 98D 4-(4-((4'-chlorobiphenyl-2-yl)methyl)piperazin-1-yl)-2-(3-(pyridin-4-yl)phenoxy)benzoic acid The title compound was prepared by substituting EXAMPLE 98C for EXAMPLE 1E in EXAMPLE 1F.

Example 98E 4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(3-pyridin-4-ylphenoxy)benzamide The title compound was prepared by substituting EXAMPLE 98D for EXAMPLE 1F and EXAMPLE 4A for EXAMPLE 1G in EXAMPLE 1H. $^1$H NMR (400 MHz, dimethylsulfoxide-$d_6$) δ 11.87 (m, 1H), 8.68 (d, 2H), 8.58 (m, 1H), 8.42 (d, 1H), 7.73 (m, 4H), 7.52 (m, 5H), 7.36 (m, 6H), 7.14 (s, 1H), 7.03 (d, 1H), 6.91 (m, 1H), 6.80 (dd, 1H), 6.55 (d, 1H), 4.22 (m, 2H), 3.89 (m, 7H), 3.41 (m, 4H), 3.15 (m, 4H), 2.91 (m, 4H), 1.94 (m, 2H).

Example 99

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-4-ylphenoxy)benzamide

Example 99A 4-(4-(benzyloxy)phenyl)pyridine

The title compound was prepared by substituting 1-(benzyloxy)-4-bromobenzene for EXAMPLE 33C and pyridin-4-ylboronic acid for 2,4-dimethyl-5-(4,4,5,5-tetramethyl-1,3,2-dioxaborolan-2-yl)thiazole in EXAMPLE 33D.

Example 99B 4-(pyridin-4-yl)phenol

The title compound was prepared by substituting EXAMPLE 99A for EXAMPLE 33A in EXAMPLE 33B.

Example 99C methyl 4-(4-((4'-chlorobiphenyl-2-yl)methyl)piperazin-1-yl)-2-(4-(pyridin-4-yl)phenoxy)benzoate The title compound was prepared by substituting EXAMPLE 99B for EXAMPLE 1D in EXAMPLE 1E.

Example 99D 4-(4-((4'-chlorobiphenyl-2-yl)methyl)piperazin-1-yl)-2-(4-(pyridin-4-yl)phenoxy)benzoic acid The title compound was prepared by substituting EXAMPLE 99C for EXAMPLE 1E in EXAMPLE 1F.

Example 99E 4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-4-ylphenoxy)benzamide The title compound was prepared by substituting EXAMPLE 99D for EXAMPLE 1F and EXAMPLE 4A for EXAMPLE 1G in EXAMPLE 1H. $^1$H NMR (400 MHz, dimethylsulfoxide-$d_6$) δ 8.80 (d, 2H), 8.55 (m, 1H), 8.49 (d, 1H), 7.93 (m, 5H), 7.74 (m, 1H), 7.53 (m, 5H), 7.36 (m, 3H), 7.13 (m, 2H), 6.93 (d, 1H), 6.83 (dd, 1H), 6.62 (d, 1H), 4.60 (s, 4H), 4.29 (m, 2H), 3.67 (s, 4H), 3.42 (m, 4H), 3.13 (m, 4H), 2.92 (m, 4H), 1.90 (m, 2H).

Example 100

4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-3-ylphenoxy)benzamide

Example 100A 3-(4-(benzyloxy)phenyl)pyridine

The title compound was prepared by substituting 1-(benzyloxy)-4-bromobenzene for EXAMPLE 33C and pyridin-3-ylboronic acid for 2,4-dimethyl-5-(4,4,5,5-tetramethyl-1,3,2-dioxaborolan-2-yl)thiazole in EXAMPLE 33D.

Example 100B 4-(pyridin-4-yl)phenol

The title compound was prepared by substituting EXAMPLE 100A for EXAMPLE 33A in EXAMPLE 33B.

Example 100C methyl 4-(4-((4'-chlorobiphenyl-2-yl)methyl)piperazin-1-yl)-2-(4-(pyridin-4-yl)phenoxy)benzoate The title compound was prepared by substituting EXAMPLE 100B for EXAMPLE 1D in EXAMPLE 1E.

Example 100D 4-(4-((4'-chlorobiphenyl-2-yl)methyl)piperazin-1-yl)-2-(4-(pyridin-4-yl)phenoxy)benzoic acid The title compound was prepared by substituting EXAMPLE 100C for EXAMPLE 1E in EXAMPLE 1F.

Example 100E 4-(4-((4'-chloro-1,1'-biphenyl-2-yl)methyl)piperazin-1-yl)-N-((4-((3-morpholin-4-ylpropyl)amino)-3-nitrophenyl)sulfonyl)-2-(4-pyridin-3-ylphenoxy)benzamide The title compound was prepared by substituting EXAMPLE 100D for EXAMPLE 1F and EXAMPLE 4A for EXAMPLE 1G in EXAMPLE 1H. $^1$H NMR (400 MHz, dimethylsulfoxide-$d_6$) δ 11.84 (s, 1H), 8.95 (d, 1H), 8.66 (d, 1H), 8.57 (m, 1H), 8.52 (d, 1H), 8.24 (d, 1H), 7.83 (dd, 1H), 7.72 (m, 5H), 7.53 (m, 5H), 7.35 (m, 3H), 7.11 (m, 1H), 6.93 (d, 2H), 6.81 (dd, 1H), 6.57 (d, 1H), 4.31 (s, 2H), 3.80 (m, 8H), 3.42 (m, 4H), 3.14 (m, 8H), 1.94 (m, 2H).

Example 101

4-(4-((4'-chloro-1,1'-biphenyl-2-yl)methyl)piperazin-1-yl)-2-(4-(2-(dimethylamino)-2-oxoethoxy)phenoxy)-N-((3-nitro-4-((tetrahydro-2H-pyran-4-ylmethyl)amino)phenyl)sulfonyl)benzamide

Example 101A 2-(4-(benzyloxy)phenoxy)-N,N-dimethylacetamide

The title compound was prepared by substituting 2-chloro-N,N-dimethylacetamide for 2-chloro-N,N-dimethylethanamine and 4-(benzyloxy)phenol for 3-(benzyloxy)phenol in EXAMPLE 39A.

Example 101B 2-(4-hydroxyphenoxy)-N,N-dimethylacetamide

The title compound was prepared by substituting EXAMPLE 101A for EXAMPLE 39A in EXAMPLE 39B.

Example 101C methyl 4-(4-((4'-chlorobiphenyl-2-yl)methyl)piperazin-1-yl)-2-(4-(2-(dimethylamino)-2-oxoethoxy)phenoxy)benzoate The title compound was prepared by substituting EXAMPLE 101B for EXAMPLE 1D in EXAMPLE 1E.

Example 101D 4-(4-((4'-chlorobiphenyl-2-yl)methyl)piperazin-1-yl)-2-(4-(2-(dimethylamino)-2-oxoethoxy)phenoxy)benzoic acid The title compound was prepared by substituting EXAMPLE 101C for EXAMPLE 1E in EXAMPLE 1F.

Example 101E 4-(4-((4'-chloro-1,1'-biphenyl-2-yl)methyl)piperazin-1-yl)-2-(4-(2-(dimethylamino)-2-oxoethoxy)phenoxy)-N-((3-nitro-4-((tetrahydro-2H-pyran-4-ylmethyl)amino)phenyl)sulfonyl)benzamide The title compound was prepared by substituting EXAMPLE 101D for EXAMPLE 1F in EXAMPLE 1H. $^1$H NMR (400 MHz, dimethylsulfoxide-$d_6$) δ 8.68 (t, 1H), 8.57

(d, 1H), 7.87 (dd, 1H), 7.72 (s, 1H), 7.53 (dd, 4H), 7.34 (m, 4H), 7.16 (d, 1H), 6.84 (m, 4H), 6.71 (dd, 1H), 6.34 (d, 1H), 4.60 (s, 2H), 3.84 (d, 2H), 3.51 (s, 10H), 3.36 (m, 2H), 3.26 (m, 2H), 2.81 (d, 6H), 1.91 (s, 1H), 1.62 (d, 2H), 1.28 (m, 2H).

Example 102

4-(4-((4'-chloro-1,1'-biphenyl-2-yl)methyl)piperazin-1-yl)-2-((1-methyl-1H-benzimidazol-5-yl)oxy)-N-((4-((3-morpholin-4-ylpropyl)amino)-3-nitrophenyl)sulfonyl)benzamide

Example 102A methyl 4-bromo-2-(1-methyl-1H-benzo[d]imidazol-5-yloxy)benzoate 1-methyl-1H-benzo[d]imidazol-5-ol (296 mg), methyl 4-bromo-2-fluorobenzoate (311 mg) and potassium carbonate (553 mg) were combined in dimethylsulfoxide and heated to 90° C. overnight. The reaction mixture was diluted with ethyl acetate and washed thoroughly with water and with brine, dried over MgSO$_4$, filtered and concentrated.

Example 102B methyl 4-(4-((2-(4-chlorophenyl)-4,4-dimethylcyclohex-1-enyl)methyl)piperazin-1-yl)-2-(1-methyl-1H-benzo[d]imidazol-5-yloxy)benzoate EXAMPLE 102A (480 mg) and EXAMPLE 1B (457 mg) were taken up in dimethoxyethane (7.5 mL) in a microwave vial. Tris(dibenzylideneacetone)dipalladium(0) (37 mg), 2-(di-tert-butylphosphino)biphenyl (48 mg) and potassium phosphate tribasic (423 mg) were added. The vial was capped and heated in a CEM Discover microwave reactor for 30 minutes at 150° C. The crude reaction mixture was filtered through celite and concentrated. The material was dissolved in 1:1 dimethylsulfoxide:methanol and purified by HPLC.

Example 102C 4-(4-((2-(4-chlorophenyl)-4,4-dimethylcyclohex-1-enyl)methyl)piperazin-1-yl)-2-(1-methyl-1H-benzo[d]imidazol-5-yloxy)benzoic acid The title compound was prepared by substituting EXAMPLE 102B for EXAMPLE 1E in EXAMPLE 1F.

Example 102D 4-(4-((4'-chloro-1,1'-biphenyl-2-yl)methyl)piperazin-1-yl)-2-((1-methyl-1H-benzimidazol-5-yl)oxy)-N-((4-((3-morpholin-4-ylpropyl)amino)-3-nitrophenyl)sulfonyl)benzamide The title compound was prepared by substituting EXAMPLE 102C for EXAMPLE 1F and EXAMPLE 4A for EXAMPLE 1G in EXAMPLE 1H. $^1$H NMR (500 MHz, pyridine-d$_5$) δ 9.34 (d, 1H), 8.99 (t, 1H), 8.91 (s, 1H), 8.55 (s, 1H), 8.48 (dd, 1H), 7.94 (t, 1H), 7.50 (m, 4H), 7.42 (m, 3H), 7.35 (m, 3H), 7.05 (s, 1H), 7.02 (d, 1H), 6.70 (m, 2H), 3.79 (t, 4H), 3.39 (s, 3H), 3.35 (m, 2H), 3.15 (m, 4H), 2.36 (m, 12H), 1.74 (m, 2H).

Example 103

4-(4-((4'-chlorobiphenyl-2-yl)methyl)piperazin-1-yl)-2-(3-(methylcarbamoyl)phenoxy)-N-(4-(3-morpholinopropylamino)-3-nitrophenylsulfonyl)benzamide

Example 103A methyl 4-(4-((4'-chlorobiphenyl-2-yl)methyl)piperazin-1-yl)-2-(3-(methylcarbamoyl)phenoxy)benzoate The title compound was prepared by substituting 3-hydroxy-N-methylbenzamide for EXAMPLE 1D in EXAMPLE 1E.

Example 103B 4-(4-((4'-chlorobiphenyl-2-yl)methyl)piperazin-1-yl)-2-(3-(methylcarbamoyl)phenoxy)benzoic acid The title compound was prepared by substituting EXAMPLE 103A for EXAMPLE 1E in EXAMPLE 1F.

Example 103C 4-(4-((4'-chlorobiphenyl-2-yl)methyl)piperazin-1-yl)-2-(3-(methylcarbamoyl)phenoxy)-N-(4-(3-morpholinopropylamino)-3-nitrophenylsulfonyl)benzamide bis(2,2,2-trifluoroacetate)

The title compound was prepared by substituting EXAMPLE 103B for EXAMPLE 50F and EXAMPLE 4A for EXAMPLE 3I in EXAMPLE 50G. $^1$H NMR (300 MHz, dimethylsulfoxide-d$_6$) δ 11.79 (v br s, 1H), 9.38 (v br s, 1H), 8.65 (t, 1H), 8.48 (d, 1H), 8.37 (q, 1H), 7.78 (dd, 1H), 7.70 (br s, 1H), 7.50 (m, 6H), 7.35 (m, 4H), 7.26 (s, 1H), 7.11 (d, 1H), 6.98 (dd, 1H), 6.79 (dd, 1H), 6.43 (s, 1H), 4.35 (v br s, 1H), 3.99 (br m, 2H), 3.70 (v br s, 1H), 3.60, 3.50, 3.40 (all br m, total 10H), 3.20, 310, 2.80 (all br s, total 8H), 2.79, 2.77 (both s, total 3H), 1.99 (m, 2H).

Example 104

4-(4-((4'-chlorobiphenyl-2-yl)methyl)piperazin-1-yl)-N-(4-(3-(dimethylamino)propylamino)-3-nitrophenylsulfonyl)-2-(3-(methylcarbamoyl)phenoxy)benzamide The title compound was prepared by substituting EXAMPLE 103B for EXAMPLE 50F and EXAMPLE 11A for EXAMPLE 3I in EXAMPLE 50G. $^1$H NMR (500 MHz, dimethylsulfoxide-d$_6$) δ 11.79 (v br s, 1H), 9.38 (v br s, 1H), 8.65 (t, 1H), 8.48 (d, 1H), 8.37 (q, 1H), 7.78 (dd, 1H), 7.70 (br s, 1H), 7.50 (m, 6H), 7.39 (m, 2H), 7.31 (m, 2H), 7.26 (s, 1H), 7.11 (d, 1H), 6.98 (dd, 1H), 6.79 (dd, 1H), 6.43 (s, 1H), 4.35 (v br s, 1H), 3.80 (v br s, 1H), 3.50, (br m, 8H), 3.10, 3.05 (m, br s, 4H), 2.81, 2.80 (both s, 6H), 2.78, 2.77 (both s, 3H), 1.96 (m, 2H).

Example 105

4-(4-((4'-chloro-1,1'-biphenyl-2-yl)methyl)piperazin-1-yl)-2-(3-(2-(dimethylamino)-2-oxoethoxy)phenoxy)-N-((3-nitro-4-((tetrahydro-2H-pyran-4-ylmethyl)amino)phenyl)sulfonyl)benzamide

Example 105A 2-(3-(benzyloxy)phenoxy)-N,N-dimethylacetamide

The title compound was prepared by substituting 2-chloro-N,N-dimethylacetamide for 2-chloro-N,N-dimethylethanamine in EXAMPLE 39A.

Example 105B 2-(3-hydroxyphenoxy)-N,N-dimethylacetamide

The title compound was prepared by substituting EXAMPLE 105A for EXAMPLE 39A in EXAMPLE 39B.

Example 105C methyl 4-(4-((4'-chlorobiphenyl-2-yl)methyl)piperazin-1-yl)-2-(3-(2-(dimethylamino)-2-oxoethoxy)phenoxy)benzoate The title compound was prepared by substituting EXAMPLE 105B for EXAMPLE 1D in EXAMPLE 1E.

Example 105D 4-(4-((4'-chlorobiphenyl-2-yl)methyl)piperazin-1-yl)-2-(3-(2-(dimethylamino)-2-oxoethoxy)phenoxy)benzoic acid The title compound was prepared by substituting EXAMPLE 105C for EXAMPLE 1E in EXAMPLE 1F.

Example 105E 4-(4-((4'-chloro-1,1'-biphenyl-2-yl)methyl)piperazin-1-yl)-2-(3-(2-(dimethylamino)-2-oxoethoxy)phenoxy)-N-((3-nitro-4-((tetrahydro-2H-pyran-4-ylmethyl)amino)phenyl)sulfonyl)benzamide The title compound was prepared by substituting EXAMPLE 105D for EXAMPLE 1F in EXAMPLE 1H. $^1$H NMR (400 MHz, dimethylsulfoxide-$d_6$) δ 8.66 (d, 1H), 8.54 (d, 1H), 7.84 (dd, 1H), 7.72 (s, 1H), 7.51 (m, 5H), 7.35 (m, 3H), 7.28 (t, 1H), 7.16 (dd, 2H), 6.75 (dd, 1H), 6.46 (m, 3H), 4.60 (s, 2H), 3.83 (d, 2H), 3.48 (s, 10H), 3.34 (m, 2H), 3.24 (m, 2H), 2.78 (s, 6H), 1.89 (s, 1H), 1.60 (d, 2H), 1.26 (m, 2H).

Example 106

4-(4-((4'-chloro-1,1'-biphenyl-2-yl)methyl)piperazin-1-yl)-2-((3-(3-(dimethylamino)propyl)-1H-indol-5-yl)oxy)-N-((3-nitro-4-((tetrahydro-2H-pyran-4-ylmethyl)amino)phenyl)sulfonyl)benzamide

Example 106A (Z)-tert-butyl 5-(benzyloxy)-3-(3-(dimethylamino)-3-oxoprop-1-enyl)-1H-indole-1-carboxylate The title compound was prepared by substituting N,N-dimethylacrylamide for 1-morpholinoprop-2-en-1-one in EXAMPLE 70A.

Example 106B tert-butyl 3-(3-(dimethylamino)-3-oxopropyl)-5-hydroxy-1H-indole-1-carboxylate The title compound was prepared by substituting EXAMPLE 106A for EXAMPLE 39A in EXAMPLE 39B.

Example 106C tert-butyl 5-(5-(4-((4'-chlorobiphenyl-2-yl)methyl)piperazin-1-yl)-2-(methoxycarbonyl)phenoxy)-3-(3-(dimethylamino)-3-oxopropyl)-1H-indole-1-carboxylate The title compound was prepared by substituting EXAMPLE 106B for EXAMPLE 1D in EXAMPLE 1E.

Example 106D methyl 4-(4-((4'-chlorobiphenyl-2-yl)methyl)piperazin-1-yl)-2-(3-(3-(dimethylamino)propyl)-1H-indol-5-yloxy)benzoate The title compound was prepared by substituting EXAMPLE 106C for EXAMPLE 70C in EXAMPLE 74A.

Example 106E 4-(4-((4'-chlorobiphenyl-2-yl)methyl)piperazin-1-yl)-2-(3-(3-(dimethylamino)propyl)-1H-indol-5-yloxy)benzoic acid The title compound was prepared by substituting EXAMPLE 106D for EXAMPLE 1E in EXAMPLE 1F.

Example 106F 4-(4-((4'-chloro-1,1'-biphenyl-2-yl)methyl)piperazin-1-yl)-2-((3-(3-(dimethylamino)propyl)-1H-indol-5-yl)oxy)-N-((3-nitro-4-((tetrahydro-2H-pyran-4-ylmethyl)amino)phenyl)sulfonyl)benzamide The title compound was prepared by substituting EXAMPLE 106E for EXAMPLE 1F in EXAMPLE 1H. $^1$H NMR (400 MHz, dimethylsulfoxide-$d_6$) δ 10.97 (d, 1H), 9.34 (s, 1H), 8.61 (m, 2H), 7.86 (dd, 1H), 7.54-7.36 (m, 8H), 7.22 (m, 4H), 6.86 (m, 1H), 6.67 (dd, 1H), 6.16 (d, 1H), 3.83 (m, 2H), 3.34-3.24 (m, 8H), 3.07 (m, 6H), 2.76 (s, 6H), 2.67 (m, 2H), 1.95 (m, 3H), 1.65 (m, 2H), 1.29 (m, 4H), 0.88 (m, 2H).

Example 107

4-(4-((4'-chloro-1,1'-biphenyl-2-yl)methyl)piperazin-1-yl)-N-((4-((3-(dimethylamino)propyl)amino)-3-nitrophenyl)sulfonyl)-2-(3-(hydroxymethyl)phenoxy)benzamide The title compound was prepared by substituting EXAMPLE 9A for EXAMPLE 50F and EXAMPLE 11A for EXAMPLE 3I in EXAMPLE 50G. $^1$H NMR (400 MHz, dimethylsulfoxide-$d_6$) δ 11.60 (v br s, 1H), 9.40 (v br s, 1H), 8.76 (t, 1H), 8.51 (d, 1H), 7.80 (dd, 1H), 7.65 (br s, 1H), 7.50 (m, 5H), 7.40 (m, 2H), 7.30 (br s, 1H), 7.20 (dd, 1H), 7.16 (d, 1H), 6.96 (d, 1H), 6.82 (s, 1H), 6.65 (d, 1H), 6.60 (d, 1H), 6.40 (s, 1H), 4.41 (s, 2H), 3.55 (m 4H), 3.40 (m, 6H), 3.13 (m, 4H), 2.80, 2.79 (both s, total 6H), 1.98 (m, 2H).

Example 108

4-(4-((4'-chloro-1,1'-biphenyl-2-yl)methyl)piperazin-1-yl)-2-((4-methoxybenzyl)oxy)-N-((3-nitro-4-((tetrahydro-2H-pyran-4-ylmethyl)amino)phenyl)sulfonyl)benzamide

Example 108A

4-Fluoro-2-(4-methoxy-benzyloxy)-benzoic acid methyl ester

Methyl 4-fluoro-2-hydroxybenzoate (1661 mg) was added to N,N-dimethylformamide (50 mL). Sodium hydride (60% in mineral oil, 430 mg) was added, the solution stirred for 15 minutes at room temperature, and 1-(bromomethyl)-4-methoxybenzene (2061 mg) was added. The solution was stirred at room temperature for three days, added to 0.01M aqueous HCl, and extracted with ethyl acetate. The organic phase was washed with water twice, washed with brine, and dried over anhydrous sodium sulfate. After filtration, the solvent was removed under vacuum.

Example 108B

4-[4-(4'-Chloro-biphenyl-2-ylmethyl)-piperazin-1-yl]-2-(4-methoxy-benzyloxy)-benzoic acid methyl ester The title compound was prepared by substituting EXAMPLE 108A for methyl 2-bromo-4-fluorobenzoate in EXAMPLE 1C.

Example 108C

4-[4-(4'-Chloro-biphenyl-2-ylmethyl)-piperazin-1-yl]-2-(4-methoxy-benzyloxy)-benzoic acid The title compound was prepared by substituting EXAMPLE 108B for EXAMPLE 1E in EXAMPLE 1F.

Example 108D 4-(4-((4'-chloro-1,1'-biphenyl-2-yl)methyl)piperazin-1-yl)-2-((4-methoxybenzyl)oxy)-N-((3-nitro-4-((tetrahydro-2H-pyran-4-ylmethyl)amino)phenyl)sulfonyl)benzamide The title compound was prepared by substituting EXAMPLE 108C for EXAMPLE 1F in EXAMPLE 1H. $^1$H NMR (300 MHz, dimethylsulfoxide-$d_6$) δ 10.79 (br s, 1H), 8.65 (t, 1H), 8.58 (d, 1H), 7.82 (dd, 1H), 7.53-7.41 (m, 7H), 7.38 (m, 2H), 7.27-7.19 (m, 2H), 6.98 (d, 2H), 6.69 (br s, 1H), 6.55 (dd, 1H), 5.16 (s, 2H), 3.84 (dd, 2H), 3.78 (s, 3H), 3.40 (s, 2H), 3.37-3.32 (m, 8H), 2.38 (m, 4H), 1.90 (m, 1H), 1.62 (dd, 2H), 1.26 (m, 2H).

Example 109

N-[(4-{[(4-aminotetrahydro-2H-pyran-4-yl)methyl]amino}-3-nitrophenyl)sulfonyl]-2-(3-chlorophenoxy)-4-(4-{[2-(4-chlorophenyl)-4,4-dimethylcyclohex-1-en-1-yl]methyl}piperazin-1-yl)benzamide

Example 109A 4-((4-aminotetrahydro-2H-pyran-4-yl)methylamino)-3-nitrobenzenesulfonamide A mixture of 4-chloro-3-nitrobenzenesulfonamide, 4-(aminomethyl)tetrahydro-2H-pyran-4-amine, hydrochloric acid and triethylamine in dioxane (10 mL) was heated at 110° C. overnight. After cooling, the mixture was diluted with water (10 mL), and filtered.

Example 109B

N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide This example was prepared by substituting EXAMPLE 6B for EXAMPLE 1F and EXAMPLE 109A for EXAMPLE 1G in EXAMPLE 1H. $^1$H NMR (500 MHz, DMSO-$d_6$) δ 8.41 (s, 1H), 8.35 (d, J=1.83 Hz, 1H), 7.70 (dd, J=9.0, 1.98 Hz, 1H), 7.64 (d, J=8.85 Hz, 1H), 7.36 (d, J=8.54 Hz, 2H), 7.11-7.18 (m, 2H), 7.07 (d, J=8.24 Hz, 2H), 6.91 (dd, J=7.93, 1.22 Hz, 1H), 6.77 (dd, J=8.85, 2.14 Hz, 1H), 6.65 (dd, J=8.09, 1.98 Hz, 1H), 6.61-6.62 (m, 1H), 6.38 (d, J=2.14 Hz, 1H), 3.67-3.71 (m, 6H), 3.11 (m, 3H), 2.77 (s, 2H), 2.18-2.24 (m, 6H), 1.97-1.99 (m, 2H), 1.76-1.79 (m, 2H), 1.65-1.67 (m, 2H), 1.39-1.42 (m, 2H), 0.94 (s, 6H).

Example 110

4-{4-[1-(4'-chloro-1,1'-biphenyl-2-yl)ethyl]piperazin-1-yl}-2-(2-chlorophenoxy)-N-({3-nitro-4-[(tetrahydro-2H-pyran-4-ylmethyl)amino]phenyl}sulfonyl)benzamide

Example 110A 1-(4'-chlorobiphenyl-2-yl)ethanone

A mixture of 1-(2-bromophenyl)ethanone (3.1 g) 4-chlorophenylboronic acid (2.92 g), bis(triphenylphosphine)palladium(II) dichloride (1.202 g) and $Na_2CO_3$ (3.30 g) in 7:2:3 dimethoxyethane/ethanol/water (50 mL) was heated at 100° C. for 3 hours and concentrated. The concentrate was suspended in dichloromethane (30 mL) and filtered. The filtrate was loaded onto a silica gel column and flash chromatographed with 0%-50% dichloromethane/hexane.

Example 110B tert-butyl 4-(1-(4'-chlorobiphenyl-2-yl)ethyl)piperazine-1-carboxylate A mixture of EXAMPLE 110A (1.9 g) in dichloromethane (3 mL) was treated with 1M titanium(IV) chloride in dichloromethane (9.06 mL), cooled to 0° C., treated with tert-butyl piperazine-1-carboxylate (3.07 g), stirred at ambient temperature for 3 hours, treated with NaCNBH$_3$ (0.828 g) in methanol (5 ml), stirred at room temperature overnight, neutralized with aqueous NaOH and concentrated. The concentrate was treated with ethyl acetate and filtered. The organic filtrate was washed with water and concentrated. The concentrate was dissolved in methanol/trifluoroacetic acid/dimethylsulfoxide, loaded onto a reverse phase C18 column and eluted with 0-80% acetonitrile in 0.1% trifluoroacetic acid water over 70 minutes.

Example 110C 1-(1-(4'-chlorobiphenyl-2-yl)ethyl)piperazine

To a solution of EXAMPLE 110B (650 mg) in dichloromethane (6 mL) at 0° C. was added trifluoroacetic acid (6 mL). The mixture was stirred at 0° C. for 50 minutes and concentrated. The concentrate was dissolved in dichloromethane, washed with aqueous NaHCO$_3$ and dried over Na$_2$SO$_4$, filtered and concentrated.

Example 110D ethyl 4-(4-(1-(4'-chlorobiphenyl-2-yl)ethyl)piperazin-1-yl)-2-(2-chlorophenoxy)benzoate EXAMPLE 110C (252 mg) and ethyl 2-(2-chlorophenoxy)-4-fluorobenzoate (272 mg) in dimethylsulfoxide (15 mL) was treated with potassium hydrogenphosphate (219 mg), stirred at 135° C. overnight, cooled, diluted with dichloromethane, washed with water and concentrated. The concentrate was dissolved in dichloromethane, loaded onto a silica gel column and eluted with 5% 10M ammonia methanol in dichloromethane.

Example 110E 4-(4-(1-(4'-chlorobiphenyl-2-yl)ethyl)piperazin-1-yl)-2-(2-chlorophenoxy)benzoic acid A mixture of EXAMPLE 110D (300 mg) in tetrahydrofuran (10 mL) and methanol (10 mL) at 50° C. was treated with 10% NaOH (2085 μL), stirred overnight, neutralized with HCl and concentrated. The concentrate was taken up in water and extracted with dichloromethane. The organic layer was dried over Na$_2$SO$_4$, filtered and concentrated.

Example 110F

4-{4-[1-(4'-chloro-1,1'-biphenyl-2-yl)ethyl]piperazin-1-yl}-2-(2-chlorophenoxy)-N-({3-nitro-4-[(tetrahydro-2H-pyran-4-ylmethyl)amino]phenyl}sulfonyl)benzamide To a mixture of EXAMPLE 110E (65 mg), Example 1G (74.9 mg) and 4-dimethylaminopyridine (58 mg) in dichloromethane (5 mL) was added 1-ethyl-3-[3-(dimethylamino)propyl]-carbodiimide hydrochloride (45.5 mg). The mixture was stirred at ambient temperature overnight and concentrated. The concentrate was purified by RP HPLC (10-70% acetonitrile in 0.1% trifluoroacetic acid water/70 min). Fractions containing product were concentrated, and the concentrate was diluted with dichloromethane, neutralized with aqueous NaHCO$_3$, dried over Na$_2$SO$_4$, filtered, and concentrated. $^1$H NMR (500 MHz, DMSO-d$_6$) δ 11.58 (s, 1H), 8.64 (t, 1H), 8.47 (d, 1H), 7.78 (dd, 1H), 7.56 (d, 1H), 7.45-7.52 (m, 3H), 7.38-7.43 (m, 2H), 7.27-7.33 (m, 3H), 7.11-7.19 (m, 3H), 6.99 (t, 1H), 6.70-6.77 (m, 2H), 6.28 (d, 1H), 3.86 (dd, 2H), 3.33-3.37 (m, 1H), 3.24-3.31 (m, 4H), 3.12 (s, 4H), 2.33-2.47 (m, 2H), 2.20-2.31 (m, 2H), 1.85-1.96 (m, 1H), 1.64 (d, 2H), 1.17-1.33 (m, 5H).

Example 111

N-{[4-{4-[(4'-chloro-1,1'-biphenyl-2-yl)methyl]piperazin-1-yl}-2-(3,5-dichlorophenoxy)phenyl]sulfonyl}-4-[(1-methylpiperidin-4-yl)amino]-3-nitrobenzamide

Example 111A 4-(1-methylpiperidin-4-ylamino)-3-nitrobenzoic acid

To a solution of ethyl 4-fluoro-3-nitrobenzoate (2.13 g) and 1-methylpiperidin-4-amine (1.14 g) in tetrahydrofuran (40 mL) was added N,N-diisopropylethylamine (5 mL). The mixture was then stirred at reflux overnight. The solvent was evaporated and the residue was dissolved in ethyl acetate (300 mL) and washed with aqueous NaHCO$_3$, water and brine. After evaporation of the solvent, the residue was dissolved in tetrahydrofuran (20 mL), methanol (10 mL) and water (10 mL). Then, LiOH H$_2$O (2 g) was added. The mixture was stirred at room temperature overnight. The mixture was then concentrated and the residue was neutralized with 5% aqueous HCl. The precipitate was filtered, washed with brine, and dried under vacuum to give the product.

Example 111B 4-(4-((4'-chlorobiphenyl-2-yl)methyl)piperazin-1-yl)-2-fluorobenzenesulfonamide To a solution of 2,4-difluorobenzenesulfonamide (1.56 g) and 1-((4'-chlorobiphenyl-2-yl)methyl)piperazine (2.32 g) in dimethylsulfoxide (20 mL) was added N,N-diisopropylethylamine (5 mL). The mixture was stirred at 120° C. overnight. The mixture was diluted with ethyl acetate (300 mL) and washed with water (3×) brine and dried over Na$_2$SO$_4$. After filtration and evaporation of the solvent, the residue was loaded on a column and eluted with 40% ethyl acetate in hexane to give the title compound.

Example 111C

N-(4-(4-((4'-chlorobiphenyl-2-yl)methyl)piperazin-1-yl)-2-fluorophenylsulfonyl)-4-(1-methylpiperidin-4-ylamino)-3-nitrobenzamide The title compound was prepared as described in EXAMPLE 1G by replacing EXAMPLE 1E and EXAMPLE 1F with EXAMPLE 111A and EXAMPLE 111B, respectively.

Example 111D

N-{[4-{4-[(4'-chloro-1,1'-biphenyl-2-yl)methyl]piperazin-1-yl}-2-(3,5-dichlorophenoxy)phenyl]sulfonyl}-4-[(1-methylpiperidin-4-yl)amino]-3-nitrobenzamide To a solution of 3,5-dichlorophenol (81 mg) and EXAMPLE 111C (72 mg) in diglyme (3 mL) was added $K_2HPO_4$ (53 mg). The mixture was stirred at 200° C. in a CEM Discover microwave reactor for 2 hours. The mixture was filtered and purified by RP HPLC (10-70% acetonitrile in 0.1% trifluoroacetic acid water/70 min). Fractions containing product were concentrated, and the concentrate was diluted with dichloromethane, neutralized with aqueous $NaHCO_3$, dried over $Na_2SO_4$, filtered, and concentrated. $^1$H NMR (300 MHz, dimethylsulfoxide-$d_6$) δ 8.56 (d, 1H), 8.12 (d, 1H), 7.94 (m, 1H), 7.84 (m, 2H), 7.51 (m, 5H), 7.36 (m, 4H), 7.17 (d, 1H), 7.05 (m, 1H), 6.94 (m, 1H), 6.71 (m, 1H), 4.36 (m, 1H), 3.92 (m, 2H), 3.15 (m, 4H), 2.79 (m, 6H), 2.22 (m, 8H), 1.29 (m, 2H).

Example 112

4-(4-{[2-(4-chlorophenyl)-4,4-dimethylcyclohex-1-en-1-yl]methyl}piperazin-1-yl)-2-(3-fluorophenoxy)-N-({4-[(1-methylpiperidin-4-yl)amino]-3-nitrophenyl}sulfonyl)benzamide

Example 112A ethyl 4-fluoro-2-(3-fluorophenoxy)benzoate

The title compound was prepared by substituting 3-fluorophenol for 2-methyl-5-indolol in EXAMPLE 3A.

Example 112B ethyl 4-(4-((2-(4-chlorophenyl)-4,4-dimethylcyclohex-1-enyl)methyl)piperazin-1-yl)-2-(3-fluorophenoxy)benzoate The title compound was prepared by substituting EXAMPLE 112A for EXAMPLE 3A in EXAMPLE 3G.

Example 112C 4-(4-((2-(4-chlorophenyl)-4,4-dimethylcyclohex-1-enyl)methyl)piperazin-1-yl)-2-(3-fluorophenoxy)benzoic acid The title compound was prepared by substituting EXAMPLE 112B for EXAMPLE 1E in EXAMPLE 1F.

Example 112D 4-(4-{[2-(4-chlorophenyl)-4,4-dimethylcyclohex-1-en-1-yl]methyl}piperazin-1-yl)-2-(3-fluorophenoxy)-N-({4-[(1-methylpiperidin-4-yl)amino]-3-nitrophenyl}sulfonyl)benzamide The title compound was prepared by substituting EXAMPLE 112C for EXAMPLE 1F and EXAMPLE 3I for EXAMPLE 1G in EXAMPLE 1H. $^1$H NMR (500 MHz, dimethylsulfoxide-$d_6$) δ 8.34 (d, 1H), 8.08 (d, 1H), 7.69 (dd, 1H), 7.60 (d, 1H), 7.36 (d, 2H), 7.14 (m, 1H), 7.06 (d, 2H), 7.03 (d, 1H), 6.72 (dd, 1H), 6.65 (m, 1H), 6.49 (dd, 1H), 6.41 (m, 2H), 3.81 (m, 1H), 3.22 (m, 2H), 3.11 (m, 4H), 2.88 (m, 2H), 2.77 (m, 2H), 2.64 (s, 3H), 2.22 (m, 6H), 2.10 (m, 2H), 1.98 (m, 2H), 1.79 (m, 2H), 1.40 (m, 2H), 0.94 (s, 6H).

Example 113

4-(4-{[2-(4-chlorophenyl)-4,4-dimethylcyclohex-1-en-1-yl]methyl}piperazin-1-yl)-2-(3-fluorophenoxy)-N-({3-nitro-4-[(1-tetrahydro-2H-pyran-4-ylpiperidin-4-yl)amino]phenyl}sulfonyl)benzamide The title compound was prepared by substituting EXAMPLE 112C for EXAMPLE 1F and EXAMPLE 49C for EXAMPLE 1G in EXAMPLE 1H. $^1$H NMR (500 MHz, dimethylsulfoxide-$d_6$) δ 8.34 (d, 1H), 8.10 (d, 1H), 7.67 (dd, 1H), 7.60 (d, 1H), 7.36 (d, 2H), 7.14 (m, 1H), 7.06 (d, 2H), 7.01 (d, 1H), 6.72 (dd, 1H), 6.65 (m, 1H), 6.49 (dd, 1H), 6.41 (m, 2H), 3.93 (dd, 2H), 3.77 (br s, 2H), 3.30 (m, 2H), 3.10 (m, 6H), 2.77 (s, 2H), 2.69 (m, 2H), 2.24 (m, 4H), 2.18 (t, 2H), 2.06 (d, 2H), 1.98 (s, 2H), 1.80 (d, 2H), 1.68 (m, 2H), 1.52 (m, 2H), 1.41 (t, 2H), 0.94 (s, 6H).

Example 114

4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide The title compound was prepared by substituting EXAMPLE 112C for EXAMPLE 1F and EXAMPLE 4A for EXAMPLE 1G in EXAMPLE 1H. $^1$H NMR (500 MHz, dimethylsulfoxide-$d_6$) δ 8.74 (br m, 1H), 8.43 (d, 1H), 7.73 (dd, 1H), 7.52 (d, 1H), 7.35 (m, 2H), 7.19 (m, 1H), 7.06 (m, 3H), 6.73 (m, 2H), 6.50 (m, 2H), 6.44 (d, 1H), 3.64 (t, 4H), 3.45 (m, 2H), 3.18 (m, 5H), 2.79 (m, 2H), 2.58 (m, 3H), 2.22 (m, 7H), 1.98 (m, 3H), 1.83 (m, 2H), 1.41 (m, 2H), 0.94 (s, 6H).

Example 115

2-(2-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 34C for EXAMPLE 1F and EXAMPLE 49C for EXAMPLE 1G in EXAMPLE 1H. $^1$H NMR (400 MHz, dimethylsulfoxide-$d_6$) δ 8.33 (d, 1H), 8.09 (s, 1H), 7.70 (d, 1H), 7.63 (d, 1H), 7.34 (m, 3H), 7.03 (m, 4H), 6.87 (t, 1H), 6.69 (m, 1H), 6.50 (d, 1H), 6.25 (d, 1H), 3.91 (d, 2H), 3.57 (s, 4H), 3.30 (m, 6H), 3.06 (s, 4H), 2.20 (d, 6H), 1.96 (d, 4H), 1.73 (s, 2H), 1.63 (s, 2H), 1.48 (s, 2H), 1.40 (t, 2H), 0.94 (s, 6H).

Example 116

2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide The title compound was prepared by substituting EXAMPLE 34C for EXAMPLE 1F and EXAMPLE 4A for EXAMPLE 1G in EXAMPLE 1H. $^1$H NMR (400 MHz, dimethylsulfoxide-$d_6$) δ 8.70 (t, 1H), 8.44 (d, 1H), 7.77 (dd, 1H), 7.54 (d, 1H), 7.40 (dd, 1H), 7.35 (m, 2H), 7.12 (m, 1H), 7.06 (m, 3H), 6.98 (td, 1H), 6.73 (dd, 1H), 6.68 (dd, 1H), 6.26 (d, 1H), 4.62 (s, 2H), 3.62 (m, 4H), 3.46 (dd, 2H), 3.11 (s, 4H), 2.75 (d, 2H), 2.47 (m, 4H), 2.20 (d, 6H), 1.97 (s, 2H), 1.82 (p, 2H), 1.40 (t, 2H), 0.94 (s, 6H).

Example 117

2-(2-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide Example 117A 4-(1-cyclopentylpiperidin-4-ylamino)-3-nitrobenzenesulfonamide The title compound was prepared by substituting 1-cyclopentylpiperidin-4-amine for 3-(N-morpholinyl)-1-propylamine in EXAMPLE 4A.

Example 117B 2-(2-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide The title compound was prepared by substituting EXAMPLE 34C for EXAMPLE 1F and EXAMPLE 117A for EXAMPLE 1G in EXAMPLE 1H. $^1$H NMR (400 MHz, dimethylsulfoxide-$d_6$) δ 8.35 (d, 1H), 8.06 (d, 1H), 7.73 (dd, 1H), 7.63 (d, 1H), 7.35 (m, 3H), 7.04 (m, 4H), 6.88 (td, 1H), 6.69 (dd, 1H), 6.53 (dd, 1H), 6.25 (d, 1H), 4.57 (s, 1H), 3.29 (s, 8H), 3.05 (d, 4H), 2.75 (s, 2H), 2.62 (s, 2H), 2.20 (d, 5H), 2.07 (s, 1H), 1.95 (d, 3H), 1.66 (s, 3H), 1.53 (s, 3H), 1.40 (t, 2H), 0.94 (s, 6H).

Example 118

4-(4-{[2-(4-chlorophenyl)-4,4-dimethylcyclohex-1-en-1-yl]methyl}piperazin-1-yl)-2-(4-fluorophenoxy)-N-({4-[(1-methylpiperidin-4-yl)amino]-3-nitrophenyl}sulfonyl)benzamide Example 118A ethyl 4-fluoro-2-(4-fluorophenoxy)benzoate The title compound was prepared by substituting 4-fluorophenol for 2-methyl-5-indolol in EXAMPLE 3A.

Example 118B ethyl 4-(4-((2-(4-chlorophenyl)-4,4-dimethylcyclohex-1-enyl)methyl)piperazin-1-yl)-2-(4-fluorophenoxy)benzoate The title compound was prepared by substituting EXAMPLE 118A for EXAMPLE 3A in EXAMPLE 3G.

Example 118C 4-(4-((2-(4-chlorophenyl)-4,4-dimethylcyclohex-1-enyl)methyl)piperazin-1-yl)-2-(4-fluorophenoxy)benzoic acid The title compound was prepared by substituting EXAMPLE 118B for EXAMPLE 1E in EXAMPLE 1F.

Example 118D 4-(4-{[2-(4-chlorophenyl)-4,4-dimethylcyclohex-1-en-1-yl]methyl}piperazin-1-yl)-2-(4-fluorophenoxy)-N-({4-[(1-methylpiperidin-4-yl)amino]-3-nitrophenyl}sulfonyl)benzamide The title compound was prepared by substituting EXAMPLE 118C for EXAMPLE 1F and EXAMPLE 3I for EXAMPLE 1G in EXAMPLE 1H. $^1$H NMR (500 MHz, dimethylsulfoxide-$d_6$) δ 8.39 (d, 1H), 8.08 (d, 1H), 7.75 (dd, 1H), 7.55 (d, 1H), 7.36 (d, 2H), 7.06 (m, 3H), 6.98 (m, 2H), 6.73 (m, 2H), 6.67 (dd, 1H), 6.29 (d, 1H), 3.82 (m, 1H), 3.18 (m, 2H), 3.08 (m, 4H), 2.80 (m, 4H), 2.60 (m, 3H), 2.22 (m, 6H), 2.07 (m, 2H), 1.97 (m, 2H), 1.77 (m, 2H), 1.40 (m, 2H), 0.94 (s, 6H).

Example 119

2-(3-chlorophenoxy)-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 36C and EXAMPLE 65A, respectively. $^1$H NMR (300 MHz, dimethylsulfoxide-$d_6$) δ 8.35 (d, 1H), 8.17 (d, 1H), 7.66 (dd, 1H), 7.58 (d, 1H), 7.36 (d, 2H), 7.15 (t, 1H), 7.05 (m, 3H), 6.88 (d, 1H), 6.74 (dd, 1H), 6.64 (m, 2H), 6.41 (d, 1H), 3.69 (m, 1H), 3.16 (m, 4H), 2.97 (m, 4H), 2.77 (m, 2H), 2.72 (s, 2H), 2.44 (m, 3H), 2.21 (m, 3H), 1.96 (m, 2H), 1.58 (m, 3H), 0.94 (s, 6H), 0.40 (m, 5H).

Example 120

2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-yl-propyl)amino]-3-nitrophenyl}sulfonyl)benzamide The title compound was prepared by substituting EXAMPLE 61D for EXAMPLE 1F and EXAMPLE 4A for EXAMPLE 1G in EXAMPLE 1H. $^1$H NMR (400 MHz, dimethylsulfoxide-$d_6$) δ 8.73 (m, 1H), 8.48 (d, 1H), 7.80 (dd, 1H), 7.51 (d, 1H), 7.36 (m, 3H), 7.07 (m, 4H), 6.75 (m, 2H), 6.25 (d, 1H), 3.63 (m, 4H), 3.47 (m, 2H), 3.12 (m, 4H), 2.77 (s, 2H), 2.21 (m, 6H), 1.97 (s, 2H), 1.82 (m, 2H), 1.41 (t, 2H), 0.94 (s, 6H).

Example 121

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2,3-difluorophenoxy)benzamide The title compound was prepared by substituting EXAMPLE 45C for EXAMPLE 1F and EXAMPLE 65A for EXAMPLE 1G in EXAMPLE 1H. $^1$H NMR (400 MHz, dimethylsulfoxide-d$_6$) δ 8.42 (d, 1H), 8.21 (d, 1H), 7.77 (dd, 1H), 7.54 (d, 1H), 7.35 (d, 2H), 7.15 (d, 1H), 7.06 (d, 2H), 6.89 (m, 2H), 6.75 (dd, 1H), 6.44 (m, 2H), 3.76 (m, 1H), 3.17 (m, 4H), 3.00 (m, 2H), 2.81 (s, 2H), 2.59 (m, 2H), 2.24 (m, 6H), 1.92 (m, 5H), 1.61 (m, 2H), 1.41 (t, 2H), 0.94 (s, 6H), 0.46 (m, 4H).

Example 122

4-(4-{[2-(4-chlorophenyl)-4,4-dimethylcyclohex-1-en-1-yl]methyl}piperazin-1-yl)-2-(2-fluorophenoxy)-N-({4-[(1-methylpiperidin-4-yl)amino]-3-nitrophenyl}sulfonyl)benzamide Example 122A methyl 4-fluoro-2-(2-fluorophenoxy)benzoate The title compound was prepared by substituting 2-fluorophenol for 2-methyl-5-indolol in EXAMPLE 3A.

Example 122B methyl 4-(4-((2-(4-chlorophenyl)-4,4-dimethylcyclohex-1-enyl)methyl)piperazin-1-yl)-2-(2-fluorophenoxy)benzoate The title compound was prepared by substituting EXAMPLE 122A for EXAMPLE 3A in EXAMPLE 3G.

Example 122C 4-(4-((2-(4-chlorophenyl)-4,4-dimethylcyclohex-1-enyl)methyl)piperazin-1-yl)-2-(2-fluorophenoxy)benzoic acid The title compound was prepared by substituting EXAMPLE 122B for EXAMPLE 1E in EXAMPLE 1F.

Example 122D 4-(4-{[2-(4-chlorophenyl)-4,4-dimethylcyclohex-1-en-1-yl]methyl}piperazin-1-yl)-2-(2-fluorophenoxy)-N-({4-[(1-methylpiperidin-4-yl)amino]-3-nitrophenyl}sulfonyl)benzamide The title compound was prepared by substituting EXAMPLE 122C for EXAMPLE 1F and EXAMPLE 3I for EXAMPLE 1G in EXAMPLE 1H. $^1$H NMR (400 MHz, dimethylsulfoxide-d$_6$) δ 11.87 (s, 1H), 9.54 (s, 1H), 8.50 (d, 1H), 8.20 (d, 1H), 7.86 (dd, 1H), 7.52 (d, 1H), 7.40 (d, 2H), 7.24 (m, 2H), 7.10 (d, 2H), 7.03 (m, 2H), 6.78 (m, 2H), 6.42 (s, 1H), 3.62 (m, 10H), 3.10 (m, 4H), 2.82 (m, 2H), 2.82 (s, 3H), 2.21 (m, 4H), 2.03 (s, 2H), 1.85 (m, 1H), 1.46 (t, 2H), 0.96 (s, 6H).

Example 123

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(2-fluorophenoxy)benzamide The title compound was prepared by substituting EXAMPLE 122C for EXAMPLE 1F and EXAMPLE 65A for EXAMPLE 1G in EXAMPLE 1H. $^1$H NMR (400 MHz, dimethylsulfoxide-d$_6$) δ 8.51 (d, 1H), 8.19 (s, 1H), 7.87 (dd, 1H), 7.53 (d, 1H), 7.40 (d, 2H), 7.24 (m, 2H), 7.11 (d, 2H), 7.03 (m, 2H), 6.78 (m, 2H), 6.43 (d, 1H), 3.97 (m, 4H), 3.21 (s, 8H), 3.21 (s, 4H), 2.83 (m, 4H), 2.22 (m, 4H), 2.06 (m, 2H), 1.81 (m, 1H), 1.47 (t, 2H), 0.96 (s, 6H).

Example 124

4-(4-{[2-(4-chlorophenyl)-4,4-dimethylcyclohex-1-en-1-yl]methyl}piperazin-1-yl)-2-(2-fluorophenoxy)-N-({3-nitro-4-[(1-tetrahydro-2H-pyran-4-yl)piperidin-4-yl)amino]phenyl}sulfonyl)benzamide The title compound was prepared by substituting EXAMPLE 122C for EXAMPLE 1F and EXAMPLE 49C for EXAMPLE 1G in EXAMPLE 1H. $^1$H NMR (400 MHz, dimethylsulfoxide-d$_6$) δ 11.90 (s, 1H), 9.59 (s, 1H), 8.51 (m, 1H), 8.20 (d, 1H), 7.87 (dd, 1H), 7.53 (d, 1H), 7.39 (d, 2H), 7.24 (m, 2H), 7.10 (d, 2H), 7.03 (m, 2H), 6.78 (m, 2H), 6.42 (s, 1H), 4.01 (m, 2H), 3.71 (m, 4H), 3.34 (m, 6H), 3.17 (m, 4H), 2.78 (m, 2H), 2.24 (m, 4H), 1.94 (m, 8H), 1.70 (m, 2H), 1.46 (t, 2H), 0.96 (s, 6H).

Example 125

4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide The title compound was prepared by substituting EXAMPLE 122C for EXAMPLE 1F and EXAMPLE 4A for EXAMPLE 1G in EXAMPLE 1H. $^1$H NMR (400 MHz, dimethylsulfoxide-d$_6$) δ 11.85 (s, 1H), 9.94 (s, 1H), 9.63 (s, 1H), 8.71 (m, 1H), 8.53 (d, 1H), 7.86 (dd, 1H), 7.53 (d, 1H), 7.40 (d, 2H), 7.26 (m, 1H), 7.19 (d, 1H), 7.07 (m, 4H), 6.80 (m, 2H), 6.41 (d, 1H), 3.97 (m, 2H), 3.54 (m, 6H), 3.31 (m, 4H), 3.19 (m, 8H), 2.22 (m, 2H), 1.99 (m, 4H), 1.47 (t, 2H), 0.97 (s, 6H).

Example 126

4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide Example 126A 4-(2-morpholinoethylamino)-3-nitrobenzenesulfonamide The title compound was prepared by substituting 2-(N-morpholinyl)-2-ethylamine for 3-(N-morpholinyl)-1-propylamine in EXAMPLE 4A.

Example 126B 4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide The title compound was prepared by substituting EXAMPLE 122C for EXAMPLE 1F and EXAMPLE 126A for EXAMPLE 1G in EXAMPLE 1H. $^1$H NMR (400 MHz, dimethylsulfoxide-d$_6$) δ 8.81 (s, 1H), 8.50 (d, 1H), 7.82 (dd, 1H), 7.50 (d, 1H), 7.36 (d, 2H), 7.23 (m, 1H), 7.04 (m, 5H), 6.79 (m, 1H), 6.73 (dd, 1H), 6.31 (d, 1H), 3.62 (m, 4H), 3.50 (q, 2H), 3.32 (m, 6H), 3.14 (m, 4H), 2.79 (s, 2H), 2.67 (m, 2H), 2.20 (m, 6H), 1.99 (m, 2H), 1.40 (t, 2H), 0.94 (s, 6H).

Example 127

2-(3-chlorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 36C for EXAMPLE 1F and EXAMPLE 49C for EXAMPLE 1G in EXAMPLE 1H. $^1$H NMR (400 MHz, dimethylsulfoxide-$d_6$) δ 8.38 (m, 1H), 8.13 (m, 1H), 7.70 (m, 1H), 7.59 (m, 1H), 7.36 (d, 2H), 7.16 (m, 1H), 7.05 (m, 3H), 6.89 (m, 1H), 6.74 (dd, 1H), 6.66 (dd, 1H), 6.61 (m, 1H), 6.42 (m, 1H), 3.94 (m, 2H), 3.26 (m, 6H), 3.15 (m, 6H), 2.78 (m, 2H), 2.18 (m, 9H), 1.98 (m, 3H), 1.86 (m, 2H), 1.74 (m, 2H), 1.57 (m, 2H), 1.41 (m, 2H), 0.93 (s, 6H).

Example 128

2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide The title compound was prepared by substituting EXAMPLE 36C for EXAMPLE 1F and EXAMPLE 4A for EXAMPLE 1G in EXAMPLE 1H. $^1$H NMR (400 MHz, dimethylsulfoxide-$d_6$) δ 8.75 (t, 1H), 8.41 (d, 1H), 7.71 (dd, 1H), 7.52 (d, 1H), 7.36 (d, 2H), 7.18 (m, 1H), 7.06 (m, 3H), 6.93 (dd, 1H), 6.77 (dd, 1H), 6.69 (m, 2H), 6.46 (d, 1H), 3.65 (t, 4H), 3.47 (q, 2H), 3.29 (m, 2H), 3.18 (m, 4H), 2.79 (s, 2H), 2.56 (m, 4H), 2.22 (m, 6H), 1.98 (m, 2H), 1.85 (m, 2H), 1.41 (t, 2H), 0.94 (s, 6H).

Example 129

4-(4-{[2-(4-chlorophenyl)-4,4-dimethylcyclohex-1-en-1-yl]methyl}piperazin-1-yl)-2-(3-fluorophenoxy)-N-({4-[(2-morpholin-4-ylethyl)amino]-3-nitrophenyl}sulfonyl)benzamide The title compound was prepared by substituting EXAMPLE 112C for EXAMPLE 1F and EXAMPLE 126A for EXAMPLE 1G in EXAMPLE 1H. $^1$H NMR (400 MHz, dimethylsulfoxide-$d_6$) δ 11.48 (m, 1H), 8.81 (t, 1H), 8.45 (d, 1H), 7.75 (dd, 1H), 7.49 (d, 1H), 7.36 (d, 2H), 7.19 (m, 1H), 7.06 (m, 3H), 6.77 (dd, 1H), 6.72 (m, 1H), 6.54 (m, 2H), 6.47 (d, 1H), 3.62 (m, 4H), 3.50 (q, 2H), 3.32 (m, 4H), 3.19 (m, 4H), 2.82 (s, 2H), 2.69 (t, 2H), 2.27 (m, 4H), 2.18 (s, 2H), 1.99 (m, 2H), 1.41 (t, 2H), 0.94 (s, 6H).

Example 130

2-(3-chlorophenoxy)-4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)benzamide The title compound was prepared by substituting EXAMPLE 36C for EXAMPLE 1F and EXAMPLE 117A for EXAMPLE 1G in EXAMPLE 1H. $^1$H NMR (400 MHz, dimethylsulfoxide-$d_6$) δ 8.35 (d, 1H), 8.08 (d, 1H), 7.69 (dd, 1H), 7.61 (d, 1H), 7.35 (d, 2H), 7.14 (m, 1H), 7.04 (m, 3H), 6.88 (dd, 1H), 6.72 (dd, 1H), 6.65 (dd, 1H), 6.60 (m, 1H), 6.39 (d, 1H), 3.87 (s, 1H), 3.11 (m, 6H), 2.93 (m, 2H), 2.77 (s, 2H), 2.21 (m, 8H), 1.98 (m, 5H), 1.69 (m, 4H), 1.56 (m, 4H), 1.41 (t, 2H), 0.94 (s, 6H).

Example 131

2-(3-chlorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide Example 131A (2-fluorophenyl)(trifluoromethyl)sulfane Methyl viologen hydrochloride (1.17 g) in N,N-dimethylformamide (80 mL) at 25° C. was saturated with trifluoromethyl iodide, treated with 2-fluorobenzenethiol (9.7 mL) and triethylamine (20 mL), stirred for 24 hours, diluted with water (240 mL) and extracted with diethyl ether. The extract was washed with 1M aqueous NaOH, saturated ammonium chloride and brine and concentrated.

Example 131B 1-fluoro-2-(trifluoromethylsulfonyl)benzene

EXAMPLE 131A (17.346 g) in 1:1:2 carbon tetrachloride:acetonitrile:water (800 mL) at 25° C. was treated with sodium periodate (56.8 g) and ruthenium(III) chloride hydrate (183 mg), stirred for 18 hours, diluted with dichloromethane (100 mL) and filtered through diatomaceous earth (Celite®). The filtrate was washed with saturated sodium bicarbonate and extracted with dichloromethane. The extract was washed with brine and dried (MgSO$_4$), filtered and concentrated. The concentrate was filtered through silica gel.

Example 131C 4-fluoro-3-(trifluoromethylsulfonyl)benzenesulfonamide

EXAMPLE 131B (37.3 g) in chlorosulfonic acid (32.8 mL) at 120° C. was stirred for 18 hours, cooled to 25° C. and pipetted onto crushed ice. The mixture was extracted with ethyl acetate, and the extract was washed with water and brine and dried (MgSO$_4$), filtered and concentrated. The crude product was taken up in isopropanol (706 mL) at −78° C., treated with ammonium hydroxide (98 mL) over 1 hour, stirred for 1 hour, quenched with 6M aqueous HCl (353 mL), warmed to 25° C. and concentrated. The concentrate was mixed with water and extracted with ethyl acetate. The extract was dried over MgSO$_4$, filtered and concentrated. The concentrate was recrystallized from ethyl acetate/hexane.

Example 131D 4-(1-methylpiperidin-4-ylamino)-3-(trifluoromethylsulfonyl)benzenesulfonamide The title compound was prepared by substituting 1-methyl-4-aminopiperidine for 3-(N-morpholinyl)-1-propylamine and EXAMPLE 131C for 4-fluoro-3-nitrobenzenesulfonamide in EXAMPLE 4A.

Example 131E 2-(3-chlorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide The title compound was prepared by substituting EXAMPLE 36C for EXAMPLE 1F and EXAMPLE 131D for EXAMPLE 1G in EXAMPLE 1H. $^1$H NMR (400 MHz, dimethylsulfoxide-$d_6$) δ 8.00 (d, 1H), 7.83 (dd, 1H), 7.61 (d, 1H), 7.36 (m, 2H), 7.19 (m, 1H), 7.07 (d, 2H), 7.01 (d, 1H), 6.93 (d, 1H), 6.72 (dd, 1H), 6.66 (m, 2H), 6.51 (d, 1H), 6.39 (d, 1H), 3.79 (none, 1H), 3.11 (m, 6H), 2.90 (t, 2H), 2.78 (s, 2H), 2.65 (s, 3H), 2.20 (m, 6H), 2.09 (m, 2H), 1.97 (m, 3H), 1.64 (m, 2H), 1.41 (t, 2H), 0.95 (s, 6H).

Example 132

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-(3-fluorophenoxy)benzamide The title compound was prepared by substituting EXAMPLE 112C for EXAMPLE 1F and EXAMPLE 65A for EXAMPLE 1G in EXAMPLE 1H. $^1$H NMR (400 MHz, dimethylsulfoxide-$d_6$) δ 8.43 (d, 1H), 8.23 (d, 1H), 7.75 (dd, 1H), 7.51 (d, 1H), 7.35 (d, 2H), 7.17 (m, 2H), 7.06 (d, 2H), 6.73 (m, 2H), 6.56 (dd, 1H), 6.51 (dd, 1H), 6.45 (d, 1H), 3.74 (m, 1H), 3.18 (m, 4H), 2.97 (m, 2H), 2.80 (s, 2H), 2.54 (m, 2H), 2.20 (m, 6H), 1.98 (m, 4H), 1.85 (m, 1H), 1.62 (m, 2H), 1.41 (t, 2H), 0.94 (s, 6H), 0.50 (m, 2H), 0.41 (m, 2H).

Example 133

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2,3-difluorophenoxy)benzamide The title compound was prepared by substituting EXAMPLE 45C for EXAMPLE 1F and EXAMPLE 117A for EXAMPLE 1G in EXAMPLE 1H. $^1$H NMR (400 MHz, dimethylsulfoxide-$d_6$) δ 8.35 (d, 1H), 8.05 (s, 1H), 7.73 (dd, 1H), 7.64 (d, 1H), 7.36 (d, 2H), 7.06 (m, 3H), 6.84 (m, 2H), 6.72 (dd, 1H), 6.43 (d, 1H), 6.31 (m, 1H), 3.89 (s, 1H), 3.12 (m, 6H), 2.97 (m, 2H), 2.77 (s, 2H), 2.21 (m, 8H), 1.98 (m, 5H), 1.63 (m, 8H), 1.41 (t, 2H), 0.95 (s, 6H).

Example 134

4-(4-{[2-(4-chlorophenyl)-4,4-dimethylcyclohex-1-en-1-yl]methyl}piperazin-1-yl)-N-({4-[(1-cyclopentylpiperidin-4-yl)amino]-3-nitrophenyl}sulfonyl)-2-(2-fluorophenoxy)benzamide The title compound was prepared by substituting EXAMPLE 122C for EXAMPLE 1F and EXAMPLE 117A for EXAMPLE 1G in EXAMPLE 1H. $^1$H NMR (400 MHz, dimethylsulfoxide-$d_6$) δ 8.39 (m, 1H), 8.07 (d, 1H), 7.76 (m, 1H), 7.61 (d, 1H), 7.34 (d, 2H), 7.18 (m, 3H), 7.07 (m, 3H), 6.91 (m, 2H), 6.68 (m, 1H), 6.28 (m, 1H), 3.26 (m, 8H), 3.17 (m, 2H), 3.05 (m, 4H), 2.75 (s, 2H), 2.23 (m, 7H), 2.00 (m, 4H), 1.64 (m, 6H), 1.40 (m, 2H), 0.94 (s, 6H).

Example 135

4-(4-{[2-(4-chlorophenyl)-4,4-dimethylcyclohex-1-en-1-yl]methyl}piperazin-1-yl)-2-(2,3-difluorophenoxy)-N-({4-[(2-morpholin-4-ylethyl)amino]-3-nitrophenyl}sulfonyl)benzamide The title compound was prepared by substituting EXAMPLE 45C for EXAMPLE 1F and EXAMPLE 126A for EXAMPLE 1G in EXAMPLE 1H. $^1$H NMR (400 MHz, dimethylsulfoxide-$d_6$) δ 8.77 (m, 1H), 8.45 (d, 1H), 7.78 (dd, 1H), 7.52 (d, 1H), 7.34 (d, 2H), 7.06 (m, 3H), 6.91 (m, 2H), 6.76 (dd, 1H), 6.45 (m, 2H), 3.62 (m, 4H), 3.49 (m, 2H), 3.18 (m, 4H), 2.81 (s, 2H), 2.68 (t, 2H), 2.23 (m, 6H), 1.97 (m, 2H), 1.41 (t, 2H), 0.94 (s, 6H).

Example 136

4-(4-{[2-(4-chlorophenyl)-4,4-dimethylcyclohex-1-en-1-yl]methyl}piperazin-1-yl)-2-(2,3-difluorophenoxy)-N-[(3-nitro-4-{[1-(thien-3-ylmethyl)piperidin-4-yl]amino}phenyl)sulfonyl]benzamide

Example 136A 4-(2-Nitro-4-sulfamoyl-phenylamino)-piperidine-1-carboxylic acid tert-butyl ester Tert-butyl 4-aminopiperidine-1-carboxylate (8.63 g) was dissolved in 1,4-dioxane (250 mL), and 4-chloro-3-nitrobenzenesulfonamide (6.00 g) was added followed by triethylamine (10.60 mL). The solution was heated at 90° C. for 20 hours and then cooled. The solvent was removed under vacuum, and the material was purified by flash column chromatography on silica gel using 50% ethyl acetate in hexanes, increasing to 100% ethyl acetate and increasing further to 20% methanol in dichloromethane.

Example 136B

3-Nitro-4-(piperidin-4-ylamino)-benzenesulfonamide

The title compound was prepared by substituting EXAMPLE 136A for EXAMPLE 1A in EXAMPLE 1B.

Example 136C 3-nitro-4-(1-(thiophen-3-ylmethyl)piperidin-4-ylamino)benzenesulfonamide The title compound was prepared by substituting thiophene-3-carbaldehyde for 4'-chlorobiphenyl-2-carboxaldehyde and EXAMPLE 136B for tert-butyl piperazine-1-carboxylate in EXAMPLE 1A.

Example 136D 4-(4-{[2-(4-chlorophenyl)-4,4-dimethylcyclohex-1-en-1-yl]methyl}piperazin-1-yl)-2-(2,3-difluorophenoxy)-N-[(3-nitro-4-{[1-(thien-3-ylmethyl)piperidin-4-yl]amino}phenyl)sulfonyl]benzamide The title compound was prepared by substituting EXAMPLE 45C for EXAMPLE 1F and EXAMPLE 136C for EXAMPLE 1G in EXAMPLE 1H. $^1$H NMR (400 MHz, dimethylsulfoxide-$d_6$) δ 8.39 (d, 1H), 8.16 (d, 1H), 7.74 (dd, 1H), 7.54 (m, 3H), 7.35 (d, 2H), 7.10 (m, 4H), 6.87 (m, 2H), 6.74 (dd, 1H), 6.40 (m, 2H), 3.84 (m, 3H), 3.15 (m, 4H), 3.03 (m, 2H), 2.79 (s, 2H), 2.62 (m, 2H), 2.23 (m, 6H), 2.02 (m, 4H), 1.73 (m, 2H), 1.41 (t, 2H), 0.94 (s, 6H).

Example 137

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(2-fluorophenoxy)benzamide EXAMPLE 122C (203 mg), EXAMPLE 11A (124 mg), 1-ethyl-3-[3-(dimethylamino)propyl]-carbodiimide hydrochloride (142 mg), and 4-dimethylaminopyridine (90 mg) were stirred in $CH_2Cl_2$ (8 mL) overnight. The reaction was concentrated and the crude was purified by preparative HPLC using a C18 column, 250×50 mm, 10μ, and eluting with a gradient of 20-100% $CH_3CN$ vs. 0.1% trifluoroacetic acid in water, giving the product as a trifluoroacetate salt. The salt was dissolved in dichloromethane (6 mL) and washed with 50% aqueous $NaHCO_3$. The organic layer was dried over anhydrous $Na_2SO_4$, filtered, and concentrated to give the title compound. $^1$H NMR (300 MHz, dimethylsulfoxide-$d_6$) δ 8.71 (br t, 1H), 8.38 (d, 1H), 7.75 (dd, 1H), 7.63 (d, 1H), 7.37 (d, 2H), 7.18 (m, 1H), 7.06 (d, 2H), 6.98 (d, 1H), 6.92 (m, 2H), 6.66 (dd, 1H), 6.60 (m, 1H), 6.26 (d, 1H), 3.47 (dd, 2H), 3.05 (br m, 4H), 2.89 (br m, 2H), 2.75 (s, 2H), 2.60 (s, 6H), 2.20 (br m, 6H), 1.98 (s, 2H), 1.88 (m, 2H) 1.40 (t, 2H), 0.93 (s, 6H).

Example 138

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(3-fluorophenoxy)benzamide The title compound was prepared by substituting EXAMPLE 112C for EXAMPLE 122C in EXAMPLE 137. $^1$H NMR (300 MHz, dimethylsulfoxide-$d_6$) δ 8.70 (br t, 1H), 8.35 (d, 1H), 7.69 (dd, 1H), 7.62 (d, 1H), 7.37 (d, 2H), 7.15 (dd, 1H), 7.06 (d, 2H), 6.95 (d, 1H), 6.70 (m, 2H), 6.50 (dd, 1H), 6.41 (m, 1H), 6.38 (d, 1H), 3.47 (dd, 2H), 3.10 (br m, 4H), 2.94 (br m, 2H), 2.78 (s, 2H), 2.62 (s, 6H), 2.23 (br m, 6H), 1.99 (s, 2H), 1.90 (m, 2H) 1.40 (t, 2H), 0.93 (s, 6H).

Example 139

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(4-fluorophenoxy)benzamide The title compound was prepared by substituting EXAMPLE 118C for EXAMPLE 122C in EXAMPLE 137. $^1$H NMR (300 MHz, dimethylsulfoxide-$d_6$) δ 8.75 (br t, 1H), 8.39 (d, 1H), 7.75 (dd, 1H), 7.58 (d, 1H), 7.37 (d, 2H), 7.06 (d, 2H), 7.00 (m, 3H), 6.75 (m, 2H), 6.66 (dd, 1H), 6.28 (d, 1H), 3.47 (dd, 2H), 3.05 (br m, 4H), 2.89 (br m, 2H), 2.75 (s, 2H), 2.60 (s, 6H), 2.20 (br m, 6H), 1.98 (s, 2H), 1.88 (m, 2H) 1.40 (t, 2H), 0.93 (s, 6H).

Example 140

4-(4-{[2-(4-chlorophenyl)-4,4-dimethylcyclohex-1-en-1-yl]methyl}piperazin-1-yl)-2-(2,3-difluorophenoxy)-N-[(4-{[1-(2-fluoroethyl)piperidin-4-yl]amino}-3-nitrophenyl)sulfonyl]benzamide

Example 140A 4-(2-Nitro-4-sulfamoyl-phenylamino)-piperidine-1-carboxylic acid tert-butyl ester Tert-butyl 4-aminopiperidine-1-carboxylate (8.63 g) was dissolved in 1,4-dioxane (250 mL), and 4-chloro-3-nitrobenzenesulfonamide (6.00 g) was added followed by triethylamine (10.60 mL). The solution was heated at 90° C. for 20 hours and then cooled. The solvent was removed under vacuum, and the material purified by flash column chromatography on silica gel using 50% ethyl acetate in hexanes, increasing to 100% ethyl acetate and increasing further to 20% methanol in dichloromethane.

Example 140B

3-Nitro-4-(piperidin-4-ylamino)-benzenesulfonamide

The title compound was prepared by substituting EXAMPLE 140A for EXAMPLE 1A in EXAMPLE 1B.

Example 140C

4-[1-(2-Fluoro-ethyl)-piperidin-4-ylamino]-3-nitro-benzenesulfonamide

To EXAMPLE 140B (1000 mg) was added N,N-dimethylformamide (10 mL). 1-Fluoro-2-iodoethane (462 mg) and triethylamine (1.18 mL) were added and the solution was heated at 70° C. for 16 hours. The solvent was removed under vacuum, and the material purified by flash column chromatography on silica gel using ethyl acetate increasing to 10% methanol in dichloromethane.

Example 140D 4-(4-{[2-(4-chlorophenyl)-4,4-dimethylcyclohex-1-en-1-yl]methyl}piperazin-1-yl)-2-(2,3-difluorophenoxy)-N-[(4-{[1-(2-fluoroethyl)piperidin-4-yl]amino}-3-nitrophenyl)sulfonyl]benzamide The title compound was prepared by substituting EXAMPLE 45C for EXAMPLE 1F and EXAMPLE 140C for EXAMPLE 1G in EXAMPLE 1H. $^1$H NMR (300 MHz, dimethylsulfoxide-$d_6$) δ 8.41 (d, 1H), 8.21 (d, 1H), 7.76 (dd, 1H), 7.56 (d, 1H), 7.37 (d, 2H), 7.14 (d, 1H), 7.07 (d, 2H), 6.94-6.82 (m, 2H), 6.76 (dd, 1H), 6.48 (d, 1H), 6.41-6.34 (m, 1H), 4.71 (t, 1H), 4.55 (t, 1H), 3.89-3.70 (m, 2H), 3.17 (br s, 4H), 3.09-2.90 (m, 4H), 2.91-2.77 (m, 3H), 2.26 (br s, 4H), 2.18 (m, 2H), 2.08-1.96 (m, 4H), 1.71 (q, 2H), 1.41 (t, 2H), 0.95 (s, 6H).

Example 141

2-(3-chlorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide The title compound was prepared by substituting EXAMPLE 36C for EXAMPLE 1F and EXAMPLE 126A for EXAMPLE 1G in EXAMPLE 1H. $^1$H NMR (300 MHz, dimethylsulfoxide-$d_6$) δ 8.81 (t, 1H), 8.44 (d, 1H), 7.73 (dd, 1H), 7.51 (d, 1H), 7.36 (d, 2H), 7.18 (t, 1H), 7.07 (d, 2H), 7.04 (d, 1H), 6.93 (dt, 1H), 6.78 (dd, 1H), 6.71 (dd, 1H), 6.69 (d, 1H), 6.47 (d, 1H), 3.62 (t, 4H), 3.50 (q, 2H), 3.20 (br s, 4H), 2.81 (br s, 2H), 2.69 (t, 2H), 2.26 (m, 4H), 2.18 (t, 2H), 2.02-1.93 (m, 4H), 1.41 (t, 2H), 1.37-1.22 (m, 2H), 0.95 (s, 6H).

Example 142

2-(3-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide The title compound was prepared by substituting EXAMPLE 36C for EXAMPLE 122C in EXAMPLE 137. $^1$H NMR (300 MHz, dimethylsulfoxide-$d_6$) δ 8.71 (br t, 1H), 8.34 (d, 1H), 7.65 (dd, 1H), 7.63 (d, 1H), 7.37 (d, 2H), 7.16 (dd, 1H), 7.07 (d, 2H), 6.93 (d, 1H), 6.89 (m, 1H), 6.73 (dd, 1H), 6.64 (dd, 1H), 6.60 (dd, 1H), 6.38 (d, 1H), 3.45 (dd, 2H), 3.09 (br m, 4H), 2.93 (br m, 2H), 2.78 (s, 2H), 2.62 (s, 6H), 2.23 (br m, 6H), 1.98 (s, 2H), 1.90 (m, 2H) 1.41 (t, 2H), 0.93 (s, 6H).

Example 143

2-(3-chlorophenoxy)-4-(4-{[2-(4-chlorophenyl)-4,4-dimethylcyclohex-1-en-1-yl]methyl}piperazin-1-yl)-N-[(4-{[3-(4-methylpiperazin-1-yl)propyl]amino}-3-nitrophenyl)sulfonyl]benzamide

Example 143A

4-[3-(4-Methyl-piperazin-1-yl)-propylamino]-3-nitro-benzenesulfonamide

The title compound was prepared by substituting 1-(3-aminopropyl)-4-methylpiperazine for tert-butyl 4-aminopiperidine-1-carboxylate in EXAMPLE 140A.

Example 143B 2-(3-chlorophenoxy)-4-(4-{[2-(4-chlorophenyl)-4,4-dimethylcyclohex-1-en-1-yl]methyl}piperazin-1-yl)-N-[(4-{[3-(4-methylpiperazin-1-yl)propyl]amino}-3-nitrophenyl)sulfonyl]benzamide The title compound was prepared by substituting EXAMPLE 36C for EXAMPLE 1F and EXAMPLE 143A for EXAMPLE 10 in EXAMPLE 1H. $^1$H NMR (300 MHz, dimethylsulfoxide-$d_6$) δ 8.55 (t, 1H), 8.39 (d, 1H), 7.67 (dd, 1H), 7.61 (d, 1H), 7.36 (d, 2H), 7.15 (t, 1H), 7.07 (d, 2H), 6.95 (d, 1H), 6.89 (dd, 1H), 6.73 (dd, 1H), 6.65 (d, 1H), 6.60 (t, 1H), 6.40 (d, 1H), 3.43 (q, 2H), 3.12 (br s, 4H), 2.89 (br s, 2H), 2.77 (s, 2H), 2.60-2.45 (m, 9H), 2.29-2.15 (m, 8H), 1.98 (br s, 2H), 1.81 (m, 2H), 1.41 (t, 2H), 0.94 (s, 6H).

Example 144

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide

Example 144A methyl 2-(3-chlorophenoxy)-4-(piperazin-1-yl)benzoate

This example was prepared by substituting piperazine for EXAMPLE 3F and EXAMPLE 36A for EXAMPLE 3A in EXAMPLE 3G.

Example 144B methyl 2-(3-chlorophenoxy)-4-(4-((4-(4-chlorophenyl)-6,6-dimethyl-5,6-dihydro-2H-pyran-3-yl)methyl)piperazin-1-yl)benzoate This example was prepared by substituting EXAMPLE 144A for EXAMPLE 38F in EXAMPLE 38G.

Example 144C 2-(3-chlorophenoxy)-4-(4-((4-(4-chlorophenyl)-6,6-dimethyl-5,6-dihydro-2H-pyran-3-yl)methyl)piperazin-1-yl)benzoic acid The title compound was prepared as described in EXAMPLE 38H by replacing EXAMPLE 38G with EXAMPLE 144B.

Example 144D 2-(3-chlorophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 144C and EXAMPLE 3I, respectively. $^1$H NMR (300 MHz, dimethylsulfoxide-$d_6$) δ 8.33 (d, 1H), 8.07 (d, 1H), 7.68 (dd, 1H), 7.62 (d, 1H), 7.40 (d, 2H), 7.15 (m, 3H), 7.01 (d, 1H), 6.86 (m, 1H), 6.72 (m, 1H), 6.64 (dd, 1H), 6.58 (m, 1H), 6.39 (d, 1H), 4.15 (s, 2H), 3.83 (m, 1H), 3.17 (m, 8H), 2.87 (s, 3H), 2.63 (m, 5H), 2.26 (m, 4H), 2.13 (m, 3H), 1.79 (m, 1H), 1.20 (s, 6H).

Example 145

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(1-methylpiperidin-4-yl)amino]-3-nitrophenyl}sulfonyl)benzamide

Example 145A methyl 2-(2,3-difluorophenoxy)-4-(piperazin-1-yl)benzoate

This example was prepared by substituting piperazine for EXAMPLE 3F and EXAMPLE 45A for EXAMPLE 3A in EXAMPLE 3G.

Example 145B methyl 2-(2,3-difluorophenoxy)-4-(4-((4-(4-chlorophenyl)-6,6-dimethyl-5,6-dihydro-2H-pyran-3-yl)methyl)piperazin-1-yl)benzoate This example was prepared by substituting EXAMPLE 145A for EXAMPLE 38F in EXAMPLE 38G.

Example 145C 4-(4-((4-(4-chlorophenyl)-6,6-dimethyl-5,6-dihydro-2H-pyran-3-yl)methyl)piperazin-1-yl)-2-(2,3-difluorophenoxy)benzoic acid The title compound was prepared as described in EXAMPLE 38H by replacing EXAMPLE 38G with EXAMPLE 145B.

Example 145D 4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 145C and EXAMPLE 3I, respectively. $^1$H NMR (300 MHz, dimethylsulfoxide-$d_6$) δ 8.32 (d, 1H), 8.06 (d, 1H), 7.71 (dd, 1H), 7.66 (d, 1H), 7.40 (d, 2H), 7.15 (s, 2H), 7.03 (d, 1H), 6.81 (m, 2H), 6.73 (m, 1H), 6.43 (m, 1H), 6.27 (m, 1H), 4.15 (m, 2H), 3.83 (m, 1H), 3.16 (m, 8H), 2.88 (s, 3H), 2.70 (m, 4H), 2.26 (s, f 4H), 2.13 (m, 4H), 1.78 (m, 1H), 1.21 (s, 6H).

Example 146

N-({4-[(1-allylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(2,3-difluorophenoxy)benzamide

Example 146A 4-(1-allylpiperidin-4-ylamino)-3-nitrobenzenesulfonamide 3-nitro-4-(piperidin-4-ylamino)benzenesulfonamide hydrochloride (0.27 g), triethylamine (0.2 mL) and 3-bromoprop-1-ene (0.1 g) was dissolved in N,N-dimethylformamide (5 mL). The mixture was stirred at room temperature overnight. The solvent was dried under vacuum. The mixture was chromatographed on silica gel with 0-20% methanol in dichloromethane.

Example 146B

N-({4-[(1-allylpiperidin-4-yl)amino]-3-nitrophenyl}sulfonyl)-4-(4-{[2-(4-chlorophenyl)-4,4-dimethylcyclohex-1-en-1-yl]methyl}piperazin-1-yl)-2-(2,3-difluorophenoxy)benzamide The title compound was prepared by substituting EXAMPLE 45C for EXAMPLE 1F and EXAMPLE 146A for EXAMPLE 1G in EXAMPLE 1H. $^1$H NMR (400 MHz, dimethylsulfoxide-$d_6$) δ 8.39 (d, 1H), 8.14 (d, 1H), 7.75 (dd, 1H), 7.59 (d, 1H), 7.35 (d, 2H), 7.08 (m, 3H), 6.86 (m, 2H), 6.74 (dd, 1H), 6.45 (d, 1H), 6.36 (m, 1H), 5.88 (m, 1H), 5.37 (m, 2H), 3.83 (m, 1H), 3.13 (m, 8H), 2.74 (m, 4H), 2.17 (m, 8H), 1.98 (s, 2H), 1.74 (m, 2H), 1.41 (t, 2H), 0.94 (s, 6H).

Example 147

2-(3-chloro-2-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 147A methyl 2-(3-chloro-2-fluorophenoxy)-4-fluorobenzoate

The title compound was prepared by substituting 3-chloro-2-fluorophenol for 2-methyl-5-indolol in EXAMPLE 3A.

Example 147B

Ethyl 2-(3-chloro-2-fluorophenoxy)-4-(piperazin-1-yl)benzoate

The title compound was prepared by substituting piperazine for EXAMPLE 3F and EXAMPLE 147A for EXAMPLE 3A in EXAMPLE 3G.

Example 147C

Ethyl 2-(3-chloro-2-fluorophenoxy)-4-(4-((2-(4-chlorophenyl)-4,4-dimethylcyclohex-1-enyl)methyl)piperazin-1-yl)benzoate The title compound was prepared by substituting EXAMPLE 60D for 4'-chlorobiphenyl-2-carboxaldehyde and EXAMPLE 147B for tert-butyl piperazine-1-carboxylate in EXAMPLE 1A.

Example 147D 2-(3-chloro-2-fluorophenoxy)-4-(4-((2-(4-chlorophenyl)-4,4-dimethylcyclohex-1-enyl)methyl)piperazin-1-yl)benzoic acid The title compound was prepared by substituting EXAMPLE 147C for EXAMPLE 1E in EXAMPLE 1F.

Example 147E 2-(3-chloro-2-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 147D for EXAMPLE 1F and EXAMPLE 3I for EXAMPLE 1G in EXAMPLE 1H. $^1$H NMR (400 MHz, dimethylsulfoxide-$d_6$) δ 8.33 (d, 1H), 8.05 (d, 1H), 7.68 (m, 2H), 7.35 (d, 2H), 7.02 (m, 4H), 6.84 (m, 1H), 6.72 (d, 1H), 6.43 (m, 2H), 3.83 (m, 1H), 3.12 (m, 6H), 2.84 (m, 4H), 2.62 (s, 3H), 2.22 (m, 6H), 2.11 (m, 2H), 1.98 (s, 2H), 1.76 (m, 2H), 1.41 (t, 2H), 0.94 (s, 6H).

Example 148

2-(3-chloro-2-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide The title compound was prepared by substituting EXAMPLE 147D for EXAMPLE 1F and EXAMPLE 4A for EXAMPLE 1G in EXAMPLE 1H. $^1$H NMR (400 MHz, dimethylsulfoxide-$d_6$) δ 8.71 (m, 1H), 8.41 (d, 1H), 7.74 (dd, 1H), 7.56 (d, 1H), 7.35 (d, 2H), 7.05 (m, 4H), 6.91 (m, 1H), 6.75 (dd, 1H), 6.56 (m, 1H), 6.47 (d, 1H), 3.64 (m, 4H), 3.47 (q, 2H), 3.17 (m, 4H), 2.79 (s, 2H), 2.55 (m, 6H), 2.22 (m, 6H), 1.98 (s, 2H), 1.84 (m, 2H), 1.41 (t, 2H), 0.95 (s, 6H).

Example 149

2-(3-chloro-2-fluorophenoxy)-4-(4-{[2-(4-chlorophenyl)-4,4-dimethylcyclohex-1-en-1-yl]methyl)}piperazin-1-yl)-N-({3-nitro-4-[(3-pyrrolidin-1-ylpropyl)amino]phenyl}sulfonyl)benzamide

Example 149A 3-nitro-4-(3-(pyrrolidin-1-yl)propylamino)benzenesulfonamide

The title compound was prepared by substituting 3-(pyrrolidin-1-yl)propan-1-amine for 3-(N-morpholinyl)-1-propylamine in EXAMPLE 4A.

Example 149B 2-(3-chloro-2-fluorophenoxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide The title compound was prepared by substituting EXAMPLE 147D for EXAMPLE 1F and EXAMPLE 149A for EXAMPLE 1G in EXAMPLE 1H. $^1$H NMR (400 MHz, dimethylsulfoxide-$d_6$) δ 8.43 (s, 1H), 8.32 (d, 1H), 7.70 (m, 2H), 7.35 (d, 2H), 7.07 (d, 2H), 6.97 (m, 2H), 6.85 (m, 1H), 6.71 (dd, 1H), 6.43 (m, 2H), 3.48 (q, 2H), 3.09 (m, 8H), 2.77 (s, 2H), 2.21 (m, 8H), 1.92 (m, 8H), 1.40 (t, 2H), 0.94 (s, 6H).

Example 150

2-(3-chloro-2-fluorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide The title compound was prepared by substituting EXAMPLE 147D for EXAMPLE 1F and EXAMPLE 126A for EXAMPLE 1G in EXAMPLE 1H. $^1$H NMR (400 MHz, dimethylsulfoxide-$d_6$) δ 8.79 (m, 1H), 8.44 (d, 1H), 7.76 (dd, 1H), 7.53 (d, 1H), 7.36 (d, 2H), 7.06 (m, 4H), 6.91 (m, 1H), 6.76 (dd, 1H), 6.58 (m, 1H), 6.48 (d, 1H), 3.62 (m, 4H), 3.50 (q, 2H), 3.19 (m, 4H), 2.81 (s, 2H), 2.69 (m, 2H), 2.23 (m, 6H), 1.98 (s, 2H), 1.41 (t, 2H), 0.94 (s, 6H).

Example 151

2-(2-chloro-6-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 151A methyl 2-(2-chloro-6-fluorophenoxy)-4-fluorobenzoate

The title compound was prepared by substituting 2-chloro-6-fluorophenol for 2-methyl-5-indolol in EXAMPLE 3A.

Example 151B methyl 2-(2-chloro-6-fluorophenoxy)-4-(4-((2-(4-chlorophenyl)-4,4-dimethylcyclohex-1-enyl)methyl)piperazin-1-yl)benzoate The title compound was prepared by substituting EXAMPLE 151A for EXAMPLE 3A in EXAMPLE 3G.

Example 151C 2-(2-chloro-6-fluorophenoxy)-4-(4-((2-(4-chlorophenyl)-4,4-dimethylcyclohex-1-enyl)methyl)piperazin-1-yl)benzoic acid The title compound was prepared by substituting EXAMPLE 151B for EXAMPLE 1E in EXAMPLE 1F.

Example 151D 2-(2-chloro-6-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 151C for EXAMPLE 1F and EXAMPLE 3I for EXAMPLE 1G in EXAMPLE 1H. $^1$H NMR (400 MHz, dimethylsulfoxide-$d_6$) δ 8.51 (d, 1H), 8.09 (d, 1H), 7.92 (dd, 1H), 7.60 (d, 1H), 7.32 (m, 5H), 7.17 (d, 1H), 7.05 (d, 2H), 6.56 (dd, 1H), 5.83 (d, 1H), 3.85 (m, 1H), 3.17 (m, 2H), 2.95 (m, 4H), 2.81 (m, 2H), 2.73 (s, 2H), 2.59 (s, 3H), 2.15 (m, 8H), 1.97 (m, 2H), 1.77 (m, 2H), 1.39 (t, 2H), 0.93 (s, 6H).

Example 152

2-(2-chloro-6-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 151C for EXAMPLE 1F and EXAMPLE 49C for EXAMPLE 1G in EXAMPLE 1H. $^1$H NMR (400 MHz, dimethylsulfoxide-$d_6$) δ 8.54 (d, 1H), 8.14 (d, 1H), 7.93 (dd, 1H), 7.58 (d, 1H), 7.34 (m, 5H), 7.20 (d, 1H), 7.04 (d, 2H), 6.59 (dd, 1H), 5.85 (d, 1H), 3.93 (dd, 2H), 3.85 (m, 1H), 3.21 (s, 6H), 2.97 (m, 4H), 2.73 (m, 4H), 2.16 (m, 8H), 1.96 (s, 2H), 1.81 (m, 2H), 1.69 (m, 2H), 1.54 (m, 2H), 1.39 (t, 2H), 0.93 (s, 6H).

Example 154

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(1-methylpiperidin-4-yl)amino]-3-nitrophenyl}sulfonyl)benzamide

Example 154A 6-fluoro-1H-indol-5-ol

The title compound was prepared from 2-fluoro-4-nitrophenol according to WO 02/12227 (page 78).

Example 154B methyl 4-fluoro-2-(6-fluoro-1H-indol-5-yloxy)benzoate

The title compound was prepared as described in EXAMPLE 3A by replacing 2-methyl-5-indolol with EXAMPLE 154A.

Example 154C methyl 2-(6-fluoro-1H-indol-5-yloxy)-4-(piperazin-1-yl)benzoate The title compound was prepared as described in EXAMPLE 3G by replacing EXAMPLE 3F and EXAMPLE 3A with piperazine and EXAMPLE 154B, respectively.

Example 154D methyl 4-(4-((2-(4-chlorophenyl)-4,4-dimethylcyclohex-1-enyl)methyl)piperazin-1-yl)-2-(6-fluoro-1H-indol-5-yloxy)benzoate The title compound was prepared as described in EXAMPLE 38G by replacing EXAMPLE 38F and EXAMPLE 38E with EXAMPLE 154C and EXAMPLE 60D, respectively.

Example 154E 4-(4-((2-(4-chlorophenyl)-4,4-dimethylcyclohex-1-enyl)methyl)piperazin-1-yl)-2-(6-fluoro-1H-indol-5-yloxy)benzoic acid The title compound was prepared as described in EXAMPLE 38H by replacing EXAMPLE 38G with EXAMPLE 154D.

Example 154F 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 154E and EXAMPLE 3I, respectively. $^1$H NMR (300 MHz, dimethylsulfoxide-$d_6$) δ 11.12 (m, 1H), 8.49 (d, 1H), 8.11 (d, 1H), 7.82 (dd, 1H), 7.55 (d, 1H), 7.33 (m, 3H), 7.28 (d, 1H), 7.11 (d, 1H), 7.05 (m, 2H), 6.59 (dd, 1H), 6.35 (m, 1H), 6.08 (m, 1H), 3.76 (m, 1H), 3.06 (m, 8H), 2.72 (m, 6H), 2.17 (s, 6H), 1.98 (m, 5H), 1.72 (s, 2H), 1.38 (t, 2H), 0.92 (s, 6H).

Example 155

2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide

Example 155A 4-((1-methylpiperidin-4-yl)methylamino)-3-nitrobenzenesulfonamide The title compound was prepared by substituting 4-aminomethyl-N-methylpiperidine for 3-(N-morpholinyl-1-propylamine in EXAMPLE 4A.

Example 155B 2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide The title compound was prepared by substituting EXAMPLE 36C for EXAMPLE 1F and EXAMPLE 155A for EXAMPLE 1G in EXAMPLE 1H. $^1$H NMR (300 MHz, dimethylsulfoxide-$d_6$) δ 8.45 (br t, 1H), 8.33 (d, 1H), 7.65 (m, 2H), 7.36 (d, 2H), 7.15 (t, 1H), 7.06 (d, 2H), 6.97 (d, 1H), 6.89 (d, 1H), 6.60 (m, 2H), 6.38 (d, 1H), 3.02-3.12 (m, 8H), 2.77 (m, 4H), 2.65 (m, 2H), 2.24 (m, 4H), 2.19 (m, 2H), 1.91 (m, 1H), 1.87 (m, 2H), 1.41 (m, 4H), 0.95 (s, 6H).

Example 156

4-(4-{[2-(4-chlorophenyl)-4,4-dimethylcyclohex-1-en-1-yl]methyl}piperazin-1-yl)-2-(2,3-difluorophenoxy)-N-[(4-{[(1-methylpiperidin-4-yl)methyl]amino}-3-nitrophenyl)sulfonyl]benzamide The title compound was prepared by substituting EXAMPLE 45C for EXAMPLE 1F and EXAMPLE 155A for EXAMPLE 1G in EXAMPLE 1H. $^1$H NMR (300 MHz, dimethylsulfoxide-$d_6$) δ 8.54 (br t, 1H), 8.37 (d, 1H), 7.72 (d, 1H), 7.60 (d, 1H), 7.36 (d, 2H), 7.07 (d, 3H), 6.88 (dd, 2H), 6.75 (d, 1H), 6.46 (s, 1H), 6.36 (br s, 1H), 3.16 (m, 8H), 2.89 (m, 2H), 2.81 (m, 2H), 2.68 (s, 3H), 2.27 (m, 4H), 2.20 (m, 2H), 1.99 (m, 2H), 1.91 (m, 3H), 1.55 (m, 2H), 1.41 (m, 2H), 0.95 (s, 6H).

Example 157

4-(4-{[2-(4-chlorophenyl)-4,4-dimethylcyclohex-1-en-1-yl]methyl}piperazin-1-yl)-2-[(4-fluoro-1H-indol-5-yl)oxy]-N-({4-[(1-methylpiperidin-4-yl)amino]-3-nitrophenyl}sulfonyl)benzamide

Example 157A 4-fluoro-1H-indol-5-ol

The title compound was prepared from 2-fluoro-4-nitrophenol according to WO 02/12227 (page 78).

Example 157B methyl 4-fluoro-2-(4-fluoro-1H-indol-5-yloxy)benzoate

The title compound was prepared as described in EXAMPLE 3A by replacing 2-methyl-5-indolol with EXAMPLE 157A.

Example 157C methyl 2-(4-fluoro-1H-indol-5-yloxy)-4-(piperazin-1-yl)benzoate The title compound was prepared as described in EXAMPLE 3G by replacing EXAMPLE 3F and EXAMPLE 3A with piperazine and EXAMPLE 157B respectively.

Example 157D methyl 4-(4-((2-(4-chlorophenyl)-4,4-dimethylcyclohex-1-enyl)methyl)piperazin-1-yl)-2-(4-fluoro-1H-indol-5-yloxy)benzoate The title compound was prepared as described in EXAMPLE 38G by replacing EXAMPLE 38F and EXAMPLE 38E with EXAMPLE 157C and EXAMPLE 60D, respectively.

Example 157E 4-(4-((2-(4-chlorophenyl)-4,4-dimethylcyclohex-1-enyl)methyl)piperazin-1-yl)-2-(4-fluoro-1H-indol-5-yloxy)benzoic acid The title compound was prepared as described in EXAMPLE 38H by replacing EXAMPLE 38G with EXAMPLE 157D.

Example 157F 4-(4-{[2-(4-chlorophenyl)-4,4-dimethylcyclohex-1-en-1-yl]methyl}piperazin-1-yl)-2-[(4-fluoro-1H-indol-5-yl)oxy]-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 157E and EXAMPLE 3I. $^1$H NMR (300 MHz, dimethylsulfoxide-$d_6$) δ 11.40 (m, 1H), 8.53 (d, 1H), 8.12 (d, 1H), 7.88 (d, 1H), 7.53 (d, 1H), 7.42 (t, 1H), 7.33 (d, 2H), 7.16 (dd, 2H), 7.05 (d, 2H), 6.83 (m, 1H), 6.52 (m, 2H), 6.02 (s, 1H), 3.77 (m, 2H), 3.03 (m, 6H), 2.70 (s, 3H), 2.04 (m, 12H), 1.71 (m, 2H), 0.92 (s, 6H).

Example 158

4-(4-{[2-(4-chlorophenyl)-4,4-dimethylcyclohex-1-en-1-yl]methyl}piperazin-1-yl)-2-[3-(methoxymethoxy)-2-methylphenoxy]-N-({4-[(1-methylpiperidin-4-yl)amino]-3-nitrophenyl}sulfonyl)benzamide

Example 158A

Ethyl 4-fluoro-2-(3-hydroxy-2-methylphenoxy)benzoate

The title compound was prepared by substituting 2-methylbenzene-1,3-diol for 2-methyl-5-indolol in EXAMPLE 3A.

Example 158B ethyl 4-(4-((2-(4-chlorophenyl)-4,4-dimethylcyclohex-1-enyl)methyl)piperazin-1-yl)-2-(3-hydroxy-2-methylphenoxy)benzoate The title compound was prepared by substituting EXAMPLE 158A for EXAMPLE 3A in EXAMPLE 3G.

Example 158C

Ethyl 4-(4-((2-(4-chlorophenyl)-4,4-dimethylcyclohex-1-enyl)methyl)piperazin-1-yl)-2-(3-(methoxymethoxy)-2-methylphenoxy)benzoate A mixture of EXAMPLE 158B (0.6 g), chloro(methoxy)methane (0.18 g) and cesium carbonate (0.9 g) was suspended in N,N-dimethylformamide (15 mL). After it stirred at room temperature for 30 minutes, the crude product was purified by preparative HPLC using a 250×50 mm C18 column and eluting with 20-100% CH$_3$CN vs. 0.1% trifluoroacetic acid in water.

Example 158D 4-(4-((2-(4-chlorophenyl)-4,4-dimethylcyclohex-1-enyl)methyl)piperazin-1-yl)-2-(3-(methoxymethoxy)-2-methylphenoxy)benzoic acid The title compound was prepared by substituting EXAMPLE 158C for EXAMPLE 1E in EXAMPLE 1F.

Example 158E 4-(4-{[2-(4-chlorophenyl)-4,4-dimethylcyclohex-1-en-1-yl]methyl}piperazin-1-yl)-2-[3-(methoxymethoxy)-2-methylphenoxy]-N-({4-[(1-methylpiperidin-4-yl)amino]-3-nitrophenyl}sulfonyl)benzamide The title compound was prepared by substituting EXAMPLE 158D for EXAMPLE 1F and EXAMPLE 3I for EXAMPLE 1G in EXAMPLE 1H. $^1$H NMR (500 MHz, dimethylsulfoxide-$d_6$) δ 8.43 (d, 1H), 8.10 (d, 1H), 7.73 (dd, 1H), 7.54 (d, 1H), 7.35 (d, 2H), 7.07 (m, 3H), 6.94 (t, 1H), 6.72 (d, 1H), 6.63 (dd, 1H), 6.19 (m, 2H), 5.21 (s, 2H), 3.79 (m, 1H), 3.40 (s, 3H), 3.09 (m, 6H), 2.73 (m, 4H), 2.56 (s, 2H), 2.19 (m, 6H), 2.07 (m, 6H), 1.96 (s, 2H), 1.74 (m, 2H), 1.40 (t, 2H), 0.94 (s, 6H).

Example 159

4-(4-{([2-(4-chlorophenyl)-4,4-dimethylcyclohex-1-en-1-yl]methyl}piperazin-1-yl)-2-(3-hydroxy-2-methylphenoxy)-N-({4-[(1-methylpiperidin-4-yl)amino]-3-nitrophenyl}sulfonyl)benzamide Into a 10 mL microwave tube was added EXAMPLE 158E (54 mg) and hydrogen chloride (1.25M in methanol) (0.5 mL) in tetrahydrofuran (4 mL) to give a solution. The mixture was stirred at 60° C. in a CEM Discover microwave reactor for 20 minutes. The solvent was dried under vacuum and the crude product was purified by preparative HPLC using a 250×50 mm C18 column and eluting with 20-100% $CH_3CN$ vs. 0.1% trifluoroacetic acid in water. The trifluoroacetic acid salt was solved in dichloromethane with ammonium and washed with saturated $Na_2CO_3$, dried over $Na_2SO_4$, filtered, and concentrated to afford the free base product. $^1H$ NMR (500 MHz, dimethylsulfoxide-$d_6$) δ 9.38 (s, 1H), 8.46 (d, 1H), 8.13 (d, 1H), 7.77 (dd, 1H), 7.52 (d, 1H), 7.35 (d, 2H), 7.08 (m, 3H), 6.83 (t, 1H), 6.60 (dd, 1H), 6.51 (d, 1H), 6.08 (m, 2H), 3.03 (m, 6H), 2.73 (m, 4H), 2.19 (m, 6H), 2.00 (m, 9H), 1.71 (m, 2H), 1.40 (t, 2H), 0.94 (s, 6H).

Example 160

2-(3-bromophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide

Example 160A methyl 2-(3-bromophenoxy)-4-fluorobenzoate

The title compound was prepared as described in EXAMPLE 3A by replacing 2-methyl-5-indolol with 3-bromophenol.

Example 160B methyl 2-(3-bromophenoxy)-4-(piperazin-1-yl)benzoate

The title compound was prepared as described in EXAMPLE 3G by replacing EXAMPLE 3F and EXAMPLE 3A with piperazine and EXAMPLE 160A, respectively.

Example 160C methyl 2-(3-bromophenoxy)-4-(4-((4-(4-chlorophenyl)-6,6-dimethyl-5,6-dihydro-2H-pyran-3-yl)methyl)piperazin-1-yl)benzoate The title compound was prepared as described in EXAMPLE 38G by replacing EXAMPLE 38F with EXAMPLE 160B.

Example 160D 2-(3-bromophenoxy)-4-(4-((4-(4-chlorophenyl)-6,6-dimethyl-5,6-dihydro-2H-pyran-3-yl)methyl)piperazin-1-yl)benzoic acid The title compound was prepared as described in EXAMPLE 38H by replacing EXAMPLE 38G with EXAMPLE 160C.

Example 160E 2-(3-bromophenoxy)-4-(4-{[4-(4-chlorophenyl)-6,6-dimethyl-5,6-dihydro-2H-pyran-3-yl]methyl}piperazin-1-yl)-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 160D and EXAMPLE 3I, respectively. $^1H$ NMR (300 MHz, dimethylsulfoxide-$d_6$) δ 8.29 (d, 1H), 8.10 (m, 2H), 7.64 (d, 1H), 7.60 (dd, 1H), 7.40 (d, 2H), 7.15 (d, 2H), 7.06 (t, 1H), 6.96 (m, 2H), 6.94 (d, 1H), 6.68 (m, 3H), 6.37 (d, 1H), 5.84 (m, 2H), 4.15 (m, 2H), 3.65 (m, 1H), 3.09 (m, 6H), 2.99 (m, 5H), 2.87 (s, 2H), 2.75 (m, 2H), 2.26 (m, 4H), 1.98 (m, 1H), 1.21 (s, 6H).

Example 161

4-(4-{[4-(4-chlorophenyl)-6,6-dimethyl-5,6-dihydro-2H-pyran-3-yl]methyl}piperazin-1-yl)-2-(3-iodophenoxy)-N-({4-[(1-methylpiperidin-4-yl)amino]-3-nitrophenyl}sulfonyl)benzamide

Example 161A methyl 4-fluoro-2-(3-iodophenoxy)benzoate

The title compound was prepared as described in EXAMPLE 3A by replacing 2-methyl-5-indolol with 3-iodophenol.

Example 161B methyl 2-(3-iodophenoxy)-4-(piperazin-1-yl)benzoate

The title compound was prepared as described in EXAMPLE 3G by replacing EXAMPLE 3F and EXAMPLE 3A with piperazine and EXAMPLE 161A, respectively.

Example 161C methyl 4-(4-((4-(4-chlorophenyl)-6,6-dimethyl-5,6-dihydro-2H-pyran-3-yl)methyl)piperazin-1-yl)-2-(3-iodophenoxy)benzoate The title compound was prepared as described in EXAMPLE 38G by replacing EXAMPLE 38F with EXAMPLE 161B.

Example 161D 4-(4-((4-(4-chlorophenyl)-6,6-dimethyl-5,6-dihydro-2H-pyran-3-yl)methyl)piperazin-1-yl)-2-(3-iodophenoxy)benzoic acid The title compound was prepared as described in EXAMPLE 38H by replacing EXAMPLE 38G with EXAMPLE 161C.

Example 161E 4-(4-{[4-(4-chlorophenyl)-6,6-dimethyl-5,6-dihydro-2H-pyran-3-yl]methyl}piperazin-1-yl)-2-(3-iodophenoxy)-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 161D and EXAMPLE 3I, respectively. ¹H NMR (300 MHz, dimethylsulfoxide-d₆) δ 8.34 (d, 1H), 8.08 (d, 1H), 7.64 (m, 2H), 7.40 (d, 2H), 7.17 (m, 3H), 6.95 (m, 3H), 6.71 (m, 2H), 6.37 (d, 1H), 4.15 (s, 2H), 3.83 (m, 1H), 3.15 (m, 8H), 2.87 (s, 3H), 2.60 (m, 4H), 2.17 (m, 8H), 1.76 (m, 1H), 1.20 (s, 6H).

Example 162

2-(3-chlorophenoxy)-4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]benzamide Example 162A tert-butyl 4-(2-nitro-4-sulfamoylphenylamino)piperidine-1-carboxylate The title compound was prepared by substituting tert-butyl 4-aminopiperidine-1-carboxylate for 3-(N-morpholinyl)-1-propylamine in EXAMPLE 4A.

Example 162B

The title compound was prepared by substituting EXAMPLE 36C for EXAMPLE 1F and EXAMPLE 162A for EXAMPLE 1G in EXAMPLE 1H.

Example 162C 2-(3-chlorophenoxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide The title compound was prepared by substituting EXAMPLE 162B for EXAMPLE 1A in EXAMPLE 1B.

Example 162D

N-(4-(1-(2-(tert-butyldimethylsilyloxy)ethyl)piperidin-4-ylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide The title compound was prepared by substituting EXAMPLE 162C for tert-butyl pieperazien-1-carboxylate and 2-(tert-butyldimethylsilyloxy)acetaldehyde for 4'-chlorobiphenyl-2-carboxaldehyde in EXAMPLE 1A.

Example 162E 2-(3-chlorophenoxy)-4-(4-{[2-(4-chlorophenyl)-4,4-dimethylcyclohex-1-en-1-yl]methyl}piperazin-1-yl)-N-[(4-{[1-(2-hydroxyethyl)piperidin-4-yl]amino}-3-nitrophenyl)sulfonyl]benzamide A mixture of EXAMPLE 162D (270 mg) in anhydrous tetrahydrofuran (5 mL) and tetrabutyl ammonium fluoride (5 mL 1M in tetrahydrofuran) was stirred at room temperature for 2 hours. The solvent was removed under vacuum. The residue was purified by reverse phase HPLC on a C18 column using a gradient of 40-70% acetonitrile/0.1% trifluoroacetic acid in water to give the title compound as the trifluoroacetate salt. The trifluoroacetate salt was dissolved in dichloromethane (6 mL) and washed with 50% aqueous NaHCO₃. The organic layer was dried over anhydrous Na₂SO₄ and concentrated to give the title compound. ¹H NMR (400 MHz, dimethylsulfoxide-d₆) δ 8.35 (d, 1H), 8.09 (d, 1H), 7.69 (dd, 1H), 7.61 (d, 1H), 7.36 (d, 2H), 7.14 (m, 1H), 7.05 (m, 3H), 6.88 (dd, 1H), 6.73 (dd, 1H), 6.65 (dd, 1H), 6.60 (m, 1H), 6.40 (d, 1H), 3.85 (m, 1H), 3.68 (m, 2H), 3.28 (m, 4H), 3.12 (m, 4H), 2.99 (m, 4H), 2.77 (s, 2H), 2.16 (m, 8H), 1.98 (s, 2H), 1.83 (m, 2H), 1.41 (t, 2H), 0.94 (s, 6H).

Example 163

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(2-phenylethyl)piperidin-4-yl]amino}phenyl)sulfonyl]benzamide The title compound was prepared by substituting EXAMPLE 162C for tert-butyl pieperazien-1-carboxylate and 2-phenylacetaldehyde for 4'-chlorobiphenyl-2-carboxaldehyde in EXAMPLE 1A. ¹H NMR (400 MHz, dimethylsulfoxide-d₆) δ 8.37 (d, 1H), 8.16 (d, 1H), 7.70 (dd, 1H), 7.59 (d, 1H), 7.30 (m, 8H), 7.16 (m, 1H), 7.07 (m, 3H), 6.89 (d, 1H), 6.74 (dd, 1H), 6.66 (dd, 1H), 6.62 (d, 1H), 6.42 (d, 1H), 3.84 (m, 1H), 3.27 (m, 6H), 2.98 (m, 8H), 2.78 (s, 2H), 2.17 (m, 8H), 1.98 (s, 2H), 1.78 (m, 2H), 1.41 (t, 2H), 0.94 (s, 6H).

Example 164

4-(4-{[2-(4-chlorophenyl)-4,4-dimethylcyclohex-1-en-1-yl]methyl}piperazin-1-yl)-2-(3,4-dichlorophenoxy)-N-({4-[(1-methylpiperidin-4-yl)amino]-3-nitrophenyl}sulfonyl)benzamide Example 164A Ethyl 2-(3,4-dichlorophenoxy)-4-fluorobenzoate The title compound was prepared by substituting 2,3-dichlorophenol for 2-methyl-5-indolol in EXAMPLE 3A.

Example 164B

Ethyl 2-(3,4-dichlorophenoxy)-4-(4-((2-(4-chlorophenyl)-4,4-dimethylcyclohex-1-enyl)methyl)piperazin-1-yl)benzoate The title compound was prepared by substituting EXAMPLE 164A for EXAMPLE 3A in EXAMPLE 3G.

Example 164C 2-(3,4-dichlorophenoxy)-4-(4-((2-(4-chlorophenyl)-4,4-dimethylcyclohex-1-enyl)methyl)piperazin-1-yl) benzoic acid The title compound was prepared by substituting EXAMPLE 164B for EXAMPLE 1E in EXAMPLE 1F.

Example 164D 4-(4-{[2-(4-chlorophenyl)-4,4-dimethylcyclohex-1-en-1-yl]methyl}piperazin-1-yl)-2-(3,4-dichlorophenoxy)-N-({4-[(1-methylpiperidin-4-yl)amino]-3-nitrophenyl}sulfonyl)benzamide The title compound was prepared by substituting EXAMPLE 164C for EXAMPLE 1F and EXAMPLE 3I for EXAMPLE 1G in EXAMPLE 1H. $^1$H NMR (300 MHz, dimethylsulfoxide-d$_6$) δ 8.35 (d, 1H), 8.06 (s, 1H), 7.62 (d, 2H), 7.31-7.40 (m, 3H), 7.04-7.10 (m, 2H), 6.98 (d, 1H), 6.98 (d, 1H), 6.70-6.81 (m, 2H), 6.64 (dd, 1H), 6.42 (d, 1H), 3.79 (s, 1H), 3.19-3.27 (m, 2H), 3.12 (s, 5H), 2.69-2.81 (m, 4H), 2.63 (s, 2H), 2.15-2.28 (m, 8H), 2.08 (s, 2H), 1.98 (s, 3H), 1.77 (s, 1H), 1.36-1.45 (m, 2H), 1.24 (s, 1H), 0.95 (s, 6H).

Example 165

2-(2-chloro-3,5-difluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide Example 165A Ethyl 2-(2-chloro-3,5-difluorophenoxy)-4-fluorobenzoate The title compound was prepared by substituting 2-chloro-3,5-difluorophenol for 2-methyl-5-indolol in EXAMPLE 3A.

Example 165B

Ethyl 2-(2-chloro-3,5-difluorophenoxy)-4-(piperazin-1-yl)benzoate

The title compound was prepared by substituting piperazine for EXAMPLE 3F and EXAMPLE 165A for EXAMPLE 3A in EXAMPLE 3G.

Example 165C

Ethyl 2-(2-chloro-3,5-difluorophenoxy)-4-(4-((2-(4-chlorophenyl)-4,4-dimethylcyclohex-1-enyl)methyl)piperazin-1-yl)benzoate The title compound was prepared by substituting EXAMPLE 60D for 4'-chlorobiphenyl-2-carboxaldehyde and EXAMPLE 165B for tert-butyl piperazine-1-carboxylate in EXAMPLE 1A.

Example 165D 2-(2-chloro-3,5-difluorophenoxy)-4-(4-((2-(4-chlorophenyl)-4,4-dimethylcyclohex-1-enyl)methyl)piperazin-1-yl)benzoic acid The title compound was prepared by substituting EXAMPLE 165C for EXAMPLE 1E in EXAMPLE 1F.

Example 165E 2-(2-chloro-3,5-difluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 165D for EXAMPLE 1F and EXAMPLE 3I for EXAMPLE 1G in EXAMPLE 1H. $^1$H NMR (500 MHz, dimethylsulfoxide-d$_6$) δ 8.30 (m, 1H), 8.06 (m, 1H), 7.68 (m, 2H), 7.36 (d, 2H), 7.07 (d, 2H), 7.00 (d, 1H), 6.78 (m, 2H), 6.45 (d, 1H), 5.93 (d, 1H), 3.77 (m, 1H), 3.12 (m, 4H), 2.76 (s, 3H), 2.21 (m, 6H), 2.07 (m, 2H), 1.98 (s, 2H), 1.72 (m, 2H), 1.41 (t, 2H), 0.94 (s, 6H).

Example 166

4-(4-{[2-(4-chlorophenyl)-4,4-dimethylcyclohex-1-en-1-yl]methyl}piperazin-1-yl)-2-(3-methoxyphenoxy)-N-({4-[(1-methylpiperidin-4-yl)amino]-3-nitrophenyl}sulfonyl)benzamide Example 166A ethyl 4-fluoro-2-(3-methoxyphenoxy)benzoate The title compound was prepared by substituting 3-methoxyphenol for 2-methyl-5-indolol in EXAMPLE 3A.

Example 166B ethyl 4-(4-((2-(4-chlorophenyl)-4,4-dimethylcyclohex-1-enyl)methyl)piperazin-1-yl)-2-(3-methoxyphenoxy)benzoate The title compound was prepared by substituting EXAMPLE 166A for EXAMPLE 3A in EXAMPLE 3G.

Example 166C 4-(4-((2-(4-chlorophenyl)-4,4-dimethylcyclohex-1-enyl)methyl)piperazin-1-yl)-2-(3-methoxyphenoxy)benzoic acid The title compound was prepared by substituting EXAMPLE 166B for EXAMPLE 1E in EXAMPLE 1F.

Example 166D 4-(4-{[2-(4-chlorophenyl)-4,4-dimethylcyclohex-1-en-1-yl]methyl}piperazin-1-yl)-2-(3-methoxyphenoxy)-N-({4-[(1-methylpiperidin-4-yl)amino]-3-nitrophenyl}sulfonyl)benzamide The title compound was prepared by substituting EXAMPLE 166C for EXAMPLE 122C and EXAMPLE 3I for EXAMPLE 11A in EXAMPLE 137. $^1$H NMR (300 MHz, dimethylsulfoxide-d$_6$) δ 8.39 (d, 1H), 8.10 (br d, 1H), 7.73 (dd, 1H), 7.57 (d, 1H), 7.37 (d, 2H), 7.05 (m, 4H), 6.68 (dd, 1H), 6.45 (dd, 1H), 6.30 (m, 3H), 3.80 (br m, 1H), 3.64 (s, 3H), 3.18 (br m, 1H), 3.07 (br m, 4H), 2.80 (br m, 1H), 2.78 (s, 2H), 2.60 (s, 2H), 2.50 (s, 3H), 2.20 (br m, 6H), 2.09 (br m, 2H), 1.98 (s, 2H), 1.78 (br m, 2H), 1.40 (br t, 2H), 0.93 (s, 6H).

Example 167

4-(4-{[2-(4-chlorophenyl)-4,4-dimethylcyclohex-1-en-1-yl]methyl}piperazin-1-yl)-2-[3-(hydroxymethyl)phenoxy]-N-({4-[(1-methylpiperidin-4-yl)amino]-3-nitrophenyl}sulfonyl)benzamide Example 167A methyl 4-(4-((2-(4-chlorophenyl)-4,4-dimethylcyclohex-1-enyl)methyl)piperazin-1-yl)-2-(3-formylphenoxy)benzoate The title compound was prepared by substituting 3-hydroxybenzaldehyde for EXAMPLE 1D and EXAMPLE 214A for EXAMPLE 1C in EXAMPLE 1E.

Example 167B 4-(4-((2-(4-chlorophenyl)-4,4-dimethylcyclohex-1-enyl)methyl)piperazin-1-yl)-2-(3-formylphenoxy)benzoic acid The title compound was prepared by substituting EXAMPLE 167A for EXAMPLE 1E in EXAMPLE 1F.

Example 167C 4-(4-((2-(4-chlorophenyl)-4,4-dimethylcyclohex-1-enyl)methyl)piperazin-1-yl)-2-(3-formylphenoxy)-N-(4-(1-methylpiperidin-4-ylamino)-3-nitrophenylsulfonyl)benzamide The title compound was prepared by substituting EXAMPLE 167B for EXAMPLE 1F and EXAMPLE 3I for EXAMPLE 1G in EXAMPLE 1H.

Example 167D 4-(4-{[2-(4-chlorophenyl)-4,4-dimethylcyclohex-1-en-1-yl]methyl}piperazin-1-yl)-2-[3-(hydroxymethyl)phenoxy]-N-({4-[(1-methylpiperidin-4-yl)amino]-3-nitrophenyl}sulfonyl)benzamide EXAMPLE 167C (107 mg) was dissolved in ethanol (3 mL) and tetrahydrofuran (9 mL), and NaBH$_4$ (13 mg) was added and the mixture stirred at room temperature for 10 minutes. After carefully adding 2N aqueous HCl (0.67 mL), the reaction was concentrated and the crude material was purified by preparative HPLC using a C18 column, 250×50 mm, 10μ, and eluting with a gradient of 20-100% CH$_3$CN vs. 0.1% trifluoroacetic acid in water, giving the product as a trifluoroacetate salt. The salt was dissolved in dichloromethane (6 mL) and washed with 50% aqueous NaHCO$_3$. The organic layer was dried over anhydrous Na$_2$SO$_4$, filtered, and concentrated to give the title compound. $^1$H NMR (500 MHz, CDCl$_3$/methanol-d$_4$) δ 8.80 (d, 1H), 8.45 (br d, 1H), 8.03 (dd, 1H), 7.86 (d, 1H), 7.39 (m, 1H), 7.27 (m, 3H), 7.09 (s, 1H), 6.95 (d, 4H), 6.60 (dd, 1H), 6.12 (d, 1H), 4.67 (s, 2H), 3.63 (br s, 1H), 3.15 (br t, 4H), 2.82 (br s, 1H), 2.80 (s, 3H), 2.35 (m, 5H), 2.28 (br t, 4H), 2.20 (br t, 2H), 2.10 (br m, 2H), 1.99 (s, 2H), 1.73 (m, 2H), 1.43 (t, 2H), 0.94 (s, 6H).

Example 168

2-(2-chlorophenoxy)-4-(4-{([2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide

Example 168A tert-butyl 4-(benzyloxycarbonylamino)-4-methylpiperidine-1-carboxylate 1-(tert-butoxycarbonyl)-4-methylpiperidine-4-carboxylic acid (5.0 g), diphenylphosphoryl azide (DPPA, 4.58 mL), triethylamine (2.86 mL), and benzyl alcohol (4.26 mL) were stirred in toluene (45 mL) at 110° C. for 24 hours. The mixture was cooled, concentrated, and chromatographed on silica gel using 10% ethyl acetate/hexanes as eluent to give the pure product.

Example 168B tert-butyl 4-amino-4-methylpiperidine-1-carboxylate

EXAMPLE 168A (4.5 g) and ethanol (100 mL) were added to 20% Pd(OH)$_2$—C, wet (0.900 g) in a 250 mL SS pressure bottle and stirred for 3 hours at 30 psi and room temperature. The mixture was filtered through a nylon membrane and concentrated to give the product.

Example 168C tert-butyl 4-methyl-4-(2-nitro-4-sulfamoylphenylamino)piperidine-1-carboxylate The title compound was prepared by substituting EXAMPLE 168B for 3-(n-morpholinyl)-1-propylamine in EXAMPLE 4A.

Example 168D 4-(4-methylpiperidin-4-ylamino)-3-nitrobenzenesulfonamide

The title compound was prepared by substituting EXAMPLE 168C for EXAMPLE 1A in EXAMPLE 1B.

Example 168E 4-(1,4-dimethylpiperidin-4-ylamino)-3-nitrobenzenesulfonamide

EXAMPLE 168D (1.33 g), iodomethane (0.29 mL), and triethylamine (0.65 mL) in acetonitrile (20 mL) were stirred for 1 hour. The mixture was concentrated and chromatographed on silica gel using 10% methanol/dichloromethane as eluent to give the product.

Example 168F 2-(2-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide The title compound was prepared by substituting EXAMPLE 34C for EXAMPLE 1F and EXAMPLE 168E for EXAMPLE 1G in EXAMPLE 1H. $^1$H NMR (300 MHz, dimethylsulfoxide-d$_6$) δ 8.55 (m, 1H), 8.43 (d, 1H), 7.82 (d, 1H), 7.52 (d, 1H), 7.43 (d, 1H), 7.38 (d, 2H), 7.18 (dd, 1H), 7.09 (d, 2H), 7.05 (m, 1H), 6.76 (d, 2H), 6.34 (d, 1H), 2.94-3.12 (m, 11H), 2.70 (m, 4H), 2.27 (m, 4H), 2.00 (s, 3H), 1.55 (s, 3H), 1.41 (m, 2H), 0.95 (s, 6H).

Example 169

2-(3-chlorophenoxy)-4-(4-{[2-(4-chlorophenyl)-4,4-dimethylcyclohex-1-en-1-yl]methyl}piperazin-1-yl)-N-({4-[(1,4-dimethylpiperidin-4-yl)amino]-3-nitrophenyl}sulfonyl)benzamide The title compound was prepared by substituting EXAMPLE 36C for EXAMPLE 1F and EXAMPLE 168E for EXAMPLE 1G in EXAMPLE 1H. $^1$H NMR (300 MHz, dimethylsulfoxide-d$_6$) δ 8.49 (m, 1H), 8.40 (d, 1H), 7.75 (d, 1H), 7.54 (d, 1H), 7.37 (d, 2H), 7.27 (m, 1H), 7.22 (t, 1H), 7.07 (d, 2H), 7.00 (d, 1H), 6.77 (d, 1H), 6.72 (d, 1H), 6.45 (d, 1H), 3.20 (m, 4H), 3.05 (m, 6H), 2.88 (m, 2H), 2.73 (m, 4H), 2.27 (m, 4H), 2.20 (m, 2H), 1.99 (s, 3H), 1.55 (s, 3H), 1.41 (t, 2H), 0.95 (s, 6H).

Example 170

2-(3-chlorophenoxy)-4-(4-{[2-(4-chlorophenyl)-4,4-dimethylcyclohex-1-en-1-yl]methyl}piperazin-1-yl)-N-{[4-({1-[2-(2-methoxyethoxy)ethyl]piperidin-4-yl}amino)-3-nitrophenyl]sulfonyl}benzamide A mixture of EXAMPLE 162C (100 mg), 1-bromo-2-(2-methoxyethoxy)ethane (52 mg), cesium carbonate (70 mg) in N,N-dimethylformamide was heated at 60° C. overnight. The solvent was removed under vacuum. The residue was purified by reverse phase HPLC on a C18 column using a gradient of 40-70% acetonitrile/0.1% TFA in water to give the title compound as the trifluoroacetate salt. The TFA salt was dissolved in dichloromethane (6 mL) and washed with 50% aqueous NaHCO$_3$. The organic layer was dried over anhydrous Na$_2$SO$_4$ and concentrated to give the title compound. $^1$H NMR (400 MHz, dimethylsulfoxide-d$_6$) 8.36 (d, 1H), 8.12 (d, 1H), 7.69 (dd, 1H), 7.59 (d, 1H), 7.35 (d, 2H), 7.14 (m, 1H), 7.05 (m, 3H), 6.89 (m, 1H), 6.74 (dd, 1H), 6.66 (dd, 1H), 6.60 (m, 1H), 6.40 (d, 1H), 3.81 (s, 1H), 3.65 (t, 2H), 3.56 (m, 2H), 3.47 (m, 2H), 3.31 (m, 2H), 3.26 (m, 3H), 3.18 (m, 2H), 3.13 (m, 2H), 2.97 (m, 2H), 2.77 (m, 4H), 2.21 (m, 7H), 2.07 (m, 2H), 1.98 (s, 2H), 1.76 (m, 2H), 1.41 (t, 2H), 0.94 (s, 6H).

Example 171

2-(2-chloro-3-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 171A 2-chloro-3-(methoxymethoxy)phenol

The title compound was prepared by substituting 2-chlorobenzene-1,3-diol for EXAMPLE 158B in EXAMPLE 158C.

Example 171B

Methyl 2-(2-chloro-3-(methoxymethoxy)phenoxy)-4-fluorobenzoate

The title compound was prepared by substituting 171A for 2-methyl-5-indolol in EXAMPLE 3A.

Example 171C

Methyl 2-(2-chloro-3-(methoxymethoxy)phenoxy)-4-(piperazin-1-yl)benzoate

The title compound was prepared by substituting piperazine for EXAMPLE 3F and EXAMPLE 171B for EXAMPLE 3A in EXAMPLE 3G.

Example 171D

Methyl 2-(2-chloro-3-(methoxymethoxy)phenoxy)-4-(4-((2-(4-chlorophenyl)-4,4-dimethylcyclohex-1-enyl)methyl)piperazin-1-yl)benzoate The title compound was prepared by substituting EXAMPLE 60D for 4'-chlorobiphenyl-2-carboxaldehyde and EXAMPLE 171C for tert-butyl piperazine-1-carboxylate in EXAMPLE 1A.

Example 171E 2-(2-chloro-3-(methoxymethoxy)phenoxy)-4-(4-((2-(4-chlorophenyl)-4,4-dimethylcyclohex-1-enyl)methyl)piperazin-1-yl)benzoic acid The title compound was prepared by substituting 171D for EXAMPLE 1E in EXAMPLE 1F.

Example 171F 2-(2-chloro-3-(methoxymethoxy)phenoxy)-4-(4-((2-(4-chlorophenyl)-4,4-dimethylcyclohex-1-enyl)methyl)piperazin-1-yl)-N-(4-(1-methylpiperidin-4-ylamino)-3-nitrophenylsulfonyl)benzamide The title compound was prepared by substituting EXAMPLE 171E for EXAMPLE 1F and EXAMPLE 3I for EXAMPLE 1G in EXAMPLE 1H.

Example 171G 2-(2-chloro-3-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 171F for EXAMPLE 158 in EXAMPLE 159. $^1$H NMR (500 MHz, dimethylsulfoxide-d$_6$) δ 10.13 (s, 1H), 8.41 (d, 1H), 8.08 (d, 1H), 7.77 (dd, 1H), 7.60 (d, 1H), 7.35 (d, 2H), 7.07 (m, 3H), 6.89 (t, 1H), 6.67 (dd, 1H), 6.59 (m, 1H), 6.19 (d, 1H), 6.08 (d, 1H), 3.80 (m, 1H), 3.09 (m, 6H), 2.79 (m, 4H), 2.57 (s, 3H), 2.21 (m, 6H), 2.08 (m, 2H), 1.97 (s, 2H), 1.74 (m, 2H), 1.40 (t, 2H), 0.94 (s, 6H).

Example 172

2-(3-chlorophenoxy)-4-(4-{[2-(4-chlorophenyl)-4,4-dimethylcyclohex-1-en-1-yl]methyl}piperazin-1-yl)-N-[(3-nitro-4-{[1-(3-phenylpropyl)piperidin-4-yl]amino}phenyl)sulfonyl]benzamide The title compound was prepared by substituting EXAMPLE 162C for tert-butyl pieperazien-1-carboxylate and 3-phenylpropanal for 4'-chlorobiphenyl-2-carboxaldehyde in EXAMPLE 1A. $^1$H NMR (400 MHz, dimethylsulfoxide-d$_6$) δ 8.36 (d, 1H), 8.10 (m, 1H), 7.69 (m, 1H), 7.59 (d, 1H), 7.36 (d, 2H), 7.31 (m, 2H), 7.22 (m, 3H), 7.14 (m, 1H), 7.07 (d, 2H), 7.02 (d, 1H), 6.88 (d, 1H), 6.74 (dd, 1H), 6.65 (dd, 1H), 6.60 (m, 1H), 6.41 (d, 1H), 3.84 (m, 1H), 3.29 (m, 4H), 3.12 (m, 4H), 2.81 (m, 5H), 2.64 (m, 2H), 2.22 (m, 6H), 2.10 (m, 2H), 1.99 (m, 2H), 1.90 (m, 2H), 1.75 (m, 2H), 1.40 (t, 2H), 0.94 (s, 6H).

Example 173

2-(3-chlorophenoxy)-4-(4-{[2-(4-chlorophenyl)-4,4-dimethylcyclohex-1-en-1-yl]methyl}piperazin-1-yl)-N-[(4-{[1-(2-methoxyethyl)piperidin-4-yl]amino}-3-nitrophenyl)sulfonyl]benzamide The title compound was prepared by substituting 1-bromo-2-methoxyethane for 1-bromo-2-(2-methoxyethoxy)ethane in EXAMPLE 170. $^1$H NMR (400 MHz, dimethylsulfoxide-$d_6$) δ 8.36 (d, 1H), 8.13 (d, 1H), 7.69 (dd, 1H), 7.59 (d, 1H), 7.36 (d, 2H), 7.15 (m, 1H), 7.06 (m, 3H), 6.89 (dd, 1H), 6.74 (dd, 1H), 6.66 (dd, 1H), 6.61 (d, 1H), 6.41 (d, 1H), 3.82 (m, 1H), 3.57 (t, 2H), 3.38 (m, 4H), 3.13 (m, 6H), 2.99 (m, 2H), 2.89 (m, 1H), 2.78 (s, 3H), 2.21 (m, 6H), 2.08 (m, 2H), 1.98 (s, 2H), 1.78 (m, 2H), 1.41 (t, 2H), 0.94 (s, 6H).

Example 174

2-(3-chlorophenoxy)-4-(4-{[2-(4-chlorophenyl)-4,4-dimethylcyclohex-1-en-1-yl]methyl}piperazin-1-yl)-N-({4-[(1-ethylpiperidin-4-yl)amino]-3-nitrophenyl}sulfonyl)benzamide The title compound was prepared by substituting EXAMPLE 36C for EXAMPLE 1F and EXAMPLE 47A for EXAMPLE 1G in EXAMPLE 1H. $^1$H NMR (300 MHz, dimethylsulfoxide-$d_6$) δ 8.34 (d, 1H), 8.07 (s, 1H), 7.58-7.71 (m, 2H), 7.36 (d, 2H), 7.00-7.14 (m, 4H), 6.85-6.94 (m, 1H), 6.73 (dd, 1H), 6.64 (dd, 1H), 6.59 (d, 1H), 6.39 (d, 1H), 3.86 (s, 1H), 3.11 (s, 5H), 2.94 (d, 2H), 2.72-2.81 (m, 3H), 2.12-2.27 (m, 8H), 1.98 (s, 2H), 1.77 (s, 2H), 1.41 (t, 2H), 1.18 (t, 3H), 0.94 (s, 6H).

Example 175

2-(3-chlorophenoxy)-4-(4-{[2-(4-chlorophenyl)-4,4-dimethylcyclohex-1-en-1-yl]methyl}piperazin-1-yl)-N-({4-[(1-isopropylpiperidin-4-yl)amino]-3-nitrophenyl}sulfonyl)benzamide The title compound was prepared by substituting EXAMPLE 36C for EXAMPLE 1F and EXAMPLE 41A for EXAMPLE 1G in EXAMPLE 1H. $^1$H NMR (300 MHz, dimethylsulfoxide-d) δ 8.98 (bs, 1H), 8.34 (d, 1H), 8.04 (s, 1H), 7.59-7.73 (m, 2H), 7.36 (d, 2H), 7.14 (t, 1H), 7.04-7.09 (m, 2H), 7.01 (d, 1H), 6.87 (d, 1H), 6.72 (dd, 1H), 6.61-6.66 (m, 1H), 6.58 (s, 1H), 6.39 (d, 1H), 3.90 (s, 1H), 3.11 (s, 6H), 2.73-2.83 (m, 2H), 2.14-2.28 (m, 9H), 1.98 (s, 3H), 1.76 (s, 2H), 1.41 (t, 3H), 1.14-1.29 (m, 6H), 0.94 (s, 6H).

Example 176

4-(4-{[2-(4-chlorophenyl)-4,4-dimethylcyclohex-1-en-1-yl]methyl}piperazin-1-yl)-2-(3-hydroxyphenoxy)-N-({4-[(1-methylpiperidin-4-yl)amino]-3-nitrophenyl}sulfonyl)benzamide

Example 176A

Ethyl 2-(3-hydroxyphenoxy)-4-fluorobenzoate

The title compound was prepared by substituting resorcinol for 2-methyl-5-indolol in EXAMPLE 3A.

Example 176B

Ethyl 2-(3-hydroxyphenoxy)-4-(4-((2-(4-chlorophenyl)-4,4-dimethylcyclohex-1-enyl)methyl)piperazin-1-yl)benzoate The title compound was prepared by substituting EXAMPLE 176A for EXAMPLE 3A in EXAMPLE 3G.

Example 176C

Ethyl 4-(4-((2-(4-chlorophenyl)-4,4-dimethylcyclohex-1-enyl)methyl)piperazin-1-yl)-2-(3-(methoxymethoxy)phenoxy)benzoate A suspension of EXAMPLE 176B (0.295 g), methoxymethyl chloride (0.117 mL) and cesium carbonate (0.334 g) in N,N-dimethylformamide (3 mL) was stirred at 60° C. for 16 hours. The reaction mixture was partitioned between dichloromethane and water. The water layer was extracted with dichloromethane. The combined organic extracts were washed with water (2×), dried over magnesium sulfate, filtered and concentrated. The crude product was purified by flash chromotography (silica gel, 5%-20% ethyl acetate/hexanes) providing the product.

Example 176D 4-(4-((2-(4-chlorophenyl)-4,4-dimethylcyclohex-1-enyl)methyl)piperazin-1-yl)-2-(3-(methoxymethoxy)phenoxy)benzoic acid The title compound was prepared by substituting EXAMPLE 176C for EXAMPLE 1E in EXAMPLE 1F.

Example 176E 4-(4-((2-(4-chlorophenyl)-4,4-dimethylcyclohex-1-enyl)methyl)piperazin-1-yl)-2-(3-(methoxymethoxy)phenoxy)-N-(4-(1-methylpiperidin-4-ylamino)-3-nitrophenylsulfonyl)benzamide The title compound was prepared by substituting EXAMPLE 176D for EXAMPLE 1F and EXAMPLE 3I for EXAMPLE 1G in EXAMPLE 1H.

Example 176F 4-(4-{[2-(4-chlorophenyl)-4,4-dimethylcyclohex-1-en-1-yl]methyl}piperazin-1-yl)-2-(3-hydroxyphenoxy)-N-({4-[(1-methylpiperidin-4-yl)amino]-3-nitrophenyl}sulfonyl)benzamide A suspension of EXAMPLE 176E (35.5 mg) in tetrahydrofuran (3 mL) and HCl (1.25M in methanol, 2 mL) was stirred for 1 hour at 60° C. The product was concentrated. The crude product was purified by RP HPLC (C8, 30%-100% CH$_3$CN/water/0.1% TFA) to yield the product. $^1$H NMR (300 MHz, dimethylsulfoxide-$d_6$) δ 9.31 (s, 1H), 8.10 (s, 1H), 7.66-7.73 (m, 2H), 7.56 (d, 1H), 7.34-7.38 (m, 2H), 7.02-7.09 (m, 2H), 6.95-7.02 (m, 1H), 6.65 (dd, 1H), 6.34 (s, 1H), 6.29 (d, 1H), 6.20 (d, 1H), 6.14 (d, 1H), 4.14 (dd, 1H), 3.75 (s, 1H), 3.05 (d, 4H), 2.68-2.80 (m, 3H), 2.20 (d, 6H), 2.08 (d, 2H), 1.97 (s, 2H), 1.69-1.79 (m, 2H), 1.63 (s, 1H), 1.39 (d, 2H), 1.21-1.36 (m, 9H), 0.94 (s, 6H).

Example 177

2-(2-chloro-3-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 177A 2-chloro-3-fluorophenol

To a solution of 2-chloro-3-fluorophenylboronic acid (5.0 g) in tetrahydrofuran (50 mL) and 1M aqueous NaOH (30 mL) at 0° C. was added 30% hydrogen peroxide solution (4 mL), and the reaction was stirred for 2 hours. The reaction was quenched with saturated aqueous $Na_2S_2O_3$ solution, acidified with concentrated aqueous HCl, and extracted twice with ethyl acetate. The combined extracts were washed with brine, concentrated, and chromatographed on silica gel using 10% ethyl acetate/hexanes as eluent to give the product.

Example 177B methyl 2-(2-chloro-3-fluorophenoxy)-4-fluorobenzoate

The title compound was prepared by substituting EXAMPLE 177A for 2-methyl-5-indolol and methyl 2,4-difluorobenzoate for ethyl 2,4-difluorobenzoate in EXAMPLE 3A.

Example 177C methyl 2-(2-chloro-3-fluorophenoxy)-4-(4-((2-(4-chlorophenyl)-4,4-dimethylcyclohex-1-enyl)methyl)piperazin-1-yl)benzoate The title compound was prepared by substituting EXAMPLE 177B for methyl 2-bromo-4-fluorobenzoate and EXAMPLE 3F for EXAMPLE 1B in EXAMPLE 1C.

Example 177D 2-(2-chloro-3-fluorophenoxy)-4-(4-((2-(4-chlorophenyl)-4,4-dimethylcyclohex-1-enyl)methyl)piperazin-1-yl)benzoic acid The title compound was prepared by substituting EXAMPLE 177C for EXAMPLE 1E in EXAMPLE 1F.

Example 177E 2-(2-chloro-3-fluorophenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 177D for EXAMPLE 1F and EXAMPLE 3I for EXAMPLE 1G in EXAMPLE 1H. $^1$H NMR (300 MHz, dimethylsulfoxide-$d_6$) δ 8.39 (d, 1H), 8.15 (m, 1H), 7.76 (d, 1H), 7.58 (d, 1H), 7.37 (d, 2H), 7.15 (d, 1H), 7.07 (d, 2H), 7.02 (m, 1H), 6.88 (t, 1H), 6.77 (d, 1H), 6.44 (s, 1H), 6.33 (d, 1H), 3.91 (m, 1H), 3.18 (m, 4H), 3.07 (m, 2H), 2.77 (m, 6H), 2.27 (m, 4H), 2.19 (m, 4H), 1.99 (s, 3H), 1.77 (m, 2H), 1.41 (t, 2H), 0.95 (s, 6H).

Example 178

2-(2-chloro-3-fluorophenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 177D for EXAMPLE 1F and EXAMPLE 49C for EXAMPLE 1G in EXAMPLE 1H. $^1$H NMR (300 MHz, dimethylsulfoxide-$d_6$) δ 8.28 (d, 1H), 8.10 (m, 1H), 7.65 (d, 1H), 7.62 (d, 1H), 7.37 (d, 2H), 7.08 (d, 2H), 6.98 (m, 2H), 6.80 (t, 1H), 6.74 (d, 1H), 6.37 (d, 1H), 6.22 (d, 1H), 3.89 (m, 1H), 3.28 (m, 4H), 3.09 (m, 6H), 2.84 (m, 4H), 2.73 (m, 3H), 2.40 (m, 2H), 2.23 (m, 6H), 2.01 (m, 1H), 1.99 (s, 3H), 1.68 (m, 2H), 1.55 (m, 4H), 1.41 (t, 2H), 0.94 (s, 6H).

Example 179

2-(2-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide The title compound was prepared by substituting EXAMPLE 34C for EXAMPLE 122C in EXAMPLE 137. $^1$H NMR (300 MHz, dimethylsulfoxide-$d_6$) δ 8.50 (br t, 1H), 8.38 (d, 1H), 7.75 (dd, 1H), 7.63 (d, 1H), 7.37 (m, 3H), 7.06 (m, 3H), 6.98 (d, 1H), 6.92 (ddd, 1H), 6.70 (dd, 1H), 6.56 (dd, 1H), 6.24 (d, 1H), 3.47 (dd, 2H), 3.05 (br m, 4H), 2.90 (br m, 2H), 2.75 (s, 2H), 2.60 (s, 6H), 2.20 (br m, 6H), 1.98 (s, 2H), 1.90 (m, 2H) 1.40 (t, 2H), 0.93 (s, 6H).

Example 180

4-(4-{[2-(4-chlorophenyl)-4,4-dimethylcyclohex-1-en-1-yl]methyl}piperazin-1-yl)-2-(2-methoxyphenoxy)-N-({4-[(1-methylpiperidin-4-yl)amino]-3-nitrophenyl}sulfonyl)benzamide

Example 180A ethyl 4-fluoro-2-(2-methoxyphenoxy)benzoate

The title compound was prepared by substituting 2-methoxyphenol for 2-methyl-5-indolol in EXAMPLE 3A.

Example 180B ethyl 4-(4-((2-(4-chlorophenyl)-4,4-dimethylcyclohex-1-enyl)methyl)piperazin-1-yl)-2-(2-methoxyphenoxy)benzoate The title compound was prepared by substituting EXAMPLE 180A for EXAMPLE 3A in EXAMPLE 3G.

Example 180C 4-(4-((2-(4-chlorophenyl)-4,4-dimethylcyclohex-1-enyl)methyl)piperazin-1-yl)-2-(2-methoxyphenoxy)benzoic acid The title compound was prepared by substituting EXAMPLE 180B for EXAMPLE 1E in EXAMPLE 1F.

Example 180D 4-(4-{[2-(4-chlorophenyl)-4,4-dimethylcyclohex-1-en-1-yl]methyl}piperazin-1-yl)-2-(2-methoxyphenoxy)-N-({4-[(1-methylpiperidin-4-yl)amino]-3-nitrophenyl}sulfonyl)benzamide The title compound was prepared by substituting EXAMPLE 180C for EXAMPLE 122C and EXAMPLE 3I for EXAMPLE 11A in EXAMPLE 137. $^1$H NMR (300 MHz, dimethylsulfoxide-$d_6$) δ 8.47 (d, 1H), 8.15 (br d, 1H), 7.83 (dd, 1H), 7.57 (d, 1H), 7.37 (d, 2H), 7.13 (d, 1H), 7.05 (m, 4H), 6.80 (m, 2H), 6.60 (dd, 1H), 6.07 (d, 1H), 3.80 (br m, 1H), 3.73 (s, 3H), 3.22 (br m, 1H), 3.05 (br m, 1H), 3.00 (br m, 4H), 2.75 (s, 2H), 2.62 (br s, 2H), 2.50 (s, 3H), 2.20 (br m, 6H), 2.04 (br m, 2H), 1.98 (s, 2H), 1.73 (br m, 2H), 1.40 (br t, 2H), 0.93 (s, 6H).

Example 181

4-(4-{[2-(4-chlorophenyl)-4,4-dimethylcyclohex-1-en-1-yl]methyl}piperazin-1-yl)-2-(2-methylphenoxy)-N-({4-[(1-methylpiperidin-4-yl)amino]-3-nitrophenyl}sulfonyl)benzamide

Example 181A ethyl 4-fluoro-2-(2-methylphenoxy)benzoate

The title compound was prepared by substituting 2-methylphenol for 2-methyl-5-indolol in EXAMPLE 3A.

Example 181B ethyl 4-(4-((2-(4-chlorophenyl)-4,4-dimethylcyclohex-1-enyl)methyl)piperazin-1-yl)-2-(2-methylphenoxy)benzoate The title compound was prepared by substituting EXAMPLE 181A for EXAMPLE 3A in EXAMPLE 3G.

Example 181C 4-(4-((2-(4-chlorophenyl)-4,4-dimethylcyclohex-1-enyl)methyl)piperazin-1-yl)-2-(2-methylphenoxy)benzoic acid The title compound was prepared by substituting EXAMPLE 181B for EXAMPLE 1E in EXAMPLE 1F.

Example 181D 4-(4-{[2-(4-chlorophenyl)-4,4-dimethylcyclohex-1-en-1-yl]methyl}piperazin-1-yl)-2-(2-methylphenoxy)-N-({4-[(1-methylpiperidin-4-yl)amino]-3-nitrophenyl}sulfonyl)benzamide The title compound was prepared by substituting EXAMPLE 181C for EXAMPLE 122C and EXAMPLE 3I for EXAMPLE 11A in EXAMPLE 137. $^1$H NMR (300 MHz, dimethylsulfoxide-$d_6$) δ 8.40 (d, 1H), 8.12 (br d, 1H), 7.73 (dd, 1H), 7.54 (d, 1H), 7.37 (d, 2H), 7.10 (m, 2H), 7.05 (d, 2H), 6.96 (m, 1H), 6.84 (m, 1H), 6.64 (dd, 1H), 6.46 (d, 1H), 6.20 (d, 1H), 3.80 (br m, 1H), 3.10 (br m, 3H), 3.05 (br m, 4H), 2.77 (s, 2H), 2.76 (br m, 2H), 2.58 (s, 2H), 2.20 (br m, 6H), 2.16 (s, 3H), 2.09 (br m, 2H), 1.98 (s, 2H), 1.78 (br m, 2H), 1.40 (br t, 2H), 0.93 (s, 6H).

Example 182

4-(4-{[2-(4-chlorophenyl)-4,4-dimethylcyclohex-1-en-1-yl]methyl}piperazin-1-yl)-2-(3-methylphenoxy)-N-({4-[(1-methylpiperidin-4-yl)amino]-3-nitrophenyl}sulfonyl)benzamide

Example 182A ethyl 4-fluoro-2-(3-methylphenoxy)benzoate

The title compound was prepared by substituting 3-methylphenol for 2-methyl-5-indolol in EXAMPLE 3A.

Example 182B ethyl 4-(4-((2-(4-chlorophenyl)-4,4-dimethylcyclohex-1-enyl)methyl)piperazin-1-yl)-2-(3-methylphenoxy)benzoate The title compound was prepared by substituting EXAMPLE 182A for EXAMPLE 3A in EXAMPLE 3G.

Example 182C 4-(4-((2-(4-chlorophenyl)-4,4-dimethylcyclohex-1-enyl)methyl)piperazin-1-yl)-2-(3-methylphenoxy)benzoic acid The title compound was prepared by substituting EXAMPLE 182B for EXAMPLE 1E in EXAMPLE 1F.

Example 182D 4-(4-{[2-(4-chlorophenyl)-4,4-dimethylcyclohex-1-en-1-yl]methyl}piperazin-1-yl)-2-(3-methylphenoxy)-N-({4-[(1-methylpiperidin-4-yl)amino]-3-nitrophenyl}sulfonyl)benzamide The title compound was prepared by substituting EXAMPLE 182C for EXAMPLE 122C and EXAMPLE 3I for EXAMPLE 11A in EXAMPLE 137. $^1$H NMR (300 MHz, dimethylsulfoxide-$d_6$) δ 8.40 (d, 1H), 8.10 (br d, 1H), 7.74 (dd, 1H), 7.56 (d, 1H), 7.36 (d, 2H), 7.05 (m, 4H), 6.73 (d, 1H), 6.67 (dd, 1H), 6.52 (m, 2H), 6.29 (d, 1H), 3.80 (br m, 1H), 3.10 (br m, 3H), 3.05 (br m, 4H), 2.77 (s, 2H), 2.76 (br m, 2H), 2.58 (s, 2H), 2.20 (br m, 6H), 2.16 (s, 3H), 2.09 (br m, 2H), 1.98 (s, 2H), 1.78 (br m, 2H), 1.40 (br t, 2H), 0.93 (s, 6H).

Example 183

2-(2-chlorophenoxy)-4-(4-{[6-(4-chlorophenyl)-1,3-benzodioxol-5-yl]methyl}piperazin-1-yl)-N-({4-[(1-methylpiperidin-4-yl)amino]-3-nitrophenyl}sulfonyl)benzamide

Example 183A 6-(4-chlorophenyl)benzo[d][1,3]dioxole-5-carbaldehyde

To a solution of 6-bromobenzo[d][1,3]dioxole-5-carbaldehyde (4.6 g), 4-chlorophenylboronic acid (3.78 g) and tetrakis(triphenylphosphine)palladium(0) (0.232 g) in toluene (80 mL) and methanol (30 mL) was added 2N aqueous $Na_2CO_3$ (30 mL). The mixture was stirred at reflux overnight. The mixture was diluted with ether (400 mL) and washed with water, brine and dried over Na₂SO₄. After filtration and concentration of the solvent, the residue was loaded on a column and eluted with 3% ethyl acetate in hexane to give the product.

Example 183B methyl 2-(2-chlorophenoxy)-4-(4-((6-(4-chlorophenyl)benzo[d][1,3]dioxol-5-yl)methyl)piperazin-1-yl)benzoate The title compound was prepared as described in EXAMPLE 38G by replacing EXAMPLE 38E with EXAMPLE 183A.

Example 183C 2-(2-chlorophenoxy)-4-(4-((6-(4-chlorophenyl)benzo[d][1,3]dioxol-5-yl)methyl)piperazin-1-yl)benzoic acid The title compound was prepared as described in EXAMPLE 38H by replacing EXAMPLE 38G with EXAMPLE 183B.

Example 183D 2-(2-chlorophenoxy)-4-(4-{[6-(4-chlorophenyl)-1,3-benzodioxol-5-yl]methyl}piperazin-1-yl)-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 183C and EXAMPLE 3I, respectively. $^1$H NMR (300 MHz, dimethylsulfoxide-d₆) δ 8.35 (d, 1H), 8.07 (d, 1H), 7.73 (dd, 1H), 7.64 (d, 1H), 7.38 (m, 6H), 7.02 (m, 3H), 6.86 (m, 1H), 6.79 (s, 1H), 6.72 (dd, 1H), 6.51 (d, 1H), 6.28 (d, 1H), 6.04 (s, 2H), 3.81 (m, 1H), 3.25 (s, 3H), 3.08 (m, 6H), 2.72 (m, 5H), 2.33 (m, 4H), 2.07 (m, 2H), 1.74 (m, 1H).

Example 184

2-(2-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide

Example 184A 4-(4-methylpiperazin-1-ylamino)-3-nitrobenzenesulfonamide

The title compound was prepared by substituting 4-methylpiperazin-1-amine for 3-(N-morpholinyl)-1-propylamine in EXAMPLE 4A.

Example 184B 2-(2-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 34C for EXAMPLE 1F and EXAMPLE 184A for EXAMPLE 1G in EXAMPLE 1H. $^1$H NMR (500 MHz, dimethylsulfoxide-d₆) δ 9.14 (s, 1H), 8.38 (d, 1H), 7.77 (dd, 1H), 7.55 (m, 2H), 7.37 (m, 3H), 7.08 (m, 3H), 6.95 (m, 1H), 6.72 (dd, 1H), 6.62 (d, 1H), 6.27 (d, 1H), 3.10 (m, 4H), 2.97 (m, 4H), 2.77 (s, 2H), 2.45 (s, 3H), 2.20 (m, 6H), 1.97 (s, 2H), 1.40 (t, 2H), 0.94 (m, 6H).

Example 185

2-(3-chlorophenoxy)-4-(4-{[4-(4-chlorophenyl)-6,6-dimethyl-5,6-dihydro-2H-pyran-3-yl]methyl}piperazin-1-yl)-N-({4-[(4-methylpiperazin-1-yl)amino]-3-nitrophenyl}sulfonyl)benzamide The title compound was prepared by substituting EXAMPLE 38H for EXAMPLE 1F and EXAMPLE 184A for EXAMPLE 1G in EXAMPLE 1H. $^1$H NMR (500 MHz, dimethylsulfoxide-d₆) δ 9.15 (s, 1H), 8.34 (d, 1H), 7.68 (dd, 1H), 7.57 (d, 1H), 7.51 (d, 1H), 7.39 (d, 2H), 7.16 (m, 3H), 6.92 (m, 1H), 6.75 (dd, 1H), 6.68 (dd, 1H), 6.64 (m, 1H), 6.43 (d, 1H), 4.15 (s, 2H), 3.15 (m, 6H), 2.99 (m, 6H), 2.88 (s, 2H), 2.49 (s, 3H), 2.26 (m, 4H), 2.17 (s, 2H), 1.20 (s, 6H).

Example 186

4-(4-{[4-(4-chlorophenyl)-6,6-dimethyl-5,6-dihydro-2H-pyran-3-yl]methyl}piperazin-1-yl)-2-(2,3-difluorophenoxy)-N-({4-[(4-methylpiperazin-1-yl)amino]-3-nitrophenyl}sulfonyl)benzamide The title compound was prepared by substituting EXAMPLE 145B for EXAMPLE 1F and EXAMPLE 184A for EXAMPLE 1G in EXAMPLE 1H. $^1$H NMR (500 MHz, dimethylsulfoxide-d₆) δ 9.15 (s, 1H), 8.34 (d, 1H), 7.74 (dd, 1H), 7.60 (d, 1H), 7.54 (d, 1H), 7.40 (d, 2H), 7.16 (d, 2H), 6.87 (m, 2H), 6.74 (dd, 1H), 6.46 (d, 1H), 6.34 (m, 1H), 4.15 (s, 2H), 3.14 (m, 6H), 3.00 (m, 4H), 2.88 (s, 2H), 2.52 (s, 3H), 2.26 (m, 4H), 2.17 (s, 2H), 1.21 (s, 6H).

Example 187

2-(3-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide

Example 187A tert-butyl 4-(4-(N-(2-(3-chlorophenoxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate The title compound was prepared by substituting EXAMPLE 36C for EXAMPLE 1F and EXAMPLE 162A for EXAMPLE 1G in EXAMPLE 1H.

Example 187B 2-(3-chlorophenoxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide EXAMPLE 187A was treated with TFA (0.5 mL) and stirred for 6 hours. The product was concentrated and purified by RP HPLC (C8, 30%-100% CH₃CN/water/0.1% TFA).

Example 187C 2-(3-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide A suspension of EXAMPLE 187B (50 mg), cyclopropanecarbaldehyde (100 mg) and MP-CNBH$_3$ resin (0.2 g, 2.43 mmol/g) in dichloromethane (4 mL)/methanol (3 mL) was shaken for 16 hours at room temperature. The product was filtered, washed with dichloromethane/methanol and concentrated. The crude product was purified by RP HPLC (C8, 30%-100% CH$_3$CN/water/0.1% TFA) to yield the product. $^1$H NMR (300 MHz, dimethylsulfoxide-d$_6$) δ 8.35 (s, 1H), 8.10 (s, 1H), 7.67-7.75 (m, 1H), 7.60 (d, 1H), 7.36 (d, 2H), 7.15 (t, 1H), 7.07 (d, 3H), 6.89 (d, 1H), 6.73 (dd, 1H), 6.63 (s, 1H), 6.60 (s, 1H), 6.40 (s, 1H), 3.86 (s, 1H), 3.12 (s, 5H), 2.71-2.80 (m, 3H), 2.13-2.28 (m, 9H), 1.98 (s, 3H), 1.79 (s, 1H), 1.41 (t, 2H), 0.99-1.11 (m, 2H), 0.94 (s, 6H), 0.84 (d, 1H), 0.63 (d, 2H), 0.33 (s, 2H).

Example 188

2-(2-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide

Example 188A tert-butyl 4-(4-(N-(2-(2-chlorophenoxy)-4-(4-((2-(4-chlorophenyl)-4,4-dimethylcyclohex-1-enyl)methyl)piperazin-1-yl)benzoyl)sulfamoyl)-2-nitrophenylamino)piperidine-1-carboxylate The title compound was prepared by substituting EXAMPLE 34C for EXAMPLE 1F and EXAMPLE 162A for EXAMPLE 1G in EXAMPLE 1H.

Example 188B 2-(3-chlorophenoxy)-4-(4-((2-(4-chlorophenyl)-4,4-dimethylcyclohex-1-enyl)methyl)piperazin-1-yl)-N-(3-nitro-4-(piperidin-4-ylamino)phenylsulfonyl)benzamide The title compound was prepared by substituting EXAMPLE 188A for EXAMPLE 187A in EXAMPLE 187B.

Example 188C 2-(2-chlorophenoxy)-4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]benzamide The title compound was prepared by substituting EXAMPLE 188B for EXAMPLE 187B in EXAMPLE 187C. $^1$H NMR (300 MHz, dimethylsulfoxide-d$_6$) δ 8.41 (d, 1H), 8.13 (s, 1H), 7.79 (dd, 1H), 7.58 (d, 1H), 7.33-7.40 (m, 3H), 7.04-7.16 (m, 4H), 6.94 (t, 1H), 6.72 (dd, 1H), 6.61 (s, 1H), 6.27 (d, 1H), 3.91 (s, 1H), 3.44 (s, 2H), 3.02-3.15 (m, 5H), 2.95 (s, 2H), 2.69-2.82 (m, 3H), 2.13-2.28 (m, 8H), 1.97 (s, 3H), 1.83 (s, 2H), 1.32-1.46 (m, 3H), 0.99-1.10 (m, 1H), 0.94 (s, 6H), 0.76-0.90 (m, 1H), 0.59-0.71 (m, 2H), 0.34 (d, 2H).

Example 189

2-(3-chlorophenoxy)-4-(4-{[2-(4-chlorophenyl)-4,4-dimethylcyclohex-1-en-1-yl]methyl}piperazin-1-yl)-N-{[4-({1-[2-(dimethylamino)-2-oxoethyl]piperidin-4-yl}amino)-3-nitrophenyl]sulfonyl}benzamide The title compound was prepared by substituting 2-chloro-N,N-dimethylacetamide for 1-bromo-2-(2-methoxyethoxy)ethane in EXAMPLE 170. $^1$H NMR (400 MHz, dimethylsulfoxide-d$_6$) δ 9.63 (s, 1H), 8.46 (s, 1H), 8.21 (m, 1H), 7.78 (m, 1H), 7.53 (d, 1H), 7.40 (d, 2H), 7.22 (m, 2H), 7.11 (d, 2H), 6.96 (d, 1H), 6.82 (dd, 1H), 6.72 (m, 2H), 6.57 (s, 1H), 4.28 (m, 2H), 3.85 (m, 8H), 3.16 (m, 4H), 2.96 (m, 7H), 2.82 (m, 2H), 2.11 (m, 8H), 1.47 (s, 2H), 0.96 (s, 6H).

Example 190

2-(3-chlorophenoxy)-4-(4-{[2-(4-chlorophenyl)-4,4-dimethylcyclohex-1-en-1-yl]methyl}piperazin-1-yl)-N-[(4-{[1-(2-morpholin-4-ylethyl)piperidin-4-yl]amino}-3-nitrophenyl)sulfonyl]benzamide The title compound was prepared by substituting EXAMPLE 162C for tert-butyl pieperazien-1-carboxylate and 2-morpholinoacetaldehyde for 4'-chlorobiphenyl-2-carboxaldehyde in EXAMPLE 1A. $^1$H NMR (400 MHz, dimethylsulfoxide-d$_6$) δ 8.46 (d, 1H), 8.29 (d, 1H), 7.78 (dd, 1H), 7.53 (d, 1H), 7.41 (d, 2H), 7.21 (m, 2H), 7.11 (d, 2H), 6.96 (dd, 1H), 6.83 (dd, 1H), 6.73 (dd, 1.83 Hz, 1H), 6.69 (m, 1H), 6.58 (s, 1H), 3.82 (m, 10H), 3.27 (m, 4H), 3.09 (m, 6H), 2.81 (m, 7H), 2.23 (m, 2H), 2.15 (m, 2H), 2.04 (s, 2H), 1.93 (m, 2H), 1.48 (t, 2H), 0.96 (s, 6H).

Example 191

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide

Example 191A 4-((4-aminotetrahydro-2H-pyran-4-yl)methylamino)-3-nitrobenzenesulfonamide The title compound was prepared by substituting 4-(aminomethyl)tetrahydro-2H-pyran-4-amine for (tetrahydropyran-4-yl)methylamine in EXAMPLE 1G.

Example 191B

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide The title compound was prepared by substituting EXAMPLE 34C for EXAMPLE 1F and EXAMPLE 191A for EXAMPLE 1G in EXAMPLE 1H. $^1$H NMR (500 MHz, dimethylsulfoxide-d$_6$) δ 8.57 (t, 1H), 8.47 (d, 1H), 8.18 (s, 3H), 7.79 (dd, 1H), 7.53 (d, 1H), 7.41 (d, 2H), 7.34 (d, 1H), 7.24 (t, 1H), 7.11 (d, 2H), 7.01-7.03 (m, 2H), 6.82 (dd, 1H), 6.73-6.76 (m, 2H), 6.56 (s, 1H), 3.85 (d, 2H), 3.71-3.73 (m, 4H), 3.14 (br s, 2H), 2.23 (s, 2H), 2.04 (m, 2H), 1.82-1.87 (m, 2H), 1.70-1.75 (m, 2H), 1.47 (t, 2H), 0.96 (s, 6H).

Example 192

2-(2-chlorophenoxy)-4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide Example 192A The title compound was prepared by substituting 4-(aminomethyl)-1-methylpiperidin-4-ol for (tetrahydropyran-4-yl)methylamine in EXAMPLE 1G.

Example 192B 2-(2-chlorophenoxy)-4-(4-({[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide The title compound was prepared by substituting EXAMPLE 34C for EXAMPLE 1F and EXAMPLE 192A for EXAMPLE 1G in EXAMPLE 1H. $^1$H NMR (500 MHz, dimethylsulfoxide-$d_6$) δ 9.38 (s, 1H), δ 8.65 (t, 1H), 8.46 (d, 1H), 7.74 (dd, 1H), 7.53 (d, 1H), 7.40 (d, 2H), 7.19-7.22 (m, 2H), 7.11 (d, 2H), 6.97 (dd, 1H), 6.82 (dd, 1H), 6.70-6.74 (m, 2H), 6.57 (s, 1H), 3.60 (d, 2H), 3.47 (d, 2H), 3.10-3.17 (m, 4H), 2.80-2.81 (m, 4H), 2.23 (s, 2H), 2.04 (s, 2H), 1.76-1.85 (m, 4H), 1.47 (t, 2H), 0.96 (s, 6H).

Example 193

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(1-tetrahydro-2H-pyran-4-ylpiperidin-4-yl)amino]phenyl}sulfonyl)benzamide The title compound was prepared as described in EXAMPLE 1H by replacing EXAMPLE 1F and EXAMPLE 1G with EXAMPLE 154E and EXAMPLE 49C, respectively. $^1$H NMR (300 MHz, dimethylsulfoxide-$d_6$) δ 11.15 (s, 1H), 8.51 (d, 1H), 8.16 (d, 1H), 7.82 (dd, 1H), 7.54 (d, 1H), 7.31 (m, 4H), 7.08 (m, 4H), 6.60 (dd, 1H), 6.36 (s, 1H), 6.08 (d, 1H), 3.92 (m, 2H), 3.74 (m, 1H), 3.04 (m, 7H), 2.71 (m, 3H), 2.16 (m, 6H), 1.99 (m, 4H), 1.49 (m, 10H), 0.92 (s, 6H).

Example 194

2-(3-chlorophenoxy)-4-(4-{[2-(4-chlorophenyl)-4,4-dimethylcyclohex-1-en-1-yl]methyl}piperazin-1-yl)-N-[(4-{[(3S)-1-methylpyrrolidin-3-yl]amino}-3-nitrophenyl)sulfonyl]benzamide Example 194A (S)-tert-butyl 3-(2-nitro-4-sulfamoylphenylamino)pyrrolidine-1-carboxylate The title compound was prepared by substituting (S)-tert-butyl 3-aminopyrrolidine-1-carboxylate for tert-butyl 4-aminopiperidine-1-carboxylate in EXAMPLE 140A.

Example 194B (S)-tert-butyl 3-(4-(N-(2-(3-chlorophenoxy)-4-(4-((2-(4-chlorophenyl)-4,4-dimethylcyclohex-1-enyl)methyl)piperazin-1-yl)benzoyl)sulfamoyl)-2-nitrophenylamino)pyrrolidine-1-carboxylate The title compound was prepared by substituting EXAMPLE 194A for EXAMPLE 1G and EXAMPLE 36C for EXAMPLE 1F in EXAMPLE 1H.

Example 194C (S)-2-(3-chlorophenoxy)-4-(4-((2-(4-chlorophenyl)-4,4-dimethylcyclohex-1-enyl)methyl)piperazin-1-yl)-N-(3-nitro-4-(pyrrolidin-3-ylamino)phenylsulfonyl)benzamide The title compound was prepared by substituting EXAMPLE 194B for EXAMPLE 1A in EXAMPLE 1B.

Example 194D 2-(3-chlorophenoxy)-4-(4-{[2-(4-chlorophenyl)-4,4-dimethylcyclohex-1-en-1-yl]methyl}piperazin-1-yl)-N-[(4-{[(3S)-1-methylpyrrolidin-3-yl]amino}-3-nitrophenyl)sulfonyl]benzamide To a solution of EXAMPLE 194C (470 mg) in tetrahydrofuran (3 mL) and acetic acid (1 mL) was added 37% formaldehyde solution in water (0.42 mL) and MP-CNBH$_3$ resin (947 mg, 2.38 mmol/g)). The reaction mixture was stirred overnight at room temperature. The resin was filtered off and reaction mixture was then concentrated. The residue was purified by flash chromatography, eluting with ethyl acetate, followed by a gradient of 3-10% methanol/dichloromethane. $^1$H NMR (500 MHz, dimethylsulfoxide-$d_6$) δ 8.42 (d, 1H), 8.34 (m, 1H), 7.78 (dd, 1H), 7.53 (d, 1H), 7.36 (d, 2H), 7.19 (t, 1H), 7.08 (m, 3H), 6.95 (m, 1H), 6.76 (dd, 1H), 6.67 (m, 2H), 6.45 (d, 1H), 3.53 (m, 2H), 3.16 (m, 7H), 2.83 (m, 4H), 2.61 (br m, 1H), 2.27 (m, 4H), 2.18 (m, 3H), 1.98 (m, 3H), 1.41 (m, 2H), 0.94 (s, 6H).

Example 195

2-(3-chlorophenoxy)-4-(4-{[2-(4-chlorophenyl)-4,4-dimethylcyclohex-1-en-1-yl]methyl}piperazin-1-yl)-N-[(4-{[(3R)-1-methylpyrrolidin-3-yl]amino}-3-nitrophenyl)sulfonyl]benzamide Example 195A (R)-tert-butyl 3-(2-nitro-4-sulfamoylphenylamino)pyrrolidine-1-carboxylate The title compound was prepared by substituting (R)-tert-butyl 3-aminopyrrolidine-1-carboxylate for tert-butyl 4-aminopiperidine-1-carboxylate in EXAMPLE 140A.

Example 195B (R)-tert-butyl 3-(4-(N-(2-(3-chlorophenoxy)-4-(4-((2-(4-chlorophenyl)-4,4-dimethylcyclohex-1-enyl)methyl)piperazin-1-yl)benzoyl)sulfamoyl)-2-nitrophenylamino)pyrrolidine-1-carboxylate The title compound was prepared by substituting EXAMPLE 195A for EXAMPLE 1G and EXAMPLE 36C for EXAMPLE 1F in EXAMPLE 1H.

Example 195C (R)-2-(3-chlorophenoxy)-4-(4-((2-(4-chlorophenyl)-4,4-dimethylcyclohex-1-enyl)methyl)piperazin-1-yl)-N-(3-nitro-4-(pyrrolidin-3-ylamino)phenylsulfonyl)benzamide The title compound was prepared by substituting EXAMPLE 195B for EXAMPLE 1A in EXAMPLE 1B.

Example 195D 2-(3-chlorophenoxy)-4-(4-{[2-(4-chlorophenyl)-4,4-dimethylcyclohex-1-en-1-yl]methyl}piperazin-1-yl)-N-[(4-{[(3R)-1-methylpyrrolidin-3-yl]amino}-3-nitrophenyl)sulfonyl]benzamide The title compound was prepared by substituting EXAMPLE 195C for EXAMPLE 194C in EXAMPLE 194D. $^1$H NMR (500 MHz, dimethylsulfoxide-$d_6$) δ 8.36 (d, 1H), 8.23 (m, 1H), 7.72 (dd, 1H), 7.59 (d, 1H), 7.36 (d, 2H), 7.16 (t, 1H), 7.06 (m, 2H), 6.98 (m, 1H), 6.90 (dd, 1H), 6.73 (dd, 1H), 6.64 (m, 2H), 6.41 (d, 1H), 4.01 (s, 1H), 3.28 (m, 2H), 3.24 (m, 1H), 3.13 (m, 5H), 2.76 (m, 2H), 2.69 (m, 3H), 2.56 (m, 1H), 2.24 (m, 7H), 1.90 (br s, 2H), 1.41 (m, 2H), 0.94 (s, 6H).

Example 197

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[3-(1H-pyrrol-2-yl)phenoxy]benzamide A mixture of EXAMPLE 161 (0.095 g), 1-(tert-butoxycarbonyl)-1H-pyrrol-2-ylboronic acid (0.025 g), tetrakis(triphenylphosphine)palladium(0) (0.012 g), and CsF (0.046 g) in dimethoxyethane (2 mL) and methanol (1 mL) was heated in a CEM Discover microwave reactor (80° C., 20 minutes). The reaction mixture was partitioned between water and ethyl acetate. The organic layer was separated, and the aqueous layer was extracted with additional ethyl acetate. The combined organic layers were washed with brine, dried over MgSO$_4$, filtered, and concentrated. The residue was then treated with 4 N HCl in dioxane. The solvent was removed, and the residue was purified by reverse phase Prep HPLC to give the title compound. $^1$H NMR (500 MHz, dimethylsulfoxide-$d_6$) δ 11.21 (s, 1H), 8.39 (s, 1H), 8.04 (d, 1H), 7.70 (d, 1H), 7.57 (d, 1H), 7.34 (d, 2H), 7.11-7.25 (m, 5H), 7.04 (d, 2H), 6.96 (d, 1H), 6.80 (s, 1H), 6.66 (d, 2H), 6.48 (d, 1H), 6.41 (s, 1H), 6.28 (s, 1H), 6.08 (d, 1H), 3.05 (s, 6H), 2.73 (s, 2H), 2.18-2.24 (m, 6H), 1.74 (s, 3H), 1.38 (t, 2H), 0.92 (s, 6H).

Example 198

4-(4-{[2-(4-chlorophenyl)-4,4-dimethylcyclohex-1-en-1-yl]methyl}piperazin-1-yl)-2-(3-fluorophenoxy)-N-[(4-{[(4-hydroxy-1-methylpiperidin-4-yl)methyl]amino}-3-nitrophenyl)sulfonyl]benzamide The title compound was prepared by substituting EXAMPLE 112C for EXAMPLE 1F and EXAMPLE 192A for EXAMPLE 1G in EXAMPLE 1H. $^1$H NMR (500 MHz, dimethylsulfoxide-$d_6$) δ 8.44 (s, 1H), 8.31 (d, 1H), 7.92 (s, 1H), 7.63-7.66 (m, 2H), 7.36 (d, 2H), 7.07 (d, 2H), 6.99 (d, 1H), 6.71 (dd, 1H), 6.62-6.65 (m, 1H), 6.47 (dd, 1H), 6.36-6.40 (m, 2H), 5.16 (s, 1H), 3.09 (s, 6H), 2.92 (br s, 2H), 2.76 (a, 2H), 2.62-2.64 (m, 2H), 2.18-2.23 (m, 6H), 1.93 (d, J=5.49 Hz, 2H), 1.72-1.76 (m, 4H), 1.41 (t, 2H), 0.94 (s, 6H).

Example 199

2-(3-chlorophenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 36C for EXAMPLE 1F and EXAMPLE 184A for EXAMPLE 1G in EXAMPLE 1H. $^1$H NMR (400 MHz, dimethylsulfoxide-$d_6$) δ 9.12 (s, 1H), 8.33 (d, 1H), 7.66 (dd, 1H), 7.57 (d, 1H), 7.50 (d, 1H), 7.36 (d, 2H), 7.17 (t, 1H), 7.07 (d, 2H), 6.91 (m, 1H), 6.75 (dd, 1H), 6.68 (dd, 1H), 6.63 (m, 1H), 6.42 (d, 1H), 3.14 (m, 4H), 2.96 (m, 6H), 2.78 (s, 2H), 2.45 (s, 3H), 2.21 (m, 6H), 1.98 (s, 2H), 1.41 (t, 2H), 0.94 (s, 6H).

Example 200

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(1-methylpiperidin-4-yl)amino]-3-nitrophenyl}sulfonyl)benzamide

Example 200A 2,3-difluoro-4-nitrophenol

A solution of 2,3-difluoro-4-nitroanisole (10 g) in 48% HBr (60 mL) and 30% HBr in acetic acid (30 mL) was stirred at 120° C. overnight. The mixture was cooled to room temperature and extracted with ethyl acetate (3×200 mL) and the combined extracts were washed with brine and dried over Na$_2$SO$_4$. Filtration and evaporation of the solvent gave the product.

Example 200B 6,7-difluoro-1H-indol-5-ol

The title compound was prepared as in EXAMPLE 154A by replacing 2-fluoro-4-nitrophenol with EXAMPLE 200A.

Example 200C methyl 2-(6,7-difluoro-1H-indol-5-yloxy)-4-fluorobenzoate

The title compound was prepared as described in EXAMPLE 3A by replacing 2-methyl-5-indolol with EXAMPLE 200B.

Example 200D methyl 2-(6,7-difluoro-1H-indol-5-yloxy)-4-(piperazin-1-yl)benzoate The title compound was prepared as described in EXAMPLE 3G by replacing EXAMPLE 3F and EXAMPLE 3A with piperazine and EXAMPLE 200C respectively.

Example 200E methyl 4-(4-((2-(4-chlorophenyl)-4,4-dimethylcyclohex-1-enyl)methyl)piperazin-1-yl)-2-(6,7-difluoro-1H-indol-5-yloxy)benzoate The title compound was prepared as described in EXAMPLE 38G by replacing EXAMPLE 38F and EXAMPLE 38E with EXAMPLE 200D and EXAMPLE 60D.

Example 200F 4-(4-((2-(4-chlorophenyl)-4,4-dimethylcyclohex-1-enyl)methyl)piperazin-1-yl)-2-(6,7-difluoro-1H-indol-5-yloxy)benzoic acid The title compound was prepared as described in EXAMPLE 38H by replacing EXAMPLE 38G with EXAMPLE 200E.

Example 200G 4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(1-methylpiperidin-4-yl)amino]-3-nitrophenyl}sulfonyl)benzamide The title compound was prepared as described in EXAMPLE 1H by replacing EXAMPLE 1F and EXAMPLE 1G with EXAMPLE 200F and EXAMPLE 3I, respectively. $^1$H NMR (300 MHz, dimethylsulfoxide-$d_6$) δ 11.63 (s, 1H), 8.40 (d, 1H), 8.06 (d, 1H), 7.72 (dd, 1H), 7.59 (d, 1H), 7.35 (m, 3H), 7.05 (d, 2H), 6.96 (d, 1H), 6.72 (d, 1H), 6.64 (dd, 1H), 6.36 (d, 1H), 6.24 (d, 1H), 3.74 (m, 1H), 3.12 (m, 8H), 2.73 (s, 3H), 2.55 (m, 2H), 2.14 (m, 10H), 1.74 (m, 3H), 1.39 (t, 2H), 0.93 (s, 6H).

Example 201

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(1-tetrahydro-2H-pyran-4-ylpiperidin-4-yl)amino]phenyl}sulfonyl)benzamide The title compound was prepared as described in EXAMPLE 1H by replacing EXAMPLE 1F and EXAMPLE 1G with EXAMPLE 200F and EXAMPLE 49C, respectively. $^1$H NMR (300 MHz, dimethylsulfoxide-$d_6$) δ 11.64 (s, 1H), 8.40 (d, 1H), 8.09 (s, 1H), 7.70 (dd, 1H), 7.58 (d, 1H), 7.35 (m, 4H), 7.05 (d, 2H), 6.92 (d, 1H), 6.64 (m, 2H), 6.36 (d, 1H), 6.23 (s, 1H), 3.92 (m, 2H), 3.67 (m, 1H), 3.01 (m, 8H), 2.73 (s, 2H), 2.25 (m, 8H), 1.97 (m, 5H), 1.53 (m, 8H), 0.94 (m, 6H).

Example 202 tert-butyl 4-(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)-1H-indole-1-carboxylate

Example 202A ethyl 2-(1H-indol-4-yloxy)-4-fluorobenzoate

The title compound was prepared by substituting 4-hydroxyindole for 2-methyl-5-indolol in EXAMPLE 3A.

Example 202B ethyl 2-(1H-indol-4-yloxy)-4-(4-((2-(4-chlorophenyl)-4,4-dimethylcyclohex-1-enyl)methyl)piperazin-1-yl)benzoate The title compound was prepared by substituting EXAMPLE 202A for EXAMPLE 3A in EXAMPLE 3G.

Example 202C 2-(1H-indol-4-yloxy)-4-(4-((2-(4-chlorophenyl)-4,4-dimethylcyclohex-1-enyl)methyl)piperazin-1-yl) benzoic acid The title compound was prepared by substituting EXAMPLE 202B for EXAMPLE 1E in EXAMPLE 1F.

Example 202D 4-(4-{[2-(4-chlorophenyl)-4,4-dimethylcyclohex-1-en-1-yl]methyl}piperazin-1-yl)-2-(1H-indol-4-yloxy)-N-({4-[(1-methylpiperidin-4-yl)amino]-3-nitrophenyl}sulfonyl)benzamide The title compound was prepared by substituting EXAMPLE 202C for EXAMPLE 1F and EXAMPLE 3I for EXAMPLE 1G in EXAMPLE 1H, except 2-10% methanol in $CH_2Cl_2$ was used for the chromatography.

Example 202E tert-butyl 4-(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)-1H-indole-1-carboxylate bis(2,2,2-trifluoroacetate)

EXAMPLE 202D (0.58 g) was dissolved in $CH_2Cl_2$ (30 mL), then di-tert-butyl dicarbonate (0.14 g) and 4-dimethylaminopyridine (0.02 g) was added and the reaction stirred at room temperature for 60 hours. The reaction was then filtered through celite, concentrated, and the crude was purified by preparative HPLC using a 250×50 mm C18 column, eluting with 20-100% $CH_3CN$ vs. 0.1% trifluoroacetic acid in water, giving the product as a trifluoroacetate salt. $^1$H NMR (300 MHz, dimethylsulfoxide-$d_6$) δ 11.80 (v br s, 1H), 9.65, 9.45 (both v br s, total 2H), 8.55 (d, 1H), 8.12 (br d, 1H), 7.80 (dd, 1H), 7.72 (d, 1H), 7.61 (d, 1H), 7.55 (d, 1H), 7.40 (d, 2H), 7.19 (d, 1H), 7.10 (m, 3H), 6.80 (dd, 1H), 6.59 (d, 1H), 6.43 (s, 1H), 6.41 (d, 1H), 4.05 (v br s, 1H), 3.85 (v br s, 1H), 3.60, 3.50, 3.40 (all v br m, total 10H), 3.10 (v br m, 2H), 2.95, 2.90

(both br m, total 5H), 2.20 br m, 4H), 2.05 (br s, 2H), 1.80 (br m, 1H), 1.67 (s, 9H), 1.45 (br t, 2H), 0.95 (s, 6H).

Example 203

2-(3-chlorophenoxy)-4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]benzamide

Example 203A 4-(4-(dimethylamino)cyclohexylamino)-3-nitrobenzenesulfonamide

The title compound was prepared by substituting $N^1,N^1$-dimethylcyclohexane-1,4-diamine for 1-isopropylpiperidin-4-amine in EXAMPLE 41A.

Example 203B 2-(3-chlorophenoxy)-4-(4-{[2-(4-chlorophenyl)-4,4-dimethylcyclohex-1-en-1-yl]methyl}piperazin-1-yl)-N-[(4-{[4-(dimethylamino)cyclohexyl]amino}-3-nitrophenyl)sulfonyl]benzamide The title compound was prepared by substituting EXAMPLE 36C for EXAMPLE 1F and EXAMPLE 203A for EXAMPLE 1G in EXAMPLE 1H. $^1$H NMR (500 MHz, pyridine-$d_5$) δ 9.16 (d, 1H), 8.31-8.39 (m, 2H), 8.03-8.07 (m, 1H), 7.46 (d, 2H), 7.08-7.17 (m, 4H), 7.00-7.04 (m, 1H), 6.91-6.99 (m, 2H), 6.82 (dd, 1H), 6.69 (d, 1H), 3.44-3.52 (m, 1H), 3.14-3.20 (m, 4H), 2.84 (s, 2H), 2.64 (s, 1H), 2.49 (s, 6H), 2.31 (t, 2H), 2.22-2.28 (m, 4H), 2.09-2.15 (m, 2H), 2.05 (s, 2H), 1.97-2.02 (m, 2H), 1.47-1.56 (m, 2H), 1.42 (t, 2H), 1.27-1.37 (m, 2H), 1.25 (s, 1H), 0.93-0.98 (m, 6H).

Example 204

2-(3-chlorophenoxy)-4-(4-{[2-(4-chlorophenyl)-4,4-dimethylcyclohex-1-en-1-yl]methyl}piperazin-1-yl)-N-[(4-{[4-(diethylamino)cyclohexyl]amino}-3-nitrophenyl)sulfonyl]benzamide

Example 204A 4-(4-(diethylamino)cyclohexylamino)-3-nitrobenzenesulfonamide

The title compound was prepared by substituting $N^1,N^1$-diethylcyclohexane-1,4-diamine for 1-isopropylpiperidin-4-amine in EXAMPLE 41A.

Example 204B 2-(3-chlorophenoxy)-4-(4-{[2-(4-chlorophenyl)-4,4-diethylcyclohex-1-en-1-yl]methyl}piperazin-1-yl)-N-[(4-{[4-(diethylamino)cyclohexyl]amino}-3-nitrophenyl)sulfonyl]benzamide The title compound was prepared by substituting EXAMPLE 36C for EXAMPLE 1F and EXAMPLE 204A for EXAMPLE 1G in EXAMPLE 1H. $^1$H NMR (500 MHz, pyridine-$d_5$) δ 9.18 (d, 1H), 8.32-8.39 (m, 2H), 8.05-8.09 (m, 1H), 7.46 (d, 2H), 7.15 (t, 1H), 7.08-7.13 (m, 3H), 6.98-7.05 (m, 2H), 6.94 (dd, 1H), 6.82 (dd, 1H), 6.69 (d, 1H), 3.43-3.50 (m, 1H), 3.13-3.19 (m, 4H), 2.84 (s, 2H), 2.72 (t, 1H), 2.63 (q, 4H), 2.31 (t, 2H), 2.22-2.28 (m, 4H), 2.11 (d, 2H), 2.00 (s, 2H), 1.91 (d, 2H), 1.40-1.48 (m, 4H), 1.24-1.34 (m, 2H), 1.10 (t, 6H), 0.93-0.99 (m, 6H).

Example 205

Trans-2-(3-chlorophenoxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide

Example 205A trans-4-(4-morpholinocyclohexylamino)-3-nitrobenzenesulfonamide The title compound was prepared by substituting trans 4-morpholinocyclohexanamine for 1-isopropylpiperidin-4-amine in EXAMPLE 41A.

Example 205B

Trans-2-(3-chlorophenoxy)-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide The title compound was prepared by substituting EXAMPLE 36C for EXAMPLE 1F and EXAMPLE 205A for EXAMPLE 1G in EXAMPLE 1H. $^1$H NMR (500 MHz, pyridine-$d_5$) δ 9.17 (d, 1H), 8.42 (d, 1H), 8.32 (dd, 1H), 8.00 (d, 1H), 7.46 (d, 2H), 7.15 (t, 1H), 7.11 (d, 2H), 7.07 (d, 1H), 7.03 (d, 1H), 6.99 (d, 1H), 6.93 (dd, 1H), 6.81 (dd, 1H), 6.69 (d, 1H), 3.73-3.78 (m, 4H), 3.43-3.50 (m, 1H), 3.15-3.21 (m, 4H), 2.84 (s, 2H), 2.50-2.54 (m, 4H), 2.31 (t, 2H), 2.21-2.27 (m, 5H), 2.11 (d, 2H), 2.00 (s, 2H), 1.91 (d, 2H), 1.36-1.43 (m, 4H), 1.28-1.34 (m, 2H), 0.96 (s, 6H).

Example 206

4-{4-[1-(4'-chloro-1,1'-biphenyl-2-yl)ethyl]piperazin-1-yl}-2-(2-chlorophenoxy)-N-({4-[(1-methylpiperidin-4-yl)amino]-3-nitrophenyl}sulfonyl)benzamide The title compound was prepared as described in EXAMPLE 137 by replacing EXAMPLE 122C with EXAMPLE and EXAMPLE 111A with EXAMPLE 31. $^1$H NMR (400 MHz, $CH_2CD_2$) δ 8.80 (s, 1H), 8.41 (d, 1H), 8.01 (d, 1H), 7.87 (d, 1H), 7.55 (t, 2H), 7.29-7.37 (m, 4H), 7.17-7.28 (m, 4H), 7.10-7.15 (m, 2H), 6.94 (d, 1H), 6.58 (d, 1H), 5.95 (s, 1H), 3.53-3.64 (m, 1H), 3.39 (q, 1H), 3.01-3.12 (m, 4H), 2.77 (t, 2H), 2.38-2.46 (m, 2H), 2.15-2.31 (m, 7H), 2.05 (d, 2H), 1.63-1.74 (m, 2H), 1.22 (d, 3H).

Example 207

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 207A 2-chloro-4-(methoxymethoxy)phenol

The title compound was prepared by substituting 2-chlorobenzene-1,4-diol for EXAMPLE 158B in EXAMPLE 158C.

Example 207B

Ethyl 2-(2-chloro-4-(methoxymethoxy)phenoxy)-4-fluorobenzoate

The title compound was prepared by substituting 207A for 2-methyl-5-indolol in EXAMPLE 3A.

Example 207C

Ethyl 2-(2-chloro-4-(methoxymethoxy)phenoxy)-4-fluorobenzoate

The title compound was prepared by substituting piperazine for EXAMPLE 3F and EXAMPLE 207B for EXAMPLE 3A in EXAMPLE 3G.

Example 207D

Ethyl 2-(2-chloro-4-(methoxymethoxy)phenoxy)-4-(4-((2-(4-chlorophenyl)-4,4-dimethylcyclohex-1-enyl)methyl)piperazin-1-yl)benzoate The title compound was prepared by substituting EXAMPLE 60D for 4'-chlorobiphenyl-2-carboxaldehyde and EXAMPLE 207C for tert-butyl piperazine-1-carboxylate in EXAMPLE 1A.

Example 207E 2-(2-chloro-4-(methoxymethoxy)phenoxy)-4-(4-((2-(4-chlorophenyl)-4,4-dimethylcyclohex-1-enyl)methyl)piperazin-1-yl)benzoic acid The title compound was prepared by substituting EXAMPLE 207D for EXAMPLE 1E in EXAMPLE 1F.

Example 207F 2-(2-chloro-4-(methoxymethoxy)phenoxy)-4-(4-((2-(4-chlorophenyl)-4,4-dimethylcyclohex-1-enyl)methyl)piperazin-1-yl)-N-(4-(1-methylpiperidin-4-ylamino)-3-nitrophenylsulfonyl)benzamide The title compound was prepared by substituting EXAMPLE 207E for EXAMPLE 1F and EXAMPLE 3I for EXAMPLE 1G in EXAMPLE 1H.

Example 207G 2-(2-chloro-4-hydroxyphenoxy)-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 207F for EXAMPLE 158 in EXAMPLE 159. $^1$H NMR (500 MHz, pyridine-$d_5$) δ 12.30 (br. s, 1H), 9.29 (d, 1H), 8.49 (d, 1H), 8.40 (dd, 1H), 8.08 (d, 1H), 7.45 (d, 2H), 7.09 (m, 3H), 7.01 (d, 1H), 6.93 (dd, 1H), 6.75 (dd, 1H), 6.58 (d, 1H), 3.54 (m, 1H), 3.13 (m, 4H), 2.81 (s, 2H), 2.65 (m, 2H), 2.29 (m, 2H), 2.21 (m, 4H), 2.16 (s, 3H), 2.07 (m, 2H), 1.96 (m, 4H), 1.66 (m, 2H), 1.41 (t, 2H), 0.95 (s, 6H).

Example 208

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide

Example 208A 2-(2-chloro-4-(methoxymethoxy)phenoxy)-4-(4-((2-(4-chlorophenyl)-4,4-dimethylcyclohex-1-enyl)methyl)piperazin-1-yl)-N-(4-(4-methylpiperazin-1-ylamino)-3-nitrophenylsulfonyl)benzamide The title compound was prepared by substituting EXAMPLE 207E for EXAMPLE 1F and EXAMPLE 184A for EXAMPLE 1G in EXAMPLE 1H.

Example 208B 2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 208A for EXAMPLE 158E in EXAMPLE 159. $^1$H NMR (500 MHz, pyridine-$d_5$) δ 12.33 (br. s, 1H), 9.28 (m, 2H), 8.44 (dd, 1H), 8.07 (d, 1H), 7.76 (d, 1H), 7.45 (d, 2H), 7.09 (m, 3H), 6.94 (dd, 1H), 6.75 (dd, 1H), 6.57 (d, 1H), 3.13 (m, 4H), 2.94 (m, 4H), 2.81 (m, 4H), 2.29 (m, 2H), 2.19 (m, 10H), 1.99 (s, 2H), 1.41 (t, 2H), 0.95 (m, 6H).

Example 209

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(1-methylpiperidin-4-yl)amino]-3-nitrophenyl}sulfonyl)benzamide

Example 209A

6-Fluoro-4-methoxy-1H-indole-2-carboxylic acid methyl ester

Sodium methoxide solution (25% by weight in methanol, 22.25 mL) and methanol (52 mL) were added to a flask and cooled to −20° C. using an acetonitrile/dry ice bath. Ethyl 2-azidoacetate (25% by weight in ethanol, 50.3 g) and 4-fluoro-2-methoxybenzaldehyde (5.00 g, dissolved in ethyl 2-azidoacetate solution) were added drop-wise to the stirring sodium methoxide solution at −20° C. The solution was then stirred at −20° C. for 3.5 hours, then at 0° C. for one hour. The solution was poured over ice, vacuum filtered, and washed with water. The filtered solid was taken up in xylenes (100 mL), washed twice with brine, and dried using anhydrous sodium sulfate and filtered. In a separate flask xylenes (50 mL) was brought to reflux. The xylene solution containing the filtered material was added drop-wise to the refluxing xylenes. The solution was then refluxed for five hours, cooled, and placed in a freezer for 16 hours. The precipitate was filtered out. The volume of the filtrate was reduced on vacuum to generate a second crop of precipitate, which was washed

Example 209B

6-Fluoro-4-methoxy-1H-indole-2-carboxylic acid

The title compound was prepared by substituting EXAMPLE 209A for EXAMPLE 1E in EXAMPLE 1F.

Example 209C

6-Fluoro-4-methoxy-1H-indole

EXAMPLE 209B (1775 mg) was dissolved in N-methylpyrrolidinone (75 mL), and copper powder (2157 mg) was added. The solution was stirred to keep the copper powder suspended and the solution was split into nine microwave reactor vials, each containing a stir bar. Each vial was heated in a CEM Discover microwave reactor at 260° C. for 25 minutes with stirring. The vials were combined, added to water, and extracted with ethyl ether. The ether was washed with brine and dried on anhydrous sodium sulfate. The solution was filtered and the filtrate was concentrated and purified by flash column chromatography on silica gel using 10% ethyl acetate in hexanes.

Example 209D

6-Fluoro-1H-indol-4-ol

Aluminum chloride (727 mg) was added to dichloromethane (20 mL), the mixture was cooled to 0° C., and benzylmercaptan (4512 mg) was added. EXAMPLE 209C (600 mg) dissolved in dichloromethane (5 mL) was added drop-wise. The solution was mixed for 30 minutes at 0° C. Benzylmercaptan (451 mg) and aluminum chloride (727 mg) were added, and the solution was stirred for 75 minutes at 0° C. The reaction was quenched by adding 1M aqueous HCl. The solution was extracted with ethyl acetate, which was subsequently washed with brine and dried on anhydrous sodium sulfate. After filtration, the filtrate was concentrated and purified by flash column chromatography on silica gel using 5% ethyl acetate in hexanes increasing to 20% ethyl acetate in hexanes and increasing again to 50% ethyl acetate in hexanes.

Example 209E

4-Fluoro-2-(6-fluoro-1H-indol-4-yloxy)-benzoic acid ethyl ester

The title compound was prepared by substituting EXAMPLE 209D for 2-methyl-5-indolol in EXAMPLE 3A.

Example 209F

4-{4-[2-(4-Chloro-phenyl)-4,4-dimethyl-cyclohex-1-enylmethyl]-piperazin-1-yl}-2-(6-fluoro-1H-indol-4-yloxy)-benzoic acid ethyl ester The title compound was prepared by substituting EXAMPLE 209E for EXAMPLE 3A in EXAMPLE 3G.

Example 209G

4-{4-[2-(4-Chloro-phenyl)-4,4-dimethyl-cyclohex-1-enylmethyl]-piperazin-1-yl}-2-(6-fluoro-1H-indol-4-yloxy)-benzoic acid The title compound was prepared by substituting EXAMPLE 209F for EXAMPLE 1E in EXAMPLE 1F.

Example 209H 4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(1-methylpiperidin-4-yl)amino]-3-nitrophenyl}sulfonyl)benzamide The title compound was prepared by substituting EXAMPLE 209G for EXAMPLE 1F and EXAMPLE 3I for EXAMPLE 1G in EXAMPLE 1H. $^1$H NMR (300 MHz, dimethylsulfoxide-$d_6$) δ 11.14 (br s, 1H), 8.37 (d, 1H), 8.08 (d, 1H), 7.68 (dd, 1H), 7.59 (d, 1H), 7.35 (d, 2H), 7.19 (t, 1H), 7.05 (d, 2H), 6.97 (d, 1H), 6.78 (dd, 1H), 6.71 (dd, 1H), 6.34 (d, 1H), 6.26 (t, 1H), 5.97 (dd, 1H), 3.74 (m, 1H), 3.18-3.09 (m, 2H), 3.05 (br s, 4H), 2.83-2.70 (m, 2H), 2.74 (br s, 2H), 2.57 (s, 3H), 2.25-2.12 (m, 6H), 2.09-2.01 (m, 2H), 1.96 (s, 2H), 1.72 (q, 2H), 1.39 (t, 2H), 0.93 (s, 6H).

Example 210

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({3-nitro-4-[(1-tetrahydro-2H-pyran-4-ylpiperidin-4-yl)amino]phenyl}sulfonyl)benzamide The title compound was prepared by substituting EXAMPLE 209G for EXAMPLE 1F and EXAMPLE 49C for EXAMPLE 1G in EXAMPLE 1H. $^1$H NMR (300 MHz, dimethylsulfoxide-$d_6$) δ 11.16 (br s, 1H), 8.39 (d, 1H), 7.64 (d, 1H), 7.57 (d, 1H), 7.38-7.32 (d, 2H), 7.21 (t, 1H), 7.05 (d, 2H), 6.99 (d, 1H), 6.80 (d, 1H), 6.73 (d, 1H), 6.35 (d, 1H), 6.26 (t, 2H), 6.00 (d, 1H), 3.99-3.89 (m, 3H), 3.76 (m, 1H), 3.26 (m, 2H), 3.07 (m, 4H), 2.72 (br s, 2H), 2.27-2.12 (m, 8H), 2.09-1.95 (m, 4H), 1.86-1.48 (m, 8H), 1.39 (t, 2H), 0.93 (s, 6H).

Example 211

2-(2-chloro-4-hydroxyphenoxy)-4-(4-{[2-(4-chlorophenyl)-4,4-dimethylcyclohex-1-en-1-yl]methyl}piperazin-1-yl)-N-({4-[(4-methylpiperazin-1-yl)amino]-3-[(trifluoromethyl)sulfonyl]phenyl}sulfonyl)benzamide

Example 211A 4-(4-methylpiperazin-1-ylamino)-3-(trifluoromethylsulfonyl)benzenesulfonamide The title compound was prepared by substituting 4-methylpiperazin-1-amine for 3-(N-morpholinyl)-1-propylamine and EXAMPLE 131C for 4-Fluoro-3-nitrobenzenesulfonamide in EXAMPLE 4A.

Example 211B 2-(2-chloro-4-(methoxymethoxy)phenoxy)-4-(4-((2-(4-chlorophenyl)-4,4-dimethylcyclohex-1-enyl)methyl)piperazin-1-yl)-N-(4-(4-methylpiperazin-1-ylamino)-3-(trifluoromethylsulfonyl)phenylsulfonyl)benzamide The title compound was prepared by substituting EXAMPLE 207E for EXAMPLE 1F and EXAMPLE 211A for EXAMPLE 1G in EXAMPLE 1H.

Example 211C 2-(2-chloro-4-hydroxyphenoxy)-4-(4-((2-(4-chlorophenyl)-4,4-dimethylcyclohex-1-enyl)methyl)piperazin-1-yl)-N-(4-(4-methylpiperazin-1-ylamino)-3-(trifluoromethylsulfonyl)phenylsulfonyl)benzamide The title compound was prepared by substituting EXAMPLE 211B for EXAMPLE 158E in EXAMPLE 159. $^1$H NMR (500 MHz, dimethylsulfoxide-$d_6$) δ 9.87 (s, 1H), 8.08 (d, 1H), 7.96 (s, 1H), 7.90 (dd, 1H), 7.54 (d, 1H), 7.48 (d, 1H), 7.36 (d, 2H), 7.07 (d, 2H), 6.89 (d, 1H), 6.83 (d, 1H), 6.73 (dd, 1H), 6.65 (dd, 1H), 6.21 (d, 1H), 3.07 (m, 4H), 2.90 (m, 6H), 2.76 (s, 2H), 2.41 (s, 3H), 2.21 (m, 6H), 1.97 (s, 2H), 1.40 (t, 3H), 0.94 (s, 6H).

Example 212

2-({1,3-bis[(4-methylpiperazin-1-yl)methyl]-1H-indol-4-yl}oxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide

Example 212A 4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-4-yloxy)benzamide The title compound was prepared by substituting EXAMPLE 202C for EXAMPLE 1F and EXAMPLE 11A for EXAMPLE 1G in EXAMPLE 1H.

Example 212B 2-({1,3-bis[(4-methylpiperazin-1-yl)methyl]-1H-indol-4-yl}oxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide EXAMPLE 212A (0.25 g) was dissolved in methanol (0.60 mL), to which was added 37% (wt) formaldehyde in water (0.22 mL) and 1-methylpiperazine (0.33 mL). The reaction was heated at 60° C. for two hours, then cooled and concentrated. The crude was purified by preparative HPLC using a C18 column, 250×50 mm, 10μ, and eluting with a gradient of 20-100% $CH_3CN$ vs. 0.1% trifluoroacetic acid in water, giving the product as a trifluoroacetate salt. The salt was dissolved in dichloromethane (6 mL) and washed with 50% aqueous $NaHCO_3$. The organic layer was dried over anhydrous $Na_2SO_4$, filtered, and concentrated to give the title compound. $^1$H NMR (300 MHz, dimethylsulfoxide-$d_6$) δ 8.68 (br t, 1H), 8.00 (s, 1H), 7.82 (d, 1H), 7.38 (m, 3H), 7.25 (d, 1H), 7.08 (d, 2H), 6.87 (d, 1H), 6.75 (d, 1H), 6.67 (m, 2H), 6.58 (s, 1H), 5.58 (d, 1H), 4.85 (s, 2H), 3.40 (m, 4H), 3.20 (v br s, 4H), 3.05 (v br s, 4H), 2.79 (s, 2H), 2.60 (v br s, 2H), 2.40 (br m, 6H), 2.20 (m, 21H), 2.09 (s, 3H), 1.98 (s, 2H), 1.80 (m, 2H), 1.42 (t, 2H), 0.95 (s, 6H).

Example 213

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-({3-[(4-methylpiperazin-1-yl)methyl]-1H-indol-4-yl}oxy)benzamide To EXAMPLE 212A (0.13 g) in methanol (0.30 mL) was added 37% (wt) formaldehyde in water (0.022 mL) and 1-methylpiperazine (0.035 mL). The reaction was heated at 60° C. for 50 minutes, then it was cooled and concentrated. The crude was purified by preparative HPLC using a C18 column, 250×50 mm, 10 t, and eluting with a gradient of 20-100% $CH_3CN$ vs. 0.1% trifluoroacetic acid in water, giving the product as a trifluoroacetate salt. The salt was dissolved in dichloromethane (6 mL) and washed with 50% aqueous $NaHCO_3$. The organic layer was dried over anhydrous $Na_2SO_4$, filtered, and concentrated to give the title compound. $^1$H NMR (300 MHz, dimethylsulfoxide-d) δ 11.23 (s, 1H), 8.68 (br t, 1H), 7.96 (s, 1H), 7.79 (d, 1H), 7.38 (d, 2H), 7.31 (s, 1H), 7.17 (br d, 1H), 7.08 (d, 2H), 6.75 (d, 2H), 6.66 (d, 1H), 6.60 (m, 2H), 5.65 (d, 1H), 4.33 (br s, 2H), 3.40 (m, 4H), 3.20 (v br s, 4H), 3.03 (v br s, 4H), 2.79 (s, 2H), 2.60 (v br s, 2H), 2.42 (br m, 2H), 2.20 (m, 15H), 1.98 (s, 2H), 1.83 (m, 2H), 1.42 (t, 2H), 0.95 (s, 6H).

Example 214

2-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)-N,N-dimethylbenzamide

Example 214A methyl 2-bromo-4-(4-((2-(4-chlorophenyl)-4,4-dimethylcyclohex-1-enyl)methyl)piperazin-1-yl)benzoate The title compound was prepared by substituting EXAMPLE 3F for EXAMPLE 1B in EXAMPLE 1C.

Example 214B methyl 4-(4-((2-(4-chlorophenyl)-4,4-dimethylcyclohex-1-enyl)methyl)piperazin-1-yl)-2-(2-(dimethylcarbamoyl)phenoxy)benzoate The title compound was prepared by substituting EXAMPLE 214A for EXAMPLE 1C and 2-hydroxy-N,N-dimethylbenzamide for EXAMPLE 1D in EXAMPLE 1E.

Example 214C 4-(4-((2-(4-chlorophenyl)-4,4-dimethylcyclohex-1-enyl)methyl)piperazin-1-yl)-2-(2-(dimethylcarbamoyl)phenoxy)benzoic acid The title compound was prepared by substituting EXAMPLE 214B for EXAMPLE 1E in EXAMPLE 1F.

Example 214D 2-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)-N,N-dimethylbenzamide The title compound was prepared by substituting EXAMPLE 214C for EXAMPLE 1F and EXAMPLE 3I for EXAMPLE 1G in EXAMPLE 1H. $^1$H NMR (400 MHz, dimethylsulfoxide-$d_6$) δ 8.35 (s, 1H), 8.07 (d, 1H), 7.72 (d, 1H), 7.61 (d, 1H), 7.36 (d, 2H), 7.12 (m, 2H), 7.06 (d, 2H), 7.02 (d, 1H), 6.93 (t, 1H), 6.68 (dd, 1H), 6.47 (d, 1H), 6.18 (d, 1H), 3.72 (m, 1H), 3.04 (m, 4H), 2.95 (m, 2H), 2.86 (s, 3H), 2.75 (s, 2H), 2.70 (s, 3H), 2.42 (m, 2H), 2.19 (m, 6H), 2.01 (m, 4H), 1.67 (m, 2H), 1.40 (t, 2H), 1.24 (s, 3H), 0.94 (s, 6H).

Example 215

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[2-(trifluoromethyl)-1H-indol-4-yl]oxy}benzamide

Example 215A methyl 2-(3-amino-2-methylphenoxy)-4-fluorobenzoate

The title compound was prepared by substituting 3-amino-2-methylphenol for 2-methyl-5-indolol in EXAMPLE 3A.

Example 215B (E)-methyl 2-(3-(1-chloro-2,2,2-trifluoroethylideneamino)-2-methylphenoxy)-4-fluorobenzoate To a mixture of triethylamine (0.476 g) and triphenylphosphine (3.05 g) in CCl$_4$ (10 mL) was added trifluoroacetic acid (0.477 g) dropwise at 0° C. The solution was stirred for 10 minutes. To this solution was added EXAMPLE 215A (1.08 g) in CCl$_4$ (5 mL). The solution was heated under reflux for 3 hours. After cooling, the reaction mixture was concentrated, and diluted with 3:7 ethyl acetate/hexanes. The solid was filtered off, and the filtrate was concentrated. The residue was purified by flash chromatography on silica gel eluting 1:10 ethyl acetate/hexane to give the title compound.

Example 215C (E)-methyl 2-(2-(bromomethyl)-3-(1-chloro-2,2,2-trifluoroethylideneamino)phenoxy)-4-fluorobenzoate A mixture of EXAMPLE 215B (1.4 g), N-bromosuccinimide (0.671 g), and benzoyl peroxide (0.044 g) in CCl$_4$ (20 mL) was heated under reflux for 4 hours. After cooling, the solid was filtered off. The filtrate was then concentrated. The residue was purified by flash chromatography on silica gel eluting 1:20 ethyl acetate/hexane to give the title compound.

Example 215D methyl 4-fluoro-2-(2-(trifluoromethyl)-1H-indol-4-yloxy)benzoate Magnesium (0.081 g) in tetrahydrofuran (10 mL) was treated with EXAMPLE 215C (1.3 g) in tetrahydrofuran (5 mL) drop-wise at 0° C. After the addition was over, a couple of I$_2$ crystals were added to the reaction. After stirring for 2 hours, the magnesium started to disappear. The reaction was stirred for another 6 hours at room temperature. The reaction was quenched with saturated aqueous NH$_4$Cl, and extracted with ethyl acetate. The aqueous layer was extracted with additional ethyl acetate. The combined organic layers were washed with brine, dried over MgSO$_4$, filtered, and concentrated. The residue was purified by flash chromatography on silica gel eluting with 1:4 ethyl acetate/hexanes to give the title compound.

Example 215E methyl 4-(4-((2-(4-chlorophenyl)-4,4-dimethylcyclohex-1-enyl)methyl)piperazin-1-yl)-2-(2-(trifluoromethyl)-1H-indol-4-yloxy)benzoate The title compound was prepared by substituting EXAMPLE 215D for EXAMPLE 3A in EXAMPLE 3G.

Example 215F

A mixture of EXAMPLE 215E (0.13 g) and lithium iodide (0.534 g) in pyridine (2 mL) was heated in a CEM Discover microwave reactor (130° C., 30 minutes). The pyridine was removed under vacuum, and the residue was partitioned between ethyl acetate and water. The aqueous layer was extracted with additional ethyl acetate. The combined organic layers were washed with brine, dried over MgSO$_4$, filtered, and concentrated. The residue was then purified by reverse phase Prep HPLC to give the desired product.

Example 215G 4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[2-(trifluoromethyl)-1H-indol-4-yl]oxy}benzamide The title compound was prepared by substituting EXAMPLE 215F for EXAMPLE 1F and EXAMPLE 49C for EXAMPLE 1G in EXAMPLE 1H. $^1$H NMR (500 MHz, dimethylsulfoxide-$d_6$) δ 12.29 (s, 1H), 8.39 (d, 1H), 8.12 (d, 1H), 7.69 (dd, 1H), 7.59 (d, 1H), 7.34 (d, 2H), 7.00-7.12 (m, 5H), 6.85 (s, 1H), 6.71 (dd, 1H), 6.34 (d, 1H), 6.29 (d, 1H), 3.93 (dd, 1H), 3.06-3.09 (m, 6H), 2.76 (s, 2H), 2.62-2.64 (m, 2H), 2.16-2.19 (m, 6H), 2.03-2.05 (m, 2H), 1.96 (s, 2H), 1.79-1.82 (m, 2H), 1.66-1.68 (m, 2H), 1.49-1.57 (m, 2H), 1.96 (t, 2H), 0.93 (s, 6H).

Example 216

2-(2-chloro-4-hydroxyphenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 216A 2-(2-chloro-4-(methoxymethoxy)phenoxy)-4-(4-((2-(4-chlorophenyl)-4,4-dimethylcyclohex-1-enyl)methyl)piperazin-1-yl)-N-(3-nitro-4-(1-(tetrahydro-2H-pyran-4-yl)piperidin-4-ylamino)phenylsulfonyl)benzamide The title compound was prepared by substituting EXAMPLE 207E for EXAMPLE 1F and EXAMPLE 49C for EXAMPLE 1G in EXAMPLE 1H.

Example 216B 2-(2-chloro-4-hydroxyphenoxy)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 216A for EXAMPLE 158E in EXAMPLE 159. $^1$H NMR (500 MHz, dimethylsulfoxide-$d_6$) δ 9.83 (br. s, 1H), 8.47 (s, 1H), 8.17 (br. s, 1H), 7.76 (d, 1H), 7.50 (d, 1H), 7.35 (d, 2H), 7.08 (m, 3H), 6.83 (m, 2H), 6.67 (m, 2H), 6.22 (d, 1H), 3.93 (m, 2H), 3.81 (m, 1H), 3.07 (m, 6H), 2.75 (s, 2H), 2.19 (m, 8H), 1.97 (s, 2H), 1.68 (m, 6H), 1.40 (t, 2H), 0.94 (s, 6H).

Example 217

4-(4-{[2-(4-chlorophenyl)-4,4-dimethylcyclohex-1-en-1-yl]methyl}piperazin-1-yl)-N-((4-[(1-methylpiperidin-4-yl)amino]-3-nitrophenyl}sulfonyl)-2-{[6-(trifluoromethyl)-1H-indol-5-yl]oxy}benzamide

Example 217A 4-nitro-2-(trifluoromethyl)phenol

The title compound was prepared as described in EXAMPLE 200A by replacing 2,3-difluoro-4-nitroanisole with 2-trifluoromethyl-4-nitroanisole.

Example 217B 6-(trifluoromethyl)-1H-indol-5-ol

The title compound was prepared analogously to that of 2-fluoro-4-nitrophenol in WO 02/12227 (page 78).

Example 217C methyl 4-fluoro-2-(6-(trifluoromethyl)-1H-indol-5-yloxy)benzoate The title compound was prepared as described in EXAMPLE 3A by replacing 2-methyl-5-indolol with EXAMPLE 217B.

Example 217D methyl 4-(piperazin-1-yl)-2-(6-(trifluoromethyl)-1H-indol-5-yloxy)benzoate The title compound was prepared as described in EXAMPLE 3G by replacing EXAMPLE 3F and EXAMPLE 3A with piperazine and EXAMPLE 217C, respectively.

Example 217E methyl 4-(4-((2-(4-chlorophenyl)-4,4-dimethylcyclohex-1-enyl)methyl)piperazin-1-yl)-2-(6-(trifluoromethyl)-1H-indol-5-yloxy)benzoate The title compound was prepared as described in EXAMPLE 38G by replacing EXAMPLE 38F and EXAMPLE 38E with EXAMPLE 217D and EXAMPLE 60D, respectively.

Example 217F 4-(4-((2-(4-chlorophenyl)-4,4-dimethylcyclohex-1-enyl)methyl)piperazin-1-yl)-2-(6-(trifluoromethyl)-1H-indol-5-yloxy)benzoic acid The title compound was prepared as described in EXAMPLE 38H by replacing EXAMPLE 38G with EXAMPLE 217E.

Example 217G 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-{[6-(trifluoromethyl)-1H-indol-5-yl]oxy}benzamide The title compound was prepared as described in EXAMPLE 1H by replacing EXAMPLE 1F and EXAMPLE 1G with EXAMPLE 217F and EXAMPLE 3I, respectively. $^1$H NMR (300 MHz, dimethylsulfoxide-$d_6$) δ 11.38 (s, 1H), 8.43 (d, 1H), 8.09 (d, 1H), 7.77 (dd, 1H), 7.67 (s, 1H), 7.55 (m, 2H), 7.33 (d, 2H), 7.02 (m, 4H), 6.67 (dd, 1H), 6.38 (s, 1H), 3.71 (m, 1H), 3.05 (m, 7H), 2.72 (s, 3H), 2.25 (m, 7H), 1.98 (m, 5H), 1.72 (m, 3H), 1.38 (t, 3H), 0.92 (s, 6H).

Example 218

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-{[6-(trifluoromethyl)-1H-indol-5-yl]oxy}benzamide The title compound was prepared as described in EXAMPLE 1H by replacing EXAMPLE 1F and EXAMPLE 1G with EXAMPLE 217F and EXAMPLE 49C, respectively. $^1$H NMR (300 MHz, dimethylsulfoxide-$d_6$) δ 11.42 (s, 1H), 8.46 (d, 1H), 8.16 (d, 1H), 7.77 (dd, 1H), 7.70 (s, 1H), 7.56 (m, 2H), 7.33 (m, 3H), 7.03 (m, 5H), 6.69 (dd, 1H), 6.40 (s, 1H), 6.14 (d, 1H), 3.91 (m, 3H), 3.72 (m, 1H), 3.02 (m, 8H), 2.72 (s, 2H), 2.25 (m, 10H), 1.95 (m, 4H), 1.48 (m, 5H), 0.92 (s, 6H).

Example 219

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 219A methyl 2-((2-aminothiazol-4-yl)methoxy)-4-fluorobenzoate

A mixture of methyl 4-fluoro-2-hydroxybenzoate (552 mg), 4-(chloromethyl)thiazol-2-amine hydrochloric acid (600 mg) and $Cs_2CO_3$ (2.64 g) in 15 mL N,N-dimethylformamide was stirred at room temperature for 24 hours. Water was added and the mixture was extracted with ethyl acetate (2×), washed with water (2×) and brine, dried over $MgSO_4$, filtered and concentrated. The residue was chromatographed on silica gel using 10-50% ethyl acetate in hexanes as eluent.

Example 219B methyl 2-((2-aminothiazol-4-yl)methoxy)-4-(4-((2-(4-chlorophenyl)-4,4-dimethylcyclohex-1-enyl)methyl)piperazin-1-yl)benzoate The title compound was prepared by substituting EXAMPLE 219A for EXAMPLE 3A in EXAMPLE 3G.

Example 219C methyl 2-((2-(tert-butoxycarbonylamino)thiazol-4-yl)methoxy)-4-(4-((2-(4-chlorophenyl)-4,4-dimethylcyclohex-1-enyl)methyl)piperazin-1-yl)benzoate To a solution of EXAMPLE 219B (280 mg), 4-(dimethylamino)pyridine (2.94 mg), triethylamine (81 μL) in 10 mL tetrahydrofuran at room temperature was added a solution of di-tert-butyl dicarbonate (134 μL) in 3 mL tetrahydrofuran via a cannula. The mixture was stirred at room temperature overnight, and partitioned between water and ethyl acetate. The aqueous phase was extracted with ethyl acetate and the combined organics were washed with brine and dried over MgSO$_4$, filtered and concentrated. The oil residue was chromatographed on silica gel with 25-60% ethyl acetate in hexanes.

Example 219D 2-((2-(tert-butoxycarbonylamino)thiazol-4-yl)methoxy)-4-(4-((2-(4-chlorophenyl)-4,4-dimethylcyclohex-1-enyl)methyl)piperazin-1-yl)benzoic acid The title compound was prepared by substituting EXAMPLE 219C for EXAMPLE 1E in EXAMPLE 1F.

Example 219E tert-butyl 4-((5-(4-((2-(4-chlorophenyl)-4,4-dimethylcyclohex-1-enyl)methyl)piperazin-1-yl)-2-(3-nitro-4-(1-(tetrahydro-2H-pyran-4-yl)piperidin-4-ylamino)phenylsulfonylcarbamoyl)phenoxy)methyl)thiazol-2-ylcarbamate The title compound was prepared by substituting EXAMPLE 219D for EXAMPLE 1F and EXAMPLE 49C for EXAMPLE 1G respectively in EXAMPLE 1H.

Example 219F 2-((2-aminothiazol-4-yl)methoxy)-4-(4-((2-(4-chlorophenyl)-4,4-dimethylcyclohex-1-enyl)methyl)piperazin-1-yl)-N-(3-nitro-4-(1-(tetrahydro-2H-pyran-4-yl)piperidin-4-ylamino)phenylsulfonyl)benzamide This EXAMPLE was prepared by substituting EXAMPLE 219E for EXAMPLE 1A in EXAMPLE 1B. $^1$H NMR (300 MHz, dimethylsulfoxide-d$_6$) δ 0.96 (s, 6H) 1.36-1.78 (m, 8H) 1.99 (m, 2H) 2.14-2.31 (m, 7H) 2.40-2.64 (m, 3H) 2.78 (m, 2H) 2.92 (d, 2H) 3.16-3.43 (m, 10H) 3.75 (m, 1H) 3.84-3.96 (m, 2H) 5.01 (s, 2H) 6.51 (d, 1H) 6.57 (s, 1H) 6.63 (s, 1H) 6.93 (s, 2H) 7.06 (d, 2H) 7.28 (d, 1H) 7.37 (d, 2H) 7.45 (d, 1H) 7.93 (dd, 1H) 8.28 (d, 1H) 8.62 (d, 1H).

Example 220

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-methylpiperazin-1-yl)amino]-3-nitrophenyl}sulfonyl)benzamide The title compound was prepared as described in EXAMPLE 1H by replacing EXAMPLE 1F and EXAMPLE 1G with EXAMPLE 200F and EXAMPLE 184A, respectively. $^1$H NMR (300 MHz, dimethylsulfoxide-d$_6$) δ 11.72 (s, 1H), 9.14 (s, 1H), 8.47 (d, 1H), 7.82 (m, 1H), 7.54 (dd, 2H), 7.41 (t, 1H), 7.34 (d, 2H), 7.04 (d, 1H), 6.92 (d, 1H), 6.66 (d, 1H), 6.42 (d, 1H), 6.21 (s, 1H), 2.98 (m, 11H), 2.73 (s, 2H), 2.40 (s, 4H), 2.17 (m, 7H), 1.95 (s, 3H), 1.38 (t, 2H), 0.93 (s, 6H).

Example 221

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide The title compound was prepared by substituting EXAMPLE 154E for EXAMPLE 1F and EXAMPLE 184A for EXAMPLE 1G in EXAMPLE 1H. $^1$H NMR (500 MHz, dimethylsulfoxide-d$_6$) δ 11.19 (s, 1H), 9.17 (s, 1H), 8.52 (d, 1H), 7.89 (dd, 1H), 7.59 (d, 1H), 7.53 (d, 1H), 7.34 (m, 4H), 7.23 (d, 1H), 7.04 (d, 2H), 6.62 (dd, 1H), 6.39 (m, 1H), 6.07 (m, 1H), 2.94 (m, 10H), 2.71 (s, 2H), 2.36 (s, 3H), 2.15 (m, 6H), 1.95 (s, 2H), 1.38 (t, 2H), 0.92 (m, 6H).

Example 222 tert-butyl 4-[(5-(4-{[2-(4-chlorophenyl)-4,4-dimethylcyclohex-1-en-1-yl]methyl}piperazin-1-yl)-2-{[({4-[(1-methylpiperidin-4-yl)amino]-3-nitrophenyl}sulfonyl)amino]carbonyl}phenoxy)methyl]-1,3-thiazol-2-ylcarbamate The title compound was prepared by substituting EXAMPLE 219D for EXAMPLE 1F and EXAMPLE 3I for EXAMPLE 1G respectively in EXAMPLE 1H. $^1$H NMR (300 MHz, dimethylsulfoxide-d$_6$) δ 0.96 (s, 6H) 1.37-1.54 (m, 12H) 1.60-1.79 (m, 2H) 1.97-2.08 (m, 3H) 2.15-2.30 (m, 7H) 2.38 (s, 3H) 2.78 (s, 2H) 2.91 (d, 2H) 3.17-3.26 (m, 5H) 3.69-3.84 (m, 1H) 5.08 (s, 2H) 6.48 (d, 1H) 6.53 (s, 1H) 7.07 (d, 2H) 7.17 (s, 1H) 7.23 (d, 1H) 7.37 (d, 2H) 7.43 (d, 1H) 7.90 (dd, 1H) 8.22 (d, 1H) 8.58 (d, 1H) 10.39 (s, 1H) 11.35 (s, 1H).

Example 223

2-[(2-amino-1,3-thiazol-4-yl)methoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 222 for EXAMPLE 1A in EXAMPLE 1B. $^1$H NMR (300 MHz, dimethylsulfoxide-d$_6$) δ 0.96 (s, 6H) 1.42 (t, 2H) 1.59-1.76 (m, 2H) 1.92-2.06 (m, 3H) 2.16-2.42 (m, 11H) 2.78 (s, 4H) 3.20-3.26 (m, 5H) 3.67-3.82 (m, 1H) 4.99 (s, 2H) 6.50 (d, 1H) 6.55 (s, 1H) 6.62 (s, 1H) 6.91 (s, 2H) 7.08 (d, 2H) 7.26 (d, 1H) 7.37 (d, 2H) 7.45 (d, 1H) 7.93 (dd, 1H) 8.24 (d, 1H) 8.60 (d, 1H).

Example 224

2-[3-(acetylamino)phenoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 224A methyl 2-(3-acetamidophenoxy)-4-(4-((4'-chlorobiphenyl-2-yl)methyl)piperazin-1-yl)benzoate The title compound was prepared by substituting 3-acetamidophenol for EXAMPLE 1D in EXAMPLE 1E.

Example 224B 2-(3-acetamidophenoxy)-4-(4-((4'-chlorobiphenyl-2-yl)methyl)piperazin-1-yl)benzoic acid The title compound was prepared by substituting EXAMPLE 224A for EXAMPLE 1E in EXAMPLE 1F.

Example 224C

2-[3-(acetylamino)phenoxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 224B for EXAMPLE 1F in EXAMPLE 1H. $^1$H NMR (300 MHz, dimethylsulfoxide-$d_6$) δ 11.48 (s, 1H), 9.89 (s, 1H), 8.59 (m, 1H), 8.50 (d, 1H), 7.71 (dd, 1H), 7.47 (m, 6H), 7.36 (m, 2H), 7.24 (m, 2H), 7.14 (m, 3H), 6.75 (dd, 1H), 6.50 (dd, 1H), 6.39 (d, 1H), 3.86 (dd, 2H), 3.37 (m, 2H), 3.30 (m, 6H), 3.16 (m, 4H), 2.35 (s, 4H), 2.00 (s, 3H), 1.89 (m, 1H), 1.63 (dd, 2H), 1.27 (m, 2H).

Example 225

2-[3-(acetylamino)phenoxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 224B for EXAMPLE 1F and EXAMPLE 49C for EXAMPLE 1G in EXAMPLE 1H. $^1$H NMR (300 MHz, dimethylsulfoxide-$d_6$) δ 9.86 (s, 1H), 8.45 (d, 1H), 8.15 (d, 1H), 7.70 (dd, 1H), 7.54 (d, 1H), 7.36 (d, 2H), 7.29 (d, 1H), 7.09 (m, 4H), 6.98 (m, 1H), 6.70 (dd, 1H), 6.45 (dd, 1H), 6.33 (d, 1H), 3.95 (dd, 2H), 3.83 (m, 1H), 3.36 (m, 3H), 3.24 (m, 2H), 3.11 (m, 4H), 2.77 (m, 4H), 2.17 (m, 8H), 1.98 (m, 5H), 1.66 (m, 6H), 1.40 (t, 2H), 0.94 (s, 6H).

Example 226

2-[(2-chlorophenyl)amino]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 226A methyl 4-(4-((2-(4-chlorophenyl)-4,4-dimethylcyclohex-1-enyl)methyl)piperazin-1-yl)-2-(2-chlorophenylamino)benzoate A solution of EXAMPLE 214A (500 mg), cesium carbonate (429 mg), palladium(II) acetate (21 mg), rac-BINAP (2,2'-bis(diphenylphosphino)-1,1'-binaphthyl) (58.5 mg) and toluene (6.4 mL) was degassed with $N_2$. The solution was stirred at 115° C. for 5 minutes. After cooling to room temperature, 2-chloroaniline (144 mg) was added and the reaction mixture was degassed again with $N_2$ and was stirred at 115° C. for 45 minutes. The solution was cooled to room temperature, diluted with ethyl acetate and was washed with water and brine, dried (MgSO$_4$), filtered and concentrated. The crude material was purified by flash chromatography on silica gel, eluting with dichloromethane/1% methanol.

Example 226B 4-(4-((2-(4-chlorophenyl)-4,4-dimethylcyclohex-1-enyl)methyl)piperazin-1-yl)-2-(2-chlorophenylamino)benzoic acid The title compound was prepared by substituting EXAMPLE 226A for EXAMPLE 1E in EXAMPLE 1F.

Example 226C 4-(4-((2-(4-chlorophenyl)-4,4-dimethylcyclohex-1-enyl)methyl)piperazin-1-yl)-2-(2-chlorophenylamino)-N-(3-nitro-4-(1-(tetrahydro-2H-pyran-4-yl)piperidin-4-ylamino)phenylsulfonyl)benzamide The title compound was prepared by substituting EXAMPLE 226B for EXAMPLE 1F and EXAMPLE 49C for EXAMPLE 1G in EXAMPLE 1H. $^1$H NMR (300 MHz, dimethylsulfoxide-$d_6$) δ 11.11 (br s, 1H), 9.15 (br s, 1H), 8.53 (d, 1H), 7.97-8.20 (m, 1H), 7.93 (d, 1H), 7.81 (d, 1H), 7.47 (d, 1H), 7.42 (dd, 1H), 7.36 (d, 2H), 7.22 (t, 1H), 7.15 (d, 1H), 7.07 (d, 2H), 6.89 (t, 1H), 6.52 (d, 1H), 6.34 (dd, 1H), 3.96 (d, 2H), 3.46-3.78 (m, 2H), 3.33-3.40 (m, 2H), 3.23-3.28 (m, 2H), 2.96-3.14 (m, 6H), 2.13-2.31 (m, 8H), 1.98 (br s, 6H), 1.65 (br s, 4H), 1.41 (t, 2H), 0.95 (s, 6H).

Example 227

4-(4-{[2-(4-chlorophenyl)-4,4-dimethylcyclohex-1-en-1-yl]methyl}piperazin-1-yl)-2-[(6-methoxy-1H-indol-5-yl)oxy]-N-({3-nitro-4-[(1-tetrahydro-2H-pyran-4-ylpiperidin-4-yl)amino]phenyl}sulfonyl)benzamide

Example 227A

6-Methoxy-1H-indol-5-ol 5-(benzyloxy)-6-methoxy-1H-indole (3.00 g) was added to methanol (100 mL) and ethyl acetate (100 mL) in a pressure bottle. Palladium hydroxide on carbon (0.832 g) was added and the solution was shaken under 30 psi of hydrogen at room temperature for 40 minutes. The mixture was filtered through a nylon membrane, the solvent removed under vacuum, the residue taken up in ethyl acetate, the solution was filtered over a pad of silica gel, and the solvent was removed from the filtrate under vacuum.

Example 227B

4-Fluoro-2-(6-methoxy-1H-indol-5-yloxy)-benzoic acid methyl ester

The title compound was prepared by substituting methyl 2,4-difluorobenzoate for ethyl 2,4-difluorobenzoate and EXAMPLE 227A for 2-methyl-5-indolol in EXAMPLE 3A.

Example 227C 2-(6-Methoxy-1H-indol-5-yloxy)-4-piperazin-1-yl-benzoic acid methyl ester The title compound was prepared by substituting piperazine for EXAMPLE 3F and EXAMPLE 227B for EXAMPLE 3A in EXAMPLE 3G.

Example 227D

4-{4-[2-(4-Chloro-phenyl)-4,4-dimethyl-cyclohex-1-enylmethyl]-piperazin-1-yl}-2-(6-methoxy-1H-indol-5-yloxy)-benzoic acid methyl ester The title compound was prepared by substituting EXAMPLE 60D for 4'-chlorobiphenyl-2-carboxaldehyde and EXAMPLE 227C for tert-butyl piperazine-1-carboxylate in EXAMPLE 1A.

Example 227E

4-{4-[2-(4-Chloro-phenyl)-4,4-dimethyl-cyclohex-1-enylmethyl]-piperazin-1-yl}-2-(6-methoxy-1H-indol-5-yloxy)-benzoic acid The title compound was prepared by substituting EXAMPLE 227D for EXAMPLE 1E in EXAMPLE 1F.

Example 227F 4-(4-{[2-(4-chlorophenyl)-4,4-dimethylcyclohex-1-en-1-yl]methyl}piperazin-1-yl)-2-[(6-methoxy-1H-indol-5-yl)oxy]-N-({3-nitro-4-[(1-tetrahydro-2H-pyran-4-ylpiperidin-4-yl)amino]phenyl}sulfonyl)benzamide The title compound was prepared by substituting EXAMPLE 227E for EXAMPLE 1F and EXAMPLE 49C for EXAMPLE 1G in EXAMPLE 1H. $^1$H NMR (300 MHz, dimethylsulfoxide-$d_6$) δ 11.02 (br s, 1H), 8.60 (d, 1H), 8.25 (d, 1H), 7.89 (dd, 1H), 7.54 (d, 1H), 7.33 (d, 2H), 7.29-7.26 (m, 2H), 7.21 (d, 1H), 7.09 (s, 1H), 7.04 (d, 2H), 6.59 (dd, 1H), 6.36 (t, 1H), 6.03 (d, 1H), 3.96-3.87 (m, 3H), 3.74 (s, 3H), 3.73 (m, 1H), 2.97 (m, 8H), 2.70 (br s, 2H), 2.13 (br s, 8H), 2.05-1.92 (m, 4H), 1.74 (m, 2H), 1.63 (m, 2H), 1.49 (m, 2H), 1.37 (t, 2H), 0.92 (s, 6H).

Example 229

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide

Example 229A methyl 2-(2-aminobenzo[d]thiazol-6-yloxy)-4-fluorobenzoate

The title compound was prepared by substituting 2-aminobenzo[d]thiazol-6-ol for 2-methyl-5-indolol in EXAMPLE 3A.

Example 229B methyl 2-(2-aminobenzo[d]thiazol-6-yloxy)-4-(4-((2-(4-chlorophenyl)-4,4-dimethylcyclohex-1-enyl)methyl)piperazin-1-yl)benzoate The title compound was prepared by substituting EXAMPLE 229A for EXAMPLE 3A in EXAMPLE 3G.

Example 229C methyl 2-(2-(tert-butoxycarbonylamino)benzo[d]thiazol-6-yloxy)-4-(4-((2-(4-chlorophenyl)-4,4-dimethylcyclohex-1-enyl)methyl)piperazin-1-yl)benzoate The title compound was prepared by substituting EXAMPLE 229B for EXAMPLE 219B in EXAMPLE 219C.

Example 229D 2-(2-(tert-butoxycarbonylamino)benzo[d]thiazol-6-yloxy)-4-(4-((2-(4-chlorophenyl)-4,4-dimethylcyclohex-1-enyl)methyl)piperazin-1-yl)benzoic acid The title compound was prepared by substituting EXAMPLE 229C for EXAMPLE 1E in EXAMPLE 1F.

Example 229E tert-butyl 6-(5-(4-((2-(4-chlorophenyl)-4,4-dimethylcyclohex-1-enyl)methyl)piperazin-1-yl)-2-(4-(1-methylpiperidin-4-ylamino)-3-nitrophenylsulfonylcarbamoyl)phenoxy)benzo[d]thiazol-2-ylcarbamate The title compound was prepared by substituting EXAMPLE 229D for EXAMPLE 1F and EXAMPLE 3I for EXAMPLE 1G respectively in EXAMPLE 1H.

Example 229F

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 229E for EXAMPLE 1A in EXAMPLE 1B. $^1$H NMR (300 MHz, dimethylsulfoxide-$d_6$) δ 0.93 (s, 6H) 1.39 (t, 2H) 1.62-1.80 (m, 2H) 1.91-2.24 (m, 10H) 2.50-2.62 (m, 4H) 2.74 (s, 4H) 2.97-3.18 (m, 5H) 3.66-3.82 (m, 1H) 6.24 (d, 1H) 6.64 (dd, 1H) 6.75 (dd, 1H) 6.92 (d, 1H) 7.01-7.12 (m, 3H) 7.20 (d, 1H) 7.31 (s, 2H) 7.35 (d, 2H) 7.52 (d, 1H) 7.61-7.71 (m, 1H) 8.09 (d, 1H) 8.44 (d, 1H).

Example 230

2-[(2-chlorophenyl)amino]-4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)benzamide The title compound was prepared by substituting EXAMPLE 226B for EXAMPLE 1F and EXAMPLE 3I for EXAMPLE 1G in EXAMPLE 1H. $^1$H NMR (300 MHz, dimethylsulfoxide-$d_6$) δ 11.11 (br s, 1H), 8.53 (d, 1H), 7.02 (br s, 1H), 7.94 (dd, 1H), 7.81 (d, 1H), 7.46 (dd, 1H), 7.42 (dd, 1H), 7.36 (d, 2H), 7.18-7.25 (m, 1H), 7.14 (d, 1H), 7.07 (d, 2H), 6.85-6.92 (m, 1H), 6.52 (d, 1H), 6.33 (dd, 1H), 3.88 (br s, 1H), 3.01-3.09 (m, 7H), 2.66-2.83 (m, 6H), 2.07-2.32 (m, 8H), 1.97 (br s, 3H), 1.78 (br s, 2H), 1.41 (t, 2H), 0.94 (s, 6H).

Example 231 tert-butyl 5-[5-(4-{[2-(4-chlorophenyl)-4,4-dimethyl-cyclohex-1-en-1-yl]methyl}piperazin-1-yl)-2-({[(4-{[3-(dimethylamino)propyl]amino}-3-nitrophenyl)sulfonyl]amino}carbonyl)phenoxy]-1H-indole-1-carboxylate

Example 231A ethyl 2-(1H-indol-5-yloxy)-4-fluorobenzoate

The title compound was prepared by substituting 5-hydroxyindole for 2-methyl-5-indolol in EXAMPLE 3A.

Example 231B ethyl 2-(1H-indol-5-yloxy)-4-(4-((2-(4-chlorophenyl)-4,4-dimethylcyclohex-1-enyl)methyl)piperazin-1-yl)benzoate The title compound was prepared by substituting EXAMPLE 231A for EXAMPLE 3A in EXAMPLE 3G.

Example 231C 2-(1H-indol-5-yloxy)-4-(4-((2-(4-chlorophenyl)-4,4-dimethylcyclohex-1-enyl)methyl)piperazin-1-yl)benzoic acid The title compound was prepared by substituting EXAMPLE 231B for EXAMPLE 1E in EXAMPLE 1F.

Example 231D 4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(1H-indol-5-yloxy)benzamide The title compound was prepared by substituting EXAMPLE 231C for EXAMPLE 1F and EXAMPLE 11A for EXAMPLE 1G in EXAMPLE 1H, except 2-10% methanol in $CH_2Cl_2$ was used for the chromatography.

Example 231E tert-butyl 5-[5-(4-{[2-(4-chlorophenyl)-4,4-dimethyl-cyclohex-1-en-1-yl]methyl}piperazin-1-yl)-2-({[(4-{[3-(dimethylamino)propyl]amino}-3-nitrophenyl)sulfonyl]amino}carbonyl)phenoxy]-1H-indole-1-carboxylate bis(2,2,2-trifluoroacetate)

The title compound was prepared by substituting EXAMPLE 231D for EXAMPLE 202D in EXAMPLE 202E. $^1$H NMR (500 MHz, dimethylsulfoxide-$d_6$) δ 11.63 (v br s, 1H), 9.40 (v br s, 2H), 8.61 (br t, 1H), 8.53 (d, 1H), 8.00 (d, 1H), 7.85 (dd, 1H), 7.70 (d, 1H), 7.54 (d, 1H), 7.40 (d, 2H), 7.10 (m, 4H), 6.97 (dd, 1H), 6.76 (dd, 1H), 6.43 (d, 1H), 6.33 (d, 1H), 3.60, 3.50, 3.30 (all v br m, total 10H), 3.10 (br m, 4H), 2.79, 2.77 (both s, total 6H), 2.20 (br m, 2H), 2.04 (s, 2H), 1.85 (br m, 2H), 1.66 (s, 9H), 1.45 (br t, 2H), 0.95 (s, 6H).

Example 232

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 232A tert-butyl 6-(5-(4-((2-(4-chlorophenyl)-4,4-dimethyl-cyclohex-1-enyl)methyl)piperazin-1-yl)-2-(3-nitro-4-(1-(tetrahydro-2H-pyran-4-yl)piperidin-4-ylamino)phenylsulfonylcarbamoyl)phenoxy)benzo[d]thiazol-2-ylcarbamate The title compound was prepared by substituting EXAMPLE 229D for EXAMPLE 1F and EXAMPLE 49C for EXAMPLE 1G respectively in EXAMPLE 1H.

Example 232B

2-[(2-amino-1,3-benzothiazol-6-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 232A for EXAMPLE 1A in EXAMPLE 1B. $^1$H NMR (300 MHz, dimethylsulfoxide-d) δ 0.95 (s, 6H) 1.44 (br. s, 2H) 1.61-1.89 (m, 3H) 1.90-2.12 (m, 5H) 2.13-2.32 (m, 4H) 2.36-2.63 (m, 2H) 2.97-3.78 (m, 16H) 4.01 (dd, 2H) 6.30 (s, 1H) 6.72 (d, 1H) 6.84 (d, 1H) 7.11 (m, 3H) 7.18-7.32 (m, 2H) 7.33-7.55 (m, 5H) 7.68-7.89 (m, 1H) 8.17 (d, 1H) 8.57 (d, 1H) 9.25 (br. s, 1H) 11.62 (br. s, 1H).

Example 233

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[3-(3-oxopiperazin-1-yl)propyl]amino}phenyl)sulfonyl]benzamide The title compound was prepared by substituting EXAMPLE 154E for EXAMPLE 122C and EXAMPLE 254A for EXAMPLE 11A in EXAMPLE 137. $^1$H NMR (500 MHz, dimethylsulfoxide-$d_6$) δ 11.20 (br s, 1H), 8.62 (br t, 1H), 8.57 (d, 1H), 7.83 (dd, 1H), 7.75 (s, 1H), 7.51 (d, 1H), 7.37 (dd, 1H), 7.34 (m, 3H), 7.26 (d, 1H), 7.08 (d, 1H), 7.04 (d, 2H), 6.63 (dd, 1H), 6.40 (s, 1H), 6.09 (s, 1H), 3.43 (dd, 2H), 3.18 (br m, 2H), 3.04 (br m, 4H), 2.95 (s, 2H), 2.70 (s, 2H), 2.55 (t, 2H), 2.45 (t, 2H), 2.17 (br m, 6H), 1.95 (s, 2H), 1.79 (m, 2H), 1.38 (t, 2H), 0.92 (s, 6H).

Example 234

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide The title compound was prepared by substituting EXAMPLE 154E for EXAMPLE 122C and EXAMPLE 205A for EXAMPLE 11A in EXAMPLE 137. $^1$H NMR (500 MHz, dimethylsulfoxide-$d_6$) δ 11.20 (s, 1H), 8.54 (s, 1H), 8.17 (br d, 1H), 7.84 (d, 1H), 7.52 (d, 1H), 7.34 (m, 4H), 7.24 (br d, 1H), 7.11 (br d, 1H), 7.04 (d, 2H), 6.64 (d, 1H), 6.40 (s, 1H), 6.09 (s, 1H), 3.62 (br m, 4H), 3.58 (v br s, 1H), 3.00 (br m, 4H), 2.73 (s, 2H), 2.65 (br m, 4H), 2.47 (v br s, 1H), 2.18 (br m, 6H), 2.06 (br m, 2H), 1.93 (br m, 4H), 1.40 (m, 6H), 0.92 (s, 6H).

Example 235

Trans-4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({4-[(4-morpholin-4-ylcyclohexyl)amino]-3-nitrophenyl}sulfonyl)benzamide The title compound was prepared by substituting EXAMPLE 200F for EXAMPLE 122C and EXAMPLE 205A for EXAMPLE 11A in EXAMPLE 137. $^1$H NMR (500 MHz, dimethylsulfoxide-$d_6$) δ 11.72 (s, 1H), 8.46 (s, 1H), 8.15 (br d, 1H), 7.78 (d, 1H), 7.52 (d, 1H), 7.40 (dd, 1H), 7.34 (d, 2H), 7.06 (br d, 1H), 7.05 (d, 2H), 6.91 (br d, 1H), 6.66 (br d, 1H), 6.40 (s, 1H), 6.25 (d, 1H), 3.62 (br m, 4H), 3.58 (v br s, 1H), 3.00 (br m, 4H), 2.73 (s, 2H), 2.65 (br m, 4H), 2.47 (v br s, 1H), 2.18 (br m, 6H), 2.06 (br m, 2H), 1.93 (br m, 4H), 1.40 (m, 6H), 0.92 (s, 6H).

Example 236

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6-fluoro-1H-indol-5-yl)oxy]benzamide

Example 236A tert-butyl 1-(cyclopropylmethyl)piperidin-4-ylcarbamate

The title compound was prepared by substituting cyclopropanecarbaldehyde for 4'-chlorobiphenyl-2-carboxaldehyde and tert-butyl piperidin-4-ylcarbamate for tert-butyl piperazine-1-carboxylate in EXAMPLE 1A.

Example 236B 1-(cyclopropylmethyl)piperidin-4-amine bis(2,2,2-trifluoroacetate)

The title compound was prepared by substituting EXAMPLE 236A for EXAMPLE 1A in EXAMPLE 1B.

Example 236C 4-(1-(cyclopropylmethyl)piperidin-4-ylamino)-3-nitrobenzenesulfonamide The title compound was prepared by substituting EXAMPLE 236B for 4-(1-isopropylpiperidin-4-ylamino)-3-nitrobenzenesulfonamide in EXAMPLE 41A.

Example 236D 4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6-fluoro-1H-indol-5-yl)oxy]benzamide The title compound was prepared by substituting EXAMPLE 154E for EXAMPLE 1F and EXAMPLE 236C for EXAMPLE 1G in EXAMPLE 1H. $^1$H NMR (500 MHz, pyridine-$d_5$) δ 12.39 (s, 1H), 9.31 (d, 1H), 8.49 (d, 1H), 8.45 (dd, 1H), 8.15 (d, 1H), 7.47-7.52 (m, 3H), 7.41-7.45 (m, 3H), 7.04 (d, 2H), 6.98 (d, 1H), 6.71 (dd, 1H), 6.57 (dd, 2H), 3.48-3.55 (m, 1H), 3.01-3.07 (m, 4H), 2.86 (d, 2H), 2.74 (s, 2H), 2.21-2.26 (m, 2H), 2.19 (d, 4H), 2.07-2.13 (m, 4H), 1.93-2.00 (m, 4H), 1.63-1.71 (m, 2H), 1.38 (t, 2H), 0.93 (s, 6H), 0.84-0.91 (m, 1H), 0.45-0.49 (m, 2H), 0.11 (q, 2H).

Example 237

4-(4-{[2-(4-chlorophenyl)-4,4-dimethylcyclohex-1-en-1-yl]methyl}piperazin-1-yl)-N-[(4-{[1-(cyclopropylmethyl)piperidin-4-yl]amino}-3-nitrophenyl)sulfonyl]-2-[(6,7-difluoro-1H-indol-5-yl)oxy]benzamide The title compound was prepared by substituting EXAMPLE 200F for EXAMPLE 1F and EXAMPLE 236C for EXAMPLE 1G in EXAMPLE 1H. $^1$H NMR (500 MHz, pyridine-$d_5$) δ 13.12 (s, 1H), 9.29 (d, 1H), 8.49 (d, 1H), 8.46 (dd, 1H), 8.11 (d, 1H), 7.42 (d, 2H), 7.19 (s, 1H), 7.04 (d, 2H), 6.98 (d, 1H), 6.75 (dd, 1H), 6.66 (d, 1H), 6.51-6.54 (m, 1H), 3.50-3.55 (m, 1H), 3.07-3.13 (m, 4H), 2.83-2.87 (m, 2H), 2.76 (s, 2H), 2.25 (t, 2H), 2.11-2.23 (m, 8H), 1.93-2.00 (m, 4H), 1.63-1.71 (m, 2H), 1.38 (t, 2H), 0.92 (s, 6H), 0.84-0.90 (m, 1H), 0.44-0.49 (m, 2H), 0.08-0.12 (m, 2H).

Example 238

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide The title compound was prepared by substituting EXAMPLE 154E for EXAMPLE 1F in EXAMPLE 1H. $^1$H NMR (500 MHz, dimethylsulfoxide-$d_6$) δ 11.23 (s, 1H), 8.63 (t, 1H), 8.60 (d, 1H), 7.87 (dd, 1H), 7.51 (d, 1H), 7.38 (t, 1H), 7.30-7.34 (m, 4H), 7.17 (d, 1H), 7.03 (d, 2H), 6.66 (dd, 1H), 6.41 (s, 1H), 6.09 (s, 1H), 3.85 (dd, 2H), 3.26 (t, 2H), 3.03 (s, 4H), 2.74 (s, 2H), 2.12-2.19 (m, 6H), 1.94 (s, 2H), 1.87-1.90 (m, 1H), 1.62 (d, 2H), 1.38 (t, 2H), 1.22-1.30 (m, 2H), 0.92 (s, 6H).

Example 239

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-[(3-nitro-4-{[3-(3-oxopiperazin-1-yl)propyl]amino}phenyl)sulfonyl]benzamide The title compound was prepared by substituting EXAMPLE 200F for EXAMPLE 122C and EXAMPLE 254A for EXAMPLE 11A in EXAMPLE 137. $^1$H NMR (500 MHz, dimethylsulfoxide-$d_6$) δ 11.68 (br s, 1H), 8.70 (v br s, 1H), 8.46 (s, 1H), 7.74 (s, 1H), 7.73 (br s, 1H), 7.52 (d, 1H), 7.37 (dd, 1H), 7.34 (d, 2H), 7.05 (d, 2H), 7.95 (v br s, 1H), 6.83 (v br s, 1H), 6.67 (dd, 1H), 6.39 (s, 1H), 6.25 (d, 1H), 3.44 (q, 2H), 3.18 (br m, 2H), 3.04 (br m, 4H), 2.97 (s, 2H), 2.73 (s, 2H), 2.57 (t, 2H), 2.47 (t, 2H), 2.18 (br m, 6H), 1.95 (s, 2H), 1.88 (m, 2H), 1.37 (t, 2H), 0.91 (s, 6H).

Example 240

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-hydroxy-1-tetrahydro-2H-pyran-4-ylethyl)amino]-3-nitrophenyl}sulfonyl)benzamide

Example 240A

N-(4-chloro-3-nitrophenylsulfonyl)-4-(4-((2-(4-chlorophenyl)-4,4-dimethylcyclohex-1-enyl)methyl)piperazin-1-yl)-2-(6-fluoro-1H-indol-5-yloxy)benzamide The title compound was prepared by substituting EXAMPLE 154E for EXAMPLE 122C and 4-chloro-3-nitrobenzenesulfonamide for EXAMPLE 11A in EXAMPLE 137.

Example 240B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-hydroxy-1-tetrahydro-2H-pyran-4-ylethyl)amino]-3-nitrophenyl}sulfonyl)benzamide EXAMPLE 240A (150 mg) was dissolved in dioxane (1.8 mL), then 2-amino-2-(tetrahydro-2H-pyran-4-yl)ethanol (35 mg) and triethylamine (0.078 mL) were added. The reaction was heated at 110° C. for 20 hours. The reaction was concentrated and the crude was purified by preparative HPLC using a C18 column, 250×50 mm, 10, and eluting with a gradient of 20-100% $CH_3CN$ vs. 0.1% trifluoroacetic acid in water, giving the product as a trifluoroacetate salt. The salt was dissolved in dichloromethane (6 mL) and washed with 50% aqueous $NaHCO_3$. The organic layer was dried over anhydrous $Na_2SO_4$, filtered, and concentrated to give the title compound. $^1$H NMR (500 MHz, dimethylsulfoxide-$d_6$) δ 11.23 (s, 1H), 8.60 (d, 1H), 8.58 (d, 1H), 7.84 (dd, 1H), 7.52 (d, 1H), 7.39 (dd, 1H), 7.33 (m, 4H), 7.29 (d, 1H), 7.04 (d, 2H), 6.64 (dd, 1H), 6.42 (s, 1H), 6.08 (s, 1H), 5.03 (t, 1H), 3.85 (m, 2H), 3.74 (m, 1H), 3.63 (m, 1H), 3.57 (m, 1H), 3.26 (dd, 2H), 3.02 (br m, 4H), 2.73 (s, 2H), 2.18 (br m, 6H), 1.95 (s, 2H), 1.94 (m, 1H), 1.61 (br m, 2H), 1.38 (m, 3H), 1.30 (m, 1H), 0.92 (s, 6H).

Example 241

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-({[4-(hydroxymethyl)tetrahydro-2H-pyran-4-yl]methyl}amino)-3-nitrophenyl]sulfonyl}benzamide

Example 241A 4-((4-(hydroxymethyl)tetrahydro-2H-pyran-4-yl)methylamino)-3-nitrobenzenesulfonamide The title compound was prepared by substituting (4-(aminomethyl)tetrahydro-2H-pyran-4-yl)methanol for (tetrahydropyran-4-yl)methylamine in EXAMPLE 1G.

Example 241B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-({[4-(hydroxymethyl)tetrahydro-2H-pyran-4-yl]methyl}amino)-3-nitrophenyl]sulfonyl}benzamide The title compound was prepared by substituting EXAMPLE 154E for EXAMPLE 1F and EXAMPLE 241 A for EXAMPLE 1G in EXAMPLE 1H. $^1$H NMR (500 MHz, dimethylsulfoxide-$d_6$) δ 11.22 (s, 2H), 9.10 (t, 1H), 8.59 (d, 1H), 7.87 (dd, 1H), 7.51 (d, 1H), 7.30-7.39 (m, 5H), 7.24 (d, 1H), 7.02-7.05 (m, 2H), 6.66 (dd, 1H), 6.41 (s, 1H), 6.08 (s, 1H), 5.22 (t, 1H), 3.51-3.62 (m, 6H), 3.41 (d, 2H), 3.03 (s, 4H), 2.73 (s, 2H), 2.09-2.18 (m, 6H), 1.95 (s, 2H), 1.45-1.51 (m, 4H), 1.38 (t, 2H), 0.92 (s, 6H).

Example 242

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 242A ethyl 2-(4-amino-2-chlorophenoxy)-4-fluorobenzoate

To a solution of ethyl 2,4-difluorobenzoate (6.48 g) and 4-amino-2-chlorophenol (5.0 g) in diglyme (40 mL) was added $K_3PO_4$ (7.39 g). The mixture was stirred at 110° C. overnight. The mixture was diluted with ethyl acetate (300 mL) and washed with water, brine and dried over $Na_2SO_4$. The mixture was filtered, and the solvent was evaporated and the residue was loaded on a column and eluted with 10% ethyl acetate in hexane to give the product.

Example 242B ethyl 2-(4-amino-2-chloro-5-iodophenoxy)-4-fluorobenzoate

To a solution of EXAMPLE 242A (8.15 g) in dichloromethane (60 mL) was added bis(pyridine)iodonium tetrafluoroborate (9.79 g). The mixture was stirred at room temperature for 4 hours. The mixture was diluted with ethyl acetate (200 mL) and washed with aqueous $Na_2S_2O_3$, water, brine and dried over $Na_2SO_4$. The mixture was filtered, and the solvent was evaporated and the residue was loaded on a column and eluted with 10% ethyl acetate in hexane to give the pure product.

Example 242C ethyl 2-(4-amino-2-chloro-5-((trimethylsilyl)ethynyl)phenoxy)-4-fluorobenzoate To a mixture of EXAMPLE 242B (3.0 g), bis(triphenylphosphine)palladium(II) dichloride (242 mg), CuI (66 mg) in triethylamine (30 mL) was added trimethylsilylacetylene (2.2 g). The mixture was stirred at room temperature overnight. The mixture was diluted with ethyl acetate (200 mL) and washed with aqueous $NH_4Cl$, water, brine and dried over $Na_2SO_4$. The mixture was filtered, and the solvent was evaporated and the residue was loaded on a column and eluted with 10% ethyl acetate in hexane to give the pure product.

Example 242D ethyl 2-(4-amino-2-chloro-5-ethynylphenoxy)-4-fluorobenzoate

To a solution of EXAMPLE 242C (2.69 g) in methanol (20 mL) was added CsF (5 g). The mixture was stirred at room temperature overnight. The solvent was evaporated and the residue was dissolved in ethyl acetate (200 mL) and washed with water, brine and dried over $Na_2SO_4$. The mixture was filtered, and the solvent was evaporated.

Example 242E ethyl 2-(6-chloro-1H-indol-5-yloxy)-4-fluorobenzoate

To a solution of EXAMPLE 242D (1.0 g) in ethanol (20 mL) was added $NaAuCl_4 \cdot 2H_2O$ (60 mg). The mixture was stirred at room temperature for 4 hours. The mixture was diluted with ethyl acetate (200 mL) and washed with water, brine and dried over $Na_2SO_4$. The mixture was filtered, and the solvent was evaporated and the residue was loaded on a column and eluted with 10% ethyl acetate in hexane to give the pure product.

Example 242F ethyl 2-(6-chloro-1H-indol-5-yloxy)-4-(piperazin-1-yl)benzoate

The title compound was prepared as described in EXAMPLE 3G by replacing EXAMPLE 3F and EXAMPLE 3A with piperazine and EXAMPLE 242E respectively.

Example 242G ethyl 2-(6-chloro-1H-indol-5-yloxy)-4-(4-((2-(4-chlorophenyl)-4,4-dimethylcyclohex-1-enyl)methyl)piperazin-1-yl)benzoate The title compound was prepared as described in EXAMPLE 38G by replacing EXAMPLE 38F and EXAMPLE 38E with EXAMPLE 242F and EXAMPLE 60D.

Example 242H 2-(6-chloro-1H-indol-5-yloxy)-4-(4-((2-(4-chlorophenyl)-4,4-dimethylcyclohex-1-enyl)methyl)piperazin-1-yl)benzoic acid The title compound was prepared as described in EXAMPLE 38H by replacing EXAMPLE 38G with EXAMPLE 242G.

Example 242I

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared as described in EXAMPLE 1H by replacing EXAMPLE 1F and EXAMPLE 1G with EXAMPLE 242H and EXAMPLE 49C, respectively. $^1$H NMR (300 MHz, dimethylsulfoxide-$d_6$) δ 11.20 (s, 1H), 8.52 (m, 1H), 8.18 (d, 1H), 7.83 (dd, 1H), 7.53 (m, 2H), 7.40 (m, 1H), 7.33 (d, 3H), 7.18 (m, 1H), 7.04 (m, 4H), 6.62 (m, 1H), 6.38 (s, 1H), 6.01 (d, 1H), 3.92 (m, 2H), 3.77 (m, 1H), 3.13 (m, 8H), 2.71 (s, 2H), 2.24 (m, 8H), 1.95 (m, 6H), 1.52 (m, 6H), 0.94 (s, 6H).

Example 243

4-(4-{[2-(4-chlorophenyl)-4,4-dimethylcyclohex-1-en-1-yl]methyl}piperazin-1-yl)-2-[(6,7-difluoro-1H-indol-5-yl)oxy]-N-({3-nitro-4-[(tetrahydro-2H-pyran-4-ylmethyl)amino]phenyl}sulfonyl)benzamide The title compound was prepared as described in EXAMPLE 1H by replacing EXAMPLE 1F with EXAMPLE 200F. $^1$H NMR (300 MHz, dimethylsulfoxide-$d_6$) δ 11.75 (s, 1H), 8.59 (t, 1H), 8.53 (d, 1H), 7.82 (dd, 1H), 7.49 (d, 1H), 7.41 (m, 1H), 7.34 (d, 3H), 7.12 (d, 1H), 7.04 (d, 2H), 6.98 (d, 1H), 6.69 (dd, 1H), 6.43 (d, 1H), 6.24 (d, 1H), 3.85 (m, 2H), 3.07 (m, 5H), 2.74 (m, 2H), 2.23 (m, 6H), 1.92 (m, 5H), 1.60 (m, 3H), 1.30 (m, 4H), 0.94 (s, 6H).

Example 244

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared as described in EXAMPLE 1H by replacing EXAMPLE 1F and EXAMPLE 1G with EXAMPLE 242H and EXAMPLE 184A, respectively. $^1$H NMR (300 MHz, dimethylsulfoxide-$d_6$) δ 11.24 (s, 1H), 9.19 (s, 1H), 8.52 (d, 1H), 7.88 (dd, 1H), 7.56 (m, 3H), 7.42 (t, 1H), 7.31 (m, 3H), 7.03 (d, 2H), 6.63 (dd, 1H), 6.41 (s, 1H), 5.98 (d, 1H), 2.94 (m, 10H), 2.70 (s, 3H), 2.37 (m, 3H), 2.14 (m, 6H), 1.94 (s, 2H), 1.37 (t, 2H), 0.91 (s, 6H).

Example 245

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[1-(1,3-thiazol-4-ylmethyl)piperidin-4-yl]amino}phenyl)sulfonyl]benzamide

Example 245A tert-butyl 1-(thiazol-4-ylmethyl)piperidin-4-ylcarbamate

The title compound was prepared by substituting thiazole-4-carbaldehyde for 4'-chlorobiphenyl-2-carbaldehyde and tert-butyl piperidin-4-ylcarbamate for tert-butyl piperazine-1-carboxylate in EXAMPLE 1A

Example 245B

The title compound was prepared by substituting EXAMPLE 245A for EXAMPLE 1A in EXAMPLE 1B.

Example 245C 3-nitro-4-(1-(thiazol-4-ylmethyl)piperidin-4-ylamino)benzenesulfonamide The title compound was prepared by substituting EXAMPLE 245B for (tetrahydropyran-4-yl)methylamine in EXAMPLE 1G.

Example 245D 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[1-(1,3-thiazol-4-ylmethyl)piperidin-4-yl]amino}phenyl)sulfonyl]benzamide The title compound was prepared by substituting EXAMPLE 154E for EXAMPLE 1F and EXAMPLE 245C for EXAMPLE 1G in EXAMPLE 1H. $^1$H NMR (500 MHz, dimethylsulfoxide-$d_6$) δ 11.16 (s, 1H), 9.08 (s, 1H), 8.20 (s, 1H), 7.91 (s, 1H), 7.82 (d, 1H), 7.29-7.34 (m, 4H), 7.18 (d, 1H), 7.15 (m, 1H), 7.04 (d, 2H), 6.60 (dd, 1H), 6.37 (s, 1H), 6.08 (s, 1H), 4.28 (s, 2H), 2.90-2.98 (m, 8H), 2.72 (s, 2H), 2.14-2.17 (m, 6H), 2.01 (m, 2H), 1.95 (s, 2H), 1.53-1.55 (m, 2H), 1.38 (t, 2H), 0.92 (s, 6H).

Example 246

2-(3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 36C for EXAMPLE 1F in EXAMPLE 1H. $^1$H NMR (500 MHz, dimethylsulfoxide-$d_6$) δ 8.60 (t, 1H), 8.42 (d, 1H), 7.71 (dd, 1H), 7.51 (d, 1H), 7.36 (d, 2H), 7.19 (t, 1H), 7.10 (d, 1H), 7.07 (d, 2H), 6.93 (dd, 1H), 6.79 (dd, 1H), 6.72 (dd, 1H), 6.69 (t, 1H), 6.47 (d, 1H), 3.87 (dd, 2H), 3.21-3.32 (m, 4H), 3.20 (s, 4H), 2.81 (s, 2H), 2.27 (s, 4H), 2.16 (br s, 2H), 1.90-1.98 (m, 3H), 1.63-1.66 (m, 2H), 1.41 (t, 2H), 1.27-1.30 (m, 2H), 0.94 (s, 6H).

Example 247

2-(4-amino-3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 40C for EXAMPLE 1F in EXAMPLE 1H. $^1$H NMR (500 MHz, dimethylsulfoxide-$d_6$) δ 11.12 (s, 1H), 8.50 (d, 2H), 7.84 (dd, 1H), 7.58 (d, 1H), 7.32-7.34 (m, 2H), 7.28 (d, 1H), 7.15 (d, 1H), 7.10 (d, 1H), 7.04 (d, 2H), 6.58 (dd, 1H), 6.34 (s, 1H), 6.07 (d, 1H), 3.63-3.70 (m, 6H), 2.96 (s, 4H), 2.71 (s, 2H), 2.12-2.16 (m, 6H), 1.95 (s, 2H), 1.72-1.76 (m, 2H), 1.55-1.60 (m, 2H), 1.38 (t, 2H), 0.94 (s, 6H).

Example 248

N-[(4-{[(4-aminotetrahydro-2H-pyran-4-yl)methyl]amino}-3-nitrophenyl)sulfonyl]-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 1F and EXAMPLE 191A for EXAMPLE 1G in EXAMPLE 1H. $^1$H NMR (500 MHz, dimethylsulfoxide-$d_6$) δ 11.12 (s, 1H), 8.50 (d, 1H), 7.84 (dd, 1H), 7.32-7.34 (m, 3H), 7.28 (d, 1H), 7.15 (d, 1H), 7.11 (d, 1H), 7.04 (d, 2H), 6.58 (dd, 1H), 6.34 (s, 1H), 6.07 (d, 1H), 3.85-3.89 (m, 4H), 3.61-3.63 (m, 2H), 3.66-3.69 (m, 4H), 3.48-3.51 (m, 2H), 2.96 (s, 4H), 2.71 (s, 2H), 2.14-2.18 (m, 6H), 1.95 (s, 2H), 1.72-1.76 (m, 2H), 1.57-1.70 (m, 2H), 1.38 (t, 2H), 0.92 (s, 6H).

Example 249

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(3S,4R)-3-hydroxy-1-(1,3-thiazol-4-ylmethyl)piperidin-4-yl]amino}-3-nitrophenyl)sulfonyl]benzamide

Example 249A

A mixture of tert-butyl (3S,4R)-1-benzyl-3-hydroxypiperidin-4-ylcarbamate (0.42 g) and palladium hydroxide on carbon (0.095 g) in ethanol (15 mL) was hydrogenated with a balloon of $H_2$. The reaction mixture was stirred for 16 hours. The solid was filtered off, and the filtrate was concentrated to give the title compound.

Example 249B tert-butyl (3R,4S)-3-hydroxy-1-(thiazol-4-ylmethyl)piperidin-4-ylcarbamate The title compound was prepared by substituting thiazole-4-carbaldehyde for 4'-chlorobiphenyl-2-carbaldehyde and EXAMPLE 249A for tert-butyl piperazine-1-carboxylate in EXAMPLE 1A.

Example 249C (3R,4S)-4-amino-1-(thiazol-4-ylmethyl)piperidin-3-ol

The title compound was prepared by substituting EXAMPLE 249B for EXAMPLE 1A in EXAMPLE 1B.

Example 249D 4-((3S,4R)-3-hydroxy-1-(thiazol-4-ylmethyl)piperidin-4-ylamino)-3-nitrobenzenesulfonamide The title compound was prepared by substituting EXAMPLE 249C for (tetrahydropyran-4-yl)methylamine in EXAMPLE 1G.

Example 249E 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(3S,4R)-3-hydroxy-1-(1,3-thiazol-4-ylmethyl)piperidin-4-yl]amino}-3-nitrophenyl)sulfonyl]benzamide The title compound was prepared by substituting EXAMPLE 154E for EXAMPLE 1F and EXAMPLE 249D for EXAMPLE 1G in EXAMPLE 1H. $^1$H NMR (500 MHz, dimethylsulfoxide-$d_6$) δ 11.20 (s, 1H), 8.64 (t, 1H), 9.07-9.09 (m, 1H), 8.60 (s, 1H), 8.57 (s, 1H), 7.82 (d, 1H), 7.80 (s, 1H), 7.51 (d, 1H), 7.19-7.32 (m, 6H), 7.04 (d, 2H), 6.62-6.64 (m, 2H), 6.39 (s, 1H), 6.08 (s, 1H), 3.82 (m, 2H), 3.01 (s, 4H), 2.77 (s, 2H), 2.12-2.16 (m, 6H), 1.81 (m, 2H), 1.38 (t, 2H), 0.92 (s, 6H).

Example 250

2-(2-chlorophenoxy)-4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide

Example 250A 4-((4-(hydroxymethyl)tetrahydro-2H-pyran-4-yl)methylamino)-3-nitrobenzenesulfonamide The title compound was prepared by substituting (4-(aminomethyl)tetrahydro-2H-pyran-4-yl)methanol for (tetrahydropyran-4-yl)methylamine in EXAMPLE 1G.

Example 250B 2-(2-chlorophenoxy)-4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide The title compound was prepared by substituting EXAMPLE 34C for EXAMPLE 1F and EXAMPLE 250A for EXAMPLE 1G in EXAMPLE 1H. $^1$H NMR (500 MHz, dimethylsulfoxide-$d_6$) δ 9.11 (s, 1H), 8.44 (d, 1H), 7.72 (dd, 1H), 7.50 (d, 1H), 7.36 (d, 2H), 7.17-7.20 (m, 2H), 7.07 (d, 2H), 6.95 (dd, 2H), 6.78 (dd, 1H), 6.72 (dd, 1H), 6.69 (t, 1H), 6.48 (d, 1H), 5.24 (t, 1H), 3.54-3.65 (m, 6H), 3.42 (d, 2H), 3.21 (s, 4H), 2.84 (s, 2H), 2.26-2.34 (m, 4H), 2.17-2.19 (m, 2H), 1.48-1.55 (m, 4H), 0.95 (s, 6H).

Example 251

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylamino)phenyl]sulfonyl}benzamide The title compound was prepared by substituting tetrahydro-2H-pyran-4-amine for 2-amino-2-(tetrahydro-2H-pyran-4-yl)ethanol in EXAMPLE 240B. $^1$H NMR (500 MHz, dimethylsulfoxide-$d_6$) δ 11.21 (s, 1H), 8.58 (d, 1H), 8.24 (d, 1H), 7.84 (dd, 1H), 7.52 (d, 1H), 7.38 (dd, 1H), 7.33 (m, 3H), 7.29 (d, 1H), 7.23 (d, 1H), 7.03 (d, 2H), 6.64 (dd, 1H), 6.40 (s, 1H), 6.08 (s, 1H), 3.90 (m, 3H), 3.47 (m, 2H), 3.03 (br m, 4H), 2.73 (s, 2H), 2.19 (br m, 6H), 1.95 (s, 2H), 1.91 (br m, 2H), 1.60 (m, 2H), 1.38 (t, 2H), 0.92 (s, 6H).

Example 252

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-(morpholin-4-ylamino)-3-nitrophenyl]sulfonyl}benzamide

Example 252A 4-(morpholinoamino)-3-nitrobenzenesulfonamide

The title compound was prepared by substituting morpholin-4-amine for 4-(1-isopropylpiperidin-4-ylamino)-3-nitrobenzenesulfonamide in EXAMPLE 41A.

Example 252B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[4-(morpholin-4-ylamino)-3-nitrophenyl]sulfonyl}benzamide The title compound was prepared by substituting EXAMPLE 154E for EXAMPLE 1F and EXAMPLE 252A for EXAMPLE 1G in EXAMPLE 1H. $^1$H NMR (500 MHz, pyridine-$d_5$) δ 12.38 (s, 1H), 9.26-9.30 (m, 2H), 8.48 (dd, 1H), 8.14 (d, 1H), 7.71 (d, 1H), 7.51 (t, 1H), 7.46-7.50 (m, 2H), 7.41-7.45 (m, 3H), 7.04 (d, 2H), 6.71 (dd, 1H), 6.54-6.58 (m, 2H), 3.86 (s, 2H), 3.71 (s, 2H), 3.01-3.07 (m, 4H), 2.89 (d, 4H), 2.74 (s, 2H), 2.23 (t, 2H), 2.07-2.13 (m, 4H), 1.96 (s, 2H), 1.38 (t, 2H), 0.92 (s, 6H).

Example 253

2-(3-chlorophenoxy)-4-(4-{[2-(4-chlorophenyl)-4,4-dimethylcyclohex-1-en-1-yl]methyl}piperazin-1-yl)-N-{[4-(morpholin-4-ylamino)-3-nitrophenyl]sulfonyl}benzamide The title compound was prepared by substituting EXAMPLE 36C for EXAMPLE 1F and EXAMPLE 252A for EXAMPLE 1G in EXAMPLE 1H. $^1$H NMR (500 MHz, pyridine-$d_5$) δ 9.26 (s, 1H), 9.13 (d, 1H), 8.31 (dd, 1H), 8.09 (d, 1H), 7.67 (d, 1H), 7.46 (d, 2H), 7.10-7.16 (m, 3H), 7.08 (t, 1H), 7.02 (d, 1H), 6.93 (dd, 1H), 6.82 (dd, 1H), 6.69 (d, 1H), 3.88 (s, 2H), 3.77 (s, 2H), 3.27 (s, 2H), 3.13-3.19 (m, 4H), 2.93 (s, 4H), 2.84 (s, 2H), 2.31 (t, 2H), 2.23-2.28 (m, 4H), 2.00 (s, 2H), 1.42 (t, 2H), 0.97 (s, 6H).

Example 254

2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide

Example 254A

3-Nitro-4-[3-(3-oxo-piperazin-1-yl)-propylamino]-benzenesulfonamide

The title compound was prepared by substituting 4-(3-aminopropyl)-piperazine-2-one for tert-butyl 4-aminopiperidine-1-carboxylate in EXAMPLE 140A.

Example 254B 2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide The title compound was prepared by substituting EXAMPLE 5B for EXAMPLE 1F and EXAMPLE 254A for EXAMPLE 1G in EXAMPLE 1H. $^1$H NMR (300 MHz, dimethylsulfoxide-$d_6$) δ 8.85 (t, 1H), 8.47 (d, 1H), 7.80-7.72 (m, 2H), 7.51 (d, 1H), 7.41 (dd, 1H), 7.36 (d, 2H), 7.18-7.03 (m, 4H), 7.00 (td, 1H), 6.75 (dd, 1H), 6.71 (d, 1H), 6.30 (d, 1H), 3.46 (q, 2H), 3.22-3.11 (m, 6H), 2.97 (s, 2H), 2.79 (br s, 2H), 2.59 (t, 2H), 2.47 (t, 2H), 2.31-2.12 (m, 6H), 1.97 (br s, 2H), 1.82 (m, 2H), 1.46 (t, 2H), 0.94 (s, 6H).

Example 255

2-(6-aminopyridin-3-yl)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 255A methyl 2-(6-aminopyridin-3-yloxy)-4-fluorobenzoate

A mixture of 5-(4,4,5,5-tetramethyl-1,3,2-dioxaborolan-2-yl)pyridin-2-amine (1.039 g), CsF (1.956 g), bis(triphenylphosphine)palladium(II)dichloride (0.301 g), and methyl 2-bromo-4-fluorobenzoate (1.0 g) in 50 mL dimethoxyethane-methanol (1:1) was heated at 80° C. for 2.5 hours. The reaction mixture was partitioned between water and ethyl acetate. The organic phase was washed with brine, dried over $MgSO_4$, filtered, ad concentrated. The residue was chromatographed on silica gel with 25-80% ethyl acetate in hexanes.

Example 255B methyl 2-(6-aminopyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 255A for EXAMPLE 3A in EXAMPLE 3G.

Example 255C methyl 2-(6-(tert-butoxycarbonylamino)pyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 255B for EXAMPLE 219B in EXAMPLE 219C.

Example 255D 2-(6-(tert-butoxycarbonylamino)pyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 255C for EXAMPLE 1E in EXAMPLE 1F.

Example 255E tert-butyl 5-(5-(4-((2-(4-chlorophenyl)-4,4-dimethylcyclohex-1-enyl)methyl)piperazin-1-yl)-2-(3-nitro-4-(1-(tetrahydro-2H-pyran-4-yl)piperidin-4-ylamino)phenylsulfonylcarbamoyl)phenoxy)pyridin-2-ylcarbamate The title compound was prepared by substituting EXAMPLE 255D for EXAMPLE 1F and EXAMPLE 49C for EXAMPLE 1G respectively in EXAMPLE 1H.

Example 255F 2-(6-aminopyridin-3-yl)-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 255E for EXAMPLE 1A in EXAMPLE 1B. $^1$H NMR (500 MHz, dimethylsulfoxide-$d_6$) δ 0.96 (s, 6H) 1.42 (t, 2H) 1.61-1.75 (m, 2H) 1.92-2.05 (m, 6H) 2.21 (s, 5H) 2.28-2.42 (m, 3H) 2.80-3.57 (m, 14H) 3.95-4.00 (m, 2H) 6.31 (d, 1H) 6.68 (d, 1H) 6.82 (dd, 1H) 7.08 (d, 2H) 7.15 (s, 1H) 7.28-7.41 (m, 4H) 7.68 (d, 1H) 7.85 (dd, 1H) 8.22 (s, 1H) 8.50 (d, 1H).

Example 256

4-(4-{1-[2-(4-chlorophenyl)-4,4-dimethylcyclohex-1-en-1-yl]ethyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide

Example 256A methyl 4-(4-(1-(2-(4-chlorophenyl)-4,4-dimethylcyclohex-1-enyl)ethyl)piperazin-1-yl)-2-(6-fluoro-1H-indol-5-yloxy)benzoate The title compound was prepared as described in EXAMPLE 110D by replacing EXAMPLE 34A with EXAMPLE 154B.

Example 256B 4-(4-(1-(2-(4-chlorophenyl)-4,4-dimethylcyclohex-1-enyl)ethyl)piperazin-1-yl)-2-(6-fluoro-1H-indol-5-yloxy)benzoic acid The title compound was prepared as described in EXAMPLE 110E by replacing EXAMPLE 110D with EXAMPLE 256A.

Example 256C 4-(4-{1-[2-(4-chlorophenyl)-4,4-dimethylcyclohex-1-en-1-yl]ethyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide The title compound was prepared as described in EXAMPLE 110F by replacing EXAMPLE 110E with EXAMPLE 256B. $^1$H NMR (500 MHz, dimethylsulfoxide-$d_6$) δ 11.29 (s, 1H), 11.22 (s, 1H), 8.60 (s, 1H), 8.57 (s, 1H), 7.86 (d, 1H), 7.52 (d, 1H), 7.27-7.40 (m, 5H), 7.15 (d, 1H), 7.02 (d, 2H), 6.60-6.68 (m, 1H), 6.40 (s, 1H), 6.08 (d, 1H), 3.84 (dd, 2H), 3.20-3.32 (m, 4H), 3.01 (s, 4H), 2.59-2.72 (m, 1H), 2.16-2.31 (m, 4H), 1.75-2.12 (m, 5H), 1.58-1.65 (m, 2H), 1.31-1.41 (m, 2H), 1.20-1.29 (m, 2H), 1.01 (d, 3H), 0.91 (s, 3H), 0.90 (s, 3H).

Example 257

4-(4-{[2-(4-chlorophenyl)-4,4-dimethylcyclohex-1-en-1-yl]methyl}piperazin-1-yl)-2-[(6-fluoro-1H-indol-4-yl)oxy]-N-[(3-nitro-4-{[3-(3-oxopiperazin-1-yl)propyl]amino}phenyl)sulfonyl]benzamide The title compound was prepared by substituting EXAMPLE 209G for EXAMPLE 1F and EXAMPLE 254A for EXAMPLE 1G in EXAMPLE 1H. $^1$H NMR (300 MHz, dimethylsulfoxide-$d_6$) δ 11.23 (br s, 1H), 8.75 (t, 1H), 8.43 (d, 1H), 7.74 (br s, 1H), 7.61 (dd, 1H), 7.51 (d, 1H), 7.35 (d, 2H), 7.24 (t, 1H), 7.05 (d, 2H), 6.95 (d, 1H), 6.85 (dd, 1H), 6.76 (dd, 1H), 6.42 (d, 1H), 6.26 (t, 1H), 6.06 (d, 1H), 3.43 (q, 2H), 3.20-3.08 (m, 6H), 2.97 (br s, 2H), 2.76 (br s, 2H), 2.57

(t, 2H), 2.47 (t, 2H), 2.27-2.12 (m, 6H), 1.97 (br s, 2H), 1.80 (m, 2H), 1.40 (t, 2H), 0.93 (s, 6H).

Example 258

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-tetrahydro-2H-pyran-3-ylmethyl]amino}phenyl)sulfonyl]benzamide

Example 258A

The title compound was prepared by substituting (tetrahydro-2H-pyran-3-yl)methanamine for 1-(tetrahydropyran-4-yl)methylamine in EXAMPLE 1G.

Example 258B (S)-3-nitro-4-((tetrahydro-2H-pyran-3-yl)methylamino)benzenesulfonamide The racemic mixture of EXAMPLE 258A was resolved by chiral SFC on an AD column (21 mm i.d.×250 mm in length) using a gradient of 10-30% 0.1% diethylamine methanol in $CO_2$ over 15 minutes (oven temperature: 40° C.; flow rate: 40 mL/minute) to provide the title compound.

Example 258C (R)-3-nitro-4-((tetrahydro-2H-pyran-3-yl)methylamino)benzenesulfonamide The racemic mixture of EXAMPLE 258A was resolved by chiral SFC on an AD column (21 mm i.d.×250 mm in length) using a gradient of 10-30% 0.1% diethylamine methanol in $CO_2$ over 15 minutes (oven temperature: 40° C.; flow rate: 40 mL/minute) to provide the title compound.

Example 258D 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-tetrahydro-2H-pyran-3-ylmethyl]amino}phenyl)sulfonyl]benzamide The title compound was prepared as described in EXAMPLE 110F by replacing EXAMPLE 110E and EXAMPLE 1G with EXAMPLE 154E and EXAMPLE 258B, respectively. $^1$H NMR (400 MHz, dimethylsulfoxide-$d_6$) δ 11.22 (s, 2H), 8.50-8.65 (m, 2H), 7.86 (dd, 1H), 7.51 (d, 1H), 7.38 (t, 1H), 7.28-7.35 (m, 4H), 7.13 (d, 1H), 7.03 (d, 2H), 6.65 (dd, 1H), 6.41 (s, 1H), 6.09 (d, 1H), 3.79 (dd, 1H), 3.68-3.74 (m, 1H), 3.14-3.32 (m, 4H), 3.03 (s, 4H), 2.73 (s, 2H), 2.08-2.25 (m, 6H), 1.78-1.97 (m, 4H), 1.55-1.66 (m, 1H), 1.41-1.52 (m, 1H), 1.23-1.40 (m, 3H), 0.92 (s, 6H).

Example 259

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3R)-tetrahydro-2H-pyran-3-ylmethyl]amino}phenyl)sulfonyl]benzamide The title compound was prepared as described in EXAMPLE 110F by replacing EXAMPLE 110E and EXAMPLE 1G with EXAMPLE 154E and EXAMPLE 258C, respectively. $^1$H NMR (400 MHz, dimethylsulfoxide-$d_6$) δ 11.22 (s, 2H), 8.50-8.65 (m, 2H), 7.86 (dd, 1H), 7.51 (d, 1H), 7.38 (t, 1H), 7.28-7.35 (m, 4H), 7.13 (d, 1H), 7.03 (d, 2H), 6.65 (dd, 1H), 6.41 (s, 1H), 6.09 (d, 1H), 3.79 (dd, 1H), 3.68-3.74 (m, 1H), 3.14-3.32 (m, 4H), 3.03 (s, 4H), 2.73 (s, 2H), 2.08-2.25 (m, 6H), 1.78-1.97 (m, 4H), 1.55-1.66 (m, 1H), 1.41-1.52 (m, 1H), 1.23-1.40 (m, 3H), 0.92 (s, 6H).

Example 260 tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-3,4-dihydro isoquinoline-2(H)-carboxylate

Example 260A tert-butyl 5-hydroxy-3,4-dihydroisoquinoline-2(1H)-carboxylate

A mixture of 1,2,3,4-tetrahydroisoquinolin-5-ol, hydrochloric acid (1.0 g), di-tert-butyl dicarbonate (1.27 g) and 1.0 N aqueous NaOH (14.5 mL) in dioxane (20 mL) was stirred at room temperature for 16 hours. The reaction mixture was partitioned between water and ethyl acetate. The aqueous layer was neutralized with 5% aqueous HCl. The combined organic layers were washed with brine, dried ($MgSO_4$), filtered, and concentrated. The residue was purified by flash chromatography on silica gel to give the title compound.

Example 260B tert-butyl 5-(2-(ethoxycarbonyl)-5-fluorophenoxy)-3,4-dihydroisoquinoline-2(1H)-carboxylate The title compound was prepared by substituting EXAMPLE 260A for 2-methyl-5-indolol in EXAMPLE 3A.

Example 260C tert-butyl 5-(5-(4-((2-(4-chlorophenyl)-4,4-dimethylcyclohex-1-enyl)methyl)piperazin-1-yl)-2-(ethoxycarbonyl)phenoxy)-3,4-dihydroisoquinoline-2(1H)-carboxylate The title compound was prepared by substituting EXAMPLE 260B for EXAMPLE 3A in EXAMPLE 3G.

Example 260D 2-(2-(tert-butoxycarbonyl)-1,2,3,4-tetrahydroisoquinolin-5-yloxy)-4-(4-((2-(4-chlorophenyl)-4,4-dimethylcyclohex-1-enyl)methyl)piperazin-1-yl) benzoic acid The title compound was prepared by substituting EXAMPLE 260C for EXAMPLE 1E in EXAMPLE 1F.

Example 260E 2-(2-(tert-butoxycarbonyl)-1,2,3,4-tetrahydroisoquinolin-5-yloxy)-4-(4-((2-(4-chlorophenyl)-4,4-dimethylcyclohex-1-enyl)methyl)piperazin-1-yl) benzoic 3-nitro-4-((tetrahydro-2H-pyran-4-yl)methylamino)benzenesulfonic anhydride The title compound was prepared by substituting EXAMPLE 260D for EXAMPLE 1F in EXAMPLE 1H. $^1$H NMR (500 MHz, dimethylsulfoxide-$d_6$) δ 8.63 (s, 1H), 8.45 (s, 1H), 7.70 (d, 1H), 7.50 (d, 1H), 7.35 (d, 1H), 7.15 (d, 1H), 7.06 (d, 2H), 6.97 (t, 1H), 6.80 (d, 1H), 6.73 (dd, 1H), 6.37 (d, 1H), 6.31 (d, 1H), 4.48 (s, 2H), 3.86 (dd, 2H), 3.53 (t, 2H), 3.14 (s, 4H), 2.67-2.75 (m, 2H), 2.16-2.30 (m, 6H), 1.63 (d, 2H), 1.43 (s, 9H), 0.94 (s, 6H).

Example 261

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide

Example 261A

4-Fluoro-2-(6-nitro-pyridin-3-yloxy)-benzoic acid methyl ester

Methyl 4-fluoro-2-hydroxybenzoate (3.00 g), 5-chloro-2-nitropyridine (3.08 g), and potassium carbonate (4.87 g) were added to dimethyl sulfoxide (50 mL), heated to 110° C. for one hour, cooled, added to water, and extracted with ethyl ether. The ether was washed with brine and dried on anhydrous sodium sulfate. The solution was filtered and concentrated and purified by flash column chromatography on silica gel using 10% ethyl acetate in hexanes increasing to 20% ethyl acetate in hexanes and increasing again to 30% ethyl acetate in hexanes.

Example 261B 2-(6-Amino-pyridin-3-yloxy)-4-fluoro-benzoic acid methyl ester

EXAMPLE 261A (1015 mg), cyclohexene (3.52 mL, 2853 mg), and 10% palladium on carbon (100 mg) were added to ethanol (12 mL) and ethyl acetate (4 mL) and heated at 75° C. for three hours. The solution was cooled and vacuum filtered over diatomaceous earth. The solvent was removed under vacuum.

Example 261C 2-(6-Amino-pyridin-3-yloxy)-4-{4-[2-(4-chlorophenyl)-4,4-dimethyl-cyclohex-1-enylmethyl]-piperazin-1-yl}-benzoic acid methyl ester The title compound was prepared by substituting EXAMPLE 261B for EXAMPLE 3A in EXAMPLE 3G.

Example 261D 2-(6-Amino-pyridin-3-yloxy)-4-{4-[2-(4-chlorophenyl)-4,4-dimethyl-cyclohex-1-enylmethyl]-piperazin-1-yl}-benzoic acid The title compound was prepared by substituting EXAMPLE 261C for EXAMPLE 1E in EXAMPLE 1F.

Example 261E

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 261D for EXAMPLE 1F and EXAMPLE 49C for EXAMPLE 1G in EXAMPLE 1H. $^1$H NMR (300 MHz, dimethylsulfoxide-$d_6$) δ 8.53 (br s, 1H), 8.19 (br s, 1H), 7.85 (dd, 1H), 7.66 (br s, 1H), 7.47 (d, 1H), 7.36 (d, 2H), 7.25-7.14 (m, 1H), 7.10 (m, 1H), 7.07 (d, 2H), 6.58 (dd, 1H), 6.43 (d, 1H), 6.10 (br s, 1H), 5.81 (m, 2H), 3.94 (d, 2H), 3.03 (br s, 6H), 2.73 (m, 2H), 2.24-2.12 (m, 8H), 2.09-2.00 (m, 2H), 1.97 (br s, 2H), 2.09-2.00 (m, 2H), 1.84-1.74 (m, 2H), 1.70-1.60 (m, 2H), 1.58-1.47 (m, 4H), 1.40 (t, 2H), 0.94 (s, 6H).

Example 262

4-(4-{[2-(4-chlorophenyl)-5,5-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide

Example 262A methyl 5,5-dimethyl-2-(trifluoromethylsulfonyloxy)cyclohex-1-enecarboxylate The title compound was prepared by substituting 4,4-dimethyl-2-methoxycarbonylcyclohexanone for 5,5-dimethyl-2-methoxycarbonylcyclohexanone in EXAMPLE 3B.

Example 262B methyl 2-(4-chlorophenyl)-5,5-dimethylcyclohex-1-enecarboxylate The title compound was prepared by substituting EXAMPLE 262A for EXAMPLE 3B in EXAMPLE 3C.

Example 262C (2-(4-chlorophenyl)-5,5-dimethylcyclohex-1-enyl)methanol

The title compound was prepared by substituting EXAMPLE 262B for EXAMPLE 3C in EXAMPLE 3D.

Example 262D 2-(4-chlorophenyl)-5,5-dimethylcyclohex-1-enecarbaldehyde

The title compound was prepared as described in EXAMPLE 53F by replacing EXAMPLE 53E with EXAMPLE 262C.

Example 262E tert-butyl 4-((2-(4-chlorophenyl)-5,5-dimethylcyclohex-1-enyl)methyl)piperazine-1-carboxylate The title compound was prepared as described in EXAMPLE 1A by replacing 4'-chlorobiphenyl-2-carboxaldehyde with EXAMPLE 262D.

Example 262F 1-((2-(4-chlorophenyl)-5,5-dimethylcyclohex-1-enyl)methyl)piperazine The title compound was prepared as described in EXAMPLE 110C by replacing EXAMPLE 110B with EXAMPLE 262E.

Example 262G methyl 4-(4-((2-(4-chlorophenyl)-5,5-dimethylcyclo-hex-1-enyl)methyl)piperazin-1-yl)-2-(6-fluoro-1H-indol-5-yloxy)benzoate The title compound was prepared as described in EXAMPLE 110D by replacing EXAMPLE 34A and EXAMPLE 110C with EXAMPLE 154B and EXAMPLE 262F, respectively.

Example 262H 4-(4-((2-(4-chlorophenyl)-5,5-dimethylcyclohex-1-enyl)methyl)piperazin-1-yl)-2-(6-fluoro-1H-indol-5-yloxy)benzoic acid The title compound was prepared as described in EXAMPLE 110E by replacing EXAMPLE 110D with EXAMPLE 262G.

Example 262I 4-(4-{[2-(4-chlorophenyl)-5,5-dimethylcyclohex-1-en-1-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide The title compound was prepared as described in EXAMPLE 110F by replacing EXAMPLE 110E with EXAMPLE 262H. $^1$H NMR (500 MHz, dimethylsulfoxide-$d_6$) δ 11.27 (s, 1H), 11.22 (s, 1H), 8.61 (t, 1H), 8.58 (d, 1H), 7.86 (dd, 1H), 7.51 (d, 1H), 7.38 (t, 1H), 7.31-7.36 (m, 3H), 7.30 (d, 1H), 7.16 (d, 1H), 7.07 (d, 2H), 6.65 (dd, 1H), 6.41 (s, 1H), 6.08 (d, 1H), 3.84 (dd, 2H), 3.22-3.32 (m, 4H), 3.02 (s, 4H), 2.68 (s, 2H), 2.17 (s, 6H), 1.84-1.96 (m, 3H), 1.57-1.65 (m, 2H), 1.39 (t, 2H), 1.20-1.31 (m, 2H), 0.92 (s, 6H).

Example 263

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-methoxyethyl)amino]-3-nitrophenyl}sulfonyl)benzamide

Example 263A 4-(2-methoxyethylamino)-3-nitrobenzenesulfonamide

The title compound was prepared by substituting 2-methoxyethanamine for 3-(N-morpholinyl)-1-propylamine in EXAMPLE 4A.

Example 263B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(2-methoxyethyl)amino]-3-nitrophenyl}sulfonyl)benzamide The title compound was prepared by substituting EXAMPLE 154E for EXAMPLE 1F and EXAMPLE 263A for EXAMPLE 1G in EXAMPLE 1H. $^1$H NMR (500 MHz, dimethylsulfoxide-$d_6$) δ 11.28 (s, 1H), 11.21 (s, 1H), 8.58 (m, 2H), 7.87 (dd, 1H), 7.50 (d, 1H), 7.32 (m, 5H), 7.15 (d, 1H), 7.03 (d, 2H), 6.65 (dd, 1H), 6.40 (m, 1H), 6.10 (m, 1H), 3.58 (m, 4H), 3.30 (s, 3H), 3.04 (m, 4H), 2.73 (s, 2H), 2.17 (m, 6H), 1.95 (s, 2H), 1.38 (t, 2H), 0.92 (s, 6H).

Example 264

4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylmethoxy)phenyl]sulfonyl}benzamide

Example 264A 3-nitro-4-((tetrahydro-2H-pyran-4-yl)methoxy)benzenesulfonamide (Tetrahydro-2H-pyran-4-yl)methanol (2.0 g) in tetrahydrofuran (20 mL) was treated with 60% NaH (1.377 g). The solution was stirred for 20 minutes at room temperature. To this solution was added 4-fluoro-3-nitrobenzenesulfonamide (2.84 g) portion-wise. The reaction was stirred for another 2 hours. The mixture was poured into water, neutralized with 10% HCl, and extracted with ethyl acetate three times. The combined organic layers were washed with brine, dried over $MgSO_4$, filtered, and concentrated. The residue was purified with flash column chromatography on silica gel eluting with 20%-60% ethyl acetate in hexanes.

Example 264B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-{[3-nitro-4-(tetrahydro-2H-pyran-4-ylmethoxy)phenyl]sulfonyl}benzamide The title compound was prepared by substituting EXAMPLE 154E for EXAMPLE 1F and EXAMPLE 264A for EXAMPLE 1G in EXAMPLE 1H. $^1$H NMR (500 MHz, dimethylsulfoxide-$d_6$) δ 11.12 (s, 1H), 8.10 (d, 1H), 7.52 (d, 1H), 7.45 (d, 1H), 7.38 (d, 1H), 7.33-7.35 (m, 3H), 7.28 (d, 1H), 7.04 (d, 2H), 6.65 (dd, 1H), 6.41 (s, 1H), 6.10 (s, 1H), 4.09 (d, 2H), 3.88 (dd, 2H), 3.05 (s, 4H), 2.80 (br s, 2H), 2.03-2.20 (m, 6H), 1.63-1.65 (m, 2H), 1.33-1.40 (m, 4H), 0.92 (s, 6H).

Example 265

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 265A ethyl 2-(1H-indol-5-yloxy)-4-fluorobenzoate

The title compound was prepared by substituting 5-indolol for 2-methyl-5-indolol in EXAMPLE 3A.

Example 265B ethyl 2-(3-chloro-1H-indol-5-yloxy)-4-fluorobenzoate

N-Chloro-succinimide (160 mg) was added portionwise to a solution of EXAMPLE 265A (300 mg) in toluene (10 mL) and the mixture was stirred at room temperature for about two hours. The mixture was chromatographed on a silica gel column with 30% ethyl acetate in hexane to give the title compound.

Example 265C ethyl 2-(3-chloro-1H-indol-5-yloxy)-4-(4-((2-(4-chlorophenyl)-4,4-dimethylcyclohex-1-enyl)methyl)piperazin-1-yl)benzoate The title compound was prepared by substituting EXAMPLE 265B for EXAMPLE 3A in EXAMPLE 3G.

Example 265D 2-(3-chloro-1H-indol-5-yloxy)-4-(4-((2-(4-chlorophenyl)-4,4-dimethylcyclohex-1-enyl)methyl)piperazin-1-yl)benzoic acid The title compound was prepared by substituting EXAMPLE 265C for EXAMPLE 1E in EXAMPLE 1F.

Example 265E 2-(3-chloro-1H-indol-5-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 265D for EXAMPLE 1F in EXAMPLE 1H. $^1$H NMR (500 MHz, dimethylsulfoxide-$d_6$) δ 11.42 (s, 1H), 11.30 (br s, 1H), 8.60 (t, 1H), 8.54 (d, 1H), 7.78 (dd, 1H), 7.55 (d, 1H), 7.50 (d, 1H), 7.42 (d, 1H), 7.34 (d, 2H), 7.09 (d, 1H), 7.04 (d, 2H), 7.00 (d, 1H), 6.92 (dd, 1H), 6.68 (dd, 1H), 6.16 (d, 1H), 3.85 (dd, 2H), 3.28 (dd, 2H), 3.07 (m, 4H), 2.75 (m, 2H), 2.25-2.15 (m, 6H), 1.95 (br.s, 2H), 1.90 (m, 1H), 1.61 (dd, 2H), 1.38 (t, 2H), 1.27 (m, 2H), 0.92 (s, 6H).

Example 266

2-[(3-chloro-1H-indol-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 266A ethyl 2-(1H-indol-4-yloxy)-4-fluorobenzoate

The title compound was prepared by substituting 4-indolol for 2-methyl-5-indolol in EXAMPLE 3A.

Example 266B ethyl 2-(3-chloro-1H-indol-4-yloxy)-4-fluorobenzoate

The title compound was prepared by substituting EXAMPLE 266A for EXAMPLE 265A in EXAMPLE 265B.

Example 266C ethyl 2-(3-chloro-1H-indol-4-yloxy)-4-(4-((2-(4-chlorophenyl)-4,4-dimethylcyclohex-1-enyl)methyl)piperazin-1-yl)benzoate The title compound was prepared by substituting EXAMPLE 266B for EXAMPLE 3A in EXAMPLE 3G.

Example 266D 2-(3-chloro-1H-indol-4-yloxy)-4-(4-((2-(4-chlorophenyl)-4,4-dimethylcyclohex-1-enyl)methyl)piperazin-1-yl)benzoic acid The title compound was prepared by substituting EXAMPLE 266C for EXAMPLE 1E in EXAMPLE 1F.

Example 266E 2-(3-chloro-1H-indol-4-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared by substituting EXAMPLE 266D for EXAMPLE 1F in EXAMPLE 1H. $^1$H NMR (500 MHz, dimethylsulfoxide-$d_6$) δ 11.56 (s, 1H), 11.00 (br s, 1H), 8.64 (t, 1H), 8.54 (d, 1H), 7.81 (dd, 1H), 7.58 (d, 1H), 7.45 (d, 1H), 7.34 (d, 2H), 7.26 (d, 1H), 7.16 (d, 2H), 7.10 (t, 1H), 7.03 (d, 2H), 6.68 (dd, 1H), 6.62 (d, 1H), 6.10 (d, 1H), 3.85 (dd, 2H), 3.26 (t, 2H), 3.02 (br.s, 4H), 2.73 (br.s, 2H), 2.20-2.10 (m, 6H), 1.95 (br.s, 2H), 1.90 (m, 1H), 1.61 (dd, 2H), 1.38 (t, 2H), 1.27 (m, 2H), 0.92 (s, 6H).

Example 267

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-5-yl)oxy]benzamide A solution of EXAMPLE 265E (38 mg) in ethanol (5 mL) and 1 N aqueous HCl (5 mL) was stirred at 85° C. for 7 hours. The mixture was cooled to ambient temperature and concentrated. The residue was purified on reverse-phase HPLC on a C18 column using a water-acetonitrile gradient with ammonium acetate buffer to give the title compound. $^1$H NMR (500 MHz, dimethylsulfoxide-$d_6$) δ 11.30 (br s, 1H), 10.33 (s, 1H), 8.61 (t, 1H), 8.54 (d, 1H), 7.84 (dd, 1H), 7.47 (d, 1H), 7.35 (d, 2H), 7.18 (d, 1H), 7.06 (d, 2H), 6.84 (s, 1H), 6.80 (d, 1H), 6.74 (d, 1H), 6.67 (dd, 1H), 6.20 (d, 1H), 3.85 (dd, 2H), 3.43 (s, 2H), 3.27 (t, 2H), 3.10 (br.s, 4H), 2.77 (br.s, 2H), 2.25-2.10 (m, 6H), 1.97 (br.s, 2H), 1.90 (m, 1H), 1.62 (dd, 2H), 1.40 (t, 2H), 1.27 (m, 2H), 0.94 (s, 6H).

Example 268

4-(4-{[2-(4-chlorophenyl)-4,4-dimethylcyclohex-1=en-1-yl]methyl}piperazin-1-yl)-N-({3-nitro-4-[(tetrahydro-2H-pyran-4-ylmethyl)amino]phenyl}sulfonyl)-2-[(2-oxo-2,3-dihydro-1H-indol-4-yl)oxy]benzamide The title compound was prepared by substituting EXAMPLE 266E for EXAMPLE 265E in EXAMPLE 267.

¹H NMR (500 MHz, dimethylsulfoxide-d₆) δ 11.50 (br s, 1H), 10.40 (s, 1H), 8.59 (t, 1H), 8.54 (d, 1H), 7.72 (d, 1H), 7.47 (d, 1H), 7.35 (d, 2H), 7.12 (d, 1H), 7.06 (d, 2H), 6.96 (t, 1H), 6.75 (dd, 1H), 6.46 (d, 1H), 6.44 (d, 1H), 6.13 (d, 1H), 3.86 (dd, 2H), 3.28 (t, 2H), 3.25 (s, 2H), 3.19 (br.s, 4H), 2.82 (br.s, 2H), 2.28 (br. s, 4H), 2.18 (m, 2H), 1.98 (br.s, 2H), 1.90 (m, 1H), 1.63 (d, 2H), 1.41 (t, 2H), 1.27 (m, 2H), 0.94 (s, 6H).

Example 269

4-(4-{[2-(4-chlorophenyl)-4,4-dimethylcyclohex-1-en-1-yl]methyl}piperazin-1-yl)-2-[(6-fluoro-1H-indol-4-yl)oxy]-N-({4-[(2-methoxyethyl)amino]-3-nitrophenyl}sulfonyl)benzamide The title compound was prepared by substituting EXAMPLE 209G for EXAMPLE 1F and EXAMPLE 263A for EXAMPLE 1G in EXAMPLE 1H. ¹H NMR (300 MHz, dimethylsulfoxide-d₆) δ 11.22 (br s, 1H), 8.55 (t, 1H), 8.43 (d, 1H), 7.61 (dd, 1H), 7.51 (d, 1H), 7.35 (d, 2H), 7.24 (t, 1H), 7.05 (d, 2H), 7.00 (d, 1H), 6.89 (dd, 1H), 6.77 (dd, 1H), 6.43 (d, 1H), 6.26 (t, 1H), 6.06 (t, 1H), 3.63-3.51 (m, 4H), 3.32 (s, 3H), 3.13 (br s, 4H), 2.78 (br s, 2H), 2.31-2.12 (m, 6H), 1.97 (br s, 2H), 1.40 (t, 2H), 0.93 (s, 6H).

Example 270 tert-butyl 5-(5-(4-{[2-(4-chlorophenyl)-4,4-dimethyl-cyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate Example 270A methyl 2-(6-(bis(tert-butoxycarbonyl)amino)pyridin-3-yloxy)-4-(4-((2-(4-chlorophenyl)-4,4-dimethylcyclohex-1-enyl)methyl)piperazin-1-yl)benzoate EXAMPLE 261C (1080 mg) was dissolved in acetonitrile (12 mL) and 4-dimethylaminopyridine (47 mg) and di-tert-butyl dicarbonate (462 mg) were added. The solution was mixed at room temperature for 16 hours, the volume of solvent reduced, and the material purified by flash column chromatography on silica gel using 30% ethyl acetate in hexanes.

Example 270B 2-(6-tert-Butoxycarbonylamino-pyridin-3-yloxy)-4-{4-[2-(4-chloro-phenyl)-4,4-dimethyl-cyclohex-1-enylmethyl]-piperazin-1-yl}-benzoic acid The title compound was prepared by substituting EXAMPLE 270A for EXAMPLE 1E in EXAMPLE 1F.

Example 270C tert-butyl 5-(5-(4-{[2-(4-chlorophenyl)-4,4-dimethyl-cyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate The title compound was prepared by substituting EXAMPLE 270B for EXAMPLE 1F in EXAMPLE 1H. ¹H NMR (300 MHz, dimethylsulfoxide-d₆) δ 9.72 (s, 1H), 8.61 (t, 1H), 8.55 (d, 1H), 7.95 (d, 1H), 7.82 (dd, 1H), 7.74 (d, 1H), 7.47 (d, 1H), 7.36 (d, 2H), 7.32 (dd, 1H), 7.19 (d, 1H), 7.06 (d, 2H), 6.70 (dd, 1H), 6.27 (d, 1H), 3.86 (dd, 2H), 3.13 (br s, 4H), 2.78 (br s, 2H), 2.54 (m, 1H), 2.45 (m, 1H), 2.29-2.13 (m, 6H), 1.97 (br s, 2H), 1.91 (m, 1H), 1.63 (d, 2H), 1.48 (s, 9H), 1.40 (t, 2H), 1.34-1.20 (m, 4H), 0.94 (s, 6H).

Example 271 tert-butyl 4-(5-(4-{[2-(4-chlorophenyl)-4,4-dimethyl-cyclohex-1-en-1-yl]methyl}piperazin-1-yl)-2-{[({3-nitro-4-[(1-tetrahydro-2H-pyran-4-ylpiperidin-4-yl)amino]phenyl}sulfonyl)amino]carbonyl}phenoxy)pyridin-2-ylcarbamate Example 271A 2-(2-Amino-pyridin-4-yloxy)-4-fluoro-benzoic acid methyl ester The title compound was prepared by substituting methyl 2,4-difluorobenzoate for ethyl 2,4-difluorobenzoate and 2-aminopyridin-4-ol for 2-methyl-5-indolol in EXAMPLE 3A, except here heating was at 130° C.

Example 271B 2-(2-Amino-pyridin-4-yloxy)-4-{4-[2-(4-chloro-phenyl)-4,4-dimethyl-cyclohex-1-enylmethyl]-piperazin-1-yl}-benzoic acid methyl ester The title compound was prepared by substituting EXAMPLE 271A for EXAMPLE 3A in EXAMPLE 3G.

Example 271C methyl 2-(2-(bis(tert-butoxycarbonyl)amino)pyridin-4-yloxy)-4-(4-((2-(4-chlorophenyl)-4,4-dimethylcyclohex-1-enyl)methyl)piperazin-1-yl)benzoate The title compound was prepared by substituting EXAMPLE 271B for EXAMPLE 261C in EXAMPLE 270A.

Example 271D 2-(2-tert-Butoxycarbonylamino-pyridin-4-yloxy)-4-{4-[2-(4-chloro-phenyl)-4,4-dimethyl-cyclohex-1-enylmethyl]-piperazin-1-yl}-benzoic acid The title compound was prepared by substituting EXAMPLE 271C for EXAMPLE 1E in EXAMPLE 1F.

Example 271E tert-butyl 4-(5-(4-{[2-(4-chlorophenyl)-4,4-dimethyl-cyclohex-1-en-1-yl]methyl}piperazin-1-yl)-2-{[({3-nitro-4-[(1-tetrahydro-2H-pyran-4-ylpiperidin-4-yl)amino]phenyl}sulfonyl)amino]carbonyl}phenoxy)pyridin-2-ylcarbamate The title compound was prepared by substituting EXAMPLE 271D for EXAMPLE 1F and EXAMPLE 49C for EXAMPLE 1G in EXAMPLE 1H. ¹H NMR (300 MHz, dimethylsulfoxide-d₆) δ 9.32 (br s, 1H), 8.42 (m, 1H), 8.21 (d, 1H), 8.02 (m, 1H), 7.76 (m, 1H), 7.58 (d, 1H), 7.40-7.34 (m, 2H), 7.26 (m, 1H), 7.20-6.95 (m, 4H), 6.67 (d, 1H), 6.30 (br s, 1H), 3.99-3.90 (m, 3H), 3.89 (m, 1H), 3.07 (br s, 4H), 2.76 (br s, 2H), 2.42-2.32 (m, 1H), 2.30-2.14 (m, 8H), 2.13-2.03

(m, 2H), 20.2-1.95 (m, 3H), 1.90-1.65 (m, 6H), 1.60-1.49 (m, 2H), 1.40 (t, 2H), 1.31 (t, 9H), 0.94 (s, 6H).

Example 272

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 270C for EXAMPLE 1A in EXAMPLE 1B. $^1$H NMR (300 MHz, dimethylsulfoxide-$d_6$) δ 8.64 (t, 1H), 8.60 (d, 1H), 7.89 (dd, 1H), 7.73 (d, 1H), 7.46 (d, 1H), 7.36 (d, 2H), 7.24 (d, 1H), 7.18 (dd, 1H), 7.06 (d, 2H), 6.61 (dd, 1H), 6.47 (d, 1H), 6.07 (d, 1H), 5.90 (br s, 2H), 3.85 (dd, 2H), 3.07 (br s, 4H), 2.75 (br s, 2H), 2.28-2.11 (m, 10H), 1.97 (br s, 2H), 1.92 (m, 1H), 1.63 (dd, 2H), 1.40 (t, 0.2H), 1.26 (m, 2H), 0.94 (s, 6H).

Example 273

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 271E for EXAMPLE 1A in EXAMPLE 1B. $^1$H NMR (300 MHz, dimethylsulfoxide-$d_6$) δ 8.49 (br s, 1H), 8.16-8.06 (m, 1H), 7.86 (dd, 1H), 7.70 (dd, 1H), 7.44 (d, 1H), 7.40-7.35 (m, 2H), 7.16-7.09 (m, 2H), 7.07 (d, 2H), 6.59 (d, 1H), 6.45 (dd, 1H), 6.19 (d, 1H), 3.96-3.89 (m, 3H), 3.81 (m, 1H), 3.00 (br s, 4H), 2.93-2.77 (m, 2H), 2.74 (br s, 2H), 2.29-2.11 (m, 8H), 2.09-1.95 (m, 4H), 1.90-1.46 (m, 8H), 1.40 (t, 2H), 0.94 (s, 6H).

Example 274

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 274A methyl 2-(5-bromopyridin-3-yloxy)-4-fluorobenzoate

To a solution of 5-bromopyridin-3-ol (1.060 g) in 2-methyltetrahydrofuran (15 mL) was added potassium tert-butoxide (6.09 mL, 1.0M in tetrahydrofuran) dropwise. After stirring for 5 minutes, methyl 2,4-difluorobenzoate (1.049 g) was added as a solution in 2-methyltetrahydrofuran (2 mL) and the reaction was heated to 75° C. N,N-Dimethylformamide (2 mL) was added to the reaction and the reaction was stirred overnight. The reaction was cooled, diluted with ethyl acetate (100 mL) and washed with water (50 mL), brine (50 mL), dried over magnesium sulfate, filtered, and concentrated. Silica gel chromatography (SF40-80) eluting with a gradient of 5% to 35% ethyl acetate/hexanes gave the product.

Example 274B methyl 2-(5-bromopyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 274A for EXAMPLE 3A in EXAMPLE 3G.

Example 274C 2-(5-bromopyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 274B for EXAMPLE 1E in EXAMPLE 1F.

Example 274D

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 274C for EXAMPLE 1F in EXAMPLE 1H. $^1$H NMR (300 MHz, dimethylsulfoxide-$d_6$) δ 11.99-11.42 (m, 1H), 8.62 (s, 1H), 8.42 (d, 1H), 8.17 (d, 1H), 8.10 (d, 1H), 7.71 (dd, 1H), 7.54 (d, 1H), 7.37 (d, 2H), 7.19 (t, 1H), 7.09 (t, 3H), 6.81 (dd, 1H), 6.59 (d, 1H), 3.87 (dd, 2H), 3.44-3.15 (m, 8H), 2.88 (s, 2H), 2.33 (s, 4H), 2.19 (s, 2H), 1.97 (d, 3H), 1.66 (d, 2H), 1.50-1.20 (m, 4H), 0.97 (d, 6H).

Example 275

2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide

Example 275A ethyl 2-(6-chloro-1H-indol-5-yloxy)-4-(4-((4-(4-chlorophenyl)-6,6-dimethyl-5,6-dihydro-2H-pyran-3-yl)methyl)piperazin-1-yl)benzoate The title compound was prepared as described in EXAMPLE 38G by replacing EXAMPLE 38F with EXAMPLE 242F.

Example 275B 2-(6-chloro-1H-indol-5-yloxy)-4-(4-((4-(4-chlorophenyl)-6,6-dimethyl-5,6-dihydro-2H-pyran-3-yl)methyl)piperazin-1-yl)benzoic acid The title compound was prepared as described in EXAMPLE 38H by replacing EXAMPLE 38G with EXAMPLE 275A.

Example 275C

2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide The title compound was prepared as described in EXAMPLE 1H by replacing EXAMPLE 1F and EXAMPLE 1G with EXAMPLE 275B and EXAMPLE 1G, respectively. $^1$H NMR (300 MHz, dimethylsulfoxide-$d_6$) δ 11.27 (s, 1H), 11.19 (m, 1H), 8.62 (t, 1H), 8.58 (d, 1H), 7.84 (dd, 1H), 7.54 (m, 3H), 7.43 (m, 1H), 7.36 (m, 3H), 7.14 (m, 3H), 6.66 (dd, 1H), 6.43 (s, 1H), 6.00 (d, 1H), 4.10 (s, 2H), 3.85 (dd, 1H), 3.24 (m, 2H), 3.02 (m, 4H), 2.85 (m, 2H), 2.16 (m, 6H), 1.90 (m, 1H), 1.62 (m, 2H), 1.28 (m, 4H), 1.18 (s, 6H).

Example 276

2-[(6-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared as described in EXAMPLE 1H by replacing EXAMPLE 1F with EXAMPLE 242H. $^1$H NMR (300 MHz, dimethylsulfoxide-$d_6$) δ 11.27 (s, 1H), 11.12 (m, 1H), 8.60 (m, 2H), 7.85 (dd, 1H), 7.54 (m, 2H), 7.44 (m, 1H), 7.33 (d, 3H), 7.16 (d, 1H), 7.03 (d, 2H), 6.66 (dd, 1H), 6.43 (s, 1H), 6.00 (d, 1H), 3.85 (m, 2H), 3.28 (m, 4H), 3.02 (m, 4H), 2.73 (s, 2H), 2.15 (m, 4H), 1.93 (m, 4H), 1.61 (m, 3H), 1.29 (m, 4H), 0.92 (s, 6H).

Example 277

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide

Example 277A methyl 4-(4-((4-(4-chlorophenyl)-6,6-dimethyl-5,6-dihydro-2H-pyran-3-yl)methyl)piperazin-1-yl)-2-(6-fluoro-1H-indol-5-yloxy)benzoate The title compound was prepared as described in EXAMPLE 38G by replacing EXAMPLE 38F with EXAMPLE 154C.

Example 277B 4-(4-((4-(4-chlorophenyl)-6,6-dimethyl-5,6-dihydro-2H-pyran-3-yl)methyl)piperazin-1-yl)-2-(6-fluoro-1H-indol-5-yloxy)benzoic acid The title compound was prepared as described in EXAMPLE 38H by replacing EXAMPLE 38G with EXAMPLE 277A.

Example 277C 4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({3-nitro-4-[(tetrahydro-2H-pyran-4-ylmethyl)amino]phenyl}sulfonyl)benzamide The title compound was prepared as described in EXAMPLE 1H by replacing EXAMPLE 1F with EXAMPLE 277B. $^1$H NMR (300 MHz, dimethylsulfoxide-$d_6$) δ 11.30 (m, 1H), 11.21 (s, 1H), 8.61 (m, 2H), 7.86 (dd, 1H), 7.51 (d, 1H), 7.37 (m, 3H), 7.30 (m, 1H), 7.15 (m, 3H), 6.66 (dd, 1H), 6.41 (m, 1H), 6.09 (d, 1H), 4.10 (s, 2H), 3.84 (dd, 2H), 3.28 (m, 4H), 3.03 (m, 4H), 2.82 (s, 2H), 2.23 (m, 5H), 1.89 (m, 1H), 1.62 (m, 2H), 1.26 (m, 4H), 1.19 (s, 6H).

Example 278 tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-ylcarbamate

Example 278A methyl 2-(5-(tert-butoxycarbonylamino)pyridin-3-yloxy)-4-(4-((2-(4-chlorophenyl)-4,4-dimethylcyclohex-1-enyl)methyl)piperazin-1-yl)benzoate EXAMPLE 274B (0.135 g), tert-butyl carbamate (0.028 g) and cesium carbonate (0.106 g) were mixed together in dioxane (2 mL). Diacetoxypalladium (2.425 mg) and (9,9-dimethyl-9H-xanthene-4,5-diyl)bis(diphenylphosphine) (0.012 g) were added and the reaction was degassed with nitrogen then sealed and heated to 85° C. The reaction was stirred for 16 hours, cooled, loaded onto silica gel (40 g) and eluted using a gradient of 0.5% to 7.5% methanol/dichloromethane to yield the product.

Example 278B 2-(5-(tert-butoxycarbonylamino)pyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 278A for EXAMPLE 1E in EXAMPLE 1F.

Example 278C tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-yl carbamate The title compound was prepared by substituting EXAMPLE 278B for EXAMPLE 1F in EXAMPLE 1H. $^1$H NMR (300 MHz, CDCl$_3$) δ 9.75 (s, 1H), 8.84 (d, 1H), 8.51 (d, 1H), 8.32 (d, 1H), 8.13 (dd, 1H), 8.08 (d, 1H), 7.92 (d, 1H), 7.87 (s, 1H), 7.24 (d, 2H), 6.92 (dd, 3H), 6.65 (s, 1H), 6.58 (dd, 1H), 6.06 (d, 1H), 4.02 (dd, 2H), 3.42 (dd, 2H), 3.32-3.21 (m, 2H), 3.14 (s, 4H), 2.77 (s, 2H), 2.22 (d, 6H), 1.98 (s, 3H), 1.70 (t, 2H), 1.56-1.36 (m, 13H), 0.95 (s, 6H).

Example 279

2-[(5-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide To EXAMPLE 278C (0.050 g) in dichloromethane (2 mL) was added trifluoroacetic acid (0.061 mL) and the reaction stirred at room temperature. After stirring for 19 hours, the reaction was concentrated then dried under high vacuum. The residue was dissolved in dichloromethane (1 mL) and neutralized with N,N-diisopropylethylamine (0.028 mL). The solution was loaded onto silica gel (GraceResolv 12 g) and the product eluted using a gradient of 0.5% methanol/dichloromethane to 5% methanol/dichloromethane over 30 minutes (Flow=30 mL/min) to give the title compound. $^1$H NMR (300 MHz, CDCl$_3$) δ 8.82 (d, 1H), 8.50 (s, 1H), 8.11 (dd, 1H), 7.98 (d, 1H), 7.91 (d, 1H), 7.82 (d, 1H), 7.30-7.14 (m, 2H), 7.01-6.83 (m, 3H), 6.69 (t, 1H), 6.58 (dd, 1H), 6.10 (d, 1H), 4.10-3.98 (m, 2H), 3.88 (s, 2H), 3.42 (dd, 2H), 3.34-3.20 (m, 2H), 3.14 (d, 4H), 2.78 (s, 2H), 2.22 (d, 6H), 1.99 (s, 3H), 1.73 (d, 2H), 1.62-1.10 (m, 4H), 0.95 (s, 6H).

Example 280 tert-butyl 4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate The title compound was prepared by substituting EXAMPLE 271D for EXAMPLE 1F in EXAMPLE 1H. $^1$H NMR (300 MHz, dimethylsulfoxide-d$_6$) δ 9.33 (br s, 1H), 8.65 (t, 1H), 8.55 (br s, 1H), 8.16 (br s, 1H), 7.82 (d, 1H), 7.57 (d, 1H), 7.44 (t, 1H), 7.35 (d, 2H), 7.32-7.13 (m, 2H), 7.11 (d, 1H), 7.06 (d, 2H), 6.71 (d, 1H), 3.86 (dd, 2H), 3.09 (br s, 4H), 2.73 (d, 2H), 2.25-2.12 (m, 8H), 1.97 (br s, 2H), 1.91 (m, 1H), 1.66-1.47 (m, 4H), 1.40 (t, 2H), 1.31 (s, 9H), 1.24 (t, 2H), 0.94 (s, 6H).

Example 281

2-[(3-chloro-1H-indol-5-yl)oxy]-4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)benzamide The title compound was prepared by substituting EXAMPLE 265D for EXAMPLE 1F and EXAMPLE 49C for EXAMPLE 1G in EXAMPLE 1H. $^1$H NMR (500 MHz, dimethylsulfoxide-d$_6$) δ 11.34 (s, 1H), 8.48 (d, 1H), 8.15 (d, 1H), 7.74 (dd, 1H), 7.53-7.51 (m, 2H), 7.37 (d, 1H), 7.34 (d, 2H), 7.04 (d, 2H), 7.00 (d, 1H), 6.87-6.85 (m, 2H), 6.64 (dd, 1H), 6.19 (d, 1H), 3.94 (dd, 2H), 3.75 (m, 1H), 3.28 (dd, 2H), 3.02 (m, 6H), 2.72 (m, 2H), 2.62 (m, 1H), 2.25-2.10 (m, 6H), 2.00 (m, 2H), 1.95 (br.s, 2H), 1.91 (m, 2H), 1.77 (d, 2H), 1.70-1.60 (m, 2H), 1.55-1.45 (m, 2H), 1.38 (m, 2H), 0.92 (s, 6l).

Example 282

2-[(2-aminopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 280 for EXAMPLE 1A in EXAMPLE 1B. $^1$H NMR (300 MHz, dimethylsulfoxide-d$_6$) δ 8.59 (t, 1H), 8.54 (d, 1H), 7.84 (dd, 1H), 7.73 (m, 1H), 7.46 (d, 1H), 7.36 (d, 2H), 7.16 (d, 1H), 7.14-7.10 (m, 1H), 7.06 (d, 2H), 6.95 (d, 1H), 6.66 (d, 2H), 6.46 (m, 1H), 6.15 (d, 1H), 3.86 (dd, 2H), 3.07 (br s, 4H), 2.76 (br s, 2H), 2.30-2.12 (m, 6H), 1.97 (br s, 2H), 1.90 (m, 1H), 1.63 (d, 2H), 1.40 (t, 2H), 1.35-1.15 (m, 6H), 0.94 (s, 6H).

Example 283

4-(4-{[2-(4-chlorophenyl)-4,4-dimethylcyclohex-1-en-1-yl]methyl}piperazin-1-yl)-2-[(6-hydroxypyridin-3-yl)oxy]-N-({3-nitro-4-[(tetrahydro-2H-pyran-4-ylmethyl)amino]phenyl}sulfonyl)benzamide

Example 283A methyl 2-(6-(benzyloxy)pyridin-3-yloxy)-4-fluorobenzoate

To 6-(benzyloxy)pyridin-3-ol (1.10 g) in 2-methyltetrahydrofuran (20 mL) was added potassium t-butoxide (5.47 mL, 1.0M in tetrahydrofuran). After stirring for 15 minutes, methyl 2,4-difluorobenzoate (1.035 g) in 2-methyltetrahydrofuran (2 mL) was added and the reaction heated to 75° C. for 1 hour. The reaction was cooled, diluted with ethyl acetate (150 mL), washed with water (50 mL), brine (50 mL), dried over magnesium sulfate, filtered and concentrated. Silica gel chromatography (SF40-80 g) eluting with a gradient of 5% to 20% ethyl acetate/hexanes gave the title compound.

Example 283B methyl 2-(6-(benzyloxy)pyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 283A for EXAMPLE 3A in EXAMPLE 3G.

Example 283C 2-(6-(benzyloxy)pyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 283B for EXAMPLE 1E in EXAMPLE 1F.

Example 283D

2-{[6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 283C for EXAMPLE 1F in EXAMPLE 1H.

Example 283E 4-(4-((2-(4-chlorophenyl)-4,4-dimethylcyclohex-1-enyl)methyl)piperazin-1-yl)-2-(6-hydroxypyridin-3-yloxy)-N-(3-nitro-4-((tetrahydro-2H-pyran-4-yl)methylamino)phenylsulfonyl)benzamide To 2-(6-(benzyloxy)pyridin-3-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide (0.132 g) in dichloromethane (1 mL) was added trifluoroacetic acid (0.33 mL) and the reaction was sealed in a vial under nitrogen and heated to 40° C. After stirring for 16 hours, the reaction was cooled, diluted with dichloromethane (50 mL) and washed with sodium carbonate (2×25 mL). The organic layer was dried over magnesium sulfate, filtered, and concentrated. Silica gel chromatography (GraceResolv 12 g) eluting with a gradient of 0.3% to 3% methanol/dichloromethane (Flow=36 mL/minute) over 30 minutes gave the title compound. $^1$H NMR (300 MHz, CDCl$_3$) δ 12.51-11.38 (m, 1H), 9.78 (s, 1H), 8.89 (d, 1H), 8.52 (t, 1H), 8.19 (dd, 1H), 7.92 (d, 1H), 7.43-7.33 (m, 2H), 7.24 (d, 2H), 7.00-6.89 (m, 3H), 6.74-6.67 (m, 1H), 6.55 (dd, 1H), 6.00 (d, 1H), 4.00 (d, 2H), 3.42 (dd, 2H), 3.34-3.23 (m, 2H), 3.16 (s, 4H), 2.79 (s, 2H), 2.24 (d, 6H), 1.99 (s, 3H), 1.72 (s, 2H), 1.55-1.33 (m, 4H), 0.96 (s, 6H).

Example 284

2-{6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared as described in EXAMPLE 283D. $^1$H NMR (300 MHz, CDCl$_3$) δ 9.93 (s, 1H), 8.88 (d, 1H), 8.52 (t, 1H), 8.17 (dd, 1H), 8.05 (d, 1H), 7.92 (d, 1H), 7.49 (d, 2H), 7.45-7.34 (m, 4H), 7.24 (d, 2H), 6.97-6.85 (m, 4H), 6.54 (dd, 1H), 5.95 (d, 1H), 5.41 (s, 2H), 4.02 (dd, 2H), 3.48-3.35 (m, 2H), 3.30-3.23 (m, 2H), 3.15-3.02 (m, 4H), 2.77 (s, 2H), 2.23 (dd, 6H), 1.95 (d, 3H), 1.71 (s, 2H), 1.59-1.33 (m, 4H), 1.03-0.89 (m, 6H).

Example 285

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-[(6-fluoro-1H-indol-5-yl)oxy]benzamide

Example 285A 4-((1,4-dioxan-2-yl)methoxy)-3-nitrobenzenesulfonamide (1,4-Dioxan-2-yl)methanol (380 mg) in tetrahydrofuran (30 mL) was treated with sodium hydride (60%, 245 mg) at room temperature for 30 minutes. The reaction mixture was cooled in an ice bath and 4-fluoro-3-nitrobenzenesulfonamide (675 mg) was added. The resulting mixture was stirred at room temperature for 2 hours and another portion of sodium hydride (60%, 245 mg) was added. The reaction mixture was stirred overnight and quenched with ice water (3 mL). The cloudy mixture was filtered and the filtrate was concentrated. The residue was triturated with methanol to give the title compound.

Example 285

4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}-2-[(6-fluoro-1H-indol-5-yl)oxy]benzamide The title compound was prepared as described in EXAMPLE 110F by replacing EXAMPLE 110E and EXAMPLE 1G with EXAMPLE 154E and EXAMPLE 285A, respectively. $^1$H NMR (500 MHz, dimethylsulfoxide-d$_6$) δ 11.21 (s, 2H), 8.38 (d, 1H), 8.10 (d, 1H), 7.52 (d, 1H), 7.47 (d, 1H), 7.38 (t, 1H), 7.32-7.36 (m, 3H), 7.27 (d, 1H), 7.04 (d, 2H), 6.65 (dd, 1H), 6.40 (s, 1H), 6.10 (d, 1H), 4.20-4.29 (m, 2H), 3.85-3.91 (m, 1H), 3.82 (dd, 1H), 3.74-3.78 (m, 1H), 3.59-3.69 (m, 2H), 3.40-3.51 (m, 2H), 3.06 (s, 4H), 2.82 (s, 2H), 2.26 (s, 4H), 2.14 (s, 2H), 1.95 (s, 2H), 1.39 (t, 2H), 0.92 (s, 6H).

Example 286

2-[(3-chloro-1H-indol-4-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 266D for EXAMPLE 1F and EXAMPLE 184A for EXAMPLE 1G in EXAMPLE 1H. $^1$H NMR (500 MHz, dimethylsulfoxide-d$_6$) δ 11.51 (s, 1H), 9.17 (s, 1H), 8.48 (s, 1H), 7.83 (d, 1H), 7.58 (d, 2H), 7.43 (s, 1H), 7.33 (d, 2H), 7.20 (d, 1H), 7.07-7.03 (m, 3H), 6.66 (d, 1H), 6.52 (m, 1H), 6.10 (s, 1H), 3.00 (m, 3H), 2.90 (m, 6H), 2.71 (br.s, 2H), 2.50 (s, 3H), 2.32 (m, 3H), 2.15 (m, 6H), 1.95 (br.s, 2H), 1.38 (t, 2H), 0.92 (s, 6H).

Example 287

4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)-2-[(2-oxo-2,3-dihydro-1H-indol-4-yl)oxy]benzamide The title compound was prepared by substituting EXAMPLE 286 for EXAMPLE 265E in EXAMPLE 267. $^1$H NMR (500 MHz, dimethylsulfoxide-d$_6$) δ 10.31 (s, 1H), 8.86 (s, 1H), 8.29 (s, 1H), 7.54 (m, 2H), 7.42 (d, 1H), 7.36 (d, 2H), 7.08 (d, 2H), 6.91 (t, 1H), 6.68 (d, 1H), 6.39 (m, 2H), 6.06 (d, 1H), 3.34 (m, 4H), 3.27 (s, 2H), 3.08 (br.s, 4H), 2.86 (m, 4H), 2.76 (s, 2H), 2.28 (s, 3H), 2.25-2.10 (m, 6H), 1.97 ((br.s, 2H), 1.40 (t, 2H), 0.94 (s, 6H).

Example 288

4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[(2-oxo-2,3-dihydro-1H-indol-4-yl)oxy]benzamide

Example 288A 2-(3-chloro-1H-indol-4-yloxy)-4-(4-((2-(4-chlorophenyl)-4,4-dimethylcyclohex-1-enyl)methyl)piperazin-1-yl)-N-(4-(1-methylpiperidin-4-ylamino)-3-nitrophenylsulfonyl)benzamide The title compound was prepared by substituting EXAMPLE 266D for EXAMPLE 1F and EXAMPLE 3I for EXAMPLE 1G in EXAMPLE 1H.

Example 288B 4-(4-{[2-(4-chlorophenyl)-4,4-dimethylcyclohex-1-en-1-yl]methyl}piperazin-1-yl)-N-({4-[(1-methylpiperidin-4-yl)amino]-3-nitrophenyl}sulfonyl)-2-[(2-oxo-2,3-dihydro-1H-indol-4-yl)oxy]benzamide The title compound was prepared by substituting EXAMPLE 288A for EXAMPLE 265E in EXAMPLE 267. $^1$H NMR (500 MHz, dimethylsulfoxide-$d_6$) δ 10.29 (s, 1H), 8.34 (s, 1H), 8.05 (br. d, 1H), 7.64 (d, 1H), 7.54 (d, 1H), 7.36 (d, 2H), 7.07 (d, 2H), 7.01 (d, 1H), 6.91 (t, 1H), 6.68 (d, 1H), 6.38 (m, 2H), 6.08 (d, 1H), 3.80 (br.s, 1H), 3.34 (m, 2H), 3.23 (s, 2H), 3.09 (br.s, 4H), 2.84 (m, 2H), 2.76 (s, 2H), 2.62 (br.s, 2H), 2.24 (s, 3H), 2.25-2.05 (m, 6H), 1.98 ((br.s, 2H), 1.76 (m, 2H), 1.40 (t, 2H), 0.94 (s, 6H).

Example 289

4-(4-{[2-(4-chlorophenyl)-4,4-dimethylcyclohex-1-en-1-yl]methyl}piperazin-1-yl)-N-({3-nitro-4-[(1-tetrahydro-2H-pyran-4-ylpiperidin-4-yl)amino]phenyl}sulfonyl)-2-[(2-oxo-2,3-dihydro-1H-indol-4-yl)oxy]benzamide

Example 289A 2-(3-chloro-1H-indol-4-yloxy)-4-(4-((2-(4-chlorophenyl)-4,4-dimethylcyclohex-1-enyl)methyl)piperazin-1-yl)-N-(3-nitro-4-(1-(tetrahydro-2H-pyran-4-yl)piperidin-4-ylamino)phenylsulfonyl)benzamide The title compound was prepared by substituting EXAMPLE 266D for EXAMPLE 1F and EXAMPLE 49C for EXAMPLE 1G in EXAMPLE 1H.

Example 289B 4-(4-((2-(4-chlorophenyl)-4,4-dimethylcyclohex-1-enyl)methyl)piperazin-1-yl)-N-(3-nitro-4-(1-(tetrahydro-2H-pyran-4-yl)piperidin-4-ylamino)phenylsulfonyl)-2-(2-oxoindolin-4-yloxy)benzamide The title compound was prepared by substituting EXAMPLE 289A for EXAMPLE 265E in EXAMPLE 267. $^1$H NMR (500 MHz, dimethylsulfoxide-$d_6$) δ 10.32 (s, 1H), 8.37 (s, 1H), 8.12 (br. s, 1H), 7.68 (d, 1H), 7.52 (d, 1H), 7.36 (d, 2H), 7.07 (m, 3H), 6.93 (t, 1H), 6.69 (d, 1H), 6.40 (m, 2H), 6.09 (d, 1H), 3.94 (m, 2H), 3.83 (br.s, 1H), 3.34 (m, 7H), 3.23 (s, 2H), 3.12 (br.s, 4H), 2.77 (s, 2H), 2.62 (s, 2H), 2.30-2.00 (m, 8H), 1.98 ((br.s, 2H), 1.85 (m, 2H), 1.73 (m, 2H), 1.54 (m, 2H), 1.40 (t, 2H), 0.94 (s, 6H).

Example 290

2-[(6-chloro-1H-indol-5-yl)oxy]-4-(4-{[2-(4-chlorophenyl)-4,4-dimethylcyclohex-1-en-1-yl]methyl}piperazin-1-yl)-N-{[4-(1,4-dioxan-2-yl-methoxy)-3-nitrophenyl]sulfonyl}benzamide The title compound was prepared as described in EXAMPLE 1H by replacing EXAMPLE 1F and EXAMPLE 1G with EXAMPLE 242H and EXAMPLE 285A, respectively. $^1$H NMR (300 MHz, dimethylsulfoxide-$d_6$) δ 11.25 (s, 1H), 8.37 (d, 1H), 8.09 (m, 1H), 7.48 (m, 4H), 7.33 (m, 3H), 7.05 (m, 3H), 6.65 (dd, 1H), 6.42 (m, 1H), 6.01 (d, 1H), 4.25 (m, 2H), 3.83 (m, 3H), 3.63 (m, 3H), 3.45 (m, 2H), 3.04 (m, 4H), 2.74 (m, 2H), 2.24 (m, 5H), 1.95 (s, 2H), 1.38 (t, 2H), 0.92 (s, 6H).

Example 291

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide

Example 291A 4-((1,4-dioxan-2-yl)methylamino)-3-nitrobenzenesulfonamide

The title compound was prepared as described in EXAMPLE 4A by replacing 3-(N-morpholinyl)-1-propylamine with C-[1,4]dioxan-2-yl-methylamine.

Example 291B

2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide The title compound was prepared as described in EXAMPLE 1H by replacing EXAMPLE 1F and EXAMPLE 1G with EXAMPLE 242H and EXAMPLE 291A, respectively. $^1$H NMR (300 MHz, dimethylsulfoxide-$d_6$) δ 11.25 (s, 1H), 8.37 (d, 1H), 8.09 (dd, 1H), 7.54 (m, 2H), 7.44 (m, 2H), 7.33 (m, 3H), 7.05 (m, 2H), 6.65 (dd, 1H), 6.42 (s, 1H), 6.01 (d, 1H), 3.83 (m, 3H), 3.63 (m, 2H), 3.45 (m, 2H), 3.04 (m, 4H), 2.74 (m, 2H), 2.24 (m, 5H), 1.95 (s, 2H), 1.38 (t, 2H), 0.92 (s, 6H).

Example 292

4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)-2-[(6-fluoro-1H-indol-5-yl)oxy]benzamide The title compound was prepared as described in EXAMPLE 1H by replacing EXAMPLE 1F and EXAMPLE 1G with EXAMPLE 154E and EXAMPLE 291A, respectively. $^1$H NMR (300 MHz, dimethylsulfoxide-$d_6$) δ 11.20 (s, 1H), 8.58 (d, 2H), 7.95 (s, 1H), 7.88 (dd, 1H), 7.51 (d, 1H), 7.34 (m, 5H), 7.15 (d, 1H), 7.03 (d, 2H), 6.65 (dd, 1H), 6.40 (s, 1H), 3.78 (m, 3H), 3.61 (m, 2H), 3.46 (m, 3H), 3.03 (m, 4H), 2.89 (s, 3H), 2.73 (m, 2H), 2.15 (m, 4H), 1.95 (m, 2H), 1.38 (t, 2H), 0.92 (s, 6H).

Example 293

Trans-2-[(6-chloro-1H-indol-5-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide The title compound was prepared as described in EXAMPLE 1H by replacing EXAMPLE 1F and EXAMPLE 1G with EXAMPLE 242H and EXAMPLE 205A, respectively. $^1$H NMR (300 MHz, dimethylsulfoxide-$d_6$) δ 11.23 (s, 1H), 8.53 (d, 1H), 8.17 (d, 1H), 7.82 (dd, 1H), 7.53 (t, 2H), 7.41 (t, 1H), 7.33 (d, 2H), 7.24 (s, 1H), 7.11 (d, 1H), 7.03 (d, 2H), 6.64 (dd, 1H), 6.40 (s, 1H), 6.01 (d, 1H), 3.60 (m, 5H), 3.02 (m, 4H), 2.71 (s, 2H), 2.57 (m, 6H), 2.03 (m, 12H), 1.39 (m, 6H), 0.92 (s, 6H).

Example 294

Trans-2-[(6-chloro-1H-indol-5-yl)oxy]-4-(4-{[4-(4-chlorophenyl)-6,6-dimethyl-5,6-dihydro-2H-pyran-3-yl]methyl}piperazin-1-yl)-N-({4-[(4-morpholin-4-ylcyclohexyl)amino]-3-nitrophenyl}sulfonyl) benzamide The title compound was prepared as described in EXAMPLE 1H by replacing EXAMPLE 1F and EXAMPLE 1G with EXAMPLE 275B and EXAMPLE 205A, respectively. $^1$H NMR (300 MHz, dimethylsulfoxide-$d_6$) δ 11.20 (s, 1H), 8.50 (d, 1H), 8.14 (d, 1H), 7.79 (dd, 1H), 7.54 (m, 2H), 7.38 (m, 3H), 7.12 (m, 4H), 6.63 (dd, 1H), 6.38 (s, 1H), 6.02 (d, 1H), 4.10 (s, 2H), 3.59 (m, 6H), 3.31 (m, 4H), 3.01 (m, 4H), 2.81 (s, 2H), 2.68 (s, 2H), 2.54 (m, 3H), 2.03 (m, 5H), 1.39 (m, 4H), 1.20 (s, 6H).

Example 295

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-morpholin-4-ylcyclohexyl)amino]-3-nitrophenyl}sulfonyl)benzamide The title compound was prepared as described in EXAMPLE 1H by replacing EXAMPLE 1F and EXAMPLE 1G with EXAMPLE 277B and EXAMPLE 205A, respectively. $^1$H NMR (300 MHz, dimethylsulfoxide-$d_6$) δ 11.17 (s, 1H), 8.53 (d, 1H), 8.16 (d, 1H), 7.83 (dd, 1H), 7.52 (d, 1H), 7.34 (m, 4H), 7.20 (dd, 1H), 7.13 (m, 3H), 6.63 (dd, 1H), 6.38 (s, 1H), 6.09 (d, 1H), 4.10 (s, 2H), 4.01 (s, 1H), 3.61 (m, 4H), 3.02 (m, 4H), 2.81 (s, 2H), 2.59 (m, 3H), 2.12 (m, 12H), 1.39 (m, 4H), 1.18 (s, 6H).

Example 296

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl) benzamide

Example 296A 1,6-dioxaspiro[2.5]octane-2-carbonitrile

A mixture of dihydro-2H-pyran-4(3H)-one (10.0 g) and 2-chloroacetonitrile (7.5 g) in tert-butanol (10 mL) was treated with 1.0 N potassium tert-butoxide (100 mL) dropwise over 20 minutes. The reaction mixture was stirred at room temperature for 16 hours. It was diluted with water (10 mL) and 10% aqueous HCl (20 mL). The reaction mixture was concentrated to one-third of its original volume, and extracted with diethyl ether four times. The combined organic layers were washed with brine, dried over MgSO$_4$, filtered, and concentrated. The residue was purified with flash column chromatography on silica gel eluting with 20-40% ethyl acetate in hexanes.

Example 296B 2-(4-fluorotetrahydro-2H-pyran-4-yl)-2-hydroxyacetonitrile

EXAMPLE 296A (11.5 g) was dissolved in dichloromethane (40 mL) in a polypropylene bottle. The bottle was cooled to 0° C. To this solution was added 70% hydrogen fluoride-pyridine (10.3 mL) slowly. The solution was allowed to warm to room temperature over 3 hours, and stirred for 24 hours. The reaction mixture was diluted with ethyl acetate (200 mL) and poured into saturated aqueous NaHCO$_3$. Additional solid NaHCO$_3$ was used to neutralize the solution carefully until bubbling ceased. The organic layer was isolated, and the aqueous layer was extracted with additional ethyl acetate three times (150 mL each). The combined organic layers were washed with 1% aqueous HCl, brine, dried (MgSO$_4$), filtered and concentrated to give the desired compound which was used directly in the next reaction.

Example 296C (4-fluorotetrahydro-2H-pyran-4-yl)methanol

EXAMPLE 296B (11.8 g) in 2-propanol (150 mL) and water (37 mL) was cooled to 0° C. To this solution was added sodium borohydride (4.2 g). The solution was stirred and allowed to warm to room temperature over 3 hours. The reaction was quenched with acetone, and stirred for another 1 hour. The clear liquid was separated from the solid by decanting. Additional ethyl acetate was used to wash the solid, and was decanted. The combined organic solutions were concentrated. The residue was purified with flash column chromatography on silica gel eluting with 20-40% ethyl acetate-hexanes.

Example 296D 4-((4-fluorotetrahydro-2H-pyran-4-yl)methoxy)-3-nitrobenzenesulfonamide EXAMPLE 296C (2.0 g) in tetrahydrofuran (20 mL) was treated with 60% NaH (1.3 g). The solution was stirred for 20 minutes at the room temperature. To this solution was added 4-fluoro-3-nitrobenzenesulfonamide (2.8 g) portion-wise. The reaction was stirred for another 2 hours. The mixture was poured into water, neutralized with 10% aqueous HCl, and extracted with ethyl acetate three times. The combined organic layers were washed with brine, dried over MgSO$_4$, filtered, and concentrated. The residue was purified with flash column chromatography on silica gel eluting with 20%-60% ethyl acetate in hexanes.

Example 296E 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl) benzamide The title compound was prepared by substituting EXAMPLE 154E for EXAMPLE 122C and EXAMPLE 296D for EXAMPLE 11A in EXAMPLE 137. $^1$H NMR (500 MHz, dimethylsulfoxide-$d_6$) δ 11.20 (s, 1H), 8.40 (s, 1H), 8.13 (br d, 1H), 7.54 (d, 1H), 7.49 (br d, 1H), 7.38 (dd, 1H), 7.33 (d, 3H), 7.28 (br d, 1H), 7.04 (d, 2H), 6.64 (d, 1H), 6.40

(s, 1H), 6.09 (s, 1H), 4.38 (d, 2H), 3.78 (m, 2H), 3.60 (m, 2H), 3.06 (v br s, 4H), 2.82 (br s, 2H), 2.27 (v br s, 4H), 2.15 (br m, 2H), 1.95 (s, 2H), 1.85 (m, 4H), 1.40 (t, 2H), 0.92 (s, 6H).

Example 297

4-(4-{[4-(4-chlorophenyl)-6,6-dimethyl-5,6-dihydro-2H-pyran-3-yl]methyl})piperazin-1-yl)-2-[(6-fluoro-1H-indol-5-yl)oxy]-N-({4-[(4-fluorotetrahydro-2H-pyran-4-yl)methoxy]-3-nitrophenyl}sulfonyl) benzamide The title compound was prepared by substituting EXAMPLE 277B for EXAMPLE 122C and EXAMPLE 296D for EXAMPLE 11A in EXAMPLE 137. $^1$H NMR (500 MHz, dimethylsulfoxide-$d_6$) δ 11.20 (s, 1H), 8.43 (s, 1H), 8.16 (br d, 1H), 7.52 (d, 2H), 7.38 (m, 4H), 7.30 (br d, 1H), 7.11 (d, 2H), 6.64 (d, 1H), 6.40 (s, 1H), 6.09 (s, 1H), 4.40 (d, 2H), 4.10 (s, 2H), 3.78 (m, 2H), 3.60 (m, 2H), 3.07 (v br s, 4H), 2.84 (br s, 2H), 2.24 (v br s, 4H), 2.16 (s, 2H), 1.85 (m, 4H), 1.18 (s, 6H).

Example 298

4-(4-{[4-(4-chlorophenyl)-6,6-dimethyl-5,6-dihydro-2H-pyran-3-yl]methyl}piperazin-1-yl)-N-{[5-cyano-6-(tetrahydro-2H-pyran-4-ylmethoxy)pyridin-3-yl] sulfonyl}-2-[(6-fluoro-1H-indol-5-yl)oxy]benzamide The title compound was prepared by substituting EXAMPLE 277B for EXAMPLE 122C and EXAMPLE 301B for EXAMPLE 11A in EXAMPLE 137. $^1$H NMR (500 MHz, dimethylsulfoxide-$d_6$) δ 11.20 (s, 1H), 8.83 (d, 1H), 8.60 (s, 1H), 7.54 (d, 1H), 7.38 (d, 2H), 7.37 (m, 1H), 7.33 (d, 1H), 7.21 (br d, 1H), 7.13 (d, 2H), 6.66 (dd, 1H), 6.38 (s, 1H), 6.12 (s, 1H), 4.30 (d, 2H), 4.10 (s, 2H), 3.85 (dd, 2H), 3.33 (m, 2H), 3.07 (v br s, 4H), 2.95 (br s, 2H), 2.31 (v br s, 4H), 2.16 (s, 2H), 2.05 (m, 1H), 1.63 (br m, 2H), 1.38 (ddd, 2H), 1.18 (s, 6H).

Example 299

2-{[3-(2-aminoethyl)-1H-indol-5-yl]oxy}-4-(4-{[2-(4-chlorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl) benzamide Example 299A tert-butyl 2-(5-hydroxy-1H-indol-3-yl)ethylcarbamate To a suspension of 3-(2-aminoethyl)-1H-indol-5-ol, hydrochloride (5 g) in dichloromethane (100 mL) was added N-ethyl-N-isopropylpropan-2-amine (3.19 g) followed by a solution of di-tert-butyl dicarbonate (5.64 g) in dichloromethane (10 mL). The mixture was stirred at ambient temperature under nitrogen 18 hours. The resulting solution was washed with brine, dried over sodium sulfate, filtered and concentrated. The crude material was purified on silica gel with 1-5% methanol in methylene chloride.

Example 299B ethyl 2-(3-(2-(tert-butoxycarbonylamino)ethyl)-1H-indol-5-yloxy)-4-fluorobenzoate The title compound was prepared by substituting EXAMPLE 299A for 2-methyl-5-indolol in EXAMPLE 3A.

Example 299C ethyl 2-(3-(2-(tert-butoxycarbonylamino)ethyl)-1H-indol-5-yloxy)-4-(4-((2-(4-chlorophenyl)-4,4-dimethylcyclohex-1-enyl)methyl)piperazin-1-yl)benzoate The title compound was prepared by substituting EXAMPLE 299B for EXAMPLE 3A in EXAMPLE 3G.

Example 299D 2-(3-(2-(tert-butoxycarbonylamino)ethyl)-1H-indol-5-yloxy)-4-(4-((2-(4-chlorophenyl)-4,4-dimethylcyclohex-1-enyl)methyl)piperazin-1-yl)benzoic acid The title compound was prepared by substituting EXAMPLE 299C for EXAMPLE 1E in EXAMPLE 1F.

Example 299E tert-butyl 2-(5-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino) phenylsulfonylcarbamoyl)phenoxy)-1H-indol-3-yl) ethylcarbamate The title compound was prepared by substituting EXAMPLE 299D for EXAMPLE 1F in EXAMPLE 1H.

Example 299F

2-{[3-(2-aminoethyl)-1H-indol-5-yl]oxy}-4-(4-{[2-(4-chlorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl) benzamide A solution of EXAMPLE 299E (146.6 mg) in dichloromethane (10 mL) was cooled in an ice bath and 2,2,2-trifluoroacetic acid (5 mL) was added dropwise over 5 minutes. The reaction mixture was stirred 15 minutes under nitrogen, the ice bath was removed and the reaction was allowed to come to ambient temperature. The reaction was stirred 1.5 hours and then concentrated. The crude material was purified by reverse phase chromatography with ammonium acetate buffer in acetonitrile to give the title compound. $^1$H NMR (300 MHz, dimethyosulfoxide-$d_6$) δ 10.86 (d, 1H), 8.39 (d, 1H), 8.33 (t, 1H), 8.06 (br s, 1H), 7.71 (dd, 1H), 7.53 (d, 1H), 7.34 (d, 2H), 7.26 (d, 1H), 7.19 (d, 1H), 7.05 (m, 3H), 6.89 (d, 1H), 6.70 (dd, 1H), 6.52 (dd, 1H), 6.15 (d, 1H), 3.83 (dd, 2H), 3.22 (m, 3H), 2.82-3.00 (m, 8H), 2.72 (s, 2H), 2.16 (m, 6H), 1.96 (s, 2H), 1.88 (m, 4H), 1.60 (d, 2H), 1.38 (m, 2H), 1.24 (m, 2H), 0.93 (s, 6H).

Example 300

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide

Example 300A tert-butyl 2-(5-(5-(4-((2-(4-chlorophenyl)-4,4-dimethylcyclohex-1-enyl)methyl)piperazin-1-yl)-2-(4-(4-methylpiperazin-1-ylamino)-3-nitrophenylsulfonylcarbamoyl)phenoxy)-1H-indol-3-yl)ethylcarbamate The title compound was prepared by substituting EXAMPLE 299D for EXAMPLE 1F and EXAMPLE 184A for EXAMPLE 1G in EXAMPLE 1H.

Example 300B

2-{[3-(2-aminoethyl)-1H-indol-5-yl]oxy}-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 300A for EXAMPLE 299E in EXAMPLE 299F. $^1$H NMR (300 MHz, dimethylsulfoxide-$d_6$) δ 10.88 (d, 1H), 8.78 (s, 1H), 8.61 (br s, 1H), 8.38 (d, 1H), 7.76 (dd, 1H), 7.52 (d, 1H), 7.42 (d, 1H), 7.34 (d, 2H), 7.27 (d, 1H), 7.20 (d, 1H), 7.05 (m, 3H), 6.71 (dd, 1H), 6.51 (dd, 1H), 6.14 (dm, 1H), 3.02-2.80 (m, 12H), 2.71 (s, 2H), 2.20-2.11 (m, 9H), 1.95 (s, 2H), 1.90 (s, 6H), 1.38 (m, 2H), 0.93 (s, 6H).

Example 301

4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide

Example 301A (Tetrahydro-2H-pyran-4-yl)methanol (0.65 g) in tetrahydrofuran (20 mL) was treated with 60% sodium hydride (0.895 g). The reaction mixture was stirred for 10 minutes. To this solution was added EXAMPLE 305A (1.519 g). The reaction mixture was stirred overnight. It was poured into water, neutralized with 10% aqueous HCl, and extracted with ethyl acetate three times. The combined organic layers were washed with brine, dried over MgSO$_4$, filtered, and concentrated. The residue was purified with flash column chromatography on silica gel eluting with 20%-60% ethyl acetate in hexanes to give the title compound.

Example 301B

A mixture of EXAMPLE 301A (0.702 g), dicyanozine (0.129 g), and tetrakis(triphenylphosphine)palladium(0) (0.231 g) in N,N-dimethylformamide (2 mL) was degassed via vacuum/nitrogen cycle three times. The reaction mixture was heated at 120° C. for 3 hours. After cooling, it was poured into water and extracted with ethyl acetate three times. The combined organic layers were washed with brine, dried over MgSO$_4$, filtered, and concentrated. The residue was purified with flash column chromatography on silica gel eluting with 20%-60% tetrakis(triphenylphosphine)palladium(0) in hexanes to give the title compound.

Example 301C 4-(4-{[2-(4-chlorophenyl)-4,4-dimethylcyclohex-1-en-1-yl]methyl}piperazin-1-yl)-N-{[5-cyano-6-(tetrahydro-2H-pyran-4-ylmethoxy)pyridin-3-yl]sulfonyl}-2-[(6-fluoro-1H-indol-5-yl)oxy]benzamide The title compound was prepared by substituting EXAMPLE 154E for EXAMPLE 1F and EXAMPLE 301B for EXAMPLE 1G in EXAMPLE 1H. $^1$H NMR (500 MHz, dimethylsulfoxide-$d_6$) δ 11.14 (s, 1H), 8.75 (s, 1H), 8.51 (s, 1H), 7.55 (d, 1H), 7.32-7.34 (m, 3H), 7.28 (d, 1H), 7.12 (d, 1H), 7.04 (d, 2H), 6.62 (dd, 1H), 6.33 (s, 1H), 6.11 (s, 1H), 4.28 (d, 2H), 3.86 (dd, 2H), 2.92-3.06 (m, 4H), 2.35-2.38 (m, 2H), 1.95-2.15 (m, 5H), 1.61-1.64 (m, 2H), 1.34-1.40 (m, 4H), 0.91 (s, 6H).

Example 302

2-[(6-amino-5-fluoropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 302A methyl 2-(6-chloro-5-fluoropyridin-3-yloxy)-4-fluorobenzoate

To a solution of 6-chloro-5-fluoropyridin-3-ol (0.977 g) in 2-methyltetrahydrofuran (12 mL) was added potassium 2-methylpropan-2-olate (1.0M in tetrahydrofuran, 7.28 mL). After stirring for 15 minutes at room temperature, methyl 2,4-difluorobenzoate (1.710 g) was added as a solution in 2-methyltetrahydrofuran (2 mL) followed by N,N-dimethylformamide (2 mL) then the reaction was heated to 75° C. under a nitrogen atmosphere. After stirring overnight the reaction was cooled, diluted with ethyl acetate (100 mL) and washed with water (50 mL) and brine (50 mL), dried over magnesium sulfate, filtered, and concentrated. Silica gel chromatography (GraceResolv 40 g) eluting with a gradient of 2% to 15% ethyl acetate/hexanes gave the title compound.

Example 302B methyl 2-(6-(tert-butoxycarbonylamino)-5-fluoropyridin-3-yloxy)-4-fluorobenzoate Methyl 2-(6-chloro-5-fluoropyridin-3-yloxy)-4-fluorobenzoate (0.875 g), tert-butyl carbamate (0.410 g), cesium carbonate (1.427 g), diacetoxypalladium (0.033 g) and (9,9-dimethyl-9H-xanthene-4,5-diyl)bis(diphenylphosphine) (0.169 g) were added to dioxane (10 mL). The reaction was degassed with nitrogen then sealed. The reaction was then heated to 85° C. After stirring for 16 hours the reaction was cooled, diluted with water (25 mL) and the product was extracted into dichloromethane (2×25 mL). The organic layer was dried over magnesium sulfate, filtered, and concentrated. Silica gel chromatography (GraceResolv 40 g) eluting with a gradient of 5% to 25% ethyl acetate/hexanes gave the title compound.

Example 302C methyl 2-(6-(tert-butoxycarbonylamino)-5-fluoropyridin-3-yloxy)-4-(piperazin-1-yl)benzoate Methyl 2-(6-(tert-butoxycarbonylamino)-5-fluoropyridin-3-yloxy)-4-fluorobenzoate (0.170 g) and piperazine (0.154 g) were dissolved in dimethylsulfoxide (2 mL) and heated to 85° C. After 1 hour, the reaction was cooled, poured into dichloromethane (75 mL), and washed with water (30 mL). The organic layer was dried over magnesium sulfate, filtered, and concentrated to give the title compound.

Example 302D methyl 2-(6-(tert-butoxycarbonylamino)-5-fluoropyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 302C for tert-butyl piperazine-1-carboxylate and EXAMPLE 60D for 4'-chlorobiphenyl-2-carboxaldehyde in EXAMPLE 1A.

Example 302E 2-(6-(tert-butoxycarbonylamino)-5-fluoropyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 302D for EXAMPLE 1E in EXAMPLE 1F.

Example 302F tert-butyl 5-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino)phenylsulfonylcarbamoyl)phenoxy)-3-fluoropyridin-2-ylcarbamate The title compound was prepared by substituting EXAMPLE 302E for EXAMPLE 1F in EXAMPLE 1H.

Example 302G 2-(6-amino-5-fluoropyridin-3-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide To EXAMPLE 302F (0.115 g) in dichloromethane (2 mL) was added TFA (0.276 mL). After stirring for 3 hours the reaction was concentrated, dissolved in dichloromethane (50 mL) and washed with aqueous saturated $NaHCO_3$ (30 mL), dried over magnesium sulfate, filtered, and concentrated. Silica gel chromatography (GraceResolv 12 g) eluting with a gradient of 0.5% to 3% methanol/dichloromethane gave the title compound. $^1$H NMR (300 MHz, $CDCl_3$) δ 9.86 (s, 1H), 8.88 (d, J=2.2, 1H), 8.52 (s, 1H), 8.17 (dd, 1H), 7.92 (d, 1H), 7.83 (d, 1H), 7.26 (s, 1H), 7.11 (dd, 1H), 6.93 (dd, 3H), 6.54 (dd, 1H), 5.98 (d, 1H), 4.69 (s, 2H), 4.02 (dd, 2H), 3.42 (d, 2H), 3.31-3.23 (m, 2H), 3.12 (s, 4H), 2.78 (s, 2H), 2.25 (s, 6H), 1.99 (s, 3H), 1.72 (s, 2H), 1.55-1.34 (m, 4H), 0.96 (s, 6H).

Example 303

4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-[(6-fluoro-1H-indol-5-yl)oxy]benzamide

Example 303A 5,6-dichloropyridine-3-sulfonamide

The title compound was prepared by substituting 5,6-dichloropyridine-3-sulfonyl chloride for 5-bromo-6-chloropyridine-3-sulfonyl chloride in EXAMPLE 305A.

Example 303B 5-chloro-6-((tetrahydro-2H-pyran-4-yl)methoxy)pyridine-3-sulfonamide The title compound was prepared by substituting EXAMPLE 303A for EXAMPLE 305A and (tetrahydro-2H-pyran-4-yl)methanol for (1,3-dioxan-4-yl)methanol in EXAMPLE 305B.

Example 303C 4-(4-{[2-(4-chlorophenyl)-4,4-dimethylcyclohex-1-en-1-yl]methyl}piperazin-1-yl)-N-{[5-chloro-6-(tetrahydro-2H-pyran-4-ylmethoxy)pyridin-3-yl]sulfonyl}-2-[(6-fluoro-1H-indol-5-yl)oxy]benzamide The title compound was prepared by substituting EXAMPLE 154E for EXAMPLE 122C and EXAMPLE 303B for EXAMPLE 11A in EXAMPLE 137. $^1$H NMR (500 MHz, dimethylsulfoxide-$d_6$) δ 11.20 (s, 1H), 8.57 (d, 1H), 8.23 (s, 1H), 7.54 (d, 1H), 7.37 (dd, 1H), 7.35 (m, 3H), 7.26 (br d, 1H), 7.05 (d, 2H), 6.64 (dd, 1H), 6.40 (s, 1H), 6.10 (s, 1H), 4.25 (d, 2H), 3.86 (dd, 2H), 3.33 (m, 2H), 3.06 (v br s, 4H), 2.86 (br s, 2H), 2.30 (v br s, 4H), 2.05 (m, 1H), 2.15 (br m, 2H), 1.95 (s, 2H), 1.63 (br d, 2H), 1.40 (t, 2H), 1.33 (ddd, 2H), 0.92 (s, 6H).

Example 304

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(1-oxo-1,2,3,4-tetrahydroisoquinolin-5-yl)oxy]benzamide

Example 304A

4-Fluoro-2-(1-oxo-1,2,3,4-tetrahydro-isoquinolin-5-yloxy)-benzoic acid methyl ester The title compound was prepared by substituting methyl 2,4-difluorobenzoate for ethyl 2,4-difluorobenzoate and 5-hydroxy-3,4-dihydro-2H-isoquinolin-1-one for 2-methyl-5-indolol in EXAMPLE 3A, except here the heating was at 130° C.

Example 304B

4-{4-[2-(4-Chloro-phenyl)-4,4-dimethyl-cyclohex-1-enylmethyl]-piperazin-1-yl}-2-(1-oxo-1,2,3,4-tetrahydro-isoquinolin-5-yloxy)-benzoic acid methyl ester The title compound was prepared by substituting EXAMPLE 304A for EXAMPLE 3A in EXAMPLE 3G.

Example 304C

4-{4-[2-(4-Chloro-phenyl)-4,4-dimethyl-cyclohex-1-enylmethyl]-piperazin-1-yl}-2-(1-oxo-1,2,3,4-tetrahydro-isoquinolin-5-yloxy)-benzoic acid The title compound was prepared by substituting EXAMPLE 304B for EXAMPLE 1E in EXAMPLE 1F.

Example 304D

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(1-oxo-1,2,3,4-tetrahydroisoquinolin-5-yl)oxy]benzamide The title compound was prepared by substituting EXAMPLE 304C for EXAMPLE 1F and EXAMPLE 205A for EXAMPLE 1G in EXAMPLE 1H. $^1$H NMR (300 MHz, dimethylsulfoxide-$d_6$) δ 8.37 (br s, 1H), 8.22-8.18 (m, 2H), 7.93-7.84 (m, 2H), 7.57-7.52 (m, 1H), 7.45 (d, 1H), 7.36 (d, 2H), 7.12-7.02 (m, 3H), 6.72 (d, 1H), 6.59 (d, 1H), 6.36 (d, 1H), 3.62 (br s, 4H), 3.13 (br s, 4H), 2.95-2.69 (m, 6H), 2.68-2.35 (m, 4H), 2.32-3.03 (m, 10H), 2.02-1.84 (m, 4H), 1.42 (m, 6H), 0.94 (t, 6H)

Example 305

4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-[(6-fluoro-1H-indol-5-yl)oxy]benzamide

Example 305A 5-bromo-6-chloropyridine-3-sulfonamide

5-Bromo-6-chloropyridine-3-sulfonyl chloride (8.2 g) in methanol (20 mL) was cooled to 0° C. To this solution was added 7N NH$_3$ in methanol (80 mL). The reaction mixture was stirred overnight. The solvent was removed at low temperature, and the residue was partitioned between ethyl acetate and water. The aqueous layer was extracted with ethyl acetate three times. The combined organic layers were washed with brine, dried (MgSO$_4$), filtered, and concentrated. The residue was purified by flash column chromatography on silica gel to give the product.

Example 305B 6-((1,4-dioxan-2-yl)methoxy)-5-bromopyridine-3-sulfonamide (1,4-Dioxan-2-yl)methanol (211 mg) in tetrahydrofuran (10 mL) was treated with 60% sodium hydride (125 mg). The reaction mixture was stirred for 10 minutes. To this solution was added EXAMPLE 305A (211 mg). The reaction mixture was stirred overnight. It was poured into water, neutralized with 10% aqueous HCl, and extracted with ethyl acetate three times. The combined organic layers were washed with brine, dried over MgSO$_4$, filtered, and concentrated to afford the product.

Example 305C 6-((1,4-dioxan-2-yl)methoxy)-5-cyanopyridine-3-sulfonamide

A mixture of EXAMPLE 305B (100 mg), dicyanozinc (20 mg), and tetrakis(triphenylphosphine)palladium(0) (40 mg) in N,N-dimethylformamide (0.5 mL) was degassed via vacuum/nitrogen cycle three times. The reaction mixture was heated at 120° C. for 3 hours. After cooling, it was poured into water and extracted with ethyl acetate three times. The combined organic layers were washed with brine, dried over MgSO$_4$, filtered, and concentrated. The residue was purified with flash column chromatography on silica gel eluting with 2%-5% methanol/dichloromethane to give the title compound.

Example 305D 4-(4-{[2-(4-chlorophenyl)-4,4-dimethylcyclohex-1-en-1-yl]methyl}piperazin-1-yl)-N-{[5-cyano-6-(1,4-dioxan-2-ylmethoxy)pyridin-3-yl]sulfonyl}-2-[(6-fluoro-1H-indol-5-yl)oxy]benzamide The title compound was prepared by substituting EXAMPLE 154E for EXAMPLE 1F and EXAMPLE 305C for EXAMPLE 1G in EXAMPLE 1H. $^1$H NMR (400 MHz, dimethylsulfoxide-$d_6$) δ 11.14 (s, 1H), 8.76 (s, 1H), 8.55 (s, 1H), 7.57 (d, 1H), 7.33 (m, 4H), 7.12 (d, 1H), 7.05 (d, 2H), 6.64 (dd, 1H), 6.34 (s, 1H), 6.14 (s, 1H), 4.44 (d, 2H), 3.91 (m, 1H), 3.80 (m, 2H), 3.63 (m, 2H), 3.46 (m, 2H), 3.33 (m, 4H), 3.09 (m, 4H), 2.35 (m, 2H), 2.17 (m, 2H), 1.98 (m, 2H), 1.40 (t, 2H), 0.94 (s, 6H).

Example 306

N-{[5-bromo-6-(1,4-dioxan-2-ylmethoxy)pyridin-3-yl]sulfonyl}-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 1F and EXAMPLE 305B for EXAMPLE 1G in EXAMPLE 1H. $^1$H NMR (400 MHz, dimethylsulfoxide-$d_6$) δ 11.19 (s, 1H), 8.58 (dd, 1H), 8.37 (d, 1H), 7.55 (d, 1H), 7.35 (m, 4H), 7.26 (d, 1H), 7.04 (d, 2H), 6.64 (dd, 1H), 6.40 (s, 1H), 6.10 (d, 1H), 4.37 (m, 2H), 3.89 (m, 1H), 3.79 (m, 2H), 3.63 (m, 2H), 3.47 (m, 2H), 3.31 (m, 2H), 3.06 (m, 4H), 2.85 (m, 2H), 2.32 (m, 2H), 2.14 (s, 2H), 1.96 (s, 2H), 1.38 (m, 2H), 0.91 (s, 6H).

Example 307

Trans-N-({5-bromo-6-[(4-morpholin-4-ylcyclohexyl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide

Example 307A

Trans-5-bromo-6-((1r,4r)-4-morpholinocyclohexylamino)pyridine-3-sulfonamide

A mixture of EXAMPLE 305A (1.0 g), trans 4-morpholinocyclohexanamine (0.95 g) and triethylamine (3.08 mL) in anhydrous dioxane (20 mL) was heated at 110° C. overnight. The organic solvent was removed under vacuum. The residue was purified with flash column chromatography on silica gel eluting with 2%-8% methanol/dichloromethane to give the title compound.

Example 307B

Trans-N-({5-bromo-6-[(4-morpholin-4-ylcyclohexyl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 1F and EXAMPLE 307A for EXAMPLE 1G in EXAMPLE 1H. $^1$H NMR (400 MHz, dimethylsulfoxide-$d_6$) δ 11.20 (m, 1H), 8.43 (d, 1H), 8.05 (d, 1H), 7.55 (d, 1H), 7.35 (m, 4H), 7.27 (d, 1H), 7.03 (d, 2H), 6.61 (dd, 1H), 6.49 (dd, 1H), 6.40 (dd, 1H), 3.93 (m, 1H), 3.60 (m, 4H), 3.38 (m, 2H), 2.98 (m, 4H), 2.70 (s, 2H), 2.60 (m, 4H), 2.34 (m, 1H), 2.15 (m, 6H), 1.92 (d, 6H), 1.37 (m, 6H), 0.92 (s, 6H).

Example 308

4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-[(6-fluoro-1H-indol-5-yl)oxy]benzamide

Example 308A 5-bromo-6-((4-fluorotetrahydro-2H-pyran-4-yl)methoxy)pyridine-3-sulfonamide The title compound was prepared by substituting EXAMPLE 296C for (tetrahydro-2H-pyran-4-yl)methanol in EXAMPLE 301A.

Example 308B 5-cyano-6-((4-fluorotetrahydro-2H-pyran-4-yl)methoxy)pyridine-3-sulfonamide The title compound was prepared by substituting EXAMPLE 308A for EXAMPLE 301A in EXAMPLE 301B.

Example 308C 4-(4-{[2-(4-chlorophenyl)-4,4-dimethylcyclohex-1-en-1-yl]methyl}piperazin-1-yl)-N-({5-cyano-6-[(4-fluorotetrahydro-2H-pyran-4-yl)methoxy]pyridin-3-yl}sulfonyl)-2-[(6-fluoro-1H-indol-5-yl)oxy]benzamide The title compound was prepared by substituting EXAMPLE 154E for EXAMPLE 1F and EXAMPLE 308B for EXAMPLE 1G in EXAMPLE 1H. $^1$H NMR (500 MHz, dimethylsulfoxide-$d_6$) δ 11.15 (s, 1H), 8.79 (s, 1H), 8.59 (s, 1H), 7.57 (d, 1H), 7.34-7.37 (m, 3H), 7.30 (d, 1H), 7.13 (d, 1H), 7.05 (d, 2H), 6.64 (dd, 1H), 6.35 (s, 1H), 6.13 (s, 1H), 4.25 (d, 2H), 3.75-3.80 (m, 2H), 3.56-3.62 (m, 2H), 3.09 (s, 4H), 2.15-2.60 (m, 4H), 1.80-21.83 (m, 2H), 1.41 (d, 2H), 0.93 (s, 6H).

Example 309

2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 309A 2-(3-chloro-5-nitrophenyl)-4,4,5,5-tetramethyl-1,3,2-dioxaborolane 1-Bromo-3-chloro-5-nitrobenzene (0.51 g), bis(pinacolato)diboron (0.60 g), potassium acetate (0.63 g), and [1,1'-bis(diphenylphosphino)ferrocene]dichloropalladium(II) (0.09 g) were combined with dimethylformamide (5.3 mL), flushed with nitrogen, heated at 60° C. overnight, diluted with ethyl acetate, washed with water and brine, dried (MgSO$_4$), filtered, concentrated and chromatographed on silica gel with 5-10% ethyl acetate in hexanes as eluent to give the product.

Example 309B 3-chloro-5-nitrophenol

EXAMPLE 309A (0.5 g) in tetrahydrofuran (10 mL) was treated with a 4N aqueous solution of sodium hydroxide (2.65 mL), heated at 50° C. for 4 hours, cooled to 0° C., treated dropwise with a 30% aqueous hydrogen peroxide solution (0.65 mL), stirred overnight while warming to room temperature and then quenched with saturated aqueous sodium thiosulfate solution. The resulting mixture was partitioned between ethyl acetate and 1N aqueous sodium hydroxide solution and the organic portion was set aside. The aqueous layer was acidified to pH 4 with 2N aqueous HCl solution and extracted with ethyl acetate (2×100 mL). These extracts were combined, washed with brine, dried (MgSO$_4$), filtered, concentrated and chromatographed on silica gel with 5-10% ethyl acetate in hexanes as eluent to give the product.

Example 309C methyl 2-(3-chloro-5-nitrophenoxy)-4-fluorobenzoate

The title compound was prepared by substituting methyl 2,4-difluorobenzoate for ethyl 2,4-difluorobenzoate and EXAMPLE 309B for 2-methyl-5-indolol in EXAMPLE 3A.

Example 309D methyl 2-(3-amino-5-chlorophenoxy)-4-fluorobenzoate

EXAMPLE 309C (0.31 g) in a 1:1 mixture of methanol and tetrahydrofuran (9.5 mL) was treated with tin(II) chloride dihydrate (1.06 g), heated at 65° C. for 4 hours and filtered through a pad of celite rinsing with ethyl acetate. The filtrate was washed with water and brine, dried (MgSO$_4$), filtered, concentrated and chromatographed on silica gel with 10-20% ethyl acetate in hexanes as eluent to give the product.

Example 309E methyl 2-(3-amino-5-chlorophenoxy)-4-(piperazin-1-yl)benzoate

The title compound was prepared by substituting piperazine for EXAMPLE 3F and EXAMPLE 309D for EXAMPLE 3A in EXAMPLE 3G.

Example 309F 1-chloro-4-(2-(chloromethyl)-5,5-dimethylcyclohex-1-enyl)benzene EXAMPLE 3D (0.251 g) in tetrahydrofuran (5 mL) at 0° C. was treated sequentially with N,N-diisopropylethylamine (0.524 mL) and methanesulfonyl chloride (0.086 mL) and then stirred for 1.5 hours. Additional N,N-diisopropylethylamine (0.524 mL) and methanesulfonyl chloride (0.086 mL) were added and stirring was continued for another hour. The reaction mixture was diluted with ethyl acetate, washed with water and brine, dried (MgSO$_4$), filtered and concentrated. The concentrate was slurried in a 1:1 mixture of diethyl ether and dichloromethane and unreacted EXAMPLE 3D was removed by filtration. The filtrate was concentrated. The mixture was swirled with diethyl ether and the liquid decanted three times. The decanted diethyl ether mixture was concentrated and dried under vacuum to give the product.

Example 309G methyl 2-(3-amino-5-chlorophenoxy)-4-(4-((2-(4-chlorophenyl)-4,4-dimethylcyclohex-1-enyl)methyl)piperazin-1-yl)benzoate EXAMPLE 309F (0.109 g) in N,N-dimethylformamide (2 mL) was treated with EXAMPLE 309E (0.15 g) and cesium carbonate (0.264 g), stirred at ambient temperature over two nights, diluted with ethyl acetate, washed with water and brine, dried (MgSO$_4$), filtered, concentrated and chromatographed on silica gel with 0 to 5% acetone in dichloromethane as eluent to give the product.

Example 309H 2-(3-amino-5-chlorophenoxy)-4-(4-((2-(4-chlorophenyl)-4,4-dimethylcyclohex-1-enyl)methyl)piperazin-1-yl)benzoic acid The title compound was prepared by substituting EXAMPLE 309G for EXAMPLE 1E in EXAMPLE 1F.

Example 309I 2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 309H for EXAMPLE 1F in EXAMPLE 1H. $^1$H NMR (300 MHz, dimethylsulfoxide-d$_6$) δ 11.42 (s, 1H), 8.62 (t, 1H), 8.52 (d, 1H), 7.74 (dd, 1H), 7.48 (d, 1H), 7.36 (d, 2H), 7.13 (d, 1H), 7.07 (d, 2H), 6.74 (dd, 1H), 6.41 (d, 1H), 6.22 (t, 1H), 5.92 (m, 2H), 5.47 (s, 2H), 3.86 (dd, 2H), 3.32 (m, 4H), 3.18 (m, 4H), 2.80 (m, 2H), 2.21 (m, 6H), 1.98 (s, 2H), 1.89 (m, 1H), 1.64 (dd, 2H), 1.41 (t, 2H), 1.26 (m, 2H), 0.95 (s, 6H).

Example 310

4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-[(6-fluoro-1H-indol-5-yl)oxy]benzamide

Example 310A 5-bromo-6-(2-morpholinoethoxy)pyridine-3-sulfonamide

The title compound was prepared by substituting 2-morpholinoethanol for (tetrahydro-2H-pyran-4-yl)methanol in EXAMPLE 301A.

Example 310B 5-cyano-6-(2-morpholinoethoxy)pyridine-3-sulfonamide

The title compound was prepared by substituting EXAMPLE 310A for EXAMPLE 301A in EXAMPLE 301B.

Example 310C 4-(4-{[2-(4-chlorophenyl)-4,4-dimethylcyclohex-1-en-1-yl]methyl}piperazin-1-yl)-N-{[5-cyano-6-(2-morpholin-4-ylethoxy)pyridin-3-yl]sulfonyl}-2-[(6-fluoro-1H-indol-5-yl)oxy]benzamide The title compound was prepared by substituting EXAMPLE 154E for EXAMPLE 1F and EXAMPLE 310B for EXAMPLE 1G in EXAMPLE 1H. $^1$H NMR (500 MHz, dimethylsulfoxide-d$_6$) δ 11.14 (s, 1H), 8.75 (d, 1H), 8.52 (d, 1H), 7.58 (d, 1H), 7.33-7.36 (m, 3H), 7.28 (d, 1H), 7.09 (d, 1H), 7.05 (d, 2H), 6.62 (dd, 1H), 6.34 (s, 1H), 6.12 (s, 1H), 4.62 (t, 2H), 3.25-3.61 (m, 4H), 3.05 (s, 4H), 2.93 (s, 4H), 2.68 (s, 4H), 2.32-2.36 (m, 4H), 2.15 (s, 2H), 1.96 (s, 2H), 1.40 (d, 2H), 0.93 (s, 6H).

Example 311

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylcyclohexyl)oxy]-3-nitrophenyl}sulfonyl)benzamide

Example 311A

Trans-4-(4-aminocyclohexyloxy)-3-nitrobenzenesulfonamide

To a solution of tert-butyl 4-hydroxycyclohexylcarbamate (0.250 g) in tetrahydrofuran (5 mL) was added sodium hydride (0.186 g). After stirring for 15 minutes, 4-fluoro-3-nitrobenzenesulfonamide (0.256 g) was added as a solution in tetrahydrofuran (1 mL). The reaction was heated to 60° C. for 1.5 hours, cooled and poured into a mixture of dichloromethane (100 mL) and water (25 mL). The aqueous layer was adjusted to pH~4 with 1N aqueous HCl and the organic layer was separated, washed with brine (50 mL), dried over magnesium sulfate and concentrated. The residue was loaded onto silica gel (GraceResolv 40 g) and eluted using a gradient of 0.5% to 7.5% methanol/dichloromethane over 30 minutes. This solid was immediately treated with HCl (4.0M in dioxane, 5 mL) at room temperature for 1 hours and concentrated to give the title compound.

Example 311B

Trans-4-(4-morpholinocyclohexyloxy)-3-nitrobenzenesulfonamide

To EXAMPLE 311A (0.220 g) and 1-bromo-2-(2-bromoethoxy)ethane (0.177 g) in N,N-dimethylformamide (3 mL) was added triethylamine (0.338 mL) and the reaction heated to 70° C. for 5 hours. The reaction was cooled and the resulting precipitate removed by filtration. The reaction was concentrated and loaded onto silica gel and eluted using a gradient of 0.5% to 7.5% methanol/dichloromethane to give the title compound.

Example 311C

Trans-2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(4-(4-morpholinocyclohexyloxy)-3-nitrophenylsulfonyl)benzamide The title compound was prepared by substituting EXAMPLE 154E for EXAMPLE 1F and EXAMPLE 311B for EXAMPLE 1G in EXAMPLE 1H. $^1$H NMR (300 MHz, dimethylsulfoxide-$d_6$) δ 11.21-11.09 (m, 1H), 8.29-8.13 (m, 2H), 8.03-7.88 (m, 1H), 7.54 (s, 1H), 7.33 (d, 4H), 7.21-7.11 (m, 1H), 7.04 (d, 2H), 6.97-6.89 (m, 1H), 6.66-6.51 (m, 1H), 6.43-6.31 (m, 1H), 6.08 (s, 1H), 4.62-4.49 (m, 1H), 3.62 (s, 4H), 2.98 (s, 4H), 2.68 (d, 7H), 2.19 (s, 8H), 1.95 (s, 4H), 1.38 (s, 6H), 0.92 (s, 6H).

Example 312

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide

Example 312A 5-bromo-6-(1-(tetrahydro-2H-pyran-4-yl)piperidin-4-ylamino)pyridine-3-sulfonamide The title compound was prepared by substituting EXAMPLE 49B for trans 4-morpholinocyclohexanamine in EXAMPLE 307A.

Example 312B

N-({5-bromo-6-[(1-tetrahydro-2H-pyran-4-ylpiperidin-4-yl)amino]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 1F and EXAMPLE 312A for EXAMPLE 1G in EXAMPLE 1H. $^1$H NMR (400 MHz, dimethylsulfoxide-$d_6$) δ 11.16 (s, 1H), 8.40 (d, 1H), 8.05 (d, 1H), 7.56 (d, 1H), 7.32 (m, 4H), 7.19 (m, 1H), 7.04 (d, 2H), 6.58 (d, 1H), 6.38 (s, 1H), 6.05 (s, 1H), 4.05 (m, 1H), 3.93 (d, 2H), 3.24 (m, 8H), 2.96 (m, 4H), 2.72 (m, 3H), 2.15 (m, 6H), 1.93 (m, 2H), 1.85 (m, 4H), 1.55 (m, 2H), 1.38 (t, 2H), 1.17 (t, 2H), 0.91 (s, 6H).

Example 313

4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-[(2-oxo-2,3-dihydro-1H-indol-4-yl)oxy]benzamide

Example 313A 2-(3-chloro-1H-indol-4-yloxy)-4-(4-((2-(4-chlorophenyl)-4,4-dimethylcyclohex-1-enyl)methyl)piperazin-1-yl)-N-(4-((4-fluorotetrahydro-2H-pyran-4-yl)methoxy)-3-nitrophenylsulfonyl)benzamide The title compound was prepared by substituting EXAMPLE 266D for EXAMPLE 1F and EXAMPLE 296D for EXAMPLE 1G in EXAMPLE 1H.

Example 313B 4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)-2-[(2-oxo-2,3-dihydro-1H-indol-4-yl)oxy]benzamide The title compound was prepared by substituting EXAMPLE 313A for EXAMPLE 265E in EXAMPLE 267. $^1$H NMR (500 MHz, methylene chloride-$d_2$) δ 8.44 (d, 1H), 8.24 (dd, 1H), 7.86 (d, 1H), 7.71 (s, 1H), 7.24 (m, 3H), 7.19 (d, 1H), 6.97 (d, 2H), 6.77 (d, 1H), 6.62 (d, 2H), 6.14 (d, 1H), 4.19 (d, 2H), 3.84 (m, 2H), 3.75 (m, 2H), 3.39 (s, 2H), 3.14 (br.s, 4H), 2.77 (s, 2H), 2.30-2.10 (m, 6H), 1.99 ((br.s, 2H), 1.95-1.87 (m, 4H), 1.55 (m, 2H), 1.43 (t, 2H), 0.95 (s, 6H).

Example 314

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-[(trifluoromethyl)sulfonyl]phenyl}sulfonyl)benzamide

Example 314A oxepan-4-one

Tetrahydro-2H-pyran-4-one (5 g) was placed in methanol (30 mL) in the presence of barium oxide (0.85 g). Nitrosomethylurethane (6.6 g) was added slowly to the reaction mixture. During the addition, barium oxide (1.0 g) was added by small portions. The reaction mixture was stirred 3 hours at room temperature and then filtrated. The methanol was evaporated, diethyl ether was then added to the residue, and a precipitate was formed. The mixture was filtrated and diethyl ether evaporated to afford the product.

Example 314B (Z)-5-chloro-2,3,6,7-tetrahydrooxepine-4-carbaldehyde

Phosphorus oxychloride (3.45 mL) was added dropwise to a cooled (0° C.) solution of EXAMPLE 314A (4.2 g) in N,N-dimethylformamide (12 mL) and dichloromethane (30 mL). The mixture was then stirred at room temperature overnight before it was diluted with ethyl acetate (300 mL) and washed with aqueous sodium acetate, water (3×), brine and dried over $Na_2SO_4$. After filtration and concentration, the crude product was used directly in the next reaction without further purification.

Example 314C (Z)-5-(4-chlorophenyl)-2,3,6,7-tetrahydrooxepine-4-carbaldehyde To a mixture of 4-chlorophenylboronic acid (6.10 g), EXAMPLE 314B (5.2 g), palladium(II) acetate (146 mg, 0.65 mmol), $K_2CO_3$ (13.5 g) and tetrabutylammonium bromide (10.5 g) was added water (200 mL). The mixture was stirred at 50° C. for 4 hours. The mixture was diluted with ethyl acetate (400 mL) and washed with water (3×) and brine and dried over $Na_2SO_4$. After filtration and concentration, the residue was loaded on a column and eluted with 5 to 20% ethyl acetate in hexane to give the pure product.

Example 314D (Z)-ethyl 2-(6-chloro-1H-indol-5-yloxy)-4-(4-((5-(4-chlorophenyl)-2,3,6,7-tetrahydrooxepin-4-yl)methyl)piperazin-1-yl)benzoate The title compound was prepared as described in EXAMPLE 38G by replacing EXAMPLE 38F and EXAMPLE 38E with EXAMPLE 242F and EXAMPLE 314C.

Example 314E (Z)-2-(6-chloro-1H-indol-5-yloxy)-4-(4-((5-(4-chlorophenyl)-2,3,6,7-tetrahydrooxepin-4-yl)methyl)piperazin-1-yl)benzoic acid The title compound was prepared as described in EXAMPLE 38G by replacing EXAMPLE 34B with EXAMPLE 314D.

Example 314F

Trans-4-(4-morpholinocyclohexylamino)-3-(trifluoromethylsulfonyl)benzenesulfonamide The title compound was prepared by substituting trans 4-morpholinocyclohexanamine for 3-(N-morpholinyl)-1-propylamine and EXAMPLE 131C for 4-fluoro-3-nitrobenzenesulfonamide in EXAMPLE 4A.

Example 314G

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-[(trifluoromethyl)sulfonyl]phenyl}sulfonyl)benzamide The title compound was prepared as described in EXAMPLE 1H by replacing EXAMPLE 1F and EXAMPLE 1G with EXAMPLE 314E and EXAMPLE 314F, respectively. $^1$H NMR (300 MHz, dimethylsulfoxide-$d_6$) δ 11.38 (s, 1H), 8.20 (m, 1H), 7.98 (dd, 1H), 7.53 (m, 4H), 7.38 (m, 3H), 7.13 (m, 3H), 6.98 (m, 1H), 6.72 (m, 3H), 6.45 (d, 1H), 3.86 (m, 12H), 3.36 (m, 3H), 3.02 (m, 6H), 2.74 (d, 8H), 2.18 (m, 4H), 1.65 (m, 2H).

Example 315

Trans-2-[(6-chloro-1H-indol-5-yl)oxy]-4-(4-{[5-(4-chlorophenyl)-2,3,6,7-tetrahydrooxepin-4-yl]methyl}piperazin-1-yl)-N-({4-[(4-morpholin-4-ylcyclohexyl)amino]-3-nitrophenyl}sulfonyl)benzamide The title compound was prepared as described in EXAMPLE 1H by replacing EXAMPLE 1F and EXAMPLE 1G with EXAMPLE 314E and EXAMPLE 205A, respectively. $^1$H NMR (300 MHz, dimethylsulfoxide-$d_6$) δ 11.09 (s, 1H), 8.38 (d, 1H), 8.01 (d, 1H), 7.70 (dd, 1H), 7.57 (d, 1H), 7.46 (s, 1H), 7.34 (m, 3H), 7.07 (d, 2H), 6.91 (m, 2H), 6.57 (m, 2H), 6.30 (s, 1H), 6.02 (d, 1H), 3.61 (m, 10H), 2.98 (m, 12H), 2.28 (m, 8H), 1.95 (m, 4H), 1.36 (m, 2H).

Example 316

4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]-N-({4-[(4-methylpiperazin-1-yl)amino]-3-nitrophenyl}sulfonyl)benzamide The title compound was prepared as described in EXAMPLE 1H by replacing EXAMPLE 1F and EXAMPLE 1G with EXAMPLE 277B and EXAMPLE 184A, respectively. $^1$H NMR (300 MHz, dimethylsulfoxide-$d_6$) δ 11.18 (s, 1H), 9.16 (s, 1H), 8.52 (d, 1H), 7.89 (dd, 1H), 7.56 (m, 2H), 7.31 (m, 5H), 7.13 (d, 2H), 6.62 (dd, 1H), 6.39 (s, 1H), 6.07 (d, 1H), 4.09 (m, 2H), 2.95 (m, 9H), 2.81 (s, 2H), 2.35 (s, 3H), 2.16 (m, 6H), 1.18 (s, 6H).

Example 317

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylbut-2-ynyl)oxy]-3-nitrophenyl}sulfonyl)benzamide

Example 317A 4-morpholinobut-2-yn-1-ol

To a solution of morpholine (4.36 g) in toluene (15 mL) was added 4-chlorobut-2-yn-1-ol (2.09 g) in toluene (5 mL). The solution was stirred at 85° C. for 3 hours. After cooling, the solid was filtered off. The filtrate was subjected to vacuum distillation to give the title compound.

Example 317B 4-(4-morpholinobut-2-ynyloxy)-3-nitrobenzenesulfonamide

The title compound was prepared by substituting EXAMPLE 317A for (tetrahydro-2H-pyran-4-yl)methanol in EXAMPLE 264A.

Example 317C 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({4-[(4-morpholin-4-ylbut-2-ynyl)oxy]-3-nitrophenyl}sulfonyl)benzamide The title compound was prepared by substituting EXAMPLE 154E for EXAMPLE 1F and EXAMPLE 317B for EXAMPLE 1G in EXAMPLE 1H. $^1$H NMR (500 MHz, dimethylsulfoxide-d$_6$) δ 11.12 (s, 1H), 8.39 (d, 1H), 8.14 (dd, 1H), 7.52-7.54 (m, 2H), 7.34-7.39 (m, 3H), 7.32-7.35 (m, 3H), 7.29 (d, 1H), 7.04 (d, 2H), 6.64 (dd, 1H), 6.41 (s, 1H), 6.09 (d, 1H), 5.16 (s, 2H), 3.52-3.55 (m, 4H), 3.05 (s, 4H), 2.82 (s, 4H), 2.37-2.39 (m, 4H), 2.26 (s, 4H), 1.95 (s, 2H), 1.39 (d, 2H), 0.92 (s, 6H).

Example 318

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide Example 318A methyl 4-fluoro-2-(6-nitropyridin-3-yloxy)benzoate To a solution of methyl 4-fluoro-2-hydroxybenzoate (23.5 g) and 2-nitro-5-chloropyridine (21.9 g) in N,N-dimethylformamide (120 mL) was added cesium carbonate (45 g). The mixture was stirred at 50° C. overnight. The mixture was diluted with ethyl acetate (800 mL) and washed with water (3×) and brine. After drying over Na$_2$SO$_4$ and filtration, the solvent was evaporated under vacuum and the residue was purified by silica gel chromatography (2% ethyl acetate in dichloromethane) to give the title compound.

Example 318B methyl 2-(6-aminopyridin-3-yloxy)-4-fluorobenzoate

EXAMPLE 318A (12.995 g) and methanol (150 mL) were added to Ra—Ni, water wet, A-7000 (6.50 g) in a 250 mL SS pressure bottle and stirred for 2 hours at 30 psi and room temperature. The mixture was filtered through a nylon membrane and concentrated to give the title compound.

Example 318C

Methyl 2-(6-amino-5-chloropyridin-3-yloxy)-4-fluorobenzoate

EXAMPLE 318B (3.0 g) and 1-chloropyrrolidine-2,5-dione (1.680 g) were stirred together in N,N-dimethylformamide (30 mL) at room temperature under nitrogen for 16 hours. The reaction was diluted with ethyl acetate (200 mL) and washed with water (75 mL), brine (75 mL), dried over magnesium sulfate, filtered and concentrated. Silica gel chromatography (GraceResolv 80 g) eluting with a gradient of 5% to 35% ethyl acetate/hexanes over 40 minutes (Flow=40 mL/min) gave the title compound.

Example 318D methyl 2-(6-amino-5-chloropyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 318C for EXAMPLE 3A in EXAMPLE 3G.

Example 318E 2-(6-amino-5-chloropyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 318D for EXAMPLE 1E in EXAMPLE 1F.

Example 318F

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 318E for EXAMPLE 1F in EXAMPLE 1H. $^1$H NMR (300 MHz, CDCl$_3$) δ 9.86 (s, 1H), 8.89 (d, 1H), 8.52 (t, 1H), 8.17 (dd, 1H), 7.96-7.83 (m, 2H), 7.36 (d, 1H), 7.23 (s, 1H), 6.99-6.86 (m, 3H), 6.54 (dd, 1H), 5.97 (d, 1H), 4.95 (s, 2H), 4.01 (d, 2H), 3.42 (d, 2H), 3.32-3.22 (m, 2H), 3.12 (s, 4H), 2.78 (s, 2H), 2.22 (d, 6H), 1.99 (s, 2H), 1.72 (s, 2H), 1.50-1.34 (m, 5H), 0.96 (s, 6H).

Example 319

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[1-(methylsulfonyl)piperidin-4-yl]amino}-3-nitrophenyl)sulfonyl]benzamide Example 319A 4-(1-Methanesulfonyl-piperidin-4-ylamino)-3-nitro-benzenesulfonamide The title compound was prepared by substituting 1-(methylsulfonyl)piperidin-4-amine for tert-butyl 4-aminopiperidine-1-carboxylate in EXAMPLE 140A.

Example 319B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[1-(methylsulfonyl)piperidin-4-yl]amino}-3-nitrophenyl)sulfonyl]benzamide The title compound was prepared by substituting EXAMPLE 154E for EXAMPLE 1F and EXAMPLE 319A for EXAMPLE 1G in EXAMPLE 1H. ¹H NMR (300 MHz, dimethylsulfoxide-$d_6$) δ 11.21 (br s, 1H), 8.59 (d, 1H), 8.26 (d, 1H), 7.89 (dd, 1H), 7.50 (d, 1H), 7.38 (t, 1H), 7.34 (d, 2H), 7.31 (t, 1H), 7.28 (d, 1H), 7.22 (d, 1H), 7.04 (d, 2H), 6.66 (dd, 1H), 6.40 (t, 1H), 6.10 (d, 1H), 3.82 (m, 1H), 3.56 (dt, 2H), 3.09 (br s, 4H), 2.96 (dd, 2H), 2.92 (s, 3H), 2.73 (m, 2H), 2.25-2.08 (m, 6H), 2.02 (dd, 2H), 1.95 (br s, 2H), 1.70 (m, 2H), 1.38 (t, 2H), 0.92 (s, 6H).

Example 320

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(2-oxo-2,3-dihydro-1H-indol-4-yl)oxy]benzamide Example 320A Trans-2-(3-chloro-1H-indol-4-yloxy)-4-(4-((2-(4-chlorophenyl)-4,4-dimethylcyclohex-1-enyl)methyl)piperazin-1-yl)-N-(4-(4-morpholinocyclohexylamino)-3-nitrophenylsulfonyl)benzamide The title compound was prepared by substituting EXAMPLE 266D for EXAMPLE 1F and EXAMPLE 205A for EXAMPLE 1G in EXAMPLE 1H.

Example 320B

Trans-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)-2-[(2-oxo-2,3-dihydro-1H-indol-4-yl)oxy]benzamide The title compound was prepared by substituting EXAMPLE 320A for EXAMPLE 265E in EXAMPLE 267. ¹H NMR (500 MHz, dimethylsulfoxide-$d_6$) δ 10.37 (s, 1H), 8.41 (s, 1H), 8.17 (d, 1H), 7.72 (d, 1H), 7.48 (d, 1H), 7.36 (d, 2H), 7.13 (d, 1H), 7.06 (d, 2H), 6.95 (t, 1H), 6.74 (d, 1H), 6.44 (m, 2H), 6.12 (d, 1H), 3.70-3.58 (m, 4H), 3.34 (m, 2H), 3.24 (s, 2H), 3.16 (br.s, 4H), 2.79 (m, 6H), 2.25 (m, 3H), 2.18 (m, 3H), 2.12 (m, 2H), 1.98 (m, 4H), 1.55-1.40 (m, 4H), 1.41 (t, 2H), 0.94 (s, 6H).

Example 321

4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-[(2-oxo-2,3-dihydro-1H-indol-4-yl)oxy]benzamide Example 321A 2-(3-chloro-1H-indol-4-yloxy)-4-(4-((2-(4-chlorophenyl)-4,4-dimethylcyclohex-1-enyl)methyl)piperazin-1-yl)-N-(4-(2-methoxyethylamino)-3-nitrophenylsulfonyl)benzamide The title compound was prepared by substituting EXAMPLE 266D for EXAMPLE 1F and EXAMPLE 263A for EXAMPLE 1G in EXAMPLE 1H.

Example 321B 4-(4-{[2-(4-chlorophenyl)-4,4-dimethylcyclohex-1-en-1-yl]methyl}piperazin-1-yl)-N-({4-[(2-methoxyethyl)amino]-3-nitrophenyl}sulfonyl)-2-[(2-oxo-2,3-dihydro-H-indol-4-yl)oxy]benzamide The title compound was prepared by substituting EXAMPLE 321A for EXAMPLE 265E in EXAMPLE 267. ¹H NMR (500 MHz, methylene chloride-$d_2$) δ 9.80 (br.s, 1H), 8.73 (d, 1H), 8.56 (t, 1H), 8.00 (dd, 1H), 7.87 (d, 1H), 7.76 (br. s, 1H), 7.25 (d, 2H), 7.22 (t, 1H), 7.96 (d, 2H), 6.94 (d, 1H), 6.74 (d, 1H), 6.62 (m, 2H), 6.16 (d, 1H), 3.68 (t, 2H), 3.54 (t, 2H), 3.41 (s, 3H), 3.37 (s, 2H), 3.13 (br.s, 4H), 2.77 (m, 2H), 2.30-2.18 (m, 6H), 1.99 (br.s, 2H), 1.43 (t, 2H), 0.95 (s, 6H).

Example 322

4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide Example 322A 6-((tetrahydro-2H-pyran-4-yl)methoxy)-5-((triisopropylsilyl)ethynyl)pyridine-3-sulfonamide EXAMPLE 301B (0.176 g), bis(triphenylphosphine)palladium(II) chloride (0.176 g), copper(I) iodide (0.010 g), N,N-dimethylacetamide (2.5 mL) and triethylamine (0.105 mL) were combined, flushed with nitrogen and stirred for 2 minutes. (Triisopropyl)acetylene (0.135 mL) was added and the reaction mixture was flushed with nitrogen again, heated at 60° C. overnight, diluted with ethyl acetate, washed with water and brine, dried (MgSO₄), filtered, concentrated and chromatographed on silica gel with 10-30% ethyl acetate in hexanes as eluent to give the product.

Example 322B 5-ethynyl-6-((tetrahydro-2H-pyran-4-yl)methoxy)pyridine-3-sulfonamide EXAMPLE 322A (0.205 g) in tetrahydrofuran (3 mL) at ambient temperature was treated with tetrabutyl ammonium fluoride (1 M in tetrahydrofuran) (0.906 mL) and stirred at ambient temperature for 4 hours. Additional tetrabutyl ammonium fluoride (1 M in tetrahydrofuran) (1.8 mL) was added and the mixture was heated at 40° C. for 45 minutes. Solid tetrabutyl ammonium fluoride (0.253 g) was added and heating was continued for 30 minutes. The reaction mixture was concentrated and then chromatographed on silica gel using 0-2% methanol in dichloromethane as eluent to give the product.

Example 322C 4-(4-{[2-(4-chlorophenyl)-4,4-dimethylcyclohex-1-en-1-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide The title compound was prepared by substituting EXAMPLE 154E for EXAMPLE 1F and EXAMPLE 322B for EXAMPLE 1G in EXAMPLE 1H. ¹H NMR (300 MHz, dimethylsulfoxide-$d_6$) δ 11.21 (s, 1H), 8.62 (d, 1H), 8.22 (d, 1H), 7.53 (d, 1H), 7.35 (m, 5H), 7.04 (d, 2H), 6.65 (dd, 1H), 6.41 (m, 1H), 6.08 (s, 1H), 4.56 (s, 1H), 4.25 (d, 2H), 3.86 (dd, 2H), 3.35 (m, 2H), 3.05 (m, 4H), 2.81 (m, 2H), 2.24 (m, 6H), 2.04 (m, 1H), 1.95 (s, 2H), 1.64 (dd, 2H), 1.36 (m, 4H), 0.92 (s, 6H).

Example 323

4-(4-{[4-(4-chlorophenyl)-6,6-dimethyl-5,6-dihydro-2H-pyran-3-yl]methyl}piperazin-1-yl)-N-{[5-ethynyl-6-(tetrahydro-2H-pyran-4-ylmethoxy)pyridin-3-yl]sulfonyl}-2-[(6-fluoro-1H-indol-5-yl)oxy]benzamide The title compound was prepared by substituting EXAMPLE 277B for EXAMPLE 1F and EXAMPLE 322B for EXAMPLE 1G in EXAMPLE 1H. $^1$H NMR (500 MHz, pyridine-$d_5$) δ 12.39 (s, 1H), 9.27 (d, 1H), 8.90 (d, 1H), 8.09 (d, 1H), 7.52 (t, 1H), 7.46 (m, 4H), 7.10 (m, 2H), 6.68 (dd, 2H), 6.60 (m, 1H), 6.50 (d, 1H), 4.49 (s, 1H), 4.38 (m, 2H), 4.22 (d, 2H), 3.95 (dd, 2H), 3.29 (td, 2H), 2.98 (m, 4H), 2.82 (s, 2H), 2.21 (m, 2H), 2.09 (m, 4H), 1.98 (m, 1H), 1.63 (dd, 2H), 1.42 (m, 2H), 1.29 (s, 6H).

Example 324

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-morpholin-4-ylcyclohexyl)amino]-3-nitrophenyl}sulfonyl)benzamide The title compound was prepared by substituting EXAMPLE 318E for EXAMPLE 1F and EXAMPLE 205A for EXAMPLE 1G in EXAMPLE 1H. $^1$H NMR (300 MHz, dimethylsulfoxide-$d_6$) δ 11.45-10.43 (m, 1H), 8.56 (d, 1H), 8.20 (d, 1H), 7.86 (d, 1H), 7.73 (d, 1H), 7.44 (d, 1H), 7.35 (d, 3H), 7.23 (d, 1H), 7.06 (d, 2H), 6.64 (d, 1H), 6.16 (d, 3H), 3.70 (s, 5H), 3.11 (s, 4H), 2.77 (s, 6H), 2.10 (d, 12H), 1.43 (d, 6H), 0.94 (s, 6H).

Example 325

4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-[(6-fluoro-1H-indol-5-yl)oxy]benzamide

Example 325A 1-(tetrahydro-2H-pyran-4-yl)piperidin-4-ol

Piperidin-4-ol (7.8 g) and dihydro-2H-pyran-4(3H)-one (5.0 g) were dissolved in titanium(IV) isopropoxide (30 mL) and the reaction was stirred at room temperature overnight. Next day methanol (40 mL) was added and the reaction was cooled to 00. Then NaBH$_4$ (3.8 g) was added in portions over one hour. After two hours 1N aqueous NaOH was added, followed by ethyl acetate addition. After filtration through celite the layers were separated, the aqueous layer extracted with ethyl acetate, and the combined organic layers were dried over Na$_2$SO$_4$. The crude material was purified by column chromatography using CH$_2$Cl$_2$ having 5-10% 7N NH$_3$ in methanol.

Example 325B 5-chloro-6-(1-(tetrahydro-2H-pyran-4-yl)piperidin-4-yloxy)pyridine-3-sulfonamide The title compound was prepared by substituting EXAMPLE 303A for EXAMPLE 305A and EXAMPLE 325A for (1,3-dioxan-4-yl)methanol in EXAMPLE 305B.

Example 325C 4-(4-{[2-(4-chlorophenyl)-4,4-dimethylcyclohex-1-en-1-yl]methyl}piperazin-1-yl)-N-({5-cyano-6-[(1-tetrahydro-2H-pyran-4-ylpiperidin-4-yl)oxy]pyridin-3-yl}sulfonyl)-2-[(6-fluoro-1H-indol-5-yl)oxy]benzamide The title compound was prepared by substituting EXAMPLE 154E for EXAMPLE 122C and EXAMPLE 325B for EXAMPLE 11A in EXAMPLE 137. $^1$H NMR (500 MHz, dimethylsulfoxide-$d_6$) δ 11.06 (s, 1H), 8.64 (s, 1H), 8.37 (s, 1H), 7.60 (d, 1H), 7.35 (d, 2H), 7.28 (s, 1H), 7.24 (d, 1H), 7.04 (d, 2H), 6.96 (d, 1H), 6.55 (d, 1H), 6.27 (s, 1H), 6.09 (s, 1H), 5.20 (m, 1H), 3.90 (d, 2H), 3.30 (m, 5H), 2.96 (br m, 6H), 2.72 (s, 2H), 2.19 (br m, 6H), 2.00 (m, 2H), 1.95 (s, 2H), 1.78 (br m, 4H), 1.47 (br m, 2H), 1.39 (t, 2H), 0.92 (s, 6H).

Example 326

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide

Example 326A 5-chloro-6-((4-fluorotetrahydro-2H-pyran-4-yl)methoxy)pyridine-3-sulfonamide The title compound was prepared by substituting EXAMPLE 303A for EXAMPLE 305A and EXAMPLE 296C for (1,3-dioxan-4-yl)methanol in EXAMPLE 305B.

Example 326B

N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 122C and EXAMPLE 326A for EXAMPLE 1A in EXAMPLE 137. $^1$H NMR (500 MHz, dimethylsulfoxide-$d_6$) δ 11.18 (s, 1H), 8.75 (s, 1H), 8.27 (s, 1H), 7.55 (d, 1H), 7.34 (m, 4H), 7.23 (br d, 1H), 7.04 (d, 2H), 6.64 (dd, 1H), 6.40 (s, 1H), 6.09 (s, 1H), 4.53 (d, 2H), 3.77 (m, 2H), 3.60 (m, 2H), 3.06 (v br s, 4H), 2.82 (br s, 2H), 2.27 (v br s, 4H), 2.15 (br m, 2H), 1.95 (s, 2H), 1.85 (m, 4H), 1.40 (t, 2H), 0.92 (s, 6H).

Example 327

4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)-2-[(6-fluoro-1H-indol-5-yl)oxy]benzamide The title compound was prepared as described in EXAMPLE 1H by replacing EXAMPLE 1F and EXAMPLE 1G with EXAMPLE 154E and EXAMPLE 65A, respectively. $^1$H NMR (300 MHz, dimethylsulfoxide-$d_6$) δ 11.21 (s, 1H), 8.57 (d, 1H), 8.24 (d, 1H), 7.87 (dd, 1H), 7.50 (d, 1H), 7.33 (m, 5H), 7.18 (d, 1H), 7.03 (d, 2H), 6.65 (dd, 1H), 6.40 (s, 1H), 6.09 (s, 1H), 3.70 (m, 1H), 2.98 (m, 6H), 2.73 (s, 2H), 2.23 (m, 6H), 1.93 (m, 4H), 1.76 (m, 1H), 1.57 (m, 2H), 1.38 (t, 2H), 0.92 (s, 6H), 0.43 (m, 5H).

Example 328

4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-[(6-fluoro-1H-indol-5-yl)oxy]benzamide

Example 328A (4-ethylmorpholin-3-yl)methanol

Morpholin-3-ylmethanol (500 mg) and iodoethane (666 mg) in N,N-dimethylformamide was treated with $K_2CO_3$ (1.1 g) overnight. The reaction mixture was diluted with water and extracted with ethyl acetate. The organic layer was dried over $Na_2SO_4$ and concentrated to provide the title compound.

Example 328B 4-((4-ethylmorpholin-3-yl)methoxy)-3-nitrobenzenesulfonamide

The title compound was prepared as described in EXAMPLE 285A by replacing (1,4-dioxan-2-yl)methanol with EXAMPLE 328A.

Example 328C 4-(4-{[2-(4-chlorophenyl)-4,4-dimethylcyclohex-1-en-1-yl]methyl}piperazin-1-yl)-N-({4-[(4-ethylmorpholin-3-yl)methoxy]-3-nitrophenyl}sulfonyl)-2-[(6-fluoro-1H-indol-5-yl)oxy]benzamide The title compound was prepared as described in EXAMPLE 110F by replacing EXAMPLE 110E and EXAMPLE 1G with EXAMPLE 154E and EXAMPLE 328B, respectively. $^1$H NMR (500 MHz, dimethylsulfoxide-$d_6$) δ 11.21 (s, 2H), 8.37 (d, 1H), 8.10 (dd, 1H), 7.52 (t, 2H), 7.37 (t, 1H), 7.31-7.36 (m, 3H), 7.26 (d, 1H), 7.04 (d, 2H), 6.64 (dd, 1H), 6.40 (s, 1H), 6.09 (d, 1H), 4.43 (dd, 1H), 4.24 (dd, 1H), 3.80 (dd, 1H), 3.64-3.74 (m, 1H), 3.49-3.61 (m, 2H), 3.03 (s, 4H), 2.92 (s, 1H), 2.78 (s, 4H), 2.52-2.60 (m, 1H), 2.45 (s, 1H), 2.23 (s, 4H), 2.14 (s, 2H), 1.95 (s, 2H), 1.38 (t, 2H), 1.00 (t, 3H), 0.92 (s, 6H).

Example 329

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-1-tetrahydro-2H-pyran-4-ylpiperidin-3-yl]amino}phenyl)sulfonyl]benzamide

Example 329A (S)-tert-butyl 1-(tetrahydro-2H-pyran-4-yl)piperidin-3-ylcarbamate The title compound was prepared by substituting dihydro-2H-pyran-4(3H)-one for 4'-chlorobiphenyl-2-carboxaldehyde and (S)-tert-butyl piperidin-3-ylcarbamate for tert-butyl piperazine-1-carboxylate on EXAMPLE 1A.

Example 329B (S)-1-(tetrahydro-2H-pyran-4-yl)piperidin-3-amine

The title compound was prepared by substituting EXAMPLE 329A for EXAMPLE 1A in EXAMPLE 1B.

Example 329C 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[(3S)-1-tetrahydro-2H-pyran-4-ylpiperidin-3-yl]amino}phenyl)sulfonyl]benzamide The title compound was prepared by substituting EXAMPLE 329B for 2-amino-2-(tetrahydro-2H-pyran-4-yl)ethanol in EXAMPLE 240B. $^1$H NMR (500 MHz, dimethylsulfoxide-$d_6$) δ 8.92 (br s, 1H), 8.58 (br s, 1H), 7.85 (m, 1H), 7.52 (d, 1H), 7.37 (m, 1H), 7.33 (m, 3H), 7.28 (br s, 1H), 7.10 (br s, 1H), 7.03 (d, 2H), 6.65 (m, 1H), 6.40 (br s, 1H), 6.08 (m, 1H), 3.98 (br s, 1H), 3.90 (m, 2H), 3.27 (m, 2H), 3.01 (m, 4H), 2.77 (m, 4H), 2.60 (m, 2H), 2.16 (m, 6H), 1.94 (m, 2H), 1.64 (m, 5H), 1.50 (m, 3H), 1.38 (m, 2H), 1.23 (m, 1H), 0.94 (s, 6H).

Example 330

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide The title compound was prepared by substituting EXAMPLE 318E for EXAMPLE 1F and EXAMPLE 296D for EXAMPLE 1G in EXAMPLE 1H. $^1$H NMR (300 MHz, $CDCl_3$) δ 9.88 (s, 1H), 8.58 (d, 1H), 8.38 (dd, 1H), 7.91 (t, 2H), 7.36 (d, 1H), 7.29-7.11 (m, 3H), 6.94 (d, 2H), 6.62-6.47 (m, 1H), 5.96 (s, 1H), 4.96 (s, 2H), 4.19 (d, 2H), 3.81 (dt, 4H), 3.13 (s, 4H), 2.78 (s, 2H), 2.22 (d, 6H), 2.07-1.78 (m, 6H), 1.44 (s, 2H), 0.97 (d, 6H).

Example 331

4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-[(6-fluoro-1H-indol-5-yl)oxy]benzamide

Example 331A 3-nitro-4-(dioxidothiomorpholinoamino)benzenesulfonamide

The title compound was prepared by substituting 4-aminothiomorpholine-1,1-dioxide for 3-(N-morpholinyl)-1-propylamine in EXAMPLE 4A.

Example 331B 4-(4-{[2-(4-chlorophenyl)-4,4-dimethylcyclohex-1-en-1-yl]methyl}piperazin-1-yl)-N-({4-[(1,1-dioxidothiomorpholin-4-yl)amino]-3-nitrophenyl}sulfonyl)-2-[(6-fluoro-1H-indol-5-yl)oxy]benzamide The title compound was prepared by substituting EXAMPLE 154E for EXAMPLE 1F and EXAMPLE 331A for EXAMPLE 1G in EXAMPLE 1H. $^1$H NMR (400 MHz, dimethylsulfoxide-$d_6$) δ 11.22 (s, 1H), 9.65 (s, 1H), 8.56 (d, 1H), 7.88 (m, 2H), 7.51 (d, 1H), 7.35 (m, 5H), 7.03 (d, 2H), 6.64 (dd, 1H), 6.41 (d, 1H), 6.07 (d, 1H), 3.46 (m, 4H), 3.18 (m, 4H), 3.02 (m, 4H), 2.73 (s, 2H), 2.15 (m, 6H), 1.95 (s, 2H), 1.38 (t, J=6.15 Hz, 2H), 0.92 (s, 6H).

Example 332

4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydrofuran-3-ylmethyl)amino]phenyl}sulfonyl)benzamide

Example 332A 3-nitro-4-((tetrahydrofuran-3-yl)methylamino)benzenesulfonamide The title compound ws prepared by substituting 2-aminomethyl-tetrahydrofuran for 3-(N-morpholinyl)-1-propylamine in EXAMPLE 4A.

Example 332B 4-(4-{[2-(4-chlorophenyl)-4,4-dimethylcyclohex-1-en-1-yl]methyl}piperazin-1-yl)-2-[(6-fluoro-1H-indol-5-yl)oxy]-N-({3-nitro-4-[(tetrahydrofuran-3-ylmethyl)amino]phenyl}sulfonyl)benzamide The title compound was prepared by substituting EXAMPLE 154E for EXAMPLE 1F and EXAMPLE 332A for EXAMPLE 1G in EXAMPLE 1H. $^1$H NMR (500 MHz, dimethylsulfoxide-$d_6$) δ 11.30 (br.s, 1H), 11.23 (s, 1H), 8.66 (t, 1H), 8.59 (d, 1H), 7.87 (dd, 1H), 7.50 (d, 1H), 7.38 (t, 1H), 7.34 (m, 3H), 7.30 (d, 1H), 7.16 (d, 1H), 7.04 (d, 2H), 6.66 (dd, 1H), 6.41 (s, 1H), 6.10 (s, 1H), 3.80 (q, 1H), 3.70 (t, 1H), 3.63 (q, 1H), 3.51 (dd, 1H), 3.40 (m, 2H), 3.06 (br.s, 4H), 2.80 (m, 2H), 2.58 (m, 2H), 2.35-2.10 (m, 5H), 2.00-1.90 (m, 3H), 1.65 (m, 1H), 1.39 (t, 2H), 0.94 (s, 6H).

Example 333

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide

Example 333A trans-4-morpholinocyclohexanol

Trans-4-aminocyclohexanol (0.5 g), 1-bromo-2-(2-bromoethoxy)ethane (1.07 g) and triethylamine (2.42 mL) were dissolved in anhydrous acetonitrile (20 mL). The reaction mixture was heated at 60° C. overnight. The organic solvent was removed under vacuum. The residue was purified by flash column chromatography on silica gel eluting with 7-10% methanol in dichloromethane to give the title compound.

Example 333B

Trans-5-bromo-6-(4-morpholinocyclohexyloxy)pyridine-3-sulfonamide

The title compound was prepared by substituting EXAMPLE 333A for (1,4-dioxan-2-yl)methanol in EXAMPLE 305B.

Example 333C

Trans-N-({5-bromo-6-[(4-morpholin-4-ylcyclohexyl)oxy]pyridin-3-yl}sulfonyl)-4-(4-{[2-(4-chlorophenyl)-4,4-dimethylcyclohex-1-en-1-yl]methyl}piperazin-1-yl)-2-[(6-fluoro-1H-indol-5-yl)oxy]benzamide The title compound was prepared by substituting EXAMPLE 154E for EXAMPLE 1F and EXAMPLE 333B for EXAMPLE 1G in EXAMPLE 1H. $^1$H NMR (400 MHz, dimethylsulfoxide-$d_6$) δ 11.15 (s, 1H), 8.51 (d, 1H), 8.30 (d, 1H), 7.57 (d, 1H), 7.33 (m, 4H), 7.18 (d, 1H), 7.05 (d, 2H), 6.60 (dd, 1H), 6.37 (s, 1H), 6.07 (d, 1H), 5.02 (m, 1H), 3.68 (m, 4H), 2.99 (m, 4H), 2.74 (m, 7H), 2.23 (m, 8H), 1.95 (m, 4H), 1.41 (m, 6H), 0.92 (s, 6H).

Example 334

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-[(6-fluoro-1H-indol-5-yl)oxy]benzamide

Example 334A tert-butyl (trans)-4-(dicyclopropylamino)cyclohexylcarbamate

A suspension of tert-butyl (trans)-4-aminocyclohexylcarbamate (1 g), molecular sieves 3A (1 g), acetic acid (2.67 mL), (1-ethoxycyclopropoxy)trimethysilane (3.74 mL) and sodium cyanoborohydride (0.880 g) in dry methanol (10 mL) was heated at reflux for 3 hours. The insolubles were filtered off, the resulting solution was basified with aqueous NaOH (6 M) to pH 14, and extracted with ether. The combined extracts were washed with brine, dried and concentrated. The residue was purified by flash chromatography (silica gel 80 g, 30-100% acetone/hexanes) providing the product.

Example 334B trans)-N$^1$,N$^1$-dicyclopropylcyclohexane-1,4-diamine bis(2,2,2-trifluoroacetate The title compound was prepared by substituting EXAMPLE 334A for EXAMPLE 1A in EXAMPLE 1B.

Example 334C

Trans-4-(4-{[2-(4-chlorophenyl)-4,4-dimethylcyclohex-1-en-1-yl]methyl}piperazin-1-yl)-N-[(4-{[4-(dicyclopropylamino)cyclohexyl]amino}-3-nitrophenyl)sulfonyl]-2-[(6-fluoro-1H-indol-5-yl)oxy]benzamide A suspension of EXAMPLE 240A (0.14 g), EXAMPLE 334B (0.110 g) and N,N-diisopropylethylamine (0.303 mL) in dioxane (3 mL) was stirred for 3 days at 100° C. The mixture was concentrated and purified by RP HPLC (C8, 30%-100% CH$_3$CN/water/0.1% TFA). $^1$H NMR (500 MHz, pyridine-d$_5$) δ 12.38 (s, 1H), 9.31 (d, 1H), 8.48 (dd, 1H), 8.38 (d, 1H), 8.15 (d, 1H), 7.47-7.53 (m, 3H), 7.41-7.46 (m, 3H), 7.01-7.08 (m, 3H), 6.72 (dd, 1H), 6.54-6.59 (m, 2H), 3.45 (ddd, 1H), 3.01-3.07 (m, 4H), 2.72-2.79 (m, 3H), 2.24 (t, 2H), 2.10 (d, 6H), 2.00-2.06 (m, 2H), 1.96 (s, 2H), 1.88 (d, 2H), 1.67 (qd, 2H), 1.34-1.40 (m, 2H), 1.20-1.29 (m, 2H), 0.93 (s, 6H), 0.48 (d, 8H).

Example 335

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(tetrahydro-2H-pyran-4-ylamino)cyclohexyl]amino}phenyl)sulfonyl]benzamide

Example 335A tert-butyl (trans)-4-(tetrahydro-2H-pyran-4-ylamino)cyclohexylcarbamate The title compound was prepared by substituting tert-butyl (trans)-4-aminocyclohexylcarbamate for tert-butyl piperazine-1-carboxylate and dihydro-2H-pyran-4(3H)-one for 4'-chlorobiphenyl-2-carboxaldehyde in EXAMPLE 1A.

Example 335B trans)-N$^1$-(tetrahydro-2H-pyran-4-yl)cyclohexane-1,4-diamine bis(2,2,2-trifluoroacetate The title compound was prepared by substituting EXAMPLE 335A for EXAMPLE 1A in EXAMPLE 1B.

Example 335C

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(tetrahydro-2H-pyran-4-ylamino)cyclohexyl]amino}phenyl)sulfonyl]benzamide The title compound was prepared by substituting EXAMPLE 335B for EXAMPLE 334B in EXAMPLE 334C.

$^1$H NMR (500 MHz, pyridine-d$_5$) δ 12.35 (s, 1H), 9.30 (d, 1H), 8.40 (dd, 1H), 8.35 (d, 1H), 8.19 (d, 1H), 7.51 (dd, 2H), 7.46-7.49 (m, 2H), 7.43 (d, 2H), 7.05 (d, 2H), 6.92 (d, 1H), 6.73 (dd, 1H), 6.54-6.59 (m, 2H), 3.99-4.04 (m, 2H), 3.45-3.52 (m, 1H), 3.41 (t, 2H), 3.10 (s, 1H), 3.01-3.07 (m, 4H), 2.91 (s, 1H), 2.75 (s, 2H), 2.21-2.26 (m, 2H), 2.11 (d, 5H), 2.08 (d, 3H), 1.96 (s, 4H), 1.59 (s, 2H), 1.54 (d, 2H), 1.30-1.40 (m, 4H), 0.93 (s, 6H).

Example 336

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(4-tetrahydro-2H-pyran-4-ylpiperazin-1-yl)cyclohexyl]amino}phenyl)sulfonyl]benzamide

Example 336A tert-butyl 4-(tetrahydro-2H-pyran-4-yl)piperazine-1-carboxylate To a solution of tert-butyl piperazine-1-carboxylate (5.15 g) and dihydro-2H-pyran-4(3H)-one (3.05 g) stirred for 24 hours at room temperature in titanium(IV) isopropoxide (16.20 mL), methanol (5 mL) was added followed by careful addition of sodium borohydride (2.092 g). The reaction mixture was quenched with water/NaOH solution, extracted with ether, dried over magnesium sulfate, filtered, and concentrated to yield the product. The crude product was used in next step.

Example 336B 1-(tetrahydro-2H-pyran-4-yl)piperazine dihydrochloride

To a solution of EXAMPLE 336A (3.92 g) in ether was added HCl (25 mL, 2M in ether) and the reaction mixture was stirred for 16 hours at room temperature. The solid product was filtered off, dried and used in next step without further purification.

Example 336C

Trans-tert-butyl 4-(4-(tetrahydro-2H-pyran-4-yl)piperazin-1-yl)cyclohexylcarbamate To a solution of EXAMPLE 336B (1 g) and tert-butyl 4-oxocyclohexylcarbamate (0.877 g) stirred for 24 hours at room temperature in titanium(IV) isopropoxide (2.410 mL), methanol (2 mL) was added followed by careful addition of sodium borohydride (0.311 g). The reaction mixture was quenched with water, extracted with ether, dried and concentrated. The crude product was purified by flash chromatography (silica 80 g, 50%-100% acetone/hexanes) providing the product.

Example 336D trans-4-(4-(tetrahydro-2H-pyran-4-yl)piperazin-1-yl)cyclohexanamine tris(2,2,2-trifluoroacetate)

The title compound was prepared by substituting EXAMPLE 336C for EXAMPLE 1A in EXAMPLE 1B.

Example 336E

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(3-nitro-4-{[4-(4-tetrahydro-2H-pyran-4-ylpiperazin-1-yl)cyclohexyl]amino}phenyl)sulfonyl]benzamide The title compound was prepared by substituting EXAMPLE 336D for EXAMPLE 334B in EXAMPLE 334C. $^1$H NMR (500 MHz, pyridine-$d_5$) δ 12.38 (s, 1H), 9.30-9.34 (m, 1H), 8.41-8.46 (m, 1H), 8.37 (d, 1H), 8.15 (d, 1H), 7.48-7.53 (m, 3H), 7.41-7.46 (m, 3H), 7.04 (d, 2H), 6.96 (t, 1H), 6.69-6.74 (m, 1H), 6.54-6.59 (m, 2H), 3.99-4.05 (m, 2H), 3.29-3.36 (m, 2H), 3.05 (s, 4H), 2.74 (s, 2H), 2.62 (s, 5H), 2.57 (s, 3H), 2.27-2.36 (m, 2H), 2.19-2.27 (m, 3H), 2.11 (s, 6H), 1.96 (s, 2H), 1.91 (s, 1H), 1.87 (s, 1H), 1.70 (s, 2H), 1.64 (s, 1H), 1.56 (td, 2H), 1.35-1.43 (m, 4H), 1.29 (s, 2H), 0.93 (s, 6H).

Example 337

4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-fluorotetrahydro-2H-pyran-4-yl)methyl]amino}-3-nitrophenyl)sulfonyl]benzamide

Example 337A (4-fluorotetrahydro-2H-pyran-4-yl)methyl methanesulfonate

A mixture of EXAMPLE 296C (1.4 g), methanesulfonyl chloride (1.054 mL), triethylamine (2.99 mL), and 4-(dimethylamino)pyridine (0.051 g) in $CH_2Cl_2$ (20 mL) was stirred at 0° C. for 2 hours, concentrated and chromatographed on silica gel with 30% ethyl acetate in hexanes as eluent to give the product.

Example 337B 2-((4-fluorotetrahydro-2H-pyran-4-yl)methyl)isoindoline-1,3-dione A mixture of EXAMPLE 337A (1.8 g) and potassium phthalimide (2.356 g) in N,N-dimethylformamide (30 mL) was heated at 150° C. overnight, diluted with ethyl acetate, washed with water and brine, dried ($MgSO_4$), filtered, concentrated and chromatographed on silica gel with 30% ethyl acetate in hexanes as eluent to give the product.

Example 337C (4-fluorotetrahydro-2H-pyran-4-yl)methanamine

A mixture of EXAMPLE 337B (1.4 g) and hydrazine (1.548 mL) in ethanol (40 mL) was heated at 70° C. overnight, cooled to room temperature, slurried with $CH_2Cl_2$ (200 mL) and the solid removed by filtration. The filtrate was concentrated and chromatographed on silica gel with 100:5:1 ethyl acetate/methanol/$NH_4OH$ as eluent to give the product.

Example 337D 4-((4-fluorotetrahydro-2H-pyran-4-yl)methylamino)-3-nitrobenzenesulfonamide A mixture of 4-fluoro-3-nitrobenzenesulfonamide (0.44 g), EXAMPLE 337C (0.266 g), and triethylamine (1.11 mL) in tetrahydrofuran (10 mL) was heated at 70° C. overnight, diluted with ethyl acetate, washed with water and brine, dried ($MgSO_4$), filtered, concentrated and chromatographed on silica gel with 50% ethyl acetate in hexanes as eluent to give the product.

Example 337E 4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-fluorotetrahydro-2H-pyran-4-yl)methyl]amino}-3-nitrophenyl)sulfonyl]benzamide The title compound was prepared by substituting EXAMPLE 154E for EXAMPLE 1F and EXAMPLE 337D for EXAMPLE 1G in EXAMPLE 1H. $^1$H NMR (300 MHz, dimethylsulfoxide-$d_6$) δ 11.21 (m, 2H), 8.63 (t, 1H), 8.59 (d, 1H), 7.88 (dd, 1H), 7.51 (d, 1H), 7.33 (m, 6H), 7.03 (m, 2H), 6.65 (dd, 1H), 6.40 (m, 1H), 6.09 (d, 1H), 3.74 (m, 4H), 3.52 (m, 2H), 3.03 (m, 4H), 2.74 (m, 2H), 2.16 (m, 6H), 1.95 (s, 2H), 1.80 (m, 4H), 1.38 (t, 2H), 0.92 (s, 6H).

Example 338

Trans-4-(4-{[2-(4-chlorophenyl)-4,4-dimethylcyclohex-1-en-1-yl]methyl}piperazin-1-yl)-2-[(6-fluoro-1H-indol-5-yl)oxy]-N-[(4-{[(4-hydroxycyclohexyl)methyl]amino}-3-nitrophenyl)sulfonyl]benzamide A mixture of EXAMPLE 240A (153 mg), trans-4-(aminomethyl)cyclohexanol (73.5 mg) and N-ethyl-N-isopropylpropan-2-amine (0.16 mL) in dioxane (2 mL) was heated at 100° C. for 20 hours and concentrated. The residue was dissolved in dimethylsulfoxide-methanol (1:1) and purified by HPLC, eluting with 40%-65% acetonitrile in 0.1% TFA water over 40 minutes to provide the title compound. $^1$H NMR (500 MHz, dimethylsulfoxide-$d_6$) δ 11.22 (s, 2H), 8.56-8.62 (m, 2H), 7.85 (dd, 1H), 7.51 (d, 1H), 7.38 (t, 1H), 7.29-7.36 (m, 4H), 7.12 (d, 1H), 7.03 (d, 2H), 6.66 (dd, 1H), 6.41 (s, 1H), 6.09 (d, 1H), 4.51 (d, 1H), 3.24 (t, 2H), 3.03 (s, 4H), 2.74 (s, 2H), 2.16 (d, 6H), 1.95 (s, 2H), 1.83 (d, 2H), 1.74 (d, 2H), 1.56 (dd, 1H), 1.38 (t, 2H), 0.95-1.16 (m, 4H), 0.92 (s, 6H).

Example 339

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({3-nitro-4-[(tetrahydro-2H-pyran-4-ylmethyl)amino]phenyl}sulfonyl)benzamide

Example 339A methyl 2-(1H-indol-4-yloxy)-4-fluorobenzoate

Methyl 2,4-difluorobenzoate (1.53 g), $K_3PO_4$ (1.89 g) and 4-hydroxyindole (1.08 g) were stirred at 110° C. in diglyme (12 mL) for 24 hours. The reaction was cooled and poured into ether. The solution was washed three times with 1 M aqueous NaOH solution, and brine, and dried over $Na_2SO_4$. The solution was then concentrated, and the crude product was chromatographed on silica gel with 20% ethyl acetate/hexanes.

Example 339B methyl 2-(H-indol-4-yloxy)-4-(piperazin-1-yl)benzoate

EXAMPLE 339A (1425 mg), piperazine (452 mg), and $HK_2PO_4$ (958 mg) were stirred in dimethylsulfoxide (20 mL) at 140° C. for 24 hours. The reaction was diluted with ethyl acetate, washed three times with water, washed with brine, dried over $Na_2SO_4$, and concentrated. The crude product was chromatographed on silica gel with a methanol/methylene chloride gradient.

Example 339C methyl 2-(3-bromo-1H-indol-4-yloxy)-4-(piperazin-1-yl)benzoate

A solution of EXAMPLE 339B (1 g) in dichloromethane (50 mL) and N,N-dimethylformamide (5 mL) was cooled in an ice bath. N-bromosuccinimide (0.582 g) was added and the mixture was stirred overnight while warming to ambient temperature. The reaction was concentrated and the crude product was chromatographed on silica gel with a methanol/methylene chloride gradient.

Example 339D tert-butyl 3-bromo-4-(5-(4-(tert-butyloxycarbonyl)piperazin-1-yl)-2-(methoxycarbonyl)phenoxy)-1H-indol-1-carboxylate EXAMPLE 339C (388 mg) and di-tert-butyl dicarbonate (590 mg) were dissolved in a mixture of acetonitrile (20 mL), and dichloromethane (20 mL). N-ethyl-N-isopropylpropan-2-amine (0.165 mL) was added followed by N,N-dimethylpyridin-4-amine (33.0 mg) and the mixture was stirred 18 hours. The reaction was concentrated and the crude product was purified on a plug of silica gel with 15% ethyl acetate in hexane.

Example 339E

E(E)-tert-butyl 4-(3-(3-(3-(dimethylamino)prop-1-enyl)-1H-indol-4-yloxy)-4-(methoxycarbonyl)phenyl)piperizine-1-carboxylate A mixture EXAMPLE 339D (175 mg), (E)-N,N-dimethyl-3-(4,4,5,5-tetramethyl-1,3,2-dioxaborolan-2-yl)prop-2-en-1-amine (103 mg), sodium carbonate (73.5 mg) and bis(triphenylphosphine)palladium(II) dichloride (9.74 mg) in a mixture of 1,2-dimethoxyethane (3.0 mL) and water (1.5 mL) was heated in a CEM Discover microwave reactor at 150° C. for 30 minutes. The reaction was partitioned between brine and ethyl acetate. The organic layer was dried over sodium sulfate, filtered and concentrated. The crude product was purified on silica gel with a 7N methanolic ammonia/methylene chloride gradient.

Example 339F tert-butyl 4-(3-(3-(3-(dimethylamino)propyl)-1H-indol-4-yloxy)-4-(methoxycarbonyl)phenyl)piperizine-1-carboxylate A mixture of EXAMPLE 339E (715 mg) and 5% palladium on carbon (143 mg) in methanol (20 mL) was hydrogenated at 30 psi for 16 hours at ambient temperature. The reaction mixture was filtered, concentrated and the crude product was chromatographed on silica gel with 7N-methanolic ammonia in methylene chloride.

Example 339G methyl 2-(3-(3-(dimethylamino)propyl)-1H-indol-4-yloxy)-4-(piperazin-1-yl)benzoate A solution of EXAMPLE 339F (484 mg) in dichloromethane (22 mL) was cooled in an ice bath and 2,2,2-trifluoroacetic acid (11 mL) was added. The reaction was stirred for 2 hours, concentrated and the crude product was chromatographed on silica gel with 7N-methanolic ammonia in methylene chloride.

Example 339H methyl 4-(4-((2-(4-chlorophenyl)-4,4-dimethylcyclohex-1-enyl)methyl)piperazin-1-yl)-2-(3-(3-(dimethylamino)propyl)-1H-indol-4-yloxy)benzoate To a solution of EXAMPLE 339G (285 mg) and EXAMPLE 60D (171 mg) in dichloromethane (20 mL) was added sodium triacetoxyborohydride (208 mg) portion wise over a few minutes. The reaction was stirred 72 hours at ambient temperature, quenched by the slow addition of saturated aqueous sodium bicarbonate solution (100 mL) and extracted with methylene chloride (75 mL). The organic layer was dried over sodium sulfate, filtered and concentrated. The crude product was purified on silica gel with 7N-methanolic ammonia in methylene chloride.

Example 339I 4-(4-((2-(4-chlorophenyl)-4,4-dimethylcyclohex-1-enyl)methyl)piperazin-1-yl)-2-(3-(3-(dimethylamino)propyl)-1H-indol-4-yloxy)benzoic acid The title compound was prepared by substituting EXAMPLE 399H for EXAMPLE 1E in EXAMPLE 1F.

Example 399J 4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({3-nitro-4-[(tetrahydro-2H-pyran-4-ylmethyl)amino]phenyl}sulfonyl)benzamide The title compound was prepared by substituting EXAMPLE 339I for EXAMPLE 1F in EXAMPLE 1H. $^1$H NMR (500 MHz, pyridine-$d_5$) δ 12.00 (s, 1H), 9.24 (s, 1H), 8.49 (m, 1H), 8.43 (d, 1H), 8.37 (d, 1H), 7.45 (m, 2H), 7.25 (m, 2H), 7.11 (d, 2H), 7.00 (t, 1H), 6.81 (m, 3H), 6.63 (d, 1H), 3.96 (d, 2H), 3.30 (t, 2H), 3.06 (m, 10H), 2.82 (m, 7H), 2.49 (m, 2H), 2.24 (m, 5H), 1.99 (m, 1H), 1.76 (m, 1H), 1.55 (m, 2H), 1.41 (m, 2H), 1.25 (m, 4H), 0.96 (m, 6H), 0.84 (m, 2H).

Example 340

4-(4-{[2-(4-chlorophenyl)-4,4-dimethylcyclohex-1-en-1-yl]methyl}piperazin-1-yl)-2-({3-[3-(dimethylamino)propyl]-1H-indol-4-yl}oxy)-N-({4-[(4-methylpiperazin-1-yl)amino]-3-nitrophenyl}sulfonyl)benzamide The title compound was prepared by substituting EXAMPLE 339I for EXAMPLE 1F and EXAMPLE 184A for EXAMPLE 1G in EXAMPLE 1H. $^1$H NMR (500 MHz, pyridine-$d_5$) δ 11.98 (s, 1H), 9.19 (d, 1H), 8.97 (s, 1H), 8.48 (m, 1H), 8.42 (m, 1H), 7.63 (d, 1H), 7.46 (d, 2H), 7.25 (m, 2H), 7.11 (d, 2H), 7.00 (m, 1H), 6.80 (m, 2H), 6.64 (m, 1H), 3.04 (m, 8H), 2.82 (m, 10H), 2.49 (m, 3H), 2.28 (m, 3H), 2.22 (m, 6H), 2.16 (m, 3H), 2.08 (m, 1H), 1.99 (m, 2H), 1.40 (t, 2H), 0.96 (m, 6H), 0.84 (m, 2H).

Example 341

4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-[(6-fluoro-1H-indol-5-yl)oxy]benzamide

Example 341A tert-butyl 4-fluoro-4-(hydroxymethyl)piperidine-1-carboxylate

1-Tert-butyl 4-ethyl 4-fluoropiperidine-1,4-dicarboxylate (1.0 g) in tetrahydrofuran (5 mL) was treated with 1.0 N LiAlH$_4$ (2.54 mL) at 0° C. The reaction mixture was stirred at room temperature for 2 hours. Water (0.6 mL) was added to the reaction mixture drop-wise, followed by 2 N aqueous NaOH (0.2 mL). The reaction was stirred for another 1 hour. The solid was removed by filtration via a pack of Celite and washed with ethyl acetate. The filtrate was washed with brine, dried over MgSO$_4$, filtered, and concentrated to give the product.

Example 341B tert-butyl 4-fluoro-4-((2-nitro-4-sulfamoylphenoxy)methyl)piperidine-1-carboxylate The title compound was prepared by substituting EXAMPLE 341A for (tetrahydro-2H-pyran-4-yl)methanol in EXAMPLE 264A.

Example 341C 4-((4-fluoropiperidin-4-yl)methoxy)-3-nitrobenzenesulfonamide

The title compound was prepared by substituting EXAMPLE 341B for EXAMPLE 1A in EXAMPLE 1B.

Example 341D 4-((1-cyclopropyl-4-fluoropiperidin-4-yl)methoxy)-3-nitrobenzenesulfonamide To EXAMPLE 341C (0.24 g) in methanol (3 mL) was added 3 Å molecular sieves (0.1 g), followed sequentially by acetic acid (0.31 mL), (1-ethoxycyclopropoxy)trimethylsilane (0.64 mL), and sodium cyanoborohydride (0.148 g). The reaction was heated under reflux overnight. After cooling, the reaction mixture was loaded onto a silica gel column. After drying, the column was eluted with 100:2:0.2 ethyl acetate/methanol/NH$_4$OH to give the title compound.

Example 341E 4-(4-{[2-(4-chlorophenyl)-4,4-dimethylcyclohex-1-en-1-yl]methyl}piperazin-1-yl)-N-({4-[(1-cyclopropyl-4-fluoropiperidin-4-yl)methoxy]-3-nitrophenyl}sulfonyl)-2-[(6-fluoro-1H-indol-5-yl)oxy]benzamide The title compound was prepared by substituting EXAMPLE 154E for EXAMPLE 1F and EXAMPLE 341D for EXAMPLE 1G in EXAMPLE 1H. $^1$H NMR (500 MHz, dimethylsulfoxide-$d_6$) δ 11.20 (s, 1H), 8.37 (d, 1H), 8.10 (d, 1H), 7.53 (d, 1H), 7.44 (d, 1H), 7.32-7.37 (m, 4H), 7.24 (d, 1H), 7.04 (d, 2H), 6.63 (dd, 1H), 6.39 (s, 1H), 6.09 (d, 1H), 4.34 (d, 2H), 3.05 (s, 4H), 2.90 (s, 2H), 2.78 (s, 2H), 2.14-2.26 (m, 6H), 1.68-1.82 (m, 4H), 1.38 (d, 2H), 0.92 (s, 6H), 0.40-0.49 (m, 4H).

Example 342

4-(4-{[2-(4-chlorophenyl)-4,4-dimethylcyclohex-1-en-1-yl]methyl}piperazin-1-yl)-2-{[1-(4-methoxybenzyl)-1H-1,2,3-benzotriazol-4-yl]oxy}-N-({3-nitro-4-[(tetrahydro-2H-pyran-4-ylmethyl)amino]phenyl}sulfonyl)benzamide

Example 342A 4-(tert-Butyl-dimethyl-silanyloxy)-1H-benzotriazole

To 4-hydroxybenzotriazole (5.000 g) in tetrahydrofuran (250 mL) was added sodium hydride (60%, 0.932 g). The solution was stirred at room temperature for 20 minutes, cooled to 0° C., tert-butyldimethylchlorosilane (5.860 g) was added, the solution was allowed to warm to room temperature, and stirred for 16 hours. Additional sodium hydride (60%, 0.500 g) was added, the solution stirred for 15 minutes, additional tert-butyldimethylchlorosilane (3.000 g) was added, and the solution stirred for three hours at room temperature. The solution was then added to saturated aqueous ammonium chloride and extracted with ethyl acetate. The organic extract was washed with brine, dried over anhydrous sodium sulfate, filtered, concentrated and purified by flash column chromatography on silica gel using 20-30% ethyl acetate in hexanes.

Example 342B 4-(tert-Butyl-dimethyl-silanyloxy)-1-(4-methoxybenzyl)-1H-benzotriazole To EXAMPLE 342A (2.00 g) in dimethylformamide (40 mL) was added sodium hydride (60%, 0.353 g). The solution was mixed for 10 minutes at room temperature and 4-methoxybenzyl chloride (1.382 g) was added. The solution was heated at 80° C. for 16 hours, cooled, added to water, and extracted with 50% ethyl acetate in hexanes. The extract was washed with brine, dried over anhydrous sodium sulfate, filtered, concentrated, and purified by flash column chromatography on silica gel using 10% ethyl acetate in hexanes.

Example 342C 1-(4-Methoxy-benzyl)-1H-benzotriazol-4-ol

To a solution of EXAMPLE 342B (2.59 g) in tetrahydrofuran (40 mL) was added tetraammonium fluoride (1M in tetrahydrofuran, 21.03 mL). The solution was mixed at room temperature for two hours. The solvent was removed under vacuum, the residue was taken up in ethyl acetate, and the solution was vacuum filtered over a pad of silica gel. The filtrate was concentrated and purified by flash column chromatography on silica gel using 35% ethyl acetate in hexanes.

Example 342D

4-Fluoro-2-[1-(4-methoxy-benzyl)-1H-benzotriazol-4-yloxy]-benzoic acid methyl ester To a solution of EXAMPLE 342C (990 mg) and methyl 2,4-difluorobenzoate (734 mg) in diglyme (40 mL) was added potassium tert-butoxide (1M in tetrahydrofuran, 4.07 mL). The solution was heated to 100° C. for 16 hours, cooled, added to saturated ammonium chloride, and extracted with 70% ethyl acetate in hexanes. The extract was washed with brine, dried over anhydrous sodium sulfate, filtered, concentrated and purified by flash column chromatography on silica gel using 30% ethyl acetate in hexanes.

Example 342E

2-[1-(4-Methoxy-benzyl)-1H-benzotriazol-4-yloxy]-4-piperazin-1-yl-benzoic acid methyl ester To a solution of EXAMPLE 342D (650 mg) in dimethylsulfoxide (12 mL) was added piperazine (618 mg). The solution was heated at 100° C. for one hour, cooled, added to dichloromethane, extracted with water three times, dried over anhydrous sodium sulfate, filtered, and the solvent was removed under vacuum.

Example 342F

4-{4-[2-(4-Chloro-phenyl)-4,4-dimethyl-cyclohex-1-enylmethyl]-piperazin-1-yl}-2-[1-(4-methoxy-benzyl)-1H-benzotriazol-4-yloxy]-benzoic acid methyl ester The title compound was prepared by substituting EXAMPLE 60D for 4'-chlorobiphenyl-2-carboxaldehyde and EXAMPLE 342E for tert-butyl piperazine-1-carboxylate in EXAMPLE 1A.

Example 342G

4-{4-[2-(4-Chloro-phenyl)-4,4-dimethyl-cyclohex-1-enylmethyl]-piperazin-1-yl}-2-[1-(4-methoxy-benzyl)-1H-benzotriazol-4-yloxy]-benzoic acid The title compound was prepared by substituting EXAMPLE 342F for EXAMPLE 1E in EXAMPLE 1F.

Example 342H 4-(4-{[2-(4-chlorophenyl)-4,4-dimethylcyclohex-1-en-1-yl]methyl}piperazin-1-yl)-2-{[1-(4-methoxy-benzyl)-1H-1,2,3-benzotriazol-4-yl]oxy}-N-({3-nitro-4-[(tetrahydro-2H-pyran-4-ylmethyl)amino]phenyl}sulfonyl)benzamide The title compound was prepared by substituting EXAMPLE 342G for EXAMPLE 1F in EXAMPLE 1H. $^1$H NMR (300 MHz, dimethylsulfoxide-$d_6$) δ 8.59 (t, 1H), 8.37 (d, 1H), 7.67 (d, 1H), 7.56 (d, 1H), 7.38-7.23 (m, 3H), 7.30 (d, 2H), 7.23 (t, 1H), 7.05 (d, 2H), 7.02 (d, 1H), 6.91 (d, 2H), 6.80 (dd, 1H), 6.51 (d, 1H), 6.37 (d, 1H), 5.87 (s, 2H), 3.85 (dd, 2H), 3.71 (s, 3H), 3.28 (m, 4H), 3.16 (bs, 2H), 2.78 (bs, 2H), 2.57 (bs, 2H), 2.29-2.14 (m, 6H), 1.97 (bs, 2H), 1.89 (m, 1H), 1.62 (dd, 2H), 1.40 (t, 2H), 1.26 (m, 2H), 0.93 (s, 6H).

Example 343

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 318E for EXAMPLE 1F and EXAMPLE 184A for EXAMPLE 1G in EXAMPLE 1H. $^1$H NMR (300 MHz, dimethylsulfoxide-$d_6$) δ 11.04-10.47 (m, 1H), 9.19 (s, 1H), 8.50 (d, 1H), 7.90-7.83 (m, 1H), 7.70 (d, 1H), 7.64 (s, 1H), 7.47 (d, 1H), 7.33 (dd, 3H), 7.06 (d, 2H), 6.63 (d, 1H), 6.20 (d, 1H), 6.07 (s, 2H), 3.08 (s, 4H), 2.95 (s, 4H), 2.75 (s, 3H), 2.42 (s, 4H), 2.19 (m, 8H), 1.97 (s, 2H), 1.41 (d, 2H), 0.94 (s, 6H).

Example 344

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-(1,4-dioxan-2-ylmethoxy)-3-nitrophenyl]sulfonyl}benzamide The title compound was prepared by substituting EXAMPLE 318E for EXAMPLE 1F and EXAMPLE 285A for EXAMPLE 1G in EXAMPLE 1H. $^1$H NMR (300 MHz, dimethylsulfoxide-$d_6$) δ 11.54-11.15 (m, 1H), 8.35 (t, 2H), 8.05 (dd, 1H), 7.75 (d, 1H), 7.45 (d, 1H), 7.30 (m, 2H), 7.20 (d, 1H), 7.05 (d, 2H), 6.62 (d, 1H), 6.21-6.15 (m, 3H), 3.85-3.75 (m, 3H), 3.51 (m, 6H), 3.12 (m, 4H), 2.79 (s, 2H), 2.21 (m, 6H), 1.97 (s, 2H), 1.40 (t, 2H), 0.94 (s, 6H).

Example 345

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide

Example 345A (4-methoxycyclohexyl)methanamine (4-Methoxyphenyl)methanamine (1 g) in ethanol (10 mL) was treated with 5% Rh—Al$_2$O$_3$ (99.8 mg) under a H$_2$ atmosphere (500 psi) at 50° C. for 16 hours. Additional 5% Rh—Al$_2$O$_3$ (0.4 g) was added. The resulting mixture was stirred under H$_2$ atmosphere (500 psi) at 60° C. for 2 hours. The insoluble material was filtered off and the filtrate was concentrated to provide a mixture of cis and trans product as an oil, which was used for next step without further purification.

Example 345B 4-((trans-4-methoxycyclohexyl)methylamino)-3-nitrobenzenesulfonamide 4-Fluoro-3-nitrobenzenesulfonamide (1.098 g) and EXAMPLE 345A (1 g) in tetrahydrofuran (20 mL) were treated with diisopropylethylamine (0.871 mL) overnight. The reaction mixture was concentrated and the residue was purified by reverse phase chromatography, and was eluted with 40-55% acetonitrile in 0.1% trifluoroacetic acid in water over 25 minutes to provide the title compound.

Example 345C

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide The title compound was prepared as described in EXAMPLE 110F by replacing EXAMPLE 110E and EXAMPLE 1G with EXAMPLE 318E and EXAMPLE 345B, respectively. $^1$H NMR (500 MHz, dimethylsulfoxide-$d_6$) δ 8.62 (t, 1H), 8.58 (d, 1H), 7.86 (dd, 1H), 7.75 (d, 1H), 7.44 (d, 1H), 7.40 (d, 1H), 7.36 (d, 2H), 7.18 (d, 1H), 7.06 (d, 2H), 6.65 (dd, 1H), 6.18 (s, 3H), 3.26-3.33 (m, 4H), 3.22 (s, 3H), 3.12 (s, 4H), 3.03-3.09 (m, 1H), 2.79 (s, 2H), 2.24 (s, 4H), 2.17 (s, 2H), 1.93-2.03 (m, 4H), 1.80 (d, 2H), 1.62 (dd, 1H), 1.40 (t, 2H), 0.98-1.14 (m, 4H), 0.94 (s, 6H).

Example 346

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide The title compound was prepared by substituting EXAMPLE 318E for EXAMPLE 1F and EXAMPLE 291A for EXAMPLE 1G in EXAMPLE 1H. $^1$H NMR (300 MHz, dimethylsulfoxide-$d_6$) δ 11.54-11.15 (m, 1H), 8.59 (t, 2H), 7.87 (dd, 1H), 7.74 (d, 1H), 7.44 (d, 1H), 7.34 (s, 3H), 7.20 (d, 1H), 7.06 (d, 2H), 6.65 (dd, 1H), 6.21-6.15 (m, 3H), 3.84-3.75 (m, 3H), 3.51 (m, 6H), 3.12 (s, 4H), 2.79 (s, 2H), 2.21 (d, 6H), 1.97 (s, 2H), 1.40 (t, 2H), 0.94 (s, 6H).

Example 347

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(3-morpholin-4-yl-propyl)amino]-3-[(trifluoromethyl)sulfonyl]phenyl}sulfonyl)benzamide

Example 347A 4-(3-morpholinopropylamino)-3-(trifluoromethylsulfonyl)benzenesulfonamide 3-Morpholinopropan-1-amine (376 mg), EXAMPLE 131C (800 mg) and N-ethyl-N-isopropylpropan-2-amine (1.4 mL) in tetrahydrofuran (15 mL) were heated at 55° C. for 3 hours. The solvent was removed and the residue was dissolved in ethyl acetate and washed with water and brine. The organic layer was dried over Na$_2$SO$_4$, filtered, and concentrated to give the title compound.

Example 347B

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(3-morpholin-4-yl-propyl)amino]-3-[(trifluoromethyl)sulfonyl]phenyl}sulfonyl)benzamide The title compound was prepared by substituting EXAMPLE 318E for EXAMPLE 1F and EXAMPLE 347A for EXAMPLE 1G in EXAMPLE 1H. $^1$H NMR (300 MHz, dimethylsulfoxide-$d_6$) δ 11.31-10.55 (m, 1H), 8.14 (s, 1H), 7.96 (d, 1H), 7.73 (d, 1H), 7.44 (d, 1H), 7.36 (d, 4H), 7.12 (d, 1H), 7.06 (d, 2H), 6.64 (d, 1H), 6.17 (d, 3H), 3.61 (s, 4H), 3.42 (d, 2H), 3.10 (s, 4H), 2.77 (s, 2H), 2.48-2.41 (m, 4H), 2.23 (s, 8H), 1.97 (s, 2H), 1.76 (s, 2H), 1.40 (s, 2H), 0.94 (s, 6H).

Example 348

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)benzamide

Example 348A 4-((4-fluorotetrahydro-2H-pyran-4-yl)methoxy)-3-(trifluoromethylsulfonyl)benzenesulfonamide To a solution of EXAMPLE 296C (0.500 g) in tetrahydrofuran (5 mL) was added sodium hydride (0.596 g). Tetrahydrofuran (25 mL) was added and the mixture was stirred for 30 minutes, and then EXAMPLE 131C (1.145 g) was added as a solution in tetrahydrofuran (5 mL). After stirring for 2 hours, the reaction was partitioned between 1N aqueous HCl (50 mL) and dichloromethane (200 mL). The dichloromethane layer was dried over magnesium sulfate, filtered, and concentrated. The resulting solid was chromatographed over silica gel (Reveleris 80 g) eluting with a gradient of 0.5% to 7.5% methanol/dichloromethane over 30 minutes (flow=40 ml/min) to give the title compound.

Example 348B

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-[(trifluoromethyl)sulfonyl]phenyl}sulfonyl)benzamide The title compound was prepared by substituting EXAMPLE 318E for EXAMPLE 1F and EXAMPLE 348A for EXAMPLE 1G in EXAMPLE 1H. $^1$H NMR (300 MHz, dimethylsulfoxide-$d_6$) δ 8.42 (s, 1H), 8.37-8.28 (m, 1H), 7.70 (s, 1H), 7.65-7.55 (m, 1H), 7.46 (d, J=8.8, 1H), 7.37 (d, J=8.4, 3H), 7.07 (d, J=8.4, 2H), 6.67 (s, 1H), 6.23 (s, 1H), 6.12 (s, 2H), 4.47 (d, J=20.7, 2H), 3.76 (s, 2H), 3.60 (s, 2H), 3.21-3.02 (m, 4H), 2.18 (s, 6H), 2.01-1.79 (m, 8H), 1.42 (s, 2H), 0.95 (s, 6H).

Example 349

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[2-(4-chlorophenyl)-4,4-dimethylcyclohex-1-en-1-yl]methyl}piperazin-1-yl)benzamide The title compound was prepared by substituting EXAMPLE 326A for EXAMPLE 1G and EXAMPLE 318E for EXAMPLE 110E in EXAMPLE 110F. $^1$H NMR (500 MHz, dimethylsulfoxide-$d_6$) δ 8.53 (s, 1H), 8.22 (s, 1H), 7.72 (s, 1H), 7.34-7.38 (m, 13H), 7.07 (d, 2H), 6.66 (dd, 1H), 6.23 (s, 1H), 6.12 (s, 2H), 4.55 (d, 2H), 3.756-3.79 (m, 2H), 3.57-3.62 (m, 2H), 3.15 (br s, 4H), 2.18 (m, 2H), 1.99 (s, 2H), 1.82-1.91 (m, 4H), 1.42 (t, 2H), 0.95 (s, 6H).

Example 350

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 350A methyl 2-(6-amino-5-bromopyridin-3-yloxy)-4-fluorobenzoate

A mixture of EXAMPLE 318B (1.6 g) in N,N-dimethylformamide (50 mL) was cooled to 0° C., followed by the addition of N-bromosuccinimide (1.195 g) in N,N-dimethylformamide (10 mL) solution. The reaction mixture was stirred at 0° C. for 1 hour, and quenched with ice-cold saturated NaHCO$_3$ aqueous solution. The reaction mixture was extracted with ethyl acetate. The combined organic phase was washed with water and brine, dried over anhydrous sodium sulfate, filtered, and concentrated. The crude material was purified using flash column purification with 30-40% ethyl acetate/hexane to provide the title compound.

Example 350B

Methyl 2-(6-amino-5-bromopyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 350A for EXAMPLE 3A in EXAMPLE 3G.

Example 350C 2-(6-Amino-5-bromopyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 350B for EXAMPLE 38G in EXAMPLE 38H.

Example 350D

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 350C for EXAMPLE 110E in EXAMPLE 110F. $^1$H NMR (400 MHz, dimethylsulfoxide-$d_6$) δ 8.52 (m, 2H), 7.79 (dd, 1H), 7.73 (d, 1H), 7.49 (d, 1H), 7.40 (s, 1H), 7.36 (d, 2H), 7.13 (d, 1H), 7.06 (d, 2H), 6.64 (dd, 1H), 6.23 (d, 1H), 5.98 (s, 2H), 3.85 (dd, 2H), 3.27 (m, 4H), 3.08 (s, 4H), 2.75 (s, 2H), 2.19 (m, 6H), 1.93 (m, 4H), 1.63 (m, 2H), 1.40 (t, 2H), 1.27 (m, 2H), 0.94 (s, 6H).

Example 351

2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)nicotinamide

Example 351A

Methyl 2-(6-amino-5-cyanopyridin-3-yloxy)-4-fluorobenzoate

EXAMPLE 350A (150 mg), zinc cyanide (28 mg) and tetrakis(triphenylphosphine)palladium(0) (61 mg) were dissolved in N,N-dimethylformamide (0.5 mL), flushed with N$_2$ three times. The reaction mixture was heated at 120° C. for 2 hours. The reaction mixture was cooled to room temperature and diluted with ethyl acetate. The organic phase was washed with water and brine, dried over anhydrous sodium sulfate, filtered, and concentrated. The crude material was purified by column chromatography on silica gel with 2.5-5% methanol/dichloromethane to provide the title compound.

Example 351B

Methyl 2-(6-amino-5-cyanopyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 351A for EXAMPLE 3A in EXAMPLE 3G.

Example 351C 2-(6-Amino-5-carbamoylpyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 351B for EXAMPLE 38G in EXAMPLE 38H.

Example 351D 2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)nicotinamide The title compound was prepared by substituting EXAMPLE 351C for EXAMPLE 110E in EXAMPLE 110F. $^1$H NMR (400 MHz, dimethylsulfoxide-$d_6$) δ 8.50 (m, 2H), 7.91 (m, 1H), 7.79 (m, 3H), 7.50 (d, 1H), 7.36 (d, 2H), 7.31 (m, 1H), 7.07 (m, 5H), 6.59 (dd, 1H), 6.16 (s, 1H), 3.84 (dd, 2H), 3.27 (m, 4H), 3.05 (s, 4H), 2.74 (s, 2H), 2.19 (m, 6H), 1.98 (m, 3H), 1.90 (m, 1H), 1.63 (m, 2H), 1.39 (m, 2H), 1.26 (m, 2H), 0.94 (s, 6H).

Example 352

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 352A 2-(6-Amino-5-cyanopyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 351B for EXAMPLE 38G in EXAMPLE 38H.

Example 352B

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 352A for EXAMPLE 110E in EXAMPLE 110F. $^1$H NMR (400 MHz, dimethylsulfoxide-$d_6$) δ 8.46 (m, 2H), 7.93 (d, 1H), 7.76 (d, 1H), 7.52 (d, 1H), 7.36 (m, 3H), 7.08 (m, 3H), 6.65 (dd, 1H), 6.59 (s, 2H), 6.28 (d, 1H), 3.85 (dd, 2H), 3.27 (m, 4H), 3.09 (s, 4H), 2.76 (s, 2H), 2.20 (m, 6H), 1.93 (m, 5H), 1.64 (m, 2H), 1.40 (t, 2H), 1.27 (m, 2H), 0.94 (s, 6H).

Example 353

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide

Example 353A (R)-tert-butyl 1-(2,2-difluoroethyl)pyrrolidin-3-ylcarbamate (R)-tert-butyl pyrrolidin-3-ylcarbamate (500 mg) was combined with 1,1-difluoro-2-iodoethane (618 mg) and N-ethyl-N-isopropylpropan-2-amine (1.4 mL) in N,N-dimethylformamide (6 mL) in a 20 mL vial. The reaction was heated to 70° C. for 48 hours. The reaction mixture was concentrated and the residue was purified by flash chromatography, eluting with a gradient of 0-5% methanol in dichloromethane to provide the title compound.

Example 353B (R)-1-(2,2-difluoroethyl)pyrrolidin-3-amine

The title compound was prepared by substituting EXAMPLE 353A for EXAMPLE 1A in EXAMPLE 1B.

Example 353C (R)-4-(1-(2,2-difluoroethyl)pyrrolidin-3-ylamino)-3-nitrobenzenesulfonamide The title compound was prepared by substituting EXAMPLE 353B for 3-(N-morpholinyl)-1-propylamine in EXAMPLE 4A.

Example 353D

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(3R)-1-(2,2-difluoroethyl)pyrrolidin-3-yl]amino}-3-nitrophenyl)sulfonyl]benzamide The title compound was prepared by substituting EXAMPLE 318E for EXAMPLE 1F and EXAMPLE 353C for EXAMPLE 1G in EXAMPLE 1H. $^1$H NMR (500 MHz, dimethylsulfoxide-$d_6$) δ 8.58 (d, 1H), 8.41 (d, 1H), 7.89 (dd, 1H), 7.73 (d, 1H), 7.43 (d, 1H), 7.36 (m, 3H), 7.18 (d, 1H), 7.06 (d, 2H), 6.65 (dd, 1H), 6.27, 6.13, 5.99 (each t, total 1H), 6.18 (d, 1H), 6.17 (br s, 2H), 4.31 (m, 1H), 3.12 (m, 4H), 2.92 (m, 5H), 2.80 (m, 3H), 2.55 (m, 1H), 2.25 (m, 4H), 2.17 (m, 2H), 1.97 (s, 2H), 1.74 (m, 1H), 1.40 (t, 2H), 0.94 (s, 6H).

Example 354

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-methylpiperidin-4-yl)amino]-3-[(trifluoromethyl)sulfonyl]phenyl}sulfonyl)benzamide The title compound was prepared by substituting EXAMPLE 318E for EXAMPLE 1F and EXAMPLE 131D for EXAMPLE 1G in EXAMPLE 1H. $^1$H NMR (500 MHz, dimethylsulfoxide-$d_6$) δ 8.07 (d, 1H), 7.90 (dd, 1H), 7.63 (d, 1H), 7.50 (d, 1H), 7.35 (d, 2H), 7.16 (s, 1H), 7.07 (m, 3H), 7.63 (dd, 1H), 6.54 (br s, 1H), 6.26 (d, 1H), 5.95 (br s, 2H), 3.78 (m, 1H), 3.19 (m, 2H), 3.06 (m, 5H), 2.86 (m, 2H), 2.76 (m, 2H), 2.63 (m, 2H), 2.23 (m, 4H), 2.18 (m, 2H), 2.07 (m, 2H), 1.97 (s, 2H), 1.63 (m, 2H), 1.40 (t, 2H), 0.94 (s, 6H).

Example 355

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 355A methyl 2-(6-aminopyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 318B for EXAMPLE 3A in EXAMPLE 3G.

Example 355B methyl 2-(6-acetamidopyridin-3-yloxy)-4-(4-((2-(4-chlorophenyl)-4,4-dimethylcyclohex-1-enyl)methyl)piperazin-1-yl)benzoate EXAMPLE 355A (200 mg) was dissolved in anhydrous tetrahydrofuran (5 mL), followed by addition of triethylamine (0.15 mL) and acetyl chloride (0.3 mL). The reaction mixture was stirred at room temperature overnight. The solvent was removed under vacuum. The residue was purified by flash column purification with 20-40% ethyl acetate/hexane to provide the title compound.

Example 355C 2-(6-acetamidopyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 355B for EXAMPLE 38G in EXAMPLE 38H.

Example 355D

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 355C for EXAMPLE 110E in EXAMPLE 110F. $^1$H NMR (400 MHz, dimethylsulfoxide-$d_6$) δ 10.36 (s, 1H), 8.39 (m, 2H), 7.92 (d, 1H), 7.83 (s, 1H), 7.64 (m, 1H), 7.57 (d, 1H), 7.36 (d, 2H), 7.15 (m, 1H), 7.07 (d, 2H), 6.98 (d, 1H), 6.68 (dd, 1H), 6.34 (d, 1H), 3.85 (dd, 2H), 3.27 (m, 4H), 3.08 (s, 4H), 2.76 (s, 2H), 2.20 (m, 6H), 2.06 (s, 3H), 1.99 (m, 3H), 1.89 (m, 1H), 1.62 (m, 2H), 1.40 (t, 2H), 1.26 (m, 2H), 0.94 (s, 6H)

Example 356

4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide

Example 356A methyl 4-(4-((2-(4-chlorophenyl)-4,4-dimethylcyclohex-1-enyl)methyl)piperazin-1-yl)-2-(6-(methylsulfonamido)pyridin-3-yloxy)benzoate The title compound was prepared by substituting methanesulfonyl chloride for acetyl chloride in EXAMPLE 355B.

Example 356B 4-(4-((2-(4-chlorophenyl)-4,4-dimethylcyclohex-1-enyl)methyl)piperazin-1-yl)-2-(6-(methylsulfonamido)pyridin-3-yloxy)benzoic acid The title compound was prepared by substituting EXAMPLE 356A for EXAMPLE 38G in EXAMPLE 38H.

Example 356C 4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide The title compound was prepared by substituting EXAMPLE 356B for EXAMPLE 110E in EXAMPLE 110F. $^1$H NMR (400 MHz, dimethylsulfoxide-$d_6$) δ 10.30 (s, 1H), 8.41 (s, 2H), 7.83 (s, 1H), 7.64 (d, 1H), 7.59 (d, 1H), 7.36 (d, 2H), 7.16 (d, 1H), 7.05 (m, 3H), 6.88 (d, 1H), 6.69 (dd, 1H), 6.35 (d, 1H), 3.84 (dd, 2H), 3.27 (m, 7H), 3.09 (s, 4H), 2.76 (s, 2H), 2.20 (m, 6H), 1.98 (m, 3H), 1.90 (m, 1H), 1.63 (m, 2H), 1.40 (t, 2H), 1.26 (m, 2H), 0.95 (s, 6H).

Example 357

4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-[(6-fluoro-1H-indol-5-yl)oxy]benzamide

Example 357A (R)-1-(1,3-difluoropropan-2-yl)pyrrolidin-3-amine

To a solution of (R)-tert-butyl pyrrolidin-3-ylcarbamate (0.500 g) and 1,3-difluoropropan-2-one (0.278 g) in dichloromethane (5 mL) was added sodium triacetoxyborohydride (0.853 g). After stirring for 1 hour, the reaction was quenched with saturated NaHCO$_3$ solution (5 mL). The product was extracted into dichloromethane (25 mL), dried over magnesium sulfate, filtered, and concentrated. The resulting crude material was treated with HCl (4.0M in dioxane, 4 mL) and methanol (1 mL) and stirred for 1 hour. The mixture was concentrated to provide the title compound.

Example 357B (R)-4-(1-(1,3-difluoropropan-2-yl)pyrrolidin-3-ylamino)-3-nitrobenzenesulfonamide To 4-fluoro-3-nitrobenzenesulfonamide (0.272 g) and (R)-1-(1,3-difluoropropan-2-yl)pyrrolidin-3-amine (0.195 g) in tetrahydrofuran (3.0 mL) was added N-ethyl-N-isopropylpropan-2-amine (0.512 mL) and the reaction was stirred at room temperature. After stirring for 6 hours, the reaction was concentrated, loaded onto silica gel (Reveleris 40 g) and the product was purified by flash chromatography using a gradient of 25% to 100% ethyl acetate/hexanes over 30 minutes to provide the title compound.

Example 357C 4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}-2-[(6-fluoro-1H-indol-5-yl)oxy]benzamide The title compound was prepared by substituting EXAMPLE 154E for EXAMPLE 1F and EXAMPLE 357B for EXAMPLE 1G in EXAMPLE 1H. $^1$H NMR (300 MHz, dimethylsulfoxide-$d_6$) δ 11.21 (s, 2H), 8.58 (d, 1H), 8.39 (d, 1H), 7.89 (d, 1H), 7.51 (d, 1H), 7.40-7.25 (m, 5H), 7.13 (d, 1H), 7.03 (d, 2H), 6.67 (s, 1H), 6.40 (s, 1H), 6.09 (s, 1H), 4.62 (dd, 4H), 4.31-4.18 (m, 1H), 3.04 (s, 6H), 2.73 (s, 4H), 2.39-2.23 (m, 2H), 2.19 (s, 6H), 1.95 (s, 2H), 1.79-1.60 (m, 1H), 1.38 (s, 2H), 0.92 (s, 6H).

Example 358

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1-cyclopropylpiperidin-4-yl)amino]-3-nitrophenyl}sulfonyl)benzamide The title compound was prepared by substituting EXAMPLE 318E for EXAMPLE 1F and EXAMPLE 65A for EXAMPLE 1G in EXAMPLE 1H. $^1$H NMR (500 MHz, dimethylsulfoxide-$d_6$) δ 8.56 (d, 1H), 8.24 (d, 1H), 7.85 (dd, 1H), 7.72 (d, 1H), 7.44 (d, 1H), 7.35 (m, 3H), 7.22 (d, 1H), 7.06 (d, 2H), 6.64 (dd, 1H), 6.19 (d, 1H), 6.12 (br s, 2H), 3.74 (m, 2H), 3.11 (m, 5H), 2.91 (m, 2H), 2.76 (m, 3H), 2.22 (m, 6H), 1.97 (m, 4H), 1.58 (m, 2H), 1.40 (t, 2H), 0.94 (s, 6H), 0.46 (m, 2H), 0.36 (m, 2H).

Example 359

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-methylpiperazin-1-yl)amino]-3-nitrophenyl}sulfonyl)benzamide The title compound was prepared by substituting EXAMPLE 350C for EXAMPLE 110E and EXAMPLE 184A for EXAMPLE 1G in EXAMPLE 110F. $^1$H NMR (400 MHz, dimethylsulfoxide-$d_6$) δ 8.96 (s, 1H), 8.41 (d, 1H), 7.77 (dd, 1H), 7.67 (d, 1H), 7.53 (dd, 2H), 7.36 (d, 2H), 7.29 (d, 1H), 7.07 (d, 2H), 6.62 (dd, 1H), 6.26 (d, 1H), 5.85 (s, 2H), 3.28 (m, 4H), 3.06 (s, 4H), 2.90 (m, 4H), 2.75 (s, 2H), 2.31 (s, 3H), 2.20 (m, 7H), 1.97 (s, 2H), 1.40 (t, 2H), 0.94 (s, 6H).

Example 360

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(4-fluorotetrahydro-2H-pyran-4-yl)methoxy]-3-nitrophenyl}sulfonyl)benzamide The title compound was prepared by substituting EXAMPLE 350C for EXAMPLE 110E and EXAMPLE 296D for EXAMPLE 1G in EXAMPLE 110F. $^1$H NMR (400 MHz, dimethylsulfoxide-$d_6$) δ 8.19 (d, 1H), 7.85 (dd, 1H), 7.62 (d, 1H), 7.57 (d, 1H), 7.36 (d, 2H), 7.31 (d, 1H), 7.22 (d, 1H), 7.08 (d, 2H), 6.63 (dd, 1H), 6.30 (d, 1H), 5.81 (s, 2H), 4.34 (d, 2H), 3.78 (m, 2H), 3.59 (m, 2H), 3.06 (s, 4H), 2.76 (s, 2H), 2.21 (m, 6H), 1.97 (s, 2H), 1.86 (m, 4H), 1.40 (t, 2H), 0.94 (s, 6H).

Example 361

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide The title compound was prepared by substituting EXAMPLE 350C for EXAMPLE 110E and EXAMPLE 291A for EXAMPLE 1G in EXAMPLE 1100F. $^1$H NMR (400 MHz, dimethylsulfoxide-$d_6$) δ 8.48 (m, 2H), 7.78 (m, 1H), 7.68 (m, 1H), 7.50 (m, 1H), 7.35 (m, 3H), 7.06 (m, 3H), 6.62 (m, 1H), 6.25 (m, 1H), 5.92 (m, 2H), 3.79 (m, 3H), 3.63 (m, 2H), 3.49 (m, 2H), 3.40 (m, 3H), 3.08 (s, 4H), 2.76 (s, 2H), 2.19 (m, 6H), 1.97 (s, 2H), 1.40 (t, 2H), 0.94 (s, 6H).

Example 362

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 362A methyl 2-(6-amino-5-methylpyridin-3-yloxy)-4-fluorobenzoate

EXAMPLE 350A (260 mg), dicyclohexyl(2',6'-dimethoxybiphenyl-2-yl)phosphine (25 mg), and palladium (II) acetate (7 mg) were suspended in anhydrous tetrahydrofuran (2 mL). The mixture was flushed with $N_2$ three times and stirred at room temperature for 5 minutes followed by addition of methylzinc(II) chloride (0.45 mL). The reaction mixture was stirred at room temperature for 3 hours. The reaction was quenched with saturated $NH_4C$ aqueous solution and diluted with ethyl acetate. The organic phase was washed with water and brine, dried over anhydrous sodium sulfate, filtered and concentrated. The residue was purified by flash column purification with 60-100% ethyl acetate/hexane to provide the title compound.

Example 362B methyl 2-(6-amino-5-methylpyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 362A for EXAMPLE 3A in EXAMPLE 3G.

Example 362C 2-(6-amino-5-methylpyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 362B for EXAMPLE 38G in EXAMPLE 38H.

Example 362D

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 362C for EXAMPLE 110E in EXAMPLE 110F. $^1$H NMR (400 MHz, dimethylsulfoxide-$d_6$) δ 8.57 (m, 2H), 7.86 (dd, 1H), 7.58 (d, 1H), 7.47 (d, 1H), 7.35 (d, 2H), 7.19 (d, 1H), 7.05 (m, 3H), 6.60 (dd, 1H), 6.10 (d, 1H), 5.61 (s, 2H), 3.85 (dd, 2H), 3.25 (m, 4H), 3.05 (s, 4H), 2.74 (s, 2H), 2.18 (m, 6H), 1.97 (m, 7H), 1.63 (m, 2H), 1.39 (t, 2H), 1.25 (m, 2H), 0.94 (s, 6H).

Example 363

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide The title compound was prepared by substituting EXAMPLE 318E for EXAMPLE 1F and EXAMPLE 337D for EXAMPLE 1G in EXAMPLE 1H. $^1$H NMR (300 MHz, dimethylsulfoxide-$d_6$) δ 11.53-11.08 (m, 1H), 8.66 (t, 1H), 8.59 (d, 1H), 7.87 (dd, 1H), 7.75 (d, 1H), 7.38 (ddd, 5H), 7.06 (d, 2H), 6.65 (dd, 1H), 6.18 (s, 3H), 3.77 (dd, 4H), 3.52 (dd, 2H), 3.12 (s, 4H), 2.81 (s, 2H), 2.22 (d, 6H), 2.03-1.67 (m, 6H), 1.40 (t, 2H), 0.94 (s, 6H).

Example 364

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)benzamide

Example 364A tert-butyl 1-(oxetan-3-yl)piperidin-4-ylcarbamate

The title compound was prepared by substituting tert-butyl piperidin-4-ylcarbamate for tert-butyl piperazine-1-carboxylate and oxetan-3-one for 4'-chlorobiphenyl-2-carboxaldehyde in EXAMPLE 1A.

Example 364B 1-(oxetan-3-yl)piperidin-4-amine

The title compound was prepared by substituting EXAMPLE 364A for EXAMPLE 1A in EXAMPLE 1B.

Example 364C 3-nitro-4-(1-(oxetan-3-yl)piperidin-4-ylamino)benzenesulfonamide The title compound was prepared by substituting EXAMPLE 364B for 1-isopropylpiperidinyl-4-amine in EXAMPLE 41A.

Example 364D

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(1-oxetan-3-ylpiperidin-4-yl)amino]phenyl}sulfonyl)benzamide The title compound was prepared by substituting EXAMPLE 318E for EXAMPLE 1F and EXAMPLE 364C for EXAMPLE 1G in EXAMPLE 1H. $^1$H NMR (500 MHz, dimethylsulfoxide-$d_6$) δ 8.57 (d, 1H), 8.28 (d, 1H), 7.86 (dd, 1H), 7.73 (d, 1H), 7.43 (d, 1H), 7.36 (m, 3H), 7.23 (d, 1H), 7.06 (d, 2H), 6.64 (dd, 1H), 6.17 (m, 3H), 4.55 (t, 2H), 4.44 (t, 2H), 3.76 (br s, 1H), 3.46 (br s, 1H), 3.11 (m, 5H), 2.77 (m, 2H), 2.67 (m, 2H), 2.20 (m, 6H), 2.08 (m, 1H), 1.97 (m, 4H), 1.65 (m, 2H), 1.40 (t, 2H), 0.94 (s, 6H).

Example 365

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 365A methyl 2-(6-amino-5-isopropylpyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 350B for EXAMPLE 350A and isopropylzinc(II) chloride for methylzinc(II) chloride in EXAMPLE 362A.

Example 365B 2-(6-amino-5-isopropylpyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 365A for EXAMPLE 38G in EXAMPLE 38H.

Example 365C

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 365B for EXAMPLE 110E in EXAMPLE 110F. $^1$H NMR (400 MHz, dimethylsulfoxide-$d_6$) δ 8.61 (m, 2H), 7.88 (m, 1H), 7.61 (dd, 1H), 7.47 (d, 1H), 7.35 (d, 2H), 7.22 (dd, 1H), 7.07 (m, 3H), 6.60 (dd, 1H), 6.06 (dd, 1H), 5.71 (d, 2H), 3.85 (dd, 1H), 3.27 (m, 4H), 3.06 (s, 4H), 2.90 (m, 1H), 2.74 (s, 2H), 2.38 (t, 1H), 2.17 (m, 6H), 1.92 (m, 3H), 1.63 (m, 2H), 1.52 (m, 1H), 1.39 (t, 2H), 1.26 (m, 2H), 1.11 (d, 6H), 0.93 (s, 6H).

Example 366

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 366A methyl 2-(6-amino-5-cyclopropylpyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 350B for EXAMPLE 350A and cyclopropylzinc(II) chloride for methylzinc(II) chloride in EXAMPLE 362A.

Example 366B 2-(6-amino-5-cyclopropylpyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 366A for EXAMPLE 38G in EXAMPLE 38H.

Example 366C

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 366B for EXAMPLE 110E in EXAMPLE 110F. $^1$H NMR (400 MHz, dimethylsulfoxide-$d_6$) δ 8.64 (t, 1H), 8.59 (d, 1H), 7.88 (dd, 1H), 7.60 (d, 1H), 7.45 (d, 1H), 7.35 (d, 2H), 7.23 (d, 1H), 7.06 (d, 2H), 6.91 (d, 1H), 6.61 (dd, 1H), 6.04 (d, 1H), 5.83 (s, 2H), 3.85 (dd, 2H), 3.27 (m, 4H), 3.06 (s, 4H), 2.75 (s, 2H), 2.18 (m, 6H), 1.97 (m, 3H), 1.65 (m, 3H), 1.40 (t, 2H), 1.26 (m, 2H), 0.94 (s, 6H), 0.87 (m, 2H), 0.49 (m, 2H).

Example 367

Trans-2-[(6-amino-5-bromopyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide The title compound was prepared by substituting EXAMPLE 350C for EXAMPLE 110E and EXAMPLE 345B for EXAMPLE 1G in EXAMPLE 110F. $^1$H NMR (400 MHz, dimethylsulfoxide-$d_6$) δ 8.50 (m, 2H), 7.78 (d, 1H), 7.73 (d, 1H), 7.48 (d, 1H), 7.40 (s, 1H), 7.36 (d, 2H), 7.07 (m, 3H), 6.64 (dd, 1H), 6.22 (s, 1H), 5.98 (s, 2H), 3.27 (m, 4H), 3.22 (s, 3H), 3.06 (m, 4H), 2.76 (s, 2H), 2.20 (m, 6H), 1.99 (m, 4H), 1.80 (d, 2H), 1.62 (s, 1H), 1.40 (t, 2H), 1.04 (m, 4H), 0.94 (s, 6H).

Example 368

4-(4-{[2-(4-chlorophenyl)-4,4-dimethylcyclohex-1-en-1-yl]methyl}piperazin-1-yl)-2-[(3-methyl-2-oxo-2,3-dihydro-1H-benzimidazol-4-yl)oxy]-N-({3-nitro-4-[(tetrahydro-2H-pyran-4-ylmethyl)amino]phenyl}sulfonyl)benzamide

Example 368A methyl 4-fluoro-2-(3-fluoro-2-nitrophenoxy)benzoate

To a solution of methyl 4-fluoro-2-hydroxybenzoate (1.225 g) in anhydrous tetrahydrofuran (25 mL) was added potassium t-butoxide (0.808 g). The mixture was stirred for 20 minutes at room temperature. A solution of 1,3-difluoro-2-nitrobenzene (0.955 g) in tetrahydrofuran (6 mL) was then added dropwise. The resulting mixture was stirred at room temperature for 1 hour, then at 80° C. overnight. The reaction mixture was quenched with water (40 mL) and extracted with dichloromethane. The organic solution was dried (MgSO$_4$), filtered and concentrated. The residue was purified on a silica gel column, eluting with 25% ethyl acetate in hexane to obtain the title compound.

Example 368B methyl 2-(3-(bis(4-methoxyphenyl)methylamino)-2-nitrophenoxy)-4-fluorobenzoate A solution of EXAMPLE 368A (1.33 g), bis(4-methoxyphenyl)methanamine (1.046 g) and N-ethyl-N-isopropylpropan-2-amine (1.127 ml) in anhydrous 1-methyl-2-pyrrolidinone (20 mL) was stirred at 120° C. overnight. The mixture was concentrated and the residue was taken up in water (100 mL) and extracted with dichloromethane. The residue was absorbed on silica and purified by chromatography on a silica gel column, eluting with 25% ethyl acetate in hexane to provide the title compound.

Example 368C methyl 2-(2-amino-3-(bis(4-methoxyphenyl)methylamino)phenoxy)-4-fluorobenzoate A solution of EXAMPLE 368B (1.1 g) in methanol was hydrogenated over Raney Ni, at 60 psi of H$_2$ at room temperature. The filtered solution was concentrated to give the title compound.

Example 368D methyl 2-(1-(bis(4-methoxyphenyl)methyl)-2-oxo-2,3-dihydro-1H-benzo[d]imidazol-4-yloxy)-4-fluorobenzoate A solution of EXAMPLE 368C (0.58 g) and N-ethyl-N-isopropylpropan-2-amine (0.804 ml) in dichloromethane (8 mL) was cooled with an ice bath. Then, a 20 wt % solution of phosgene in toluene (0.850 ml) was added dropwise. The mixture was stirred at room temperature overnight. The mixture was diluted with dichloromethane and washed with 5% aq. NaHCO$_3$. The material was then absorbed on silica and purified on a silica gel column eluting with 50% ethyl acetate in hexane to provide the title compound.

Example 368E methyl 2-(1-(bis(4-methoxyphenyl)methyl)-3-methyl-2-oxo-2,3-dihydro-1H-benzo[d]imidazol-4-yloxy)-4-fluorobenzoate To a solution of EXAMPLE 368D (250 mg) in anhydrous N,N-dimethylformamide (6 mL) was added sodium hydride (34.1 mg). The mixture was stirred at 50° C. for 30 minutes. Then, iodomethane (35.6 µl) was added and the mixture was stirred at 50° C. overnight. The reaction mixture was quenched with water (30 mL), then extracted with ethyl acetate. The solution was dried (MgSO$_4$), filtered and concentrated to give the title compound.

Example 368F methyl 2-(1-(bis(4-methoxyphenyl)methyl)-3-methyl-2-oxo-2,3-dihydro-1H-benzo[d]imidazol-4-yloxy)-4-(piperazin-1-yl)benzoate A flask was charged with EXAMPLE 368E (281 mg), anhydrous N,N-dimethylformamide (6 mL) and piperazine (268 mg). The mixture was stirred at 75° C. overnight. The solvent was evaporated and the residue was re-dissolved in ethyl acetate. The crude product was purified on a silica gel column eluting with 5% methanol in dichloromethane to provide the title compound.

Example 368G methyl 2-(1-(bis(4-methoxyphenyl)methyl)-3-methyl-2-oxo-2,3-dihydro-1H-benzo[d]imidazol-4-yloxy)-4-(4-((2-(4-chlorophenyl)-4,4-dimethylcyclohex-1-enyl)methyl)piperazin-1-yl)benzoate To a solution of EXAMPLE 368F (275 mg) and EXAMPLE 60D (169 mg) in anhydrous dichloromethane (5 mL) was added sodium triacetoxyborohydride (172 mg) in several portions over 5 minutes. The resulting mixture was stirred at ambient temperature overnight. The mixture was quenched with 5% aqueous $Na_2CO_3$ solution (10 mL) and extracted with dichloromethane. The crude product was purified on a silica gel column eluted with 45% ethyl acetate in hexane to provide the title compound.

Example 368H 2-(1-(bis(4-methoxyphenyl)methyl)-3-methyl-2-oxo-2,3-dihydro-1H-benzo[d]imidazol-4-yloxy)-4-(4-((2-(4-chlorophenyl)-4,4-dimethylcyclohex-1-enyl)methyl)piperazin-1-yl)benzoic acid This example was prepared by substituting EXAMPLE 368G for EXAMPLE 38G in EXAMPLE 38H.

Example 368I 2-(1-(bis(4-methoxyphenyl)methyl)-3-methyl-2-oxo-2,3-dihydro-1H-benzo[d]imidazol-4-yloxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide This example was prepared by substituting by substituting EXAMPLE 368H for EXAMPLE 1F in EXAMPLE 1H.

Example 368J 4-(4-{[2-(4-chlorophenyl)-4,4-dimethylcyclohex-1-en-1-yl]methyl}piperazin-1-yl)-2-[(3-methyl-2-oxo-2,3-dihydro-1H-benzimidazol-4-yl)oxy]-N-({3-nitro-4-[(tetrahydro-2H-pyran-4-ylmethyl)amino]phenyl}sulfonyl)benzamide A solution of EXAMPLE 368I (140 mg) in dichloromethane (10 mL) was cooled with an ice bath. Trifluoroacetic acid (10 mL) was added. The resulting solution was allowed to warm to room temperature and stirred for 48 hours. The solution was concentrated and the residue was triturated with diethyl ether. The resulting solid was purified by reverse-phase HPLC using a Waters Preparative LC4000 system with Phenomenex Luna C18 column and a water-acetonitrile mobile phase buffered with ammonium acetate to provide the title compound. $^1$H NMR (500 MHz, pyridine-$d_5$) δ 12.34 (s, 1H), 9.20 (d, 1H), 8.87 (t, 1H), 8.44 (dd, 1H), 8.01 (d, 1H), 7.44 (d, 2H), 7.08 (d, 2H), 7.01 (d, 1H), 6.86-6.79 (m, 3H), 6.74 (d, 1H), 6.52 (dd, 1H), 3.96 (dd, 2H), 3.65 (s, 3H), 3.30 (d, 2H), 3.24 (m, 2H), 3.19 (m, 4H), 2.81 (s, 2H), 2.30-2.28 (m, 2H), 2.23 (m, 4H), 1.97 (s, 2H), 1.85-1.75 (m, 1H), 1.58 (d, 2H), 1.40 (t, 2H), 1.33 (dq, 2H), 0.94 (s, 6H).

Example 369

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide

Example 369A tert-butyl 2-((2-nitro-4-sulfamoylphenylamino)methyl)morpholine-4-carboxylate The title compound was prepared by substituting tert-butyl 2-(aminomethyl)morpholine-4-carboxylate for 3-(N-morpholinyl)-1-propylamine in EXAMPLE 4A.

Example 369B 4-(morpholin-2-ylmethylamino)-3-nitrobenzenesulfonamide

A solution of EXAMPLE 369A (0.8 g) in methylene chloride (10 mL) and trifluoroacetic acid (10 mL) was stirred at room temperature for 2 hours. The solvents were evaporated and the residue was triturated with diethyl ether. The resulting solid was dissolved in 5% aqueous sodium carbonate solution (20 mL). The mixture was concentrated to dryness and the resulting solid was triturated with a solution of 10% methanol in methylene chloride several times. Evaporation of the organic solvent provided the title compound.

Example 369C 4-((4-cyclopropylmorpholin-2-yl)methylamino)-3-nitrobenzenesulfonamide A solution of EXAMPLE 369B (0.633 g) and (1-ethoxycyclopropoxy)trimethylsilane (1.601 mL) in anhydrous methanol (15 mL) and acetic acid (1.717 mL) was refluxed for 30 minutes and allowed to cool to room temperature. Sodium cyanoborohydride (0.377 g) was then added and the mixture was stirred at ambient temperature overnight. The reaction mixture was concentrated to dryness. The residue was mixed with 5% aqueous $Na_2CO_3$ solution (25 mL) and extracted with ethyl acetate. The crude product was purified on a silica gel column eluting with 5% to 10% methanol in dichloromethane to provide the title compound.

Example 369D

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide The title compound was prepared by substituting EXAMPLE 318E for EXAMPLE 1F and EXAMPLE 369C for EXAMPLE 1G in EXAMPLE 1H. $^1$H NMR (500 MHz, dimethylsulfoxide-$d_6$) δ 11.34 (br s, 1H), 8.63 (t, 1H), 8.58 (d, 1H), 7.86 (dd, 1H), 7.73 (d, 1H), 7.45 (d, 1H), 7.38 (d, 1H), 7.36 (d, 2H), 7.20 (d, 1H), 7.06 (d, 2H), 6.65 (dd, 1H), 6.19 (d, 1H), 6.17 (br s, 2H), 3.83 (m, 1H), 3.64 (m, 1H), 3.56 (m, 1H), 3.45 (m, 2H), 3.12 (m, 4H), 2.91 (m, 1H), 2.74 (m, 3H), 2.26 (m, 5H), 2.15 (m, 3H), 1.97 (m, 2H), 1.66 (m, 1H), 1.40 (t, 2H), 0.94 (s, 6H), 0.42 (m, 2H), 0.33 (m, 2H).

Example 370

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-[(4-{[(3R)-1-cyclopropylpyrrolidin-3-yl]amino}-3-nitrophenyl)sulfonyl] benzamide

Example 370A (R)-tert-butyl 1-cyclopropylpyrrolidin-3-ylcarbamate

The title compound was prepared by substituting (R)-tert-butyl pyrrolidin-3-ylcarbamate for tert-butyl (trans)-4-aminocyclohexylcarbamate in EXAMPLE 334A.

Example 370B (R)-1-cyclopropylpyrrolidin-3-amine

The title compound was prepared by substituting EXAMPLE 370A for EXAMPLE 1A in EXAMPLE 1B.

Example 370C (R)-4-(1-cyclopropylpyrrolidin-3-ylamino)-3-nitrobenzenesulfonamide The title compound was prepared by substituting EXAMPLE 370B for 1-isopropylpiperidinyl-4-amine in EXAMPLE 41A.

Example 370D

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-[(4-{[(3R)-1-cyclopropylpyrrolidin-3-yl]amino}-3-nitrophenyl)sulfonyl] benzamide The title compound was prepared by substituting EXAMPLE 318E for EXAMPLE 1F and EXAMPLE 370C for EXAMPLE 1G in EXAMPLE 1H. $^1$H NMR (500 MHz, dimethylsulfoxide-$d_6$) δ 8.52 (d, 1H), 8.33 (d, 1H), 7.84 (dd, 1H), 7.69 (d, 1H), 7.46 (d, 1H), 7.36 (m, 2H), 7.30 (d, 1H), 7.10 (d, 1H), 7.06 (d, 2H), 6.64 (dd, 1H), 6.21 (d, 1H), 6.09 (br s, 2H), 4.27 (m, 1H), 3.09 (m, 4H), 3.01 (m, 1H), 2.91 (m, 1H), 2.76 (m, 3H), 2.62 (m, 1H), 2.22 (m, 6H), 1.97 (m, 2H), 1.76 (m, 1H), 1.68 (m, 1H), 1.40 (t, 2H), 0.94 (s, 6H), 0.43 (m, 2H), 0.37 (m, 2H).

Example 371

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-{[4-({4-fluoro-1-[2-fluoro-1-(fluoromethyl)ethyl]piperidin-4-yl}methoxy)-3-nitrophenyl]sulfonyl}benzamide

Example 371A 4-((1-(1,3-difluoropropan-2-yl)-4-fluoropiperidin-4-yl)methoxy)-3-nitrobenzenesulfonamide To a suspension of EXAMPLE 341C (0.100 g) and 1,3-difluoropropan-2-one (0.025 g) in dichloromethane (2 mL) was added sodium triacetoxyborohydride (0.071 g). After 15 minutes, N,N-dimethylformamide was added dropwise until an orange solution resulted (~15 drops). After stirring overnight additional 1,3-difluoropropan-2-one and sodium triacetoxyborohydride were added. After 3 hours, the reaction was loaded onto silica gel (Reveleris 40 g) and eluted with a gradient of 0.5-5% methanol/dichloromethane over 30 minutes (flow=40 ml/minutes) to provide the title compound.

Example 371B

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-{[4-({(4-fluoro-1-[2-fluoro-1-(fluoromethyl)ethyl]piperidin-4-yl}methoxy)-3-nitrophenyl]sulfonyl}benzamide The title compound was prepared by substituting EXAMPLE 318E for EXAMPLE 1F and EXAMPLE 371A for EXAMPLE 1G in EXAMPLE 1H. $^1$H NMR (300 MHz, dimethylsulfoxide-$d_6$) δ 12.05-10.74 (m, 1H), 8.38 (s, 1H), 8.08 (s, 1H), 7.73 (d, 1H), 7.50 (dd, 2H), 7.37 (d, 3H), 7.07 (d, 2H), 6.65 (d, 1H), 6.18 (d, 3H), 4.62 (dd, 4H), 4.38 (d, 2H), 3.16 (s, 5H), 2.97-2.60 (m, 8H), 2.18 (s, 4H), 2.07-1.60 (m, 6H), 1.42 (s, 2H), 0.94 (s, 6H).

Example 372 tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl) amino]phenyl}sulfonyl)amino]carbonyl}phenoxy) pyridin-2-ylcarbamate

Example 372A 2-(2,6-Dibromo-pyridin-4-yloxy)-4-fluoro-benzoic acid methyl ester A solution of methyl 4-fluoro-2-hydroxybenzoate (2.00 g), 2,6-dibromo-4-nitropyridine (3.65 g), and cesium carbonate (4.21 g) in N,N-dimethylformamide (100 mL) was heated to 55° C. for 16 hours, cooled, added to water, and extracted with 50% ethyl acetate in hexanes. The organic extract was washed with brine, dried over anhydrous sodium sulfate, filtered, concentrated and purified by flash column chromatography on silica gel using 30-50% ethyl acetate in hexanes.

Example 372B 2-(2-Bromo-6-tert-butoxycarbonylamino-pyridin-4-yloxy)-4-fluoro-benzoic acid methyl ester EXAMPLE 372A (1400 mg), tert-butyl carbamate (405 mg), and cesium carbonate (1689 mg) were added to 1,4-dioxane (24 mL). The solution was degassed and flushed with nitrogen three times. Palladium(II) acetate (39 mg) and 4,5-bis(diphenylphosphino)-9,9-dimethylxanthene (200 mg) were added, and the solution was heated at 80° C. for 2.5 hours, cooled, added to water, and extracted with 50% ethyl acetate in hexanes. The extract was washed with brine, dried over anhydrous sodium sulfate, filtered, concentrated and

Example 372C 2-(2-Bromo-6-tert-butoxycarbonylamino-pyridin-4-yloxy)-4-piperazin-1-yl-benzoic acid methyl ester The title compound was prepared by substituting EXAMPLE 372B for EXAMPLE 342D in EXAMPLE 342E.

Example 372D 2-(2-Bromo-6-tert-butoxycarbonylamino-pyridin-4-yloxy)-4-{4-[2-(4-chloro-phenyl)-4,4-dimethyl-cyclohex-1-enylmethyl]-piperazin-1-yl}-benzoic acid methyl ester The title compound was prepared by substituting EXAMPLE 60D for 4'-chlorobiphenyl-2-carboxaldehyde and EXAMPLE 372C for tert-butyl piperazine-1-carboxylate in EXAMPLE 1A.

Example 372E 2-(2-Bromo-6-tert-butoxycarbonylamino-pyridin-4-yloxy)-4-{4-[2-(4-chloro-phenyl)-4,4-dimethyl-cyclohex-1-enylmethyl]-piperazin-1-yl}-benzoic acid The title compound was prepared by substituting EXAMPLE 372D for EXAMPLE 1E in EXAMPLE 1F.

Example 372F tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate The title compound was prepared by substituting EXAMPLE 372E for EXAMPLE 1F in EXAMPLE 1H. $^1$H NMR (300 MHz, dimethylsulfoxide-$d_6$) δ 9.93 (s, 1H), 8.58 (bs, 1H), 8.47 (d, 1H), 7.70 (d, 1H), 7.57 (d, 1H), 7.37 (d, 2H), 7.18 (d, 1H), 7.08 (d, 1H), 7.07 (d, 2H), 6.83 (dd, 1H), 6.63 (bs, 1H), 6.40 (d, 1H), 3.87 (dd, 2H), 3.35-3.25 (m, 8H), 2.85 (bs, 2H), 2.40-2.15 (m, 6H), 1.97 (bs, 2H), 1.93 (m, 1H), 1.65 (d, 2H), 1.41 (t, 2H), 1.40 (s, 9H), 1.36-1.22 (m, 2H), 0.95 (s, 6H).

Example 373

4-(4-{[2-(4-chlorophenyl)-4,4-dimethylcyclohex-1-en-1-yl]methyl}piperazin-1-yl)-2-[(2,6-Bis-tert-butoxycarbonylamino-pyridin-4-yl)oxy]-N-({3-nitro-4-[(tetrahydro-2H-pyran-4-ylmethyl)amino]phenyl}sulfonyl)benzamide

Example 373A 2-(2,6-Bis-tert-butoxycarbonylamino-pyridin-4-yloxy)-4-fluoro-benzoic acid methyl ester The title compound was prepared during the synthesis of EXAMPLE 372B.

Example 373B 2-(2,6-Bis-tert-butoxycarbonylamino-pyridin-4-yloxy)-4-piperazin-1-yl-benzoic acid methyl ester The title compound was prepared by substituting EXAMPLE 373A for EXAMPLE 342D in EXAMPLE 342E.

Example 373C 2-(2,6-Bis-tert-butoxycarbonylamino-pyridin-4-yloxy)-4-(4-{[2-(4-chloro-phenyl)-4,4-dimethyl-cyclohex-1-enylmethyl]-piperazin-1-yl}-benzoic acid methyl ester The title compound was prepared by substituting EXAMPLE 60D for 4'-chlorobiphenyl-2-carboxaldehyde and EXAMPLE 373B for tert-butyl piperazine-1-carboxylate in EXAMPLE 1A.

Example 373D 2-(2,6-Bis-tert-butoxycarbonylamino-pyridin-4-yloxy)-4-{4-[2-(4-chloro-phenyl)-4,4-dimethyl-cyclohex-1-enylmethyl]-piperazin-1-yl}-benzoic acid The title compound was prepared by substituting EXAMPLE 373C for EXAMPLE 1E in EXAMPLE 1F.

Example 373E 4-(4-{[2-(4-chlorophenyl)-4,4-dimethylcyclohex-1-en-1-yl]methyl}piperazin-1-yl)-2-[(2,6-Bis-tert-butoxycarbonylamino-pyridin-4-yl)oxy]-N-({3-nitro-4-[(tetrahydro-2H-pyran-4-ylmethyl)amino]phenyl}sulfonyl)benzamide The title compound was prepared by substituting EXAMPLE 373D for EXAMPLE 1F in EXAMPLE 1H. $^1$H NMR (300 MHz, dimethylsulfoxide-$d_6$) δ 9.12 (bs, 2H), 8.57 (m, 1H), 8.50 (d, 1H), 7.72 (dd, 1H), 7.53 (d, 1H), 7.36 (d, 2H), 7.12 (d, 1H), 7.06 (d, 2H), 6.86 (s, 2H), 6.79 (dd, 1H), 6.56 (bs, 1H), 3.86 (dd, 2H), 3.27-3.18 (m, 8H), 2.79 (bs, 2H), 2.31-2.15 (m, 6H), 1.97 (bs, 2H), 1.93 (m, 1H), 1.64 (d, 2H), 1.42 (t, 2H), 1.41 (s, 18H), 1.33-1.23 (m, 2H), 0.94 (s, 6H).

Example 374

4-(4-{[2-(4-chlorophenyl)-4,4-dimethylcyclohex-1-en-1-yl]methyl}piperazin-1-yl)-2-{[6-(cyclopropylamino)pyridin-3-yl]oxy}-N-({3-nitro-4-[(tetrahydro-2H-pyran-4-ylmethyl)amino]phenyl}sulfonyl)benzamide

Example 374A methyl 2-(6-(cyclopropylamino)pyridin-3-yloxy)-4-fluorobenzoate The title compound was prepared by substituting cyclopropyl amine for tert-butyl carbamate in EXAMPLE 377B.

Example 374B methyl 2-(6-(cyclopropylamino)pyridin-3-yloxy)-4-(piperazin-1-yl)benzoate The title compound was prepared by substituting EXAMPLE 374A for EXAMPLE 377E in EXAMPLE 377F.

Example 374C methyl 4-(4-((2-(4-chlorophenyl)-4,4-dimethylcyclohex-1-enyl)methyl)piperazin-1-yl)-2-(6-(cyclopropylamino)pyridin-3-yloxy)benzoate The title compound was prepared by substituting EXAMPLE 374B for tert-butyl piperazine-1-carboxylate and EXAMPLE 60D for 4'-chlorobiphenyl-2-carboxaldehyde in EXAMPLE 1A.

Example 374D 4-(4-((2-(4-chlorophenyl)-4,4-dimethylcyclohex-1-enyl)methyl)piperazin-1-yl)-2-(6-(cyclopropylamino)pyridin-3-yloxy)benzoic acid The title compound was prepared by substituting EXAMPLE 374C for EXAMPLE 38G in EXAMPLE 38H.

Example 374E 4-(4-{[2-(4-chlorophenyl)-4,4-dimethylcyclohex-1-en-1-yl]methyl}piperazin-1-yl)-2-{[6-(cyclopropylamino)pyridin-3-yl]oxy}-N-({3-nitro-4-[(tetrahydro-2H-pyran-4-ylmethyl)amino]phenyl}sulfonyl)benzamide The title compound was prepared by substituting EXAMPLE 374D for EXAMPLE 110E in EXAMPLE 110F. $^1$H NMR (400 MHz, dimethylsulfoxide-$d_6$) δ 8.54 (m, 2H), 7.85 (m, 1H), 7.77 (d, 1H), 7.48 (d, 1H), 7.36 (d, 2H), 7.17 (m, 2H), 7.06 (d, 2H), 6.60 (m, 3H), 6.13 (d, 1H), 3.85 (dd, 2H), 3.26 (m, 4H), 3.05 (s, 4H), 2.74 (s, 2H), 2.47 (m, 2H), 2.18 (m, 6H), 1.92 (m, 3H), 1.61 (m, 2H), 1.40 (t, 2H), 1.27 (m, 2H), 0.94 (s, 6H), 0.68 (m, 2H), 0.41 (m, 2H).

Example 375

Trans-4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide

Example 375A methyl 2-(6-(2,2-difluoroethylamino)pyridin-3-yloxy)-4-fluorobenzoate The title compound was prepared by substituting 2,2-difluoroethanamine for tert-butyl carbamate in EXAMPLE 377B.

Example 375B methyl 2-(6-(2,2-difluoroethylamino)pyridin-3-yloxy)-4-(piperazin-1-yl)benzoate The title compound was prepared by substituting EXAMPLE 375A for EXAMPLE 377E in EXAMPLE 377F.

Example 375C methyl 4-(4-((2-(4-chlorophenyl)-4,4-dimethylcyclohex-1-enyl)methyl)piperazin-1-yl)-2-(6-(2,2-difluoroethylamino)pyridin-3-yloxy)benzoate The title compound was prepared by substituting EXAMPLE 375B for tert-butyl piperazine-1-carboxylate and EXAMPLE 60D for 4'-chlorobiphenyl-2-carboxaldehyde in EXAMPLE 1A.

Example 375D 4-(4-((2-(4-chlorophenyl)-4,4-dimethylcyclohex-1-enyl)methyl)piperazin-1-yl)-2-(6-(2,2-difluoroethylamino)pyridin-3-yloxy)benzoic acid The title compound was prepared by substituting EXAMPLE 375C for EXAMPLE 38G in EXAMPLE 38H.

Example 375E

Trans-4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide The title compound was prepared by substituting EXAMPLE 375D for EXAMPLE 110E and EXAMPLE 345B for EXAMPLE 1G in EXAMPLE 110F. $^1$H NMR (400 MHz, dimethylsulfoxide-$d_6$) δ 8.52 (m, 2H), 7.84 (dd, 1H), 7.75 (d, 1H), 7.47 (d, 1H), 7.35 (m, 2H), 7.16 (m, 2H), 7.05 (d, 2H), 6.87 (t, 1H), 6.60 (m, 2H), 6.10 (m, 2H), 3.66 (m, 2H), 3.27 (m, 4H), 3.23 (s, 3H), 3.05 (s, 4H), 2.74 (s, 2H), 2.18 (m, 6H), 1.99 (m, 4H), 1.79 (m, 2H), 1.61 (m, 1H), 1.40 (t, 2H), 1.07 (m, 4H), 0.94 (s, 6H).

Example 376

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-({3-nitro-4-[(tetrahydro-2H-pyran-4-ylmethyl)amino]phenyl}sulfonyl)benzamide The title compound was prepared by substituting EXAMPLE 375D for EXAMPLE 110E in EXAMPLE 110F. $^1$H NMR (400 MHz, dimethylsulfoxide-$d_6$) δ 8.55 (m, 2H), 7.86 (dd, 1H), 7.76 (d, 1H), 7.47 (d, 1H), 7.35 (d, 2H), 7.18 (m, 2H), 7.06 (d, 2H), 6.89 (m, 1H), 6.61 (m, 2H), 6.10 (m, 2H), 3.85 (dd, 2H), 3.66 (m, 2H), 3.27 (m, 4H), 3.06 (s, 4H), 2.74 (s, 2H), 2.18 (m, 6H), 1.94 (m, 4H), 1.62 (d, 2H), 1.40 (t, 2H), 1.28 (m, 2H), 0.94 (s, 6H).

Example 377

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide

Example 377A methyl 2-(6-chloropyridin-3-yloxy)-4-fluorobenzoate

To a solution of 6-chloropyridin-3-ol (2.41 g) in 2-methyltetrahydrofuran (20 mL) and N,N-dimethylformamide (4 mL) was added potassium tert-butoxide (1.0M in tetrahydrofuran) (18.60 mL). The reaction was stirred for 15 minutes, then methyl 2,4-difluorobenzoate (3.52 g) was added as a solution in 2-methyltetrahydrofuran (2 mL). The reaction was then heated to 80° C. and stirred under a nitrogen atmosphere for 3 days. The reaction was cooled, diluted with ethyl acetate (100 mL), washed with water (50 mL), 1N aqueous HCl (50 mL), and brine (50 mL), dried over magnesium sulfate, filtered, and concentrated. Silica gel chromatography (Reveleris 80 g), eluting with 10% ethyl acetate/hexanes provided the title compound.

Example 377B methyl 2-(6-(tert-butoxycarbonylamino)pyridin-3-yloxy)-4-fluorobenzoate To EXAMPLE 377A (3.30 g), tert-butyl carbamate (1.51 g) and cesium carbonate (5.73 g) in dioxane (30 mL) was added diacetoxypalladium (0.079 g) and (9,9-dimethyl-9H-xanthene-4,5-diyl)bis(diphenylphosphine) (0.41 g) and the reaction was heated to 85° C. overnight under an atmosphere of nitrogen. The reaction was cooled, diluted with ethyl acetate (100 mL) and washed with water (75 mL) and brine (75 mL) dried over magnesium sulfate, filtered, and concentrated. Silica gel chromatography (Reveleris 80 g) eluting with 10% ethyl acetate/hexanes over 20 minutes provided the title compound.

Example 377C methyl 2-(6-(tert-butoxycarbonyl(methyl)amino)pyridin-3-yloxy)-4-fluorobenzoate To a solution of EXAMPLE 377B (0.750 g) in N,N-dimethylformamide (5 mL) was added sodium hydride (0.091 g). The reaction was stirred for 30 minutes at room temperature and then iodomethane (0.142 mL) was added to the reaction and stirring was continued at room temperature for 2 hours. The reaction was quenched with water (25 mL) and extracted with ethyl acetate (75 mL). The organic layer was separated, washed with brine (50 mL), dried over magnesium sulfate, filtered, and concentrated. The residue was loaded onto silica gel (Reveleris 40 g) and eluted with a gradient of 5-15% ethyl acetate/hexanes over 30 minutes (flow=40 ml/min) to provide the title compound.

Example 377D methyl 4-fluoro-2-(6-(methylamino)pyridin-3-yloxy)benzoate

To EXAMPLE 377C (0.714 g) in dichloromethane (10 mL) was added trifluoroacetic acid (1.5 mL). After stirring for 3 hours, the reaction was concentrated, dissolved in dichloromethane (100 mL), washed with saturated aqueous NaHCO$_3$ (2×75 mL) and brine (75 mL), dried over magnesium sulfate, filtered, and concentrated to provide the title compound.

Example 377E methyl 2-(5-chloro-6-(methylamino)pyridin-3-yloxy)-4-fluorobenzoate A solution of EXAMPLE 377D (0.450 g) and N-chlorosuccinimide (0.239 g) was stirred together in N,N-dimethylformamide (10 mL) at room temperature. The reaction was stirred for 48 hours, diluted with ethyl acetate (100 mL), washed with water (2×50 mL) and brine (50 mL), dried over magnesium sulfate, filtered, and concentrated. Silica gel chromatography (Reveleris 40 g) eluting with a gradient of 5-30% ethyl acetate/hexanes over 30 minutes (flow=40 ml/min) provided the title compound.

Example 377F methyl 2-(5-chloro-6-(methylamino)pyridin-3-yloxy)-4-(piperazin-1-yl)benzoate A solution of EXAMPLE 377E (0.230 g) and piperazine (0.255 g) in dimethylsulfoxide (3 mL) was heated to 85° C. for 1 hour. The reaction was cooled and diluted with ethyl acetate (75 mL). The organic layer was washed with water (3×50 mL) and brine (50 mL), dried over magnesium sulfate, filtered, and concentrated to give the title compound.

Example 377G methyl 2-(5-chloro-6-(methylamino)pyridin-3-yloxy)-4-(4-((2-(4-chlorophenyl)-4,4-dimethylcyclohex-1-enyl)methyl)piperazin-1-yl)benzoate To a solution of EXAMPLE 377F (0.230 g) and EXAMPLE 60D (0.182 g) in dichloromethane (2 mL) was added sodium triacetoxyborohydride (0.194 g) and the reaction was allowed to stir at room temperature overnight. The reaction was quenched with saturated aqueous NaHCO$_3$ solution (25 mL) and extracted into dichloromethane (75 mL). The organic layer was washed with brine (25 mL), dried over magnesium sulfate, filtered, and concentrated. Silica gel chromatography (Reveleris 40 g) eluting with a gradient of 5-30% ethyl acetate/hexanes over 30 minutes provided the title compound.

Example 377H 2-(5-chloro-6-(methylamino)pyridin-3-yloxy)-4-(4-((2-(4-chlorophenyl)-4,4-dimethylcyclohex-1-enyl)methyl)piperazin-1-yl)benzoic acid To a solution of EXAMPLE 377G (0.295 g) in tetrahydrofuran (5 mL) and methanol (2 mL) was added 1.0M aqueous LiOH (1.452 mL) and the reaction was heated to 55° C. After stirring for 3 hours, the reaction was cooled, diluted with dichloromethane (75 mL) and water (15 mL) and quenched with 1N aqueous HCl (1.45 mL). The organic layer was separated, washed with brine (15 mL), dried over magnesium sulfate, filtered, and concentrated to provide the title compound.

Example 377I

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 377H for EXAMPLE 1F in EXAMPLE 1H. $^1$H NMR (300 MHz, dimethylsulfoxide-$d_6$) δ 11.52-11.16 (m, 1H), 8.63 (s, 1H), 8.57 (d, 1H), 7.87 (dd, 1H), 7.82 (d, 1H), 7.49-7.39 (m, 2H), 7.36 (d, 2H), 7.21 (d, 1H), 7.06 (d, 2H), 6.65 (d, 1H), 6.43 (d, 1H), 6.18 (d, 1H), 3.85 (d, 2H), 3.41-3.19 (m, 4H), 3.12 (s, 4H), 2.84 (d, 3H), 2.79 (s, 2H), 2.20 (d, 6H), 1.97 (s, 3H), 1.62 (d, 2H), 1.41 (d, 2H), 1.29 (dd, 2H), 0.94 (s, 6H).

Example 378

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[({4-[2-fluoro-1-(fluoromethyl)ethyl]morpholin-2-yl}methyl)amino]-3-nitrophenyl}sulfonyl)benzamide

Example 378A tert-butyl (4-(1,3-difluoropropan-2-yl)morpholin-2-yl)methylcarbamate The title compound was prepared by substituting tert-butyl morpholin-2-ylmethylcarbamate for tert-butyl piperazine-1-carboxylate and 1,3-difluoropropan-2-one for 4'-chlorobiphenyl-2-carboxaldehyde in EXAMPLE 1A

Example 378B (4-(1,3-difluoropropan-2-yl)morpholin-2-yl)methanamine

The title compound was prepared by substituting EXAMPLE 378A for EXAMPLE 1A in EXAMPLE 1B.

Example 378C 4-((4-(1,3-difluoropropan-2-yl)morpholin-2-yl)methylamino)-3-nitrobenzenesulfonamide The title compound was prepared by substituting EXAMPLE 378B for 3-(N-morpholinyl)-1-propylamine in EXAMPLE 4A.

Example 378D

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[({4-[2-fluoro-1-(fluoromethyl)ethyl]morpholin-2-yl}methyl)amino]-3-nitrophenyl}sulfonyl)benzamide The title compound was prepared by substituting EXAMPLE 318E for EXAMPLE 1F and EXAMPLE 378C for EXAMPLE 1G in EXAMPLE 1H. $^1$H NMR (500 MHz, dimethylsulfoxide-$d_6$) δ 11.30 (br s, 1H), 8.63 (t, 1H), 8.58 (d, 1H), 7.86 (dd, 1H), 7.74 (d, 1H), 7.44 (d, 1H), 7.38 (d, 1H), 7.36 (d, 2H), 7.20 (d, 1H), 7.06 (d, 2H), 6.65 (dd, 1H), 6.19 (d, 1H), 6.17 (br s, 2H), 4.68 (t, 2H), 4.56 (t, 2H), 3.83 (d, 1H), 3.71 (m, 1H), 3.51 (m, 4H), 3.12 (m, 4H), 2.90 (d, 1H), 2.80 (m, 2H), 2.73 (m, 1H), 2.57 (t, 1H), 2.42 (t, 1H), 2.25 (m, 4H), 2.17 (m, 2H), 1.97 (m, 2H), 1.40 (t, 2H), 0.94 (s, 6H).

Example 379

2-[(2-amino-6-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide EXAMPLE 372F (137 mg) was dissolved in dichloromethane (2 mL), and trifluoroacetic acid (0.21 mL) was added. The mixture was stirred at room temperature for 16 hours, diluted with dichloromethane, extracted with saturated aqueous sodium bicarbonate, dried over anhydrous sodium sulfate, and concentrated under vacuum to provide the title compound. $^1$H NMR (300 MHz, dimethylsulfoxide-$d_6$) δ 8.57 (bs, 1H), 8.48 (bs, 1H), 7.69 (dd, 1H), 7.54 (d, 1H), 7.37 (d, 2H), 7.08 (d, 1H), 7.07 (d, 2H), 6.80 (dd, 1H), 6.55 (bs, 1H), 6.23 (d, 2H), 6.03 (d, 1H), 5.59 (d, 1H), 3.86 (dd, 2H), 3.24 (m, 8H), 2.81 (bs, 2H), 2.35-2.15 (m, 6H), 1.97 (bs, 2H), 1.93 (m, 1H), 1.65 (d, 2H), 1.42 (t, 2H), 1.35-1.21 (m, 2H), 0.95 (s, 6H).

Example 380

4-(4-{[2-(4-chlorophenyl)-4,4-dimethylcyclohex-1-en-1-yl]methyl}piperazin-1-yl)-2-[(2,6-diaminopyridin-4-yl)oxy]-N-({3-nitro-4-[(tetrahydro-2H-pyran-4-ylmethyl)amino]phenyl}sulfonyl)benzamide The title compound was prepared by substituting EXAMPLE 373E for EXAMPLE 372F in EXAMPLE 379. $^1$H NMR (300 MHz, dimethylsulfoxide-$d_6$) δ 8.36 (d, 1H), 8.34 (t, 1H), 7.70 (dd, 1H), 7.62 (d, 1H), 7.37 (d, 2H), 7.36 (t, 1H), 7.09 (d, 1H), 7.08 (d, 2H), 6.97 (d, 1H), 6.64 (dd, 1H), 6.28 (d, 1H), 5.21 (bs, 4H), 3.84 (dd, 2H), 3.25 (m, 2H), 3.06 (m, 4H), 2.76 (m, 2H), 2.29-2.15 (m, 8H), 1.98 (bs, 2H), 1.91 (m, 1H), 1.63 (d, 2H), 1.41 (t, 2H), 1.34-1.17 (m, 2H), 0.95 (s, 6H).

Example 381

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[3-nitro-4-(tetrahydro-2H-pyran-4-ylmethoxy)phenyl]sulfonyl}benzamide The title compound was prepared by substituting EXAMPLE 318E for EXAMPLE 1F and EXAMPLE 264A for EXAMPLE 1G in EXAMPLE 1H. $^1$H NMR (300 MHz, dimethylsulfoxide-d) δ 11.78-11.08 (m, 1H), 8.35 (s, 1H), 8.07 (s, 1H), 7.73 (d, 1H), 7.54-7.43 (m, 2H), 7.36 (d, 3H), 7.07 (d, 2H), 6.65 (d, 1H), 6.18 (d, 3H), 4.13 (d, 2H), 3.88 (d, 2H), 3.35 (d, 2H), 3.14 (s, 4H), 2.99-2.78 (m, 2H), 2.08 (t, 9H), 1.66 (d, 2H), 1.45-1.22 (m, 4H), 0.94 (s, 6H).

Example 382

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]piperidin-3-yl}amino)-3-nitrophenyl]sulfonyl}benzamide

Example 382A (R)-1-(1,3-difluoropropan-2-yl)piperidin-3-amine hydrogen chloride A solution of (R)-tert-butyl piperidin-3-ylcarbamate (0.500 g), 1,3-difluoropropan-2-one (0.258 g) and sodium triacetoxyhydroborate (0.794 g) were stirred together in dichloromethane (5 mL) overnight. The reaction was quenched with saturated aqueous NaHCO$_3$ (10 mL) and extracted with dichloromethane (30 mL). The organic layer was washed with brine (20 mL), dried over magnesium sulfate, filtered, and concentrated. The crude material was treated with HCl (4.0M dioxane, 2 mL) in methanol (2 mL). After stirring for 2 hours, the reaction was concentrated to provide the title compound.

Example 382B (R)-4-(1-(1,3-difluoropropan-2-yl)piperidin-3-ylamino)-3-nitrobenzenesulfonamide To EXAMPLE 382A (0.590 g) and 4-chloro-3-nitrobenzenesulfonamide (0.611 g) in dioxane (10 mL) was added N-ethyl-N-isopropylpropan-2-amine (1.641 mL) and the reaction heated to 90° C. The reaction was concentrated, loaded onto silica gel (Reveleris 80 g) and eluted using a gradient of 35% to 100% ethyl acetate/hexanes over 30 minutes to give the title compound.

Example 382C

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]piperidin-3-yl}amino)-3-nitrophenyl]sulfonyl}benzamide The title compound was prepared by substituting EXAMPLE 318E for EXAMPLE 1F and EXAMPLE 382B for EXAMPLE 1G in EXAMPLE 1H. $^1$H NMR (300 MHz, dimethylsulfoxide-d$_6$) δ 11.62-11.06 (m, 1H), 8.91 (d, 1H), 8.60 (d, 1H), 7.87 (d, 1H), 7.75 (d, 1H), 7.47-7.32 (m, 4H), 7.19 (d, 1H), 7.06 (d, 2H), 6.65 (d, 1H), 6.18 (s, 3H), 4.64 (dt, 4H), 4.00 (s, 1H), 3.27-3.08 (m, 5H), 2.90-2.58 (m, 6H), 2.20 (d, 6H), 1.97 (s, 2H), 1.60 (s, 4H), 1.40 (s, 2H), 0.94 (s, 6H).

Example 383 tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate

Example 383A 2-(2-Amino-5-bromo-pyridin-4-yloxy)-4-fluoro-benzoic acid methyl ester EXAMPLE 271A (600 mg), potassium bromide (300 mg), and ammonium molybdate (85 mg) were added to acetic acid (6 mL). Sodium perborate tetrahydrate (387 mg) was added. The mixture stirred at room temperature for 16 hours and added to water. The pH was adjusted to 12 using 1M aqueous sodium hydroxide, and the solution was extracted with ethyl acetate. The extract was washed with brine, dried over anhydrous sodium sulfate, filtered, concentrated and purified by flash column chromatography on silica gel using 30-70% ethyl acetate in hexanes.

Example 383B 2-(5-Bromo-2-tert-butoxycarbonylamino-pyridin-4-yloxy)-4-fluoro-benzoic acid methyl ester EXAMPLE 383A (726 mg), di-tert-butyl dicarbonate (557 mg), and 4-(dimethylamino)pyridine (26 mg) were added to acetonitrile (15 mL) and stirred at room temperature for 16 hours. The solution was concentrated and purified by flash column chromatography on silica gel using 20% ethyl acetate in hexanes to provide the title compound.

Example 383C 2-(5-Bromo-2-tert-butoxycarbonylamino-pyridin-4-yloxy)-4-piperazin-1-yl-benzoic acid methyl ester The title compound was prepared by substituting EXAMPLE 383B for EXAMPLE 342D in EXAMPLE 342E.

Example 383D 2-(5-Bromo-2-tert-butoxycarbonylamino-pyridin-4-yloxy)-4-{4-[2-(4-chloro-phenyl)-4,4-dimethyl-cyclohex-1-enylmethyl]-piperazin-1-yl}-benzoic acid methyl ester The title compound was prepared by substituting EXAMPLE 60D for 4'-chlorobiphenyl-2-carboxaldehyde and EXAMPLE 383C for tert-butyl piperazine-1-carboxylate in EXAMPLE 1A.

Example 383E 2-(5-Bromo-2-tert-butoxycarbonylamino-pyridin-4-yloxy)-4-{4-[2-(4-chloro-phenyl)-4,4-dimethyl-cyclohex-1-enylmethyl]-piperazin-1-yl}-benzoic acid The title compound was prepared by substituting EXAMPLE 383D for EXAMPLE 1E in EXAMPLE 1F.

Example 383F tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate The title compound was prepared by substituting EXAMPLE 383E for EXAMPLE 1F in EXAMPLE 1H. $^1$H NMR (300 MHz, dimethylsulfoxide-d$_6$) δ 9.62 (bs, 1H), 8.58 (bs, 1H), 8.48 (bs, 1H), 8.18 (s, 1H), 7.72 (m, 1H), 7.59 (m, 1H), 7.36 (d, 2H), 7.15-6.98 (m, 4H), 6.82 (d, 1H), 6.62 (bs, 1H), 3.87 (d, 2H), 3.35-3.20 (m, 8H), 2.79 (m, 2H), 2.30-2.16 (m, 6H), 1.97 (bs, 2H), 1.92 (m, 1H), 1.64 (d, 2H), 1.41 (t, 2H), 1.32 (s, 9H), 1.30 (m, 2H), 0.95 (s, 6H).

Example 384

4-(4-{[2-(4-chlorophenyl)-4,4-dimethylcyclohex-1-en-1-yl]methyl}piperazin-1-yl)-2-[(4-chloro-1H-pyrrolo[2,3-b]pyridin-5-yl)oxy]-N-({3-nitro-4-[(tetrahydro-2H-pyran-4-ylmethyl)amino]phenyl}sulfonyl)benzamide

Example 384A 2-(4-Chloro-1H-pyrrolo[2,3-b]pyridin-5-yloxy)-4-fluoro-benzoic acid methyl ester The title compound was prepared by substituting 4-chloro-1H-pyrrolo[2,3-B]pyridin-5-ol for EXAMPLE 342C in EXAMPLE 342D.

Example 384B 2-(4-Chloro-1H-pyrrolo[2,3-b]pyridin-5-yloxy)-4-piperazin-1-yl-benzoic acid methyl ester The title compound was prepared by substituting EXAMPLE 384A for EXAMPLE 342D in EXAMPLE 342E.

Example 384C

4-{4-[2-(4-Chloro-phenyl)-4,4-dimethyl-cyclohex-1-enylmethyl]-piperazin-1-yl}-2-(4-chloro-1H-pyrrolo[2,3-b]pyridin-5-yloxy)-benzoic acid methyl ester The title compound was prepared by substituting EXAMPLE 60D for 4'-chlorobiphenyl-2-carboxaldehyde and EXAMPLE 384B for tert-butyl piperazine-1-carboxylate in EXAMPLE 1A.

Example 384D

4-{4-[2-(4-Chloro-phenyl)-4,4-dimethyl-cyclohex-1-enylmethyl]-piperazin-1-yl}-2-(4-chloro-1H-pyrrolo[2,3-b]pyridin-5-yloxy)-benzoic acid The title compound was prepared by substituting EXAMPLE 384C for EXAMPLE 1E in EXAMPLE 1F.

Example 384E 4-(4-{[2-(4-chlorophenyl)-4,4-dimethylcyclohex-1-en-1-yl]methyl}piperazin-1-yl)-2-[(4-chloro-1H-pyrrolo[2,3-b]pyridin-5-yl)oxy]-N-({3-nitro-4-[(tetrahydro-2H-pyran-4-ylmethyl)amino]phenyl}sulfonyl)benzamide The title compound was prepared by substituting EXAMPLE 384D for EXAMPLE 1F in EXAMPLE 1H. $^1$H NMR (300 MHz, dimethylsulfoxide-$d_6$) δ 12.07 (s, 1H), 8.60 (t, 1H), 8.58 (d, 1H), 8.07 (s, 1H), 7.88 (dd, 1H), 7.65 (t, 1H), 7.51 (d, 1H), 7.34 (d, 2H), 7.18 (d, 1H), 7.04 (d, 2H), 6.66 (dd, 1H), 6.50 (dd, 1H), 6.03 (d, 1H), 3.84 (dd, 2H), 3.26 (m, 4H), 3.13-2.96 (m, 4H), 2.73 (m, 2H), 2.16 (m, 6H), 1.95 (bs, 2H), 1.91 (m, 1H), 1.61 (d, 2H), 1.38 (t, 2H), 1.36-1.21 (m, 2H), 0.92 (s, 6H).

Example 385

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide

Example 385A methyl 2-(6-(tert-butoxycarbonyl(2,2,2-trifluoroethyl)amino)pyridin-3-yloxy)-4-fluorobenzoate The title compound was prepared by substituting 1,1,1-trifluoro-2-iodoethane for methyl iodide in EXAMPLE 377C.

Example 385B methyl 2-(6-(tert-butoxycarbonyl(2,2,2-trifluoroethyl)amino)pyridin-3-yloxy)-4-(piperazin-1-yl)benzoate The title compound was prepared by substituting EXAMPLE 385A for EXAMPLE 377E in EXAMPLE 377F.

Example 385C methyl 2-(6-(tert-butoxycarbonyl(2,2,2-trifluoroethyl)amino)pyridin-3-yloxy)-4-(4-((2-(4-chlorophenyl)-4,4-dimethylcyclohex-1-enyl)methyl)piperazin-1-yl)benzoate The title compound was prepared by substituting EXAMPLE 385B for tert-butyl piperazine-1-carboxylate and EXAMPLE 60D for 4'-chlorobiphenyl-2-carboxaldehyde in EXAMPLE 1A.

Example 385D 2-(6-(tert-butoxycarbonyl(2,2,2-trifluoroethyl)amino)pyridin-3-yloxy)-4-(4-((2-(4-chlorophenyl)-4,4-dimethylcyclohex-1-enyl)methyl)piperazin-1-yl)benzoic acid The title compound was prepared by substituting EXAMPLE 385C for EXAMPLE 38G in EXAMPLE 38H.

Example 385E tert-butyl 5-(5-(4-((2-(4-chlorophenyl)-4,4-dimethylcyclohex-1-enyl)methyl)piperazin-1-yl)-2-(3-nitro-4-((tetrahydro-2H-pyranyl)methylamino)phenylsulfonylcarbamoyl)-phenoxy)pyridin-2-yl(2,2,2-trifluoroethyl)carbamate The title compound was prepared by substituting EXAMPLE 385D for EXAMPLE 110E in EXAMPLE 110F.

Example 385F 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide EXAMPLE 385E (20 mg) was dissolved in anhydrous dichloromethane and trifluoroacetic acid (0.1 mL) was added.

The reaction mixture was stirred at room temperature for 1.5 hours. The solvent was removed under vacuum. The residue was dissolved in ethyl acetate, washed with NaHCO$_3$ aqueous solution and brine, dried over anhydrous sodium sulfate, filtered, and concentrated to provide the title compound. $^1$H NMR (400 MHz, dimethylsulfoxide-d$_6$) δ 8.56 (m, 2H), 7.86 (dd, 1H), 7.79 (d, 1H), 7.69 (m, 1H), 7.47 (d, 1H), 7.35 (d, 2H), 7.21 (m, 2H), 7.08 (m, 3H), 6.63 (m, 2H), 6.13 (d, 1H), 4.13 (m, 2H), 3.85 (dd, 2H), 3.27 (m, 4H), 3.06 (s, 4H), 2.74 (s, 2H), 2.18 (m, 6H), 1.97 (m, 3H), 1.61 (m, 2H), 1.40 (t, 2H), 1.27 (m, 2H), 0.94 (s, 6H).

Example 386

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide Example 386A trans-4-(aminomethyl)cyclohexanol Tert-butyl trans-(4-hydroxycyclohexyl)methylcarbamate (1 g) in dichloromethane (10 ml) was treated with trifluoroacetic acid (10 ml) at 0° C. for two hours. The reaction mixture was concentrated and the residue was dried under vacuum to provide the title compound.

Example 386B 4-(trans-(4-hydroxycyclohexyl)methylamino)-3-nitrobenzenesulfonamide The title compound was prepared by substituting EXAMPLE 386A for 1-(tetrahydropyran-4-yl)methylamine in EXAMPLE 1G.

Example 386C

Trans-2-(6-amino-5-chloropyridin-3-yloxy)-4-(4-((2-(4-chlorophenyl)-4,4-dimethylcyclohex-1-enyl)methyl)piperazin-1-yl)-N-(4-((4-hydroxycyclohexyl)methylamino)-3-nitrophenylsulfonyl)benzamide The title compound was prepared as described in EXAMPLE 110F by replacing EXAMPLE 110E and EXAMPLE 1G with EXAMPLE 318E and EXAMPLE 386B. $^1$H NMR (400 MHz, dimethylsulfoxide-d$_6$) δ 8.61 (t, 1H), 8.58 (d, 1H), 7.86 (dd, 1H), 7.75 (d, 1H), 7.44 (d, 1H), 7.40 (d, 1H), 7.36 (d, 2H), 7.18 (d, 1H), 7.06 (d, 2H), 6.65 (dd, 1H), 6.18 (s, 3H), 4.52 (d, 1H), 3.24-3.30 (m, 4H), 3.12 (s, 4H), 2.79 (s, 2H), 2.25 (s, 4H), 2.17 (s, 21H), 1.97 (s, 2H), 1.79-1.89 (m, 2H), 1.75 (d, 2H), 1.50-1.64 (m, 1H), 1.40 (t, 2H), 0.97-1.17 (m, 4H), 0.94 (s, 6H).

Example 387

2-[(6-amino-5-chloropyridin-3-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide Example 387A methyl 2-(6-amino-5-chloropyridin-3-yloxy)-4-(piperazin-1-yl)benzoate A solution of EXAMPLE 318C (8.90 g) and piperazine (10.34 g) in dimethylsulfoxide (100 mL) was heated to 85° C.

After stirring for 3 hours, the reaction mixture was cooled, diluted with ethyl acetate (400 mL), washed with water (2×250 mL) and brine (250 mL), dried over magnesium sulfate, filtered, and concentrated to provide the title compound.

Example 387B methyl 2-(6-amino-5-chloropyridin-3-yloxy)-4-(4-((4-(4-chlorophenyl)-6,6-dimethyl-5,6-dihydro-2H-pyran-3-yl)methyl)piperazin-1-yl)benzoate To a solution of EXAMPLE 387A (0.344 g) and EXAMPLE 38E (0.238 g) in dichloromethane (5 mL) was added sodium triacetoxyhydroborate (0.302 g) and the reaction stirred at room temperature overnight. The reaction was quenched with saturated aqueous NaHCO$_3$ (10 mL) and extracted with dichloromethane (50 mL). The organic layers were combined, dried over magnesium sulfate, filtered, and concentrated. Silica gel chromatography (Reveleris 40 g) eluting with a gradient of 10-75% ethyl acetate/hexanes over 30 minutes (flow=40 ml/min) provided the title compound.

Example 387C 2-(6-amino-5-chloropyridin-3-yloxy)-4-(4-((4-(4-chlorophenyl)-6,6-dimethyl-5,6-dihydro-2H-pyran-3-yl)methyl)piperazin-1-yl)benzoic acid To a solution of EXAMPLE 387B (0.300 g) in tetrahydrofuran (5 mL) and methanol (1 mL) was added 1.0M lithium hydroxide (1.506 mL) and the suspension was heated to 55° C. After 3 hours, the reaction was cooled, diluted with dichloromethane (20 mL) and water (10 mL), and quenched with 1N aqueous HCl (1.5 mL). The organic layer was separated and the aqueous layer was extracted with 20 ml of dichloromethane. The combined organic extracts were washed with brine (25 mL), dried over magnesium sulfate, filtered, and concentrated to give the title compound.

Example 387D

2-[(6-amino-5-chloropyridin-3-yl)oxy]-4-(4-{[4-(4-chlorophenyl)-6,6-dimethyl-5,6-dihydro-2H-pyran-3-yl]methyl}piperazin-1-yl)-N-({3-nitro-4-[(tetrahydro-2H-pyran-4-ylmethyl)amino]phenyl}sulfonyl)benzamide The title compound was prepared by substituting EXAMPLE 387B for EXAMPLE 1F in EXAMPLE 1H. $^1$H NMR (300 MHz, dimethylsulfoxide-d$_6$) δ 11.40 (s, 1H), 8.64 (t, 1H), 8.59 (d, 1H), 7.87 (dd, 1H), 7.75 (d, 1H), 7.47-7.35 (m, 4H), 7.23 (d, 1H), 7.19-7.11 (m, 2H), 6.65 (dd, 1H), 6.18 (s, 3H), 4.14 (s, 2H), 3.85 (dd, 2H), 3.44-3.21 (m, 4H), 3.11 (s, 4H), 2.87 (s, 2H), 2.24 (s, 4H), 2.16 (s, 2H), 1.91 (s, 1H), 1.63 (d, 2H), 1.38-1.15 (m, 8H).

Example 388

N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide The title compound was prepared by substituting EXAMPLE 277B for EXAMPLE 1F and EXAMPLE 326A for EXAMPLE 1G in EXAMPLE 1H. $^1$H NMR (500 MHz, dimethylsulfoxide-$d_6$) δ 11.22 (s, 1H), 8.60 (d, 1H), 8.30 (d, 1H), 7.55 (d, 1H), 7.38 (m, 4H), 7.29 (br d, 1H), 7.13 (d, 2H), 6.64 (d, 1H), 6.41 (s, 1H), 6.09 (s, 1H), 4.53 (d, 2H), 4.10 (s, 2H), 3.78 (m, 2H), 3.60 (m, 2H), 3.07 (v br s, 4H), 2.86 (br s, 2H), 2.25 (v br s, 4H), 2.15 (s, 2H), 1.85 (m, 4H), 1.18 (s, 6H).

Example 389

2-[(6-amino-5-chloropyridin-3-yl)oxy]-4-(4-{[2-(4-chlorophenyl)-4,4-dimethylcyclohex-1-en-1-yl] methyl}piperazin-1-yl)-N-({3-nitro-4-[(tetrahydrofuran-3-ylmethyl)amino]phenyl}sulfonyl)benzamide The title compound was prepared by substituting EXAMPLE 318E for EXAMPLE 1F and EXAMPLE 332A for EXAMPLE 1G in EXAMPLE 1H. $^1$H NMR (300 MHz, dimethylsulfoxide-$d_6$) δ 11.52-11.11 (m, 1H), 8.65 (s, 1H), 8.58 (d, 1H), 7.87 (d, 1H), 7.74 (d, 1H), 7.47-7.32 (m, 4H), 7.22 (d, 1H), 7.06 (d, 2H), 6.65 (d, 1H), 6.17 (s, 3H), 3.86-3.38 (m, 6H), 3.12 (s, 4H), 2.79 (s, 2H), 2.61 (s, 1H), 2.21 (d, 6H), 1.97 (s, 3H), 1.65 (d, 1H), 1.40 (s, 2H), 0.94 (s, 6H).

Example 390

2-[(6-amino-5-chloropyridin-3-yl)oxy]-N-({5-chloro-6-[(4-fluorotetrahydro-2H-pyran-4-yl)methoxy]pyridin-3-yl}sulfonyl)-4-(4-{[4-(4-chlorophenyl)-6,6-dimethyl-5,6-dihydro-2H-pyran-3-yl] methyl}piperazin-1-yl)benzamide The title compound was prepared by substituting EXAMPLE 387C for EXAMPLE 1F and EXAMPLE 326A for EXAMPLE 1G in EXAMPLE 1H. $^1$H NMR (300 MHz, dimethylsulfoxide-$d_6$) δ 11.94-11.04 (m, 1H), 8.58 (d, 1H), 8.26 (d, 1H), 7.75 (d, 1H), 7.48 (d, 1H), 7.40 (d, 3H), 7.16 (d, 2H), 6.66 (d, 1H), 6.18 (d, 3H), 4.56 (d, 2H), 4.15 (s, 2H), 3.77 (dd, 2H), 3.67-3.51 (m, 2H), 3.14 (s, 4H), 2.95 (s, 2H), 2.33 (s, 4H), 2.17 (s, 2H), 1.87 (td, 4H), 1.20 (s, 6H).

Example 391

2-[(6-amino-5-chloropyridin-3-yl)oxy]-4-[4-({9-(4-chlorophenyl)-3-[2-fluoro-1-(fluoromethyl)ethyl]-3-azaspiro[5.5]undec-8-en-8-yl}methyl)piperazin-1-yl]-N-({3-nitro-4-[(tetrahydro-2H-pyran-4-ylmethyl) amino]phenyl}sulfonyl)benzamide Example 391A benzyl 4-(piperidin-1-ylmethylene)piperidine-1-carboxylate To a solution of benzyl 4-formylpiperidine-1-carboxylate (22.35 g) in toluene (300 mL) was added piperidine (11.55 g). The mixture was stirred at reflux under a Dean-Stark trap overnight. The mixture was then concentrated under vacuum and the residue was used directly in the next step.

Example 391B benzyl 9-oxo-3-azaspiro[5.5]undec-7-ene-3-carboxylate

To a solution of crude EXAMPLE 391A (35.5 g) in ethanol (300 mL) was added but-3-enone (8.71 g). The mixture was stirred at reflux overnight. Acetic acid (50 mL) was added to the mixture which was stirred at reflux again overnight. The mixture was then concentrated under vacuum and the residue was diluted with ethyl acetate (600 mL) and washed with water, brine and dried over $Na_2SO_4$. After filtration and evaporation of the solvent, silica gel chromatography using 5-20% ethyl acetate in hexanes provided the title compound.

Example 391C benzyl 9-hydroxy-3-azaspiro[5.5]undecane-3-carboxylate

EXAMPLE 391B (21 g) and tetrahydrofuran (160 mL) were added to wet 5% Pt—C (3.15 g) in a 250 mL SS pressure bottle and the mixture was stirred for 24 hours at 30 psi $H_2$. The mixture was filtered through a nylon membrane and concentrated to afford the product.

Example 391D benzyl 9-oxo-3-azaspiro[5.5]undecane-3-carboxylate

To a solution of EXAMPLE 391C (23.66 g) in dichloromethane (350 mL) was added Dess-Martin Periodinane (33.1 g). The mixture was stirred overnight. The mixture was diluted with ethyl acetate (600 mL) and washed with 2N aqueous NaOH, water, and brine. After drying over $Na_2SO_4$, the mixture was filtered and concentrated to provide the title compound.

Example 391E benzyl 9-chloro-8-formyl-3-azaspiro[5.5]undec-8-ene-3-carboxylate

Phosphorus oxychloride (5.68 mL) was added dropwise to a cooled (0° C.) solution of EXAMPLE 391D (18.37 g) in N,N-dimethylformamide (20 mL) and dichloromethane (80 mL). The mixture was then stirred overnight before it was diluted with ethyl acetate (600 mL) and washed with aqueous sodium acetate, water (3×), and brine and dried over $Na_2SO_4$. After filtration and concentration, the crude product was used directly in the next reaction without further purification.

Example 391F benzyl 9-(4-chlorophenyl)-8-formyl-3-azaspiro[5.5] undec-8-ene-3-carboxylate To a mixture of 4-chlorophenylboronic acid (11.34 g, 72.5 mmol), EXAMPLE 391E (21.01 g), palladium(II) acetate (271 mg), $K_2CO_3$ (25.05 g) and tetrabutylammonium bromide (19.5 g) was added water (120 mL). The mixture was stirred at 50° C. overnight. The mixture was diluted with ethyl acetate (400 mL) and washed with water (3×) and brine and dried over $Na_2SO_4$. After filtration and concentration, the residue was loaded on a column and eluted with 5-20% ethyl acetate in hexane to provide the title compound.

Example 391G benzyl 8-((4-(3-(6-amino-5-chloropyridin-3-yloxy)-4-(methoxycarbonyl)phenyl)piperazin-1-yl)methyl)-9-(4-chlorophenyl)-3-azaspiro[5.5]undec-8-ene-3-carboxylate To a solution of EXAMPLE 387A (498 mg) in dichloromethane (10 mL) was added EXAMPLE 391F (582 mg)

409 and sodium triacetoxyborohydride (436 mg). The mixture was stirred overnight. The reaction mixture was diluted with ethyl acetate (300 mL) and washed with 2N aqueous NaOH and brine, and dried over $Na_2SO_4$. Filtration, evaporation of the solvent, and flash chromatography (2% methanol in dichloromethane) provided the title compound.

Example 391H methyl 2-(6-amino-5-chloropyridin-3-yloxy)-4-(4-((9-(4-chlorophenyl)-3-azaspiro[5.5]undec-8-en-8-yl)methyl)piperazin-1-yl)benzoate To a solution of EXAMPLE 391G (1.02 g) in ethanol (20 mL) was added Pd/C (10%, 150 mg). The mixture was stirred for 5 hours. The mixture was filtered and the filtrate was concentrated to provide the title compound.

Example 391I 2-(6-amino-5-chloropyridin-3-yloxy)-4-(4-((9-(4-chlorophenyl)-3-(1,3-difluoropropan-2-yl)-3-azaspiro[5.5]undec-8-en-8-yl)methyl)piperazin-1-yl)benzoic acid To a solution of EXAMPLE 391H (318 mg) in dichloromethane (4 mL) was added 1,3-difluoropropan-2-one (282 mg) and sodium acetoxyborohydride (318 mg). The mixture was stirred overnight. The reaction mixture was diluted with ethyl acetate (300 mL) and washed with 2N aqueous NaOH and brine, and dried over $Na_2SO_4$. Filtration and concentration gave the crude product which was dissolved in tetrahydrofuran (10 mL), methanol (5 mL) and water (5 mL). $LiOH.H_2O$ (450 mg) was added and the mixture was stirred overnight. The mixture was neutralized with 2N aqueous HCl and extracted with ethyl acetate (300 mL) and dichloromethane (300 mL) respectively. The organic extracts were combined and dried over $Na_2SO_4$. Filtration and concentration provided the title compound.

Example 391J

2-[(6-amino-5-chloropyridin-3-yl)oxy]-4-[4-({9-(4-chlorophenyl)-3-[2-fluoro-1-(fluoromethyl)ethyl]-3-azaspiro[5.5]undec-8-en-8-yl}methyl)piperazin-1-yl]-N-({3-nitro-4-[(tetrahydro-2H-pyran-4-ylmethyl)amino]phenyl}sulfonyl)benzamide The title compound was prepared as described in EXAMPLE 1H, replacing EXAMPLE 1F with EXAMPLE 391I. $^1$H NMR (300 MHz, dimethylsulfoxide-$d_6$) δ 8.62 (t, 1H), 8.57 (d, 1H), 7.86 (dd, 1H), 7.75 (d, 1H), 7.44 (d, 1H), 7.36 (m, 4H), 7.21 (d, 1H), 7.08 (m, 3H), 6.65 (dd, 1H), 6.17 (m, 3H), 4.69 (d, 2H), 4.53 (d, 2H), 3.85 (dd, 2H), 3.10 (m, 6H), 2.71 (m, 9H), 2.25 (m, 8H), 2.06 (m, 2H), 1.91 (m, 1H), 1.62 (m, 2H), 1.48 (m, 4H), 1.25 (m, 2H).

410

Example 392

2-[(6-amino-5-chloropyridin-3-yl)oxy]-4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)benzamide Example 392A 2-(6-amino-5-chloropyridin-3-yloxy)-4-(4-((9-(4-chlorophenyl)-3-isopropyl-3-azaspiro[5.5]undec-8-en-8-yl)methyl)piperazin-1-yl)benzoic acid The title compound was prepared as in EXAMPLE 391I by replacing difluoropropan-2-one with acetone.

Example 392B

2-[(6-amino-5-chloropyridin-3-yl)oxy]-4-(4-{[9-(4-chlorophenyl)-3-isopropyl-3-azaspiro[5.5]undec-8-en-8-yl]methyl}piperazin-1-yl)-N-({3-nitro-4-[(tetrahydro-2H-pyran-4-ylmethyl)amino]phenyl}sulfonyl)benzamide The title compound was prepared as in EXAMPLE 1H by replacing EXAMPLE 1F with EXAMPLE 392A. $^1$H NMR (300 MHz, dimethylsulfoxide-$d_6$) δ 8.40 (m, 2H), 7.71 (dd, 1H), 7.60 (d, 1H), 7.54 (d, 1H), 7.38 (d, 3H), 7.11 (d, 4H), 7.00 (d, 1H), 6.62 (dd, 1H), 6.28 (d, 1H), 5.88 (s, 2H), 3.84 (dd, 3H), 3.04 (m, 7H), 2.73 (m, 4H), 2.23 (m, 9H), 1.90 (m, 2H), 1.63 (m, 10H), 1.27 (m, 6H)

Example 393

2-[(6-amino-5-chloropyridin-3-yl)oxy]-N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide Example 393A tert-butyl 4-fluoro-4-(hydroxymethyl)piperidine-1-carboxylate 1-Tert-butyl 4-ethyl 4-fluoropiperidine-1,4-dicarboxylate (1.0 g) in tetrahydrofuran (10 mL) at 0° C. was treated with a 1 N solution of $LiAlH_4$ in tetrahydrofuran (2.54 mL), stirred 2 hours at room temperature, treated sequentially dropwise with water (0.2 mL) and a 2 N aqueous solution of NaOH (0.6 mL) and stirred for 1 hour. The solid was removed by filtration through a pad of diatomaceous earth, rinsing with ethyl acetate. The filtrate was washed with water and brine, dried ($MgSO_4$), filtered and concentrated to provide the title compound.

Example 393B tert-butyl 4-((3-chloro-5-sulfamoylpyridin-2-yloxy)methyl)-4-fluoropiperidine-1-carboxylate The title compound was prepared by substituting EXAMPLE 393A for (tetrahydro-2H-pyran-4-yl)methanol and EXAMPLE 303A for 4-fluoro-3-nitrobenzenesulfonamide in EXAMPLE 264A.

Example 393C 5-chloro-6-((4-fluoropiperidin-4-yl)methoxy)pyridine-3-sulfonamide, 2•trifluoroacetic acid salt The title compound was prepared by substituting EXAMPLE 393B for EXAMPLE 1A in EXAMPLE 1B.

Example 393D 5-chloro-6-((1-(2-(dimethylamino)acetyl)-4-fluoropiperidin-4-yl)methoxy)pyridine-3-sulfonamide 5-chloro-6-((4-fluoropiperidin-4-yl)methoxy)pyridine-3-sulfonamide, 2•trifluoroacetic acid (0.131 g), 2-(dimethylamino)acetyl chloride, hydrochloric acid (0.139 g), and sodium carbonate (0.048 g) were combined in a 5-mL vial with N,N-dimethylformamide (3 mL) and stirred overnight at room temperature. Additional sodium carbonate (0.048 g) was added followed by 2-(dimethylamino)acetyl chloride, hydrochloric acid (0.139 g) and stirring was continued over a second night. The reaction mixture was concentrated under high vacuum, slurried in $CH_2Cl_2$, filtered, concentrated, chromatographed on amine functionalized silica gel with 0 to 4% methanol in $CH_2Cl_2$ as the eluent and dried in a vacuum oven at 80° C.

Example 393E

2-[(6-amino-5-chloropyridin-3-yl)oxy]-N-[(5-chloro-6-{[1-(N,N-dimethylglycyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide The title compound was prepared by substituting EXAMPLE 318E for EXAMPLE 110E and EXAMPLE 393D for EXAMPLE 1G in EXAMPLE 110F. $^1$H NMR (500 MHz, PYRIDINE-$d_5$) δ 9.14 (d, 1H), 8.75 (d, 1H), 8.08 (d, 1H), 8.02 (d, 1H), 7.45 (m, 2H), 7.40 (d, 1H), 7.09 (m, 2H), 6.73 (dd, 1H), 6.53 (d, 1H), 4.66 (d, 1H), 4.57 (d, 1H), 4.53 (d, 1H), 4.08 (d, 1H), 3.40 (m, 2H), 3.27 (m, 1H), 3.11 (m, 5H), 2.80 (s, 2H), 2.33 (s, 6H), 2.29 (t, 2H), 2.19 (m, 4H), 2.06 (m, 2H), 1.99 (s, 2H), 1.84 (m, 2H), 1.41 (t, 2H), 0.95 (s, 6H).

Example 394

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[4-({(3R)-1-[2-fluoro-1-(fluoromethyl)ethyl]pyrrolidin-3-yl}amino)-3-nitrophenyl]sulfonyl}benzamide This example was prepared by substituting EXAMPLE 318E for EXAMPLE 1F and EXAMPLE 357B for EXAMPLE 1G in EXAMPLE 1H. $^1$H NMR (500 MHz, dimethylsulfoxide-$d_6$) δ 8.58 (d, 1H), 8.41 (d, 1H), 7.89 (d, 1H), 7.73 (d, 1H), 7.44 (d, 1H), 7.37 (m, 3H), 7.19 (d, 1H), 7.06 (d, 2H), 6.65 (dd, 1H), 6.18 (m, 3H), 4.67 (d, 2H), 4.58 (d, 2H), 4.30 (m, 1H), 3.11 (m, 5H), 2.95 (m, 2H), 2.78 (m, 4H), 2.23 (m, 7H), 1.97 (m, 2H), 1.72 (m, 1H), 1.40 (t, 2H), 0.94 (s, 6H).

Example 395

2-[(2-amino-5-bromopyridin-4-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide This example was prepared by substituting EXAMPLE 383F for EXAMPLE 372F in EXAMPLE 379. $^1$H NMR (300 MHz, dimethylsulfoxide-$d_6$) δ 8.61 (t, 1H), 8.49 (d, 1H), 7.81 (s, 1H), 7.74 (dd, 1H), 7.54 (d, 1H), 7.37 (d, 2H), 7.12 (d, 1H), 7.08 (d, 2H), 6.82 (dd, 1H), 5.65 (bs, 1H), 5.93 (bs, 2H), 5.49 (s, 1H), 3.87 (dd, 2H), 3.31-3.19 (m, 8H), 2.84 (m, 2H), 2.40-2.15 (m, 6H), 1.99 (bs, 2H), 1.94 (m, 1H), 1.64 (d, 2H), 1.42 (t, 2H), 1.35-1.21 (m, 2H), 0.95 (s, 6H).

Example 396

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide

Example 396A tert-butyl (4,4-difluorocyclohexyl)methylcarbamate

Tert-butyl (4-oxocyclohexyl)methylcarbamate (5 g) and diethylaminosulphurtrifluoride (7.45 g) were stirred in dichloromethane (100 mL) for 24 hours. The mixture was quenched with pH 7 buffer (100 mL), and poured into ether (400 mL). The resulting solution was separated, and the organic layer was washed twice with water and brine, and concentrated to give the crude product and fluoroolefin in a 3:2 ratio. The crude product was taken up in tetrahydrofuran (70 mL) and water (30 mL), and N-methylmorpholine-N-oxide (1.75 g) and $OsO_4$ (2.5 wt % solution in t-butanol) were added, and the mixture was stirred for 24 hours. $Na_2S_2O_3$ (10 g) was then added, and the mixture was stirred for 30 minutes. The mixture was then diluted with ether (300 mL), and the resulting solution was separated, and rinsed twice with water and brine, and concentrated. The crude product was chromatographed on silica gel using 5-10% ethyl acetate in hexanes to give the title compound.

Example 396B (4,4-difluorocyclohexyl)methanamine

A solution of EXAMPLE 396A (3 g) in dichloromethane (35 mL), trifluoroacetic acid (15 mL), and triethylsilane (1 mL) was stirred for 2 hours. The solution was concentrated, then condensed from toluene, and left under high vacuum for 24 hours. The semi-solid was taken up in ether/hexane and filtered to give the title compound as its TFA salt.

Example 396C 4-((4,4-difluorocyclohexyl)methylamino)-3-nitrobenzenesulfonamide This example was prepared by substituting EXAMPLE 396B for 1-isopropylpiperidin-4-amine in EXAMPLE 41A.

Example 396D

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide This example was prepared by substituting EXAMPLE 318E for EXAMPLE 1F and EXAMPLE 396C for EXAMPLE 1G in EXAMPLE 1H. $^1$H NMR (400 MHz, dimethylsulfoxide-d$_6$) δ 8.67 (t, 1H), 8.58 (d, 1H), 7.86 (dd, 1H), 7.75 (d, 1H), 7.45 (d, 1H), 7.40 (d, 1H), 7.35 (d, 2H), 7.22 (d, 1H), 7.06 (d, 2H), 6.65 (dd, 1H), 6.17 (m, 3H), 3.35 (m, 2H), 3.12 (v br m, 4H), 2.80 (br s, 2H), 2.25 (v br m, 4H), 2.17 (br t, 2H), 2.01 (br m, 2H), 1.98 (s, 2H), 1.80 (br m, 5H), 1.40 (t, 2H), 1.28 (br m, 2H), 0.93 (s, 6H).

Example 397

[3-chloro-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)-2-iminopyridin-1(2H)-yl]methyl dihydrogen phosphate A mixture of EXAMPLE 318F (93 mg), di-tert-butyl chloromethyl phosphate (82 mg) and N,N-diisopropylethylamine (0.12 mL) in 3 mL of acetonitrile was heated at 90° C. in a Biotage microwave synthesizer for 3 hours, cooled and concentrated. The residue was dissolved in dichloromethane (3 mL) and trifluoroacetic acid (2 mL) was added. The resulting solution was stirred at room temperature and concentrated. The residue was dissolved in a mixture of dimethylsulfoxide and methanol, purified by HPLC, eluting with 40-55% acetonitrile in 0.1% trifluoroacetic acid in water over 40 minutes. The title compound was obtained as a TFA salt. $^1$H NMR (500 MHz, dimethylsulfoxide-d$_6$) δ 8.67 (t, 1H), 8.59 (d, 1H), 8.21 (d, 1H), 8.12 (d, 1H), 7.89 (dd, 1H), 7.50 (d, 1H), 7.41 (d, 2H), 7.28 (d, 1H), 7.11 (d, 2H), 6.74 (dd, 1H), 6.39 (d, 1H), 5.77 (d, 2H), 3.86 (dd, 4H), 3.32-3.42 (m, 4H), 3.27 (dd, 4H), 2.99 (s, 4H), 2.23 (s, 2H), 2.04 (s, 2H), 1.91 (dd, 1H), 1.63 (d, 2H), 1.47 (t, 2H), 1.20-1.33 (m, 2H), 0.96 (s, 6H).

Example 398

2-[(6-amino-5-chloropyridin-3-yl)oxy]-4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)benzamide

Example 398A

4'-chloro-3-hydroxybiphenyl-2-carbaldehyde

2-Bromo-6-hydroxybenzaldehyde (2.0 g), 4-chlorophenylboronic acid (1.86 g) and tetrakis(triphenylphosphine)palladium(0) (0.575 g) were suspended in a mixed solvent of dimethoxyethane (7 mL), ethanol (2 mL) and 2N Na$_2$CO$_3$ aqueous solution (5 mL). The reaction mixture was heated at 90° C. for 2 hours. The reaction mixture was diluted with ethyl acetate and poured into water. The organic layer was washed with water and with brine, dried over anhydrous sodium sulfate, filtered, and concentrated. The resulting solid was triturated with methanol and filtered to afford the title compound.

Example 398B

4'-chloro-3-(2-(dimethylamino)ethoxy)biphenyl-2-carbaldehyde

EXAMPLE 398A (250 mg) and 2-chloro-N,N-dimethylethanamine hydrochloride salt (310 mg) was dissolved in mixed solvent of dichloromethane (5 mL) and 50% sodium hydroxide aqueous solution (0.5 mL), followed by addition of tetrabutylammonium iodide (79 mg). The reaction mixture was stirred at room temperature overnight. The reaction mixture was diluted with ethyl acetate and washed with water and brine. The organic phase was dried over anhydrous sodium sulfate, filtered, and concentrated. Flash column purification was performed with 0-5% methanol/dichloromethane to afford the title compound.

Example 398C

2-[(6-amino-5-chloropyridin-3-yl)oxy]-4-[4-({4'-chloro-3-[2-(dimethylamino)ethoxy]-1,1'-biphenyl-2-yl}methyl)piperazin-1-yl]-N-({3-nitro-4-[(tetrahydro-2H-pyran-4-ylmethyl)amino]phenyl}sulfonyl)benzamide This example was prepared by substituting EXAMPLE 398B for EXAMPLE 1F in EXAMPLE 1H. $^1$H NMR (300 MHz, DMSO) δ 11.67-11.61 (m, 1H), 9.91-9.71 (m, 1H), 9.13-8.93 (m, 1H), 8.68-8.65 (m, 1H), 8.59 (d, 1H), 7.85 (s, 1H), 7.75 (d, 1H), 7.54 (d, 3H), 7.47 (d, 1H), 7.41 (d, 1H), 7.38 (s, 2H), 7.24 (d, 2H), 6.98 (s, 1H), 6.71-6.64 (m, 1H), 6.21 (s, 2H), 4.45 (s, 8H), 3.83 (s, 3H), 3.60 (s, 3H), 3.31 (d, 6H), 2.92 (s, 4H), 1.99-1.82 (m, 1H), 1.60 (s, 2H), 1.36-1.18 (m, 2H).

Example 399

2-[(6-amino-5-chloropyridin-3-yl)oxy]-N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)benzamide

Example 399A (R)-5-chloro-6-((1-(1,3-difluoropropan-2-yl)pyrrolidin-3-yl)methoxy)pyridine-3-sulfonamide EXAMPLE 400B (278 mg) and 1,3-difluoropropan-2-one (94 mg) were suspended in 1,2-dichloroethane (10 mL). N,N-Dimethylformamide (1.5 mL) was added drop wise until a milky suspension formed. The reaction mixture was stirred at room temperature for 15 minutes followed by the addition of sodium triacetoxyborohydride (424 mg). The reaction mixture was stirred at room temperature overnight. The solvent was removed under vacuum. Flash column purification with 2.5-5% methanol/dichloromethane provided the title compound.

Example 399B

2-[(6-amino-5-chloropyridin-3-yl)oxy]-N-{[5-chloro-6-({(3R)-1-[2-fluoro-1-(fluoromethyl)ethyl]pyrrolidin-3-yl}methoxy)pyridin-3-yl]sulfonyl}-4-(4-{[2-(4-chlorophenyl)-4,4-dimethylcyclohex-1-en-1-yl]methyl}piperazin-1-yl)benzamide This example was prepared by substituting EXAMPLE 318E for EXAMPLE 110E and EXAMPLE 399A for EXAMPLE 1G in EXAMPLE 110F. $^1$H NMR (400 MHz, dimethylsulfoxide-$d_6$) δ 8.37 (d, 1H), 8.06 (d, 1H), 7.62 (d, 1H), 7.54 (d, 1H), 7.36 (m, 2H), 7.17 (d, 1H), 7.07 (m, 2H), 6.63 (dd, 1H), 6.27 (d, 1H), 5.92 (bs, 2H), 4.65 (m, 2H), 4.53 (m, 2H), 4.28 (m, 2H), 3.07 (s, 4H), 2.90 (m, 2H), 2.76 (m, 4H), 2.58 (m, 2H), 2.20 (m, 6H), 1.99 (m, 3H), 1.54 (m, 1H), 1.41 (t, 2H), 0.94 (s, 6H).

Example 400

2-[(6-amino-5-chloropyridin-3-yl)oxy]-N-[(5-chloro-6-{[(3R)-1-(2,2-difluoroethyl)pyrrolidin-3-yl]methoxy}pyridin-3-yl)sulfonyl]-4-(4-{[2-(4-chlorophenyl)-4,4-dimethylcyclohex-1-en-1-yl]methyl}piperazin-1-yl)benzamide

Example 400A (R)-tert-butyl 3-((3-chloro-5-sulfamoylpyridin-2-yloxy)methyl)pyrrolidine-1-carboxylate This example was prepared by substituting (R)-tert-butyl 3-(hydroxymethyl)pyrrolidine-1-carboxylate for (tetrahydro-2H-pyran-4-yl)methanol in EXAMPLE 303B.

Example 400B (R)-5-chloro-6-(pyrrolidin-3-ylmethoxy)pyridine-3-sulfonamide

EXAMPLE 400A (480 mg) was dissolved in anhydrous tetrahydrofuran (10 mL) followed by addition of hydrogen chloride in dioxane solution (4M, 2.5 mL). The reaction mixture was stirred at room temperature overnight. The solvent was removed under vacuum to provide the title compound.

Example 400C (R)-5-chloro-6-((1-(2,2-difluoroethyl)pyrrolidin-3-yl)methoxy)pyridine-3-sulfonamide A reaction mixture of EXAMPLE 400B (353 mg), 1,1-difluoro-2-iodoethane (268 mg) and $Na_2CO_3$ (283 mg) in N,N-dimethylformamide (10 mL) was heated at 80° C. overnight. The reaction mixture was cooled to room temperature and diluted with ethyl acetate. The organic phase was washed with water and brine, dried over anhydrous sodium sulfate, filtered, and concentrated. Flash column purification with 2.5-3% methanol/dichloromethane provided the title compound.

Example 400D

2-[(6-amino-5-chloropyridin-3-yl)oxy]-N-[(5-chloro-6-{[(3R)-1-(2,2-difluoroethyl)pyrrolidin-3-yl]methoxy}pyridin-3-yl)sulfonyl]-4-(4-({[2-(4-chlorophenyl)-4,4-dimethylcyclohex-1-en-1-yl]methyl}piperazin-1-yl)benzamide This example was prepared by substituting EXAMPLE 318E for EXAMPLE 110E and EXAMPLE 400C for EXAMPLE 1G in EXAMPLE 110F. $^1$H NMR (400 MHz, dimethylsulfoxide-$d_6$) δ 8.37 (d, 1H), 8.05 (d, 1H), 7.62 (d, 1H), 7.54 (d, 1H), 7.36 (m, 2H), 7.17 (d, 1H), 7.07 (d, 2H), 6.62 (dd, 1H), 6.27 (d, 1H), 6.07 (m, 3H), 4.27 (m, 2H), 3.07 (s, 4H), 2.83 (m, 5H), 2.64 (m, 3H), 2.20 (m, 6H), 1.99 (m, 4H), 1.54 (m, 1H), 1.41 (t, 2H), 0.94 (s, 6H).

Example 401

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide

Example 401A 2-(trans-4-(aminomethyl)cyclohexyl)acetonitrile

To a solution of tert-butyl (trans-4-(cyanomethyl)cyclohexyl)methylcarbamate (500 mg) in dichloromethane (5 mL) was slowly added trifluoroacetic acid (3 mL) at 0° C. The mixture was warmed to room temperature, stirred for 1 hour and concentrated. The residue was dried under vacuum to provide the title compound.

Example 401B 4-((trans-4-cyanocyclohexyl)methylamino)-3-nitrobenzenesulfonamide The title compound was prepared by substituting EXAMPLE 401A for 1-(tetrahydropyran-4-yl)methylamine in EXAMPLE 1G.

Example 401C

Trans-2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide The title compound was prepared as described in EXAMPLE 110F by replacing EXAMPLE 110E and EXAMPLE 1G with EXAMPLE 318E and EXAMPLE 401B. $^1$H NMR (400 MHz, dimethylsulfoxide-$d_6$) δ 8.63 (t, 1H), 8.58 (d, 1H), 7.85 (dd, 1H), 7.75 (d, 1H), 7.44 (d, 1H), 7.40 (d, 1H), 7.36 (d, 2H), 7.19 (d, 1H), 7.06 (d, 2H), 6.65 (dd, 1H), 6.19 (s, 3H), 3.24-3.31 (m, 4H), 3.12 (s, 4H), 2.79 (s, 2H), 2.58-2.69 (m, 1H), 2.25 (s, 4H), 2.17 (s, 2H), 1.92-2.07 (m, 4H), 1.79 (d, 2H), 1.60-1.73 (m, 1H), 1.34-1.55 (m, 4H), 0.97-1.12 (m, 2H), 0.94 (s, 6H).

Example 402

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide

Example 402A 5-bromo-3-fluoro-2-((4-fluorotetrahydro-2H-pyran-4-yl)methoxy)pyridine This example was prepared by substituting EXAMPLE 296C for (tetrahydro-2H-pyran-4-yl)methanol and 5-bromo-2,3-difluoropyridine for 4-fluoro-3-nitrobenzenesulfonamide in EXAMPLE 264A.

Example 402B tert-butyl 5-fluoro-6-((4-fluorotetrahydro-2H-pyran-4-yl)methoxy)pyridin-3-ylcarbamate EXAMPLE 402A (0.658 g), tert-butyl carbamate (0.300 g), palladium(II) acetate (0.024 g), 4,5-bis(diphenylphosphino)-9,9-dimethylxanthene (0.093 g) and cesium carbonate (1.044 g) were combined in a 20 mL vial with dioxane (10.7 ml). The vial was flushed with nitrogen, capped and stirred at 100° C. overnight. The reaction mixture was diluted with ethyl acetate, washed with water and brine, dried (MgSO$_4$), filtered, concentrated and chromatographed on silica gel with 20% ethyl acetate in hexanes as eluent.

Example 402C 5-fluoro-6-((4-fluorotetrahydro-2H-pyran-4-yl)methoxy)pyridine-3-sulfonyl chloride Under ice-cooling, thionyl chloride (1.563 mL) was added dropwise over 20 minutes to water (9 mL). The mixture was stirred for 12 hours to give a SO$_2$-containing solution. Separately, EXAMPLE 402B (0.295 g) was added to a mixture of dioxane (3.2 mL) and concentrated HCl (8 ml) at 0° C. The solution was stirred for 15 minutes, treated with a solution of sodium nitrite (0.065 g) in water (2 mL) dropwise at 0° C. and stirred at 0° C. for 3 hours. The SO$_2$-containing solution was cooled to 0° C., treated sequentially with copper (1) chloride (0.042 g) and the diazotized mixture, and stirred for 30 minutes. The reaction mixture was then extracted with ethyl acetate and the organic layer was dried (MgSO$_4$), filtered and concentrated. The residue was chromatographed on silica gel with 5-10% ethyl acetate in hexanes as the eluent.

Example 402D 5-fluoro-6-((4-fluorotetrahydro-2H-pyran-4-yl)methoxy)pyridine-3-sulfonamide EXAMPLE 402C (0.08 g) in isopropanol (2 mL) at 0° C. was treated with ammonium hydroxide (1.70 mL) and stirred overnight. The reaction mixture was concentrated, slurried in water, filtered, rinsed with water and dried under vacuum.

Example 402E

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({5-fluoro-6-[(4-fluorotetrahydro-2H-pyran-4-yl)methoxy]pyridin-3-yl}sulfonyl)benzamide This example was prepared by substituting EXAMPLE 402D for EXAMPLE 1G and EXAMPLE 318E for EXAMPLE 110E in EXAMPLE 1100F. $^1$H NMR (400 MHz, pyridine-d$_5$) δ 9.05 (d, 1H), 8.49 (dd, 1H), 8.03 (d, 1H), 8.00 (d, 1H), 7.45 (m, 2H), 7.39 (d, 1H), 7.09 (m, 2H), 6.73 (dd, 1H), 6.52 (d, 1H), 4.59 (d, 2H), 3.81 (m, 4H), 3.12 (m, 4H), 2.80 (s, 2H), 2.29 (t, 2H), 2.18 (m, 4H), 1.99 (s, 2H), 1.88 (m, 4H), 1.41 (t, 2H), 0.95 (s, 6H).

Example 403

2-[(6-amino-5-chloropyridin-3-yl)oxy]-N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide

Example 403A

EXAMPLE 393C (0.263 g), 1,1-difluoro-2-iodoethane (0.23 g), and sodium carbonate (0.254 g) were combined in a 20 mL vial with N,N-dimethylformamide (6 mL) and the mixture stirred at 70° C. overnight. The reaction mixture was concentrated under high vacuum, chromatographed on silica gel with 0-5% methanol in dichloromethane as the eluent, and dried overnight in a vacuum oven at 80° C.

Example 403B

2-[(6-amino-5-chloropyridin-3-yl)oxy]-N-[(5-chloro-6-{[1-(2,2-difluoroethyl)-4-fluoropiperidin-4-yl]methoxy}pyridin-3-yl)sulfonyl]-4-(4-{[2-(4-chlorophenyl)-4,4-dimethylcyclohex-1-en-1-yl]methyl}piperazin-1-yl)benzamide This example was prepared by substituting EXAMPLE 403A for EXAMPLE 1G and EXAMPLE 318E for EXAMPLE 110E in EXAMPLE 110F. $^1$H NMR (400 MHz, pyridine-d$_5$) δ 9.15 (d, 1H), 8.75 (d, 1H), 8.02 (d, 1H), 8.00 (d, 1H), 7.45 (m, 2H), 7.38 (d, 1H), 7.09 (m, 2H), 6.72 (dd, 1H), 6.50 (d, 1H), 6.18 (tt, 1H), 4.55 (d, 2H), 3.12 (m, 4H), 2.80 (m, 6H), 2.60 (td, 2H), 2.28 (t, 2H), 2.17 (m, 4H), 1.93 (m, 6H), 1.41 (t, 2H), 0.95 (s, 6H).

Example 404

2-[(6-amino-5-chloropyridin-3-yl)oxy]-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide

Example 404A 3-chloro-4-((4-fluorotetrahydro-2H-pyran-4-yl)methoxy)benzenesulfonamide To a solution of EXAMPLE 296C (0.175 g) in tetrahydrofuran (5 ml) was added sodium hydride (0.209 g) and the reaction stirred at room temperature for 15 minutes. 3-Chloro-4-fluorobenzenesulfonamide (0.273 g) was added and the reaction stirred for 3 hours. To the thick suspension was added tetrahydrofuran (2 ml) and N,N-dimethylformamide (3 ml). The reaction was stirred for 3 hours at 60° C. then poured into dichloromethane (50 ml) and 1N aqueous HCl (50 ml). The organic layer was washed with brine (35 ml) dried over magnesium sulfate, filtered, and concentrated. Silica gel chromatography (Reveleris 40 g) eluting with a

Example 404B

2-[(6-amino-5-chloropyridin-3-yl)oxy]-N-({3-chloro-4-[(4-fluorotetrahydro-2H-pyran-4-yl)methoxy]phenyl}sulfonyl)-4-(4-{[2-(4-chlorophenyl)-4,4-dimethylcyclohex-1-en-1-yl]methyl}piperazin-1-yl)benzamide This example was prepared by substituting EXAMPLE 318E for EXAMPLE 1F and EXAMPLE 404A for EXAMPLE 1G in EXAMPLE 1H. $^1$H NMR (300 MHz, DMSO) δ 11.44-11.17 (m, 1H), 7.91 (d, 1H), 7.83 (dd, 1H), 7.77 (d, 1H), 7.44 (d, 2H), 7.35 (dd, 3H), 7.06 (d, 2H), 6.66 (d, 1H), 6.19 (d, 3H), 4.31 (d, 2H), 3.84-3.73 (m, 2H), 3.66-3.55 (m, 2H), 3.13 (s, 4H), 2.81 (s, 2H), 2.26 (s, 4H), 2.17 (s, 2H), 2.02-1.74 (m, 6H), 1.41 (t, 2H), 0.94 (s, 6H).

Example 405

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}benzamide

Example 405A 5-nitro-3-(trifluoromethyl)pyridin-2-ol 3-(Trifluoromethyl)pyridin-2-ol (2.3 g) was added to concentrated sulfuric acid (15 mL) at 0° C. The mixture was stirred at 0° C. for 5 minutes. To this solution was added nitric acid (fuming, 6 mL) dropwise over 5 minutes. The reaction mixture was stirred at room temperature for 2 hours, and then heated at 50° C. for 3 hours. After cooling, the reaction mixture was poured into ice (200 g), and the mixture was extracted with ethyl acetate three times. The combined organic layers were washed with brine, dried over MgSO$_4$, filtered, and concentrated under reduced pressure to give the title compound.

Example 405B 2-chloro-5-nitro-3-(trifluoromethyl)pyridine

A mixture of EXAMPLE 405A (1.69 g), phosphorus pentachloride (2.03 g), and phosphoryl trichloride (0.97 mL) was heated at 90° C. for 3 hours. After cooling, the reaction mixture was poured into ice, and extracted with ethyl acetate three times. The extract was washed with brine, dried over MgSO$_4$, filtered, and concentrated under reduced pressure. The residue was purified by flash column chromatography on silica gel eluting with 1:9 ethyl acetate\hexanes to give the title compound.

Example 405C

A mixture of iron (1.5 g) and ammonium chloride (2.38 g) in water (40 mL) was stirred at room temperature for 5 minutes. To this suspension was added EXAMPLE 405B in methanol (40 mL). The reaction mixture was stirred at room temperature for 1 hour. More iron (1.8 g) was added to the reaction mixture, and it was stirred for another 3 hours. The solid from the reaction mixture was filtered off, and the filtrate was partitioned between water and ethyl acetate. The combined organic layers were washed with brine, dried over MgSO$_4$, filtered, and concentrated under reduced pressure. The residue was purified by flash column chromatography on silica gel eluting with 1:4 ethyl acetate\hexanes to give the title compound.

Example 405D 6-chloro-5-(trifluoromethyl)pyridine-3-sulfonyl chloride

Under ice-cooling, thionyl chloride (4 mL) was added dropwise over 20 minutes to water (27 mL). The mixture was stirred overnight for 12 hours to give a SO$_2$ containing solution. Separately, EXAMPLE 405C (1.14 g) in dioxane (5 mL) was added to concentrated HCl (20 mL) at 0° C. The solution was stirred for 5 minutes. To this suspension/solution was added sodium nitrite (0.44 g) in water (6 mL) dropwise at 0° C. The solution stirred at 0° C. for 3 hours. To the SO$_2$ containing solution was added copper(I) chloride (0.115 g). Then, to this solution was added the diazotized EXAMPLE 405C at 0° C. The solution was stirred for 30 minutes. The reaction mixture was extracted with ethyl acetate. The combined organic layers were washed with brine, dried over MgSO$_4$, filtered, and concentrated under reduced pressure. The residue was purified by flash column chromatography on silica gel eluting with 1:20 ethyl acetate\hexanes to give the title compound.

Example 405E 6-chloro-5-(trifluoromethyl)pyridine-3-sulfonamide

This example was prepared by substituting EXAMPLE 405D for 5-bromo-6-chloropyridine-3-sulfonyl chloride in EXAMPLE 305A.

Example 405F tert-butyl 4-fluoro-4-((5-sulfamoyl-3-(trifluoromethyl)pyridin-2-yloxy)methyl)piperidine-1-carboxylate This example was prepared by substituting EXAMPLE 405E for EXAMPLE 305A and EXAMPLE 341A for (1,4-dioxan-2-yl)methanol in EXAMPLE 305B.

Example 405G 6-((4-fluoropiperidin-4-yl)methoxy)-5-(trifluoromethyl)pyridine-3-sulfonamide This example was prepared by substituting EXAMPLE 405F for EXAMPLE 400A in EXAMPLE 400B.

Example 405H 6-((1-(1,3-difluoropropan-2-yl)-4-fluoropiperidin-4-yl)methoxy)-5-(trifluoromethyl)pyridine-3-sulfonamide This example was prepared by substituting EXAMPLE 405G for EXAMPLE 400B in EXAMPLE 399A.

Example 4051

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-{[6-({4-fluoro-1-[2-fluoro-1-(fluoromethyl)ethyl]piperidin-4-yl}methoxy)-5-(trifluoromethyl)pyridin-3-yl]sulfonyl}benzamide This example was prepared by substituting EXAMPLE 318E for EXAMPLE 110E and EXAMPLE 405H for EXAMPLE 1G in EXAMPLE 110F. $^1$H NMR (400 MHz, dimethylsulfoxide-$d_6$) δ 8.62 (d, 1H), 8.29 (d, 1H), 7.57 (m, 2H), 7.36 (d, 2H), 7.09 (m, 3H), 6.62 (dd, 1H), 6.29 (d, 1H), 5.86 (bs, 2H), 4.67 (d, 2H), 4.53 (m, 4H), 3.08 (m, 5H), 2.74 (m, 6H), 2.19 (m, 6H), 1.89 (m, 6H), 1.41 (t, 2H), 0.94 (s, 6H).

Example 406

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide

Example 406A 2-(2-bromophenoxy)-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide The title compound was prepared as described in EXAMPLE 110F by replacing EXAMPLE 110E with EXAMPLE 42C.

Example 406B 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide A mixture of EXAMPLE 406A (57 mg), tert-butyl 4-(4,4,5,5-tetramethyl-1,3,2-dioxaborolan-2-yl)-1H-pyrazole-1-carboxylate (27.7 mg), dichlorobis(triphenylphosphine)palladium(II) (6.61 mg), $K_2CO_3$ (0.2 ml) in a dimethoxyethane/ethanol/water (7:2:3) was heated at 160° C. for 10 minutes in a Biotage microwave synthesizer and concentrated. The residue was dissolved in dimethylsulfoxide:methanol (1:1) and purified by HPLC, eluting with 40-65% acetonitrile in 0.1% TFA water over 40 minutes to provide the title compound as a TFA salt. The TFA salt was dissolved in dichloromethane and washed with saturated $NaHCO_3$ aqueous solution. The organic layer was dried over $Na_2SO_4$, filtered, and concentrated to provide the title compound. $^1$H NMR (400 MHz, dimethylsulfoxide-$d_6$) δ 12.87 (s, 1H), 11.55 (s, 1H), 8.58 (t, 1H), 8.47 (d, 1H), 8.11 (s, 1H), 7.85 (s, 1H), 7.76 (dd, 1H), 7.59-7.67 (m, 1H), 7.48 (d, 1H), 7.34 (d, 2H), 7.00-7.11 (m, 5H), 6.73 (dd, 1H), 6.67 (dd, 1H), 6.08 (d, 1H), 3.85 (dd, 2H), 3.20-3.29 (m, 4H), 3.04 (s, 4H), 2.77 (s, 2H), 2.17 (d, 6H), 1.96 (s, 2H), 1.80-1.92 (m, 1H), 1.55-1.70 (m, 2H), 1.39 (t, 2H), 1.19-1.32 (m, 2H), 0.93 (s, 6H).

Example 407

2-[2-(2-aminopyridin-3-yl)phenoxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide The title compound was prepared as described in EXAMPLE 406B by replacing tert-butyl 4-(4,4,5,5-tetramethyl-1,3,2-dioxaborolan-2-yl)-1H-pyrazole-1-carboxylate with tert-butyl 3-(4,4,5,5-tetramethyl-1,3,2-dioxaborolan-2-yl)pyridin-2-ylcarbamate. $^1$H NMR (400 MHz, dimethylsulfoxide-$d_6$) δ 8.57 (t, 1H), 8.41 (d, 1H), 7.92 (dd, 1H), 7.74 (dd, 1H), 7.60 (d, 1H), 7.41 (d, 1H), 7.36 (d, 2H), 7.18 (dd, 1H), 7.02-7.13 (m, 5H), 6.97 (t, 1H), 6.70 (dd, 1H), 6.61-6.67 (m, 1H), 6.55 (d, 1H), 6.31 (d, 1H), 3.84 (dd, 2H), 3.21-3.30 (m, 4H), 3.15 (s, 4H), 2.83 (s, 2H), 2.23-2.34 (m, 4H), 2.17 (s, 2H), 1.84-2.02 (m, 3H), 1.63 (dd, 2H), 1.40 (t, 2H), 1.20-1.33 (m, 2H), 0.94 (s, 6H).

Example 408

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-5-yl)phenoxy]benzamide The title compound was prepared as described in EXAMPLE 406B by replacing tert-butyl 4-(4,4,5,5-tetramethyl-1,3,2-dioxaborolan-2-yl)-1H-pyrazole-1-carboxylate with 1H-pyrazol-5-ylboronic acid. $^1$H NMR (400 MHz, dimethylsulfoxide-$d_6$) δ 12.95 (s, 1H), 8.60 (s, 1H), 8.52 (s, 1H), 7.85 (s, 2H), 7.57-7.73 (m, 1H), 7.48 (d, 1H), 7.22-7.37 (m, 4H), 7.00-7.15 (m, 4H), 6.56-6.70 (m, 2H), 5.96 (s, 2H), 3.85 (dd, 2H), 3.21-3.28 (m, 4H), 3.02 (s, 4H), 2.70-2.85 (m, 2H), 2.10-2.30 (m, 5H), 1.83-1.99 (m, 3H), 1.62 (d, 2H), 1.39 (t, 2H), 1.19-1.31 (m, 2H), 0.92 (s, 6H).

Example 409

2-[(6-amino-5-chloropyridin-3-yl)oxy]-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide

Example 409A (4,4-difluorocyclohexyl)methanol

Lithium aluminum hydride (0.24 g) was added to diethyl ether (15 mL), to which was then added dropwise ethyl 4,4-difluorocyclohexanecarboxylate (1.0 g) in diethyl ether (2 mL), and the reaction was stirred at reflux under nitrogen for 4 hours. The reaction was cooled to 0° C., followed by the careful addition of water (0.24 mL), 4N aqueous NaOH (0.24 mL), and additional water (0.72 mL). Then $Na_2SO_4$ and diethyl ether (40 mL) were added and the mixture was stirred for 30 minutes. After filtration through diatomaceous earth and concentration, the title compound was used in the next step without further purification.

Example 409B 5-chloro-6-((4,4-difluorocyclohexyl)methoxy)pyridine-3-sulfonamide This example was prepared by substituting EXAMPLE 409A for (1,4-dioxan-2-yl)methanol and EXAMPLE 303A for EXAMPLE 305A in EXAMPLE 305B.

Example 409C

2-[(6-amino-5-chloropyridin-3-yl)oxy]-N-({5-chloro-6-[(4,4-difluorocyclohexyl)methoxy]pyridin-3-yl}sulfonyl)-4-(4-{[2-(4-chlorophenyl)-4,4-dimethylcyclohex-1-en-1-yl]methyl}piperazin-1-yl)benzamide This example was prepared by substituting EXAMPLE 318E for EXAMPLE 122C and EXAMPLE 409B for EXAMPLE 11A in EXAMPLE 137. $^1$H NMR (500 MHz, dimethylsulfoxide-d$_6$) δ 8.54 (s, 1H), 8.20 (2, 1H), 7.73 (d, 1H), 7.50 (d, 1H), 7.37 (m, 3H), 7.07 (d, 2H), 6.66 (dd, 1H), 6.22 (s, 1H), 6.13 (br s, 2H), 4.30 (d, 2H), 3.17 (v br m, 4H), 2.98 (v br s, 2H), 2.43 (v br m, 4H), 2.18 (br t, 2H), 2.05 (br m, 3H), 1.98 (s, 2H), 1.8 (br m, 4H), 1.43 (t, 2H), 1.35 (br m, 2H), 0.94 (s, 6H).

Example 410

N-({5-chloro-6-[(4,4-difluorocyclohexyl)methoxy]pyridin-3-yl}sulfonyl)-4-(4-{[4-(4-chlorophenyl)-6,6-dimethyl-5,6-dihydro-2H-pyran-3-yl]methyl}piperazin-1-yl)-2-[(6-fluoro-1H-indol-5-yl)oxy]benzamide This example was prepared by substituting EXAMPLE 277B for EXAMPLE 122C and EXAMPLE 409B for EXAMPLE 11A in EXAMPLE 137. $^1$H NMR (500 MHz, dimethylsulfoxide-d$_6$) δ 11.22 (s, 1H), 8.60 (d, 1H), 8.26 (d, 1H), 7.54 (d, 1H), 7.38 (m, 4H), 7.29 (br d, 1H), 7.13 (d, 2H), 6.64 (d, 1H), 6.41 (s, 1H), 6.09 (s, 1H), 4.30 (d, 2H), 4.10 (s, 2H), 3.05 (v br s, 4H), 2.86 (v br s, 2H), 2.25 (v br s, 4H), 2.15 (s, 2H), 2.03 (br m, 2H), 1.96 (br m, 1H), 1.85 (br m, 4H), 1.36 (m, 2H), 1.18 (s, 6H).

Example 411

4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]-2-[(6-fluoro-1H-indol-5-yl)oxy]benzamide This example was prepared by substituting EXAMPLE 154E for EXAMPLE 122C and EXAMPLE 396C for EXAMPLE 11A in EXAMPLE 137. $^1$H NMR (400 MHz, dimethylsulfoxide-d$_6$) δ 11.22 (s, 1H), 8.65 (t, 1H), 8.60 (d, 1H), 7.88 (dd, 1H), 7.52 (d, 1H), 7.39 (dd, 1H), 7.35 (m, 4H), 7.18 (d, 1H), 7.03 (d, 2H), 6.65 (dd, 1H), 6.21 (s, 1H), 6.08 (s, 1H), 3.04 (v br m, 4H), 2.76 (br s, 2H), 2.20 (v br m, 4H), 2.13 (br t, 2H), 2.00 (br m, 3H), 1.95 (s, 2H), 1.81 (br m, 6H), 1.39 (t, 2H), 1.24 (br m, 2H), 0.91 (s, 6H).

What is claimed is:
1. A compound having Formula (II)

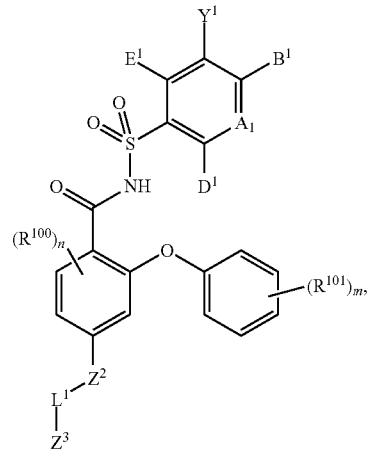

or a therapeutically acceptable salt thereof,
wherein
R$^{100}$ is absent;
n is 0;
m is 1, 2, 3, 4, or 5;
A$^1$ is C(A$^2$);
A$^2$ is H;
B$^1$ is NHR$^1$;
D$^1$ and E$^1$ are each H;
R$^1$ is R$^3$, wherein R$^5$ is alkyl which is unsubstituted or substituted with one or two or three substituents independently selected from R$^6$, R$^7$, OR$^7$, SR$^7$, S(O)R$^7$, SO$_2$R$^7$, NHR$^7$, N(R$^7$)$_2$, C(O)R$^7$, C(O)NH$_2$, C(O)NHR$^7$, C(O)N(R$^7$)$_2$, NHC(O)R$^7$, NR$^7$C(O)R$^7$, NHSO$_2$R$^7$, NHC(O)OR$^7$, SO$_2$NH$_2$, SO$_2$NHR$^7$, SO$_2$N(R$^7$)$_2$, NHC(O)NH$_2$, NHC(O)NHR$^7$, NHC(O)CH(CH$_3$)NHC(O)CH(CH$_3$)NH$_2$, OH, (O), C(O)OH, N$_3$, CN, NH$_2$, CF$_3$, CF$_2$CF$_3$, F, Cl, Br and I;
Y$^1$ is NO$_2$;
Z$^2$ is R$^{30}$, wherein R$^{30}$ is unfused piperazinyl;
L$^1$ is R$^{37}$, wherein R$^{37}$ is methylene;
Z$^3$ is R$^{40}$, wherein R$^{40}$ is unfused cyclohexenyl;
R$^6$ is C$_2$-C$_5$-spiroalkyl, which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;
R$^7$ is R$^8$, R$^9$, R$^{10}$ or R$^{11}$;
R$^8$ is phenyl, which is unfused or fused with benzene, heteroarene or R$^{8A}$; R$^{8A}$ is cycloalkane, cycloalkene, heterocycloalkane or heterocycloalkene;
R$^9$ is heteroaryl, which is unfused or fused with benzene, heteroarene or R$^{9A}$; R$^{9A}$ is cycloalkane, cycloalkene, heterocycloalkane or heterocycloalkene;
R$^{10}$ is cycloalkyl, cycloalkenyl, heterocycloalkyl or heterocycloalkenyl each of which is unfused or fused with benzene, heteroarene or R$^{10A}$; R$^{10A}$ is cycloalkane, cycloalkene, heterocycloalkane or heterocycloalkene;
R$^{11}$ is alkyl, alkenyl or alkynyl, each of which is unsubstituted or substituted with one or two or three independently selected R$^{12}$, OR$^{12}$, SR$^{12}$, S(O)R$^{12}$, SO$_2$R$^{12}$, C(O)R$^{12}$, CO(O)R$^{12}$, OC(O)R$^{12}$, OC(O)OR$^{12}$, NH$_2$, NHR$^{12}$, N(R$^{12}$)$_2$, NHC(O)R$^{12}$, NR$^{12}$C(O)R$^{12}$, NHS(O)$_2$R$^{12}$, NR$^{12}$S(O)$_2$R$^{12}$, NHC(O)OR$^{12}$, NR$^{12}$C(O)OR$^{12}$, NHC(O)NH$_2$, NHC(O)NHR$^{12}$, NHC(O)N ($R^{12}$)$_2$, $NR^{12}C(O)NHR^{12}$, $NR^{12}C(O)N(R^{12})_2$, $C(O)$ $NH_2$, $C(O)NHR^{12}$, $C(O)N(R^{12})_2$, $C(O)NHOH$, $C(O)$ $NHOR^{12}$, $C(O)NHSO_2R^{12}$, $C(O)NR^{12}SO_2R^{12}$, $SO_2NH_2$, $SO_2NHR^{12}$, $SO_2N(R^{12})_2$, $C(O)H$, $C(O)OH$, $C(N)NH_2$, $C(N)NHR^{12}$, $C(N)N(R^{12})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{12}$ is $R^{13}$, $R^{14}$, $R^{15}$ or $R^{16}$;

$R^{13}$ is phenyl, which is unfused or fused with benzene, heteroarene or $R^{13A}$; $R^{13A}$ is cycloalkane, cycloalkene, heterocycloalkane or heterocycloalkene;

$R^{14}$ is heteroaryl, which is unfused or fused with benzene, heteroarene or $R^{14A}$; $R^{14A}$ is cycloalkane, cycloalkene, heterocycloalkane or heterocycloalkene;

$R^{15}$ is cycloalkane, cycloalkene, heterocycloalkane or heterocycloalkene, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkynyl;

$R^{101}$ is selected from the group consisting of $R^{50}$, $OR^{50}$, $SR^{50}$, $S(O)R^{50}$, $SO_2R^{50}$, $C(O)R^{50}$, $CO(O)R^{50}$, $OC(O)R^{50}$, $OC(O)OR^{50}$, $NH_2$, $NHR^{50}$, $N(R^{50})_2$, $NHC(O)R^{50}$, $NR^{50}C(O)R^{50}$, $NHS(O)_2R^{50}$, $NR^{50}S(O)_2R^{50}$, $NHC(O)OR^{50}$, $NR^{50}C(O)OR^{50}$, $NHC(O)NH_2$, $NHC(O)NHR^{50}$, $NHC(O)N(R^{50})_2$, $NR^{50}C(O)NHR^{50}$, $NR^{50}C(O)N(R^{50})_2$, $C(O)NH_2$, $C(O)NHR^{50}$, $C(O)N(R^{50})_2$, $C(O)NHOH$, $C(O)NHOR^{50}$, $C(O)NHSO_2R^{50}$, $C(O)NR^{50}SO_2R^{50}$, $SO_2NH_2$, $SO_2NHR^{50}$, $SO_2N(R^{50})_2$, $C(O)H$, $C(O)OH$, $C(N)NH_2$, $C(N)NHR^{50}$, $C(N)N(R^{50})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br and I;

$R^{50}$ is $R^{51}$, $R^{52}$, $R^{53}$ or $R^{54}$;

$R^{51}$ is phenyl, which is unfused or fused with benzene, heteroarene or $R^{51A}$; $R^{51A}$ is cycloalkane, cycloalkene, heterocycloalkane or heterocycloalkene;

$R^{52}$ is heteroaryl, which is unfused or fused with benzene, heteroarene or $R^{52A}$; $R^{52A}$ is cycloalkane, cycloalkene, heterocycloalkane or heterocycloalkene;

$R^{53}$ is cycloalkyl, cycloalkenyl, heterocycloalkyl or heterocycloalkenyl, each of which is unfused or fused with benzene, heteroarene or $R^{53A}$; $R^{53A}$ is cycloalkane, cycloalkene, heterocycloalkane or heterocycloalkene;

$R^{54}$ is alkyl, alkenyl or alkynyl, each of which is unsubstituted or substituted with one or two or three of independently selected $R^{55}$, $OR^{55}$, $SR^{55}$, $S(O)R^{55}$, $SO_2R^{55}$, $C(O)R^{55}$, $CO(O)R^{55}$, $OC(O)R^{55}$, $OC(O)OR^{55}$, $NH_2$, $NHR^{55}$, $N(R^{55})_2$, $NHC(O)R^{55}$, $NR^{55}C(O)R^{55}$, $NHS(O)_2R^{55}$, $NR^{55}S(O)_2R^{55}$, $NHC(O)OR^{55}$, $NR^{55}C(O)OR^{55}$, $NHC(O)NH_2$, $NHC(O)NHR^{55}$, $NHC(O)N(R^{55})_2$, $NR^{55}C(O)NHR^{55}$, $NR^{55}C(O)N(R^{55})_2$, $C(O)NH_2$, $C(O)NHR^{55}$, $C(O)N(R^{55})_2$, $C(O)NHOH$, $C(O)NHOR^{55}$, $C(O)NHSO_2R^{55}$, $C(O)NR^{55}SO_2R^{55}$, $SO_2NH_2$, $SO_2NHR^{55}$, $SO_2N(R^{55})_2$, $C(O)H$, $C(O)OH$, $C(N)NH_2$, $C(N)NHR^{55}$, $C(N)N(R^{55})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{55}$ is alkyl, alkenyl, alkynyl, phenyl, heteroaryl, cycloalkyl, cycloalkenyl, heterocycloalkyl or heterocycloalkenyl;

wherein each cyclic moiety represented by $R^8$, $R^9$, $R^{10}$, $R^{13}$, $R^{14}$, $R^{15}$, $R^{40}$, $R^{51}$, $R^{52}$, $R^{53}$ and $R^{55}$ is independently unsubstituted, substituted or further substituted with one or two or three or four or five of independently selected $R^{57A}$, $R^{57}$, $OR^{57}$, $SR^{57}$, $S(O)R^{57}$, $SO_2R^{57}$, $C(O)R^{57}$, $CO(O)R^{57}$, $OC(O)R^{57}$, $OC(O)OR^{57}$, $NH_2$, $NHR^{57}$, $N(R^{57})_2$, $NHC(O)R^{57}$, $NR^{57}C(O)R^{57}$, $NHS(O)_2R^{57}$, $NR^{57}S(O)_2R^{57}$, $NHC(O)OR^{57}$, $NR^{57}C(O)OR^{57}$, $NHC$ $(O)NH_2$, $NHC(O)NHR^{57}$, $NHC(O)N(R^{57})_2$, $NR^{57}C(O)NHR^{57}$, $NR^{57}C(O)N(R^{57})_3$, $C(O)NH_2$, $C(O)NHR^{57}$, $C(O)N(R^{57})_2$, $C(O)NHOH$, $C(O)NHOR^{57}$, $C(O)NHSO_2R^{57}$, $C(O)NR^{57}SO_2R^{57}$, $SO_2NH_2$, $SO_2NHR^{57}$, $SO_2N(R^{57})_2$, $C(O)H$, $C(O)OH$, $C(N)NH_2$, $C(N)NHR^{57}$, $C(N)N(R^{57})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I;

$R^{57A}$ is spirocyclyl;

$R^{57}$ is $R^{58}$, $R^{59}$, $R^{60}$ or $R^{61}$;

$R^{58}$ is phenyl, which is unfused or fused with benzene, heteroarene or $R^{58A}$; $R^{58A}$ is cycloalkane, cycloalkene, heterocycloalkane or heterocycloalkene;

$R^{59}$ is heteroaryl, which is unfused or fused with benzene, heteroarene or $R^{59A}$; $R^{59A}$ is cycloalkane, cycloalkene, heterocycloalkane or heterocycloalkene;

$R^{60}$ is cycloalkyl, cycloalkenyl, heterocycloalkyl or heterocycloalkenyl, each of which is unfused or fused with benzene, heteroarene or $R^{60A}$; $R^{60A}$ is cycloalkane, cycloalkene, heterocycloalkane or heterocycloalkene;

$R^{61}$ is alkyl, alkenyl or alkynyl, each of which is unsubstituted or substituted with one or two or three of independently selected $R^{62}$, $OR^{62}$, $SR^{62}$, $S(O)R^{62}$, $SO_2R^{62}$, $C(O)R^{62}$, $CO(O)R^{62}$, $OC(O)R^{62}$, $OC(O)OR^{62}$, $NH_2$, $NHR^{62}$, $N(R^{62})_2$, $NHC(O)R^{62}$, $NR^{62}C(O)R^{62}$, $NHS(O)_2R^{62}$, $NR^{62}S(O)_2R^{62}$, $NHC(O)OR^{62}$, $NR^{62}C(O)OR^{62}$, $NHC(O)NH_2$, $NHC(O)NHR^{62}$, $NHC(O)N(R^{62})_2$, $NR^{62}C(O)NHR^{62}$, $NR^{62}C(O)N(R^{62})_2$, $C(O)NH_2$, $C(O)NHR^{62}$, $C(O)N(R^{62})_2$, $C(O)NHOH$, $C(O)NHOR^{62}$, $C(O)NHSO_2R^{62}$, $C(O)NR^{62}SO_2R^{62}$, $SO_2NH_2$, $SO_2NHR^{62}$, $SO_2N(R^{62})_2$, $C(O)H$, $C(O)OH$, $C(N)NH_2$, $C(N)NHR^{62}$, $C(N)N(R^{62})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, C, Br or I;

$R^{62}$ is $R^{63}$, $R^{64}$, $R^{65}$ or $R^{66}$;

$R^{63}$ is phenyl, which is unfused or fused with benzene, heteroarene or $R^{63A}$; $R^{63A}$ is cycloalkane, cycloalkene, heterocycloalkane or heterocycloalkene;

$R^{64}$ is heteroaryl, which is unfused or fused with benzene, heteroarene or $R^{64A}$; $R^{64A}$ is cycloalkane, cycloalkene, heterocycloalkane or heterocycloalkene;

$R^{65}$ is cycloalkyl, cycloalkenyl, heterocycloalkyl or heterocycloalkenyl, each of which is unfused or fused with benzene, heteroarene or $R^{65A}$; $R^{65A}$ is cycloalkane, cycloalkene, heterocycloalkane or heterocycloalkene;

$R^{66}$ is alkyl, alkenyl or alkynyl, each of which is unsubstituted or substituted with one or two or three of independently selected $R^{67}$, $OR^{67}$, $SR^{67}$, $S(O)R^{67}$, $SO_2R^{67}$, $C(O)R^{67}$, $CO(O)R^{67}$, $OC(O)R^7$, $OC(O)OR^{67}$, $NH_2$, $NHR^7$, $N(R^{67})_2$, $NHC(O)R^{67}$, $NR^{67}C(O)R^{67}$, $NHS(O)_2R^{67}$, $NR^{67}S(O)_2R^{67}$, $NHC(O)OR^{67}$, $NR^{67}C(O)OR^{67}$, $NHC(O)NH_2$, $NHC(O)NHR^{67}$, $NHC(O)N(R^{67})_2$, $NR^{67}C(O)NHR^{67}$, $NR^{67}C(O)N(R^{67})_2$, $C(O)NH_2$, $C(O)NHR^{67}$, $C(O)N(R^{67})_2$, $C(O)NHOH$, $C(O)NHOR^{67}$, $C(O)NHSO_2R^{67}$, $C(O)NR^{67}SO_2R^{67}$, $SO_2NH_2$, $SO_2NHR^{67}$, $SO_2N(R^{67})_2$, $C(O)H$, $C(O)OH$, $C(N)NH_2$, $C(N)NHR^{67}$, $C(N)N(R^{67})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{67}$ is alkyl, alkenyl, alkynyl, phenyl, heteroaryl, cycloalkyl, cycloalkenyl, heterocycloalkyl or heterocycloalkenyl;

wherein the moieties represented by $R^{57A}$, $R^{58}$, $R^{59}$, $R^{60}$, $R^{63}$, $R^{64}$, $R^{65}$, and $R^{67}$ are unsubstituted or substituted with one or two or three or four of independently selected $R^{68}$, $OR^{68}$, $SR^{68}$, $S(O)R$, $SO_2R^{68}$, $C(O)R^{68}$, $CO(O)R^{68}$, $OC(O)R^{68}$, $OC(O)OR^{68}$, $NH_2$, $NHR^{68}$, $N(R^{68})_2$, $NHC(O)R$, $NR^{68}C(O)R^{68}$, $NHS(O)_2R^{68}$, NR⁶⁸S(O)₂R⁶⁸, NHC(O)OR⁶⁸, NR⁶⁸C(O)OR⁶⁸, NHC(O)NH₂, NHC(O)NHR⁶⁸, NHC(O)N(R⁶⁸)₂, NR⁶⁸C(O)NHR⁶⁸, NR⁶⁸C(O)N(R⁶⁸)₂, C(O)NH₂, C(O)NHR⁶⁸, C(O)N(R⁶⁸)₂, C(O)NHOH, C(O)NHOR⁶⁸, C(O)NHSO₂R⁶⁸, C(O)NR⁶⁸SO₂R⁶⁸, SO₂NH₂, SO₂NHR⁶⁸, SO₂N(R⁶⁸)₂, C(O)H, C(O)OH, C(N)NH₂, C(N)NHR⁶⁸, C(N)N(R⁶⁸)₂, CNOH, CNOCH₃, OH, (O), CN, N₃, NO₂, CF₃, CF₂CF₃, OCF₃, OCF₂CF₃, F, Cl, Br or I;

R⁶⁸ is R⁶⁹, R⁷⁰, R⁷¹ or R⁷²;

R⁶⁹ is phenyl, which is unfused or fused with benzene, heteroarene or R⁶⁹ᴬ; R⁶⁹ᴬ is cycloalkane, cycloalkene, heterocycloalkane or heterocycloalkene;

R⁷⁰ is heteroaryl, which is unfused or fused with benzene, heteroarene or R⁷⁰ᴬ; R⁷⁰ᴬ is cycloalkane, cycloalkene, heterocycloalkane or heterocycloalkene;

R⁷¹ is cycloalkyl, cycloalkenyl, heterocycloalkyl or heterocycloalkenyl, each of which is unfused or fused with benzene, heteroarene or R⁷¹ᴬ; R⁷¹ᴬ is cycloalkane, cycloalkene, heterocycloalkane or heterocycloalkene;

R⁷² is alkyl, alkenyl or alkynyl, each of which is unsubstituted or substituted with one or two or three of independently selected R⁷³, OR⁷³, SR⁷³, S(O)R⁷³, SO₂R⁷³, C(O)R⁷³, CO(O)R⁷³, OC(O)R⁷³, OC(O)OR⁷³, NH₂, NHR⁷³, N(R⁷³)₂, NHC(O)R⁷³, NR⁷³C(O)R⁷³, NHS(O)₂R⁷³, NR⁷³S(O)₂R⁷³, NHC(O)OR⁷³, NR⁷³C(O)OR⁷³, NHC(O)NH, NHC(O)NHR⁷³, NHC(O)N(R⁷³)₂, NR⁷³C(O)NHR⁷³, NR⁷³C(O)N(R⁷³)₂, C(O)NH₂, C(O)NHR⁷³, C(O)N(R⁷³)₂, C(O)NHOH, C(O)NHOR⁷³, C(O)NHSO₂R⁷³, C(O)NR⁷³SO₂R⁷³, SO₂NH₂, SO₂NHR⁷³, SO₂N(R⁷³)₂, C(O)H, C(O)OH, C(N)NH₂, C(N)NHR⁷³, C(N)N(R⁷³)₂, CNOH, CNOCH₃, OH, (O), CN, N₃, NO₂, CF₃, CF₂CF₃, OCF₃, OCF₂CF₃, F, Cl, Br or I;

R⁷³ is alkyl, alkenyl, alkynyl, phenyl, heteroaryl, cycloalkyl, cycloalkenyl, heterocycloalkyl or heterocycloalkenyl; and the moieties represented by R⁶⁹, R⁷⁰, and R⁷¹ are unsubstituted or substituted with one or two or three or four of independently selected NH₂, C(O)NH₂, C(O)NHOH, SO₂NH₂, CF₃, CF₂CF₃, C(O)H, C(O)OH, C(N)NH₂, OH, (O), CN, N₃, NO₂, OCF₃, OCF₂CF₃, F, Cl, Br or I.

2. A compound having Formula (V)

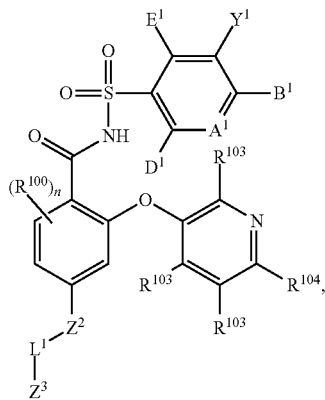

(V)

or a therapeutically acceptable salt thereof, wherein

R¹⁰⁰ is absent;
n is 0;
A² is H;
B¹ is NHR¹;
D¹ and E¹ are each H;
R¹ is R⁵, wherein R⁵ is alkyl which is unsubstituted or substituted with one or two or three substituents independently selected from R⁶, R⁷, OR⁷, SR⁷, S(O)R⁷, SO₂R⁷, NHR⁷, N(R⁷)₂, C(O)R⁷, C(O)NH₂, C(O)NHR⁷, C(O)N(R⁷)₂, NHC(O)R⁷, NR⁷C(O)R⁷, NHSO₂R⁷, NHC(O)OR⁷, SO₂NH, SO₂NHR⁷, SO₂N(R⁷)₂, NHC(O)NH₂, NHC(O)NHR⁷, NHC(O)CH(CH₃)NHC(O)CH(CH₃)NH₂, OH, (O), C(O)OH, N₃, CN, NH₂, CF₃, CF₂CF₃, F, Cl, Br and I;

Y¹ is NO₂;
Z² is R³⁰, wherein R³⁰ is unfused piperazinyl;
L¹ is R³⁷, wherein R³⁷ is methylene;
Z³ is R⁴⁰, wherein R⁴⁰ is unfused cyclohexenyl;
R⁶ is C₂-C₅-spiroalkyl, which is unsubstituted or substituted with OH, (O), N₃, CN, CF₃, CF₂CF₃, F, C, Br, I, NH₂, NH(CH₃) or N(CH₃)₂;
R⁷ is R⁸, R⁹, R¹⁰ or R¹¹;
R⁸ is phenyl, which is unfused or fused with benzene, heteroarene or R⁸ᴬ; R⁸ᴬ is cycloalkane, cycloalkene, heterocycloalkane or heterocycloalkene;
R⁹ is heteroaryl, which is unfused or fused with benzene, heteroarene or R⁹ᴬ; R⁹ᴬ is cycloalkane, cycloalkene, heterocycloalkane or heterocycloalkene;
R¹⁰ is cycloalkyl, cycloalkenyl, heterocycloalkyl or heterocycloalkenyl each of which is unfused or fused with benzene, heteroarene or R¹⁰ᴬ; R¹⁰ᴬ is cycloalkane, cycloalkene, heterocycloalkane or heterocycloalkene;
R¹¹ is alkyl, alkenyl or alkynyl, each of which is unsubstituted or substituted with one or two or three of independently selected R¹², OR¹², SR¹², S(O)R¹², SO₂R¹², C(O)R¹², CO(O)R¹², OC(O)R¹², OC(O)OR¹², NH₂, NHR¹², N(R¹²)₂, NHC(O)R¹², NR¹²C(O)R¹², NHS(O)₂R¹², NR¹²S(O)₂R¹², NHC(O)OR¹², NR¹²C(O)OR¹², NHC(O)NH₂, NHC(O)NHR¹², NHC(O)N(R¹²)₂, NR¹²C(O)NHR¹², NR¹²C(O)N(R¹²)₂, C(O)NH₂, C(O)NHR¹², C(O)N(R¹²)₂, C(O)NHOH, C(O)NHOR¹², C(O)NHSO₂R¹², C(O)NR¹²SO₂R¹², SO₂NH₂, SO₂NHR¹², SO₂N(R¹²)₂, C(O)H, C(O)OH, C(N)NH₂, C(N)NHR¹², C(N)N(R¹²)₂, CNOH, CNOCH₃, OH, (O), CN, N₃, NO₂, CF₃, CF₂CF₃, OCF₃, OCF₂CF₃, F, Cl, Br or I;
R¹² is R¹³, R¹⁴, R¹⁵ or R¹⁶;
R¹³ is phenyl, which is unfused or fused with benzene, heteroarene or R¹³ᴬ; R¹³ᴬ is cycloalkane, cycloalkene, heterocycloalkane or heterocycloalkene;
R¹⁴ is heteroaryl, which is unfused or fused with benzene, heteroarene or R¹⁴ᴬ; R¹⁴ᴬ is cycloalkane, cycloalkene, heterocycloalkane or heterocycloalkene;
R¹⁵ is cycloalkane, cycloalkene, heterocycloalkane or heterocycloalkene, each of which is unfused or fused with benzene, heteroarene or R¹⁵ᴬ; R¹⁵ᴬ is cycloalkane, cycloalkene, heterocycloalkane or heterocycloalkene;
R¹⁶ is alkyl, alkenyl or alkynyl;
at least one of R¹⁰³ or R¹⁰⁴ is selected from the group consisting of R⁵⁰, OR⁵⁰, SR⁵⁰, S(O)R⁵⁰, SO₂R⁵⁰, C(O)R⁵⁰, CO(O)R⁵⁰, OC(O)R⁵⁰, OC(O)OR⁵⁰, NH₂, NHR⁵⁰, N(R⁵⁰)₂, NHC(O)R⁵⁰, NR⁵⁰C(O)R⁵⁰, NHS(O)₂R⁵⁰, NR⁵⁰S(O)₂R⁵⁰, NHC(O)OR⁵⁰, NR⁵⁰C(O)OR⁵⁰, NHC(O)NH₂, NHC(O)NHR⁵⁰, NHC(O)N(R⁵⁰)₂, NR⁵⁰C(O)NHR⁵⁰, NR⁵⁰C(O)N(R⁵⁰)₂, C(O)NH₂, C(O)NHR⁵⁰, C(O)N(R⁵⁰)₂, C(O)NHOH, C(O)NHOR⁵⁰, NHSO₂R⁵⁰, C(O)NR⁵⁰SO₂R⁵⁰, SO₂NH₂, SO₂NHR⁵⁰, SO₂N(R⁵⁰)₂, C(O)H, C(O)OH, C(N)NH₂, C(N)NHR⁵⁰, C(N)N(R⁵⁰)₂, CNOH, CNOCH₃, OH, (O), CN, N₃, NO$_2$, CF$_3$, CF$_2$CF$_3$, OCF$_3$, OCF$_2$CF$_3$, F, Cl, Br and I, and the remainder of R$^{103}$ or R$^{104}$ are H;

R$^{50}$ is R$^{51}$, R$^{52}$, R$^{53}$ or R$^{54}$;

R$^{51}$ is phenyl, which is unfused or fused with benzene, heteroarene or R$^{51A}$; R$^{51A}$ is cycloalkane, cycloalkene, heterocycloalkane or heterocycloalkene;

R$^{52}$ is heteroaryl, which is unfused or fused with benzene, heteroarene or R$^{52A}$; R$^{52A}$ is cycloalkane, cycloalkene, heterocycloalkane or heterocycloalkene;

R$^{53}$ is cycloalkyl, cycloalkenyl, heterocycloalkyl or heterocycloalkenyl, each of which is unfused or fused with benzene, heteroarene or R$^{53A}$; R$^{53A}$ is cycloalkane, cycloalkene, heterocycloalkane or heterocycloalkene;

R$^{54}$ is alkyl, alkenyl or alkynyl, each of which is unsubstituted or substituted with one or two or three of independently selected R$^{55}$, OR$^{55}$, SR$^{55}$, S(O)R$^{55}$, SO$_2$R$^{55}$, C(O)R$^{55}$, CO(O)R$^{55}$, OC(O)R$^{55}$, OC(O)OR$^{55}$, NH$_2$, NHR$^{55}$, N(R$^{55}$)$_2$, NHC(O)R$^{55}$, NR$^{55}$C(O)R$^{55}$, NHS(O)$_2$R$^{55}$, NR$^{55}$S(O)$_2$R$^{55}$, NHC(O)OR$^{55}$, NR$^{55}$C(O)OR$^{55}$, NHC(O)NH$_2$, NHC(O)NHR$^{55}$, NHC(O)N(R$^{55}$)$_2$, NR$^{55}$C(O)NHR$^{55}$, NR$^{55}$C(O)N(R$^{55}$)$_2$, C(O)NH$_2$, C(O)NHR$^{55}$, C(O)N(R$^{55}$)$_2$, C(O)NHOH, C(O)NHOR$^{55}$, C(O)NHSO$_2$R$^{55}$, C(O)NR$^{55}$SO$_2$R$^{55}$, SO$_2$NH$_2$, SO$_2$NHR$^{55}$, SO$_2$N(R$^{55}$)$_2$, C(O)H, C(O)OH, C(N)NH$_2$, C(N)NHR$^{55}$, C(N)N(R$^{55}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{55}$ is alkyl, alkenyl, alkynyl, phenyl, heteroaryl, cycloalkyl, cycloalkenyl, heterocycloalkyl or heterocycloalkenyl;

wherein each cyclic moiety represented by R$^8$, R$^9$, R$^{10}$, R$^{13}$, R$^{14}$, R$^{15}$, R$^{40}$, R$^{51}$, R$^{52}$, R$^{53}$ and R$^{55}$ is independently unsubstituted, substituted or further substituted with one or two or three or four or five of independently selected R$^{57A}$, R$^{57}$, OR$^{57}$, SR$^{57}$, S(O)R$^{57}$, SO$_2$R$^{57}$, C(O)R$^{57}$, CO(O)R$^{57}$, OC(O)R$^{57}$, OC(O)OR$^{57}$, NH$_2$, NHR$^{57}$, N(R$^{57}$)$_2$, NHC(O)R$^{57}$, NR$^{57}$C(O)R$^{57}$, NHS(O)$_2$R$^{57}$, NR$^{57}$S(O)$_2$R$^{57}$, NHC(O)OR$^{57}$, NR$^{57}$C(O)OR$^{57}$, NHC(O)NH$_2$, NHC(O)NHR$^{57}$, NHC(O)N(R$^{57}$)$_2$, NR$^{57}$C(O)NHR$^{57}$, NR$^{57}$C(O)N(R$^{57}$)$_2$, C(O)NH$_2$, C(O)NHR$^{57}$, C(O)N(R$^{57}$)$_2$, C(O)NHOH, C(O)NHOR$^{57}$, C(O)NHSO$_2$R$^{57}$, C(O)NR$^{57}$SO$_2$R$^{57}$, SO$_2$NH$_2$, SO$_2$NHR$^{57}$, SO$_2$N(R$^{57}$)$_2$, C(O)H, C(O)OH, C(N)NH$_2$, C(N)NHR$^{57}$, C(N)N(R$^{57}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{57A}$ is spirocyclyl;

R$^{57}$ is R$^{58}$, R$^{59}$, R$^{60}$ or R$^{61}$;

R$^{58}$ is phenyl, which is unfused or fused with benzene, heteroarene or R$^{58A}$; R$^{58A}$ is cycloalkane, cycloalkene, heterocycloalkane or heterocycloalkene;

R$^{59}$ is heteroaryl, which is unfused or fused with benzene, heteroarene or R$^{59A}$; R$^{59A}$ is cycloalkane, cycloalkene, heterocycloalkane or heterocycloalkene;

R$^{60}$ is cycloalkyl, cycloalkenyl, heterocycloalkyl or heterocycloalkenyl, each of which is unfused or fused with benzene, heteroarene or R$^{60A}$; R$^{60A}$ is cycloalkane, cycloalkene, heterocycloalkane or heterocycloalkene;

R$^{61}$ is alkyl, alkenyl or alkynyl, each of which is unsubstituted or substituted with one or two or three of independently selected R$^{62}$, OR$^{62}$, SR$^{62}$, S(O)R$^{62}$, SO$_2$R$^{62}$, C(O)R$^{62}$, CO(O)R$^{62}$, OC(O)R$^{62}$, OC(O)OR$^{62}$, NH$_2$, NHR$^{62}$, N(R$^{62}$)$_2$, NHC(O)R$^{62}$, NR$^{62}$C(O)R$^{62}$, NHS(O)$_2$R$^{62}$, NR$^{62}$S(O)$_2$R$^{62}$, NHC(O)OR$^{62}$, NR$^{62}$C(O)OR$^{62}$, NHC(O)NH$_2$, NHC(O)NHR$^{62}$, NHC(O)N(R$^{62}$)$_2$, NR$^{62}$C(O)NHR$^{62}$, NR$^{62}$C(O)N(R$^{62}$)$_2$, C(O)NH$_2$, C(O)NHR$^{62}$, C(O)N(R$^{62}$)$_2$, C(O)NHOH, C(O)NHOR$^{62}$, C(O)NHSO$_2$R$^{62}$, C(O)NR$^{62}$SO$_2$R$^{62}$, SO$_2$NH$_2$, SO$_2$NHR$^{62}$, SO$_2$N(R$^{62}$)$_2$, C(O)H, C(O)OH, C(N)NH$_2$, C(N)NHR$^{62}$, C(N)N(R$^{62}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{62}$ is R$^{63}$, R$^{64}$, R$^{65}$ or R$^{66}$;

R$^{63}$ is phenyl, which is unfused or fused with benzene, heteroarene or R$^{63A}$; R$^{63A}$ is cycloalkane, cycloalkene, heterocycloalkane or heterocycloalkene;

R$^{64}$ is heteroaryl, which is unfused or fused with benzene, heteroarene or R$^{64A}$; R$^{64A}$ is cycloalkane, cycloalkene, heterocycloalkane or heterocycloalkene;

R$^{65}$ is cycloalkyl, cycloalkenyl, heterocycloalkyl or heterocycloalkenyl, each of which is unfused or fused with benzene, heteroarene or R$^{65A}$; R$^{65A}$ is cycloalkane, cycloalkene, heterocycloalkane or heterocycloalkene;

R$^{66}$ is alkyl, alkenyl or alkynyl, each of which is unsubstituted or substituted with one or two or three of independently selected R$^{67}$, OR$^{67}$, SR$^{67}$, S(O)R$^{67}$, SO$_2$R$^{67}$, C(O)R$^{67}$, CO(O)R$^{67}$, OC(O)R$^{67}$, OC(O)OR$^{67}$, NH$_2$, NHR$^{67}$, N(R$^{67}$)$_2$, NHC(O)R$^{67}$, NR$^{67}$C(O)R$^{67}$, NHS(O)$_2$R$^{67}$, NR$^{67}$S(O)$_2$R$^{67}$, NHC(O)OR$^{67}$, NR$^{67}$C(O)OR$^{67}$, NHC(O)NH$_2$, NHC(O)NHR$^{67}$, NHC(O)N(R$^{67}$)$_2$, NR$^{67}$C(O)NHR$^{67}$, NR$^{67}$C(O)N(R$^{67}$)$_2$, C(O)NH$_2$, C(O)NHR$^{67}$, C(O)N(R$^{67}$)$_2$, C(O)NHOH, C(O)NHOR$^{67}$, C(O)NHSO$_2$R$^{67}$, C(O)NR$^{67}$SO$_2$R$^{67}$, SO$_2$NH$_2$, SO$_2$NHR$^{67}$, SO$_2$N(R$^{67}$)$_2$, C(O)H, C(O)OH, C(N)NH$_2$, C(N)NHR$^{67}$, C(N)N(R$^{67}$)$_2$, CNOH, CNOCH$_3$, OH, (O), CN, N$_3$, NO$_2$, CF$_3$, CF$_2$CF$_3$, OCF$_3$, OCF$_2$CF$_3$, F, C, Br or I substituents;

R$^{67}$ is alkyl, alkenyl, alkynyl, phenyl, heteroaryl, cycloalkyl, cycloalkenyl, heterocycloalkyl or heterocycloalkenyl;

wherein the moieties represented by R$^{57A}$, R$^{58}$, R$^{59}$, R$^{60}$, R$^{63}$, R$^{64}$, R$^{65}$, and R$^{67}$ are unsubstituted or substituted with one or two or three or four of independently selected R$^{68}$, OR$^{68}$, SR$^{68}$, S(O)R$^{68}$, SO$_2$R$^{68}$, C(O)R$^{68}$, CO(O)R$^{68}$, OC(O)R$^{68}$, OC(O)OR$^{68}$, NH$_2$, NHR$^{68}$, N(R$^{68}$)$_2$, NHC(O)R$^6$, NR$^{68}$C(O)R$^{68}$, NHS(O)$_2$R$^{68}$, NR$^{68}$S(O)$_2$R$^{68}$, NHC(O)OR$^{68}$, NR$^{68}$C(O)OR$^{68}$, NHC(O)NH$_2$, NHC(O)NHR$^{68}$, NHC(O)N(R$^{68}$)$_2$, NR$^{68}$C(O)NHR$^{68}$, NR$^{68}$C(O)N(R$^{68}$)$_2$, C(O)NH$_2$, C(O)NHR$^{68}$, C(O)N(R$^{68}$)$_2$, C(O)NHOH, C(O)NHOR$^{68}$, C(O)NHSO$_2$R$^{68}$, C(O)NR$^{68}$SO$_2$R$^{68}$, SO$_2$NH$_2$, SO$_2$NHR$^{68}$, SO$_2$N(R$^{68}$)$_2$, C(O)H, C(O)OH, C(N)NH$_2$, C(N)NHR$^{68}$, C(N)N(R$^6$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{68}$ is R$^{69}$, R$^{70}$, R$^{71}$ or R$^{72}$;

R$^{69}$ is phenyl, which is unfused or fused with benzene, heteroarene or R$^{69A}$; R$^{69A}$ is cycloalkane, cycloalkene, heterocycloalkane or heterocycloalkene;

R$^{70}$ is heteroaryl, which is unfused or fused with benzene, heteroarene or R$^{70A}$; R$^{70A}$ is cycloalkane, cycloalkene, heterocycloalkane or heterocycloalkene;

R$^{71}$ is cycloalkyl, cycloalkenyl, heterocycloalkyl or heterocycloalkenyl, each of which is unfused or fused with benzene, heteroarene or R$^{71A}$; R$^{71A}$ is cycloalkane, cycloalkene, heterocycloalkane or heterocycloalkene;

R$^{72}$ is alkyl, alkenyl or alkynyl, each of which is unsubstituted or substituted with one or two or three of independently selected R$^{73}$, OR$^{73}$, SR$^{73}$, S(O)R$^{73}$, SO$_2$R$^{73}$, C(O)R$^{73}$, CO(O)R$^{73}$, OC(O)R$^{73}$, OC(O)OR$^{73}$, NH$_2$, NHR$^{73}$, N(R$^{73}$)$_2$, NHC(O)R$^{73}$, NR$^{73}$C(O)R$^{73}$, NHS(O)$_2$R$^{73}$, NR$^{73}$S(O)$_2$R$^{73}$, NHC(O)OR$^{73}$, NR$^{73}$C(O)OR$^{73}$, NHC(O)NH$_2$, NHC(O)NHR$^{73}$, NHC(O)N(R$^{73}$)$_2$, NR$^{73}$C(O)NHR$^{73}$, NR$^{73}$C(O)N(R$^{73}$)$_2$, C(O)NH$_2$, C(O)NHR$^{73}$, C(O)N(R$^{73}$)$_2$, C(O)NHOH, C(O)NHOR$^{73}$, C(O)NHSO$_2$R$^{73}$, C(O)NR$^{73}$SO$_2$R$^{73}$, SO₂NH₂, SO₂NHR⁷³, SO₂N(R⁷³)₂, C(O)H, C(O)OH, C(N)NH₂, C(N)NHR⁷³, C(N)N(R⁷³)₂, CNOH, CNOCH₃, OH, (O), CN, N₃, NO₂, CF₃, CF₂CF₃, OCF₃, OCF₂CF₃, F, Cl, Br or I;

R⁷³ is alkyl, alkenyl, alkynyl, phenyl, heteroaryl, cycloalkyl, cycloalkenyl, heterocycloalkyl or heterocycloalkenyl; and the moieties represented by R⁶⁹, R⁷⁰, and R⁷¹ are unsubstituted or substituted with one or two or three or four of independently selected NH₂, C(O)NH₂, C(O)NHOH, SO₂NH₂, CF₃, CF₂CF₃, C(O)H, C(O)OH, C(N)NH₂, OH, (O), CN, N₃, NO₂, OCF₃, OCF₂CF₃, F, Cl, Br or I.

3. A compound or a therapeutically acceptable salt thereof, wherein the compound is selected from the group consisting of:

4-(4-{[2-(4-chlorophenyl)-4,4-dimethylcyclohex-1-en-1-yl]methyl}piperazin-1-yl)-2-(2,3-difluorophenoxy)-N-({4-[(3-morpholin-4-ylpropyl)amino]-3-nitrophenyl}sulfonyl)benzamide;

2-(4-amino-3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2,5-dichlorophenoxy)-N-({4-[(3-morpholin-4-ylpropyl)amino]-3-nitrophenyl}sulfonyl)benzamide;

N-(4-((4-aminotetrahydro-2H-pyran-4-yl)methylamino)-3-nitrophenylsulfonyl)-2-(3-chlorophenoxy)-4-(4-((2-(4-chlorophenyl)-4,4-dimethylcyclohex-1-enyl)methyl)piperazin-1-yl)benzamide;

4-(4-{[2-(4-chlorophenyl)-4,4-dimethylcyclohex-1-en-1-yl]methyl}piperazin-1-yl)-2-(3-fluorophenoxy)-N-({4-[(3-morpholin-4-ylpropyl)amino]-3-nitrophenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(2-chloro-4-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2-fluorophenoxy)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(3-fluorophenoxy)-N-({4-[(2-morpholin-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-2-(2,3-difluorophenoxy)-N-({4-[(2-morpholin-4-ylethyl)amino]-3-nitrophenyl}sulfonyl)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(2-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(3-fluorophenoxy)benzamide;

4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]-2-(4-fluorophenoxy)benzamide;

2-(3-chlorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl methyl}piperazin-1-yl)-N-[(4-{[3-(dimethylamino)propyl]amino}-3-nitrophenyl)sulfonyl]benzamide;

2-(3-chlorophenoxy)-4-(4-{2-(4-chlorophenyl)-4,4-dimethylcyclohex-1-en-1-yl]methyl}piperazin-1-yl)-N-[(4-{[3-(4-methylpiperazin-1-yl)propyl]amino}-3-nitrophenyl)sulfonyl]benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(3-morpholin-4-ylpropyl)amino]-3-nitrophenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({3-nitro-4-[(3-pyrrolidin-1-ylpropyl)amino]phenyl}sulfonyl)benzamide;

2-(3-chloro-2-fluorophenoxy)-4-(4-{[2-(4-chlorophenyl)-4,4-dimethylcyclohex-1-en-1-yl]methyl}piperazin-1-yl)-N-({4-[(2-morpholin-4-ylethyl)amino]-3-nitrophenyl}sulfonyl)benzamide;

2-(3-chlorophenoxy)-4-(4-{[2-(4-chlorophenyl)-4,4-dimethylcyclohex-1-en-1-yl]methyl}piperazin-1-yl)-N-[(4-{[(1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(2,3-difluorophenoxy)-N-[(4-{[(1-methylpiperidin-4-yl)methyl]amino}-3-nitrophenyl)sulfonyl]benzamide;

2-(2-chlorophenoxy)-4-(4-{[2-(4-chlorophenyl)-4,4-dimethylcyclohex-1-en-1-yl]methyl}piperazin-1-yl)-N-[(4-{[3-(dimethylamino)propyl]amino}-3-nitrophenyl)sulfonyl]benzamide;

N-[(4-{[(4-aminotetrahydro-2H-pyran-4-yl)methyl]amino}-3-nitrophenyl)sulfonyl]-2-(2-chlorophenoxy)-4-(4-{[2-(4-chlorophenyl)-4,4-dimethylcyclohex-1-en-1-yl]methyl}piperazin-1-yl)benzamide;

2-(2-chlorophenoxy)-4-(4-{[2-(4-chlorophenyl)-4,4-dimethylcyclohex-1-en-1-yl]methyl}piperazin-1-yl)-N-[(4-{[(4-hydroxy-1-methylpiperidin-4-yl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-(3-fluorophenoxy)-N-[(4-{[(4-hydroxy-1-methylpiperidin-4-yl)methyl]amino}-3-nitrophenyl)sulfonyl]benzamide;

2-(3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(4-amino-3-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-yl methyl)amino]phenyl}sulfonyl)benzamide;

2-(2-chlorophenoxy)-4-(4-{[2-(4-chlorophenyl)-4,4-dimethylcyclohex-1-en-1-yl]methyl}piperazin-1-yl)-N-{[4-({[4-(hydroxymethyl)tetrahydro-2H-pyran-4-yl]methyl}amino)-3-nitrophenyl]sulfonyl}benzamide;

2-(2-chlorophenoxy)-4-(4-{[2-(4-chlorophenyl)-4,4-dimethylcyclohex-1-en-1-yl]methyl}piperazin-1-yl)-N-[(3-nitro-4-{[3-(3-oxopiperazin-1-yl)propyl]amino}phenyl)sulfonyl]benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

2-[(6-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-3-ylcarbamate;

2-[(5-aminopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

tert-butyl 4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

4-(4-{[2-(4-chlorophenyl)-4,4-dimethylcyclohex-1-en-1-yl]methyl}piperazin-1-yl)-2-[(6-hydroxypyridin-3-yl)oxy]-N-({3-nitro-4-[(tetrahydro-2H-pyran-4-ylmethyl)amino]phenyl}sulfonyl)benzamide;

2-{[6-(benzyloxy)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-fluoropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-amino-5-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)nicotinamide;

2-[(6-amino-5-cyanopyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-{[6-(acetylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({6-[(methylsulfonyl)amino]pyridin-3-yl}oxy)-N-({3-nitro-4-[(tetrahydro-2H-pyran-4-ylmethyl)amino]phenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-({4-[(1,4-dioxan-2-ylmethyl)amino]-3-nitrophenyl}sulfonyl)benzamide;

2-[(6-amino-5-methylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-fluorotetrahydro-2H-pyran-4-yl)methyl]amino}-3-nitrophenyl)sulfonyl]benzamide;

2-[(6-amino-5-isopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-cyclopropylpyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-bromopyridin-3-yl)oxy]-4-(4-{[2-(4-chlorophenyl)-4,4-dimethylcyclohex-1-en-1-yl]methyl}piperazin-1-yl)-N-[(4-{[(4-methoxycyclohexyl)methyl]amino}-3-nitrophenyl)sulfonyl]benzamide;

2-[(6-amino-5-chloropyridin-3-yl)oxy]-4-(4-{[2-(4-chlorphenyl)-4,4-dimethylcyclohex-1-en-1-yl]methyl}piperazin-1-yl)-N-[(4-{[(4-cyclopropylmorpholin-2-yl)methyl]amino}-3-nitrophenyl)sulfonyl]benzamide;

tert-butyl 6-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

tert-butyl 4-(5-(4-((2-(4-chlorophenyl)-4,4-dimethylcyclohex-1-enyl)methyl)piperazin-1-yl)-2-(3-nitro-4-((tetrahydro-2H-pyran-4-yl)methylamino))phenylsulfonylcarbamoyl)phenoxy)pyridine-2,6-diyldicarbamate;

4-(4-{[2-(4-chlorophenyl)-4,4-dimethylcyclohex-1-en-1-yl]methyl}piperazin-1-yl)-2-{[6-(cyclopropylamino)pyridin-3-yl]oxy}-N-({3-nitro-4-[(tetrahydro-2H-pyran-4-ylmethyl)amino]phenyl}sulfonyl)benzamide;

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-[(4-{[(4-methoxycyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-2-({6-[(2,2-difluoroethyl)amino]pyridin-3-yl}oxy)-N-({3-nitro-4-[(tetrahydro-2H-pyran-4-ylmethyl)amino]phenyl}sulfonyl)benzamide;

2-{[5-chloro-6-(methylamino)pyridin-3-yl]oxy}-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-(({4-[({4-[2-fluoro-1-(fluoromethyl)ethyl]morpholin-2-yl}methyl)amino]-3-nitrophenyl}sulfonyl)benzamide;

tert-butyl 5-bromo-4-(5-(4-{[2-(4-chlorophenyl)-4,4-dimethylcyclohex-1-en-1-yl]methyl}piperazin-1-yl)-2-{[({3-nitro-4-[(tetrahydro-2H-pyran-4-ylmethyl)amino]phenyl}sulfonyl)amino]carbonyl}phenoxy)pyridin-2-ylcarbamate;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-({6-[(2,2,2-trifluoroethyl)amino]pyridin-3-yl}oxy)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-hydroxycyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydrofuran-3-ylmethyl)amino]phenyl}sulfonyl)benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4,4-difluorocyclohexyl)methyl]amino}-3-nitrophenyl)sulfonyl]benzamide;

2-[(6-amino-5-chloropyridin-3-yl)oxy]-4-(4-{[2-(4-chlorophenyl)-4,4-dimethylcyclohex-1-en-1-yl]methyl}piperazin-1-yl)-N-[(4-{[(4-cyanocyclohexyl)methyl]amino}-3-nitrophenyl)sulfonyl]benzamide;

4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-4-yl)phenoxy]benzamide;

2-[2-(2-aminopyridin-3-yl)phenoxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide; and 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-[2-(1H-pyrazol-5-yl)phenoxy]benzamide.

4. The compound of claim 1, or therapeutically acceptable salt thereof, wherein the compound is 2-(3-amino-5-chlorophenoxy)-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide.

5. The compound of claim 2, or therapeutically acceptable salt thereof, wherein the compound is 2-[(6-amino-5-chloropyridin-3-yl)oxy]-4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)benzamide.

\* \* \* \* \*

UNITED STATES PATENT AND TRADEMARK OFFICE
CERTIFICATE OF CORRECTION

PATENT NO.      : 8,952,157 B2
APPLICATION NO. : 13/952278
DATED           : February 10, 2015
INVENTOR(S)     : Ding et al.

Page 1 of 1

It is certified that error appears in the above-identified patent and that said Letters Patent is hereby corrected as shown below:

In the Claims

Column 424, line 34, claim 1: "$R^3$," to read as --$R^5$,--

Column 426, line 02, claim 1: "$(R^{57})_3$," to read as --$(R^{57})_2$,--

Column 426, line 48, claim 1: "$R^7$," to read as --$R^{67}$,--

Column 426, line 49, claim 1: "$NHR^7$," to read as --$NHR^{67}$,--

Column 426, line 65, claim 1: "$S(O)R$," to read as --$S(O)R^{68}$,--

Column 426, line 67, claim 1: "$NHC(O)R$," to read as --$NHC(O)R^{68}$,--

Column 427, line 27, claim 1: "NH," to read as --$NH_2$,--

Column 427, line 67, claim 2: Add the missing element - "$A^1$ is $C(A^2)$;"

Column 428, line 08, claim 2: "$SO_2NH$," to read as --$SO_2NH_2$,--

Column 428, line 18, claim 2: "C," to read as --Cl,--

Column 430, line 29, claim 2: "C," to read as --Cl,--

Column 430, line 38, claim 2: "$NHC(O)R^6$," to read as --$NHC(O)R^{68}$,--

Column 430, line 45, claim 2: "$(R^6)_2$," to read as --$(R^{68})_2$,--

Column 432, line 15, claim 3: "-yl" to read as -- -yl]--

Column 432, line 18, claim 3: "{2-" to read as --{[2- --

Column 435, line 19, claim 3: "(({4-" to read as --({4- --

Signed and Sealed this
Twenty-fourth Day of November, 2015

Michelle K. Lee
*Director of the United States Patent and Trademark Office*